United States Patent
Boezio et al.

(10) Patent No.: US 9,346,798 B2
(45) Date of Patent: May 24, 2016

(54) DIHYDROBENZOXAZINE AND TETRAHYDROQUINOXALINE SODIUM CHANNEL INHIBITORS

(71) Applicant: AMGEN INC., Thousand Oaks, CA (US)

(72) Inventors: Christiane Boezio, Somerville, CA (US); Alessandro Boezio, Somerville, MA (US); Howard Bregman, Melrose, MA (US); Nagasree Chakka, Lexington, MA (US); James R. Coats, Oak Harbor, WA (US); Katrina Woodin Copeland, Sudbury, MA (US); Erin F. Dimauro, Cambridge, MA (US); Thomas Dineen, Somerville, MA (US); Hua Gao, Canton, MA (US); Daniel La, Brookline, MA (US); Isaac E. Marx, Cambridge, MA (US); Hanh Nho Nguyen, Arlington, MA (US); Emily Anne Peterson, Cambridge, MA (US); Matthew Weiss, Boston, MA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/377,478

(22) PCT Filed: Feb. 12, 2013

(86) PCT No.: PCT/US2013/025668
§ 371 (c)(1),
(2) Date: Aug. 7, 2014

(87) PCT Pub. No.: WO2013/122897
PCT Pub. Date: Aug. 22, 2013

(65) Prior Publication Data
US 2015/0057271 A1    Feb. 26, 2015

Related U.S. Application Data

(60) Provisional application No. 61/598,136, filed on Feb. 13, 2012.

(51) Int. Cl.
| | |
|---|---|
| *C07D 413/12* | (2006.01) |
| *C07D 417/12* | (2006.01) |
| *C07D 413/14* | (2006.01) |
| *C07D 471/04* | (2006.01) |
| *C07D 417/14* | (2006.01) |

(52) U.S. Cl.
CPC ............ *C07D 417/14* (2013.01); *C07D 413/12* (2013.01); *C07D 413/14* (2013.01); *C07D 417/12* (2013.01); *C07D 471/04* (2013.01)

(58) Field of Classification Search
CPC .. C07D 417/14; C07D 417/12; C07D 413/12; C07D 413/14; C07D 471/04
USPC ...................... 544/105; 514/230.5
See application file for complete search history.

(56) References Cited

U.S. PATENT DOCUMENTS 7,173,030 B2 *   2/2007 Pyring et al. ............... 514/236.2
2008/0200495 A1   8/2008 Boubia et al.

FOREIGN PATENT DOCUMENTS

| RU | 2261246 C1 | 9/2005 |
| WO | 2004/103980 A1 | 12/2004 |
| WO | 2006/051662 A1 | 5/2006 |
| WO | 2009/012241 A1 | 1/2009 |
| WO | 2010/026365 A1 | 3/2010 |
| WO | 2011/137089 A1 | 11/2011 |
| WO | 2013/006596 A1 | 1/2013 |

OTHER PUBLICATIONS

Database Registry [Online] 1,3-5,7,17,19 Chemical Abstracts Service, Columbus, Ohio, US; Jul. 11, 2006, XP002694732, Database accession No. 891935-81-2 Compounds of the following Registry Nos. 891935-81-2, 891936-13-3, 891936-21-3, 891940-34-4, 891940-42-4, 891944-38-0, 891945-17-8.

Database Registry [Online] 1,3,7,16-19 Chemical Abstracts Service, Columbus, Ohio, US; Aug. 17, 2006, XP002694733, Database accession No. 902485-35-2 Compound of the following Registry No. 902485-35-2.

Database Registry [Online] 1,3,7,16-19 Chemical Abstracts Service, Columbus, Ohio, US; Aug. 18, 2006, XP002694734, Database accession No. 902566-77-2 Compound of the following Registry No. 902566-77-2.

(Continued)

*Primary Examiner* — Kahsay Habte
(74) *Attorney, Agent, or Firm* — Elsa D. Lemoine

(57) ABSTRACT

The present invention provides compounds of Formula I, or pharmaceutically acceptable salts thereof, that are inhibitors of voltage-gated sodium channels, in particular Nav 1.7. The compounds are useful for the treatment of diseases treatable by inhibition of sodium channels such as pain disorders. Also provided are pharmaceutical compositions containing compounds of the present invention.

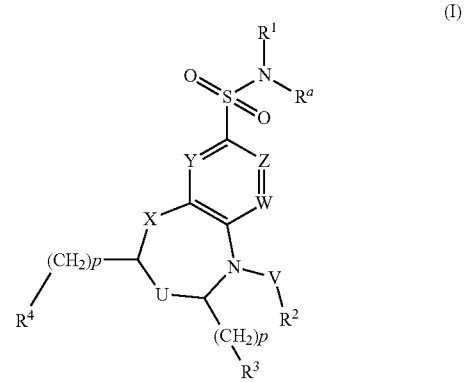

19 Claims, No Drawings

(56) References Cited

OTHER PUBLICATIONS

Database Registry [Online] 1,3-7,16,17,19 Chemical Abstracts Service, Columbus, Ohio, US; Aug. 21, 2006, XP002694735, Database accession No. 902885-28-3 Compounds of the following Registry Nos. 902885-28-3, 902885-36-3, 902885-38-5, 902885-40-9, 902886-50-4.
Database Registry [Online] 1,3,6,7,16,18,19 Chemical Abstracts Service, Columbus, Ohio, US; Apr. 17, 2007, XP002694736, Database accession No. 930524-18-8 Compound of the following Registry No. 930524-18-8.
Database Registry [Online] 1,3,4,7,17-19 Chemical Abstracts Service, Columbus, Ohio, US; Apr. 20, 2007, XP002694737, Database accession No. 931314-73-7 Compound of the following Registry No. 931314-73-7.
Database Registry [Online] 1,3-5,7,17,19 Chemical Abstracts Service, Columbus, Ohio, US; Apr. 22, 2007, XP002694738, Database accession No. 931703-87-6 Compound of the following Registry No. 931703-87-6.
Database Registry [Online] 1,3,6,8,16,18,19 Chemical Abstracts Service, Columbus, Ohio, US; Mar. 13, 2008, XP002694740, Database accession No. 1007664-85-8 Compounds of the following Registry Nos. 1007664-85-8, 1007665-10-2.
Database Registry [Online] 1,3-5,7,17-19 Chemical Abstracts Service, Columbus, Ohio, US; Jun. 22, 2008, XP002694741, Database accession No. 1029777-73-8 Compound of the following Registry No. 1029777-73-8.
Database Registry [Online] 1,3,4,7,17-19 Chemical Abstracts Service, Columbus, Ohio, US; May 20, 2009, XP002694742, Database accession No. 1147642-90-7 Compound of the following Registry No. 1147642-90-7.
Database Registry [Online] 1,3,6,16-19 Chemical Abstracts Service, Columbus, Ohio, US; Sep. 15, 2010, XP002694743, Database accession No. 1241200-98-5 Compound of the following Registry No. 1241200-98-5.
Database Registry [Online] 1,3,6,8,16-19 Chemical Abstracts Service, Columbus, Ohio, US; Sep. 16, 2010, XP002694744, Database accession No. 1241616-76-1 Compound of the following Registry No. 1241616-76-1.
Database Registry [Online] 1,3-6,16-19 Chemical Abstracts Service, Columbus, Ohio, US; Apr. 14, 2011, XP002694745, Database accession No. 1279855-48-9 Compound of the following Registry No. 1279855-48-9.
Database Registry [Online] 1,3,4,7,17,19 Chemical Abstracts Service, Columbus, Ohio, US; Feb. 29, 2012, XP002694746, Database accession No. 1358500-50-1 Compound of the following Registry No. 1358500-50-1.
Database Registry [Online] 1,3,4,7,17,19 Chemical Abstracts Service, Columbus, Ohio, US; Mar. 1, 2012, XP002694747, Database accession No. 1359082-84-0 Compound of the following Registry No. 1359082-84-0.
Database Registry [Online] 1,3,4,17-19 Chemical Abstracts Service, Columbus, Ohio, US; Jul. 27, 2012, XP002694748, Database accession No. 1384699-84-6 Compound of the following Registry No. 1384699-84-6.
Database Registry [Online] 1,3,4,7,17-19 Chemical Abstracts Service, Columbus, Ohio, US; Sep. 18, 2012, XP002694749, Database accession No. 1394647-82-5 Compound of the following Registry No. 1394647-82-5.
Valentina Zuliani et al: "Sodium channel blockers for neuropathic pain", Expert Opinion on Therapeutic Patents, Informa Healthcare, GB, vol. 20, No. 6, Jun. 2010, pp. 755-779, XP009152755, I SSN: 1354-3776.
SciFinder®—Bioorganic & Medicinal Chemistry Letters, vol. 19, Issue: 22, pp. 6452-6458, Journal, 2009, Coden: BMCLE8, ISSN:0960-894X, DOI: 10.1016/j.bmcl.2009.09.027.

* cited by examiner

DIHYDROBENZOXAZINE AND TETRAHYDROQUINOXALINE SODIUM CHANNEL INHIBITORS

RELATED APPLICATIONS

This application is a national stage application under 35 U.S.C. §371 of International Application No. PCT/US2013/025668, having an international filing date of Feb. 12, 2013, which claims the benefit of, and priority to, U.S. Provisional Patent Application No. 61/598,136, filed on Feb. 13, 2012, which is hereby incorporated herein by reference in its entirety.

FIELD OF THE INVENTION

The present invention provides compounds that are inhibitors of voltage-gated sodium channels (Nav), in particular Nav 1.7, and are useful for the treatment of diseases treatable by inhibition of sodium channels such as pain disorders. Also provided are pharmaceutical compositions containing compounds of the present invention.

BACKGROUND OF THE INVENTION

Chronic pain by definition involves abnormal electrical spiking of neurons in the pain pathways: peripheral sensory neurons, spinal cord neurons, neurons in the pain matrix of the brain (e.g., somatosensory cortex, insular cortex, anterior cingular cortex), and/or neurons in brainstem. Although firing of these neurons is modulated and governed by many different receptors, enzymes, and growth factors, in most neurons the fast upstroke of the electrical spike is produced by entry of sodium ions through voltage-gated sodium channels (Hille B, Ion Channels of Excitable Membranes. Sinauer Associates, Inc.: Sunderland Mass., $3^{rd}$ Ed. 2001). There are nine different isoforms of voltage-gated sodium channel (Nav 1.1-Nav 1.9), and they have distinct expression patterns in tissues including neurons and cardiac and skeletal muscle (Goldin, A. L, "Resurgence of sodium channel research," Ann Rev Physiol 63:871-894, 2001;
Wood, J. N. and, Boorman, J. "Voltage-gated sodium channel blockers; target validation and therapeutic potential," Curr. Top Med. Chem. 5:529-537, 2005). Nonselective sodium channel inhibitors such as lidocaine, mexiletine, and carbamazepine show clinical efficacy in chronic pain, including neuropathic pain, but they are limited in dose and in use, likely due to effects on sodium channels outside the pain pathway.

Recent evidence from several independent genetic studies has shown that the tetrodotoxin-sensitive voltage-gated sodium ion channel Nav 1.7 (SCN9A) is required to sense pain. Rare genetic forms of severe chronic pain, Primary Erythromelalgia and Paroxysmal Extreme Pain Disorder, result from mutations that increase the activity of Nav 1.7 (Fertleman C. R., Baker M. D., Parker K. A., Moffatt S., et al., "SCN9A mutations in paroxysmal extreme pain disorder: allelic variants underlie distinct channel defects and phenotypes," Neuron 52:767-774, 2006; Yang Y., Wang Y., Li S, et al., "Mutations in SCN9A, encoding a sodium channel alpha subunit, in patients with primary erythermalgia," J. Med. Genet. 41:171-174, 2004; Drenth J. P. H., to Morsche R. H. M., Guillet G., Taieb A., et al., "SCN9A mutations define primary erythermalgia as a neuropathic disorder of voltage gated sodium channels," J Invest Dermatol 124:1333-1338). Conversely, two separate clinical studies have determined that the root cause of the genetic disorder Congenital Indifference to Pain (CIP) is a loss of function of Nav 1.7 via mutations that truncate the protein and destroy function (Cox J. J., Reimann F, Nicholas A. K., et al. "An SCN9A channelopathy causes congenital inability to experience pain," Nature 444:894-898, 2006; Goldberg Y. P., MacFarlane J., MacDonald M. L., Thompson J., et al. "Loss-of-function mutations in the Nav1.7 gene underlie congenital indifference to pain in multiple human populations," Clin Genet 71:311-319, 2007). The disorder is inherited in Mendelian recessive manner with 100% penetrance. The phenotype associated with CIP is extreme: affected individuals are reported to have experienced painless burns, childbirth, appendicitis, and bone fractures, as well as to have insensitivity to clinical measures of pain such as pinprick or tendon pressure. Yet sensory, motor, autonomic, and other measured functions are normal, with the only reported abnormality being anosmia (inability to smell). These studies indicate that among the many possible targets in the pain pathway, Nav 1.7 governs one or more control points critical for pain perception.

Nav 1.7 intervention may also be implicated in respiratory and respiratory tract diseases. In general, a cough results from various kinds of respiratory conditions and diseases. The cough reflex primarily protects the airway from possible harm via the clearance of foreign particulate and uninvited debris. Within the respiratory epithelium, nerve endings, sensing incoming irritants, transmit information regarding the presence of tussive stimuli to the brain, thereby inducing a cough reflex or cough response. When the cough progresses to a chronic cough, believed to be dry and unproductive, it is frequently associated with the development of lung damage, which is typically irreversible and commonly referred to as chronic pulmonary obstructive disease (CPOD). Such conditions (COPD) become a nuisance and progressively deteriorate one's quality of life. It has been shown that Nav 1.7 inhibitors have the potential to treat such respiratory and respiratory tract conditions, including post viral cough, viral cough and acute viral cough (PCT Publication WO2013006596). Accordingly, a therapeutic agent that inhibits Nav 1.7 should effectively treat pain and/or cough in humans. The present invention provides compounds that are inhibitors of Nav 1.7.

SUMMARY OF THE INVENTION

In embodiment 1, the present invention provides compounds of Formula I, or pharmaceutically acceptable salts thereof,

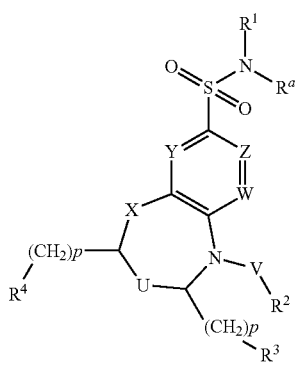

I wherein:
R$^a$ is hydrogen, C$_{1-6}$alkyl or a three to eight membered cycloalkyl group, where the cycloalkyl group may be unsubstituted or substituted with from 1 to 3 substituents independently selected from halo, C$_{1-6}$alkyl, —CN, —CF$_3$, —OH, —OCF$_3$ or —OC$_{1-6}$alkyl;

X is NR$^b$, O, S, S(=O) or S(=O)$_2$;

W, Y and Z are independently selected from CR$^5$ or N;

U is absent or —CH(R$^3$)—;

V is absent, —C(R$^d$)$_2$—, (C=O) or —(C=O)N(R$^d$)—;

R$^b$ is hydrogen, C$_{1-6}$alkyl, —(C=O)NR$^d$R$^d$, —S(=O)$_2$NR$^d$ or —(C=O)C$_{1-6}$alkyl;

R$^1$ is a five to six membered heteroaryl group having from one to three heteroatoms independently selected from O, N or S, where the heteroaryl group may be unsubstituted or substituted with from 1 to 3 substituents independently selected from a B group, halo, C$_{1-6}$alkyl, —CN, —CF$_3$, —OH, —OCF$_3$, —OC$_{1-6}$alkyl or —(CH$_2$)$_n$NR$^d$R$^d$;

R$^2$ is hydrogen, C$_{1-6}$ alkyl, a five to ten membered aryl group or a five to ten membered heteroaryl group having from one to three heteroatoms independently selected from O, N or S, where the aryl or heteroaryl group may be unsubstituted or substituted with from 1 to 3 substituents independently selected from an A group, halo, —N$_3$, —CF$_3$, —OH, —OCF$_3$, C$_{1-6}$alkyl, —OC$_{1-6}$alkyl, —CN, —(CH$_2$)$_n$NR$^d$R$^d$, —O(CH$_2$)$_m$OR$^c$, —N(R$^d$)$_2$, —NR$^d$ five to ten membered aryl, —NR$^d$ five to ten membered heteroaryl, —CO$_2$H, —SR$^d$, —S(=O)$_2$R$^d$, —O-three to eight membered cycloalkyl or —NR$^d$(CH$_2$)$_m$OR$^c$, and heteroaryl group having from one to three heteroatoms independently selected from O, N or S, and the aryl, heteroaryl or cycloalkyl group can be unsubstituted or substituted with from 1 to 3 substituents independently selected from halo, C$_{1-6}$alkyl, —CN, —CF$_3$, —OH, —OCF$_3$, —OC$_{1-6}$alkyl or —(CH$_2$)$_n$NR$^d$R$^d$;

A is a five to six membered aryl group, a five to six membered heteroaryl group, a three to six membered cycloalkyl group or a three to six membered heterocycloalkyl group, wherein the heteroaryl or heterocycloalkyl group has from one to three heteroatoms independently selected from O, N or S, and where the aryl, heteroaryl cycloalkyl or heterocycloalkyl group may be unsubstituted or substituted with from 1 to 4 substituents independently selected from halo, —CF$_3$, —OH, —OCF$_3$, C$_{1-6}$alkyl, —OC$_{1-6}$alkyl, —CN, —(CH$_2$)$_n$NR$^d$R$^d$, —O(CH$_2$)$_m$OR$^c$, —(C=O)NR$^d$R$^d$, —S(=O)$_2$NR$^d$, —N(R$^d$)$_2$, —NR$^d$(C=O)NR$^d$R$^d$, —NR$^d$S(=O)$_2$NR$^d$, —(C=N)OC$_{1-6}$alkyl, —S(=O)$_2$R$^d$ or —NR$^d$(CH$_2$)$_m$OR$^c$;

B is a five to six membered aryl group, a five to six membered heteroaryl group, a three to six membered cycloalkyl group or a three to six membered heterocycloalkyl group, wherein the heteroaryl or heterocycloalkyl group has from one to three heteroatoms independently selected from O, N or S, and where the aryl, heteroaryl cycloalkyl or heterocycloalkyl group may be unsubstituted or substituted with from 1 to 4 substituents independently selected from halo, —CF$_3$, —OH, —OCF$_3$, C$_{1-6}$alkyl, —OC$_{1-6}$alkyl, —CN, —(CH$_2$)$_n$NR$^d$R$^d$, —O(CH$_2$)$_m$OR$^c$, —(C=O)NR$^d$R$^d$, —S(=O)$_2$NR$^d$, —N(R$^d$)$_2$, —NR$^d$(C=O)NR$^d$R$^d$, —NR$^d$S(=O)$_2$NR$^d$, —(C=N)OC$_{1-6}$alkyl, —S(=O)$_2$R$^d$ or —NR$^d$(CH$_2$)$_m$OR$^c$;

each R$^c$ is independently hydrogen, C$_{1-6}$alkyl, a three to eight membered cycloalkyl group, a five to 10 membered aryl group, a five to ten membered heteroaryl group or a three to eight membered heteroacylcoalkyl group; where the heteroaryl or heterocycloalkyl group has from one to three heteroatoms independently selected from O, N or S, and where the aryl, heteroaryl, cycloalkyl or heterocycloalkyl group may be unsubstituted or substituted with from 1 to 4 substituents independently selected from halo, —CF$_3$, —OH, —OCF$_3$, —OH, C$_{1-6}$alkyl, —OC$_{1-6}$alkyl, —CN, —(CH$_2$)$_n$NR$^d$R$^d$, —O(CH$_2$)$_m$OR$^c$, —(C=O)NR$^d$R$^d$, —S(=O)$_2$NR$^d$, —N(R$^d$)$_2$—NR$^d$(C=O)NR$^d$R$^d$, —NR$^d$S(=O)$_2$NR$^d$, —(C=N)OC$_{1-6}$alkyl, —S(=O)$_2$R$^d$ or —NR$^d$(CH$_2$)$_m$OR$^c$;

each R$^d$ is independently hydrogen or C$_{1-6}$alkyl, -aryl, —Oaryl, heteroaryl, —Oheteroaryl, cycloalkyl or heterocycloalkyl group, where the —Oaryl, heteroaryl, —Oheteroaryl, cycloalkyl or heterocycloalkyl group may be unsubstituted or substituted with from 1 to 4 substituents independently selected from halo, —CF$_3$, —OH, —CH$_2$F, —CF$_2$H, —OH, —OCF$_3$, C$_{1-6}$alkyl, —OC$_{1-6}$alkyl, or —CN;

each R$^3$ is independently hydrogen, C$_{1-6}$alkyl, —OC$_{1-6}$alkyl, C$_{1-6}$haloalkyl, —OC$_{1-6}$haloalkyl, a five or six membered aryl or —Oaryl group, or a five or six membered heteroaryl or —Oheteroaryl group, a three to eight membered cycloalkyl group or a three to eight membered heterocycloalkyl group, where the heteroaryl, —Oheteroaryl or heterocycloalkyl group has from one to three heteroatoms independently selected from O, N or S, and where the aryl, —Oaryl, heteroaryl, —Oheteroaryl, cycloalkyl or heterocycloalkyl group may be unsubstituted or substituted with from 1 to 4 substituents independently selected from halo, —CF$_3$, —OH, —CH$_2$F, —CF$_2$H, —OH, —OCF$_3$, C$_{1-6}$alkyl, —OC$_{1-6}$alkyl, —CN, —(CH$_2$)$_n$NR$^d$R$^d$, or R$^3$ together with the ring carbon to which it is attached can be a (C=O) group;

each R$^4$ is independently hydrogen, C$_{1-6}$alkyl, —OC$_{1-6}$alkyl, C$_{1-6}$haloalkyl, —OC$_{1-6}$haloalkyl, a five or six membered aryl or —Oaryl group, or a five or six membered heteroaryl or —Oheteroaryl group, a three to eight membered cycloalkyl group or a three to eight membered heterocycloalkyl group, where the heteroaryl, —Oheteroaryl or heterocycloalkyl group has from one to three heteroatoms independently selected from O, N or S, and where the aryl, —Oaryl, heteroaryl, —Oheteroaryl, cycloalkyl or heterocycloalkyl group may be unsubstituted or substituted with from 1 to 4 substituents independently selected from halo, —CF$_3$, —OH, —CH$_2$F, —CF$_2$H, —OH, —OCF$_3$, C$_{1-6}$alkyl, —OC$_{1-6}$alkyl, —CN, —(CH$_2$)$_n$NR$^d$R$^d$, or R$^3$ together with the ring carbon to which it is attached can be a (C=O) group;

each R$^5$ is independently hydrogen, halo, —CN, —OC$_{1-6}$alkyl, C$_{1-6}$alkyl, —CF$_3$, —OH, —CF$_2$H, —OCF$_3$, —OCF$_2$H, or —OCFH$_2$;

each n is independently 0 to 3;

each m is independently 1 to 3, and each p is independently 0 to 3, provided that the compound of Formula I is not N-(5-chloro-1,3-thiazol-2-yl)-4-(2-chloro-4-(trifluoromethyl)phenyl)-3,4-dihydro-2H-1,4-benzoxazine-7-sulfonamide;

4-(2-chloro-4-(trifluoromethyl)phenyl)-N-(3-methyl-1,2,4-oxadiazol-5-yl)-3,4-dihydro-2H-1,4-benzoxazine-7-sulfonamide;

4-(2-chloro-4-(trifluoromethyl)phenyl)-N-(3-cyano-1,2,4-thiadiazol-5-yl)-3,4-dihydro-2H-1,4-benzoxazine-7-sulfonamide;

4-(2-chloro-4-(trifluoromethyl)phenyl)-N-(5-methyl-1,2,4-oxadiazol-3-yl)-3,4-dihydro-2H-1,4-benzoxazine-7-sulfonamide;

4-(2-chloro-4-(trifluoromethyl)phenyl)-N-(5-methyl-4-(trifluoromethyl)-1,3-thiazol-2-yl)-3,4-dihydro-2H-1,4-benzoxazine-7-sulfonamide;
4-(2-chloro-4-(trifluoromethyl)phenyl)-N-1,3-thiazol-5-yl-3,4-dihydro-2H-1,4-benzoxazine-7-sulfonamide;
4-(2-chloro-4-(trifluoromethyl)phenyl)-N-(5-methyl-3-isoxazolyl)-3,4-dihydro-2H-1,4-benzoxazine-7-sulfonamide;
4-(2-chloro-4-(trifluoromethyl)phenyl)-N-(1-methyl-1H-imidazol-4-yl)-3,4-dihydro-2H-1,4-benzoxazine-7-sulfonamide;
4-(2-chloro-4-(trifluoromethyl)phenyl)-N-(5-methyl-1,3,4-oxadiazol-2-yl)-3,4-dihydro-2H-1,4-benzoxazine-7-sulfonamide;
4-(2-chloro-4-(trifluoromethyl)phenyl)-N-(2,4-difluorophenyl)-3,4-dihydro-2H-1,4-benzoxazine-7-sulfonamide;
4-(2-chloro-4-(trifluoromethyl)phenyl)-N-4-isoxazolyl-3,4-dihydro-2H-1,4-benzoxazine-7-sulfonamide;
4-(2-chloro-4-(trifluoromethyl)phenyl)-N-1,3,4-oxadiazol-2-yl-3,4-dihydro-2H-1,4-benzoxazine-7-sulfonamide;
4-(2-bromo-4-(trifluoromethyl)phenyl)-N-1,3-thiazol-5-yl-3,4-dihydro-2H-1,4-benzoxazine-7-sulfonamide;
4-(2-(1,2,3,6-tetrahydro-4-pyridinyl)-4-(trifluoromethyl)phenyl)-N-1,3-thiazol-5-yl-3,4-dihydro-2H-1,4-benzoxazine-7-sulfonamide;
6-chloro-N-(3,4-dimethylphenyl)-3-oxo-3,4-dihydro-2H-benzo[1,4]oxazine-7-sulfonamide;
6-bromo-N-(3,4-dimethylphenyl)-3-oxo-3,4-dihydro-2H-benzo[1,4]oxazine-7-sulfonamide; or
6-methyl-N-(3,4-dimethylphenyl)-3-oxo-3,4-dihydro-2H-benzo[1,4]oxazine-7-sulfonamide.

In embodiment 2, the present invention provides compounds, or pharmaceutically acceptable salts thereof, in accordance with embodiment 1 wherein:

each $R^a$ is independently hydrogen or $C_{1-6}$alkyl;
X is $NR^b$ or O;
Y, Z and W are CH;
U is absent;
V is absent;
$R^b$ is hydrogen, $C_{1-6}$alkyl or —(C═O)$C_{1-6}$alkyl;
$R^1$ is a five to six membered heteroaryl group having from one to three heteroatoms independently selected from O, N or S, where the heteroaryl group may be unsubstituted or substituted with from 1 to 3 substituents independently selected from halo, $C_{1-6}$alkyl, —CN, —CF$_3$, —OCF$_3$ or —(CH$_2$)$_n$NR$^d$R$^d$;
$R^2$ is a five to 10 membered aryl group or heteroaryl group having from one to three heteroatoms independently selected from O, N or S, where the aryl or heteroaryl group may be unsubstituted or substituted with from 1 to 3 substituents independently selected from an A group, halo, —N$_3$, —CF$_3$, —OH, —OCF$_3$, $C_{1-6}$alkyl, —OC$_{1-6}$alkyl, —CN, —(CH$_2$)$_n$NR$^d$R$^d$, —O(CH$_2$)$_m$OR$^c$ or —NR$^d$(CH$_2$)$_m$OR$^c$;
A is a five to six membered aryl group, or a five to six membered heteroaryl or three to six membered heterocycloalkyl group, where the heteroaryl or heterocycloalkyl group has from one to three heteroatoms independently selected from O, N or S, and where the aryl, heteroaryl or heterocycloalkyl group may be unsubstituted or substituted with from 1 to 3 substituents independently selected from halo, —CF$_3$, —OH, —OCF$_3$, $C_{1-6}$alkyl, —OC$_{1-6}$alkyl, —CN, —(CH$_2$)$_n$NR$^d$R$^d$, —O(CH$_2$)$_m$OR, or —NR$^d$(CH$_2$)$_m$OR$^c$;
each $R^c$ is independently hydrogen or $C_{1-6}$alkyl;
each $R^3$ is independently hydrogen, $C_{1-6}$alkyl, —OC$_{1-6}$alkyl, a five to six membered aryl group, or a five to six membered heteroaryl group having from one to three heteroatoms independently selected from O, N or S;
each $R^4$ is independently hydrogen, $C_{1-6}$alkyl, —OC$_{1-6}$alkyl, a five or six membered aryl group, or a five or six membered heteroaryl group having from one to three heteroatoms independently selected from O, N or S;
each $R^5$ is independently hydrogen, halo, —CN, —OC$_{1-6}$alkyl, $C_{1-6}$alkyl, —CF$_3$ or —OCF$_3$;
each n is independently 0 to 3;
each m is independently 1 to 3; and
each p is 0.

In embodiment 3, the present invention provides compounds, or pharmaceutically acceptable salts thereof, in accordance with any one of embodiments 1 or 2 wherein $R^a$ is hydrogen.

In embodiment 4, the present invention provides compounds, or pharmaceutically acceptable salts thereof, in accordance with any one of embodiments 1 to 3 wherein X is O.

In embodiment 5, the present invention provides compounds, or pharmaceutically acceptable salts thereof, in accordance with any one of embodiments 1 to 3 wherein X is $NR^b$.

In embodiment 6, the present invention provides compounds, or pharmaceutically acceptable salts thereof, in accordance with any one of embodiments 1 to 5 wherein $R^3$ is hydrogen.

In embodiment 7, the present invention provides compounds, or pharmaceutically acceptable salts thereof, in accordance with any one of embodiments 1 to 6 wherein $R^4$ is hydrogen.

In embodiment 8, the present invention provides compounds, or pharmaceutically acceptable salts thereof, in accordance with any one of embodiments 1 to 7 wherein $R^5$ is hydrogen.

In embodiment 9, the present invention provides compounds, or pharmaceutically acceptable salts thereof, in accordance with any one of embodiments 1 to 8 wherein $R^1$ is a five membered heteroaryl group having from one to three heteroatoms independently selected from O, N or S, where the heteroaryl group may be unsubstituted or substituted with from 1 to 3 substituents independently selected from halo, $C_{1-6}$alkyl or —(CH$_2$)$_n$NR$^d$R$^d$.

In embodiment 10, the present invention provides compounds, or pharmaceutically acceptable salts thereof, in accordance with any one of embodiments 1 to 8 wherein $R^1$ is a six membered heteroaryl group having from one to three heteroatoms independently selected from O, N or S, where the heteroaryl group may be unsubstituted or substituted with from 1 to 3 substituents independently selected from halo, $C_{1-6}$alkyl, or —(CH$_2$)$_n$NR$^d$R$^d$.

In embodiment 11, the present invention provides compounds, or pharmaceutically acceptable salts thereof, in accordance with embodiment 9 wherein $R^1$ is selected from

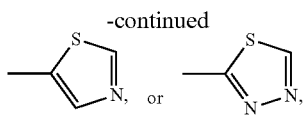 or which may be unsubstituted or substituted with from 1 to 3 substituents independently selected from halo, $C_{1-6}$alkyl, or $—(CH_2)_nNR^dR^d$.

In embodiment 12, the present invention provides compounds, or pharmaceutically acceptable salts thereof, in accordance with embodiment 10 wherein $R^1$ is selected from

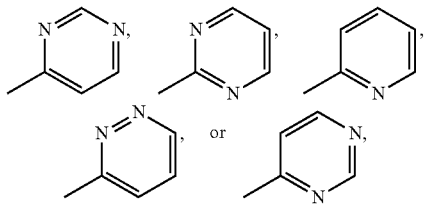

which may be unsubstituted or substituted with from 1 to 3 substituents independently selected from halo, $C_{1-6}$alkyl, or $—(CH_2)_nNR^dR^d$.

In embodiment 13, the present invention provides compounds, or pharmaceutically acceptable salts thereof, in accordance with any one of embodiments 1 to 12 wherein $R^2$ is substituted phenyl.

In embodiment 14, the present invention provides compounds, or pharmaceutically acceptable salts thereof, in accordance with any one of embodiments 1 to 12 wherein $R^2$ is disubstituted phenyl, where the substituents are located at the ortho and para positions with respect to the point of attachment of the phenyl ring to the rest of the molecule.

In embodiment 15, the present invention provides compounds, or pharmaceutically acceptable salts thereof, in accordance with any one of embodiments 1 to 12 wherein $R^2$ is substituted phenyl having at least one A substituent.

In embodiment 16, the present invention provides compounds, or pharmaceutically acceptable salts thereof, in accordance with embodiment 15 wherein A is selected from pyrazolyl, dihydropyridinyl, tetrahydropyridinyl, pyridinyl, piperazinyl, or pyrimidinyl, which groups may be unsubstituted or substituted with from 1 to 3 substituents independently selected from halo, $—CF_3$, $—OCF_3$, $C_{1-6}$alkyl, $—OC_{1-6}$alkyl, $—CN$, $—(CH_2)_nNR^dR^d$, $—O(CH_2)_mOR^c$, or $—NR^d(CH_2)_mOR^c$.

In embodiment 17, the present invention provides compounds, or pharmaceutically acceptable salts thereof, in accordance with embodiment 15 wherein A is selected from pyrazolyl, dihydropyridinyl, tetrahydropyridinyl, pyridinyl, piperazinyl, or pyrimidinyl, which groups are unsubstituted.

In embodiment 18, the present invention provides compounds, or pharmaceutically acceptable salts thereof, in accordance with any one of embodiments 1 to 12 wherein $R^2$ is substituted phenyl wherein one substituent is an A group located at an ortho position with respect to the point of attachment of the phenyl ring to the rest of the molecule and any other substituents are located at the remaining positions.

In embodiment 19, the present invention provides compounds, or pharmaceutically acceptable salts thereof, in accordance with any one of embodiments 1 to 12 wherein $R^2$ is

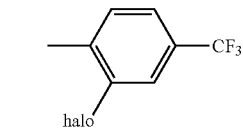

In embodiment 20, the present invention provides compounds, or pharmaceutically acceptable salts thereof, in accordance with any one of embodiments 1 to 12 wherein $R^2$ is selected from unsubstituted or substituted quinoline, isoquinoline, naphthalene, quinoxaline, or benozothiazole.

In embodiment 21, the present invention provides compounds, or pharmaceutically acceptable salts thereof, in accordance with any one of embodiments 1 to 12 wherein $R^2$ is selected from unsubstituted quinoline, isoquinoline, naphthalene, quinoxaline, or benozothiazole.

In embodiment 22, the present invention provides compounds, or pharmaceutically acceptable salts thereof, in accordance with any one of embodiments 1 and 3 to 21 wherein Y, Z and W are CH.

In embodiment 23, the present invention provides compounds, or pharmaceutically acceptable salts thereof, in accordance with any one of embodiments 1 and 3 to 22 wherein U is absent.

In embodiment 24, the present invention provides compounds, or pharmaceutically acceptable salts thereof, in accordance with any one of embodiments 1 and 3 to 23 wherein V is absent.

In embodiment 25, the present invention provides compounds, or pharmaceutically acceptable salts thereof, in accordance with any one of embodiments 1 and 3 to 24 wherein p is 0.

In embodiment 26, the present invention provides compounds, or pharmaceutically acceptable salts thereof, selected from:
4-(2-bromo-4-(trifluoromethyl)phenyl)-N-(1,2,4-thiadiazol-5-yl)-3,4-dihydro-2H-benzo[b][1,4]oxazine-7-sulfonamide;
4-(2-chloro-4-(trifluoromethyl)phenyl)-N-(1,2,4-thiadiazol-5-yl)-3,4-dihydro-2H-benzo[b][1,4]oxazine-7-sulfonamide;
4-(2-(1-methyl-1H-pyrazol-5-yl)-4-(trifluoromethyl)phenyl)-N-(1,2,4-thiadiazol-5-yl)-3,4-dihydro-2H-benzo[b][1,4]oxazine-7-sulfonamide;
4-(2-(1H-pyrazol-4-yl)-4-(trifluoromethyl)phenyl)-N-(1,2,4-thiadiazol-5-yl)-3,4-dihydro-2H-benzo[b][1,4]oxazine-7-sulfonamide;
4-(2-chloro-4-(trifluoromethyl)phenyl)-N-(thiazol-2-yl)-3,4-dihydro-2H-benzo[b][1,4]oxazine-7-sulfonamide;
tert-butyl 4-(2-(7-(n-(1,2,4-thiadiazol-5-yl)sulfamoyl)-2H-benzo[b][1,4]oxazin-4(3H)-yl)-5-(trifluoromethyl)phenyl)-5,6-dihydropyridine-1(2H)-carboxylate;
4-(2-(1,2,3,6-tetrahydropyridin-4-yl)-4-(trifluoromethyl)phenyl)-N-(1,2,4-thiadiazol-5-yl)-3,4-dihydro-2H-benzo[b][1,4]oxazine-7-sulfonamide;
N-(3-(aminomethyl)-1,2,4-thiadiazol-5-yl)-4-(2-chloro-4-(trifluoromethyl)phenyl)-3,4-dihydro-2H-benzo[b][1,4]oxazine-7-sulfonamide;
4-(2-chloro-4-(trifluoromethyl)phenyl)-N-(6-chloropyrimidin-4-yl)-3,4-dihydro-2H-benzo[b][1,4]oxazine-7-sulfonamide;
4-(2-chloro-4-(trifluoromethyl)phenyl)-N-(3-methyl-1,2,4-thiadiazol-5-yl)-3,4-dihydro-2H-benzo[b][1,4]oxazine-7-sulfonamide;

4-(2-chloro-4-(trifluoromethyl)phenyl)-N-(thiazol-4-yl)-3,4-dihydro-2H-benzo[b][1,4]oxazine-7-sulfonamide;

4-(2-chloro-4-(trifluoromethyl)phenyl)-N-(5-methylthiazol-2-yl)-3,4-dihydro-2H-benzo[b][1,4]oxazine-7-sulfonamide;

4-(2-chloro-4-(trifluoromethyl)phenyl)-N-(isoxazol-3-yl)-3,4-dihydro-2H-benzo[b][1,4]oxazine-7-sulfonamide;

4-(2-chloro-4-(trifluoromethyl)phenyl)-N-(1-(2-(dimethylamino)ethyl)-1H-pyrazol-3-yl)-3,4-dihydro-2H-benzo[b][1,4]oxazine-7-sulfonamide;

4-(2-chloro-4-(trifluoromethyl)phenyl)-N-(1-methyl-1H-pyrazol-3-yl)-3,4-dihydro-2H-benzo[b][1,4]oxazine-7-sulfonamide;

4-(2-chloro-4-(trifluoromethyl)phenyl)-N-(pyrimidin-2-yl)-3,4-dihydro-2H-benzo[b][1,4]oxazine-7-sulfonamide;

4-(2-chloro-4-(trifluoromethyl)phenyl)-N-(5-fluoropyridin-2-yl)-3,4-dihydro-2H-benzo[b][1,4]oxazine-7-sulfonamide;

1-(2-chloro-4-(trifluoromethyl)phenyl)-N-(1,2,4-thiadiazol-5-yl)-1,2,3,4-tetrahydroquinoxaline-6-sulfonamide;

1-(2-chloro-4-(trifluoromethyl)phenyl)-4-methyl-N-(1,2,4-thiadiazol-5-yl)-1,2,3,4-tetrahydroquinoxaline-6-sulfonamide;

4-acetyl-1-(2-chloro-4-(trifluoromethyl)phenyl)-N-(1,2,4-thiadiazol-5-yl)-1,2,3,4-tetrahydroquinoxaline-6-sulfonamide;

4-(2-(pyridin-3-yl)-4-(trifluoromethyl)phenyl)-N-(1,2,4-thiadiazol-5-yl)-3,4-dihydro-2H-benzo[b][1,4]oxazine-7-sulfonamide;

4-(2-(1-methyl-1,2,3,6-tetrahydropyridin-4-yl)-4-(trifluoromethyl)phenyl)-N-(1,2,4-thiadiazol-5-yl)-3,4-dihydro-2H-benzo[b][1,4]oxazine-7-sulfonamide;

4-(2-(pyrimidin-5-yl)-4-(trifluoromethyl)phenyl)-N-(1,2,4-thiadiazol-5-yl)-3,4-dihydro-2H-benzo[b][1,4]oxazine-7-sulfonamide;

4-(2-chloro-4-(trifluoromethyl)phenyl)-N-(oxazol-2-yl)-3,4-dihydro-2H-benzo[b][1,4]oxazine-7-sulfonamide;

4-(2-(3,6-dihydro-2H-pyran-4-yl)-4-(trifluoromethyl)phenyl)-N-(1,2,4-thiadiazol-5-yl)-3,4-dihydro-2H-benzo[b][1,4]oxazine-7-sulfonamide;

4-(2-(pyridin-4-yl)-4-(trifluoromethyl)phenyl)-N-(1,2,4-thiadiazol-5-yl)-3,4-dihydro-2H-benzo[b][1,4]oxazine-7-sulfonamide;

4-(2-chloro-4-(trifluoromethyl)phenyl)-N-(pyridazin-3-yl)-3,4-dihydro-2H-benzo[b][1,4]oxazine-7-sulfonamide;

4-(2-chloro-4-(trifluoromethyl)phenyl)-N-(1,3,4-thiadiazol-2-yl)-3,4-dihydro-2H-benzo[b][1,4]oxazine-7-sulfonamide;

4-(2-(2-aminopyridin-4-yl)-4-(trifluoromethyl)phenyl)-N-(1,2,4-thiadiazol-5-yl)-3,4-dihydro-2H-benzo[b][1,4]oxazine-7-sulfonamide;

4-phenyl-N-(1,2,4-thiadiazol-5-yl)-3,4-dihydro-2H-benzo[b][1,4]oxazine-7-sulfonamide;

4-(2-cyano-4-(trifluoromethyl)phenyl)-N-(1,2,4-thiadiazol-5-yl)-3,4-dihydro-2H-benzo[b][1,4]oxazine-7-sulfonamide;

4-(2-chloro-4-(trifluoromethyl)phenyl)-N-(pyrimidin-4-yl)-3,4-dihydro-2H-benzo[b][1,4]oxazine-7-sulfonamide;

4-(quinolin-5-yl)-N-(1,2,4-thiadiazol-5-yl)-3,4-dihydro-2H-benzo[b][1,4]oxazine-7-sulfonamide;

3-phenyl-N-(1,2,4-thiadiazol-5-yl)-4-(4-(trifluoromethyl)phenyl)-3,4-dihydro-2H-benzo[b][1,4]oxazine-7-sulfonamide;

N-(1,2,4-thiadiazol-5-yl)-4-(3-(trifluoromethoxy)phenyl)-3,4-dihydro-2H-benzo[b][1,4]oxazine-7-sulfonamide;

4-(naphthalen-1-yl)-N-(1,2,4-thiadiazol-5-yl)-3,4-dihydro-2H-benzo[b][1,4]oxazine-7-sulfonamide;

4-(4-methoxyphenyl)-N-(1,2,4-thiadiazol-5-yl)-3,4-dihydro-2H-benzo[b][1,4]oxazine-7-sulfonamide;

4-(2-(1,2,3,6-tetrahydropyridin-4-yl)-4-(trifluoromethyl)phenyl)-N-(thiazol-2-yl)-3,4-dihydro-2H-benzo[b][1,4]oxazine-7-sulfonamide;

4-(4-(2-methoxyethoxyl)phenyl)-N-(1,2,4-thiadiazol-5-yl)-3,4-dihydro-2H-benzo[b][1,4]oxazine-7-sulfonamide;

4-(4-chlorophenyl)-N-(thiazol-2-yl)-3,4-dihydro-2H-benzo[b][1,4]oxazine-7-sulfonamide;

4-(3-chlorophenyl)-N-(thiazol-2-yl)-3,4-dihydro-2H-benzo[b][1,4]oxazine-7-sulfonamide;

4-(2-(1-methyl-1H-pyrazol-5-yl)-4-(trifluoromethyl)phenyl)-N-(thiazol-2-yl)-3,4-dihydro-2H-benzo[b][1,4]oxazine-7-sulfonamide;

4-(2-bromo-4-(trifluoromethyl)phenyl)-N-(thiazol-2-yl)-3,4-dihydro-2H-benzo[b][1,4]oxazine-7-sulfonamide;

4-(2-(1-methyl-1,2,3,6-tetrahydropyridin-4-yl)-4-(trifluoromethyl)phenyl)-N-(thiazol-2-yl)-3,4-dihydro-2H-benzo[b][1,4]oxazine-7-sulfonamide;

N-(pyrimidin-4-yl)-4-(2-(1,2,3,6-tetrahydropyridin-4-yl)-4-(trifluoromethyl)phenyl)-3,4-dihydro-2H-benzo[b][1,4]oxazine-7-sulfonamide;

4-(2-chlorophenyl)-N-(thiazol-2-yl)-3,4-dihydro-2H-benzo[b][1,4]oxazine-7-sulfonamide;

4-(2-bromo-4-(trifluoromethyl)phenyl)-N-(pyrimidin-4-yl)-3,4-dihydro-2H-benzo[b][1,4]oxazine-7-sulfonamide;

4-(2-(2-methoxyethyl)amino)-4-(trifluoromethyl)phenyl)-N-(pyrimidin-4-yl)-3,4-dihydro-2H-benzo[b][1,4]oxazine-7-sulfonamide;

4-(2-cyano-4-(trifluoromethyl)phenyl)-N-(thiazol-2-yl)-3,4-dihydro-2H-benzo[b][1,4]oxazine-7-sulfonamide;

4-(2-(4-methylpiperazin-1-yl)-4-(trifluoromethyl)phenyl)-N-(thiazol-2-yl)-3,4-dihydro-2H-benzo[b][1,4]oxazine-7-sulfonamide;

4-(2-(1-methyl-1,2,3,6-tetrahydropyridin-4-yl)-4-(trifluoromethyl)phenyl)-N-(pyrimidin-4-yl)-3,4-dihydro-2H-benzo[b][1,4]oxazine-7-sulfonamide;

4-(4-chloro-2-(1,2,3,6-tetrahydropyridin-4-yl)phenyl)-N-(thiazol-2-yl)-3,4-dihydro-2H-benzo[b][1,4]oxazine-7-sulfonamide;

4-(2-(pyridin-4-yl)-4-(trifluoromethyl)phenyl)-N-(thiazol-2-yl)-3,4-dihydro-2H-benzo[b][1,4]oxazine-7-sulfonamide;

4-(2-(pyrimidin-5-yl)-4-(trifluoromethyl)phenyl)-N-(thiazol-2-yl)-3,4-dihydro-2H-benzo[b][1,4]oxazine-7-sulfonamide;

4-(2-chloro-4-(trifluoromethyl)phenyl)-N-(isoxazol-5-yl)-3,4-dihydro-2H-benzo[b][1,4]oxazine-7-sulfonamide;

4-(4-chloro-2-cyanophenyl)-N-(thiazol-2-yl)-3,4-dihydro-2H-benzo[b][1,4]oxazine-7-sulfonamide;

4-(2-cyanophenyl)-N-(1,2,4-thiadiazol-5-yl)-3,4-dihydro-2H-benzo[b][1,4]oxazine-7-sulfonamide;

4-(2-cyanophenyl)-N-(thiazol-2-yl)-3,4-dihydro-2H-benzo[b][1,4]oxazine-7-sulfonamide;

4-(2-(1,2,3,6-tetrahydropyridin-4-yl)phenyl)-N-(thiazol-2-yl)-3,4-dihydro-2H-benzo[b][1,4]oxazine-7-sulfonamide;

4-(2-bromo-4-(trifluoromethyl)phenyl)-N-(pyridin-2-yl)-3,4-dihydro-2H-benzo[b][1,4]oxazine-7-sulfonamide;

4-(2-bromo-4-(trifluoromethyl)phenyl)-N-(thiazol-4-yl)-3,4-dihydro-2H-benzo[b][1,4]oxazine-7-sulfonamide;

N-(pyridin-2-yl)-4-(2-(1,2,3,6-tetrahydropyridin-4-yl)-4-(trifluoromethyl)phenyl)-3,4-dihydro-2H-benzo[b][1,4]oxazine-7-sulfonamide;

4-(2-(1,2,3,6-tetrahydropyridin-4-yl)-4-(trifluoromethyl)phenyl)-N-(thiazol-4-yl)-3,4-dihydro-2H-benzo[b][1,4]oxazine-7-sulfonamide;

4-(4-azido-2-bromophenyl)-N-(thiazol-2-yl)-3,4-dihydro-2H-benzo[b][1,4]oxazine-7-sulfonamide;
4-(4-azido-2-(1,2,3,6-tetrahydropyridin-4-yl)phenyl)-N-(thiazol-2-yl)-3,4-dihydro-2H-benzo[b][1,4]oxazine-7-sulfonamide;
4-(quinolin-6-yl)-N-(thiazol-2-yl)-3,4-dihydro-2H-benzo[b][1,4]oxazine-7-sulfonamide;
4-(2-chloro-5-methylphenyl)-N-(thiazol-2-yl)-3,4-dihydro-2H-benzo[b][1,4]oxazine-7-sulfonamide;
4-(isoquinolin-8-yl)-N-(thiazol-2-yl)-3,4-dihydro-2H-benzo[b][1,4]oxazine-7-sulfonamide;
4-(quinoxalin-6-yl)-N-(thiazol-2-yl)-3,4-dihydro-2H-benzo[b][1,4]oxazine-7-sulfonamide;
4-(benzo[d]thiazol-5-yl)-N-(thiazol-2-yl)-3,4-dihydro-2H-benzo[b][1,4]oxazine-7-sulfonamide;
4-(benzo[d]thiazol-6-yl)-N-(thiazol-2-yl)-3,4-dihydro-2H-benzo[b][1,4]oxazine-7-sulfonamide;
4-(benzo[d]thiazol-4-yl)-N-(thiazol-2-yl)-3,4-dihydro-2H-benzo[b][1,4]oxazine-7-sulfonamide;
4-(6-methylisoquinolin-5-yl)-N-(thiazol-2-yl)-3,4-dihydro-2H-benzo[b][1,4]oxazine-7-sulfonamide;
4-(3,4-dichlorophenyl)-N-(thiazol-2-yl)-3,4-dihydro-2H-benzo[b][1,4]oxazine-7-sulfonamide;
N-(thiazol-2-yl)-4-(m-tolyl)-3,4-dihydro-2H-benzo[b][1,4]oxazine-7-sulfonamide;
4-(4-cyanophenyl)-N-(thiazol-2-yl)-3,4-dihydro-2H-benzo[b][1,4]oxazine-7-sulfonamide;
4-(3-methoxyphenyl)-N-(thiazol-2-yl)-3,4-dihydro-2H-benzo[b][1,4]oxazine-7-sulfonamide;
4-(3-fluoro-2-methylphenyl)-N-(thiazol-2-yl)-3,4-dihydro-2H-benzo[b][1,4]oxazine-7-sulfonamide;
4-(5-fluoro-2-methylphenyl)-N-(thiazol-2-yl)-3,4-dihydro-2H-benzo[b][1,4]oxazine-7-sulfonamide;
4-(2-fluoro-5-methylphenyl)-N-(thiazol-2-yl)-3,4-dihydro-2H-benzo[b][1,4]oxazine-7-sulfonamide;
4-(4-fluoro-3-methylphenyl)-N-(thiazol-2-yl)-3,4-dihydro-2H-benzo[b][1,4]oxazine-7-sulfonamide;
4-(3-fluoro-4-methylphenyl)-N-(thiazol-2-yl)-3,4-dihydro-2H-benzo[b][1,4]oxazine-7-sulfonamide;
4-(2,5-difluorophenyl)-N-(thiazol-2-yl)-3,4-dihydro-2H-benzo[b][1,4]oxazine-7-sulfonamide;
4-(3,4-difluorophenyl)-N-(thiazol-2-yl)-3,4-dihydro-2H-benzo[b][1,4]oxazine-7-sulfonamide;
4-(2-(1,2,3,6-tetrahydropyridin-4-yl)-4-(trifluoromethyl)phenyl)-N-(thiazol-5-yl)-3,4-dihydro-2H-benzo[b][1,4]oxazine-7-sulfonamide;
N-(pyrimidin-2-yl)-4-(2-(1,2,3,6-tetrahydropyridin-4-yl)-4-(trifluoromethyl)phenyl)-3,4-dihydro-2H-benzo[b][1,4]oxazine-7-sulfonamide;
N-(pyridazin-3-yl)-4-(2-(1,2,3,6-tetrahydropyridin-4-yl)-4-(trifluoromethyl)phenyl)-3,4-dihydro-2H-benzo[b][1,4]oxazine-7-sulfonamide;
N-(pyrazin-2-yl)-4-(2-(1,2,3,6-tetrahydropyridin-4-yl)-4-(trifluoromethyl)phenyl)-3,4-dihydro-2H-benzo[b][1,4]oxazine-7-sulfonamide;
4-(2-cyano-4-(trifluoromethyl)phenyl)-N-(pyrimidin-4-yl)-3,4-dihydro-2H-benzo[b][1,4]oxazine-7-sulfonamide;
4-(2-cyano-4-(trifluoromethyl)phenyl)-N-(oxazol-2-yl)-3,4-dihydro-2H-benzo[b][1,4]oxazine-7-sulfonamide;
4-(2-cyano-4-(trifluoromethyl)phenyl)-N-(isoxazol-5-yl)-3,4-dihydro-2H-benzo[b][1,4]oxazine-7-sulfonamide; or
4-(3-chlorophenyl)-3-oxo-N-(1,3,4-thiadiazol-2-yl)-3,4-dihydro-2H-benzo[b][1,4]oxazine-7-sulfonamide.

In embodiment 27, the present invention provides methods of treating pain, the methods comprising administering to a patient in need thereof a therapeutically effective amount of a compound, or a pharmaceutically acceptable salt thereof, in accordance with any one of embodiments 1 to 26, or a pharmaceutically acceptable salt thereof.

In embodiment 28, the present invention provides methods of embodiment 27 wherein the treatment is for chronic pain, acute pain, neuropathic pain, pain associated with rheumatoid arthritis, pain associated with osteoarthritis, pain associated with cancer or a cough selected from the group consisting of post viral cough, viral cough, and acute viral cough.

In embodiment 29, the present invention provides pharmaceutical compositions comprising a compound, or a pharmaceutically acceptable salt thereof, in accordance with any one of embodiments 1 to 26, or a pharmaceutically acceptable salt thereof, and a pharmaceutically acceptable excipient.

DETAILED DESCRIPTION OF THE INVENTION

The invention further provides compounds, and pharmaceutically acceptable salts thereof, such as embodiment 30 having a Formula II

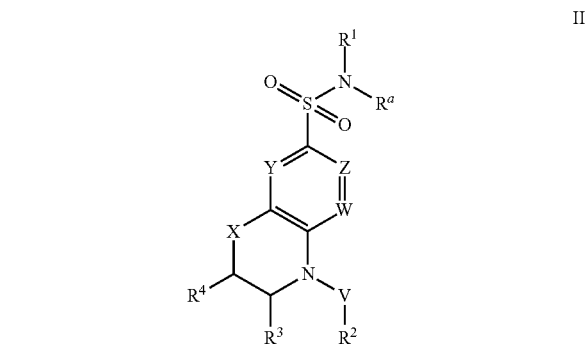

wherein
$R^a$ is hydrogen or $C_{1-6}$alkyl;
X is $NR^b$ or O;
W, Y and Z are independently selected from $CR^5$ or N;
V is absent, —$C(R^d)_2$— or (C=O);
$R^b$ is hydrogen, $C_{1-6}$alkyl or —(C=O)$C_{1-6}$alkyl;
$R^1$ is a five to six membered heteroaryl group having from one to three heteroatoms independently selected from O, N or S, where the heteroaryl group may be unsubstituted or substituted with from 1 to 3 substituents independently selected from a halo, $C_{1-6}$alkyl, —CN, —$CF_3$, —OH, —$OCF_3$, —$OC_{1-6}$alkyl or —$(CH_2)_n NR^d R^d$;
$R^2$ is hydrogen, $C_{1-6}$ alkyl, a five to ten membered aryl group or a five to ten membered heteroaryl group having from one to three heteroatoms independently selected from O, N or S, where the aryl or heteroaryl group may be unsubstituted or substituted with from 1 to 3 substituents independently selected from an A group, halo, —$N_3$, —$CF_3$, —OH, —$OCF_3$, $C_{1-6}$alkyl, —$OC_{1-6}$alkyl, —CN, —$(CH_2)_n NR^d R^d$, —$O(CH_2)_m OR^c$, —$N(R^d)_2$, —$NR^d$ five to ten membered aryl, —$NR^d$ five to ten membered heteroaryl, —$CO_2H$, —$SR^d$, —$S(=O)_2 R^d$, —O-three to eight membered cycloalkyl or —$NR^d(CH_2)_m OR^c$, and heteroaryl group having from one to three heteroatoms independently selected from O, N or S, and the aryl, heteroaryl or cycloalkyl group can be unsubstituted or substituted with from 1 to 3 substituents independently selected from halo, $C_{1-6}$alkyl, —CN, —$CF_3$, —OH, —$OCF_3$, —$OC_{1-6}$alkyl or —$(CH_2)_n NR^d R^d$;
A is a five to six membered aryl group, a five to six membered heteroaryl group, a three to six membered cycloalkyl group or a three to six membered heterocycloalkyl group, wherein the heteroaryl or heterocycloalkyl group has from one to three heteroatoms independently selected from O, N or S, and where the aryl, heteroaryl cycloalkyl or heterocycloalkyl group may be unsubstituted or substituted with from 1 to 4 substituents independently selected from halo, —$CF_3$, —OH, —$OCF_3$, $C_{1-6}$alkyl, —$OC_{1-6}$alkyl, —CN, —$(CH_2)_nNR^dR^d$, —$O(CH_2)_mOR^c$, —$(C=O)NR^dR^d$, —$S(=O)_2NR^d$, —$N(R^d)_2$, —$NR^d(C=O)NR^dR^d$, —$NR^dS(=O)_2NR^d$, —$(C=N)OC_{1-6}$alkyl, —$S(=O)_2R^d$ or —$NR^d(CH_2)_mOR^c$;

each $R^c$ is independently hydrogen, $C_{1-6}$alkyl, a three to eight membered cycloalkyl group, a five to 10 membered aryl group, a five to ten membered heteroaryl group or a three to eight membered heteroacylcoalkyl group; where the heteroaryl or heterocycloalkyl group has from one to three heteroatoms independently selected from O, N or S, and where the aryl, heteroaryl, cycloalkyl or heterocycloalkyl group may be unsubstituted or substituted with from 1 to 4 substituents independently selected from halo, —$CF_3$, —OH, —$OCF_3$, —OH, $C_{1-6}$alkyl, —$OC_{1-6}$alkyl, —CN, —$(CH_2)_nNR^dR^d$, —$O(CH_2)_mOR^c$, —$(C=O)NR^dR^d$, —$S(=O)_2NR^d$, —$N(R^d)_2$—$NR^d(C=O)NR^dR^d$, —$NR^dS(=O)_2NR^d$, —$(C=N)OC_{1-6}$alkyl, —$S(=O)_2R^d$ or —$NR^d(CH_2)_mOR^c$;

each $R^d$ is independently hydrogen or $C_{1-6}$alkyl;

$R^3$ is hydrogen, $C_{1-6}$alkyl, —$OC_{1-6}$alkyl, $C_{1-6}$haloalkyl or —$OC_{1-6}$haloalkyl, or $R^3$ together with the ring carbon to which it is attached can be a (C=O) group;

$R^4$ is independently hydrogen, $C_{1-6}$alkyl, —$OC_{1-6}$alkyl, $C_{1-6}$haloalkyl, —$OC_{1-6}$haloalkyl;

each $R^5$ is independently hydrogen, halo, —CN, —$OC_{1-6}$alkyl, $C_{1-6}$alkyl, —$CF_3$, —OH, —$CF_2H$, —$OCF_3$, —$OCF_2H$ or —$OCFH_2$;

each n is independently 0 to 3; and
each m is independently 1 to 3, provided that the compound of Formula II is not N-(5-chloro-1,3-thiazol-2-yl)-4-(2-chloro-4-(trifluoromethyl)phenyl)-3,4-dihydro-2H-1,4-benzoxazine-7-sulfonamide;

4-(2-chloro-4-(trifluoromethyl)phenyl)-N-(3-methyl-1,2,4-oxadiazol-5-yl)-3,4-dihydro-2H-1,4-benzoxazine-7-sulfonamide;

4-(2-chloro-4-(trifluoromethyl)phenyl)-N-(3-cyano-1,2,4-thiadiazol-5-yl)-3,4-dihydro-2H-1,4-benzoxazine-7-sulfonamide;

4-(2-chloro-4-(trifluoromethyl)phenyl)-N-(5-methyl-1,2,4-oxadiazol-3-yl)-3,4-dihydro-2H-1,4-benzoxazine-7-sulfonamide;

4-(2-chloro-4-(trifluoromethyl)phenyl)-N-(5-methyl-4-(trifluoromethyl)-1,3-thiazol-2-yl)-3,4-dihydro-2H-1,4-benzoxazine-7-sulfonamide;

4-(2-chloro-4-(trifluoromethyl)phenyl)-N-1,3-thiazol-5-yl-3,4-dihydro-2H-1,4-benzoxazine-7-sulfonamide;

4-(2-chloro-4-(trifluoromethyl)phenyl)-N-(5-methyl-3-isoxazolyl)-3,4-dihydro-2H-1,4-benzoxazine-7-sulfonamide;

4-(2-chloro-4-(trifluoromethyl)phenyl)-N-(1-methyl-1H-imidazol-4-yl)-3,4-dihydro-2H-1,4-benzoxazine-7-sulfonamide;

4-(2-chloro-4-(trifluoromethyl)phenyl)-N-(5-methyl-1,3,4-oxadiazol-2-yl)-3,4-dihydro-2H-1,4-benzoxazine-7-sulfonamide;

4-(2-chloro-4-(trifluoromethyl)phenyl)-N-(2,4-difluorophenyl)-3,4-dihydro-2H-1,4-benzoxazine-7-sulfonamide;

4-(2-chloro-4-(trifluoromethyl)phenyl)-N-4-isoxazolyl-3,4-dihydro-2H-1,4-benzoxazine-7-sulfonamide;

4-(2-chloro-4-(trifluoromethyl)phenyl)-N-1,3,4-oxadiazol-2-yl-3,4-dihydro-2H-1,4-benzoxazine-7-sulfonamide;

4-(2-bromo-4-(trifluoromethyl)phenyl)-N-1,3-thiazol-5-yl-3,4-dihydro-2H-1,4-benzoxazine-7-sulfonamide;

4-(2-(1,2,3,6-tetrahydro-4-pyridinyl)-4-(trifluoromethyl)phenyl)-N-1,3-thiazol-5-yl-3,4-dihydro-2H-1,4-benzoxazine-7-sulfonamide, 6-chloro-N-(3,4-dimethylphenyl)-3-oxo-3,4-dihydro-2H-benzo[1,4]oxazine-7-sulfonamide;

6-bromo-N-(3,4-dimethylphenyl)-3-oxo-3,4-dihydro-2H-benzo[1,4]oxazine-7-sulfonamide; or 6-methyl-N-(3,4-dimethylphenyl)-3-oxo-3,4-dihydro-2H-benzo[1,4]oxazine-7-sulfonamide.

In embodiment 31, the present invention provides compounds, or pharmaceutically acceptable salts thereof, in accordance with any one of embodiment 1 to 12 and 30, wherein $R^2$ is $C_{1-6}$ alkyl, a five to ten membered aryl group or a five to ten membered heteroaryl group having from one to three heteroatoms independently selected from O, N or S, where the aryl or heteroaryl group may be unsubstituted or substituted with from 1 to 3 substituents independently selected from an A group, halo, —$N_3$, —$CF_3$, —OH, —$OCF_3$, $C_{1-6}$alkyl, —$OC_{1-6}$alkyl, —CN, —$(CH_2)_nNR^dR^d$, —$O(CH_2)_mOR^c$, —$N(R^d)_2$, —$NR^d$ five to ten membered aryl, —$NR^d$ five to ten membered heteroaryl, —$CO_2H$, —$SR^d$, —$S(=O)_2R^d$, —O-three to eight membered cycloalkyl or —$NR^d(CH_2)_mOR^c$, and heteroaryl group having from one to three heteroatoms independently selected from O, N or S, and the $C_{1-6}$ alkyl, aryl, heteroaryl or cycloalkyl group can be unsubstituted or substituted with from 1 to 3 substituents independently selected from halo, $C_{1-6}$alkyl, —CN, —$CF_3$, —OH, —$OCF_3$, —$OC_{1-6}$alkyl or —$(CH_2)_nNR^dR^d$.

In embodiment 32, the present invention provides compounds, or pharmaceutically acceptable salts thereof, in accordance with any one of embodiment 1 to 12, 30 and 31, wherein $R^2$ is $C_{1-6}$ alkyl or a ring selected from phenyl, naphthyl, pyridyl, pyrimidyl, pyrazinyl, pyridazinyl or triazinyl, and the $C_{1-6}$ alkyl and ring can be unsubstituted or substituted with from 1 to 3 substituents independently selected from halo, $C_{1-6}$alkyl, hydroxy$C_{1-6}$alkyl, dihydroxy$C_{1-6}$alkyl, —CN, —$CF_3$, —OH, —$OCF_3$, —$OC_{1-6}$alkyl or —$(CH_2)_nNR^dR^d$.

In embodiment 33, the present invention provides compounds of Formula II, or pharmaceutically acceptable salts thereof, in accordance with any one of embodiments 30-32 wherein $R^1$ is selected from

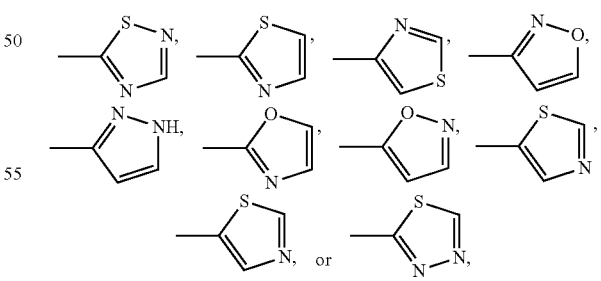

which may be unsubstituted or substituted with from 1 to 3 substituents independently selected from halo, $C_{1-6}$alkyl, or —$(CH_2)_nNR^dR^d$.

In embodiment 34, the present invention provides compounds of Formula II, or pharmaceutically acceptable salts thereof, in accordance with any one of embodiments 30-32 wherein $R^1$ is selected from

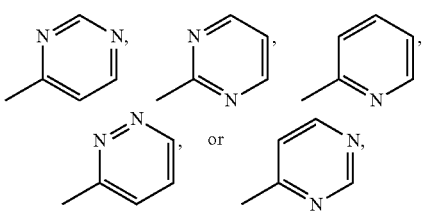

which may be unsubstituted or substituted with from 1 to 3 substituents independently selected from halo, $C_{1-6}$alkyl, or —$(CH_2)_n NR^d R^d$.

In embodiment 35, the present invention provides compounds of Formula II, or pharmaceutically acceptable salts thereof, in accordance with any one of embodiments 30-32 wherein $R^1$ is selected from

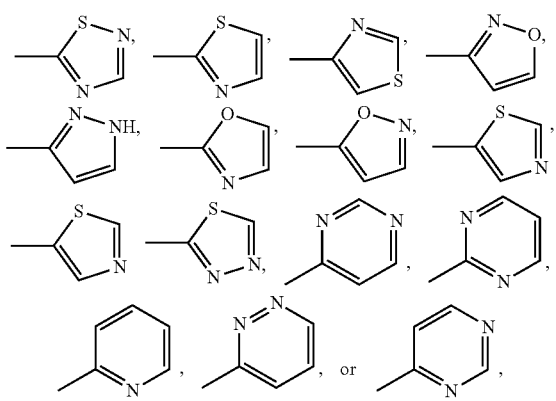

each of which may be unsubstituted or substituted with from 1 to 3 substituents independently selected from halo, $C_{1-6}$alkyl, or —$(CH_2)_n NR^d R^d$;

$R^2$ is $C_{1-6}$ alkyl, a five to ten membered aryl group or a five to ten membered heteroaryl group having from one to three heteroatoms independently selected from O, N or S, where the aryl or heteroaryl group may be unsubstituted or substituted with from 1 to 3 substituents independently selected from an A group, halo, —$N_3$, —$CF_3$, —OH, —$OCF_3$, $C_{1-6}$alkyl, —$OC_{1-6}$alkyl, —CN, —$(CH_2)_n NR^d R^d$, —$O(CH_2)_m OR^c$, —$N(R^d)_2$, —$NR^d$ five to ten membered aryl, —$NR^d$ five to ten membered heteroaryl, —$CO_2H$, —$SR^d$, —$S(=O)_2 R^d$, —O-three to eight membered cycloalkyl or —$NR^d(CH_2)_m OR^c$, and heteroaryl group having from one to three heteroatoms independently selected from O, N or S, and the $C_{1-6}$ alkyl, aryl, heteroaryl or cycloalkyl group can be unsubstituted or substituted with from 1 to 3 substituents independently selected from halo, $C_{1-6}$alkyl, —CN, —$CF_3$, —OH, —$OCF_3$, —$OC_{1-6}$alkyl or —$(CH_2)_n NR^d R^d$;

X is $NR^b$ or O;

W, Y and Z are independently selected from $CR^5$ or N;

A is a five to six membered aryl group, a five to six membered heteroaryl group, a three to six membered cycloalkyl group or a three to six membered heterocycloalkyl group, wherein the heteroaryl or heterocycloalkyl group has from one to three heteroatoms independently selected from O, N or S, and where the aryl, heteroaryl cycloalkyl or heterocycloalkyl group may be unsubstituted or substituted with from 1 to 4 substituents independently selected from halo, —$CF_3$, —OH, —$OCF_3$, $C_{1-6}$alkyl, —$OC_{1-6}$alkyl, —CN, —$(CH_2)_n NR^d R^d$, —$O(CH_2)_m OR^c$, —$(C=O)NR^d R^d$, —$S(=O)_2 NR^d$, —$N(R^d)_2$, —$NR^d(C=O)NR^d R^d$, —$NR^d S(=O)_2 NR^d$, —$(C=N)OC_{1-6}$alkyl, —$S(=O)_2 R^d$ or —$NR^d(CH_2)_m OR^c$;

each $R^c$ is independently hydrogen, $C_{1-6}$alkyl, a three to eight membered cycloalkyl group, a five to 10 membered aryl group, a five to ten membered heteroaryl group or a three to eight membered heteroacylcoalkyl group; where the heteroaryl or heterocycloalkyl group has from one to three heteroatoms independently selected from O, N or S, and where the aryl, heteroaryl, cycloalkyl or heterocycloalkyl group may be unsubstituted or substituted with from 1 to 4 substituents independently selected from halo, —$CF_3$, —OH, —$OCF_3$, —OH, $C_{1-6}$alkyl, —$OC_{1-6}$alkyl, —CN, —$(CH_2)_n NR^d R^d$, —$O(CH_2)_m OR^c$, —$(C=O)NR^d R^d$, —$S(=O)_2 NR^d$, —$N(R^d)_2$—$NR^d(C=O)NR^d R^d$, —$NR^d S(=O)_2 NR^d$, —$(C=N)OC_{1-6}$alkyl, —$S(=O)_2 R^d$ or —$NR^d(CH_2)_m OR^c$;

each $R^d$ is independently hydrogen or $C_{1-6}$alkyl;

$R^3$ is hydrogen, $C_{1-6}$alkyl, —$OC_{1-6}$alkyl, $C_{1-6}$haloalkyl or —$OC_{1-6}$haloalkyl, or $R^3$ together with the ring carbon to which it is attached can be a (C=O) group;

$R^4$ is independently hydrogen;

each $R^5$ is independently hydrogen or F, each n is independently 0 to 3; and each m is independently 1 to 3, provided that the compound of Formula II is not N-(5-chloro-1,3-thiazol-2-yl)-4-(2-chloro-4-(trifluoromethyl)phenyl)-3,4-dihydro-2H-1,4-benzoxazine-7-sulfonamide;

4-(2-chloro-4-(trifluoromethyl)phenyl)-N-(3-methyl-1,2,4-oxadiazol-5-yl)-3,4-dihydro-2H-1,4-benzoxazine-7-sulfonamide;

4-(2-chloro-4-(trifluoromethyl)phenyl)-N-(3-cyano-1,2,4-thiadiazol-5-yl)-3,4-dihydro-2H-1,4-benzoxazine-7-sulfonamide;

4-(2-chloro-4-(trifluoromethyl)phenyl)-N-(5-methyl-1,2,4-oxadiazol-3-yl)-3,4-dihydro-2H-1,4-benzoxazine-7-sulfonamide;

4-(2-chloro-4-(trifluoromethyl)phenyl)-N-(5-methyl-4-(trifluoromethyl)-1,3-thiazol-2-yl)-3,4-dihydro-2H-1,4-benzoxazine-7-sulfonamide;

4-(2-chloro-4-(trifluoromethyl)phenyl)-N-1,3-thiazol-5-yl-3,4-dihydro-2H-1,4-benzoxazine-7-sulfonamide;

4-(2-chloro-4-(trifluoromethyl)phenyl)-N-(5-methyl-3-isoxazolyl)-3,4-dihydro-2H-1,4-benzoxazine-7-sulfonamide;

4-(2-chloro-4-(trifluoromethyl)phenyl)-N-(1-methyl-1H-imidazol-4-yl)-3,4-dihydro-2H-1,4-benzoxazine-7-sulfonamide;

4-(2-chloro-4-(trifluoromethyl)phenyl)-N-(5-methyl-1,3,4-oxadiazol-2-yl)-3,4-dihydro-2H-1,4-benzoxazine-7-sulfonamide;

4-(2-chloro-4-(trifluoromethyl)phenyl)-N-(2,4-difluorophenyl)-3,4-dihydro-2H-1,4-benzoxazine-7-sulfonamide;

4-(2-chloro-4-(trifluoromethyl)phenyl)-N-4-isoxazolyl-3,4-dihydro-2H-1,4-benzoxazine-7-sulfonamide;

4-(2-chloro-4-(trifluoromethyl)phenyl)-N-1,3,4-oxadiazol-2-yl-3,4-dihydro-2H-1,4-benzoxazine-7-sulfonamide;

4-(2-bromo-4-(trifluoromethyl)phenyl)-N-1,3-thiazol-5-yl-3,4-dihydro-2H-1,4-benzoxazine-7-sulfonamide; or 4-(2-(1,2,3,6-tetrahydro-4-pyridinyl)-4-(trifluoromethyl) phenyl)-N-1,3-thiazol-5-yl-3,4-dihydro-2H-1,4-benzoxazine-7-sulfonamide.

The invention further provides compounds, and pharmaceutically acceptable salts thereof, such as embodiment 36 having a Formula II-A

II-A

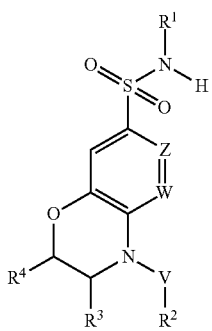

wherein $R^1$ is selected from

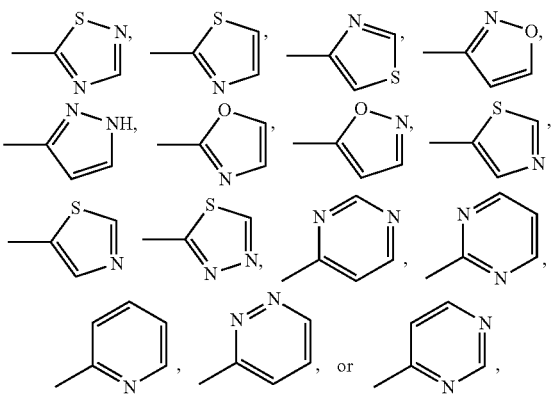

each of which may be unsubstituted or substituted with from 1 to 3 substituents independently selected from halo, $C_{1-6}$alkyl, or —$(CH_2)_nNR^dR^d$;

$R^2$ is $C_{1-6}$ alkyl, a five to ten membered aryl group or a five to ten membered heteroaryl group having from one to three heteroatoms independently selected from O, N or S, where the aryl or heteroaryl group may be unsubstituted or substituted with from 1 to 3 substituents independently selected from an A group, halo, —$N_3$, —$CF_3$, —OH, —$OCF_3$, $C_{1-6}$alkyl, —$OC_{1-6}$alkyl, —CN, —$(CH_2)_nNR^dR^d$, —$O(CH_2)_mOR^c$, —$N(R^d)_2$, —$NR^d$ five to ten membered aryl, —$NR^d$ five to ten membered heteroaryl, —$CO_2H$, —$SR^d$, —$S(=O)_2R^d$, —O-three to eight membered cycloalkyl or —$NR^d(CH_2)_mOR^c$, and heteroaryl group having from one to three heteroatoms independently selected from O, N or S, and the $C_{1-6}$ alkyl, aryl, heteroaryl or cycloalkyl group can be unsubstituted or substituted with from 1 to 3 substituents independently selected from halo, $C_{1-6}$alkyl, —CN, —$CF_3$, —OH, —$OCF_3$, —$OC_{1-6}$alkyl or —$(CH_2)_nNR^dR^d$;

W and Z are independently selected from $CR^5$ or N;

A is a five to six membered aryl group, a five to six membered heteroaryl group, a three to six membered cycloalkyl group or a three to six membered heterocycloalkyl group, wherein the heteroaryl or heterocycloalkyl group has from one to three heteroatoms independently selected from O, N or S, and where the aryl, heteroaryl cycloalkyl or heterocycloalkyl group may be unsubstituted or substituted with from 1 to 4 substituents independently selected from halo, —$CF_3$, —OH, —$OCF_3$, $C_{1-6}$alkyl, —$OC_{1-6}$alkyl, —CN, —$(CH_2)_nNR^dR^d$, —$O(CH_2)_mOR^c$, —$(C=O)NR^dR^d$, —$O(CH_2)_m(C=O)NR^dR^d$, —$S(=O)_2NR^d$, —$N(R^d)_2$, —$NR^d(C=O)NR^dR^d$, —$NR^dS(=O)_2NR^d$, —$(C=N)OC_{1-6}$alkyl, —$S(=O)_2R^d$ or —$NR^d(CH_2)_mOR^c$;

each $R^c$ is independently hydrogen, $C_{1-6}$alkyl, a three to eight membered cycloalkyl group, a five to 10 membered aryl group, a five to ten membered heteroaryl group or a three to eight membered heteroacylcoalkyl group; where the heteroaryl or heterocycloalkyl group has from one to three heteroatoms independently selected from O, N or S, and where the aryl, heteroaryl, cycloalkyl or heterocycloalkyl group may be unsubstituted or substituted with from 1 to 4 substituents independently selected from halo, —$CF_3$, —OH, —$OCF_3$, $C_{1-6}$alkyl, —$OC_{1-6}$alkyl, —CN, —$(CH_2)_nNR^dR^d$, —$O(CH_2)_mR^c$, —$(C=O)NR^dR^d$, —$S(=O)_2NR^d$, —$N(R^d)_2$—$NR^d(C=O)NR^dR^d$, —$NR^dS(=O)_2NR^d$, —$(C=N)OC_{1-6}$alkyl, —$S(=O)_2R^d$ or —$NR^d(CH_2)_mOR^c$;

each $R^d$ is independently hydrogen or $C_{1-6}$alkyl, -aryl, —Oaryl, heteroaryl, —Oheteroaryl, cycloalkyl or heterocycloalkyl group, where the —Oaryl, heteroaryl, —Oheteroaryl, cycloalkyl or heterocycloalkyl group may be unsubstituted or substituted with from 1 to 4 substituents independently selected from halo, —$CF_3$, —OH, —$CH_2F$, —$CF_2H$, —OH, —$OCF_3$, $C_{1-6}$alkyl-$OC_{1-6}$alkyl, or —CN;

$R^3$ is hydrogen, $C_{1-6}$alkyl, —$OC_{1-6}$alkyl, $C_{1-6}$haloalkyl or —$OC_{1-6}$haloalkyl, or $R^3$ together with the ring carbon to which it is attached can be a (C=O) group;

$R^4$ is independently hydrogen;

each $R^5$ is independently hydrogen or F, each n is independently 0 to 3; and each m is independently 1 to 3, provided that the compound of Formula II is not N-(5-chloro-1,3-thiazol-2-yl)-4-(2-chloro-4-(trifluoromethyl)phenyl)-3,4-dihydro-2H-1,4-benzoxazine-7-sulfonamide;

4-(2-chloro-4-(trifluoromethyl)phenyl)-N-(3-methyl-1,2,4-oxadiazol-5-yl)-3,4-dihydro-2H-1,4-benzoxazine-7-sulfonamide;

4-(2-chloro-4-(trifluoromethyl)phenyl)-N-(3-cyano-1,2,4-thiadiazol-5-yl)-3,4-dihydro-2H-1,4-benzoxazine-7-sulfonamide;

4-(2-chloro-4-(trifluoromethyl)phenyl)-N-(5-methyl-1,2,4-oxadiazol-3-yl)-3,4-dihydro-2H-1,4-benzoxazine-7-sulfonamide;

4-(2-chloro-4-(trifluoromethyl)phenyl)-N-(5-methyl-4-(trifluoromethyl)-1,3-thiazol-2-yl)-3,4-dihydro-2H-1,4-benzoxazine-7-sulfonamide;

4-(2-chloro-4-(trifluoromethyl)phenyl)-N-1,3-thiazol-5-yl-3,4-dihydro-2H-1,4-benzoxazine-7-sulfonamide;

4-(2-chloro-4-(trifluoromethyl)phenyl)-N-(5-methyl-3-isoxazolyl)-3,4-dihydro-2H-1,4-benzoxazine-7-sulfonamide;

4-(2-chloro-4-(trifluoromethyl)phenyl)-N-(1-methyl-1H-imidazol-4-yl)-3,4-dihydro-2H-1,4-benzoxazine-7-sulfonamide;

4-(2-chloro-4-(trifluoromethyl)phenyl)-N-(5-methyl-1,3,4-oxadiazol-2-yl)-3,4-dihydro-2H-1,4-benzoxazine-7-sulfonamide;

4-(2-chloro-4-(trifluoromethyl)phenyl)-N-(2,4-difluorophenyl)-3,4-dihydro-2H-1,4-benzoxazine-7-sulfonamide;

4-(2-chloro-4-(trifluoromethyl)phenyl)-N-4-isoxazolyl-3,4-dihydro-2H-1,4-benzoxazine-7-sulfonamide;

4-(2-chloro-4-(trifluoromethyl)phenyl)-N-1,3,4-oxadiazol-2-yl-3,4-dihydro-2H-1,4-benzoxazine-7-sulfonamide;

4-(2-bromo-4-(trifluoromethyl)phenyl)-N-1,3-thiazol-5-yl-3,4-dihydro-2H-1,4-benzoxazine-7-sulfonamide; or 4-(2-(1,2,3,6-tetrahydro-4-pyridinyl)-4-(trifluoromethyl)phenyl)-N-1,3-thiazol-5-yl-3,4-dihydro-2H-1,4-benzoxazine-7-sulfonamide.

In embodiment 37, the present invention provides compounds of Formula II, or pharmaceutically acceptable salts thereof, in accordance with any one of embodiments 36 wherein each $R^d$ is independently hydrogen or $C_{1-6}$alkyl.

In embodiment 38, the invention further provides the following compounds, or a pharmaceutically acceptable salt thereof, selected from (2S)-4-(2-cyano-4-(trifluoromethyl)phenyl)-2-methyl-N-1,3-thiazol-2-yl-3,4-dihydro-2H-1,4-benzoxazine-7-sulfonamide;

(2R)-4-(2-cyano-4-(trifluoromethyl)phenyl)-2-methyl-N-1,3-thiazol-2-yl-3,4-dihydro-2H-1,4-benzoxazine-7-sulfonamide;

(3R)-4-(2-cyano-4-(trifluoromethyl)phenyl)-3-methyl-N-1,3-thiazol-2-yl-3,4-dihydro-2H-1,4-benzoxazine-7-sulfonamide;

(3S)-4-(2-cyano-4-(trifluoromethyl)phenyl)-3-methyl-N-1,3-thiazol-2-yl-3,4-dihydro-2H-1,4-benzoxazine-7-sulfonamide;

(2R)-4-(4-chloro-2-methoxyphenyl)-2-methyl-N-1,3-thiazol-2-yl-3,4-dihydro-2H-1,4-benzoxazine-7-sulfonamide;

(2R)-4-(4-cyano-2-methoxyphenyl)-2-methyl-N-1,3-thiazol-2-yl-3,4-dihydro-2H-1,4-benzoxazine-7-sulfonamide;

(2S)-4-(4-cyano-2-methoxyphenyl)-2-methyl-N-1,3-thiazol-2-yl-3,4-dihydro-2H-1,4-benzoxazine-7-sulfonamide;

4-(5-chloro-2-methoxy-3-pyridinyl)-N-1,3-thiazol-2-yl-3,4-dihydro-2H-1,4-benzoxazine-7-sulfonamide;

4-(2-methoxy-5-(trifluoromethyl)phenyl)-N-1,3-thiazol-2-yl-3,4-dihydro-2H-1,4-benzoxazine-7-sulfonamide;

4-(3-cyano-5-methylphenyl)-N-1,3-thiazol-2-yl-3,4-dihydro-2H-1,4-benzoxazine-7-sulfonamide;

4-(2-cyano-5-(trifluoromethoxy)phenyl)-N-1,3-thiazol-2-yl-3,4-dihydro-2H-1,4-benzoxazine-7-sulfonamide;

4-(2,2-difluoro-1,3-benzodioxol-4-yl)-N-1,3-thiazol-2-yl-3,4-dihydro-2H-1,4-benzoxazine-7-sulfonamide;

4-(2,5-dimethoxyphenyl)-N-1,3-thiazol-2-yl-3,4-dihydro-2H-1,4-benzoxazine-7-sulfonamide;

4-(2-methyl-4-(trifluoromethoxy)phenyl)-N-1,3-thiazol-2-yl-3,4-dihydro-2H-1,4-benzoxazine-7-sulfonamide;

4-(4-(1H-pyrazol-1-yl)phenyl)-N-1,3-thiazol-2-yl-3,4-dihydro-2H-1,4-benzoxazine-7-sulfonamide;

4-(2-methoxy-5-(trifluoromethyl)-3-pyridinyl)-N-1,3-thiazol-2-yl-3,4-dihydro-2H-1,4-benzoxazine-7-sulfonamide;

4-(2-(4-pyridinyl)phenyl)-N-1,3-thiazol-2-yl-3,4-dihydro-2H-1,4-benzoxazine-7-sulfonamide;

4-(2-(1-methyl-1H-pyrazol-5-yl)phenyl)-N-1,3-thiazol-2-yl-3,4-dihydro-2H-1,4-benzoxazine-7-sulfonamide;

4-(4-fluoro-2-methoxyphenyl)-N-1,3-thiazol-2-yl-3,4-dihydro-2H-1,4-benzoxazine-7-sulfonamide;

4-(5-fluoro-2-methoxyphenyl)-N-1,3-thiazol-2-yl-3,4-dihydro-2H-1,4-benzoxazine-7-sulfonamide;

4-(2,3-dichlorophenyl)-N-1,3-thiazol-2-yl-3,4-dihydro-2H-1,4-benzoxazine-7-sulfonamide;

4-(3-(difluoromethoxy)phenyl)-N-1,3-thiazol-2-yl-3,4-dihydro-2H-1,4-benzoxazine-7-sulfonamide;

N-1,3-thiazol-2-yl-4-(3-(trifluoromethyl)phenyl)-3,4-dihydro-2H-1,4-benzoxazine-7-sulfonamide;

4-(3-(cyanomethyl)phenyl)-N-1,3-thiazol-2-yl-3,4-dihydro-2H-1,4-benzoxazine-7-sulfonamide;

4-(3-cyano-4-fluorophenyl)-N-1,3-thiazol-2-yl-3,4-dihydro-2H-1,4-benzoxazine-7-sulfonamide;

4-(2,4-difluorophenyl)-N-1,3-thiazol-2-yl-3,4-dihydro-2H-1,4-benzoxazine-7-sulfonamide;

4-(2-cyano-4-fluorophenyl)-N-1,3-thiazol-2-yl-3,4-dihydro-2H-1,4-benzoxazine-7-sulfonamide;

4-(5-chloro-2-methylphenyl)-N-1,3-thiazol-2-yl-3,4-dihydro-2H-1,4-benzoxazine-7-sulfonamide;

4-(2-(difluoromethoxy)phenyl)-N-1,3-thiazol-2-yl-3,4-dihydro-2H-1,4-benzoxazine-7-sulfonamide;

4-(2,5-dichlorophenyl)-N-1,3-thiazol-2-yl-3,4-dihydro-2H-1,4-benzoxazine-7-sulfonamide;

4-(4-cyano-2-methoxyphenyl)-N-1,3-thiazol-2-yl-3,4-dihydro-2H-1,4-benzoxazine-7-sulfonamide;

4-(2-methoxy-4-(trifluoromethyl)phenyl)-N-1,3-thiazol-2-yl-3,4-dihydro-2H-1,4-benzoxazine-7-sulfonamide;

N-1,3-thiazol-2-yl-4-(5-(trifluoromethyl)-2-pyridinyl)-3,4-dihydro-2H-1,4-benzoxazine-7-sulfonamide;

4-(2-cyano-5-(trifluoromethyl)phenyl)-N-1,3-thiazol-2-yl-3,4-dihydro-2H-1,4-benzoxazine-7-sulfonamide;

4-(4-chloro-2-methoxyphenyl)-N-1,3-thiazol-2-yl-3,4-dihydro-2H-1,4-benzoxazine-7-sulfonamide;

4-(2-cyano-5-fluorophenyl)-N-1,3-thiazol-2-yl-3,4-dihydro-2H-1,4-benzoxazine-7-sulfonamide;

4-(5-chloro-2-cyanophenyl)-N-1,3-thiazol-2-yl-3,4-dihydro-2H-1,4-benzoxazine-7-sulfonamide;

4-(4-chloro-2-(difluoromethoxy)phenyl)-N-1,3-thiazol-2-yl-3,4-dihydro-2H-1,4-benzoxazine-7-sulfonamide;

4-(2-cyano-5-methylphenyl)-N-1,3-thiazol-2-yl-3,4-dihydro-2H-1,4-benzoxazine-7-sulfonamide;

4-(4-chloro-2-methylphenyl)-N-1,3-thiazol-2-yl-3,4-dihydro-2H-1,4-benzoxazine-7-sulfonamide;

4-(3-cyano-3'-fluoro-4-biphenylyl)-N-1,3-thiazol-2-yl-3,4-dihydro-2H-1,4-benzoxazine-7-sulfonamide;

4-(3'-fluoro-3-methoxy-4-biphenylyl)-N-1,3-thiazol-2-yl-3,4-dihydro-2H-1,4-benzoxazine-7-sulfonamide;

4-(2-cyano-4-(1-methylethyl)phenyl)-N-1,3-thiazol-2-yl-3,4-dihydro-2H-1,4-benzoxazine-7-sulfonamide;

4-(2-cyano-4-ethylphenyl)-N-1,3-thiazol-2-yl-3,4-dihydro-2H-1,4-benzoxazine-7-sulfonamide;

4-(2-((1R)-1,2-dihydroxyethyl)-4-(trifluoromethyl)phenyl)-N-1,3-thiazol-2-yl-3,4-dihydro-2H-1,4-benzoxazine-7-sulfonamide;

4-(2-((1S)-1,2-dihydroxyethyl)-4-(trifluoromethyl)phenyl)-N-1,3-thiazol-2-yl-3,4-dihydro-2H-1,4-benzoxazine-7-sulfonamide;

4-(2-methoxyphenyl)-N-1,3-thiazol-2-yl-3,4-dihydro-2H-1,4-benzoxazine-7-sulfonamide;

4-(2-(hydroxymethyl)-4-(trifluoromethyl)phenyl)-N-1,3-thiazol-2-yl-3,4-dihydro-2H-1,4-benzoxazine-7-sulfonamide;

4-(2-((2R)-2,3-dihydroxypropyl)-4-(trifluoromethyl)phenyl)-N-1,3-thiazol-2-yl-3,4-dihydro-2H-1,4-benzoxazine-7-sulfonamide;

4-(2-((2S)-2,3-dihydroxypropyl)-4-(trifluoromethyl)phenyl)-N-1,3-thiazol-2-yl-3,4-dihydro-2H-1,4-benzoxazine-7-sulfonamide;

4-(4-chloro-2-((2R)-2,3-dihydroxypropyl)phenyl)-N-1,3-thiazol-2-yl-3,4-dihydro-2H-1,4-benzoxazine-7-sulfonamide;

4-(4-chloro-2-((2S)-2,3-dihydroxypropyl)phenyl)-N-1,3-thiazol-2-yl-3,4-dihydro-2H-1,4-benzoxazine-7-sulfonamide;

6-chloro-4-(2-cyano-4-(trifluoromethyl)phenyl)-N-1,3-thiazol-2-yl-3,4-dihydro-2H-1,4-benzoxazine-7-sulfonamide;

4-(2-methoxy-6-(trifluoromethyl)-3-pyridinyl)-N-1,3-thiazol-2-yl-3,4-dihydro-2H-1,4-benzoxazine-7-sulfonamide;

4-(2-cyano-4-(trifluoromethyl)phenyl)-6-fluoro-N-1,3-thiazol-2-yl-3,4-dihydro-2H-1,4-benzoxazine-7-sulfonamide;

4-(2-cyano-4-(trifluoromethyl)phenyl)-8-fluoro-N-1,3-thiazol-2-yl-3,4-dihydro-2H-1,4-benzoxazine-7-sulfonamide;

4-(4-cyano-2-methoxyphenyl)-6-fluoro-N-1,3-thiazol-2-yl-3,4-dihydro-2H-1,4-benzoxazine-7-sulfonamide;

4-(2-cyano-4-(trifluoromethyl)phenyl)-5-fluoro-N-1,3-thiazol-2-yl-3,4-dihydro-2H-1,4-benzoxazine-7-sulfonamide; and 4-(2-methoxy-4-(trifluoromethyl)phenyl)-3-oxo-N-1,3-thiazol-2-yl-3,4-dihydro-2H-1,4-benzoxazine-7-sulfonamide.

In embodiment 39, the invention provides each individual compound, or a pharmaceutically acceptable salt thereof, or a sub-set of compounds, as described in the examples herein.

The present invention provides compounds of Formula I and Formula II, as defined above, or pharmaceutically acceptable salts thereof. The present invention also provides pharmaceutical compositions comprising a compound of Formula I and Formula II, or pharmaceutically acceptable salts thereof, and methods of treating diseases and/or conditions, such as pain, using compounds of Formula I, or pharmaceutically acceptable salts thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "perfluoroalkyl" means an alkyl group in which all of the hydrogen atoms have been replaced with fluorine atoms. Common perfluoroalkyl groups are $C_{1-8}$perfluoroalkyl. An example of a common perfluoroalkyl group is $CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heteroatoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 2 heterotaoms are particularly common.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "hydroxyoalkyl" means an "alkyl" group wherein one or more of the carbon atoms are substituted with a hydroxyl (—OH) group. Similarly, the term "dihydroxyalkyl" means an alkyl group in which two (2) hydrogen atoms have been replaced by two (2) hydroxyl groups, ie., the alkyl has 2 hydroxyl substituents.

The term "substituted" means that a hydrogen atom on a molecule or group is replaced with a group or atom. Typical substitutents include: halogen, $C_{1-5}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —$NR^xR^x$, the $R^x$ groups may be joined together with the nitrogen atom to form a ring.

The term "oxo", when used as a substituent, means the =O group, which is typically attached to a carbon atom.

A group or atom that replaces a hydrogen atom is also called a substituent.

Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of the present invention or a formulation containing a compound of the present invention, or a particular excipient, are suitable for administration to a patient.

The terms "treating", "treat" or "treatment" and the like include preventative (e.g., prophylactic) and palliative treatment.

The term "patient in need thereof" means a patient who has or is at risk of having a disease and/or condition that can be treated by inhibition of Nav 1.7, such as chronic pain.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered by a tablet, while another is administered by injection or orally as a syrup. All combinations, delivery methods and administration sequences are contemplated.

The compounds of the present invention may be used in the manufacture of a medicament for the treatment of a disease and/or condition mediated by Nav 1.7, such as pain.

Pain is typically divided into primary types: chronic and acute pain based on the duration of the pain. Typically, chronic pain lasts for longer than 3 months. Examples of chronic pain include pain associated with rheumatoid arthritis, osteoarthritis, lumbosacral radiculopathy or cancer. Chronic pain also includes idiopathic pain, which is pain that has no identified cause. An example of idiopathic pain is fibromyalgia.

Another type of pain is nociceptive pain. Nociceptive pain is caused by stimulation of peripheral nerve fibers that respond to highly noxious events such as thermal, mechanical or chemical stimuli.

Still another type of pain is neuropathic pain. Neuropathic pain is pain that is caused by damage or disease affecting a part of the nervous system. Phantom limb pain is a type of neuropathic pain. In phantom limb pain, the body detects pain from a part of a body that no longer exists. For example, a person who has had a leg amputated may feel leg pain even though the leg no longer exists.

In one embodiment of the methods of treatment provided by the present invention using the compounds of Formula I, or pharmaceutically acceptable salts thereof, the disease is chronic pain. In another aspect, the chronic pain is associated with, but are not limited to, post-herpetic neuralgia (shingles), rheumatoid arthritis, osteoarthritis, diabetic neuropathy, complex regional pain syndrome (CRPS), cancer or chemotherapy-induced pain, chronic back pain, phantom limb pain, trigeminal neuralgia, HIV-induced neuropathy, cluster headache disorders, and migraine, primary erythromelalgia, and paroxysmal extreme pain disorder. Other indications for Nav 1.7 inhibitors include, but are not limited to, depression (Morinville et al., *J Comp Neurol.*, 504:680-689 (2007)), bipolar and other CNS disorders (Ettinger and Argoff, *Neurotherapeutics*, 4:75-83 (2007)), epilepsy: ibid., and Gonzalez, Termin, Wilson, *Methods and Principles in Medicinal Chemistry*, 29:168-192 (2006)), multiple sclerosis (Waxman, *Nature Neurosci.* 7:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M., et. al., *Exp. Neurol.* 184(2):830-838, 2003), anxiety, depression: McKinney B. C, et. al., *Genes Brain Behav.* 7(6):629-638, 2008), learning and memory, cognition (Woodruff-Pak D. S., et. al., *Behav. Neurosci.* 120(2):229-240, 2006), cardiac arrhythmia and fibrillation, contractility, congestive heart failure, sick sinus syndrome (Haufe V., et. al., *J. Mol. Cell Cardiol.* 42(3): 469-477, 2007), schizophrenia, neuroprotection after stroke, drug and alcohol abuse (Johannessen L. C., *CNS Drugs* 22(1) 27-47, 2008), Alzheimer's (Kim D Y., et. al., *Nat. Cell. Biol.* 9(7):755-764, 2007), and cancer (Gillet L., et. al., *J Biol Chem* 2009, January 28 (epub)).

Another aspect of the invention relates to a method of treating acute and/or chronic inflammatory and neuropathic pain, dental pain, general headache, migraine, cluster headache, mixed-vascular and non-vascular syndromes, tension headache, general inflammation, arthritis, rheumatic diseases, rheumatoid arthritis, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to the present invention. A preferred type of pain to be treated is chronic neuropathic pain. Another preferred type of pain to be treated is chronic inflammatory pain.

In another aspect of the invention, the compounds of the present invention can be used in combination with other compounds that are used to treat pain. Examples of such other compounds include, but are not limited to aspirin, celecoxib, hydrocodone, oxycodone, codeine, fentanyl, ibuprofen, ketoprofen, naproxen, acetaminophen, gabapentin and pregabalin. Examples of classes of medicines that contain compounds that can be used in combination with the compounds of the present invention include non-steroidal anti-inflammatory compounds (NSAIDS), steroidal compounds, cycloxogenase inhibitors and opiod analgesics.

The compounds of the present invention may also be used to treat obesity and facilitate weight loss.

The compounds of the present invention may be used in combination with other pharmaceutically active compounds. It is noted that the term "pharmaceutically active compounds" can include biologics, such as proteins, antibodies and peptibodies.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed by said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and non-aqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, cocrystyals, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N, N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$) alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

In addition, if a compound of the present invention comprises a sulfonamide moiety, a prodrug can be formed by replacement of the sulfonamide N(H) with a group such as —CH$_2$P(O)(O($C_1$-$C_6$)alkyl)$_2$ or —CH$_2$OC(O)($C_1$-$C_6$)alkyl.

The compounds of the present invention also include tautomeric forms of prodrugs.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention. Another example of tautomerism is as follows:

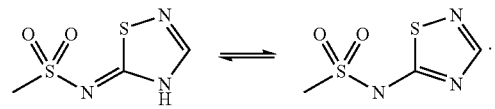

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{31}$P, $^{32}$P, $^{35}$S, $^{18}$F, and $^{36}$Cl. In another aspect, the compounds of the present invention contain one or more deuterium atoms (2H) in place of one or more hydrogen atoms.

Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents and other publications recited herein are hereby incorporated by reference in their entirety.

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity can be measured using high performance liquid chromatography (HPLC) system with UV detection at 254 nm and 215 nm (System A: Agilent Zorbax Eclipse XDB-C8 4.6×150 mm, 5 μm, 5 to 100% $CH_3CN$ in $H_2O$ with 0.1% TFA for 15 min at 1.5 mL/min; System B: Zorbax SB-C8, 4.6×75 mm, 10 to 90% $CH_3CN$ in $H_2O$ with 0.1% formic acid for 12 min at 1.0 mL/min) (Agilent Technologies, Santa Clara, Calif.). Silica gel chromatography was generally performed with pre-packed silica gel cartridges (Biotage, Uppsala, Sweden or Teledyne-Isco, Lincoln, Nebr.). $^1H$ NMR spectra were recorded on a Bruker AV-400 (400 MHz) spectrometer (Bruker Corporation, Madison, Wis.) or a Varian (Agilent Technologies, Santa Clara, Calif.) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, Calif.) LCMS with UV detection at 254 nm and 215 nm and a low resonance electrospray mode (ESI).

The following abbreviations may be used herein:
AmPhos 4-(di-tert-butylphosphino)-N,N-dimethylaniline
AcCl acetyl chloride
ACN acetonitrile
AcOH acetic acid
aq or aq. aqueous
BOC or Boc tert-butyloxycarbonyl
Bn benzyl
DBU 1,8-diazabicyclo[5.4.0]undec-7-ene
DCM dichloromethane
DMAP 4-dimethylaminopyridine
DMB dimethoxybenzyl
DME dimethoxyethane
DMF N,N-dimethylformamide
DMSO dimethyl sulfoxide
Dppf, DPPF or dppf 1,1'-bis(diphenylphosphino)ferrocene
ESI or ES electrospray ionization
Et ethyl
$Et_2O$ diethyl ether
$Et_3N$ triethylamine
EtOAc ethyl acetate
eq or eq. equivalent
g grams
h hour
HPLC high pressure liquid chromatography
iPr isopropyl
$iPr_2NEt$ N-ethyl diisopropylamine (Hunig's base)
KOAc potassium acetate
LC MS, LCMS, LC-MS or LC/MS liquid chromatography mass spectroscopy
LHMDS or LiHMDS lithium hexamethyldisilazide
m/z mass divided by charge
Me methyl
MeOH methanol
MeCN or ACN acetonitrile
mg milligrams
min minutes
mL milliliters
MPLC medium pressure liquid chromatography
MS mass spectra
NBS N-bromosuccinimide
NCS N-chlorosuccinimide
n-BuLi n-butyllithium
NMR nuclear magnetic resonance
$Pd_2(dba)_3$ tris(dibenzylideneacetone)dipalladium(0)
Ph phenyl
PMB p-methoxybenzyl
RT or rt room temperature
SEM 2-(trimethylsilyl)ethoxymethyl
SFC supercritical fluid chromatography
TBAF tetra-n-butylammonium fluoride
t-BuOH tert-butanol
TIPS-Cl triisopropylsilyl chloride
TFA trifluoroacetic acid
THF tetrahydrofuran
UV ultraviolet
xantphos 4,5-bis(diphenylphosphino)-9,9-dimethylxanthene
X-Phos 2-dicyclohexylphosphino-2',4',6'-triisopropyl-1,1'-biphenyl

EXAMPLES

General Synthetic Schemes

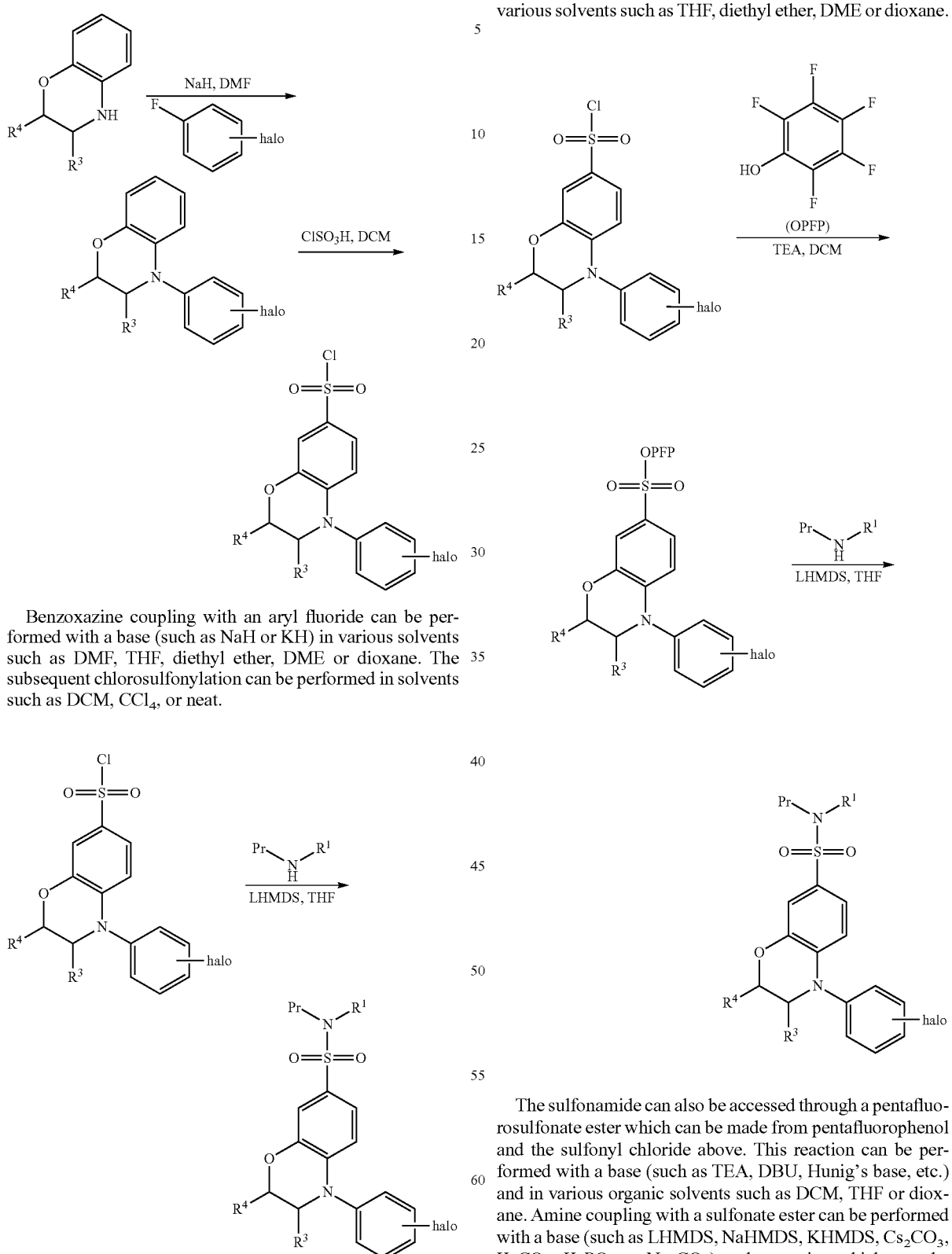

Benzoxazine coupling with an aryl fluoride can be performed with a base (such as NaH or KH) in various solvents such as DMF, THF, diethyl ether, DME or dioxane. The subsequent chlorosulfonylation can be performed in solvents such as DCM, CCl$_4$, or neat.

Amine coupling with a sulfonyl chloride can be performed with a base (such as LHMDS, NaHMDS, KHMDS, Cs$_2$CO$_3$, K$_2$CO$_3$, K$_3$PO$_4$ or Na$_2$CO$_3$) and an amine which may be protected with a benzyl, DMB, PMB, SEM or allyl group (Pr is a protecting group). This reaction can be performed in various solvents such as THF, diethyl ether, DME or dioxane.

The sulfonamide can also be accessed through a pentafluorosulfonate ester which can be made from pentafluorophenol and the sulfonyl chloride above. This reaction can be performed with a base (such as TEA, DBU, Hunig's base, etc.) and in various organic solvents such as DCM, THF or dioxane. Amine coupling with a sulfonate ester can be performed with a base (such as LHMDS, NaHMDS, KHMDS, Cs$_2$CO$_3$, K$_2$CO$_3$, K$_3$PO$_4$ or Na$_2$CO$_3$) and an amine which may be protected with a benzyl, DMB, PMB, SEM or allyl group (Pr is a protecting group). This reaction can be performed in various solvents such as THF, diethyl ether, DME or dioxane.

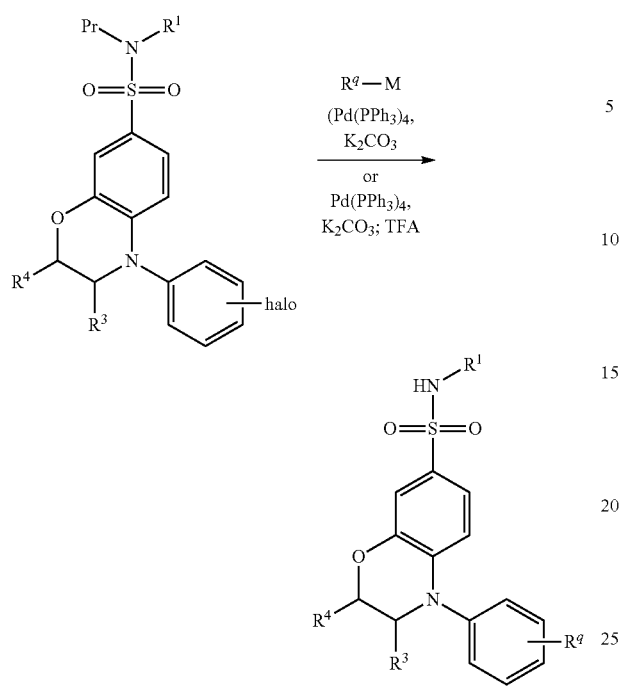

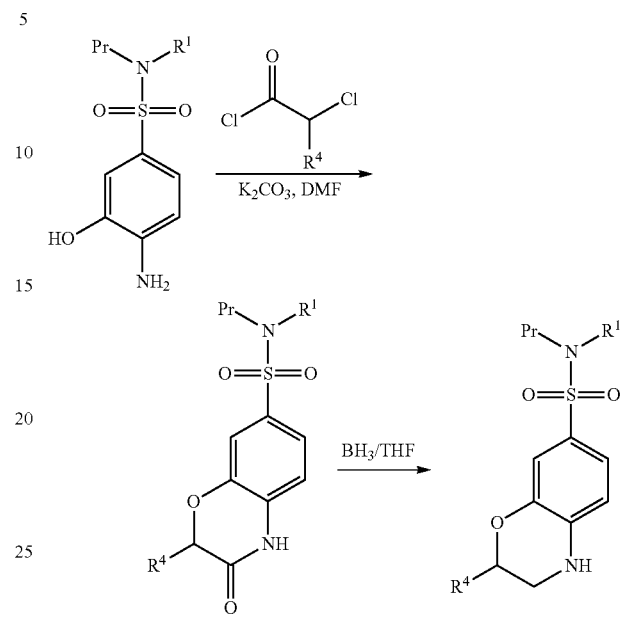

hol). The nitro group can then be reduced through various means (such as reduction with iron in acetic acid or Pd/C in $H_2(g)$).

The coupling above can be performed with various reaction partners (M) to install an $R^q$ group (such as boronic acids, Grignard or zinc reagents) and catalysts (such as Pd(AmPhos)$_2$Cl$_2$, Pd(dppf)Cl$_2$ or Pd(PPh$_3$)$_4$). The removal of the protecting group can be done thermally during the coupling reaction or by using acid or reductive conditions (such as TFA, HCl, Pd/C in hydrogen atmosphere, etc.).

Formation of the benzoxazinone can be accomplished from the aminophenol through reaction with chloro or bromo acetylchloride (or substituted version thereof —$R^4$) in the presence of a base (such as Cs$_2$CO$_3$, K$_2$CO$_3$, K$_3$PO$_4$ or Na$_2$CO$_3$) in an organic solvent (such as DMF, DME, THF, etc.). Reduction of the benzoxazinone can be accomplished with a variety of reductants or reducing conditions) such as BH$_3$/THF, NaBH$_4$/BF$_3$Et$_2$O, LAH, BH$_3$.DMS, etc.).

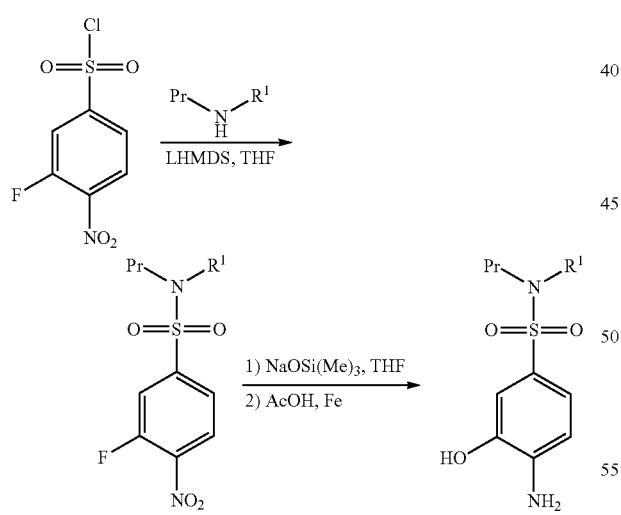

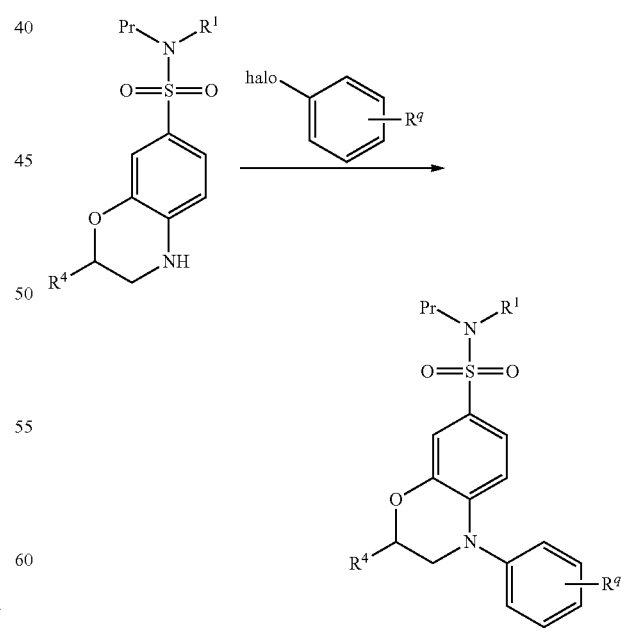

The amine coupling above with a sulfonyl chloride can be performed with a base (such as LHMDS, NaHMDS, KHMDS, Cs$_2$CO$_3$, K$_2$CO$_3$, K$_3$PO$_4$ or Na$_2$CO$_3$) and an amine which may be protected with a benzyl, DMB, PMB, SEM or allyl group (Pr is a protecting group). This reaction can be performed in various solvents such as THF, diethyl ether, DME or dioxane. The fluoride can subsequently be displaced with a nucleophilic oxygen source (such as NaOTMS or an alcohol that can be deprotected such as BnOH or allylalco- The coupling above can be performed with various catalysts (such as Pd(AmPhos)$_2$Cl$_2$, Pd(dppf)Cl$_2$, Xantphos, Pd$_2$dba$_3$, or Pd(PPh$_3$)$_4$). The removal of the protecting group can be done thermally during the coupling reaction or by using acid or reductive conditions (such as TFA, HCl, Pd/C in hydrogen atmosphere, etc.).

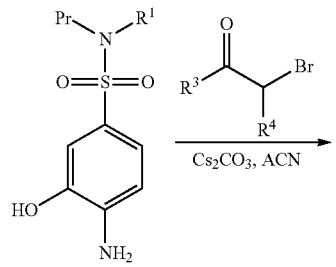

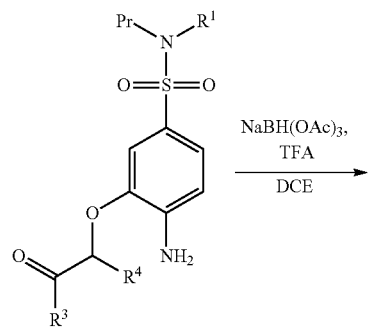

Formation of the benzoxazinone can also be accomplished from the aminophenol through a reaction with a substituted or unsubstituted α-halo ketone in the presence of a base (such as $Cs_2CO_3$, $K_2CO_3$ or NaH). This reaction can be performed in the presence of an aprotic solvent (such as ACN, THF, DME or dioxane). The cyclization/reductive amination step can be performed employing an acid such as TFA and a reductant (such as $NaBH(OAc)_3$ or $NaBH_4$).

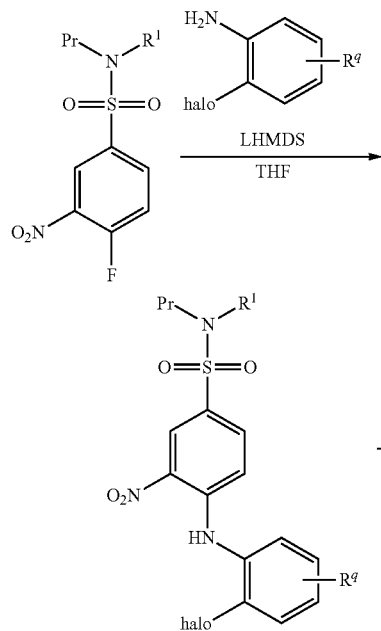

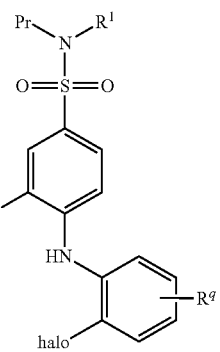

The tetrahydroquinoxalines can be made through displacement of a fluoride with a substituted aniline through a coupling promoted by a base (such as LHMDS, NaHMDS or KHMDS) in an organic solvent (such as THF, DME or dioxane). The resulting nitro group can be reduced by employing reductive conditions (such as Fe powder or Pd/C in hydrogen atmosphere, etc.).

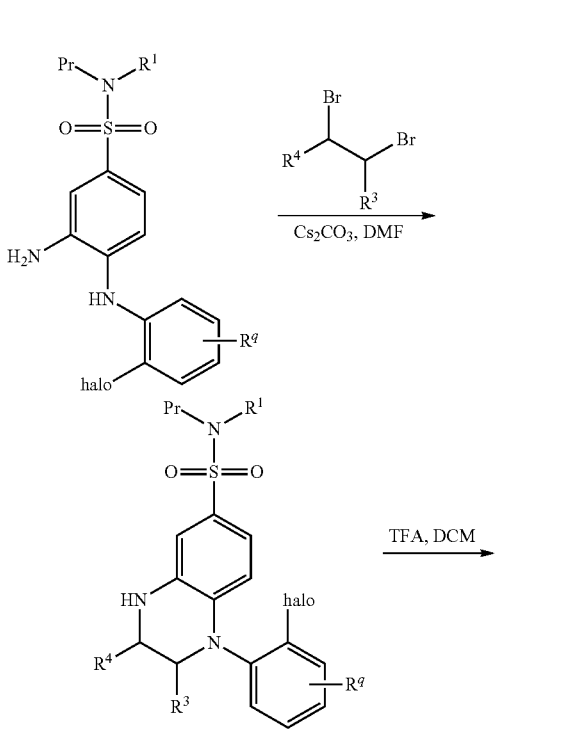

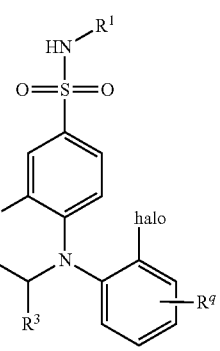

Cyclization to a tetrahydroquinoxaline can occur with dibromoethane in the presence of a base (such as $Cs_2CO_3$, $K_2CO_3$ or NaH). The resulting product can be deprotected employing conditions such as TFA, HCl or Pd/C in hydrogen atmosphere, etc.

Intermediate A

N-(2,4-Dimethoxybenzyl)-1,2,4-Thiadiazol-5-Amine

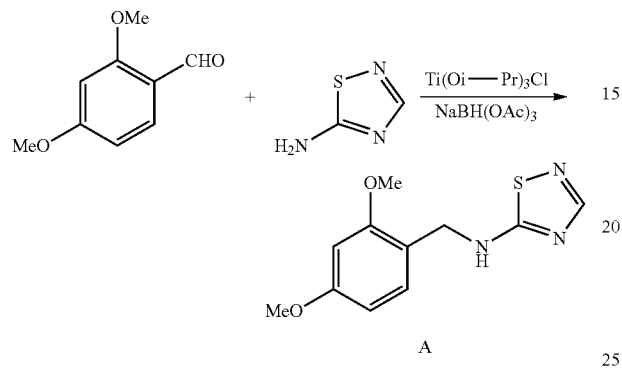

A

To a solution of 1,2,4-thiadiazol-5-amine (150 g, 1.48 mol, 1.1 eq) and 2,4-dimethoxybenzaldehyde (224.1 g, 1.35 mol, 1 eq) in anhydrous DCM (6 L) was added chlorotitanium triisopropoxide (771.3 g, 2.96 mol, 2.2 eq) slowly over 15 minutes. The resulting yellow solution was stirred for 30 minutes and then treated with sodium triacetoxyborohydride (715.3 g, 3.38 mol, 2.5 eq.) portionwise (Note: the reaction temperature increased from RT to 34° C.). After 2 hours, LC-MS analysis showed that INTERMEDIATE A was formed as the major product. The reaction mixture was cooled using an ice-water bath and neutralized with saturated aqueous $NaHCO_3$ to a pH of about 7. The resulting thick slurry was passed through a short Celite® (diatomaceous earth) pad and washed with DCM. The white solid left on the pad was collected, put into flask, charged with DCM and water and then stirred well. The resulting slurry was again passed through a short Celite® (diatomaceous earth) pad and washed with DCM. All the filtrates were combined. The organic layer was separated, dried, filtered, and concentrated. The oily residue was purified by column chromatography, affording INTERMEDIATE A (160 g) as a white solid. MS (ESI, positive) m/z: 252.3. $^1$H NMR (400 MHz, DMSO-$d_6$): δ ppm $^1$H NMR (400 MHz, DMSO-$d_6$) δ 8.68 (s, 1 H), 7.89 (s, 1 H), 7.17 (d, J=8.2 Hz, 1 H), 6.57 (s, 1 H), 6.49 (d, J=8.3 Hz, 1 H), 4.37 (d, J=5.2 Hz, 2 H), 3.80 (s, 3 H), 3.75 (s, 3 H).

Intermediates B, C and D

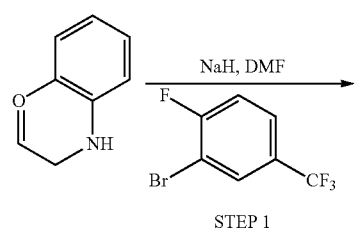

STEP 1

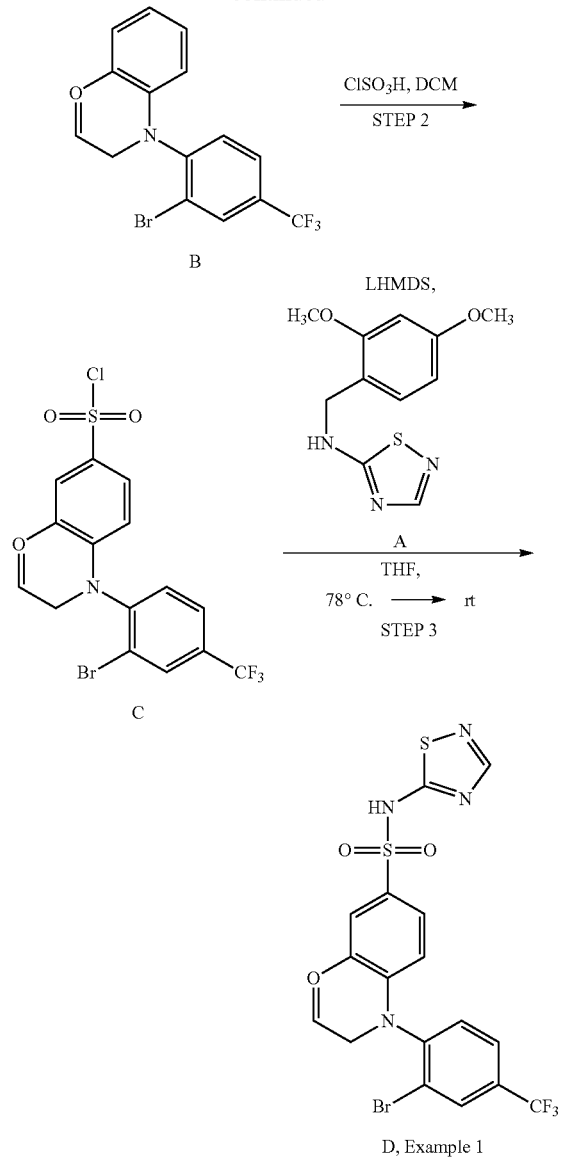

Step 1, Intermediate B: 4-(2-Bromo-4-(Trifluoromethyl)Phenyl)-3,4-Dihydro-2H-Benzo[B][1,4]Oxazine

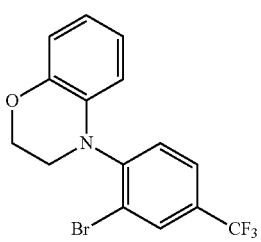

B

To a flask under nitrogen, 3,4-dihydro-2H-benzo[b][1,4] oxazine (Tyger Scientific Inc., Ewing, N.J., 0.457 mL, 3.70 mmol) was dissolved in DMF (18.50 mL) and at room temperature, NaH (60% dispersion in mineral oil) (0.326 g, 8.14 mmol) was added, and the reaction was stirred for 15 minutes. 2-Bromo-1-fluoro-4-(trifluoromethyl)benzene (Alfa Aesar, Ward Hill, Mass., 0.790 mL, 5.55 mmol) was then added, and the reaction was stirred overnight at room temperature until complete conversion to the desired product. The reaction was then quenched with saturated aqueous ammonium chloride solution, and extracted with EtOAc (×2). The combined organics were washed with brine, dried over sodium sulfate, and concentrated to give material, which was purified via silica gel MPLC (Biotage Isolera One; PuriFlash HP, 15μ, 25 g (Biotage, Uppsala, Sweden)), eluting with 0 to 100% ethyl acetate in heptanes. Fractions containing clean product were collected and concentrated under a vacuum to yield 1.73 g of 4-(2-bromo-4-(trifluoromethyl)phenyl)-3,4-dihydro-2H-benzo[b][1,4]oxazine (INTERMEDIATE B) as an orange oil. $^1$H NMR (400 MHz, DMSO-$d_6$) δ ppm 3.62-3.69 (m, 2H) 4.28 (t, J=4.21 Hz, 2H) 6.30 (dd, J=7.87, 1.71 Hz, 1 H) 6.71 (dtd, J=18.67, 7.42, 7.42, 1.71 Hz, 2H) 6.85 (dd, J=7.78, 1.81 Hz, 1 H) 7.59 (d, J=8.41 Hz, 1 H) 7.81 (dd, J=8.41, 1.56 Hz, 1 H) 8.13 (d, J=1.66 Hz, 1 H). m/z (ESI) 357.0 (M+H)$^+$.

Step 2, Intermediate C: 4-(2-Bromo-4-(Trifluoromethyl)Phenyl)-3,4-Dihydro-2H-Benzo[B][1,4]Oxazine-7-Sulfonyl Chloride

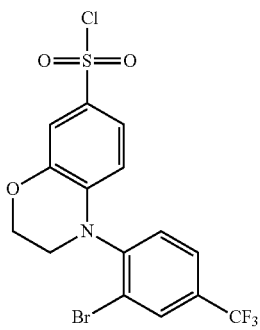

C

A solution of INTERMEDIATE B (1.325 g, 3.70 mmol) in DCM (7.40 mL) was cooled to 0° C. in an ice-water bath, and chlorosulfonic acid (1.230 mL, 18.50 mmol) was added dropwise. The resulting solution was stirred at RT for 4 hours until complete conversion to the desired product occurred. The reaction mixture was then slowly added dropwise to well-stirred ice water and subsequently neutralized to a pH of about 7 with saturated aqueous sodium bicarbonate solution. After extraction with EtOAc (×3), the combined organics were washed with water and brine, dried over magnesium sulfate, filtered and concentrated to provide INTERMEDIATE C. The material was taken forward without further purification. m/z (ESI) 477.8 (M+Na)$^+$.

Step 3, Intermediate D (Example 1): 4-(2-Bromo-4-(Trifluoromethyl)Phenyl)-N-(1,2,4-Thiadiazol-5-YL)-3,4-Dihydro-2H-Benzo[B][1,4]Oxazine-7-Sulfonamide Intermediate D Example 1

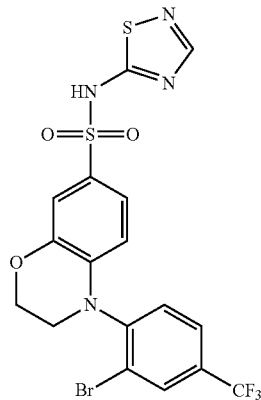

A round-bottom flask was charged with N-(2,4-dimethoxybenzyl)-1,2,4-thiadiazol-5-amine (INTERMEDIATE A, 3.49 g, 13.90 mmol) and THF (50.4 mL), and the vessel was cooled to −78° C. for 15 minutes. LHMDS (1.0 M in THF) (13.90 mL, 13.90 mmol) was then added dropwise over 1 minute. The reaction was stirred for 10 minutes, and then a solution of 4-(2-bromo-4-(trifluoromethyl)phenyl)-3,4-dihydro-2H-benzo[b][1,4]oxazine-7-sulfonyl chloride (INTERMEDIATE C, 4.60 g, 10.07 mmol) in THF (5.93 mL, 10.07 mmol) was added dropwise over 1 minute. The bath was removed, and the resulting mixture was stirred for 45 minutes, until complete conversion to 4-(2-bromo-4-(trifluoromethyl)phenyl)-N-(2,4-dimethoxybenzyl)-N-(1,2,4-thiadiazol-5-yl)-3,4-dihydro-2H-benzo[b][1,4]oxazine-7-sulfonamide. The reaction was diluted with saturated ammonium chloride (aq.) solution (30 mL), and was washed with ethyl acetate (20 mL×3). The organic layers were combined, dried over magnesium sulfate, filtered and concentrated. The resulting material was further purified (to remove the excess amine) using a 50 g SCX (strong cation exchange) column. (4-(2-bromo-4-(trifluoromethyl)phenyl)-N-(2,4-dimethoxybenzyl)-N-(1,2,4-thiadiazol-5-yl)-3,4-dihydro-2H-benzo[b][1,4]oxazine-7-sulfonamide eluted with minor impurities. The material was further purified via silica gel MPLC (Biotage Isolera One; PuriFlash HP, 15μ, 80 g), eluting with 0 to 100% ethyl acetate in heptanes to provide a mixture of 4-(2-bromo-4-(trifluoromethyl)phenyl)-N-(2,4-dimethoxybenzyl)-N-(1,2,4-thiadiazol-5-yl)-3,4-dihydro-2H-benzo[b][1,4]oxazine-7-sulfonamide and 4-(2-bromo-4-(trifluoromethyl)phenyl)-N-(1,2,4-thiadiazol-5-yl)-3,4-dihydro-2H-benzo[b][1,4]oxazine-7-sulfonamide (INTERMEDIATE D, Example 1). $^1$H NMR (400 MHz, DMSO-$d_6$) δ ppm 3.43-3.52 (m, 2H) 4.31-4.42 (m, 2H) 6.25 (d, J=8.51 Hz, 1 H) 7.12-7.16 (m, 1 H) 7.17 (d, J=2.15 Hz, 1 H) 7.74 (d, J=7.73 Hz, 1 H) 7.90 (dd, J=8.26, 1.61 Hz, 1 H) 8.20 (d, J=1.86 Hz, 1 H) 8.42 (s, 1 H). m/z (ESI) 520.9 (M+H)$^+$.

Intermediates F and G

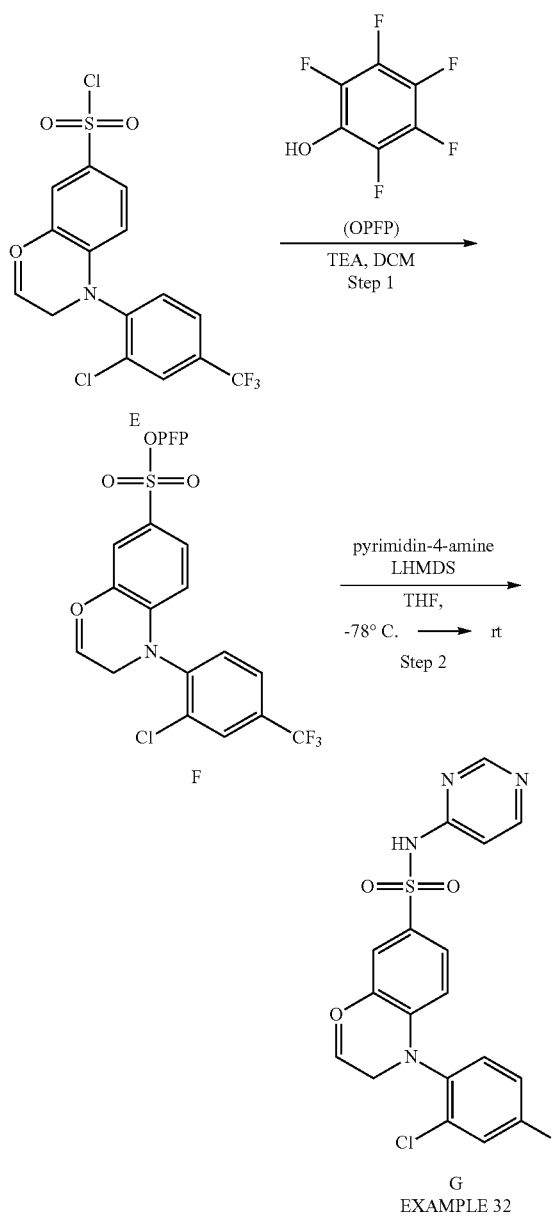

Step 1, Intermediate F: Perfluorophenyl 4-(2-Chloro-4-(Trifluoromethyl)Phenyl)-3,4-Dihydro-2H-Benzo[B][1,4]Oxazine-7-Sulfonate

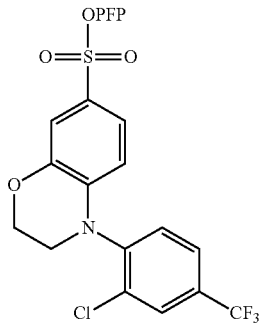

INTERMEDIATE F was prepared from 4-(2-chloro-4-(trifluoromethyl)phenyl)-3,4-dihydro-2H-benzo[b][1,4]oxazine-7-sulfonyl chloride (INTERMEDIATE E), which was prepared in an analogous fashion to INTERMEDIATE C, except using 2-chloro-1-fluoro-4-(trifluoromethyl)benzene instead of 2-bromo-1-fluoro-4-(trifluoromethyl)benzene in STEP 1. A 25 mL septa/cap vial under Argon was charged with INTERMEDIATE E (0.400 g, 0.970 mmol), and dissolved in DCM (3.6 mL). 2,3,4,5,6-Pentafluorophenol (PFP) (0.268 g, 1.456 mmol) was added, followed by dropwise addition of triethylamine (0.202 mL, 1.46 mmol). The reaction was stirred for 1 hour at room temperature. The resulting material was concentrated, dissolved in minimal DCM and purified via column chromatography (silica gel 40 g, gradient elution 0 to 40% EtOAc:Heptane; product eluted at 30%) to afford perfluorophenyl 4-(2-chloro-4-(trifluoromethyl)phenyl)-3,4-dihydro-2H-benzo[b][1,4]oxazine-7-sulfonate (0.543 g, 0.970 mmol) as a clear colorless oil. m/z (ESI) 391.8 (M-PFP)⁻.

Step 2, Intermediate G (Example 32): 4-(2-Chloro-4-(Trifluoromethyl)Phenyl)-N-(Pyrimidin-4-Y1)-3,4-Dihydro-2H-Benzo[B][1,4]Oxazine-7-Sulfonamide

EXAMPLE 32

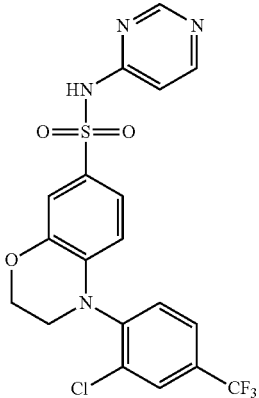

A sealable vial was charged with 4-aminopyrimidine (0.101 g, 1.067 mmol) sealed with a septa cap and placed under an N₂ atmosphere. THF (2 mL) was added and the solution was cooled to −78° C. Lithium bis(trimethylsilyl)amide, 1.0 M in THF (1.067 mL, 1.067 mmol) was added dropwise and the solution was maintained at −78° C. for 15 min. Perfluorophenyl 4-(2-chloro-4-(trifluoromethyl)phenyl)-3,4-dihydro-2H-benzo[b][1,4]oxazine-7-sulfonate (INTERMEDIATE F, 0.543 g, 0.970 mmol) was added as a solution in THF (3 mL) and the solution was allowed to warm to rt, and the mixture was stirred for 40 min. To the solution was added acetic acid (0.2 mL) to provide a bright yellow/orange mixture. The mixture was concentrated to dryness. The residue was absorbed onto a plug of silica gel and purified by chromatography through a silica gel column (40 g), eluting with a gradient of 10% to 100% EtOAc in heptane, to provide 4-(2-chloro-4-(trifluoromethyl)phenyl)-N-(pyrimidin-4-yl)-3,4-dihydro-2H-benzo[b][1,4]oxazine-7-sulfonamide (0.050 g, 0.106 mmol) as tan solid. ¹H NMR (400 MHz, DMSO-d₆) δ ppm 3.60-3.84 (m, 2 H) 4.24-4.48 (m, 2 H) 6.32 (d, J=8.51 Hz, 1 H) 6.98-7.05 (m, 1 H) 7.24-7.31 (m, 1 H) 7.34 (s, 1 H) 7.71-7.79 (m, 1 H) 7.82-7.89 (m, 1 H) 8.03-8.11 (m, 1 H) 8.31-8.43 (m, 1 H) 8.56-8.75 (m, 1 H). m/z (ESI) 471.0 (M+H)⁺.

Intermediates H, I, J, K and L

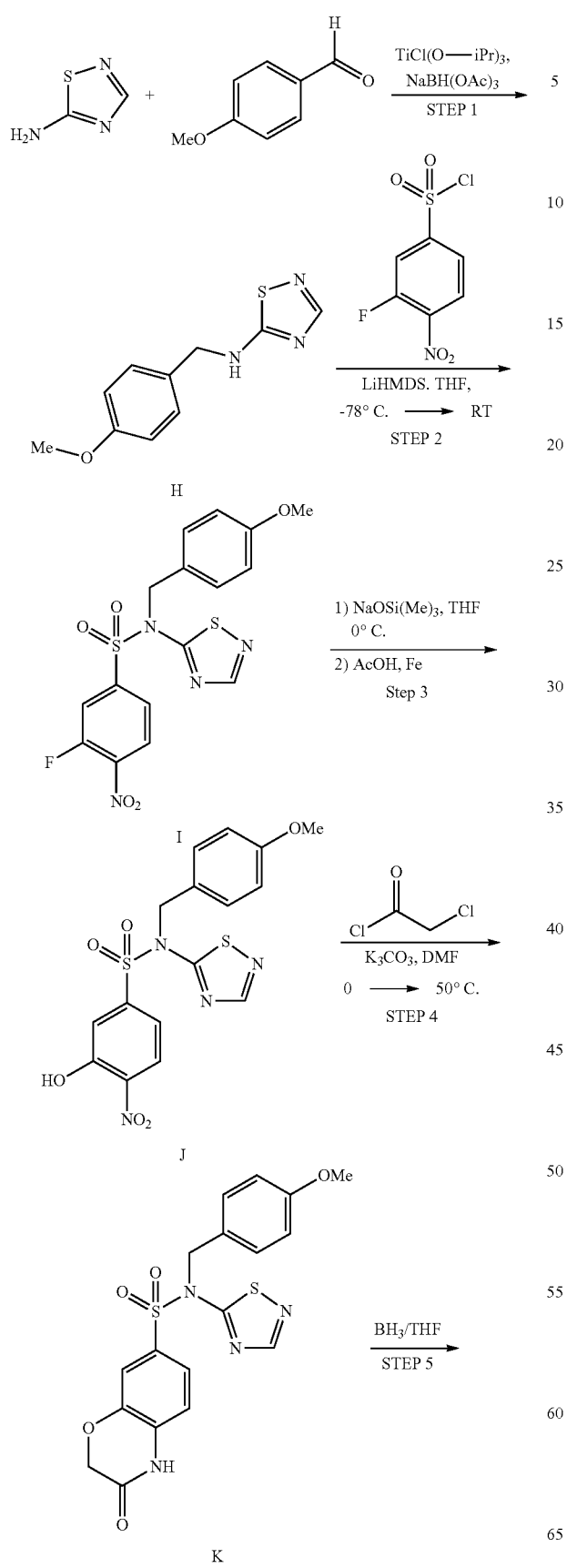

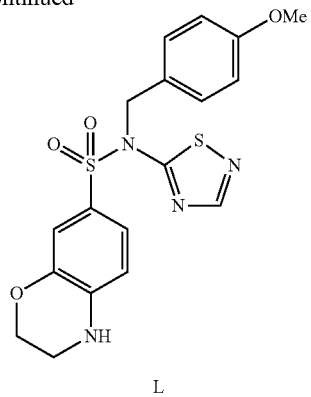

Step 1, Intermediate H: N-(4-Methoxybenzyl)-1,2,4-Thiadiazol-5-Amine

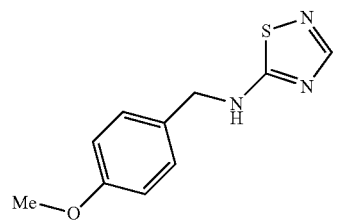

To a suspension of 4-methoxybenzaldehyde (10.0 g, 73.4 mmol) and 1,2,4-thiadiazol-5-amine (7.40 g, 73.4 mmol) in dichloromethane (200 mL) was added chlorotitanium triisopropoxide (28.6 g, 110 mmol) portionwise over 5 min. After stirring for 3 hours, sodium triacetoxyborohydride (38.9 g, 184 mmol) was added portionwise at 0° C. and allowed to stir for additional 1 hour. The reaction was cooled in ice/water mixture quenched with saturated NaHCO₃ solution (300 mL) and extracted with dichloromethane (2×300 mL). The organic layer was separated, dried over Na₂SO₄, filtered and concentrated to obtain the product, which was purified by column chromatography using silica gel (100 to 200 mesh) and 0 to 30% ethyl acetate in hexane to give 5.5 g of INTERMEDIATE H as an off-white solid. MS (ESI, positive) m/z: 222.1; $^1$H NMR (400 MHz, DMSO-$d_6$) δ 8.89 (s, 1 H), 7.92 (s, 1 H), 7.27 (d, J=8.5 Hz, 2 H), 6.91 (d, J=8.5 Hz, 2 H), 4.42 (d, J=5.4 Hz, 2 H), 3.73 (s, 3 H).

Step 2, Intermediate I: 3-Fluoro-N-(4-Methoxybenzyl)-4-Nitro-N-(1,2,4-Thiadiazol-5-Yl)Benzenesulfonamide

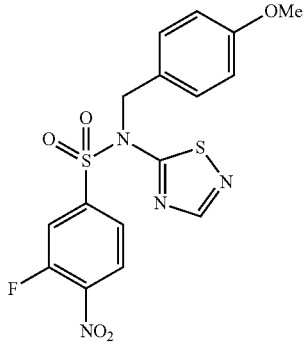

A 250-mL round bottom flask was charged with N-(4-methoxybenzyl)-1,2,4-thiadiazol-5-amine (INTERMEDIATE H, 2.032 g, 9.18 mmol) and THF (30 mL). The flask was cooled to −78° C. and lithium bis(trimethylsilyl)amide (1M in THF) (10.02 mL, 10.02 mmol) was added dropwise, rapidly. The flask was placed in an ice/water bath for 10 minutes, and then returned to −78° C., at which time a solution of 3-fluoro-4-nitrobenzenesulfonyl chloride (Matrix Scientific, Columbia, S.C., 2.000 g, 8.35 mmol) in THF (5 mL with a 1 mL wash) was added dropwise. After 15 minutes, the reaction was complete, and was quenched with aqueous saturated ammonium chloride solution. The mixture was warmed to RT and extracted with EtOAc. The organics were combined and dried over sodium sulfate, filtered and concentrated. The solids were taken up in methanol, and after triturating, were filtered and washed with methanol to yield 3-fluoro-N-(4-methoxybenzyl)-4-nitro-N-(1,2,4-thiadiazol-5-yl)benzenesulfonamide. (INTERMEDIATE I) (2.76 g, 6.50 mmol) as a light yellow solid. m/z (ESI) 446.7 (M+Na)$^+$.

Step 3, Intermediate J: 4-Amino-3-Hydroxy-N-(4-Methoxybenzyl)-N-(1,2,4-Thiadiazol-5-Yl)Benzenesulfonamide

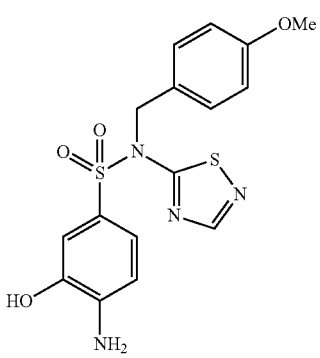

J

A 250-mL round bottom flask was charged with INTERMEDIATE I (2.76 g, 6.50 mmol) and THF (32.5 mL) to give a clear, yellow solution. The flask was cooled to 0° C. for 10 minutes, after which sodium trimethylsilanolate, 1.0M solution in tetrahydrofuran (13.01 mL, 13.01 mmol) was added dropwise rapidly over 1 minute to give an orange solution. The reaction was complete after 50 minutes (with M+H corresponding to the phenol). 1N HCl (aq, 70 mL) was added, followed quickly by EtOAc (70 mL). The layers were separated, and the aqueous portion was extracted (3×) with EtOAc (40 mL). The organics were combined, dried over sodium sulfate, filtered and concentrated to give a yellow solid. The solid was then dissolved in THF (20 mL) and acetic acid (20.47 mL, 358 mmol), and iron (3.63 g, 65.0 mmol) was added. The flask was sealed and heated to 70° C. for 40 minutes. The reaction was cooled to RT, diluted with THF, and filtered through Celite® (diatomaceous earth), washing with THF. The filtrate was concentrated, and partitioned between sat. aq. sodium bicarbonate solution and EtOAc. The layers were separated, and the aqueous was then extracted with EtOAc. The combined organics were washed with brine, dried over sodium sulfate, filtered and concentrated to yield 4-amino-3-hydroxy-N-(4-methoxybenzyl)-N-(1,2,4-thiadiazol-5-yl)benzenesulfonamide (INTERMEDIATE J) (2.45 g, 6.24 mmol). $^1$H NMR (400 MHz, DMSO-$d_6$) δ ppm 3.72 (s, 3 H) 4.94 (s, 2 H) 5.86 (s, 2 H) 6.65 (d, J=8.41 Hz, 1 H) 6.81-6.90 (m, 2 H) 7.09 (d, J=2.25 Hz, 1 H) 7.21 (dd, J=8.41, 2.25 Hz, 1 H) 7.29 (m, J=8.80 Hz, 2 H) 8.34 (s, 1 H) 9.92 (s, 1 H). m/z (ESI) 392.7 (M+H)$^+$.

Step 4, Intermediate K: N-(4-Methoxybenzyl)-3-Oxo-N-(1,2,4-Thiadiazol-5-Yl)-3,4-Dihydro-2H-Benzo[B][1,4]Oxazine-7-Sulfonamide

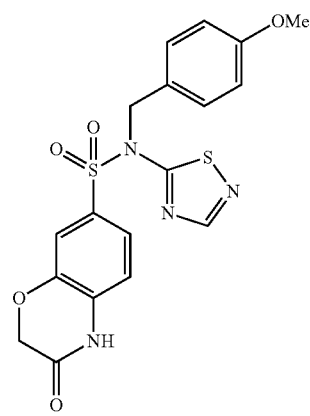

K

A 250 mL round bottom flask was charged with 4-amino-3-hydroxy-N-(4-methoxybenzyl)-N-(1,2,4-thiadiazol-5-yl)benzenesulfonamide (INTERMEDIATE J, 2.450 g, 6.24 mmol) and $K_2CO_3$ (2.59 g, 18.73 mmol), and diluted with DMF (62.4 mL) under an inert atmosphere. The reaction mixture was cooled to 0° C. in an ice-water bath, and 2-chloroacetyl chloride (0.596 mL, 7.49 mmol) was added (color change from orange to light yellow suspension). After stirring for 5 minutes, the reaction was warmed to rt. After 30 minutes, complete conversion to the first alkylation was observed (M+H=468), along with some fully cyclized material. The reaction was heated to 50° C. for 2 h until complete conversion to the cyclized oxazinone. The reaction was cooled to rt, and diluted with sat aq. ammonium chloride and then extracted with ethyl acetate. The organics were washed with brine, then dried over magnesium sulfate and concentrated under a vacuum. Upon attempts to transfer using DCM and a small amount of ether, it was observed that a solid crashed out of solution. The solids were filtered, and washed with ether to yield 1.37 g of N-(4-methoxybenzyl)-3-oxo-N-(1,2,4-thiadiazol-5-yl)-3,4-dihydro-2H-benzo[b][1,4]oxazine-7-sulfonamide (INTERMEDIATE K) as a light pink solid. $^1$H NMR (400 MHz, DMSO-$d_6$) δ ppm 3.72 (s, 3 H) 4.67 (s, 2 H) 5.13 (s, 2 H) 6.83-6.92 (m, 2 H) 7.04 (d, J=8.41 Hz, 1 H) 7.30 (d, J=8.80 Hz, 2 H) 7.37 (d, J=2.05 Hz, 1 H) 7.56 (dd, J=8.41, 2.15 Hz, 1 H) 8.41 (s, 1 H) 11.21 (s, 1 H). m/z (ESI) 432.9 (M+H)$^+$.

Step 5, Intermediate L: N-(4-Methoxybenzyl)-N-(1,2,4-Thiadiazol-5-Yl)-3,4-Dihydro-2H-Benzo[B][1,4]Oxazine-7-Sulfonamide

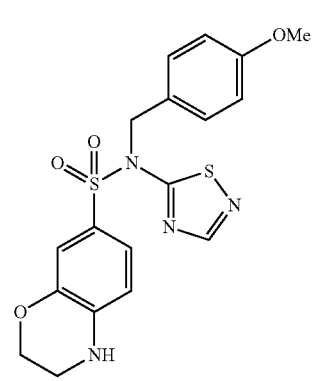

L

A solution of borane tetrahydrofuran complex, 1.0 M in tetrahydrofuran (4.76 mL, 4.76 mmol) was added dropwise to a mixture of N-(4-methoxybenzyl)-3-oxo-N-(1,2,4-thiadiazol-5-yl)-3,4-dihydro-2H-benzo[b][1,4]oxazine-7-sulfonamide (INTERMEDIATE K, 1.372 g, 3.17 mmol) in THF (15.86 mL) to form a heterogeneous mixture at 0° C. Gas evolution was observed upon addition, as well as gradual solubilization. After the addition, the reaction was warmed to RT for 5 h. The reaction was then quenched with MeOH (16.0 mL) and stirred overnight at room temperature. The reaction was then concentrated under a vacuum, and re-diluted with MeOH, and concentrated (×2). The resulting material was diluted once more in methanol and the solids were triturated and filtered, washing with methanol to yield 1.122 g of INTERMEDIATE L, N-(4-methoxybenzyl)-N-(1,2,4-thiadiazol-5-yl)-3,4-dihydro-2H-benzo[b][1,4]oxazine-7-sulfonamide (1.122 g, 2.68 mmol, 85%). $^1$H NMR (400 MHz, DMSO-d$_6$) δ ppm 3.34-3.38 (m, 2 H) 3.72 (s, 3 H) 4.10 (t, J=4.40 Hz, 2 H) 5.03 (s, 2 H) 6.62-6.66 (m, 1 H) 6.82-6.89 (m, 2 H) 7.04 (d, J=2.35 Hz, 1 H) 7.16-7.21 (m, 1 H) 7.25-7.31 (m, 2 H) 8.35 (s, 1 H). m/z (ESI) 418.8 (M+H)$^+$.

Intermediate M

N-(4-Methoxybenzyl)-N-(Thiazol-2-Yl)-3,4-Dihydro-2H-Benzo[B][1,4]Oxazine-7-Sulfonamide

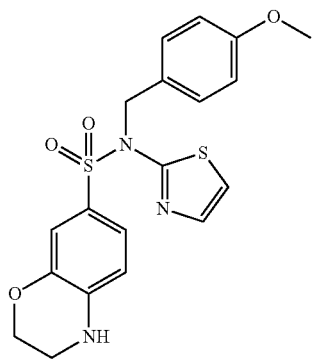

INTERMEDIATE M was synthesized in an analogous manner to INTERMEDIATE L, using N-(4-methoxybenzyl)thiazol-2-amine (INTERMEDIATE W) instead of N-(4-methoxybenzyl)-1,2,4-thiadiazol-5-amine in STEP 2. $^1$H NMR (400 MHz, DMSO-d$_6$) δ ppm 3.32-3.37 (m, 2 H) 3.70 (s, 3 H) 4.10 (t, J=4.35 Hz, 2 H) 4.97 (s, 2 H) 6.61 (d, J=8.51 Hz, 1 H) 6.82-6.88 (m, 2 H) 6.96 (d, J=2.15 Hz, 1 H) 7.00 (br. s., 1 H) 7.15 (dd, J=8.46, 2.20 Hz, 1 H) 7.24 (d, J=8.61 Hz, 2 H) 7.30 (d, J=3.62 Hz, 1 H) 7.40 (d, J=3.62 Hz, 1 H). m/z (ESI) 417.9 (M+H)$^+$.

Intermediate N

3-Bromo-N-(4-Methoxybenzyl)-1,2,4-Thiadiazol-5-Amine

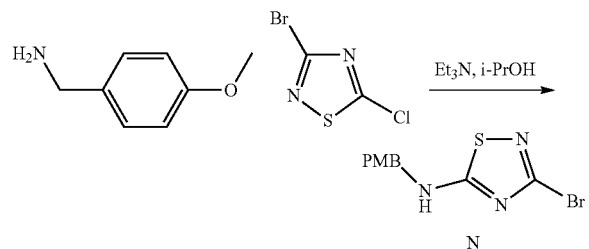

A round bottom flask was charged with 3-bromo-5-chloro-1,2,4-thiadiazole (Acros, 2.73 g, 13.69 mmol), i-PrOH (25 mL), and triethylamine (3.82 mL, 27.4 mmol) to give a clear solution. 4-methoxybenzylamine (Sigma Aldrich, St. Louis, Mo., 2.132 mL, 16.42 mmol) was added dropwise, and the resulting mixture was stirred for 2.5 hours. The reaction mixture was diluted with EtOAc and washed with saturated aq. sodium bicarbonate solution, washed with water, washed with brine, dried over sodium sulfate, filtered, and concentrated. The product was purified by chromatography on silica gel (0 to 40% EtOAc/Heptane) to give a white solid. The solid was suspended in heptane, then filtered. The collected solid was washed with heptane (3×), then dried under a stream of N$_2$ (g) overnight to give 3-bromo-N-(4-methoxybenzyl)-1,2,4-thiadiazol-5-amine (INTERMEDIATE N) (2.774 g, 9.24 mmol) as a white, fluffy solid. $^1$H NMR (400 MHz, DMSO-d$_6$) δ=9.20 (br. s., 1 H), 7.33-7.20 (m, 2 H), 7.01-6.84 (m, 2 H), 4.43 (br. s., 2 H), 3.74 (s, 3 H). m/z (ESI) 300.0 (M+H)$^+$.

Intermediate O

N-(3-Bromo-1,2,4-Thiadiazol-5-Yl)-4-(2-Chloro-4-(Trifluoromethyl)Phenyl)-N-(4-Methoxybenzyl)-3,4-Dihydro-2H-Benzo[B][1,4]Oxazine-7-Sulfonamide

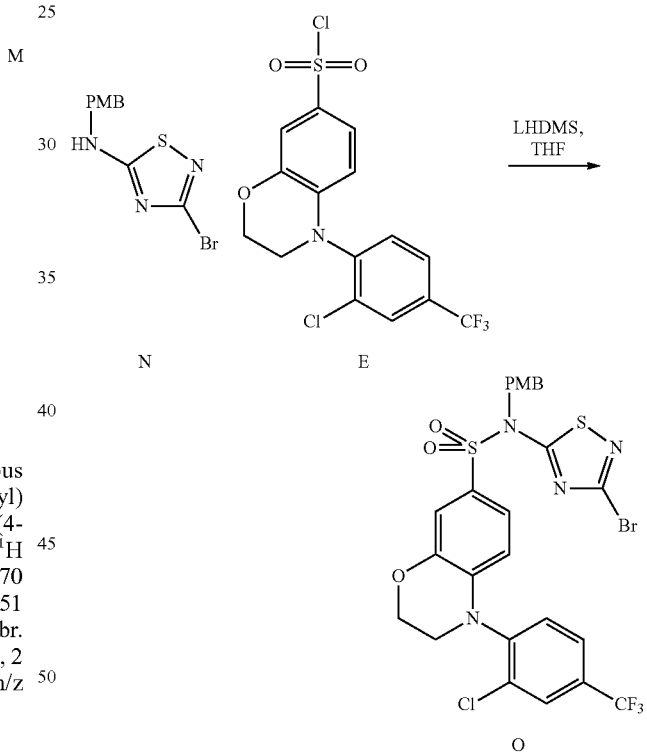

A 25-mL round bottom flask was charged with 3-bromo-N-(4-methoxybenzyl)-1,2,4-thiadiazol-5-amine (INTERMEDIATE N) (1.369 g, 4.56 mmol) and THF (20 mL) to give a clear solution. The flask was cooled To −78° C. for 10 min, then lithium bis(trimethylsilyl)amide (1M in THF) (5.61 mL, 5.61 mmol) was added dropwise. The resulting clear solution was stirred for 20 minutes, then a solution of 4-(2-chloro-4-(trifluoromethyl)phenyl)-3,4-dihydro-2H-benzo[b][1,4]oxazine-7-sulfonyl chloride (INTERMEDIATE E, 1.4457 g, 3.51 mmol) in THF (2 mL with a 1 mL syringe/flask wash) was added dropwise over 2 minutes. After a few minutes, the flask was lowered into an ice-water bath for 25 min. The reaction mixture was then diluted with saturated aq ammonium chloride solution and warmed to room temperature. The biphasic mixture was extracted with EtOAc, and the organic extract was washed with brine, dried over sodium sulfate, filtered, and concentrated. The product was purified by chromatography on silica gel (0 to 40% EtOAc/Heptane) to give N-(3-bromo-1,2,4-thiadiazol-5-yl)-4-(2-chloro-4-(trifluoromethyl)phenyl)-N-(4-methoxybenzyl)-3,4-dihydro-2H-benzo[b][1,4]oxazine-7-sulfonamide (INTERMEDIATE O) (2.009 g, 2.97 mmol) as a white foam. $^1$H NMR (400 MHz, DMSO-d$_6$) δ=8.11 (d, J=1.7 Hz, 1 H), 7.93-7.85 (m, 1 H), 7.78 (d, J=8.3 Hz, 1 H), 7.37-7.16 (m, 4 H), 6.96-6.79 (m, 2 H), 6.27 (d, J=8.5 Hz, 1 H), 5.04 (s, 2 H), 4.37 (d, J=16.6 Hz, 2 H), 3.87-3.65 (m, 5 H). m/z (ESI) 675.0 (M+H)$^+$.

Intermediate P 4-(2-Chloro-4-(Trifluoromethyl)Phenyl)-N-(3-Cyano-1,2,4-Thiadiazol-5-Yl)-N-(4-Methoxybenzyl)-3,4-Dihydro-2H-Benzo[B][1,4]Oxazine-7-Sulfonamide

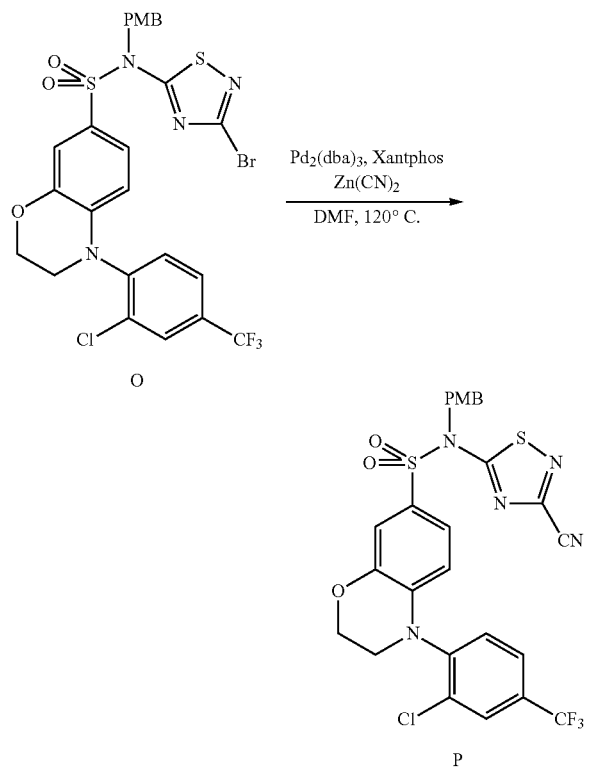

A 15-mL resealable vessel was charged with xantphos (51.4 mg, 0.089 mmol) and Pd$_2$(dba)$_3$ (40.6 mg, 0.044 mmol). The vessel was flushed with Ar (g), then DMF (4438 μL) was added. The vessel was sealed and placed in a 120° C. bath for 10 min. The mixture was cooled, then a solid mixture of N-(3-bromo-1,2,4-thiadiazol-5-yl)-4-(2-chloro-4-(trifluoromethyl)phenyl)-N-(4-methoxybenzyl)-3,4-dihydro-2H-benzo[b][1,4]oxazine-7-sulfonamide (INTERMEDIATE 0, 300 mg, 0.444 mmol) and dicyanozinc (261 mg, 2.219 mmol) was added. DMF (1 mL) was washed down the sides of the vessel, and the vessel was sealed and placed in a 120° C. bath for 2.5 hours. The mixture was cooled to room temperature, then diluted with EtOAc, water, and brine. layers were separated, and the organic layer was washed with brine, dried over sodium sulfate, filtered, and concentrated. The product was purified by chromatography on silica gel (0 to 40% EtOAc/Heptane) to give 4-(2-chloro-4-(trifluoromethyl)phenyl)-N-(3-cyano-1,2,4-thiadiazol-5-yl)-N-(4-methoxybenzyl)-3,4-dihydro-2H-benzo[b][1,4]oxazine-7-sulfonamide (INTERMEDIATE P) (155.63 mg, 0.250 mmol). m/z (ESI) 622.2 (M+H)$^+$.

Intermediate Q

4-Amino-N-(4-Methoxybenzyl)-3-(2-Oxo-2-Phenylethoxy)-N-(1,2,4-Thiadiazol-5-Yl)Benzenesulfonamide

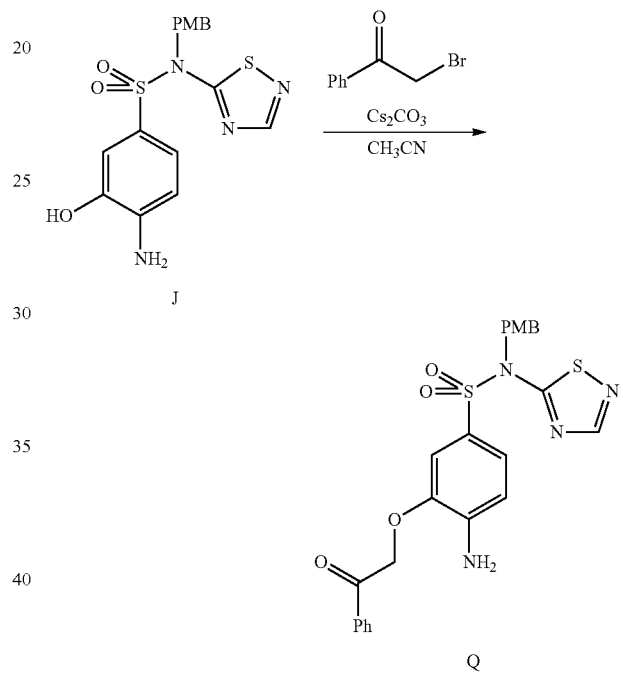

A round-bottom flask was charged with 4-amino-3-hydroxy-N-(4-methoxybenzyl)-N-(1,2,4-thiadiazol-5-yl)benzenesulfonamide (INTERMEDIATE J, 852 mg, 2.171 mmol), acetonitrile (7237 μL), cesium carbonate (707 mg, 2.171 mmol), and 2-bromo-1-phenylethanone (475 mg, 2.388 mmol). The resulting mixture was stirred for 2 hours, then was diluted with THF and filtered. The filter pad was washed successively with THF, then with DCM. The filtrate was concentrated, and the residue was concentrated from DCM. The residual solid was taken up in DCM and filtered. The solid was washed with DCM, then dried under vacuum to give 459 mg of a white solid. The filtrate was concentrated and the process repeated to yield an additional crop of product. The two crops of product were combined to give 4-amino-N-(4-methoxybenzyl)-3-(2-oxo-2-phenylethoxy)-N-(1,2,4-thiadiazol-5-yl)benzenesulfonamide (INTERMEDIATE Q) (377.62 mg, 0.740 mmol) as a white solid. $^1$H NMR (400 MHz, DMSO-d$_6$) δ=8.44 (s, 1 H), 8.05 (d, J=7.2 Hz, 2 H), 7.67-7.52 (m, 6 H), 7.40 (d, J=2.1 Hz, 1 H), 7.32 (d, J=8.7 Hz, 2 H), 6.88 (d, J=8.8 Hz, 2 H), 5.35 (s, 2 H), 5.19 (s, 2 H), 3.71 (s, 3 H).

Intermediate R

Rac-N-(4-Methoxybenzyl)-3-Phenyl-N-(1,2,4-Thiadiazol-5-Yl)-3,4-Dihydro-2H-Benzo[B][1,4]Oxazine-7-Sulfonamide

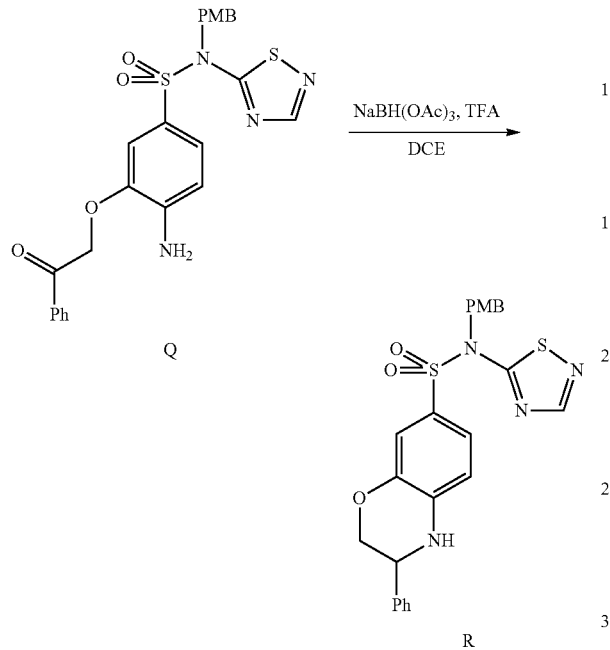

A round-bottom flask was charged with INTERMEDIATE Q (328.14 mg, 0.643 mmol), DCE (6427 μl), and sodium triacetoxyborohydride (272 mg, 1.285 mmol) to give a thick, white slurry. Trifluoroacetic acid (49.5 μl, 0.643 mmol) was added dropwise, and the resulting white mixture was stirred vigorously for 4 hours. The reaction mixture was quenched by the dropwise addition of saturated aq. sodium bicarbonate solution, then diluted with water. The biphasic mixture was extracted with DCM (2×), and the combined organic extracts were dried over sodium sulfate, filtered, and concentrated. The product was purified by chromatography on silica gel (10 to 60% EtOAc/Heptane) to give N-(4-methoxybenzyl)-3-phenyl-N-(1,2,4-thiadiazol-5-yl)-3,4-dihydro-2H-benzo[b][1,4]oxazine-7-sulfonamide (INTERMEDIATE R) (311.1 mg, 0.629 mmol) as a white foam. $^1$H NMR (400 MHz, DMSO-d$_6$) δ=8.37 (s, 1 H), 7.68 (s, 1 H), 7.44-7.26 (m, 8 H), 7.12 (d, J=2.2 Hz, 1 H), 6.91-6.84 (m, 2 H), 6.79 (d, J=8.6 Hz, 1 H), 5.07 (s, 2 H), 4.62 (s, 1 H), 4.26 (dd, J=3.0, 10.9 Hz, 1 H), 3.94 (dd, J=6.8, 10.7 Hz, 1 H), 3.71 (s, 3 H). m/z (ESI) 495.0 (M+H)$^+$.

Intermediates S, T, U, V

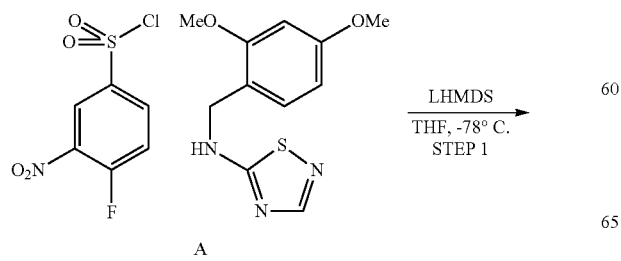

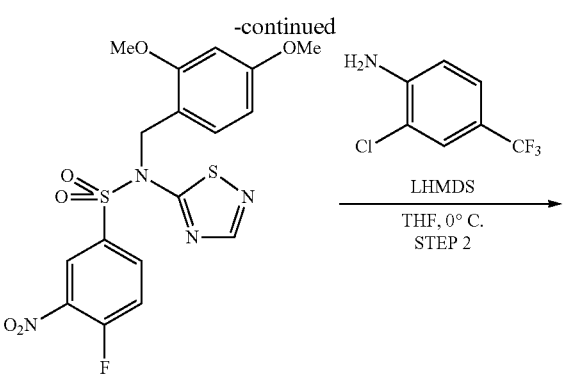

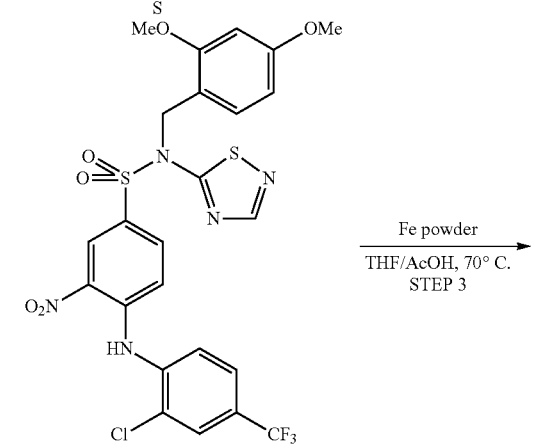

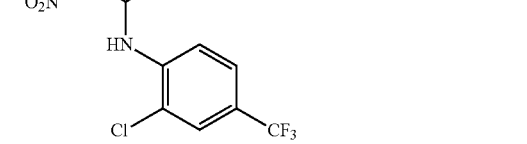

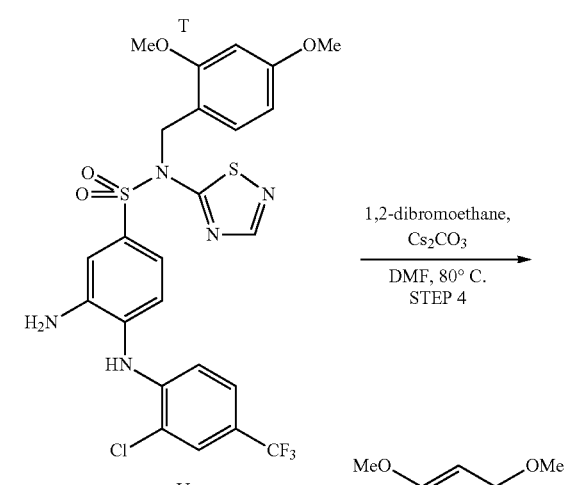

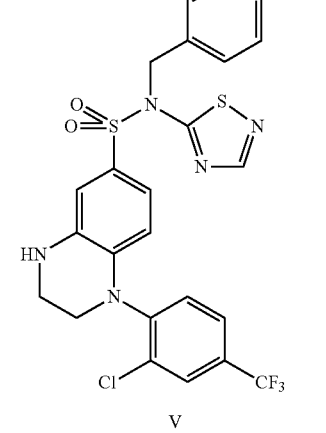

Step 1, Intermediate S: N-(2,4-Dimethoxybenzyl)-4-Fluoro-3-Nitro-N-(1,2,4-Thiadiazol-5-Yl)Benzenesulfonamide

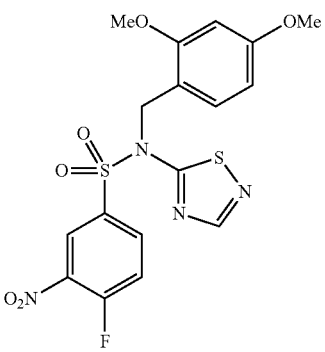

S

A 100-mL round-bottom flask was charged with N-(2,4-dimethoxybenzyl)-1,2,4-thiadiazol-5-amine (INTERMEDIATE A, 1.478 g, 5.88 mmol) and THF (10 mL) to give a clear, light-yellow solution. The flask was cooled in a dry ice-acetone bath for 10 min, then lithium bis(trimethylsilyl)amide (1M in THF) (5.88 mL, 5.88 mmol) was added dropwise over 2 min. The cooling bath was removed for 5 minutes, then re-cooled for 5 min. A solution of 4-fluoro-3-nitrobenzene-1-sulfonyl chloride (1.281 g, 5.35 mmol) in THF (3 mL with a 1 mL flask/syringe wash) was added dropwise over 2 minutes. The cooling bath was removed and the reaction was warmed to room temperature. The mixture was diluted with water and extracted with EtOAc. The organic extract was washed with brine, dried over sodium sulfate, filtered, and concentrated. The material was concentrated from EtOAc (2×), then taken up in EtOAc, sonicated for 1 min, and filtered through a membrane filter. The resulting solid was transferred to a sonication vial, then put under high vacuum at 60° C. for 10 min to give N-(2,4-dimethoxybenzyl)-4-fluoro-3-nitro-N-(1,2,4-thiadiazol-5-yl)benzenesulfonamide (INTERMEDIATE S) as a yellow solid. $^1$H NMR (400 MHz, CHLOROFORM-d) δ=8.24 (s, 1 H), 8.18 (dd, J=2.4, 6.7 Hz, 1 H), 7.99 (ddd, J=2.4, 3.9, 8.8 Hz, 1H), 7.33-7.28 (m, 1 H), 7.09 (d, J=8.4 Hz, 1 H), 6.32 (dd, J=2.3, 8.4 Hz, 1 H), 6.21 (d, J=2.4 Hz, 1 H), 5.37 (s, 2 H), 3.76 (s, 3 H), 3.63 (s, 3 H). m/z (ESI) 477.0 (M+Na)$^+$.

Step 2, Intermediate T: 4-((2-Chloro-4-(Trifluoromethyl)Phenyl)Amino)-N-(2,4-Dimethoxybenzyl)-3-Nitro-N-(1,2,4-Thiadiazol-5-Yl)Benzenesulfonamide

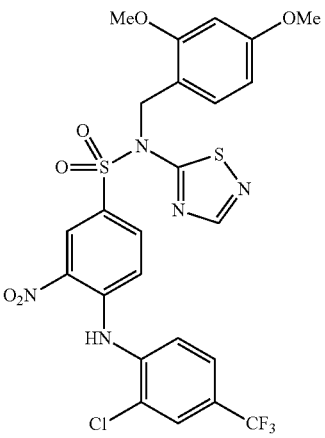

T

A 50-mL round-bottom flask was charged with INTERMEDIATE S (0.645 g, 1.419 mmol), 4-amino-3-chlorobenzotrifluoride (0.235 mL, 1.703 mmol), and THF (7.10 mL) to give a yellow solution. The flask was cooled in an ice-bath for 5 min, then lithium bis(trimethylsilyl)amide (1M in THF) (4.26 mL, 4.26 mmol) was added dropwise over 1 minute to give a dark maroon mixture. The reaction was stirred for 30 minutes at 0° C. The mixture was diluted with saturated aq ammonium chloride solution, then with water, and extracted with EtOAc (3×). The combined organic extracts were dried over sodium sulfate, filtered, and concentrated. The residue was chromatographed on a 40 g silica gel column with 0 to 50% EtOAc/Heptane gradient elution to give 4-((2-chloro-4-(trifluoromethyl)phenyl)amino)-N-(2,4-dimethoxybenzyl)-3-nitro-N-(1,2,4-thiadiazol-5-yl)benzenesulfonamide (0.332 g, 0.527 mmol) (INTERMEDIATE T) as a bright-yellow solid. m/z (ESI) 652.1 (M+Na)$^+$.

Step 3, Intermediate U: 4-((2-Chloro-4-(Trifluoromethyl)Phenyl)Amino)-N-(2,4-Dimethoxybenzyl)-3-Nitro-N-(1,2,4-Thiadiazol-5-Yl)Benzenesulfonamide

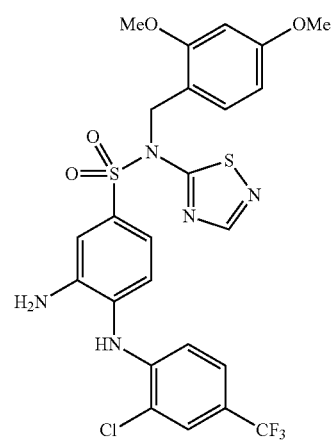

U

A vial was charged with INTERMEDIATE T (0.250 g, 0.397 mmol), iron (0.222 g, 3.97 mmol), THF (0.25 mL), and acetic acid (0.25 mL). The vial was sealed and stirred at 70° C. for one hour. The mixture was diluted with DCM and MeOH, then filtered through a pad of Celite® (diatomaceous earth) and concentrated. The material was purified via silica gel chromatography (40 g, gradient elution 0 to 50% EtOAc: Heptane) to afford 3-amino-4-((2-chloro-4-(trifluoromethyl)phenyl)amino)-N-(2,4-dimethoxybenzyl)-N-(1,2,4-thiadiazol-5-yl)benzenesulfonamide (INTERMEDIATE U) as an off-white solid. m/z (ESI) 621.8 (M+Na)$^+$.

Step 4, Intermediate V: 1-(2-Chloro-4-(Trifluoromethyl)Phenyl)-N-(2,4-Dimethoxybenzyl)-N-(1,2,4-Thiadiazol-5-Yl)-1,2,3,4-Tetrahydroquinoxaline-6-Sulfonamide

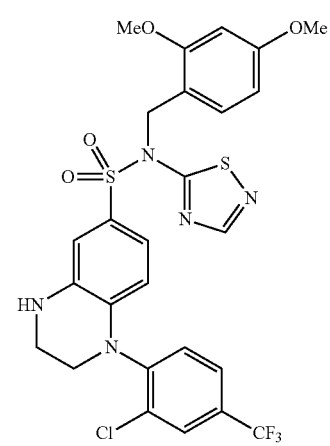

V

3-Amino-4-((2-chloro-4-(trifluoromethyl)phenyl)amino)-N-(2,4-dimethoxybenzyl)-N-(1,2,4-thiadiazol-5-yl)benzenesulfonamide (INTERMEDIATE V, 0.100 g, 0.167 mmol) and cesium carbonate (0.543 g, 1.667 mmol) were dissolved in DMF (1.667 mL) and stirred for 2 minutes. 1,2-Dibromoethane (0.144 mL, 1.667 mmol) was added and the reaction was stirred for 90 minutes at 80° C. The reaction was diluted with ethyl acetate and washed with water. The aqueous layer was extracted with ethyl acetate, and the combined organic layers were dried with sodium sulfate, filtered, and concentrated. The material was purified via silica gel chromatography (12 g, gradient elution 0 to 50% EtOAc: Heptane) to afford 1-(2-chloro-4-(trifluoromethyl)phenyl)-N-(2,4-dimethoxybenzyl)-N-(1,2,4-thiadiazol-5-yl)-1,2,3,4-tetrahydroquinoxaline-6-sulfonamide (INTERMEDIATE V) as a red solid. $^1$H NMR (400 MHz, DMSO-d$_6$) δ=8.31 (s, 1 H), 8.05 (d, J=1.7 Hz, 1 H), 7.84 (dd, J=2.0, 8.7 Hz, 1 H), 7.70 (d, J=8.1 Hz, 1 H), 7.04 (d, J=2.3 Hz, 1 H), 6.90 (dd, J=2.3, 8.6 Hz, 1 H), 6.86 (d, J=8.5 Hz, 1 H), 6.54 (d, J=2.3 Hz, 1 H), 6.47 (s, 1 H), 6.42 (dd, J=2.3, 8.5 Hz, 1 H), 6.04 (d, J=8.6 Hz, 1 H), 4.97 (s, 2 H), 3.78 (s, 3 H), 3.72 (s, 3 H), 3.63 (br. s., 2 H), 3.41 (br. s., 2 H). m/z (ESI) 625.8 (M+H)$^+$.

Intermediates W, X

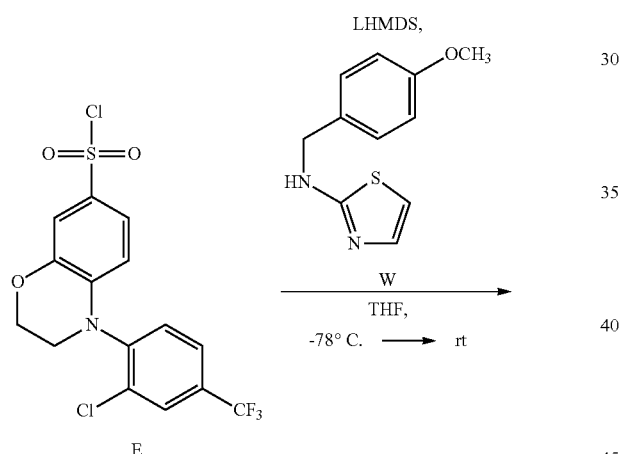

Intermediate W

N-(4-Methoxybenzyl)Thiazol-2-Amine

N-(4-methoxybenzyl)thiazol-2-amine (INTERMEDIATE W) was prepared in a manner analogous to INTERMEDIATE A wherein 1,2,4-thiadiazol-5-amine was replaced with thiazole-2-amine

Intermediate X 4-(2-Chloro-4-(Trifluoromethyl)Phenyl)-N-(4-Methoxybenzyl)-N-(Thiazol-2-Yl)-3,4-Dihydro-2H-Benzo[B][1,4]Oxazine-7-Sulfonamide

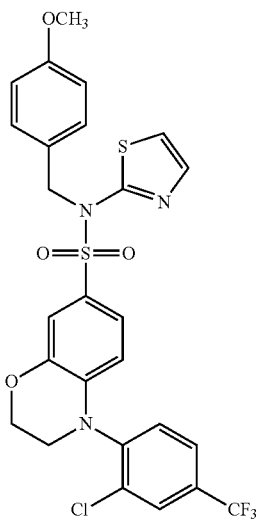

4-(2-chloro-4-(trifluoromethyl)phenyl)-N-(4-methoxybenzyl)-N-(thiazol-2-yl)-3,4-dihydro-2H-benzo[b][1,4]oxazine-7-sulfonamide (INTERMEDIATE X) was prepared in the same manner as INTERMEDIATE D, STEP 3, except employing INTERMEDIATE E and INTERMEDIATE W (N-(4-methoxybenzyl)thiazol-2-amine) m/z (ESI) 595.8 (M+H)$^+$.

Intermediate Y

N-(2,4-Dimethoxybenzyl)-1,3,4-Thiadiazol-2-Amine

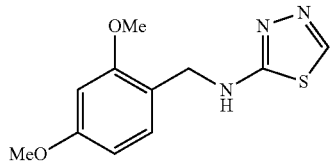

N-(2,4-dimethoxybenzyl)-1,3,4-thiadiazol-2-amine (INTERMEDIATE Y) was prepared in a manner analogous to INTERMEDIATE A wherein 1,2,4-thiadiazol-5-amine was replaced with 1,3,4-thiadiazol-2-amine.

Intermediate Z

N-(1,2,4-Thiadiazol-5-Yl)-3,4-Dihydro-2H-Benzo[B][1,4]Oxazine-7-Sulfonamide

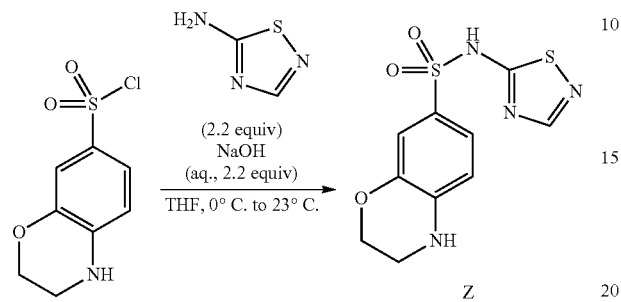

Z

A vial was charged with 3,4-dihydro-2H-benzo[b][1,4]oxazine-7-sulfonyl chloride (from HangZhou Trylead Chemical, Hangzhou, China) (74.42 mg, 0.318 mmol), 1,2,4-thiadiazol-5-amine (70.9 mg, 0.701 mmol), and THF (1991 µL) to give a cloudy solution. The vial was cooled in an ice-bath for 5 min, then sodium hydroxide (6N aq.) (117 µL, 0.701 mmol) was added dropwise. After 45 min, the mixture was allowed to warm to room temperature with the bath. The mixture was diluted with 1N aq. HCl and extracted with EtOAc (3×). The combined organic extracts were dried over sodium sulfate, filtered, and concentrated. The residue was purified by chromatography on silica gel (4% MeOH/DCM). Several mixed fractions at the tail end of the elution were discarded, and the remainder that contained product were combined and concentrated to give N-(1,2,4-thiadiazol-5-yl)-3,4-dihydro-2H-benzo[b][1,4]oxazine-7-sulfonamide (33.19 mg, 0.111 mmol) as a white foam. m/z (ESI) 299.2 (M+H)$^+$.

Intermediate AA

Tert-Butyl 4-(2-(7-((Perfluorophenoxy)Sulfonyl)-2H-Benzo[B][1,4]Oxazin-4(3H)-Yl)-5-(Trifluoromethyl)Phenyl)-5,6-Dihydropyridine-1(2H)-Carboxylate

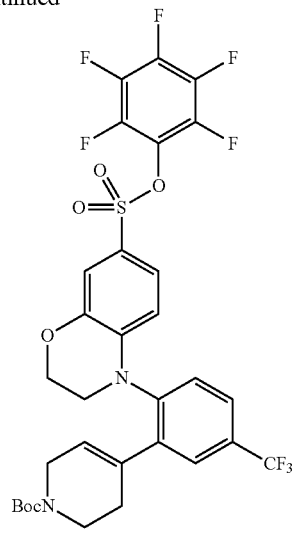

AA

A vial was charged with perfluorophenyl 4-(2-bromo-4-(trifluoromethyl)phenyl)-3,4-dihydro-2H-benzo[b][1,4]oxazine-7-sulfonate (EXAMPLE 46, STEP 1) (134.9 mg, 0.223 mmol), tert-butyl 4-(4,4,5,5-tetramethyl-1,3,2-dioxaborolan-2-yl)-5,6-dihydropyridine-1(2H)-carboxylate (104 mg, 0.335 mmol), Pd(AmPhos)$_2$Cl$_2$ (7.90 mg, 0.011 mmol), potassium phosphate (142 mg, 0.670 mmol), dioxane (1116 µL), and water (372 µL). The vial as sealed and heated in a microwave reactor for 1 h at 100° C. The mixture was extracted with EtOAc (3×). The combined organic extracts were concentrated, and the residue was purified by chomatography on silica gel (12 g, 0 to 40% EtOAc/Heptane) to give tert-butyl 4-(2-(7-((perfluorophenoxy)sulfonyl)-2H-benzo[b][1,4]oxazin-4(3H)-yl)-5-(trifluoromethyl)phenyl)-5,6-dihydropyridine-1(2H)-carboxylate (125.5 mg, 0.178 mmol) as a clear oil. m/z (ESI) 729.4 (M+H)$^+$.

Intermediate AB

Perfluorophenyl 4-(2-Cyano-4-(Trifluoromethyl)Phenyl)-3,4-Dihydro-2H-Benzo[B][1,4]Oxazine-7-Sulfonate

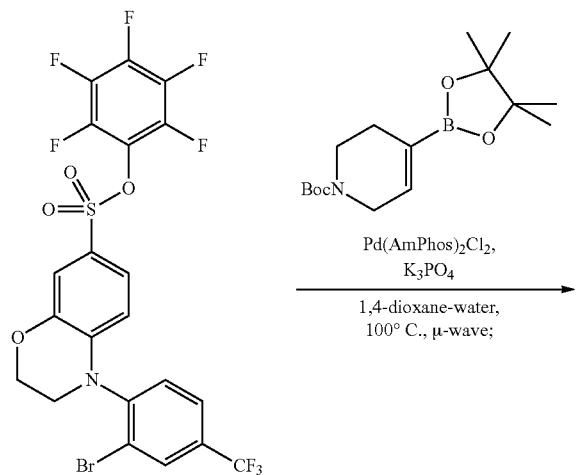

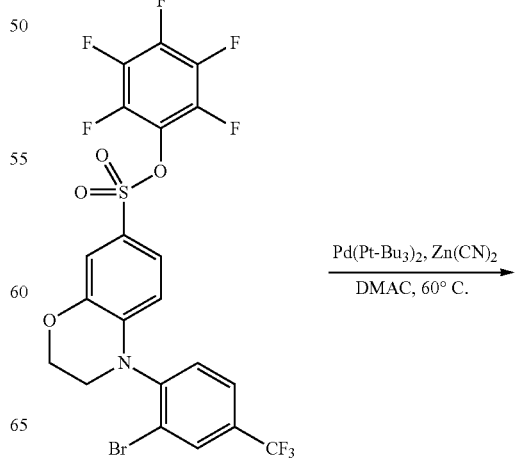

-continued

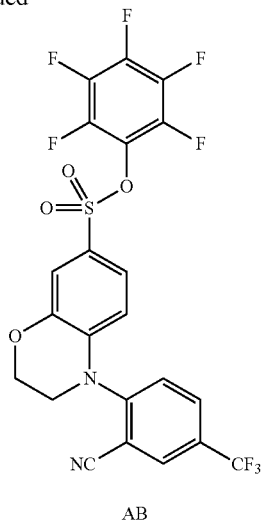

AB

A round bottom flask was charged with perfluorophenyl 4-(2-bromo-4-(trifluoromethyl)phenyl)-3,4-dihydro-2H-benzo[b][1,4]oxazine-7-sulfonate (see EXAMPLE 46, STEP 1) (391 mg, 0.647 mmol), dicyanozinc (380 mg, 3.24 mmol), and palladum (0) bis(tri-tert-butylphosphine) (33.1 mg, 0.065 mmol). The flask was flushed with Ar (g), then DMAC (3235 µL) was added. A reflux condenser was attached, and the flask was lowered into a 60° C. heating bath overnight. The mixture was cooled to room temperature and diluted with water and EtOAc. A small portion of brine was added to break up an emulsion, and the layers were separated. The aq. layer was extracted with EtOAc (2×), and the combined organic extracts were dried over sodium sulfate, filtered, and concentrated. The product was purified by chromatography on silica gel (40 g, 0 to 30% EtOAc/Heptane) to give perfluorophenyl 4-(2-cyano-4-(trifluoromethyl)phenyl)-3,4-dihydro-2H-benzo[b][1,4]oxazine-7-sulfonate (327 mg, 0.594 mmol) as a white solid. $^1$H NMR (400 MHz, DMSO-$d_6$) δ ppm 8.50 (d, J=2.2 Hz, 1 H), 8.26-8.13 (m, 1 H), 7.85 (d, J=8.5 Hz, 1 H), 7.43 (d, J=2.2 Hz, 1 H), 7.33 (dd, J=2.3, 8.8 Hz, 1 H), 6.80 (d, J=8.8 Hz, 1 H), 4.45-4.40 (m, 2 H), 3.94 (t, J=4.2 Hz, 2 H). m/z (ESI) 573.2 (M+H)$^+$.

Example 1 (INTERMEDIATE D)

4-(2-Bromo-4-(Trifluoromethyl)Phenyl)-N-(1,2,4-Thiadiazol-5-Yl)-3,4-Dihydro-2H-Benzo[B][1,4] Oxazine-7-Sulfonamide Intermediate D

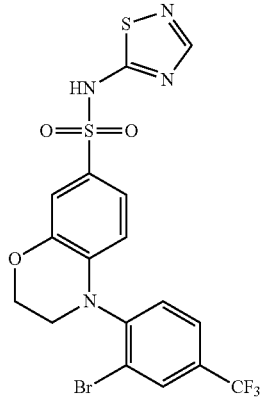

Example 1

EXAMPLE 1 was synthesized as described for INTERMEDIATE D. $^1$H NMR (400 MHz, DMSO-$d_6$) δ ppm 3.43-3.52 (m, 2 H) 4.31-4.42 (m, 2 H) 6.25 (d, J=8.51 Hz, 1 H) 7.12-7.16 (m, 1 H) 7.17 (d, J=2.15 Hz, 1 H) 7.74 (d, J=7.73 Hz, 1 H) 7.90 (dd, J=8.26, 1.61 Hz, 1 H) 8.20 (d, J=1.86 Hz, 1 H) 8.42 (s, 1 H). m/z (ESI) 520.9 (M+H)$^+$.

Example 2

4-(2-Chloro-4-(Trifluoromethyl)Phenyl)-N-(1,2,4-Thiadiazol-5-Yl)-3,4-Dihydro-2H-Benzo[B][1,4] Oxazine-7-Sulfonamide

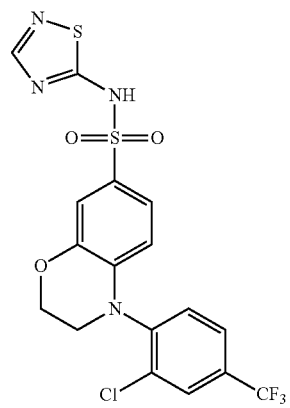 [SMILES: O=S(=O)(Nc1ncns1)c1ccc2c(c1)OCCN2c1ccc(C(F)(F)F)cc1Cl]

A round bottom flask was charged with N-(2,4-dimethoxybenzyl)-1,2,4-thiadiazol-5-amine (0.566 g, 2.253 mmol) and THF (9.01 mL), and the flask was cooled to −78° C. LiHMDS (1.0 M in THF) (2.253 mL, 2.253 mmol) was then added, dropwise, over 1 minute. The solution was stirred for 5 minutes, and a solution of Intermediate E (0.743 g, 1.802 mmol) in THF (1.060 mL, 1.802 mmol) was added dropwise over 1 minute. The bath was removed, and the resulting mixture was stirred for 30 minutes. The reaction was diluted with sat. aq. NH$_4$Cl (30 mL), and was washed with ethyl acetate (3×20 mL). The organic layers were combined, dried over magnesium sulfate, filtered and concentrated to yield 1.14 g of a light orange oily solid. The material was passed through a 10 g SCX column to provide 4-(2-chloro-4-(trifluoromethyl) phenyl)-N-(2,4-dimethoxybenzyl)-N-(1,2,4-thiadiazol-5-yl)-3,4-dihydro-2H-benzo[b][1,4]oxazine-7-sulfonamide with minimal impurities. This material was further purified via silica gel MPLC, eluting with 0 to 100% ethyl acetate in heptanes to provide clean 4-(2-chloro-4-(trifluoromethyl) phenyl)-N-(2,4-dimethoxybenzyl)-N-(1,2,4-thiadiazol-5-yl)-3,4-dihydro-2H-benzo[b][1,4]oxazine-7-sulfonamide, which was taken up in dichloromethane (7.30 mL) and treated with trifluoroacetic acid (5.63 mL, 73.0 mmol). After 5 minutes, the reaction mixture was concentrated under a vacuum. Upon dissolving the material in DMSO for reverse-phase preparative HPLC purification, insoluble solids were filtered off, and the filtrate was purified by reverse-phase preparative HPLC using 0.1% TFA in CH$_3$CN/H$_2$O, gradient 25% to 90% over 22 min to provide 4-(2-chloro-4-(trifluoromethyl)phenyl)-N-(1,2,4-thiadiazol-5-yl)-3,4-dihydro-2H-benzo[b][1,4]oxazine-7-sulfonamide as a white solid. $^1$H NMR (400 MHz, DMSO-$d_6$) δ ppm 3.74 (br. t, J=1.00, 1.00 Hz, 2 H) 4.36 (br. t, J=1.00, 1.00 Hz, 2 H) 6.32 (d, J=8.51 Hz, 1 H) 7.15 (dd, J=1.00 Hz, 1H) 7.18 (d, J=2.05 Hz, 1 H) 7.75 (d, J=8.31 Hz, 1 H) 7.82-7.87 (m, 1 H) 8.07 (d, J=1.66 Hz, 1 H) 8.44 (s, 1 H). m/z (ESI) 477.0 (M+H)$^+$.

Example 3

4-(2-(1-Methyl-1H-Pyrazol-5-Yl)-4-(Trifluoromethyl)Phenyl)-N-(1,2,4-Thiadiazol-5-Yl)-3,4-Dihydro-2H-Benzo[B][1,4]Oxazine-7-Sulfonamide

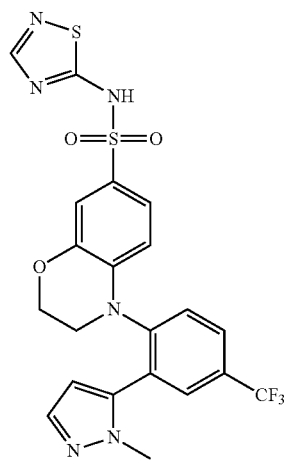 [SMILES: Cn1nccc1-c1cc(C(F)(F)F)ccc1N1CCOc2cc(S(=O)(=O)Nc3ncns3)ccc21]

A microwave vial was charged with INTERMEDIATE D (0.100 g, 0.192 mmol), 1-methyl-5-(4,4,5,5-tetramethyl-1,3,2-dioxaborolan-2-yl)-1H-pyrazole (Sigma Aldrich, St. Louis, Mo., 0.060 g, 0.288 mmol), tetrakis(triphenylphosphine)palladium(0) (0.022 g, 0.019 mmol), and $K_2CO_3$ (0.133 g, 0.959 mmol). The solids were diluted with dioxane (1.279 mL) and water (0.639 mL), and the reaction was heated under microwave irradiation at 100° C. for 60 minutes (starting material remained, but the reaction was moved forward). The reaction mixture was diluted with water, and washed with DCM. Equal partitioning between both layers was observed, so the organic and aqueous layers were combined and concentrated. The material was taken up in methanol, and acidified with HCl (1N) (3.84 mL, 3.84 mmol), and then re-concentrated under a vacuum. The solids were taken up in DCM, and washed with water. The organic layer was then dried using a phase separator, concentrated under a vacuum and purified by reverse-phase preparative HPLC (Column: Phenomenex 150×30 mm, 5 micron, $C_{18}$ column; 0.1% TFA in $CH_3CN/H_2O$, gradient 25% to 90% over 20 min (Phenomenex, Torrance, Calif.)) to provide 4-(2-(1-methyl-1H-pyrazol-5-yl)-4-(trifluoromethyl)phenyl)-N-(1,2,4-thiadiazol-5-yl)-3,4-dihydro-2H-benzo[b][1,4]oxazine-7-sulfonamide (0.018 g, 0.034 mmol) as a white solid. $^1$H NMR (400 MHz, DMSO-$d_6$) δ ppm 3.66 (s, 3 H) 4.14 (br. s., 2 H) 6.31 (d, J=1.66 Hz, 1 H) 6.68 (d, J=8.51 Hz, 1 H) 7.07-7.16 (m, 2H) 7.42 (d, J=1.76 Hz, 1 H) 7.72 (d, J=8.41 Hz, 1 H) 7.86 (s, 1 H) 7.90 (d, J=8.61 Hz, 1 H) 8.44 (s, 1 H). m/z (ESI) 523.0 (M+H)$^+$.

Example 4

4-(2-(1H-Pyrazol-4-Yl)-4-(Trifluoromethyl)Phenyl)-N-(1,2,4-Thiadiazol-5-Yl)-3,4-Dihydro-2H-Benzo[B][1,4]Oxazine-7-Sulfonamide

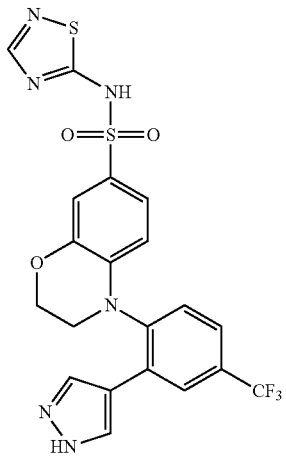 [SMILES: O=S(=O)(Nc1ncns1)c1ccc2c(c1)OCCN2c1ccc(C(F)(F)F)cc1-c1cn[nH]c1]

A microwave vial was charged with INTERMEDIATE D (0.100 g, 0.192 mmol), tert-butyl 4-(4,4,5,5-tetramethyl-1,3,2-dioxaborolan-2-yl)-1H-pyrazole-1-carboxylate (Sigma-Aldrich, St. Louis, Mo., 0.113 g, 0.384 mmol), tetrakis(triphenylphosphine)palladium(0) (0.022 g, 0.019 mmol), and $K_2CO_3$ (0.133 g, 0.959 mmol). The solids were diluted with dioxane (1.279 mL) and water (0.639 mL), and the reaction was heated under microwave irradiation at 100° C. for 30 minutes. The reaction mixture was lyophilized overnight and the material was then taken up in methanol, and acidified with HCl (1N) (3.84 mL, 3.84 mmol). The mixture was concentrated onto silica gel, and purified via silica gwel MPLC (Biotage Isolera One; PuriFlash HP, 15µ, 25 g), eluting with 0 to 100% ethyl acetate in heptane to yield slightly impure material. The material was loaded onto a 500 mg SCX column and the product was eluted (with impurity) in the ammonia wash. The resulting material was then purified by reverse-phase preparative HPLC (Column: Phenomenex 150×30 mm, 5 micron, C18 column; 0.1% TFA in $CH_3CN/H_2O$, gradient 25% to 90% over 20 min) to provide 4-(2-(1H-pyrazol-4-yl)-4-(trifluoromethyl)phenyl)-N-(1,2,4-thiadiazol-5-yl)-3,4-dihydro-2H-benzo[b][1,4]oxazine-7-sulfonamide (0.022 g, 0.043 mmol) as a white solid. $^1$H NMR (400 MHz, DMSO-$d_6$) δ ppm 3.47 (m, J=12.80 Hz, 2H) 4.28-4.37 (m, 2H) 6.25 (d, J=8.51 Hz, 1 H) 7.08 (dd, J=8.56, 2.20 Hz, 1 H) 7.14 (d, J=2.15 Hz, 1 H) 7.59-7.64 (m, 1 H) 7.65-7.70 (m, 1 H) 7.96 (s, 2 H) 8.02 (d, J=1.37 Hz, 1 H) 8.43 (s, 1 H). m/z (ESI) 509.0 (M+H)$^+$.

Example 5

4-(2-Chloro-4-(Trifluoromethyl)Phenyl)-N-(Thiazol-2-Yl)-3,4-Dihydro-2H-Benzo[B][1,4]Oxazine-7-Sulfonamide

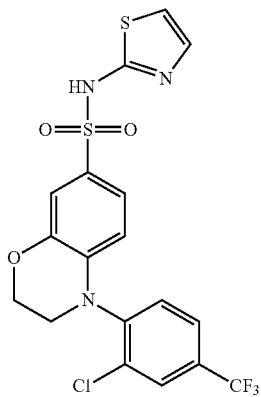 [SMILES: O=S(=O)(Nc1nccs1)c1ccc2c(c1)OCCN2c1ccc(C(F)(F)F)cc1Cl]

4-(2-Chloro-4-(trifluoromethyl)phenyl)-N-(thiazol-2-yl)-3,4-dihydro-2H-benzo[b][1,4]oxazine-7-sulfonamide (EXAMPLE 5) was prepared in the same manner as INTERMEDIATE D, step 3, starting from 4-(2-chloro-4-(trifluoromethyl)phenyl)-3,4-dihydro-2H-benzo[b][1,4]oxazine-7-sulfonyl chloride and using thiazol-2-amine instead of intermediate A. $^1$H NMR (400 MHz, DMSO-d$_6$) δ ppm 3.73 (br. s., 2 H) 4.36 (t, J=4.45 Hz, 2 H) 6.32 (d, J=8.41 Hz, 1 H) 6.79 (d, J=4.50 Hz, 1 H) 7.14 (dd, J=8.61, 2.15 Hz, 1 H) 7.17-7.26 (m, 2 H) 7.73 (d, J=8.31 Hz, 1 H) 7.81-7.88 (m, 1 H) 8.06 (s, 1 H) 12.58 (br. s., 1 H).

Example 6

Tert-Butyl 4-(2-(7-(N-(1,2,4-Thiadiazol-5-Yl)Sulfamoyl)-2H-Benzo[B][1,4]Oxazin-4(3H)-Yl)-5-(Trifluoromethyl)Phenyl)-5,6-Dihydropyridine-1(2H)-Carboxylate

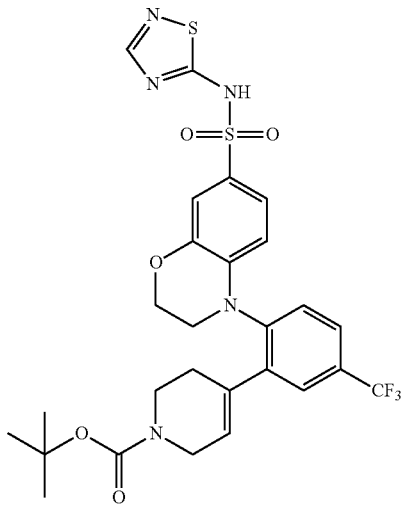 [SMILES: CC(C)(C)OC(=O)N1CC=C(c2cc(C(F)(F)F)ccc2N2CCOc3cc(S(=O)(=O)Nc4ncns4)ccc32)CC1]

A microwave vial was charged with INTERMEDIATE D (0.100 g, 0.192 mmol), (N-tert-butoxycarbonyl)-1,2,3,6-tetrahydropyridine-4-boronic acid pinacol ester (Maybridge Chemicals, Cornwall, UK, 0.059 mL, 0.192 mmol), tetrakis(triphenylphosphine)palladium(0) (0.022 g, 0.019 mmol), and K$_2$CO$_3$ (0.133 g, 0.959 mmol). The solids were diluted with dioxane (1.279 mL) and water (0.639 mL), and the reaction was heated under microwave irradiation at 100° C. for 10 minutes (starting material remained, but moved forward). The reaction mixture was diluted with water, and washed with DCM. Equal partitioning between both layers was observed (and an emulsion formed), so the organic and aqueous were combined and concentrated until just the water remained. The aqueous was washed with DCM (×3) and the organics were then combined and dried using a phase separator. After concentration, the material was purified by reverse-phase preparative HPLC (Column: Phenomenex 150×30 mm, 5 micron, C$_{18}$ column; 0.1% TFA in CH$_3$CN/H$_2$O, gradient 25% to 90% over 20 min) to provide tert-butyl 4-(2-(7-(N-(1,2,4-thiadiazol-5-yl)sulfamoyl)-2H-benzo[b][1,4]oxazin-4(3 H)-yl)-5-(trifluoromethyl)phenyl)-5,6-dihydropyridine-1(2 H)-carboxylate (0.035 g, 0.056 mmol) as a light-yellow solid. $^1$H NMR (400 MHz, DMSO-d$_6$) δ ppm 1.37 (s, 9 H) 2.16-2.37 (m, 2 H) 3.51-3.72 (m, 4 H) 3.81-3.90 (m, 2 H) 4.22-4.34 (m, 2 H) 5.84 (br. s., 1 H) 6.38-6.46 (m, 1 H) 7.10-7.17 (m, 2 H) 7.56 (d, J=8.31 Hz, 1 H) 7.65 (d, J=2.05 Hz, 1 H) 7.72 (dd, J=8.41, 2.15 Hz, 1 H) 8.42 (s, 1 H). m/z (ESI) 524.0 (Boc group falls off in LCMS).

Example 7

4-(2-(1,2,3,6-Tetrahydropyridin-4-Yl)-4-(Trifluoromethyl)Phenyl)-N-(1,2,4-Thiadiazol-5-Yl)-3,4-Dihydro-2H-Benzo[B][1,4]Oxazine-7-Sulfonamide

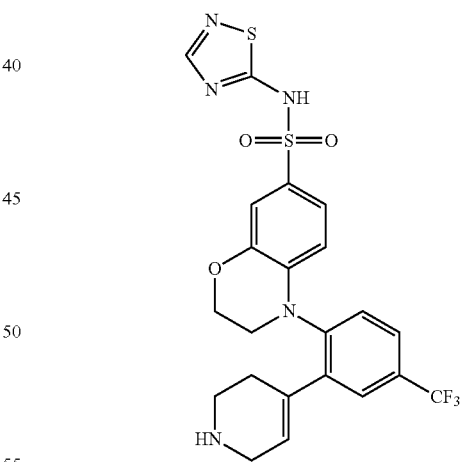

Tert-butyl 4-(2-(7-(N-(1,2,4-thiadiazol-5-yl)sulfamoyl)-2H-benzo[b][1,4]oxazin-4(3H)-yl)-5-(trifluoromethyl)phenyl)-5,6-dihydropyridine-1(2H)-carboxylate (EXAMPLE 5, 30 mg) was diluted with 0.5 mL of DCM and TFA (0.5 mL) was added. After 5 minutes, complete conversion to the desired deprotected product was observed. The material was concentrated under a vacuum and purified via reverse-phase HPLC (Column: Phenomenex 150×30 mm, 5 micron, C$_{18}$ column; 0.1% TFA in CH$_3$CN/H$_2$O, gradient 25% to 90% over 20 min) to yield 4-(2-(1,2,3,6-tetrahydropyridin-4-yl)-4-(trifluoromethyl)phenyl)-N-(1,2,4-thiadiazol-5-yl)-3,4-dihydro-2H-benzo[b][1,4]oxazine-7-sulfonamide as a light yellow solid. ¹H NMR (400 MHz, DMSO-d₆) δ ppm 2.39 (m, J=17.50 Hz, 2 H) 3.19 (m, J=12.90 Hz, 2 H) 3.59 (m, J=3.80 Hz, 2 H) 3.65-3.71 (m, 2 H) 4.30 (m, J=4.90 Hz, 2 H) 5.88 (s, 1 H) 6.48 (d, J=8.41 Hz, 1 H) 7.11-7.19 (m, 2 H) 7.59 (d, J=8.12 Hz, 1 H) 7.63 (d, J=2.05 Hz, 1 H) 7.76 (dd, J=8.41, 1.66 Hz, 1 H) 8.39 (s, 1 H) 8.77 (br. s., 2 H). m/z (ESI) 524.0 (M+H)⁺.

Example 8

N-(3-(Aminomethyl)-1,2,4-Thiadiazol-5-Yl)-4-(2-Chloro-4-(Trifluoromethyl)Phenyl)-3,4-Dihydro-2H-Benzo[B][1,4]Oxazine-7-Sulfonamide 2,2,2-Trifluoroacetate

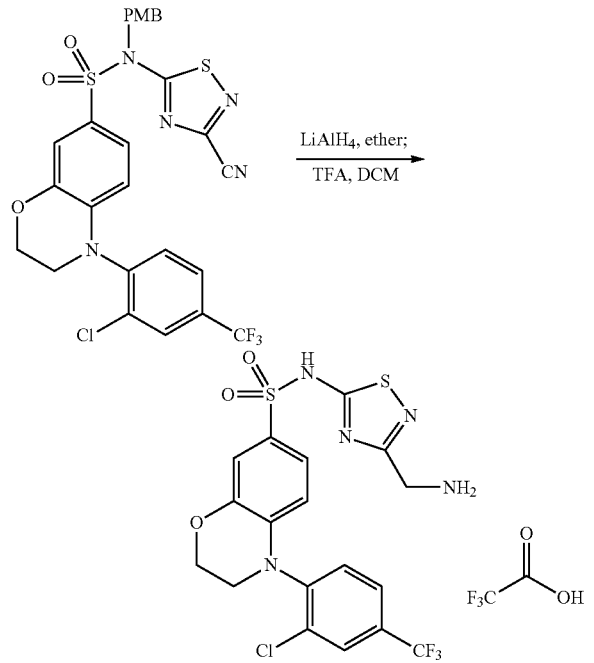

A flask was charged with 4-(2-chloro-4-(trifluoromethyl)phenyl)-N-(3-cyano-1,2,4-thiadiazol-5-yl)-N-(4-methoxybenzyl)-3,4-dihydro-2H-benzo[b][1,4]oxazine-7-sulfonamide (94 mg, 0.151 mmol) and ether (2 mL) to give a clear solution. The flask was lowered into an ice-bath for 10 min, then lithium aluminum hydride (2M in THF) (151 μL, 0.302 mmol) was added dropwise. The mixture was stirred for 20 min before being carefully quenched by the addition of sodium sulfate decahydrate (60 mg). The mixture was stirred for 5 minutes, then the cooling bath was removed. When it had achieved room temperature, 2-methyltetrahydrofuran (2 mL) was added. The mixture was stirred for 10 min, then filtered through Celite® (diatomaceous earth) with the aid of EtOAc. The filtrate was concentrated, and the residue dissolved in DCM (1 mL) and TFA (0.5 mL). The resulting mixture was stirred overnight. In the morning, the mixture was concentrated, and the residue was taken up in ether. The resulting suspension was sonicated, then filtered. The collected solid was washed with ether (2×), then dried under vacuum. The solid was re-suspended with DCM, and the resulting suspension was sonciated, then filtered. The collected solid was dried under vacuum to give N-(3-(aminomethyl)-1,2,4-thiadiazol-5-yl)-4-(2-chloro-4-(trifluoromethyl)phenyl)-3,4-dihydro-2H-benzo[b][1,4]oxazine-7-sulfonamide 2,2,2-trifluoroacetate (29.8 mg, 0.048 mmol) as an orange solid. ¹H NMR (400 MHz, DMSO-d₆) δ=8.27 (br. s., 3 H), 8.05 (s, 1 H), 7.89-7.78 (m, 1 H), 7.70 (d, J=8.1 Hz, 1 H), 7.16 (d, J=2.2 Hz, 1 H), 7.10 (dd, J=2.1, 8.6 Hz, 1 H), 6.28 (d, J=8.5 Hz, 1 H), 4.33 (t, J=4.1 Hz, 2 H), 3.97 (d, J=2.6 Hz, 2 H), 3.71 (br. s., 2 H). m/z (ESI) 506.1 (M+H)⁺.

Example 9

4-(2-Chloro-4-(Trifluoromethyl)Phenyl)-N-(6-Chloropyrimidin-4-Yl)-3,4-Dihydro-2H-Benzo[B][1,4]Oxazine-7-Sulfonamide

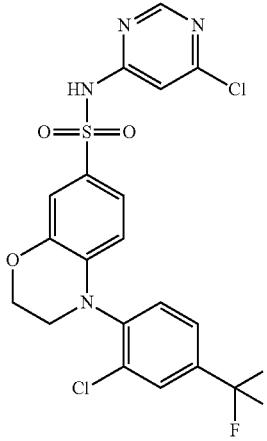

EXAMPLE 9 was prepared in the same manner as EXAMPLE 5 using 6-chloropyrimidin-4-amine (Sigma-Aldrich, St. Louis, Mo.) instead of thiazol-2-amine 1H NMR (500 MHz, DMSO-d₆) δ ppm—3.67 (br. s., 1 H), 3.74 (br. s., 2H), 4.28 (d, J=4.70 Hz, 1 H), 4.37 (br. s., 1 H), 6.32 (d, J=8.71 Hz, 1 H), 7.02 (s, 1H), 7.29-7.37 (m, 2 H), 7.76 (d, J=8.36 Hz, 1 H), 7.80-7.87 (m, 1 H), 8.07 (s, 1H), 8.59 (s, 1 H).

Example 10

4-(2-Chloro-4-(Trifluoromethyl)Phenyl)-N-(3-Methyl-1,2,4-Thiadiazol-5-Yl)-3,4-Dihydro-2H-Benzo[B][1,4]Oxazine-7-Sulfonamide

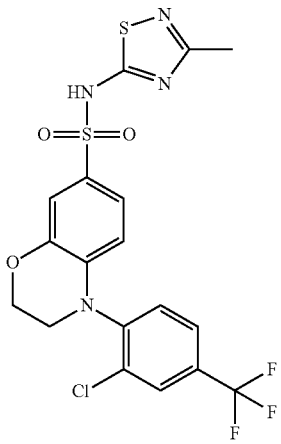 [SMILES: Cc1nsc(NS(=O)(=O)c2ccc3c(c2)OCCN3c2ccc(C(F)(F)F)cc2Cl)n1]

EXAMPLE 10 was prepared in the same manner as EXAMPLE 5 using 3-methyl-1,2,4-thiadiazol-5-amine (Maybridge Chemicals, Cornwall, UK) instead of thiazol-2-amine $^1$H NMR (500 MHz, DMSO-$d_6$) δ ppm 2.27 (s, 3 H) 3.59 (br. s., 1 H) 3.73 (br. s., 2 H) 4.36 (br. s., 2 H) 6.31 (d, J=8.48 Hz, 1 H) 7.12-7.18 (m, 2 H) 7.74 (d, J=8.36 Hz, 1 H) 7.84 (dd, J=8.31, 1.66 Hz, 1 H) 8.04-8.08 (m, 1 H).

Example 11

4-(2-Chloro-4-(Trifluoromethyl)Phenyl)-N-(Thiazol-4-Yl)-3,4-Dihydro-2H-Benzo[B][1,4]Oxazine-7-Sulfonamide

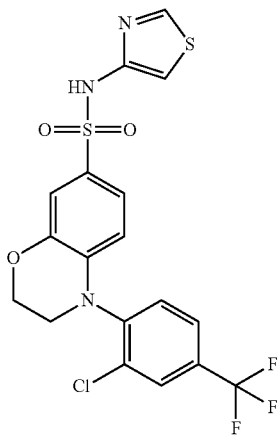 [SMILES: O=S(=O)(Nc1cscn1)c1ccc2c(c1)OCCN2c1ccc(C(F)(F)F)cc1Cl]

EXAMPLE 11 was prepared in the same manner as EXAMPLE 5 using thiazol-4-amine (J&W Pharmlab, LLC, Levittown, Pa.) instead of thiazol-2-amine $^1$H NMR (500 MHz, DMSO-$d_6$) δ ppm—3.73 (br. s., 2 H) 4.35 (br. s., 2 H) 6.28 (d, J=8.59 Hz, 1 H) 6.96 (d, J=2.06 Hz, 1 H) 7.13-7.19 (m, 1 H) 7.25 (d, J=2.18 Hz, 1 H) 7.73 (d, J=8.13 Hz, 1 H) 7.79-7.89 (m, 1 H) 8.05 (d, J=1.60 Hz, 1 H) 8.87 (d, J=2.18 Hz, 1 H) 10.86 (s, 1 H).

Example 12

4-(2-Chloro-4-(Trifluoromethyl)Phenyl)-N-(5-Methylthiazol-2-Yl)-3,4-Dihydro-2H-Benzo[B][1,4]Oxazine-7-Sulfonamide

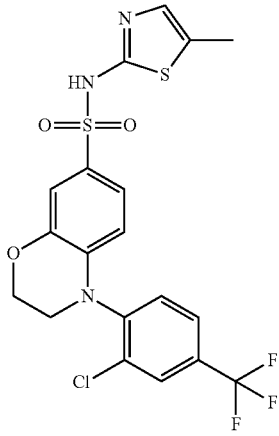 [SMILES: Cc1cnc(NS(=O)(=O)c2ccc3c(c2)OCCN3c2ccc(C(F)(F)F)cc2Cl)s1]

EXAMPLE 12 was prepared in the same manner as EXAMPLE 5 using 5-methylthiazol-2-amine (Sigma-Aldrich, St. Louis, Mo.) instead of thiazol-2-amine $^1$H NMR (500 MHz, DMSO-d6) δ ppm 2.16 (d, J=1.37 Hz, 3H) 3.58 (br. s., 2 H) 3.61-3.81 (m, 2 H) 4.34 (t, J=4.12 Hz, 1 H) 6.24-6.32 (m, 1 H) 6.93-6.97 (m, 1 H) 7.10-7.19 (m, 1 H) 7.70-7.78 (m, 1 H) 8.04 (s, 1H) 8.05 (s, 1H).

Example 13

4-(2-Chloro-4-(Trifluoromethyl)Phenyl)-N-(Isoxazol-3-Yl)-3,4-Dihydro-2H-Benzo[B][1,4]Oxazine-7-Sulfonamide

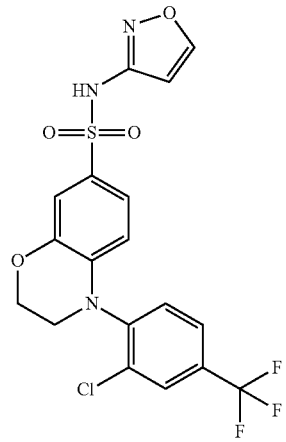 [SMILES: O=S(=O)(Nc1ccon1)c1ccc2c(c1)OCCN2c1ccc(C(F)(F)F)cc1Cl]

EXAMPLE 13 was prepared in the same manner as EXAMPLE 5 using isoxazol-3-amine (Sigma-Aldrich, St. Louis, Mo.) instead of thiazol-2-amine $^1$H NMR (500 MHz, DMSO-$d_6$) δ ppm 3.74 (br. s., 2 H) 4.36 (br. s., 2 H) 6.31 (d, J=8.59 Hz, 1 H) 6.41 (d, J=1.72 Hz, 1 H) 7.19 (dd, J=8.59, 2.18 Hz, 1 H) 7.26 (d, J=2.18 Hz, 1 H) 7.76 (d, J=8.25 Hz, 1 H) 7.80-7.92 (m, 1 H) 8.04-8.11 (m, 1 H) 8.70 (d, J=1.72 Hz, 1 H) 11.30 (s, 1 H).

Example 14

4-(2-Chloro-4-(Trifluoromethyl)Phenyl)-N-(1-(2-(Dimethylamino)Ethyl)-1H-Pyrazol-3-Yl)-3,4-Dihydro-2H-Benzo[B][1,4]Oxazine-7-Sulfonamide 2,2,2-Trifluoroacetate

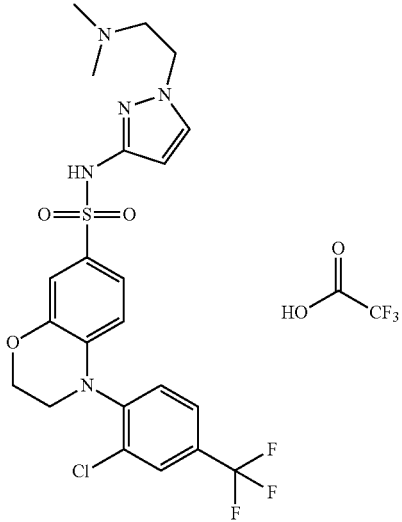 [SMILES: CN(C)CCn1ccc(NS(=O)(=O)c2ccc3c(c2)OCCN3c2ccc(C(F)(F)F)cc2Cl)n1 ; O=C(O)C(F)(F)F]

EXAMPLE 14 was prepared in the same manner as EXAMPLE 5 using 1-(2-(dimethylamino)ethyl)-1H-pyrazol-3-amine (Ryan Scientific, Inc., Mt. Pleasant, S.C.) instead of thiazol-2-amine. $^1$H NMR (500 MHz, DMSO-d$_6$) δ ppm 2.70 (s, 4 H) 3.63 (br. s., 9 H) 3.72 (br. s., 2 H) 4.35 (t, J=6.19 Hz, 3 H) 5.97 (d, J=2.29 Hz, 1 H) 6.29 (d, J=8.59 Hz, 1 H) 7.12 (dd, J=8.53, 2.12 Hz, 1 H) 7.20 (d, J=2.18 Hz, 1 H) 7.64 (d, J=2.29 Hz, 1 H) 7.73 (d, J=8.25 Hz, 1 H) 7.83-7.89 (m, 1 H) 8.05-8.08 (m, 1 H) 9.87 (br. s., 1 H) 10.36 (s, 1 H).

Example 15

4-(2-Chloro-4-(Trifluoromethyl)Phenyl)-N-(1-Methyl-1H-Pyrazol-3-Yl)-3,4-Dihydro-2H-Benzo[B][1,4]Oxazine-7-Sulfonamide

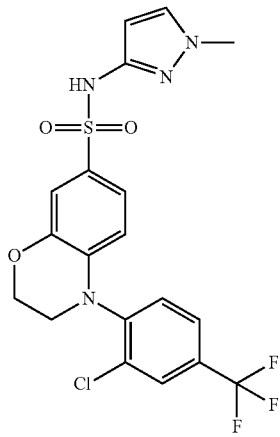 [SMILES: Cn1ccc(NS(=O)(=O)c2ccc3c(c2)OCCN3c2ccc(C(F)(F)F)cc2Cl)n1]

EXAMPLE 15 was prepared in the same manner as EXAMPLE 5 using 1-methyl-1H-pyrazol-3-amine instead of thiazol-2-amine $^1$H NMR (500 MHz, DMSO-d$_6$) δ ppm 3.68 (br. s., 2 H) 3.64 (s, 6 H) 3.78 (br. s., 1 H) 4.35 (br. s., 1 H) 5.89 (d, J=2.18 Hz, 1 H) 6.29 (d, J=8.59 Hz, 1 H) 7.11 (dd, J=8.53, 2.12 Hz, 1 H) 7.20 (d, J=2.06 Hz, 1 H) 7.46 (d, J=2.18 Hz, 1 H) 7.73 (d, J=8.36 Hz, 1 H) 7.80-7.86 (m, 1 H) 8.03-8.07 (m, 1 H) 10.22 (s, 1 H).

Example 16

4-(2-Chloro-4-(Trifluoromethyl)Phenyl)-N-(Pyrimidin-2-Yl)-3,4-Dihydro-2H-Benzo[B][1,4]Oxazine-7-Sulfonamide

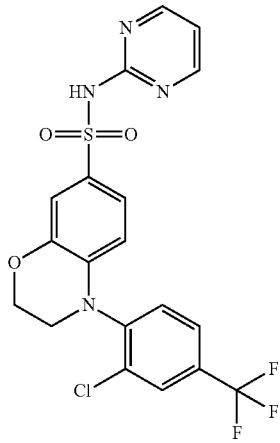 [SMILES: O=S(=O)(Nc1ncccn1)c1ccc2c(c1)OCCN2c1ccc(C(F)(F)F)cc1Cl]

EXAMPLE 16 was prepared in the same manner as EXAMPLE 5 using pyrimidin-2-amine instead of thiazol-2-amine $^1$H NMR (500 MHz, DMSO-d$_6$) δ ppm—3.67 (d, J=4.01 Hz, 1 H) 3.73 (br. s., 1 H) 4.35 (br. s., 2 H) 6.31 (d, J=8.59 Hz, 1 H) 7.04 (t, J=4.87 Hz, 1 H) 7.32 (dd, J=8.59, 2.18 Hz, 1 H) 7.40 (d, J=2.06 Hz, 1 H) 7.74 (d, J=8.25 Hz, 1 H) 7.84 (dd, J=8.42, 1.78 Hz, 1 H) 8.06 (d, J=1.60 Hz, 1 H) 8.51 (d, J=4.93 Hz, 2 H) 11.44 (br. s., 1 H).

Example 17

4-(2-Chloro-4-(Trifluoromethyl)Phenyl)-N-(5-Fluoropyridin-2-Yl)-3,4-Dihydro-2H-Benzo[B][1,4]Oxazine-7-Sulfonamide

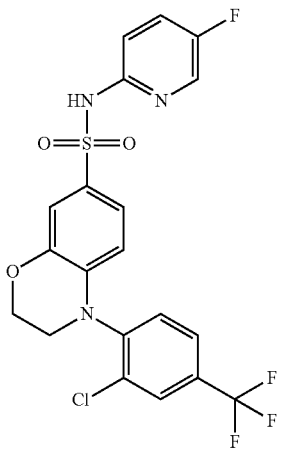 [SMILES: O=S(=O)(Nc1ccc(F)cn1)c1ccc2c(c1)OCCN2c1ccc(C(F)(F)F)cc1Cl]

EXAMPLE 17 was prepared in the same manner as EXAMPLE 5 using 5-fluoropyridin-2-amine (Sigma-Aldrich, St. Louis, Mo.) instead of thiazol-2-amine $^1$H NMR (500 MHz, DMSO-d$_6$) δ ppm 3.94 (d, J=5.38 Hz, 1 H) 4.35 (br. s., 1 H) 6.29 (d, J=8.59 Hz, 1 H) 7.13 (dd, J=9.05, 3.78 Hz, 1 H) 7.19-7.28 (m, 1 H) 7.30 (d, J=2.18 Hz, 1 H) 7.64 (td, J=8.65, 3.09 Hz, 1 H) 7.73 (d, J=8.25 Hz, 1 H) 7.83 (dd, J=8.48, 1.72 Hz, 1 H) 8.03-8.06 (m, 1 H) 8.19 (d, J=3.09 Hz, 1 H) 10.83 (d, J=15.92 Hz, 1 H).

Example 18

1-(2-Chloro-4-(Trifluoromethyl)Phenyl)-N-(1,2,4-Thiadiazol-5-Yl)-1,2,3,4-Tetrahydroquinoxaline-6-Sulfonamide

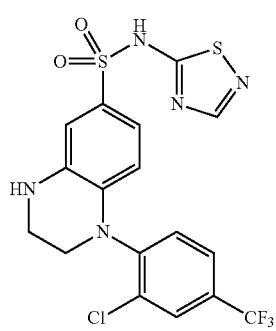 [SMILES: O=S(=O)(Nc1ncns1)c1ccc2c(c1)NCCN2c1ccc(C(F)(F)F)cc1Cl]

1-(2-Chloro-4-(trifluoromethyl)phenyl)-N-(2,4-dimethoxybenzyl)-N-(1,2,4-thiadiazol-5-yl)-1,2,3,4-tetrahydroquinoxaline-6-sulfonamide (INTERMEDIATE V, 0.068 g, 0.108 mmol) was dissolved in 1 mL of DCM and TFA (0.1 mL, 1.298 mmol) was added. The reaction was stirred for 10 minutes. The material was concentrated, dissolved in acetonitrile and loaded onto an ion exchange column (pre-wetted with acetonitrile). The column was flushed several times with acetonitrile, then the product was liberated by flushing the column several times with about 1M HCl solution in MeOH/EtOAc (made by adding acetyl chloride to a MeOH/EtOAc mixture). The second filtrate was concentrated to afford 1-(2-chloro-4-(trifluoromethyl)phenyl)-N-(1,2,4-thiadiazol-5-yl)-1,2,3,4-tetrahydroquinoxaline-6-sulfonamide as a purple solid. $^1$H NMR (400 MHz, DMSO-$d_6$) δ=8.42 (s, 1 H), 7.99 (s, 1 H), 7.80 (d, J=8.1 Hz, 1 H), 7.63 (d, J=8.0 Hz, 1 H), 7.01 (d, J=2.1 Hz, 1 H), 6.80 (dd, J=1.9, 8.3 Hz, 1 H), 6.08 (d, J=8.4 Hz, 1 H), 3.61 (t, J=4.0 Hz, 2 H), 3.40 (t, J=4.4 Hz, 2 H). m/z (ESI) 475.8 (M+H)$^+$.

Example 19

1-(2-Chloro-4-(Trifluoromethyl)Phenyl)-4-Methyl-N-(1,2,4-Thiadiazol-5-Yl)-1,2,3,4-Tetrahydroquinoxaline-6-Sulfonamide

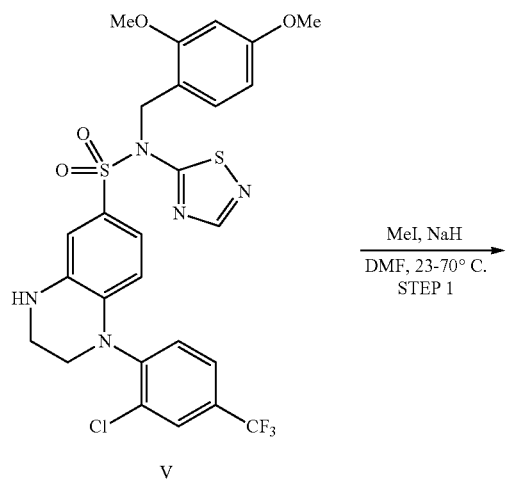

V

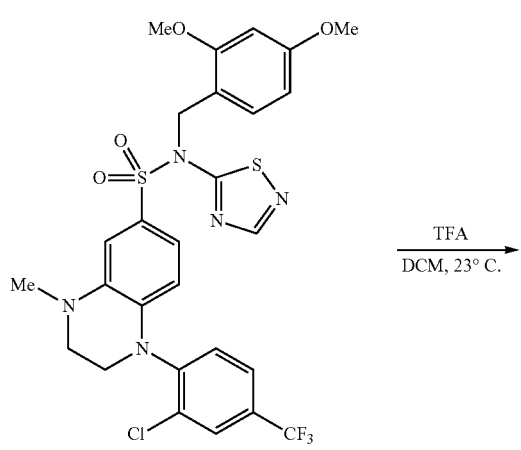

Step 1: 1-(2-Chloro-4-(Trifluoromethyl)Phenyl)-N-(2,4-Dimethoxybenzyl)-4-Methyl-N-(1,2,4-Thiadiazol-5-Yl)-1,2,3,4-Tetrahydroquinoxaline-6-Sulfonamide


A solution of 1-(2-chloro-4-(trifluoromethyl)phenyl)-N-(2,4-dimethoxybenzyl)-N-(1,2,4-thiadiazol-5-yl)-1,2,3,4-tetrahydroquinoxaline-6-sulfonamide (INTERMEDIATE V, 0.045 g, 0.072 mmol) in DMF (0.719 mL) was treated with sodium hydride (4.31 mg, 0.108 mmol) to afford a dark brown solution. Iodomethane (6.74 µL, 0.108 mmol) was added dropwise to give a light-yellow solution. The reaction was stirred for 40 minutes. Additional iodomethane (6.74 µL, 0.108 mmol) was added and the reaction was heated to 70° C. and stirred for one hour. The mixture was diluted with water and a small amount of brine (to break up an emulsion) then extracted with EtOAc (2x). The combined organic extracts were dried over sodium sulfate, filtered, and concentrated. The material was purified via silica gel chromatography (12 g column, gradient elution 0 to 50% EtOAc:Heptane) to afford 1-(2-chloro-4-(trifluoromethyl)phenyl)-N-(2,4-dimethoxybenzyl)-4-methyl-N-(1,2,4-thiadiazol-5-yl)-1,2,3,4-tetrahydroquinoxaline-6-sulfonamide as a white solid. m/z (ESI) 639.8 (M+H)$^+$.

Step 2: 1-(2-Chloro-4-(Trifluoromethyl)Phenyl)-4-Methyl-N-(1,2,4-Thiadiazol-5-Yl)-1,2,3,4-Tetrahydroquinoxaline-6-Sulfonamide

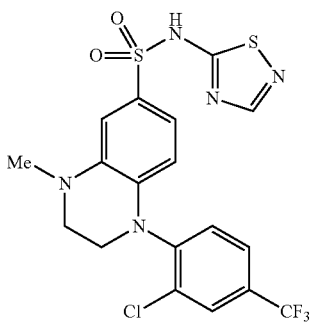 [SMILES: CN1CCN(c2ccc(C(F)(F)F)cc2Cl)c2ccc(S(=O)(=O)Nc3ncns3)cc21]

1-(2-Chloro-4-(trifluoromethyl)phenyl)-N-(2,4-dimethoxybenzyl)-4-methyl-N-(1,2,4-thiadiazol-5-yl)-1,2,3,4-tetrahydroquinoxaline-6-sulfonamide (0.046 g, 0.072 mmol) was dissolved in 1 mL of DCM and TFA (0.1 mL, 1.298 mmol) was added. The reaction was stirred for 30 minutes at room temperature. The solution was concentrated, dissolved in acetonitrile and loaded onto an ion exchange column (pre-wetted with acetonitrile). The column was flushed several times with acetonitrile, then the product was liberated by flushing the column several times with about 1M HCl solution in MeOH/EtOAc (made by adding acetyl chloride to a MeOH/EtOAc mixture). The second filtrate was concentrated to afford 1-(2-chloro-4-(trifluoromethyl)phenyl)-4-methyl-N-(1,2,4-thiadiazol-5-yl)-1,2,3,4-tetrahydroquinoxaline-6-sulfonamide as a light pink solid. $^1$H NMR (400 MHz, DMSO-$d_6$) δ=8.41 (s, 1 H), 8.02 (d, J=1.8 Hz, 1 H), 7.82 (dd, J=1.8, 8.7 Hz, 1 H), 7.67 (d, J=8.1 Hz, 1 H), 6.91 (qd, J=2.2, 4.4 Hz, 2 H), 6.03 (d, J=8.9 Hz, 1 H), 3.71 (t, J=4.8 Hz, 2 H), 3.40 (t, J=4.8 Hz, 2 H), 2.91 (s, 3H). m/z (ESI) 489.8 (M+H)$^+$.

Example 20

4-Acetyl-1-(2-Chloro-4-(Trifluoromethyl)Phenyl)-N-(1,2,4-Thiadiazol-5-Yl)-1,2,3,4-Tetrahydroquinoxaline-6-Sulfonamide

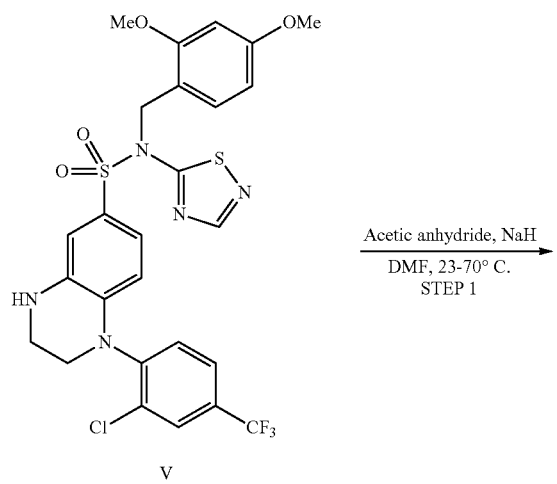

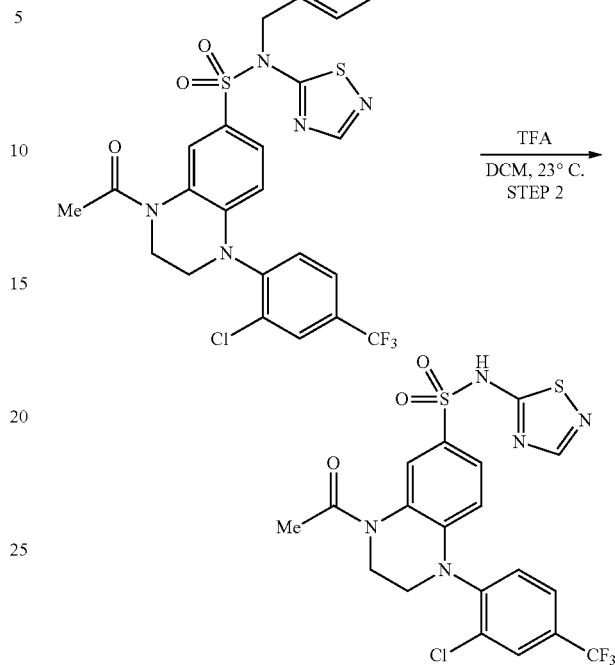

Step 1: 4-Acetyl-1-(2-Chloro-4-(Trifluoromethyl)Phenyl)-N-(2,4-Dimethoxybenzyl)-N-(1,2,4-Thiadiazol-5-Yl)-1,2,3,4-Tetrahydroquinoxaline-6-Sulfonamide

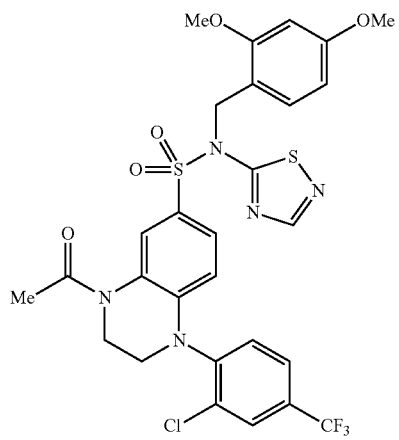 [SMILES: COc1ccc(CN(c2ncns2)S(=O)(=O)c2ccc3c(c2)N(C(C)=O)CCN3c2ccc(C(F)(F)F)cc2Cl)c(OC)c1]

A vial was charged with 1-(2-chloro-4-(trifluoromethyl)phenyl)-N-(2,4-dimethoxybenzyl)-N-(1,2,4-thiadiazol-5-yl)-1,2,3,4-tetrahydroquinoxaline-6-sulfonamide (INTERMEDIATE V, 0.045 g, 0.072 mmol) and DMF (0.719 mL). Sodium hydride (60% in mineral oil) (4.31 mg, 0.108 mmol) was added to give a dark brown solution. Acetic anhydride (0.014 mL, 0.144 mmol) was added dropwise, and the mixture lightened significantly and thickened up. After stirring for 30 minutes at room temperature, additional acetic anhydride (0.014 mL, 0.144 mmol) was added and the reaction was heated to 50° C. and stirred for one hour. Additional sodium hydride (60% in mineral oil) (4.31 mg, 0.108 mmol) and acetic anhydride (0.014 mL, 0.144 mmol) were added and the reaction was stirred at 70° C. for one hour. The mixture was diluted with water and EtOAc, then with brine to break up an emulsion. The layers were separated, and the aqueous layer was extracted with EtOAc. The organic extracts were combined, dried over sodium sulfate, and concentrated. The material was purified via silica gel chromatography (12 g column, gradient elution 0 to 100% EtOAc:Heptane) to afford 4-acetyl-1-(2-chloro-4-(trifluoromethyl)phenyl)-N-(2,4-dimethoxybenzyl)-N-(1,2,4-thiadiazol-5-yl)-1,2,3,4-tetrahydroquinoxaline-6-sulfonamide as a white solid. m/z (ESI) 667.7 (M+H)$^+$.

Step 2, Example 20: 4-Acetyl-1-(2-Chloro-4-(Trifluoromethyl)Phenyl)-N-(1,2,4-Thiadiazol-5-Yl)-1,2,3,4-Tetrahydroquinoxaline-6-Sulfonamide

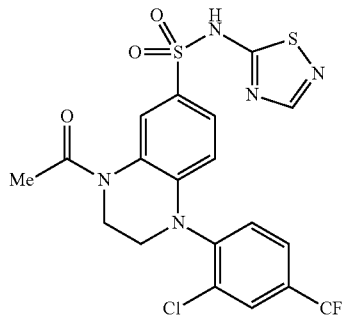

4-Acetyl-1-(2-chloro-4-(trifluoromethyl)phenyl)-N-(2,4-dimethoxybenzyl)-N-(1,2,4-thiadiazol-5-yl)-1,2,3,4-tetrahydroquinoxaline-6-sulfonamide (0.048 g, 0.072 mmol) was dissolved in 1 mL of DCM and TFA (0.1 mL, 1.298 mmol) was added. The reaction was stirred for 30 minutes. The material was concentrated, dissolved in acetonitrile and loaded onto an ion exchange column (pre-wetted with acetonitrile). The column was flushed several times with acetonitrile, then the product was liberated by flushing the column several times with about 1M HCl solution in MeOH/EtOAc (made by adding acetyl chloride to a MeOH/EtOAc mixture). The second filtrate was concentrated to afford 4-acetyl-1-(2-chloro-4-(trifluoromethyl)phenyl)-N-(1,2,4-thiadiazol-5-yl)-1,2,3,4-tetrahydroquinoxaline-6-sulfonamide as a light pink solid. $^1$H NMR (400 MHz, DMSO-d$_6$) δ=8.42 (s, 1 H), 8.12 (d, J=1.7 Hz, 1 H), 7.90 (dd, J=1.6, 8.4 Hz, 1 H), 7.81 (d, J=8.5 Hz, 1 H), 7.31 (d, J=7.9 Hz, 1 H), 6.21 (d, J=8.8 Hz, 1 H), 3.96 (t, J=4.6 Hz, 2 H), 3.68 (br. s., 2 H), 2.24 (s, 3 H). m/z (ESI) 517.8 (M+H)$^+$.

Example 21

4-(2-(Pyridin-3-Yl)-4-(Trifluoromethyl)Phenyl)-N-(1,2,4-Thiadiazol-5-Yl)-3,4-Dihydro-2H-Benzo[B][1,4]Oxazine-7-Sulfonamide

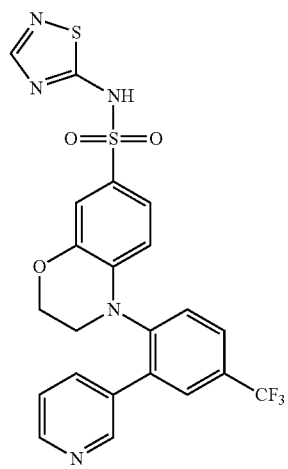 [SMILES: O=S(=O)(Nc1ncns1)c1ccc2c(c1)OCCN2c1ccc(C(F)(F)F)cc1-c1cccnc1]

EXAMPLE 21 was synthesized in the same manner as EXAMPLE 23, instead using 3-pyridylboronic acid (Boron Molecular Inc., Research Triangle, NC). $^1$H NMR (400 MHz, DMSO-d$_6$) δ ppm 3.36 (d, J=12.23 Hz, 1 H) 3.66-3.76 (m, 1 H) 4.06 (m, J=8.50 Hz, 1 H) 4.25-4.33 (m, 1 H) 6.43-6.50 (m, 1 H) 7.02-7.08 (m, 2 H) 7.52 (dd, J=7.73, 4.99 Hz, 1 H) 7.74 (d, J=8.02 Hz, 1 H) 7.89-7.96 (m, 2 H) 8.01 (d, J=7.82 Hz, 1 H) 8.45 (s, 1 H) 8.56 (dd, J=4.99, 1.56 Hz, 1H) 8.71 (d, J=1.76 Hz, 1 H). m/z (ESI) 519.8 (M+H)$^+$.

Example 22

4-(2-(1-Methyl-1,2,3,6-Tetrahydropyridin-4-Yl)-4-(Trifluoromethyl)Phenyl)-N-(1,2,4-Thiadiazol-5-Yl)-3,4-Dihydro-2H-Benzo[B][1,4]Oxazine-7-Sulfonamide 2,2,2-Trifluoroacetate

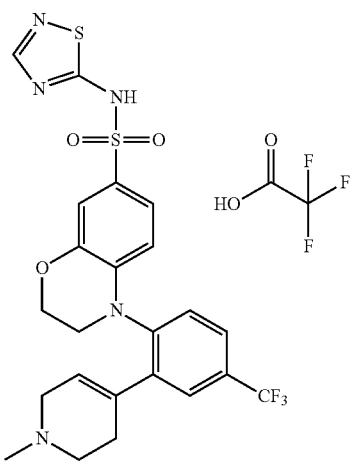 [SMILES: CN1CC=C(c2cc(C(F)(F)F)ccc2N2CCOc3cc(S(=O)(=O)Nc4ncns4)ccc32)CC1 ; O=C(O)C(F)(F)F]

EXAMPLE 22 was synthesized in the same manner as EXAMPLE 23, instead using 1-methyl-1,2,3,6-tetrahydropyridine-4-boronic acid pinacol ester (Sigma-Aldrich, St. Louis, Mo.). $^1$H NMR (400 MHz, DMSO-d$_6$) δ ppm 2.79 (s, 3 H) 3.32-3.79 (m, 6 H) 3.81-4.00 (m, 2 H) 4.22-4.40 (m, 2 H) 5.88 (br. s., 1H) 6.41-6.52 (m, 1 H) 7.09-7.19 (m, 2 H) 7.60 (d, J=8.41 Hz, 1 H) 7.64-7.70 (m, 1 H) 7.78 (dd, J=8.46, 2.01 Hz, 1 H) 8.40 (s, 1 H) 9.80 (br. s., 1 H). m/z (ESI) 537.8 (M+H)$^+$.

Example 23

4-(2-(Pyrimidin-5-Yl)-4-(Trifluoromethyl)Phenyl)-N-(1,2,4-Thiadiazol-5-Yl)-3,4-Dihydro-2H-Benzo[B][1,4]Oxazine-7-Sulfonamide

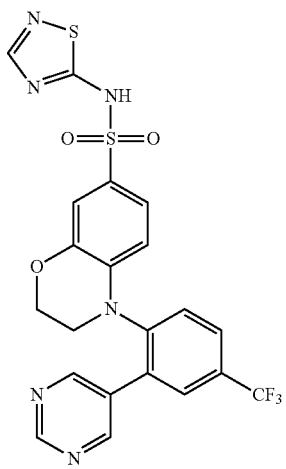 [SMILES: O=S(=O)(Nc1ncns1)c1ccc2c(c1)OCCN2c1ccc(C(F)(F)F)cc1-c1cncnc1]

A microwave vial was charged with INTERMEDIATE D (0.100 g, 0.192 mmol), pyrimidin-5-ylboronic acid (Small Molecules, Inc., Hoboken, N.J., 0.036 g, 0.288 mmol), tetrakis(triphenylphosphine)palladium(0) (0.022 g, 0.019 mmol), and $K_2CO_3$ (0.133 g, 0.959 mmol). The solids were diluted with dioxane (1.279 mL) and water (0.639 mL), and the reaction was heated under microwave irradiation at 100° C. for 30 minutes. The reaction mixture was diluted with water, and washed with ether (the ether layer was extracted once more with water). The combined aqueous layers were acidified with 1.0N HCl, and then washed with DCM (×2). The combined organics were dried using a phase separator and concentrated. After concentration, the material was purified by reverse-phase preparative HPLC (Column: Phenomenex 150×30 mm, 5 micron, $C_{18}$ column; 0.1% TFA in $CH_3CN/H_2O$, gradient 25% to 90% over 20 min) to provide 4-(2-(pyrimidin-5-yl)-4-(trifluoromethyl)phenyl)-N-(1,2,4-thiadiazol-5-yl)-3,4-dihydro-2H-benzo[b][1,4]oxazine-7-sulfonamide (0.040 g, 0.077 mmol) as a light-yellow solid. $^1$H NMR (400 MHz, DMSO-$d_6$) δ ppm 3.45 (m, J=13.00 Hz, 1H) 3.76 (m, J=11.20 Hz, 1 H) 4.06-4.15 (m, 1 H) 4.31 (m, J=10.50 Hz, 1 H) 6.38 (d, J=8.22 Hz, 1 H) 6.98-7.00 (m, 1 H) 7.01-7.03 (m, 1 H) 7.73 (d, J=8.41 Hz, 1H) 7.94 (dd, J=8.56, 2.01 Hz, 1 H) 7.99 (m, J=1.70 Hz, 1 H) 8.26 (s, 1 H) 8.90 (s, 2 H) 9.07 (s, 1 H). m/z (ESI) 520.8 (M+H)$^+$.

Example 24

4-(2-Chloro-4-(Trifluoromethyl)Phenyl)-N-(Oxazol-2-Yl)-3,4-Dihydro-2H-Benzo[B][1,4]Oxazine-7-Sulfonamide

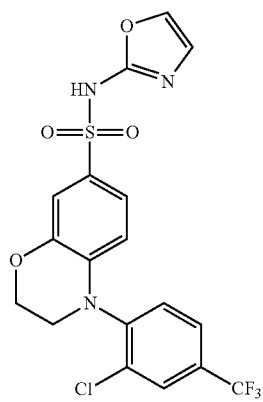

EXAMPLE 24 was prepared in the same manner as EXAMPLE 5 using 1,3-oxazol-2-amine (Small Molecules, Inc., Hoboken, N.J.) instead of thiazol-2-amine $^1$H NMR (400 MHz, DMSO-$d_6$) δ ppm 3.71 (br. s., 2 H) 4.34 (t, J=4.35 Hz, 2 H) 6.29 (d, J=8.61 Hz, 1 H) 7.11-7.22 (m, 2 H) 7.25 (d, J=2.15 Hz, 1 H) 7.56 (d, J=1.56 Hz, 1 H) 7.72 (d, J=8.41 Hz, 1 H) 7.82 (dd, J=8.66, 1.81 Hz, 1 H) 8.04 (d, J=1.86 Hz, 1 H) 11.90 (br. s., 1 H).

Example 25

4-(2-(3,6-Dihydro-2H-Pyran-4-Yl)-4-(Trifluoromethyl)Phenyl)-N-(1,2,4-Thiadiazol-5-Yl)-3,4-Dihydro-2H-Benzo[B][1,4]Oxazine-7-Sulfonamide

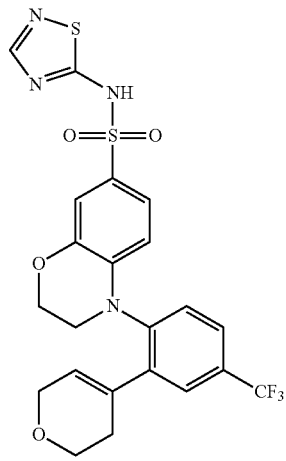 [SMILES: O=S(=O)(Nc1ncns1)c1ccc2c(c1)OCCN2c1ccc(C(F)(F)F)cc1C1=CCOCC1]

EXAMPLE 25 was synthesized in the same manner as EXAMPLE 23, instead using 2-(3,6-dihydro-2H-pyran-4-yl)-4,4,5,5-tetramethyl-1,3,2-dioxaborolane. (Sigma-Aldrich, St. Louis, Mo.)$^1$H NMR (400 MHz, DMSO-$d_6$) δ ppm 2.21-2.31 (m, 2 H) 3.61 (m, J=4.10 Hz, 2 H) 3.65-3.74 (m, 2 H) 4.07 (d, J=2.74 Hz, 2 H) 4.26-4.33 (m, 2 H) 5.85-5.95 (m, 1 H) 6.39-6.47 (m, 1 H) 7.10-7.17 (m, 2 H) 7.56 (d, J=8.31 Hz, 1 H) 7.65 (d, J=2.15 Hz, 1 H) 7.73 (dd, J=8.46, 1.81 Hz, 1 H) 8.44 (s, 1 H). m/z (ESI) 524.8 (M+H)$^+$.

Example 26

4-(2-(Pyridin-4-Yl)-4-(Trifluoromethyl)Phenyl)-N-(1,2,4-Thiadiazol-5-Yl)-3,4-Dihydro-2H-Benzo[B][1,4]Oxazine-7-Sulfonamide

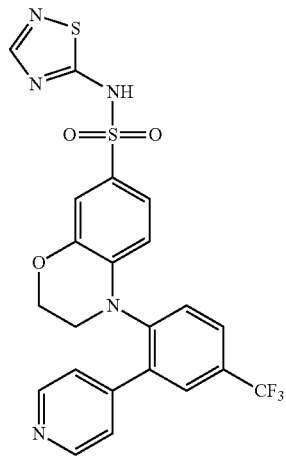 [SMILES: O=S(=O)(Nc1ncns1)c1ccc2c(c1)OCCN2c1ccc(C(F)(F)F)cc1-c1ccncc1]

EXAMPLE 26 was synthesized in the same manner as EXAMPLE 23 instead using 4-pyridineboronic acid (Maybridge Chemicals, Cornwall, UK). $^1$H NMR (400 MHz, DMSO-d$_6$) δ ppm 3.34 (m, J=14.10 Hz, 1 H) 3.58-3.68 (m, 1 H) 4.06-4.17 (m, 1 H) 4.21-4.31 (m, 1 H) 6.50-6.58 (m, 1 H) 7.03-7.09 (m, 2H) 7.69 (d, J=5.97 Hz, 2 H) 7.76 (d, J=8.31 Hz, 1 H) 7.91 (s, 1 H) 7.96 (dd, J=8.66, 2.01 Hz, 1 H) 8.44 (s, 1 H) 8.65-8.73 (m, 2 H). m/z (ESI) 519.8 (M+H)$^+$.

Example 27

4-(2-Chloro-4-(Trifluoromethyl)Phenyl)-N-(Pyridazin-3-Yl)-3,4-Dihydro-2H-Benzo[B][1,4]Oxazine-7-Sulfonamide

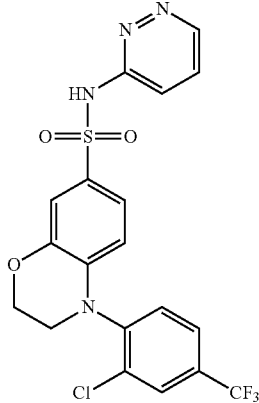 [SMILES: O=S(=O)(Nc1cccnn1)c1ccc2c(c1)OCCN2c1ccc(C(F)(F)F)cc1Cl]

EXAMPLE 27 was prepared in the same manner as EXAMPLE 5 using 3-aminopyridazine (Sigma-Aldrich, St. Louis, Mo.) instead of thiazol-2-amine $^1$H NMR (400 MHz, DMSO-d$_6$) δ ppm 3.71 (br. s., 2 H) 4.34 (br. s., 3 H) 6.29 (d, J=8.51 Hz, 1 H) 7.08 (d, J=2.05 Hz, 1 H) 7.10-7.29 (m, 2 H) 7.63 (dd, J=9.44, 4.25 Hz, 1 H) 7.71 (d, J=8.22 Hz, 1 H) 7.82 (dd, J=8.66, 2.01 Hz, 2 H) 8.04 (d, J=1.56 Hz, 1 H).

Example 28

4-(2-Chloro-4-(Trifluoromethyl)Phenyl)-N-(1,3,4-Thiadiazol-2-Yl)-3,4-Dihydro-2H-Benzo[B][1,4]Oxazine-7-Sulfonamide

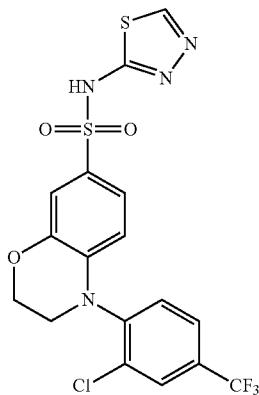 [SMILES: O=S(=O)(Nc1nncs1)c1ccc2c(c1)OCCN2c1ccc(C(F)(F)F)cc1Cl]

EXAMPLE 28 was prepared in the same manner as EXAMPLE 5 using 2-amino-1,3,4-thiadiazole (Sigma-Aldrich, St. Louis, Mo.) instead of thiazol-2-amine $^1$H NMR (400 MHz, DMSO-d$_6$) δ ppm 3.79 (br. s., 2 H) 4.42 (br. s., 2 H) 6.37 (d, J=8.51 Hz, 1 H) 7.04 (s, 1 H) 7.11-7.24 (m, 2 H) 7.29 (s, 1 H) 7.80 (d, J=8.22 Hz, 1 H) 7.90 (dd, J=8.41, 1.66 Hz, 1 H) 8.11 (s, 1 H) 8.78 (s, 1 H).

Example 29

4-(2-(2-Aminopyridin-4-Yl)-4-(Trifluoromethyl)Phenyl)-N-(1,2,4-Thiadiazol-5-Yl)-3,4-Dihydro-2H-Benzo[B][1,4]Oxazine-7-Sulfonamide

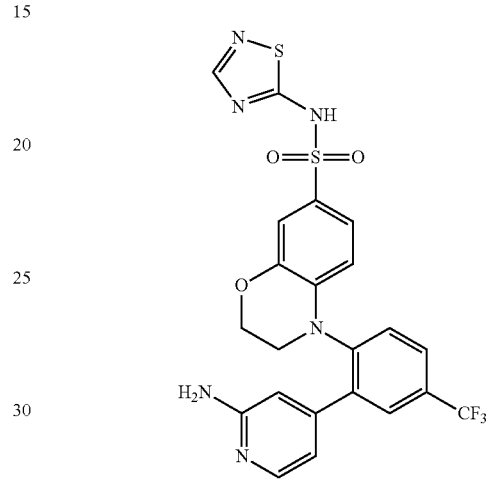

EXAMPLE 29 was synthesized in the same manner as EXAMPLE 23, instead using 2-aminopyridine-4-boronic acid pinacol ester (CombiPhos Catalysts (Ryan Scientific, Inc., Mt. Pleasant, S.C.). $^1$H NMR (400 MHz, DMSO-d$_6$) δ ppm 3.41 (m, J=13.30 Hz, 1 H) 3.60-3.68 (m, 1 H) 4.24 (d, J=16.63 Hz, 2 H) 6.60 (d, J=8.31 Hz, 1 H) 6.87 (dd, J=6.55, 1.66 Hz, 1 H) 7.00-7.02 (m, 1 H) 7.07-7.13 (m, 2 H) 7.75 (d, J=8.22 Hz, 1 H) 7.87-7.94 (m, 3 H) 7.96 (dd, J=8.56, 2.01 Hz, 2 H) 8.42 (s, 1 H). m/z (ESI) 534.8 (M+H)$^+$.

Example 30

4-Phenyl-N-(1,2,4-Thiadiazol-5-Yl)-3,4-Dihydro-2H-Benzo[B][1,4]Oxazine-7-Sulfonamide

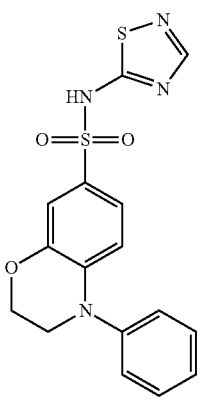 [SMILES: O=S(=O)(Nc1ncns1)c1ccc2c(c1)OCCN2c1ccccc1]

A microwave vial was charged with INTERMEDIATE L (0.099 g, 0.237 mmol), xantphos (0.023 g, 0.039 mmol), bromobenzene (0.021 mL, 0.197 mmol), $Pd_2(dba)_3$ (0.018 g, 0.020 mmol) and sodium tert-butoxide (0.038 g, 0.395 mmol). The mixture was diluted with toluene (1.974 mL), and purged with nitrogen, and heated at 130° C. under microwave irradiation for 30 minutes, until clean conversion to the desired product. The reaction was diluted with water, and washed with DCM. The organics were dried using a phase separator and concentrated under a vacuum. The reaction was then diluted with DCM (1.5 mL) and TFA (2.0 mL) was added. The reaction was stirred for 1.5 h until complete removal of the dimethoxybenzyl protecting group. The reaction was concentrated under a vacuum, and then purified via reverse-phase preparative HPLC (Column: Phenomenex 150×30 mm, 5 micron, $C_{18}$ column; 0.1% TFA in $CH_3CN$/$H_2O$, gradient 25% to 90% over 20 min) to provide 4-phenyl-N-(1,2,4-thiadiazol-5-yl)-3,4-dihydro-2H-benzo[b][1,4]oxazine-7-sulfonamide (0.023 g, 0.061 mmol) as an off-white solid. $^1$H NMR (400 MHz, DMSO-$d_6$) δ ppm 3.69-3.78 (m, 2 H) 4.27-4.36 (m, 2 H) 6.67-6.78 (m, 1 H) 7.10-7.17 (m, 2 H) 7.18-7.26 (m, 1 H) 7.29-7.36 (m, 2 H) 7.39-7.51 (m, 2 H) 8.43 (s, 1 H). m/z (ESI) 374.8 (M+H)$^+$.

Example 31

4-(2-Cyano-4-(Trifluoromethyl)Phenyl)-N-(1,2,4-Thiadiazol-5-Yl)-3,4-Dihydro-2H-Benzo[B][1,4]Oxazine-7-Sulfonamide

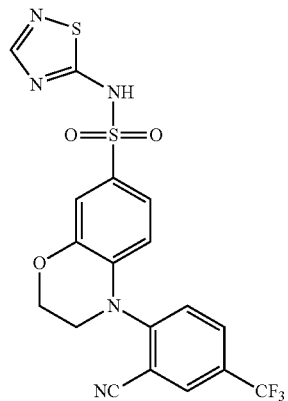 [SMILES: N#Cc1cc(C(F)(F)F)ccc1N1CCOc2cc(S(=O)(=O)Nc3ncns3)ccc21]

EXAMPLE 31 was synthesized in the same manner as EXAMPLE 30, instead using 2-bromo-5-(trifluoromethyl)benzonitrile (Apollo Scientific, Cheshire, UK) in place of bromobenzene. $^1$H NMR (400 MHz, DMSO-$d_6$) δ ppm 3.81-3.90 (m, 2 H) 4.29-4.39 (m, 2 H) 6.81 (d, J=8.61 Hz, 1 H) 7.19 (dd, J=8.56, 2.20 Hz, 1 H) 7.23 (d, J=2.15 Hz, 1 H) 7.74 (d, J=8.61 Hz, 1 H) 8.08 (dd, J=8.70, 2.15 Hz, 1 H) 8.41 (d, J=1.86 Hz, 1 H) 8.44 (s, 1 H). m/z (ESI) 468.0 (M+H)$^+$.

Example 32

(Intermediate G) 4-(2-Chloro-4-(Trifluoromethyl)Phenyl)-N-(Pyrimidin-4-Yl)-3,4-Dihydro-2H-Benzo[B][1,4]Oxazine-7-Sulfonamide

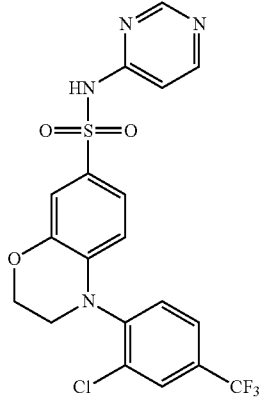 [SMILES: O=S(=O)(Nc1ccncn1)c1ccc2c(c1)OCCN2c1ccc(C(F)(F)F)cc1Cl]

EXAMPLE 32 was prepared from INTERMEDIATE F as described in the preparation of INTERMEDIATE G. $^1$H NMR (400 MHz, DMSO-$d_6$) δ ppm 3.60-3.84 (m, 2 H) 4.24-4.48 (m, 2 H) 6.32 (d, J=8.51 Hz, 1 H) 6.98-7.05 (m, 1 H) 7.24-7.31 (m, 1 H) 7.34 (s, 1 H) 7.71-7.79 (m, 1 H) 7.82-7.89 (m, 1 H) 8.03-8.11 (m, 1 H) 8.31-8.43 (m, 1 H) 8.56-8.75 (m, 1 H). m/z (ESI) 471.0 (M+H)$^+$.

Example 33

4-(Quinolin-5-Yl)-N-(1,2,4-Thiadiazol-5-Yl)-3,4-Dihydro-2H-Benzo[B][1,4]Oxazine-7-Sulfonamide

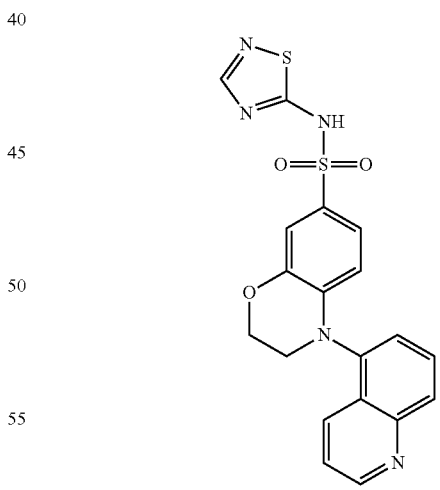

EXAMPLE 33 was synthesized in the same manner as EXAMPLE 30, instead using 5-bromoquinoline (Indofine Chemical Company, Inc., Hillsborough, N.J.) in place of bromobenzene. $^1$H NMR (400 MHz, DMSO-$d_6$) δ ppm 3.68-3.77 (m, 1 H) 3.87-3.96 (m, 1 H) 4.40-4.49 (m, 1 H) 4.50-4.60 (m, 1 H) 6.00 (d, J=8.61 Hz, 1 H) 7.02 (dd, J=8.56, 2.20 Hz, 1 H) 7.18 (d, J=2.15 Hz, 1 H) 7.56 (dd, J=8.51, 4.21 Hz, 1 H) 7.68 (dd, J=7.34, 0.88 Hz, 1 H) 7.88 (dd, J=8.36, 7.48 Hz, 1 H)

8.07 (d, J=8.41 Hz, 1 H) 8.30 (d, J=8.31 Hz, 1 H) 8.42 (s, 1 H) 8.98 (dd, J=4.16, 1.61 Hz, 1 H). m/z (ESI) 425.7 (M+H)+.

Example 34

3-Phenyl-N-(1,2,4-Thiadiazol-5-Yl)-4-(4-(Trifluoromethyl)Phenyl)-3,4-Dihydro-2H-Benzo[B][1,4]Oxazine-7-Sulfonamide

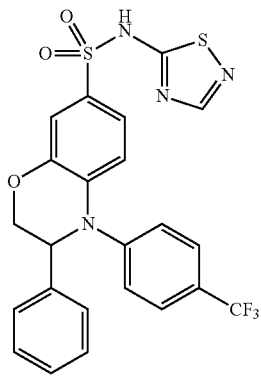 [SMILES: O=S(=O)(Nc1ncns1)c1ccc2c(c1)OCC(c1ccccc1)N2c1ccc(C(F)(F)F)cc1]

A vial was charged with N-(4-methoxybenzyl)-3-phenyl-N-(1,2,4-thiadiazol-5-yl)-3,4-dihydro-2H-benzo[b][1,4]oxazine-7-sulfonamide (INTERMEDIATE R, 93.6 mg, 0.189 mmol), xantphos (21.89 mg, 0.038 mmol), Pd$_2$(dba)$_3$ (17.32 mg, 0.019 mmol), toluene (1891 µL), 1-bromo-4-(trifluoromethyl)benzene (31.8 µl, 0.227 mmol), and sodium tert-butoxide (36.4 mg, 0.378 mmol). The vial was sealed and placed in a 130° C. heating bath for 10 min. The reaction mixture was cooled to room temperature, diluted with water, and extracted with EtOAc (3×). The combined organic extracts were dried over sodium sulfate, filtered, and concentrated. The residue was dissolved in DCM (0.5 mL) and TFA (0.5 mL). The resulting mixture was stirred for 20 minutes, then concentrated. The product was purified by chromatography on silica gel (0 to 5% MeOH/DCM) to give a yellow foam. The material was dissolved in MeOH/DCM and loaded onto a 1 g anion exchange column. The column was eluted with MeOH, then with 10% HCl/MeOH (prepared by dissolving 1 mL of conc. HCl in 9 mL of MeOH). The acidic fractions were concentrated, and the residue was concentrated from DCM to give 3-phenyl-N-(1,2,4-thiadiazol-5-yl)-4-(4-(trifluoromethyl)phenyl)-3,4-dihydro-2H-benzo[b][1,4]oxazine-7-sulfonamide (52.2 mg, 0.101 mmol) as a yellow solid. $^1$H NMR (400 MHz, DMSO-d$_6$) δ ppm 8.44 (s, 1 H), 7.71 (d, J=8.8 Hz, 2 H), 7.44 (d, J=8.4 Hz, 2 H), 7.37-7.23 (m, 6H), 7.16 (dd, J=3.3, 5.4 Hz, 2 H), 5.28-5.23 (m, 1 H), 4.60 (dd, J=2.4, 11.2 Hz, 1 H), 4.40 (dd, J=2.8, 11.3 Hz, 1 H). m/z (ESI) 519.0 (M+H)+.

Example 35

N-(1,2,4-Thiadiazol-5-Yl)-4-(3-(Trifluoromethoxy)Phenyl)-3,4-Dihydro-2H-Benzo[B][1,4]Oxazine-7-Sulfonamide

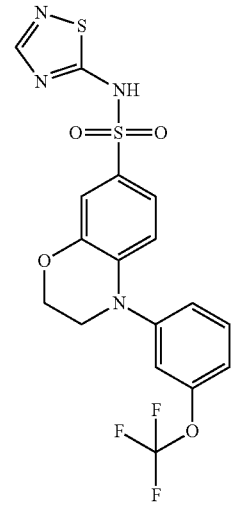 [SMILES: O=S(=O)(Nc1ncns1)c1ccc2c(c1)OCCN2c1cccc(OC(F)(F)F)c1]

EXAMPLE 35 was synthesized in the same manner as EXAMPLE 30, instead using 1-bromo-3-(trifluoromethoxy)benzene in place of bromobenzene. $^1$H NMR (400 MHz, DMSO-d$_6$) δ ppm 3.73-3.81 (m, 2 H) 4.27-4.37 (m, 2 H) 6.87-6.94 (m, 1 H) 7.14-7.21 (m, 3 H) 7.30-7.46 (m, 3 H) 7.50-7.57 (m, 1 H) 8.44 (s, 1 H). m/z (ESI) 458.8 (M+H)+.

Example 36

4-(Naphthalen-1-Yl)-N-(1,2,4-Thiadiazol-5-Yl)-3,4-Dihydro-2H-Benzo[B][1,4]Oxazine-7-Sulfonamide

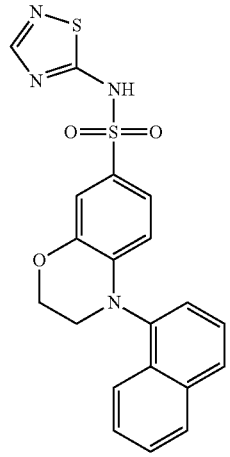

EXAMPLE 36 was synthesized in the same manner as EXAMPLE 30, using 1-bromonaphthalene in place of bromobenzene. $^1$H NMR (400 MHz, DMSO-d$_6$) δ ppm 3.67-3.76 (m, 1 H) 3.90 (ddd, J=12.45, 7.36, 3.08 Hz, 1 H) 4.41-4.58 (m, 2 H) 5.96 (d, J=8.51 Hz, 1 H) 7.02 (dd, J=8.61, 2.15 Hz, 1 H) 7.17 (d, J=2.15 Hz, 1 H) 7.50-7.67 (m, 4 H) 7.85 (d, J=8.31 Hz, 1 H) 7.98 (d, J=8.02 Hz, 1 H) 8.05 (d, J=7.53 Hz, 1 H) 8.42 (s, 1 H). m/z (ESI) 424.8 (M+H)⁺.

Example 37

4-(4-Methoxyphenyl)-N-(1,2,4-Thiadiazol-5-Yl)-3,4-Dihydro-2H-Benzo[B][1,4]Oxazine-7-Sulfonamide

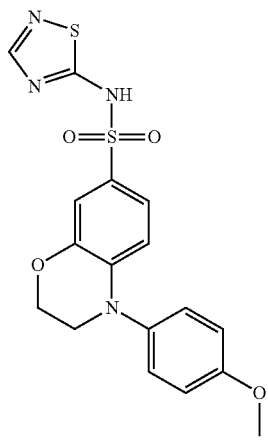 [SMILES: COc1ccc(N2CCOc3cc(S(=O)(=O)Nc4ncns4)ccc32)cc1]

EXAMPLE 37 was synthesized in the same manner as EXAMPLE 30, using 1-bromo-4-methoxybenzene in place of bromobenzene. ¹H NMR (400 MHz, DMSO-d₆) δ ppm 3.65-3.70 (m, 2 H) 3.78 (s, 3 H) 4.29-4.35 (m, 2 H) 6.50 (d, J=8.31 Hz, 1 H) 6.99-7.05 (m, 2 H) 7.08-7.14 (m, 2 H) 7.23-7.28 (m, 2 H) 8.43 (s, 1 H). m/z (ESI) 404.8 (M+H)⁺.

Example 38

4-(2-(1,2,3,6-Tetrahydropyridin-4-Yl)-4-(Trifluoromethyl)Phenyl)-N-(Thiazol-2-Yl)-3,4-Dihydro-2H-Benzo[B][1,4]Oxazine-7-Sulfonamide 2,2,2-Trifluoroacetate

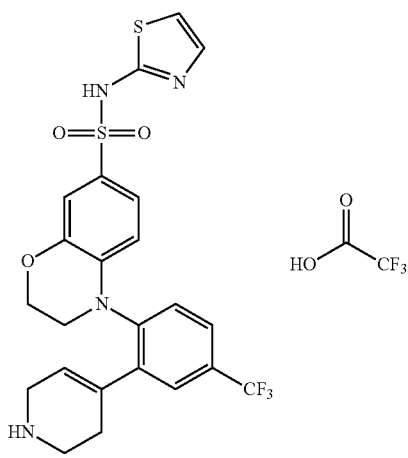 [SMILES: O=S(=O)(Nc1nccs1)c1ccc2c(c1)OCCN2c1ccc(C(F)(F)F)cc1C1=CCNCC1 ; O=C(O)C(F)(F)F]

A 5-mL glass microwave reaction vessel was charged with 4-(2-chloro-4-(trifluoromethyl)phenyl)-N-(4-methoxybenzyl)-N-(thiazol-2-yl)-3,4-dihydro-2H-benzo[b][1,4]oxazine-7-sulfonamide (INTERMEDIATE X, 0.150 g, 0.252 mmol), (n-tert-butoxycarbonyl)-1,2,3,6-tetrahydropyridine-4-boronic acid pinacol ester (0.195 mL, 0.629 mmol), 1,1-bis[(di-t-butyl-p-methylaminophenyl]palladium(II) chloride (0.027 g, 0.038 mmol), and potassium phosphate (0.083 mL, 1.007 mmol). The vessel was sealed and flushed with N₂. Dioxane (1 mL) and water (0.32 mL) were added via syringe and the mixture was sparged with N₂ for 5 min. The reaction mixture was stirred and heated in a microwave reactor at 112° C. for 3 h. After cooling to rt, the reaction was diluted with EtOAc and the organic layer was decanted from aqueous layer at the bottom of the vial. The organic layer was concentrated and absorbed onto a 5 g loading cartridge and passed through a silica gel column (12 g) using a gradient from 0% to 60% EtOAc in Heptanes to provide tert-butyl 4-(2-(7-(N-(4-methoxybenzyl)-N-(thiazol-2-yl)sulfamoyl)-2H-benzo[b][1,4]oxazin-4(3H)-yl)-5-(trifluoromethyl)phenyl)-5,6-dihydropyridine-1(2H)-carboxylate. This product was dissolved in DCM (5 mL) and the solution was cooled to 0° C. Trifluoroacetic acid (1 mL) was added dropwise to generate a bright pink solution. The cold bath was removed and the solution was stirred for 30 min. Additional trifluoroacetic acid (1 mL) was added dropwise and the solution was maintained at rt for 5 min. The solution was partitioned between ice/brine and DCM. The layers were separated and the aqueous layer was extracted with DCM (3×). The combined organic layers were dried (Na₂SO₄) and concentrated. The resulting residue was dissolved in MeOH/DMSO and purified by reverse-phase preparative HPLC using 0.1% TFA in CH₃CN/H₂O, gradient 10% to 80% over 15 min to provide 4-(2-(1,2,3,6-tetrahydropyridin-4-yl)-4-(trifluoromethyl)phenyl)-N-(thiazol-2-yl)-3,4-dihydro-2H-benzo[b][1,4]oxazine-7-sulfonamide 2,2,2-trifluoroacetate (0.075 g, 0.118 mmol) as a white solid. ¹H NMR (500 MHz, DMSO-d₆) δ ppm 3.20 (br. s., 4 H) 3.52-3.62 (m, 2 H) 3.69 (br. s., 2 H) 4.28 (br. s., 2 H) 5.89 (br. s., 1 H) 6.48 (d, J=8.55 Hz, 1 H) 6.79 (d, J=4.59 Hz, 1 H) 7.08-7.26 (m, 3 H) 7.53-7.66 (m, 2 H) 7.70-7.80 (m, 1 H) 8.67-8.87 (m, 2 H) 12.46-12.62 (m, 1 H).

Example 39

4-(4-(2-Methoxyethoxy)Phenyl)-N-(1,2,4-Thiadiazol-5-Yl)-3,4-Dihydro-2H-Benzo[B][1,4]Oxazine-7-Sulfonamide

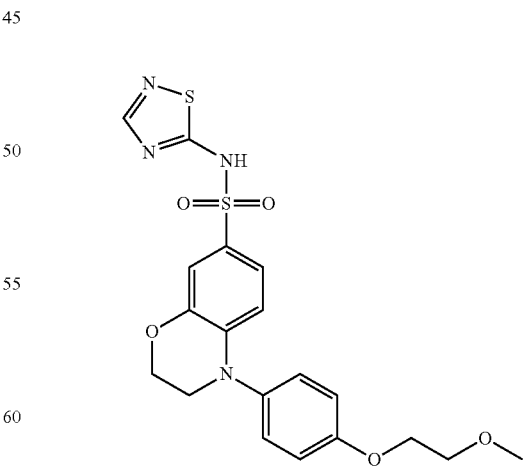

EXAMPLE 39 was synthesized in the same manner as EXAMPLE 30, using 1-bromo-4-(2-methoxyethoxy)benzene in place of bromobenzene. ¹H NMR (400 MHz, DMSO-d₆) δ ppm 3.31 (s, 3 H) 3.63-3.70 (m, 4 H) 4.11 (m, J=6.00, 2.90 Hz, 2 H) 4.27-4.36 (m, 2 H) 6.50 (dd, J=8.17, 2.20 Hz, 1 H) 7.02 (dd, J=8.95, 2.40 Hz, 2 H) 7.08-7.14 (m, 2 H) 7.24 (dd, J=8.90, 2.45 Hz, 2 H) 8.42 (d, J=2.45 Hz, 1 H). m/z (ESI) 448.8 (M+H)⁺.

Example 40

4-(4-Chlorophenyl)-N-(Thiazol-2-Yl)-3,4-Dihydro-2H-Benzo[B][1,4]Oxazine-7-Sulfonamide

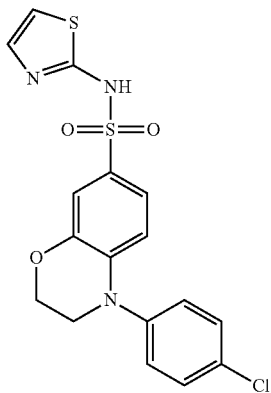 [SMILES: O=S(=O)(Nc1nccs1)c1ccc2c(c1)OCCN2c1ccc(Cl)cc1]

EXAMPLE 40 was synthesized in the same manner as EXAMPLE 41, using 1-bromo-4-chlorobenzene in place of 1-bromo-3-chlorobenzene. ¹H NMR (400 MHz, DMSO-d₆) δ ppm 3.69-3.74 (m, 2 H) 4.26-4.33 (m, 2 H) 6.75-6.82 (m, 2 H) 7.11-7.17 (m, 2 H) 7.23 (d, J=4.60 Hz, 1 H) 7.30-7.36 (m, 2 H) 7.43-7.51 (m, 2 H) 12.58 (br. s., 1 H). m/z (ESI) 407.8 (M+H)⁺.

Example 41

4-(3-Chlorophenyl)-N-(Thiazol-2-Yl)-3,4-Dihydro-2H-Benzo[B][1,4]Oxazine-7-Sulfonamide

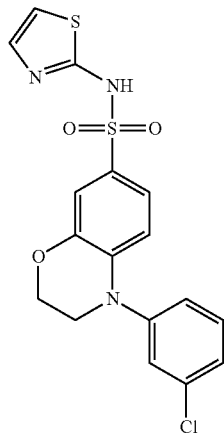 [SMILES: O=S(=O)(Nc1nccs1)c1ccc2c(c1)OCCN2c1cccc(Cl)c1]

A microwave vial was charged with INTERMEDIATE M (0.100 g, 0.240 mmol), xantphos (0.028 g, 0.048 mmol), 1-bromo-3-chlorobenzene (0.031 mL, 0.263 mmol), Pd₂(dba)₃ (0.022 g, 0.024 mmol) and sodium tert-butoxide (0.046 g, 0.479 mmol). The mixture was diluted with toluene (2.395 mL), purged with nitrogen, and heated at 130° C. under microwave irradiation for 30 minutes, until clean conversion to the desired product. The reaction was diluted with water and washed with DCM. The organics were dried using a phase separator, and concentrated under a vacuum. The reaction was then diluted with 1.5 mL of DCM, and 2.0 mL of TFA was added. The reaction was stirred for 1 h until complete removal of the protecting group. The reaction was concentrated under a vacuum, and then purified via reverse-phase preparative HPLC (Column: Phenomenex 150×30 mm, 5 micron, C₁₈ column; 0.1% TFA in CH₃CN/H₂O, gradient 25% to 90% over 20 min) to provide 4-(3-chlorophenyl)-N-(thiazol-2-yl)-3,4-dihydro-2H-benzo[b][1,4]oxazine-7-sulfonamide (0.003 g, 7.35 μmol) as an orange solid. ¹H NMR (400 MHz, DMSO-d₆) δ ppm 3.72-3.77 (m, 2 H) 4.26-4.33 (m, 2 H) 6.79 (d, J=4.50 Hz, 1 H) 6.83-6.87 (m, 1 H) 7.14-7.18 (m, 2 H) 7.20-7.25 (m, 2 H) 7.28 (dd, J=8.12, 1.27 Hz, 1 H) 7.38 (t, J=2.05 Hz, 1 H) 7.40-7.46 (m, 1 H) 12.59 (br. s., 1 H). m/z (ESI) 407.8 (M+H)⁺.

Example 42

4-(2-(1-Methyl-1H-Pyrazol-5-Yl)-4-(Trifluoromethyl)Phenyl)-N-(Thiazol-2-Yl)-3,4-Dihydro-2H-Benzo[B][1,4]Oxazine-7-Sulfonamide

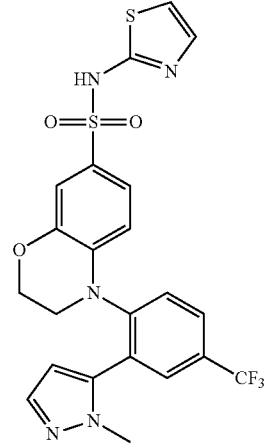 [SMILES: Cn1nccc1-c1cc(C(F)(F)F)ccc1N1CCOc2cc(S(=O)(=O)Nc3nccs3)ccc21]

A 5-mL glass microwave reaction vessel was charged with 4-(2-chloro-4-(trifluoromethyl)phenyl)-N-(4-methoxybenzyl)-N-(thiazol-2-yl)-3,4-dihydro-2H-benzo[b][1,4]oxazine-7-sulfonamide (INTERMEDIATE X, 0.150 g, 0.252 mmol), 1-methyl-1H-pyrazole-5-boronic acid pinacol ester (0.131 g, 0.629 mmol), 1,1-bis[(di-t-butyl-p-methylaminophenyl]palladium(II) chloride (0.027 g, 0.038 mmol), and potassium phosphate (0.083 mL, 1.007 mmol). The vial was sealed and flushed with N₂ and dioxane (1 mL) and water (0.32 mL) were added. The mixture was sparged with N₂ for 5 min and heated microwave reactor at 112° C. for 3 h. The mixture was diluted with EtOAc and the organic layer was decanted, concentrate and absorbed onto a 5 g loading cartridge and passed through a silica gel column (12 g) using a gradient from 0% to 80% EtOAc in Heptanes to provide N-(4-methoxybenzyl)-4-(2-(1-methyl-1H-pyrazol-5-yl)-4-(trifluoromethyl)phenyl)-N-(thiazol-2-yl)-3,4-dihydro-2H-benzo[b][1,4]oxazine-7-sulfonamide. This product was dissolved in DCM (1 mL), cooled to 0° C., and trifluoroacetic acid was added (0.5 mL) dropwise. The solution was maintained at rt for 15 min, then concentrated to dryness. The residue was taken up in DCM and passed through an SCX column (10 g column), flushing with DCM. The product was released by treatment of the SCX column with ammonia (2.0 M) in methanol to afford EXAMPLE 42: 4-(2-(1-methyl-1H- pyrazol-5-yl)-4-(trifluoromethyl)phenyl)-N-(thiazol-2-yl)-3,4-dihydro-2H-benzo[b][1,4]oxazine-7-sulfonamide (0.030 g, 0.058 mmol). $^1$H NMR (500 MHz, DMSO-d$_6$) δ ppm 3.66 (s, 2 H) 3.90 (s, 4 H) 4.11 (br. s., 1 H) 6.33 (d, J=1.82 Hz, 1 H) 6.49 (s, 1 H) 6.62-6.73 (m, 1 H) 7.05-7.15 (m, 2 H) 7.43 (d, J=1.82 Hz, 1 H) 7.67 (d, J=8.44 Hz, 1 H) 7.80 (s, 1 H) 7.85 (d, J=8.44 Hz, 1 H).

Example 43

4-(2-Bromo-4-(Trifluoromethyl)Phenyl)-N-(Thiazol-2-Yl)-3,4-Dihydro-2H-Benzo[B][1,4]Oxazine-7-Sulfonamide

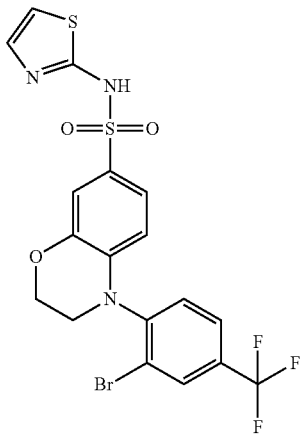 [SMILES: O=S(=O)(Nc1nccs1)c1ccc2c(c1)OCCN2c1ccc(C(F)(F)F)cc1Br]

EXAMPLE 43 was synthesized in the same manner as EXAMPLE 41, instead using 2-bromo-1-iodo-4-trifluoromethyl-benzene (Oakwood Products, Inc., West Columbia, S.C.) in place of 1-bromo-3-chlorobenzene. $^1$H NMR (400 MHz, DMSO-d$_6$) δ ppm 3.71 (m, J=10.80 Hz, 2 H) 4.27-4.44 (m, 2 H) 6.24 (d, J=8.51 Hz, 1 H) 6.79 (d, J=4.60 Hz, 1 H) 7.08-7.26 (m, 3 H) 7.72 (d, J=8.31 Hz, 1 H) 7.88 (d, J=8.31 Hz, 1 H) 8.19 (s, 1 H) 12.59 (br. s, 1 H). m/z (ESI) 519.6 (M+H)$^+$.

Example 44

4-(2-(1-Methyl-1,2,3,6-Tetrahydropyridin-4-Yl)-4-(Trifluoromethyl)Phenyl)-N-(Thiazol-2-Yl)-3,4-Dihydro-2H-Benzo[B][1,4]Oxazine-7-Sulfonamide

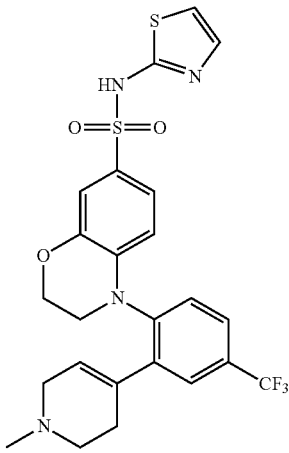 [SMILES: CN1CC=C(c2cc(C(F)(F)F)ccc2N2CCOc3cc(S(=O)(=O)Nc4nccs4)ccc32)CC1]

EXAMPLE 44 was prepared by charging a 10-mL round bottomed flask with 4-(2-(1,2,3,6-tetrahydropyridin-4-yl)-4-(trifluoromethyl)phenyl)-N-(thiazol-2-yl)-3,4-dihydro-2H-benzo[b][1,4]oxazine-7-sulfonamide, (EXAMPLE 38, 0.040 g, 0.077 mmol). The reaction vessel was then flushed with N$_2$ gas and the solid starting materials were dissolved in methanol (0.4 mL). To the resulting solution, formaldehyde 37% wt in water (0.085 mL, 1.148 mmol) was added and the mixture was stirred for 5 min at room temperature. Sodium triacetoxyborohydride (0.243 g, 1.148 mmol) was added portion wise and the resulting solution was stirred for 10 min. The reaction mixture was poured into a sep. funnel containing sat. NaHCO$_3$ and EtOAc. The aqueous layer was washed with EtOAc (3×25 mL), the organic layers were combined and dried over Na$_2$SO$_4$. The organic layer was filtered and concentrated to give pure 4-(2-(1-methyl-1,2,3,6-tetrahydropyridin-4-yl)-4-(trifluoromethyl)phenyl)-N-(thiazol-2-yl)-3,4-dihydro-2H-benzo[b][1,4]oxazine-7-sulfonamide (0.030 g, 0.056 mmol) as a white solid. $^1$H NMR (400 MHz, DMSO-d$_6$) δ ppm 2.18 (d, J=5.58 Hz, 3 H) 2.41 (br. s., 2 H) 2.91 (br. s., 2 H) 3.57 (br. s., 3 H) 4.25 (br. s., 2 H) 5.22 (s, 1 H) 5.80 (br. s., 1 H) 6.40 (t, J=8.61 Hz, 1 H) 6.60 (d, J=3.62 Hz, 1 H) 6.85 (d, J=4.70 Hz, 1 H) 7.03-7.12 (m, 1 H) 7.13-7.22 (m, 1 H) 7.35 (d, J=4.50 Hz, 1 H) 7.46-7.63 (m, 2 H) 7.64-7.78 (m, 1 H).

Example 45

N-(Pyrimidin-4-Yl)-4-(2-(1,2,3,6-Tetrahydropyridin-4-Yl)-4-(Trifluoromethyl)Phenyl)-3,4-Dihydro-2H-Benzo[B][1,4]Oxazine-7-Sulfonamide 2,2,2-Trifluoroacetate

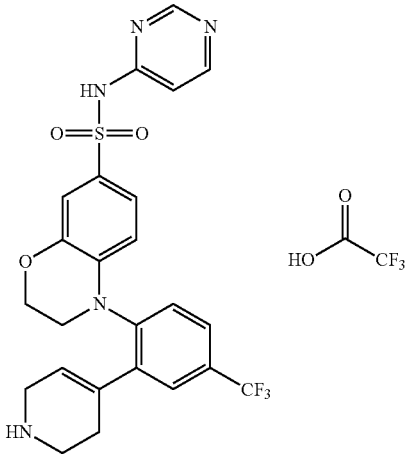 [SMILES: O=S(=O)(Nc1ccncn1)c1ccc2c(c1)OCCN2c1ccc(C(F)(F)F)cc1C1=CCNCC1 ; O=C(O)C(F)(F)F]

A 5-mL glass microwave reaction vessel was charged with 4-(2-chloro-4-(trifluoromethyl)phenyl)-N-(pyrimidin-4-yl)-3,4-dihydro-2H-benzo[b][1,4]oxazine-7-sulfonamide (0.075 g, 0.159 mmol), (N-tert-butoxycarbonyl)-1,2,3,6-tetrahydropyridine-4-boronic acid pinacol ester (0.123 mL, 0.398 mmol), 1,1-bis[(di-t-butyl-p-methylaminophenyl]palladium (II) chloride (0.017 g, 0.024 mmol), potassium phosphate (0.053 mL, 0.637 mmol) and sealed with a septa cap. The reaction head space was flushed with nitrogen and dioxane (0.6 mL) and water (0.2 mL) were added. The mixture was sparged with nitrogen for 5 min. The reaction mixture was stirred and heated in a microwave reactor at 115° C. for 3 h. The reaction mixture was diluted with EtOAc and the organic layer was decanted from the aqueous layer at the bottom of the vial by pipet. The organic layer was concentrated and absorbed onto a 5 g loading cartridge and passed through a silica gel column (12 g) using a gradient from 0% to 70% EtOAc in Heptanes to provide tert-butyl 4-(2-(7-(N-(pyrimidin-4-yl)sulfamoyl)-2H-benzo[b][1,4]oxazin-4(3 H)-yl)-5-(trifluoromethyl)phenyl)-5,6-dihydropyridine-1(2 H)-carboxylate. This product was taken up in 0.5 mL DCM and 0.5 mL of trifluoroacetic acid was added and the solution was maintained at rt for 10 min. The solution was concentrated to dryness and then triturated with ether and IPA to give N-(pyrimidin-4-yl)-4-(2-(1,2,3,6-tetrahydropyridin-4-yl)-4-(trifluoromethyl)phenyl)-3,4-dihydro-2H-benzo[b][1,4]oxazine-7-sulfonamide 2,2,2-trifluoroacetate (0.005 g, 7.92 μmol) as a white solid. $^1$H NMR (400 MHz, DMSO-$d_6$) δ ppm 3.13-3.25 (m, 3 H) 3.57-3.64 (m, 3 H) 3.65-3.72 (m, 3 H) 4.24-4.40 (m, 2 H) 5.82-5.94 (m, 1 H) 6.42-6.55 (m, 1 H) 7.01-7.14 (m, 1 H) 7.24-7.38 (m, 2 H) 7.53-7.67 (m, 2 H) 7.72-7.82 (m, 1 H) 8.32-8.47 (m, 1 H) 8.63-8.72 (m, 1 H) 8.73-8.86 (m, 2 H).

Example 46

4-(2-Chlorophenyl)-N-(Thiazol-2-Yl)-3,4-Dihydro-2H-Benzo[B][1,4]Oxazine-7-Sulfonamide

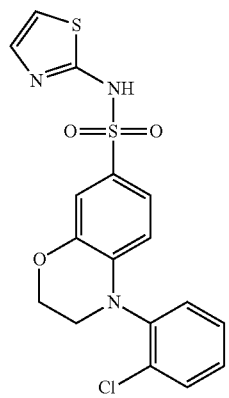 [SMILES: O=S(=O)(Nc1nccs1)c1ccc2c(c1)OCCN2c1ccccc1Cl]

EXAMPLE 46 was synthesized in the same manner as EXAMPLE 41, using 1-bromo-2-chlorobenzene in place of 1-bromo-3-chlorobenzene. $^1$H NMR (400 MHz, DMSO-$d_6$) δ ppm 3.58-3.74 (m, 2 H) 4.24-4.43 (m, 2 H) 6.12 (d, J=8.51 Hz, 1 H) 6.78 (d, J=4.50 Hz, 1 H) 7.11 (dd, J=8.51, 2.15 Hz, 1 H) 7.15 (d, J=2.05 Hz, 1 H) 7.22 (d, J=4.69 Hz, 1 H) 7.37-7.44 (m, 1 H) 7.44-7.55 (m, 2 H) 7.65 (dd, J=7.92, 1.47 Hz, 1 H) 12.55 (br. s., 1 H). m/z (ESI) 408.0 (M+H)$^+$.

Example 47

4-(2-Bromo-4-(Trifluoromethyl)Phenyl)-N-(Pyrimidin-4-Yl)-3,4-Dihydro-2H-Benzo[B][1,4]Oxazine-7-Sulfonamide

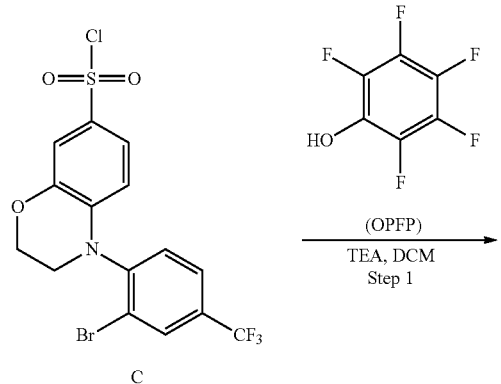

Step 1: Perfluorophenyl 4-(2-Bromo-4-(Trifluoromethyl)Phenyl)-3,4-Dihydro-2H-Benzo[B][1,4]Oxazine-7-Sulfonate

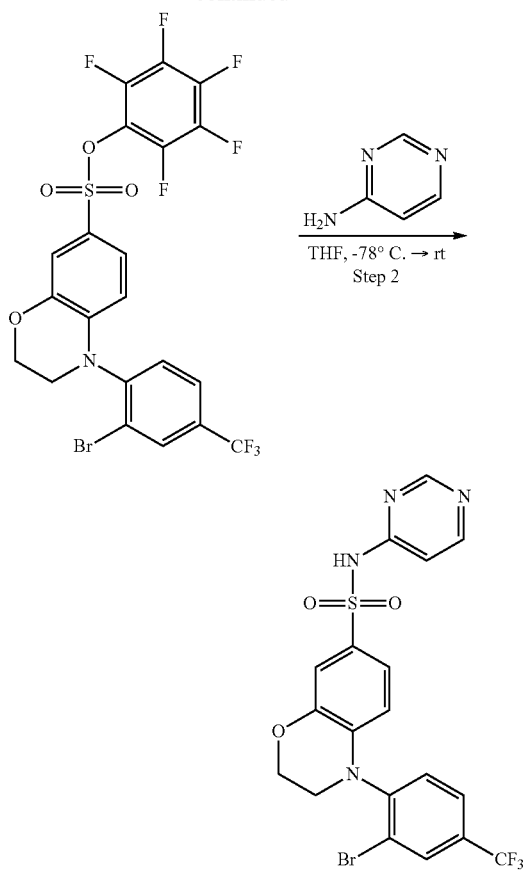

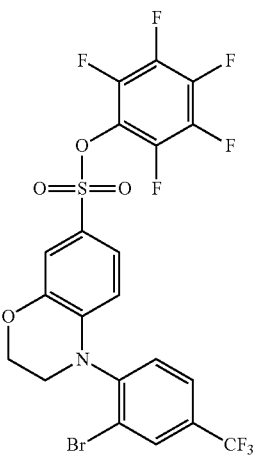 [SMILES: O=S(=O)(Oc1c(F)c(F)c(F)c(F)c1F)c1ccc2c(c1)OCCN2c1ccc(C(F)(F)F)cc1Br]

Perfluorophenyl 4-(2-bromo-4-(trifluoromethyl)phenyl)-3,4-dihydro-2H-benzo[b][1,4]oxazine-7-sulfonate was prepared from INTERMEDIATE C according to the procedure used to prepare INTERMEDIATE F. MS (ESI, positive) m/z: 625.8 (M+Na).

Step 2, Example 47: 4-(2-Bromo-4-(Trifluoromethyl)Phenyl)-N-(Pyrimidin-4-Yl)-3,4-Dihydro-2H-Benzo[B][1,4]Oxazine-7-Sulfonamide

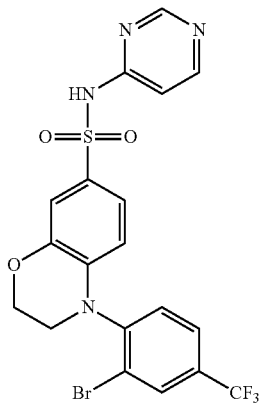 [SMILES: O=S(=O)(Nc1ccncn1)c1ccc2c(c1)OCCN2c1ccc(C(F)(F)F)cc1Br]

EXAMPLE 47 was prepared from perfluorophenyl 4-(2-bromo-4-(trifluoromethyl)phenyl)-3,4-dihydro-2H-benzo[b][1,4]oxazine-7-sulfonate in the same manner as describe for INTERMEDIATE G. $^1$H NMR (500 MHz, DMSO-d$_6$) δ ppm 3.60-3.85 (m, 2 H) 4.27-4.46 (m, 2 H) 6.19-6.31 (m, 1 H) 6.97-7.10 (m, 1 H) 7.23-7.38 (m, 2 H) 7.68-7.79 (m, 1 H) 7.84-7.93 (m, 1 H) 8.13-8.25 (m, 1 H) 8.33-8.44 (m, 1 H) 8.60-8.73 (m, 1 H). MS (ESI, positive) m/z: 516.9.

Example 48

4-(2-((2-Methoxyethyl)Amino)-4-(Trifluoromethyl)Phenyl)-N-(Pyrimidin-4-Yl)-3,4-Dihydro-2H-Benzo[B][1,4]Oxazine-7-Sulfonamide

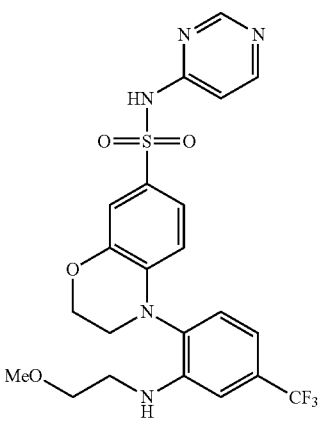 [SMILES: COCCNc1cc(C(F)(F)F)ccc1N1CCOc2cc(S(=O)(=O)Nc3ccncn3)ccc21]

To a 5-mL septa/cap vial was charged with 4-(2-bromo-4-(trifluoromethyl)phenyl)-N-(pyrimidin-4-yl)-3,4-dihydro-2H-benzo[b][1,4]oxazine-7-sulfonamide (EXAMPLE 47, 0.050 g, 0.097 mmol), tris (dibenzylideneacetone)dipalladium (0) (0.018 g, 0.019 mmol), (+/−)-2,2'-bis(diphenylphosphino)-1,1-binaphthalene (0.024 g, 0.039 mmol) and cesium carbonate (0.031 mL, 0.388 mmol). The vial was flushed with nitrogen gas. Dioxane (0.970 mL) followed by 2-methoxyethanamine (10.12 μL, 0.116 mmol) were added via syringe. The resulting reaction mixture was heated to 95° C. on a hot plate for 18 h. The reaction mixture was absorbed onto a 5 g plug of silica gel and eluted through a silica gel column (12 g), eluting with a gradient of 0% to 60% MeOH in CH$_2$CL$_2$. The product was further purified by reverse-phase preparative HPLC using 0.1% TFA in CH$_3$CN/H$_2$O, gradient 10% to 85% over 15 min to provide 4-(2-(2-methoxyethyl)amino)-4-(trifluoromethyl)phenyl)-N-(pyrimidin-4-yl)-3,4-dihydro-2H-benzo[b][1,4]oxazine-7-sulfonamide (0.010 g, 0.020 mmol) as a white solid. $^1$H NMR (400 MHz, DMSO-d$_6$) δ ppm 3.19 (s, 3 H) 3.32 (br. s., 2 H) 3.42 (d, J=3.42 Hz, 2 H) 3.64 (br. s., 2 H) 4.29-4.41 (m, 1 H) 4.44-4.57 (m, 1 H) 6.17 (d, J=8.51 Hz, 1 H) 6.86-7.15 (m, 4 H) 7.18-7.42 (m, 4 H) 8.42 (br. s., 1 H) 8.68 (s, 1 H) MS (ESI, positive) m/z: 510.0.

Example 49

4-(2-Cyano-4-(Trifluoromethyl)Phenyl)-N-(Thiazol-2-Yl)-3,4-Dihydro-2H-Benzo[B][1,4]Oxazine-7-Sulfonamide

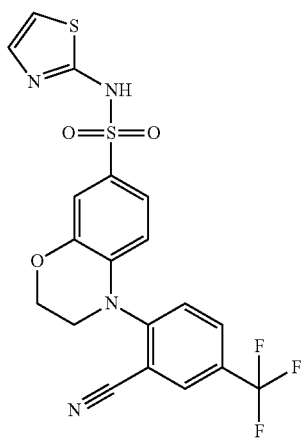 [SMILES: N#Cc1cc(C(F)(F)F)ccc1N1CCOc2cc(S(=O)(=O)Nc3nccs3)ccc21]

A microwave vial was charged with N-(4-methoxybenzyl)-N-(thiazol-2-yl)-3,4-dihydro-2H-benzo[b][1,4]oxazine-7-sulfonamide (INTERMEDIATE M, 0.150 g, 0.359 mmol), xantphos (0.042 g, 0.072 mmol), 2-bromo-5-(trifluoromethyl)benzonitrile (Apollo Scientific) (0.135 g, 0.539 mmol), Pd$_2$(dba)$_3$ (0.033 g, 0.036 mmol) and sodium tert-butoxide (0.069 g, 0.719 mmol). The mixture was diluted with toluene (3.59 mL), purged with nitrogen, and heated at 130° C. in the microwave for 1.5 h. After cooling to rt, trifluoroacetic acid (0.554 mL, 7.19 mmol) was carefully added and the reaction was stirred for 1 h. The reaction mixture was diluted with water, and washed with DCM (×2). organics were dried via phase separator, and concentrated under a vacuum. The material was then purified via reverse-phase preparative HPLC, 0.1% TFA in CH$_3$CN/H$_2$O, gradient 25% to 90% over 25 min to provide 4-(2-cyano-4-(trifluoromethyl)phenyl)-N-(thiazol-2-yl)-3,4-dihydro-2H-benzo[b][1,4]oxazine-7-sulfonamide (0.045 g, 0.096 mmol) as an off-white solid. $^1$H NMR (400 MHz, DMSO-d$_6$) δ ppm 3.82-3.91 (m, 2 H) 4.28-4.39 (m, 2 H) 6.76-6.85 (m, 2 H) 7.18 (dd, J=8.56, 2.10 Hz, 1 H) 7.21-7.28 (m, 2 H) 7.71 (d, J=8.70 Hz, 1 H) 8.06 (dd, J=8.71, 2.15 Hz, 1 H) 8.40 (d, J=1.27 Hz, 1 H) 12.66 (br. s., 1 H). m/z (ESI) 467.0 (M+H)$^+$.

Example 50

4-(2-(4-Methylpiperazin-1-Yl)-4-(Trifluoromethyl)Phenyl)-N-(Thiazol-2-Yl)-3,4-Dihydro-2H-Benzo[B][1,4]Oxazine-7-Sulfonamide 2,2,2-Trifluoroacetate

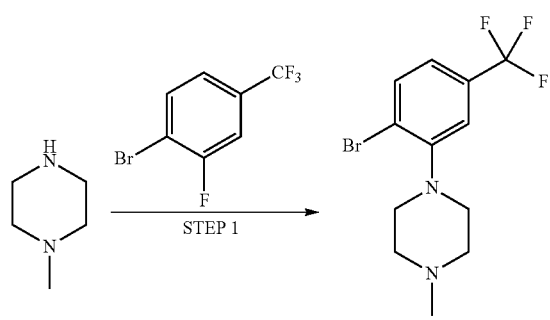

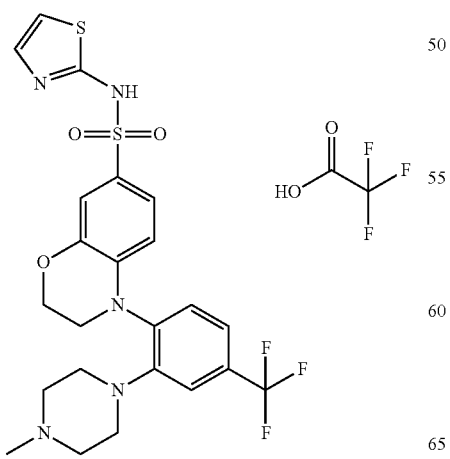

Step 1: 1-(2-Bromo-5-(Trifluoromethyl)Phenyl)-4-Methylpiperazine

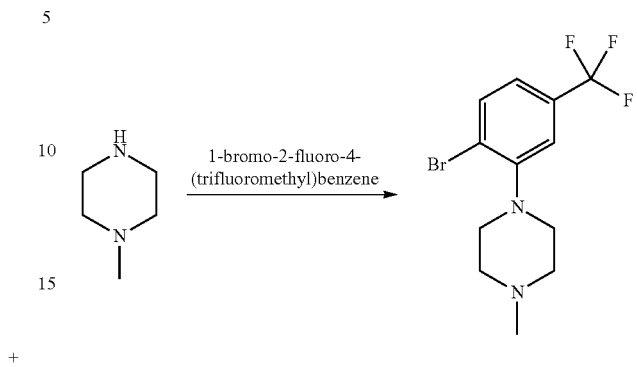

A microwave vial was charged with 1-methylpiperazine (1.371 mL, 12.35 mmol) and 4-bromo-3-fluorobenzotrifluoride (1.000 mL, 4.12 mmol), and was heated under microwave irradiation at 180° C. for 90 minutes. The reaction was concentrated under a vacuum, and the solids were then filtered and washed with DCM (solids contained only minor amounts of product). The filtrate was then concentrated under a vacuum to yield 1-(2-bromo-5-(trifluoromethyl)phenyl)-4-methylpiperazine, mixed with starting bromide. Material was used without further purification.

Step 2, Example 50: 4-(2-(4-Methylpiperazin-1-Yl)-4-(Trifluoromethyl)Phenyl)-N-(Thiazol-2-Yl)-3,4-Dihydro-2H-Benzo[B][1,4]Oxazine-7-Sulfonamide 2,2,2-Trifluoroacetate

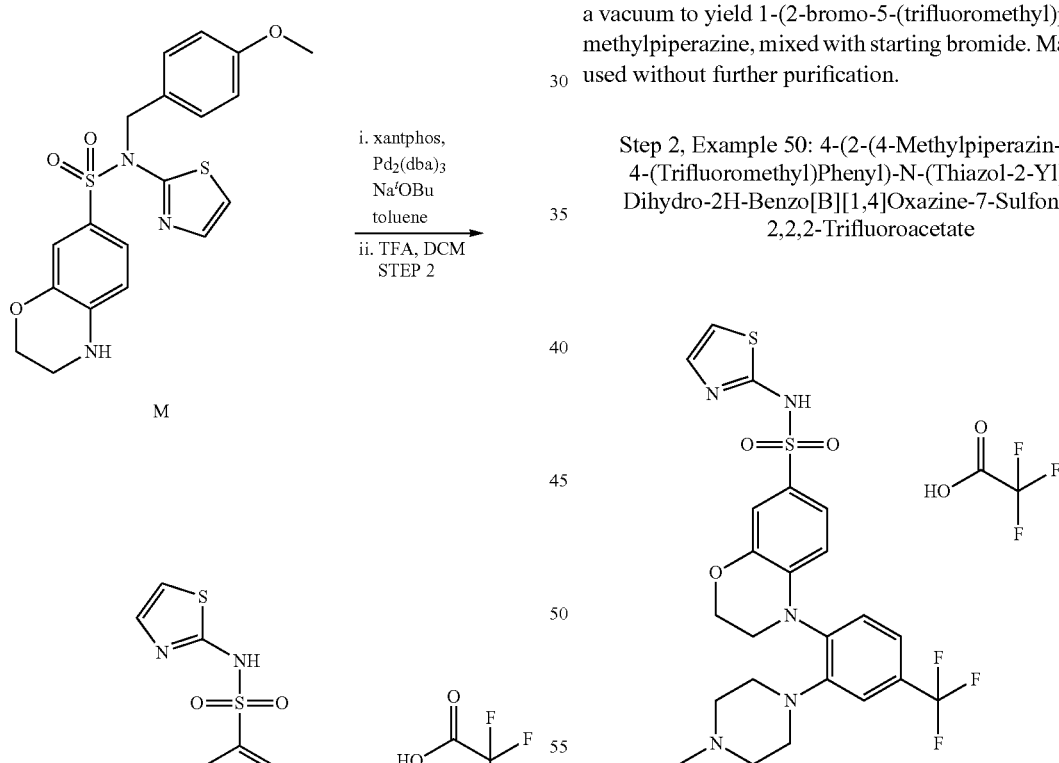

EXAMPLE 50 was synthesized in the same manner as EXAMPLE 49, instead using 1-(2-bromo-5-(trifluoromethyl)phenyl)-4-methylpiperazine in place of 2-bromo-5-(trifluoromethyl)benzonitrile. $^1$H NMR (400 MHz, DMSO-d$_6$) δ ppm 2.76 (s, 3 H) 2.82-3.14 (m, 4 H) 3.34-3.85 (m, 6 H) 4.23-4.35 (m, 2 H) 6.58 (d, J=8.41 Hz, 1 H) 6.80 (d, J=4.60 Hz, 1 H) 7.13-7.21 (m, 2 H) 7.24 (d, J=4.60 Hz, 1 H) 7.35-7.50 (m, 3 H) 9.74 (br. s., 1 H) 12.60 (br. s., 1 H). m/z (ESI) 540.0 (M+H)$^+$.

Example 51

4-(2-(1-Methyl-1,2,3,6-Tetrahydropyridin-4-Yl)-4-(Trifluoromethyl)Phenyl)-N-(Pyrimidin-4-Yl)-3,4-Dihydro-2H-Benzo[B][1,4]Oxazine-7-Sulfonamide

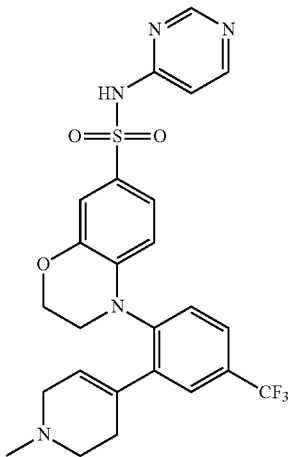 [SMILES: CN1CC=C(c2cc(C(F)(F)F)ccc2N2CCOc3cc(S(=O)(=O)Nc4ccncn4)ccc32)CC1]

EXAMPLE 51 was prepared from N-(pyrimidin-4-yl)-4-(2-(1,2,3,6-tetrahydropyridin-4-yl)-4-(trifluoromethyl)phenyl)-3,4-dihydro-2H-benzo[b][1,4]oxazine-7-sulfonamide (EXAMPLE 45) as described in EXAMPLE 41. $^1$H NMR (400 MHz, DMSO-d$_6$) δ ppm 2.19 (s, 3 H) 2.26-2.46 (m, 4 H) 2.93 (br. s., 2 H) 3.58 (d, J=14.28 Hz, 2 H) 4.16-4.34 (m, 2 H) 5.78 (br. s., 1 H) 6.37 (d, J=8.51 Hz, 1 H) 6.75 (d, J=5.58 Hz, 1 H) 7.16 (dd, J=8.56, 2.01 Hz, 1 H) 7.22 (s, 1 H) 7.51 (d, J=8.31 Hz, 1 H) 7.57 (s, 1 H) 7.68 (d, J=6.55 Hz, 1 H) 8.07 (d, J=6.16 Hz, 1 H) 8.43 (s, 1 H); m/z (ESI) 533.1 (M+2 H)$^+$.

Example 52

4-(4-Chloro-2-(1,2,3,6-Tetrahydropyridin-4-Yl)Phenyl)-N-(Thiazol-2-Yl)-3,4-Dihydro-2H-Benzo[B][1,4]Oxazine-7-Sulfonamide

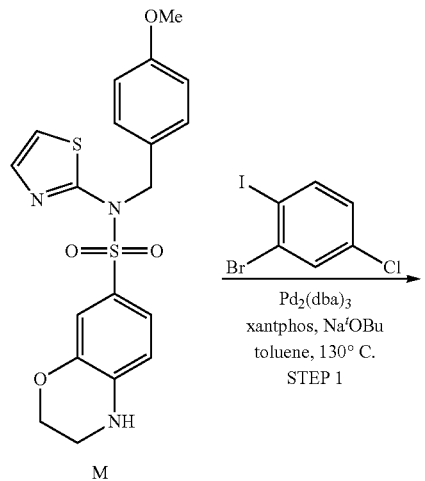

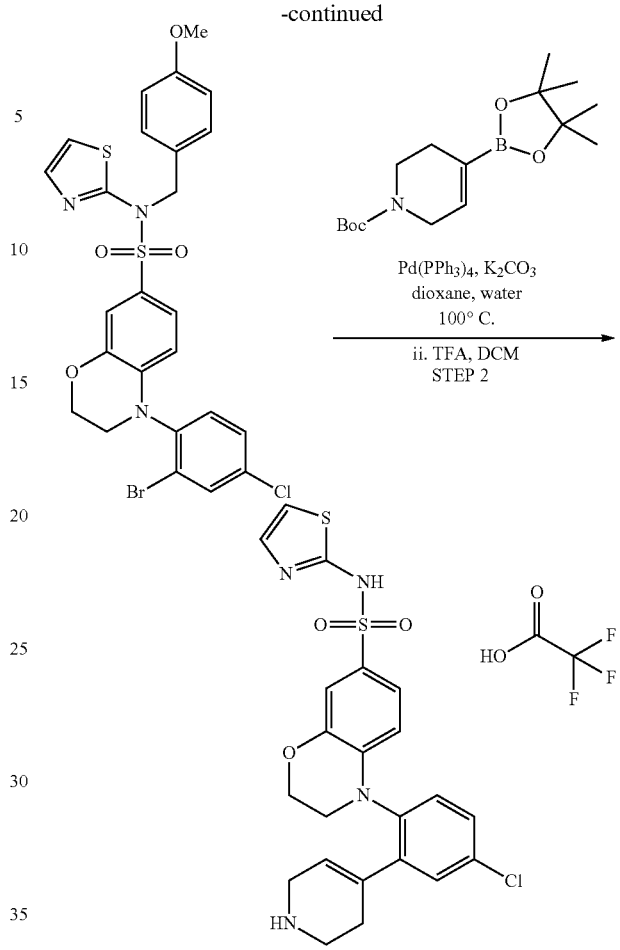

Step 1: 4-(2-Bromo-4-Chlorophenyl)-N-(4-Methoxybenzyl)-N-(Thiazol-2-Yl)-3,4-Dihydro-2H-Benzo[B][1,4]Oxazine-7-Sulfonamide

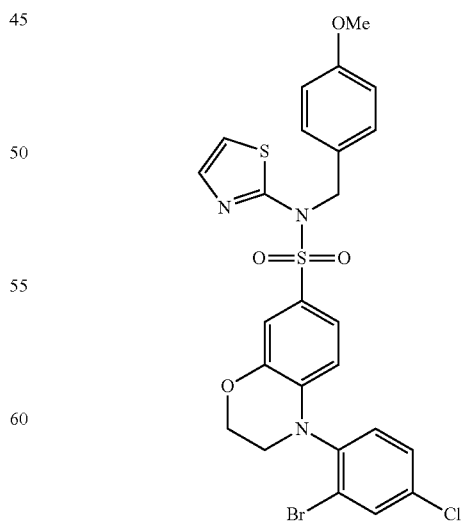

A microwave vial was charged with INTERMEDIATE M (0.500 g, 1.198 mmol), xantphos (0.139 g, 0.240 mmol), 2-bromo-4-chloro-1-iodobenzene (0.570 g, 1.796 mmol), Pd₂(dba)₃ (0.110 g, 0.120 mmol) and sodium tert-butoxide (0.230 g, 2.395 mmol). The mixture was diluted with toluene (11.98 mL), and purged with nitrogen, and stirred at 130° C. in the microwave for 15 minutes. After completion, the reaction was diluted with water, and washed with DCM. The organics were dried using a phase separator and concentrated under a vacuum. The material was then purified via silica gel MPLC, eluting with 0 to 50% ethyl acetate in heptanes to yield 4-(2-bromo-4-chlorophenyl)-N-(4-methoxybenzyl)-N-(thiazol-2-yl)-3,4-dihydro-2H-benzo[b][1,4]oxazine-7-sulfonamide (0.576 g, 0.949 mmol) as a light yellow solid.

Step 2, Example 52: 4-(4-Chloro-2-(1,2,3,6-Tetrahydropyridin-4-Yl)Phenyl)-N-(Thiazol-2-Yl)-3,4-Dihydro-2H-Benzo[B][1,4]Oxazine-7-Sulfonamide 2,2,2-Trifluoroacetate

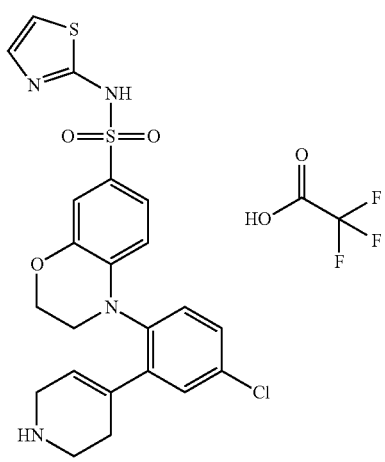 [SMILES: O=S(=O)(Nc1nccs1)c1ccc2c(c1)OCCN2c1ccc(Cl)cc1C1=CCNCC1 ; O=C(O)C(F)(F)F]

A microwave vial was charged with 4-(2-bromo-4-chlorophenyl)-N-(4-methoxybenzyl)-N-(thiazol-2-yl)-3,4-dihydro-2H-benzo[b][1,4]oxazine-7-sulfonamide (0.576 g, 0.949 mmol), (N-tert-butoxycarbonyl)-1,2,3,6-tetrahydropyridine-4-boronic acid pinacol ester (0.293 g, 0.949 mmol), tetrakis(triphenylphosphine)palladium(0) (0.110 g, 0.095 mmol), and K₂CO₃ (0.656 g, 4.75 mmol). The solids were diluted with dioxane (6.33 mL) and water (3.16 mL), and the reaction was heated under microwave irradiation at 100° C. for 30 minutes. The reaction was diluted with water and DCM, and the layers separated. The aqueous was washed once more with DCM, and the organics were combined and dried using a phase separator to yield material. The material was then further purified via silica gel MPLC eluting with 0 to 100% ethyl acetate in heptane to yield tert-butyl 4-(5-chloro-2-(7-(N-(4-methoxybenzyl)-N-(thiazol-2-yl)sulfamoyl)-2H-benzo[b][1,4]oxazin-4(3H)-yl)phenyl)-5,6-dihydropyridine-1(2H)-carboxylate as a red oil. A portion of material (117 mg) was diluted with 1.00 mL of DCM, and TFA (1.00 mL) and the reaction was stirred at RT for 5 minutes. The material was concentrated under a vacuum and purified via HPLC to yield 4-(4-chloro-2-(1,2,3,6-tetrahydropyridin-4-yl)phenyl)-N-(thiazol-2-yl)-3,4-dihydro-2H-benzo[b][1,4]oxazine-7-sulfonamide 2,2,2-trifluoroacetate (0.073 g, 0.121 mmol, 12.76% yield) as a white solid. ¹H NMR (400 MHz, DMSO-d₆) δ ppm 2.30-2.43 (m, 1 H) 2.54 (m, J=0.60 Hz, 1 H) 3.15-3.23 (m, 2 H) 3.52 (m, J=3.30 Hz, 2 H) 3.63-3.70 (m, 2 H) 4.25-4.32 (m, 2 H) 5.82 (br. s., 1 H) 6.33 (d, J=8.31 Hz, 1 H) 6.79 (d, J=4.50 Hz, 1 H) 7.09-7.15 (m, 2 H) 7.23 (d, J=4.60 Hz, 1 H) 7.36-7.41 (m, 2 H) 7.45-7.50 (m, 1 H) 8.79 (br. s., 2 H) 12.55 (br. s., 1H). m/z (ESI) 489.0 (M+H)⁺.

Example 53

4-(2-(Pyridin-4-Yl)-4-(Trifluoromethyl)Phenyl)-N-(Thiazol-2-Yl)-3,4-Dihydro-2H-Benzo[B][1,4]Oxazine-7-Sulfonamide 2,2,2-Trifluoroacetate

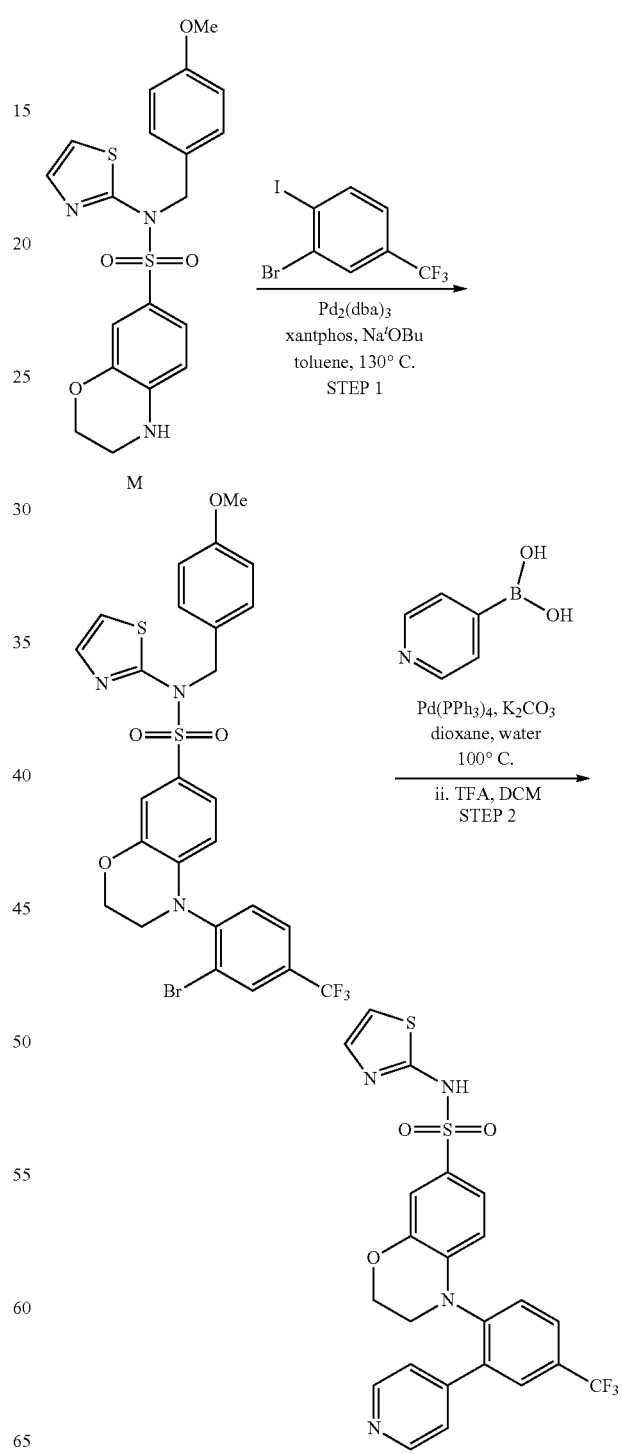

Step 1: 4-(2-Bromo-4-(Trifluoromethyl)Phenyl)-N-(4-Methoxybenzyl)-N-(Thiazol-2-Yl)-3,4-Dihydro-2H-Benzo[B][1,4]Oxazine-7-Sulfonamide

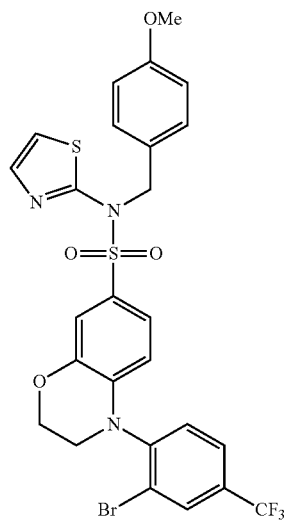 [SMILES: COc1ccc(CN(c2nccs2)S(=O)(=O)c2ccc3c(c2)OCCN3c2ccc(C(F)(F)F)cc2Br)cc1]

A microwave vial was charged with INTERMEDIATE M (0.573 g, 1.372 mmol), Xantphos (0.159 g, 0.274 mmol), 2-bromo-1-iodo-4-trifluoromethyl-benzene (0.722 g, 2.059 mmol), Pd$_2$(dba)$_3$ (0.126 g, 0.137 mmol) and sodium tert-butoxide (0.264 g, 2.74 mmol). The mixture was diluted with toluene (13.72 mL), and purged with nitrogen, and stirred at 130° C. in the microwave for 30 minutes. The reaction was diluted with water, and washed with DCM. The organics were dried using a phase separator, and concentrated under a vacuum. The material was then purified via silica gel MPLC, eluting with 0 to 50% ethyl acetate in heptanes to yield 4-(2-bromo-4-(trifluoromethyl)phenyl)-N-(4-methoxybenzyl)-N-(thiazol-2-yl)-3,4-dihydro-2H-benzo[b][1,4]oxazine-7-sulfonamide as a light yellow solid.

Step 2, Example 53: 4-(2-(Pyridin-4-Yl)-4-(Trifluoromethyl)Phenyl)-N-(Thiazol-2-Yl)-3,4-Dihydro-2H-Benzo[B][1,4]Oxazine-7-Sulfonamide 2,2,2-Trifluoroacetate

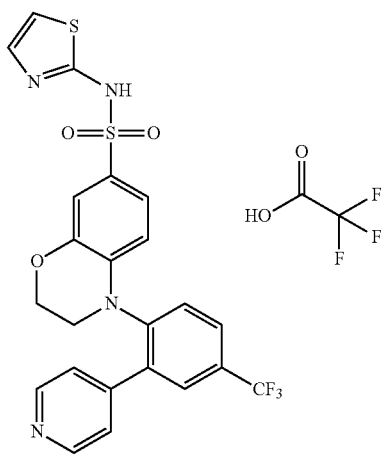 [SMILES: O=S(=O)(Nc1nccs1)c1ccc2c(c1)OCCN2c1ccc(C(F)(F)F)cc1-c1ccncc1 ; O=C(O)C(F)(F)F]

EXAMPLE 53 was obtained in the same manner as STEP 2 of EXAMPLE 52, using pyridin-4-ylboronic acid instead of (N-tert-butoxycarbonyl)-1,2,3,6-tetrahydropyridine-4-boronic acid pinacol ester. $^1$H NMR (400 MHz, DMSO-d$_6$) δ ppm 3.33 (m, 1 H) 3.55-3.67 (m, 1 H) 4.09-4.19 (m, 1 H) 4.20-4.30 (m, 1 H) 6.55 (d, J=8.22 Hz, 1 H) 6.79 (d, J=4.60 Hz, 1 H) 7.03-7.10 (m, 2 H) 7.23 (d, J=4.69 Hz, 1 H) 7.70-7.81 (m, 3 H) 7.89-7.93 (m, 1 H) 7.95 (m, J=8.40 Hz, 1H) 8.73 (d, J=6.06 Hz, 2 H) 12.58 (br. s., 1 H). m/z (ESI) 519.0 (M+H)$^+$.

Example 54

4-(2-(Pyrimidin-5-Yl)-4-(Trifluoromethyl)Phenyl)-N-(Thiazol-2-Yl)-3,4-Dihydro-2H-Benzo[B][1,4]Oxazine-7-Sulfonamide 2,2,2-Trifluoroacetate

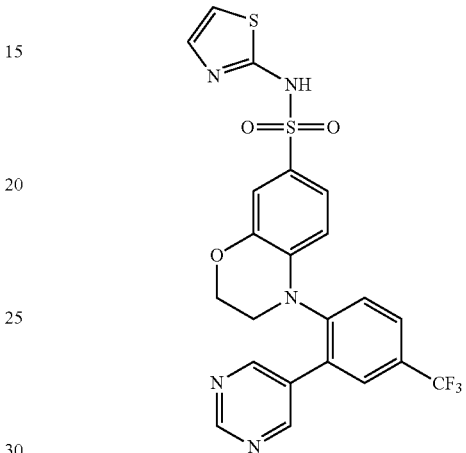

EXAMPLE 54 was synthesized in the same manner as STEP 2, EXAMPLE 52 using pyrimidin-5-ylboronic acid instead of (N-tert-butoxycarbonyl)-1,2,3,6-tetrahydropyridine-4-boronic acid pinacol ester. $^1$H NMR (400 MHz, DMSO-d$_6$) δ ppm 3.47 (m, J=10.50 Hz, 1 H) 3.70-3.84 (m, 1 H) 4.03-4.18 (m, 1 H) 4.32 (m, J=10.00 Hz, 1 H) 6.37 (d, J=8.31 Hz, 1 H) 6.80 (d, J=4.50 Hz, 1 H) 6.94-7.09 (m, 2 H) 7.23 (d, J=4.60 Hz, 1 H) 7.73 (d, J=8.22 Hz, 1 H) 7.88-8.03 (m, 2 H) 8.90 (s, 2 H) 9.05 (s, 1 H) 12.59 (br. s., 1 H). m/z (ESI) 520.0 (M+H)$^+$.

Example 55

4-(2-Chloro-4-(Trifluoromethyl)Phenyl)-N-(Isoxazol-5-Yl)-3,4-Dihydro-2H-Benzo[B][1,4]Oxazine-7-Sulfonamide

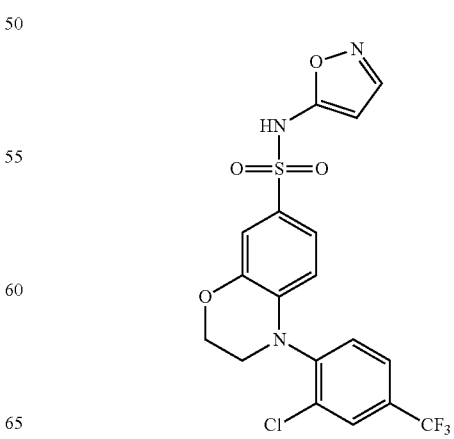

EXAMPLE 55 was prepared in the same manner as INTERMEDIATE G using isoxazol-5-ylamine (Ryan Scientific, Inc., Mt. Pleasant, S.C.) instead of 4-aminopyrimidine. $^1$H NMR (400 MHz, DMSO-d$_6$) δ ppm 3.59-3.93 (m, 2 H) 4.37 (br. s., 2 H) 7.20 (dd, J=8.56, 2.20 Hz, 1 H) 7.25 (d, J=2.25 Hz, 1 H) 7.74-7.80 (m, 1 H) 7.86 (dd, J=8.36, 1.91 Hz, 1 H) 8.09 (d, J=1.56 Hz, 1 H) 8.35 (d, J=1.86 Hz, 1 H); m/z (ESI) 460.1 (M+H)$^+$.

Example 56

4-(4-Chloro-2-Cyanophenyl)-N-(Thiazol-2-Yl)-3,4-Dihydro-2H-Benzo[B][1,4]Oxazine-7-Sulfonamide

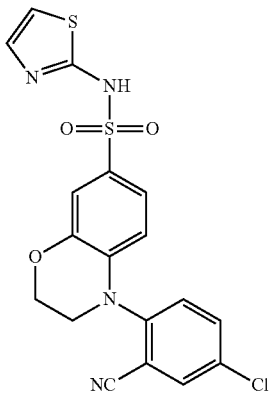 [SMILES: N#Cc1cc(Cl)ccc1N1CCOc2cc(S(=O)(=O)Nc3nccs3)ccc21]

EXAMPLE 56 was synthesized in the same manner as EXAMPLE 41, using 2-bromo-5-chlorobenzonitrile instead of 1-bromo-3-chlorobenzene. $^1$H NMR (400 MHz, DMSO-d$_6$) δ ppm 3.71-3.80 (m, 2 H) 4.29-4.36 (m, 2 H) 6.56 (d, J=8.61 Hz, 1 H) 6.80 (d, J=4.50 Hz, 1 H) 7.15 (dd, J=8.51, 2.05 Hz, 1 H) 7.19 (d, J=2.15 Hz, 1 H) 7.23 (d, J=4.60 Hz, 1 H) 7.58 (d, J=8.80 Hz, 1 H) 7.84 (dd, J=8.75, 2.59 Hz, 1 H) 8.14 (d, J=2.54 Hz, 1 H) 12.63 (br. s., 1 H). m/z (ESI) 433.0 (M+H)$^+$.

Example 57

4-(2-Cyanophenyl)-N-(1,2,4-Thiadiazol-5-Yl)-3,4-Dihydro-2H-Benzo[B][1,4]Oxazine-7-Sulfonamide

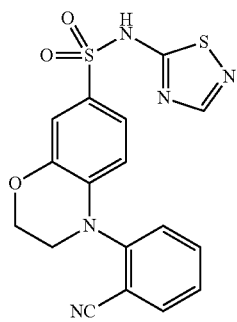 [SMILES: N#Cc1ccccc1N1CCOc2cc(S(=O)(=O)Nc3ncns3)ccc21]

A vial was charged with N-(1,2,4-thiadiazol-5-yl)-3,4-dihydro-2H-benzo[b][1,4]oxazine-7-sulfonamide (INTERMEDIATE Z, 36 mg, 0.121 mmol), 2-bromobenzonitrile (32.9 mg, 0.181 mmol, Sigma-Aldrich, St. Louis, Mo.), Xantphos (13.96 mg, 0.024 mmol), Pd$_2$(dba)$_3$ (11.05 mg, 0.012 mmol), cesium carbonate (118 mg, 0.362 mmol), and toluene (1207 nl). The vial was sealed and placed in a 100° C. heating bath for 20 min, then 1,4-dioxane (1 mL) and cesium carbonate (180 mg) were added. The vial was heated overnight at 120° C., then the mixture was diluted with THF, EtOAc, and 1N aq. HCl. The mixture was extracted with EtOAC (3×), and the combined organic extracts were dried over sodium sulfate, filtered, and concentrated. The product was purified by chromatography on silica gel (12 g column, 0 to 10% MeOH/DCM to give 4-(2-cyanophenyl)-N-(1,2,4-thiadiazol-5-yl)-3,4-dihydro-2H-benzo[b][1,4]oxazine-7-sulfonamide (9.98 mg, 0.025 mmol) as an off-white solid. $^1$H NMR (400 MHz, DMSO-d$_6$) δ=8.43 (s, 1 H), 8.01-7.92 (m, 1 H), 7.80 (dt, J=1.6, 7.8 Hz, 1 H), 7.59 (d, J=7.6 Hz, 1 H), 7.50 (dt, J=1.0, 7.7 Hz, 1 H), 7.23-7.05 (m, 2 H), 6.47 (d, J=8.4 Hz, 1 H), 4.40-4.24 (m, 2 H), 3.83-3.73 (m, 2 H). m/z (ESI) 400.2 (M+H)$^+$.

Example 58

4-(2-Cyanophenyl)-N-(Thiazol-2-Yl)-3,4-Dihydro-2H-Benzo[B][1,4]Oxazine-7-Sulfonamide 2,2,2-Trifluoroacetate

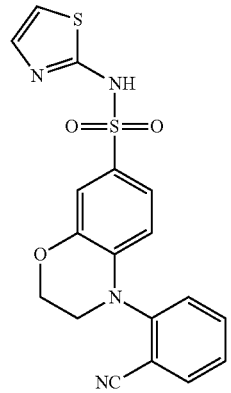 [SMILES: N#Cc1ccccc1N1CCOc2cc(S(=O)(=O)Nc3nccs3)ccc21]

EXAMPLE 58 was synthesized in the same manner as EXAMPLE 49, using 2-iodobenzonitrile instead of 2-bromo-5-(trifluoromethyl)benzonitrile. $^1$H NMR (400 MHz, DMSO-d$_6$) δ ppm 3.74-3.81 (m, 2 H) 4.31-4.37 (m, 2 H) 6.47 (d, J=8.51 Hz, 1 H) 6.80 (d, J=4.60 Hz, 1 H) 7.15 (dd, J=8.51, 2.15 Hz, 1 H) 7.19 (d, J=2.05 Hz, 1 H) 7.23 (d, J=4.60 Hz, 1 H) 7.48 (td, J=7.65, 1.03 Hz, 1 H) 7.57 (d, J=7.53 Hz, 1 H) 7.79 (td, J=7.87, 1.56 Hz, 1 H) 7.95 (dd, J=7.78, 1.42 Hz, 1 H) 12.62 (br. s., 1 H). m/z (ESI) 399.0 (M+H)$^+$.

Example 59

4-(2-(1,2,3,6-Tetrahydropyridin-4-Yl)Phenyl)-N-(Thiazol-2-Yl)-3,4-Dihydro-2H-Benzo[B][1,4]Oxazine-7-Sulfonamide 2,2,2-Trifluoroacetate

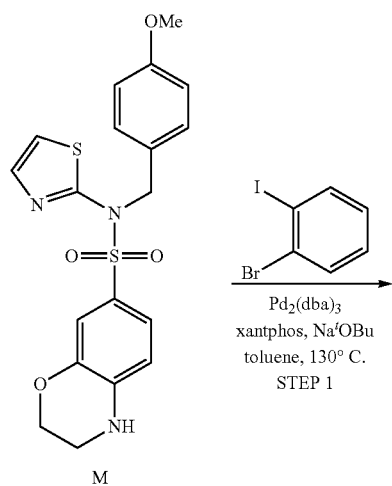

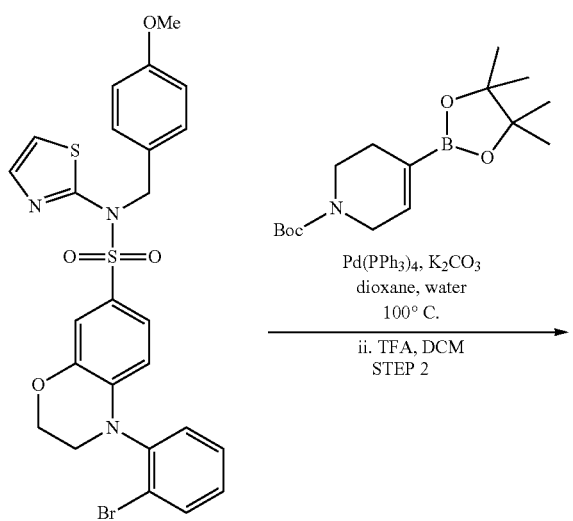

Step 1: 4-(2-Bromophenyl)-N-(4-Methoxybenzyl)-N-(Thiazol-2-Yl)-3,4-Dihydro-2H-Benzo[B][1,4]Oxazine-7-Sulfonamide

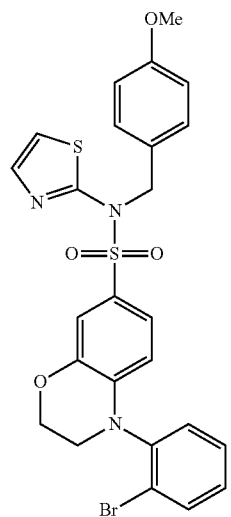 [SMILES: COc1ccc(CN(c2nccs2)S(=O)(=O)c2ccc3c(c2)OCCN3c2ccccc2Br)cc1]

A microwave vial was charged with INTERMEDIATE M (0.100 g, 0.240 mmol), Xantphos (0.028 g, 0.048 mmol), 1-bromo-2-iodobenzene (0.045 mL, 0.359 mmol), Pd$_2$(dba)$_3$ (0.022 g, 0.024 mmol) and sodium tert-butoxide (0.046 g, 0.479 mmol). The mixture was diluted with toluene (2.395 mL), and purged with nitrogen, and stirred at 130° C. in the microwave for 20 minutes. After completion, the reaction was diluted with water, and washed with DCM. The organics were dried via phase separator, and concentrated under a vacuum. The material was then purified via 2 g SCX column. The material was concentrated to provide 4-(2-bromophenyl)-N-(4-methoxybenzyl)-N-(thiazol-2-yl)-3,4-dihydro-2H-benzo[b][1,4]oxazine-7-sulfonamide, which was taken forward without further purification.

Step 2, Example 59: 4-(2-(1,2,3,6-Tetrahydropyridin-4-Yl)Phenyl)-N-(Thiazol-2-Yl)-3,4-Dihydro-2H-Benzo[B][1,4]Oxazine-7-Sulfonamide 2,2,2-Trifluoroacetate

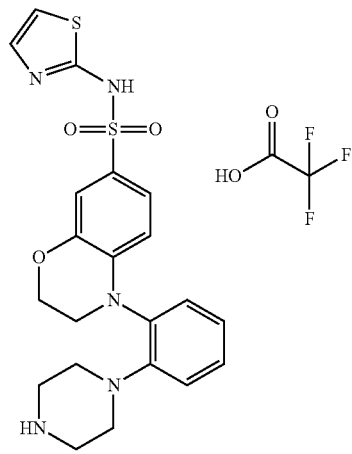 [SMILES: O=S(=O)(Nc1nccs1)c1ccc2c(c1)OCCN2c1ccccc1N1CCNCC1 ; O=C(O)C(F)(F)F]

The compound was synthesized in the same manner as STEP 2 of the synthesis of EXAMPLE 52. $^1$H NMR (400 MHz, DMSO-d$_6$) δ ppm 2.27-2.45 (m, 1 H) 2.53-2.70 (m, 1 H) 3.19 (br. s., 2 H) 3.49-3.58 (m, 2 H) 3.63-3.70 (m, 2 H) 4.24-4.35 (m, 2 H) 5.74 (br. s., 1 H) 6.29 (d, J=8.41 Hz, 1 H)

6.78 (d, J=4.50 Hz, 1 H) 7.07-7.15 (m, 2 H) 7.23 (d, J=4.60 Hz, 1 H) 7.30-7.45 (m, 4 H) 8.77 (br. s., 2H) 12.53 (br. s., 1 H). m/z (ESI) 455.0 (M+H)⁺.

Example 60

4-(2-Bromo-4-(Trifluoromethyl)Phenyl)-N-(Pyridin-2-Yl)-3,4-Dihydro-2H-Benzo[B][1,4]Oxazine-7-Sulfonamide

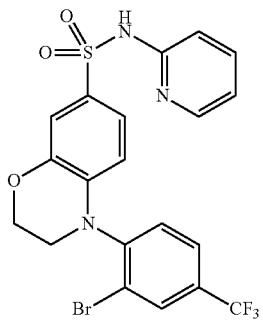 [SMILES: O=S(=O)(Nc1ccccn1)c1ccc2c(c1)OCCN2c1ccc(C(F)(F)F)cc1Br]

A round bottom flask was charged with 4-(2-bromo-4-(trifluoromethyl)phenyl)-3,4-dihydro-2H-benzo[b][1,4]oxazine-7-sulfonyl chloride (INTERMEDIATE C, 330.62 mg, 0.724 mmol), pyridin-2-amine (82 mg, 0.869 mmol), and THF (3620 µl) to give a clear, lightly-colored solution. The flask was cooled in an ice-bath for 5 min, then lithium bis(trimethylsilyl)amide (1M in THF) (1520 µl, 1.520 mmol) was added dropwise over 30 s to give a light-yellow solution. The mixture was allowed to warm to room temperature with the ice-water bath. The mixture was quenched by the addition of aq. 1N hydrochloric acid and extracted with EtOAc (3×). The combined organic extracts were dried over sodium sulfate, filtered, and concentrated. The residue was purified by chromatography on a 40 g silica gel column with 0 to 5% MeOH/DCM to 4-(2-bromo-4-(trifluoromethyl)phenyl)-N-(pyridin-2-yl)-3,4-dihydro-2H-benzo[b][1,4]oxazine-7-sulfonamide (278.5 mg, 0.541 mmol). ¹H NMR (400 MHz, DMSO-d₆) δ=11.97-10.63 (m, 1 H), 8.19 (d, J=1.8 Hz, 1 H), 8.06 (d, J=4.3 Hz, 1 H), 7.88 (dd, J=2.0, 8.4 Hz, 1 H), 7.75-7.66 (m, 2 H), 7.29 (d, J=2.1 Hz, 1 H), 7.21 (dd, J=2.2, 8.6 Hz, 1 H), 7.12 (d, J=8.6 Hz, 1 H), 6.89 (t, J=6.2 Hz, 1 H), 6.23 (d, J=8.5 Hz, 1 H), 4.35 (d, J=12.0 Hz, 2 H), 3.79-3.62 (m, 2 H). m/z (ESI) 514.2 (M+H)⁺.

Example 61

4-(2-Bromo-4-(Trifluoromethyl)Phenyl)-N-(Thiazol-4-Yl)-3,4-Dihydro-2H-Benzo[B][1,4]Oxazine-7-Sulfonamide

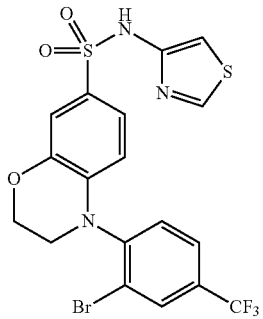

A round-bottom flask was charged with 4-(2-bromo-4-(trifluoromethyl)phenyl)-3,4-dihydro-2H-benzo[b][1,4]oxazine-7-sulfonyl chloride (INTERMEDIATE C, 299.84 mg, 0.657 mmol), thiazol-4-amine (79 mg, 0.788 mmol), and THF (3283 nl) to give a brown mixture. The flask was cooled in an ice-bath for 10 min, then lithium bis(trimethylsilyl)amide (1M in THF) (1379 µl, 1.379 mmol) was added dropwise over 30 s. After 30 min, the cooling bath was removed, and the mixture was allowed to warm to room temperature. The reaction mixture was quenched by the addition of aq. 1N hydrochloric acid and a small amount of brine and extracted with EtOAc (3×, emulsion). The combined organic extracts were dried over sodium sulfate, filtered, and concentrated. The residue was purified by silica gel chromatography on a 40 g column with 0 to 10% MeOH/DCM. The desired product was repurified again by chromatography on a 40 g silica gel column, this time with 0 to 40% EtOAc/Heptane to give 4-(2-bromo-4-(trifluoromethyl)phenyl)-N-(thiazol-4-yl)-3,4-dihydro-2H-benzo[b][1,4]oxazine-7-sulfonamide (73.1 mg, 0.140 mmol) as a cream-colored solid. ¹H NMR (400 MHz, DMSO-d₆) δ=10.88 (s, 1 H), 8.88 (d, J=2.2 Hz, 1 H), 8.20 (d, J=1.5 Hz, 1 H), 7.89 (dd, J=1.6, 8.5 Hz, 1 H), 7.73 (d, J=8.4 Hz, 1 H), 7.25 (d, J=2.2 Hz, 1 H), 7.16 (dd, J=2.2, 8.6 Hz, 1 H), 6.96 (d, J=2.2 Hz, 1 H), 6.22 (d, J=8.6 Hz, 1 H), 4.36 (d, J=15.8 Hz, 2 H), 3.78-3.63 (m, 2 H). m/z (ESI) 520.2 (M+H)⁺.

Example 62

N-(Pyridin-2-Yl)-4-(2-(1,2,3,6-Tetrahydropyridin-4-Yl)-4-(Trifluoromethyl)Phenyl)-3,4-Dihydro-2H-Benzo[B][1,4]Oxazine-7-Sulfonamide

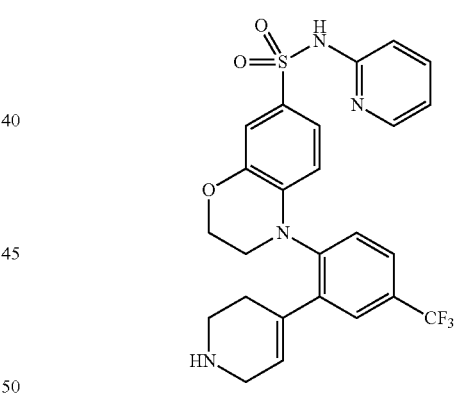

A vial was charged with 4-(2-bromo-4-(trifluoromethyl)phenyl)-N-(pyridin-2-yl)-3,4-dihydro-2H-benzo[b][1,4]oxazine-7-sulfonamide (EXAMPLE 60, 84 mg, 0.163 mmol), tert-butyl 4-(4,4,5,5-tetramethyl-1,3,2-dioxaborolan-2-yl)-5,6-dihydropyridine-1(2H)-carboxylate (76 mg, 0.245 mmol), Pd(AmPhos)₂Cl₂ (5.78 mg, 8.17 µmol), potassium phosphate (104 mg, 0.490 mmol), dioxane (817 µl), and water (272 µl). The vial as sealed and heated in a microwave reactor for 2.5 h at 100° C. Additional portions of boronic acid (200 mg) and potassium phosphate (150 mg) were added, and the mixture was heated for 1 h at 100° C. in the microwave. An additional portion of catalyst (9.5 mg) was added, and the vial was heated in the microwave for 1 h at 120° C. The mixture was extracted with EtOAc (3×). The combined organic extracts were concentrated, and the residue was purified by chromatography on silica gel (12 g column, 25 to 75% EtOAc/

Heptane) to give about 71 mg of a clear oil. The residue was dissolved in DCM (1 mL) and TFA (0.5 mL). After 1 h, the mixture was concentrated. The residue was dissolved in MeOH and loaded onto a 1 g cation exchange column (Biotage, LLC). The column was eluted with MeOH, then with 2N ammonia in methanol. The basic fraction was concentrated to give N-(pyridin-2-yl)-4-(2-(1,2,3,6-tetrahydropyridin-4-yl)-4-(trifluoromethyl)phenyl)-3,4-dihydro-2H-benzo[b][1,4]oxazine-7-sulfonamide as a cream-colored solid. The material was the further purified by chromatography on a 12 g silica gel column, eluting with 10% MeOH/DCM, then with 20% of a 2N ammonia in MeOH solution dissolved in DCM to give N-(pyridin-2-yl)-4-(2-(1,2,3,6-tetrahydropyridin-4-yl)-4-(trifluoromethyl)phenyl)-3,4-dihydro-2H-benzo[b][1,4]oxazine-7-sulfonamide (32 mg, 0.062 mmol) as a white solid after concentration from DCM/heptane. $^1$H NMR (400 MHz, DMSO-$d_6$) δ=8.05 (dd, J=1.2, 5.2 Hz, 1 H), 7.73-7.62 (m, 2H), 7.58-7.48 (m, 2 H), 7.25 (d, J=2.2 Hz, 1 H), 7.19 (dd, J=2.1, 8.6 Hz, 1 H), 7.09 (d, J=8.5 Hz, 1 H), 6.90-6.82 (m, 1 H), 6.39 (d, J=8.6 Hz, 1 H), 5.79 (br. s., 1 H), 4.26 (t, J=4.4 Hz, 2 H), 3.60 (br. s., 2 H), 3.23 (br. s., 2 H), 2.71 (t, J=5.4 Hz, 2 H), 2.25-2.07 (m, 2 H). m/z (ESI) 517.4 (M+H)$^+$.

Example 63

4-(2-(1,2,3,6-Tetrahydropyridin-4-Yl)-4-(Trifluoromethyl)Phenyl)-N-(Thiazol-4-Yl)-3,4-Dihydro-2H-Benzo[B][1,4]Oxazine-7-Sulfonamide

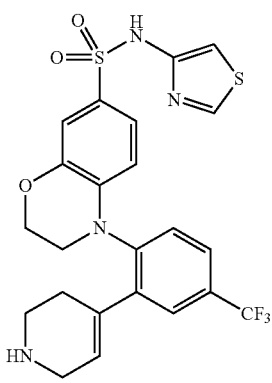 [SMILES: O=S(=O)(Nc1cscn1)c1ccc2c(c1)OCCN2c1ccc(C(F)(F)F)cc1C1=CCNCC1]

A vial was charged with 4-(2-bromo-4-(trifluoromethyl)phenyl)-N-(thiazol-4-yl)-3,4-dihydro-2H-benzo[b][1,4]oxazine-7-sulfonamide (EXAMPLE 61, 66 mg, 0.127 mmol), tert-butyl 4-(4,4,5,5-tetramethyl-1,3,2-dioxaborolan-2-yl)-5,6-dihydropyridine-1(2H)-carboxylate (118 mg, 0.381 mmol), Pd(AmPhos)$_2$Cl$_2$ (8.98 mg, 0.013 mmol), potassium phosphate (135 mg, 0.634 mmol), dioxane (634 µL), and water (211 µL). The vial was sealed and placed in a 120° C. heating bath for 40 min. The mixture was cooled to room temperature and extracted with EtOAc (3×). The combined organic extracts were concentrated, and the residue was purified by chomatography on silica gel (12 g column, 10-60% EtOAc/Heptane) to give 61.9 mg of a yellow oil. The residue was dissolved in DCM (1 mL) and TFA (0.5 mL). After 1 h, the mixture was concentrated. The product was purified by chromatography on silica gel (12 g column, 10% MeOH/DCM, then 20% of a 2N ammonia in methanol solution dissolved in DCM). The fractions containing product were combined and concentrated. The residue was taken up in DCM, and this solution was filtered through cotton. The filtrate was concentrated, then concentrated again from DCM/heptane to give 4-(2-(1,2,3,6-tetrahydropyridin-4-yl)-4-(trifluoromethyl)phenyl)-N-(thiazol-4-yl)-3,4-dihydro-2H-benzo[b][1,4]oxazine-7-sulfonamide (32.36 mg, 0.062 mmol) as an off-white solid. $^1$H NMR (400 MHz, DMSO-$d_6$) δ ppm 8.89 (d, J=2.2 Hz, 1 H), 7.76 (dd, J=2.0, 8.4 Hz, 1 H), 7.62 (d, J=2.1 Hz, 1 H), 7.57 (d, J=8.1 Hz, 1 H), 7.24 (d, J=2.2 Hz, 1 H), 7.17 (dd, J=2.2, 8.6 Hz, 1 H), 6.99 (d, J=2.2 Hz, 1 H), 6.46 (d, J=8.6 Hz, 1 H), 5.87 (br. s., 1 H), 4.34-4.25 (m, J=6.7 Hz, 2 H), 3.66 (d, J=2.2 Hz, 2 H), 3.59 (t, J=4.3 Hz, 2 H), 3.22-3.12 (m, 2 H), 2.62-2.53 (m, 1 H), 2.45-2.29 (m, 1 H). m/z (ESI) 523.3 (M+H)$^+$.

Example 64

4-(4-Azido-2-Bromophenyl)-N-(Thiazol-2-Yl)-3,4-Dihydro-2H-Benzo[B][1,4]Oxazine-7-Sulfonamide 2,2,2-Trifluoroacetate

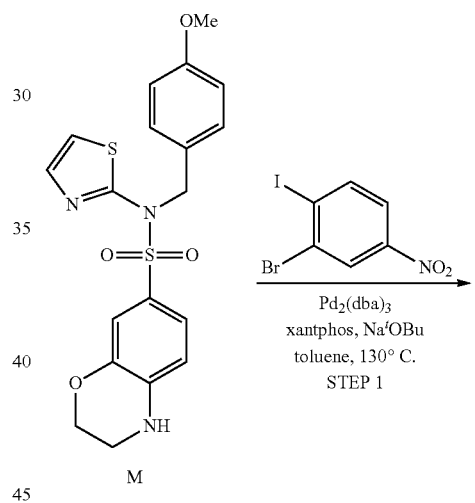

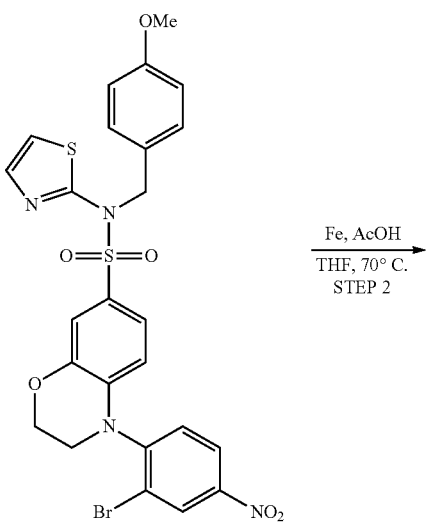

113

-continued

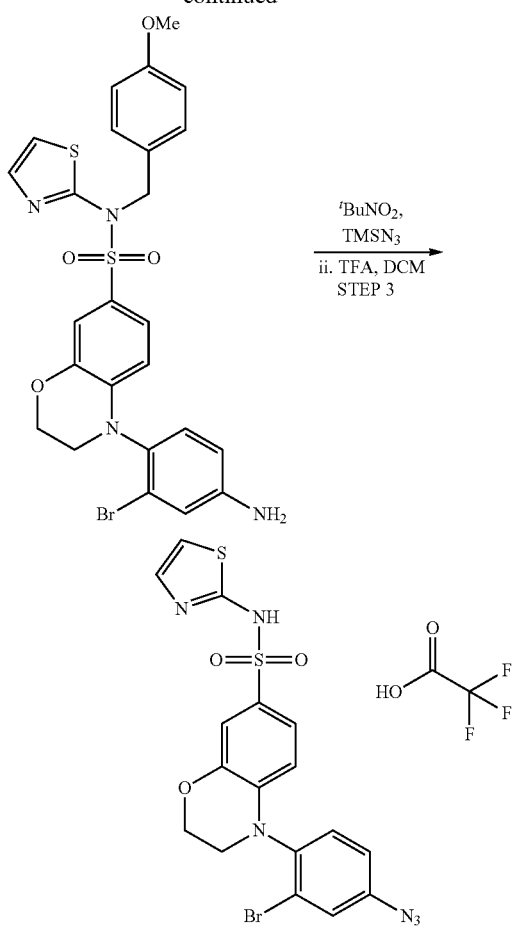

Step 1: 4-(2-Bromo-4-Nitrophenyl)-N-(4-Methoxybenzyl)-N-(Thiazol-2-Yl)-3,4-Dihydro-2H-Benzo[B][1,4]Oxazine-7-Sulfonamide

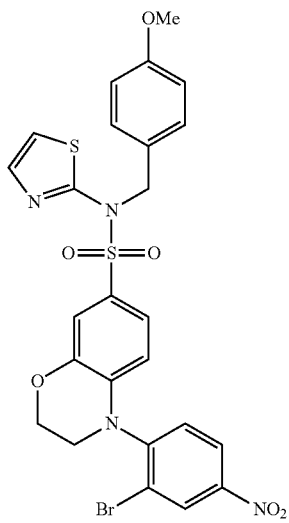 [SMILES: COc1ccc(CN(c2nccs2)S(=O)(=O)c2ccc3c(c2)OCCN3c2ccc(N)cc2Br)cc1]

4-(2-Bromo-4-nitrophenyl)-N-(4-methoxybenzyl)-N-(thiazol-2-yl)-3,4-dihydro-2H-benzo[b][1,4]oxazine-7-sulfonamide was synthesized in the same manner as STEP 1 of EXAMPLE 53, using 2-bromo-1-iodo-4-nitrobenzene instead of 2-bromo-1-iodo-4-trifluoromethyl-benzene. m/z (ESI) 616.9 (M+H)$^+$.

Step 2: 4-(4-Amino-2-Bromophenyl)-N-(4-Methoxybenzyl)-N-(Thiazol-2-Yl)-3,4-Dihydro-2H-Benzo[B][1,4]Oxazine-7-Sulfonamide

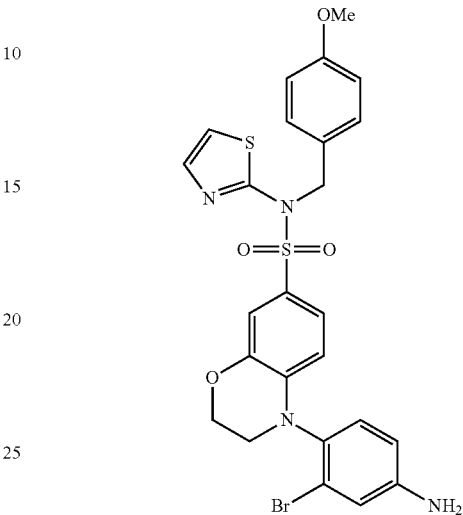

4-(2-bromo-4-nitrophenyl)-N-(4-methoxybenzyl)-N-(thiazol-2-yl)-3,4-dihydro-2H-benzo[b][1,4]oxazine-7-sulfonamide (0.025 g, 0.040 mmol) was dissolved in THF (0.135 mL) and acetic acid (0.127 mL, 2.227 mmol), and iron (0.023 g, 0.405 mmol) was added. The flask was sealed and heated to 70° C. for 1 hour. The reaction was cooled to rt, diluted with THF, and filtered through Celite® (diatomaceous earth), washing well with THF. The filtrate was concentrated, and partitioned between saturated aqueous sodium bicarbonate solution and EtOAc. The layers were separated, and the aqueous was then extracted (×2) with EtOAc. The combined organics were washed with brine, dried over sodium sulfate, filtered and concentrated to yield 4-(4-amino-2-bromophenyl)-N-(4-methoxybenzyl)-N-(thiazol-2-yl)-3,4-dihydro-2H-benzo[b][1,4]oxazine-7-sulfonamide as a light brown solid. The material was carried forward without further purification. m/z (ESI) 587.1 (M+H)$^+$.

Step 3, Example 64: 4-(4-Azido-2-Bromophenyl)-N-(Thiazol-2-Yl)-3,4-Dihydro-2H-Benzo[B][1,4]Oxazine-7-Sulfonamide 2,2,2-Trifluoroacetate

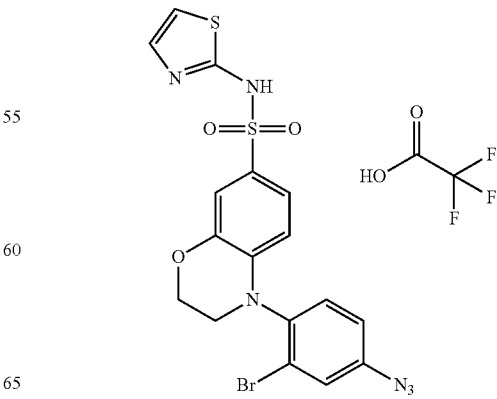

To a solution of 4-(4-amino-2-bromophenyl)-N-(4-methoxybenzyl)-N-(thiazol-2-yl)-3,4-dihydro-2H-benzo[b][1,4]oxazine-7-sulfonamide (0.095 g, 0.162 mmol) in dry acetonitrile (1.617 mL) at 0° C. was added tert-butyl nitrite (0.027 mL, 0.226 mmol), followed by dropwise addition of azidotrimethylsilane (0.026 mL, 0.194 mmol). The resulting mixture was stirred for 20 minutes at RT. The reaction was concentrated under a vacuum, and purified via silica gel MPLC, eluting with a gradient of 0% to 100% ethyl acetate in heptanes to provide 4-(4-azido-2-bromophenyl)-N-(4-methoxybenzyl)-N-(thiazol-2-yl)-3,4-dihydro-2H-benzo[b][1,4]oxazine-7-sulfonamide as tan solid. The material was taken up in DCM (1.5 mL), and TFA (0.125 mL, 1.617 mmol) was added. The reaction was stirred at RT for 1.5 h, after which the reaction was concentrated under a vacuum. The material was purified by reverse-phase preparative HPLC using a Phenomenex Luna column, 5 micron, $C_{18}$(2), 100 Å, 150×30 mm, 0.1% TFA in $CH_3CN/H_2O$, gradient 30% to 90% over 20 min to provide 4-(4-azido-2-bromophenyl)-N-(thiazol-2-yl)-3,4-dihydro-2H-benzo[b][1,4]oxazine-7-sulfonamide 2,2,2-trifluoroacetate (0.0308 g, 0.051 mmol) as a tan solid. $^1$H NMR (400 MHz, DMSO-$d_6$) δ ppm 3.55-3.63 (m, 1 H) 3.64-3.72 (m, 1 H) 4.27-4.34 (m, 1 H) 4.35-4.41 (m, 1 H) 6.10 (d, J=8.41 Hz, 1 H) 6.78 (d, J=4.69 Hz, 1H) 7.08-7.15 (m, 2 H) 7.22 (d, J=4.60 Hz, 1 H) 7.28 (dd, J=8.51, 2.54 Hz, 1 H) 7.53 (d, J=8.51 Hz, 1 H) 7.56 (d, J=2.54 Hz, 1 H) 12.55 (br. s., 1 H). m/z (ESI) 493.0 (M+H)$^+$.

Example 65

4-(4-Azido-2-(1,2,3,6-Tetrahydropyridin-4-Yl)Phenyl)-N-(Thiazol-2-Yl)-3,4-Dihydro-2H-Benzo[B][1,4]Oxazine-7-Sulfonamide Bis(2,2,2-Trifluoroacetate)

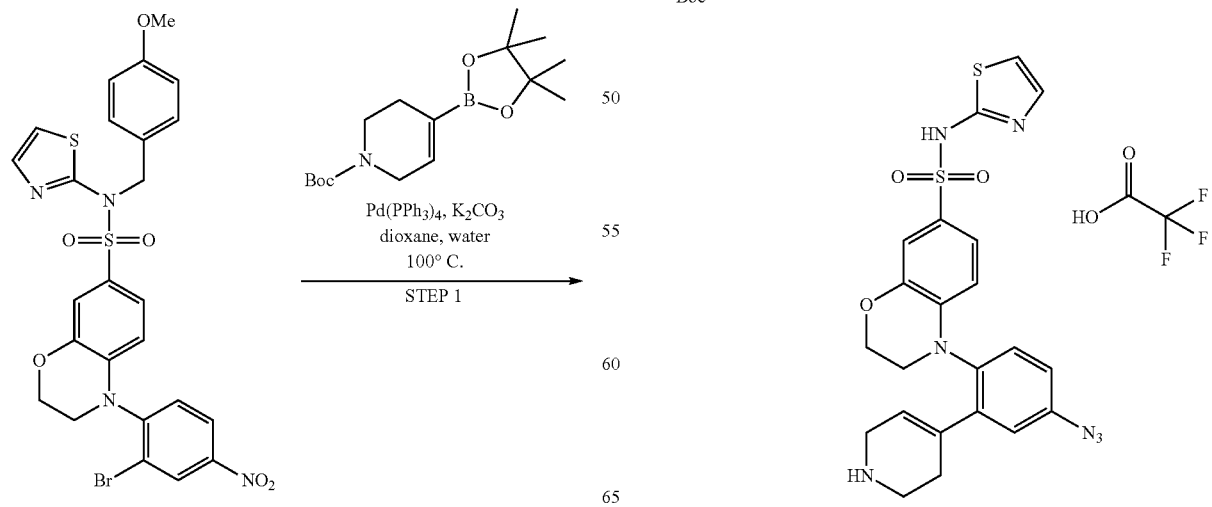

Step 1: Tert-Butyl 4-(2-(7-(N-(4-Methoxybenzyl)-N-(Thiazol-2-Yl)Sulfamoyl)-2H-Benzo[B][1,4]Oxazin-4(3H)-Yl)-5-Nitrophenyl)-5,6-Dihydropyridine-1(2H)-Carboxylate

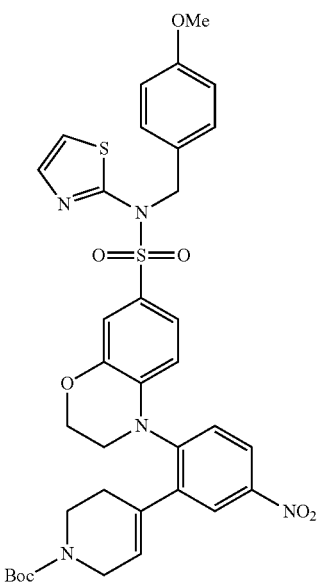 [SMILES: COc1ccc(CN(c2nccs2)S(=O)(=O)c2ccc3c(c2)OCCN3c2ccc([N+](=O)[O-])cc2C2=CCN(C(=O)OC(C)(C)C)CC2)cc1]

A microwave vial was charged with 4-(2-bromo-4-nitrophenyl)-N-(4-methoxybenzyl)-N-(thiazol-2-yl)-3,4-dihydro-2H-benzo[b][1,4]oxazine-7-sulfonamide (0.136 g, 0.220 mmol) (STEP 1, EXAMPLE 64), 3,6-dihydro-2h-pyridine-1-N-boc-4-boronic acid pinacol ester (0.136 g, 0.440 mmol), tetrakis(triphenylphosphine)palladium(0) (0.025 g, 0.022 mmol), and K$_2$CO$_3$ (0.152 g, 1.101 mmol). The solids were diluted with dioxane (1.468 mL) and water (0.734 mL), and the reaction was heated under microwave irradiation at 100° C. for 30 minutes. The reaction was diluted with water and DCM, the layers separated. The aqueous was washed once more with DCM, and the organics were combined and dried using a phase separator to yield material. After concentration under a vacuum, the material was taken up in methanol (and a small amount of DCM) and purified via 5 g SCX column to provide tert-butyl 4-(2-(7-(N-(4-methoxybenzyl)-N-(thiazol-2-yl)sulfamoyl)-2H-benzo[b][1,4]oxazin-4(3H)-yl)-5-nitrophenyl)-5,6-dihydropyridine-1(2H)-carboxylate, which was taken forward without further purification. m/z (ESI) 720.0 (M+H)$^+$.

Step 2: Tert-Butyl 4-(5-Amino-2-(7-(N-(4-Methoxybenzyl)-N-(Thiazol-2-Yl)Sulfamoyl)-2H-Benzo[B][1,4]Oxazin-4(3H)-Yl)Phenyl)-5,6-Dihydropyridine-1(2H)-Carboxylate

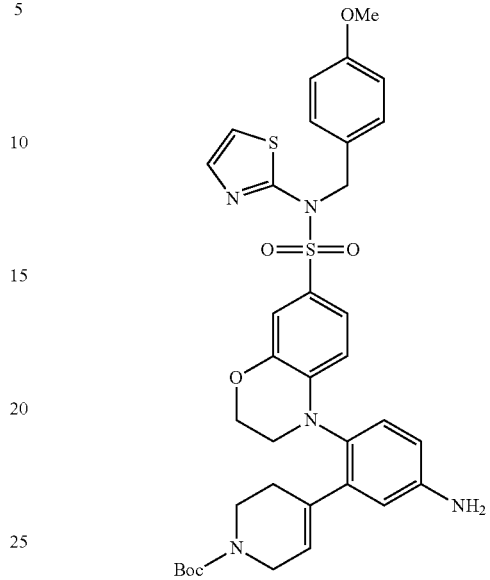

To a solution of tert-butyl 4-(2-(7-(N-(4-methoxybenzyl)-N-(thiazol-2-yl)sulfamoyl)-2H-benzo[b][1,4]oxazin-4(3H)-yl)-5-nitrophenyl)-5,6-dihydropyridine-1(2H)-carboxylate (0.159 g, 0.221 mmol) in methanol (1.104 mL) was added tin(II) chloride (0.168 g, 0.884 mmol) and the reaction was stirred at RT for 1 h. The reaction was then heated to 60° C. for 1.5 h. The reaction mixture was concentrated under a vacuum. The residue was taken up in EtOAc, and washed with 1N NaOH (to a pH that is basic) and the layers were separated. The organic layer was washed with brine and dried over magnesium sulfate, filtered, and concentrated under a vacuum. The material was dissolved in methanol and purified via 2 g SCX column to provide tert-butyl 4-(5-amino-2-(7-(N-(4-methoxybenzyl)-N-(thiazol-2-yl)sulfamoyl)-2H-benzo[b][1,4]oxazin-4(3H)-yl)phenyl)-5,6-dihydropyridine-1(2H)-carboxylate, which was taken forward without further purification. m/z (ESI) 690.2 (M+H)$^+$.

Step 3, Example 65: 4-(4-Azido-2-(1,2,3,6-Tetrahydropyridin-4-Yl)Phenyl)-N-(Thiazol-2-Yl)-3,4-Dihydro-2H-Benzo[B][1,4]Oxazine-7-Sulfonamide Bis(2,2,2-Trifluoroacetate)

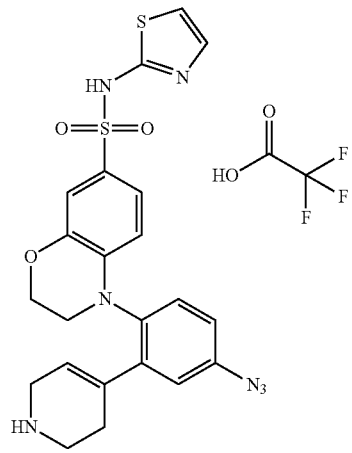 [SMILES: [N-]=[N+]=Nc1ccc(N2CCOc3cc(S(=O)(=O)Nc4nccs4)ccc32)c(C2=CCNCC2)c1 ; O=C(O)C(F)(F)F]

To a solution of tert-butyl 4-(5-amino-2-(7-(N-(4-methoxybenzyl)-N-(thiazol-2-yl)sulfamoyl)-2H-benzo[b][1,4]oxazin-4(3H)-yl)phenyl)-5,6-dihydropyridine-1(2H)-carboxylate (0.105 g, 0.152 mmol) in dry acetonitrile (1.522 mL) at 0° C. was added tert-butyl nitrite (0.026 mL, 0.213 mmol) followed by dropwise addition of azidotrimethylsilane (0.024 mL, 0.183 mmol). The resulting mixture was stirred for 20 minutes, at which time no conversion to the desired was observed. Additional tert-butyl nitrite (0.052 mL) and azidotrimethylsilane (0.048 mL) were added at 0° C. and the reaction was once again stirred at RT for 1 h. Conversion was observed, but starting material was still the major reaction component, so the reaction was recooled to 0° C. and 0.156 mL of t-Bu nitrite was added, followed by dropwise addition of 0.144 mL of TMS-azide. After 20 minutes at RT, the reaction was complete and was concentrated under a vacuum. DCM (1.0 mL) was added, followed by TFA (0.235 mL, 3.04 mmol), and the reaction was stirred at RT for 1 h. The material was concentrated under a vacuum and purified by reverse-phase preparative HPLC using a Phenomenex Luna column, 5 micron, $C_{18}$(2), 100 Å, 150×30 mm, 0.1% TFA in $CH_3CN/H_2O$, gradient 25% to 90% over 20 min to provide 4-(4-azido-2-(1,2,3,6-tetrahydropyridin-4-yl)phenyl)-N-(thiazol-2-yl)-3,4-dihydro-2H-benzo[b][1,4]oxazine-7-sulfonamide bis(2,2,2-trifluoroacetate) (0.028 g, 0.039 mmol) as a brown solid. $^1$H NMR (400 MHz, DMSO-$d_6$) δ ppm 2.30-2.44 (m, 2 H) 3.19 (m, J=5.20 Hz, 2 H) 3.47-3.56 (m, 2 H) 3.62-3.70 (m, 2 H) 4.29 (t, J=4.25 Hz, 2 H) 5.76-5.83 (m, 1 H) 6.29 (d, J=8.31 Hz, 1 H) 6.79 (d, J=4.50 Hz, 1 H) 7.02 (d, J=2.74 Hz, 1 H) 7.08-7.15 (m, 2 H) 7.17 (dd, J=8.56, 2.69 Hz, 1 H) 7.22 (d, J=4.60 Hz, 1 H) 7.38 (d, J=8.51 Hz, 1 H) 8.76 (br. s., 2 H) 12.53 (br. s., 1H); m/z (ESI) 496.0 (M+H)$^+$.

Example 66

4-(Quinolin-6-Yl)-N-(Thiazol-2-Yl)-3,4-Dihydro-2H-Benzo[B][1,4]Oxazine-7-Sulfonamide 2,2,2-Trifluoroacetate

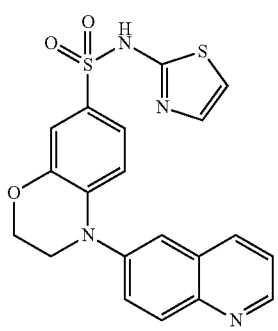 [SMILES: O=S(=O)(Nc1nccs1)c1ccc2c(c1)OCCN2c1ccc2ncccc2c1]

EXAMPLE 66 was synthesized in the same manner as EXAMPLE 49, using 6-bromoquinoline instead of 2-bromo-5-(trifluoromethyl)benzonitrile. $^1$H NMR (500 MHz, DMSO-$d_6$) δ ppm 3.86-3.92 (m, 2 H) 4.35-4.39 (m, 2 H) 6.80 (d, J=4.58 Hz, 1 H) 7.03 (d, J=8.59 Hz, 1 H) 7.18 (dd, J=8.59, 2.06 Hz, 1 H) 7.21-7.26 (m, 2 H) 7.72 (dd, J=8.31, 4.53 Hz, 1 H) 7.87-7.98 (m, 2 H) 8.11 (d, J=8.93 Hz, 1 H) 8.58 (d, J=8.71 Hz, 1 H) 8.97 (d, J=4.47 Hz, 1 H) 12.58 (br. s, 1 H). m/z (ESI) 425.0 (M+H)$^+$.

Example 67

4-(2-Chloro-5-Methylphenyl)-N-(Thiazol-2-Yl)-3,4-Dihydro-2H-Benzo[B][1,4]Oxazine-7-Sulfonamide 2,2,2-Trifluoroacetate

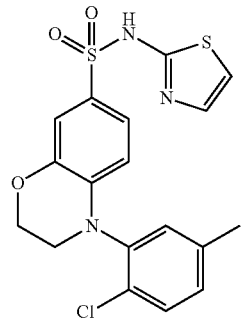 [SMILES: Cc1ccc(Cl)c(N2CCOc3cc(S(=O)(=O)Nc4nccs4)ccc32)c1]

EXAMPLE 67 was synthesized in the same manner as EXAMPLE 49, using 2-bromo-1-chloro-4-methylbenzene instead of 2-bromo-5-(trifluoromethyl)benzonitrile. $^1$H NMR (500 MHz, DMSO-$d_6$) δ ppm 2.31 (s, 3H) 3.56-3.76 (m, 2 H) 4.24-4.40 (m, 2 H) 6.13 (d, J=8.48 Hz, 1 H) 6.77 (d, J=4.58 Hz, 1 H) 7.08-7.16 (m, 2 H) 7.21 (m, J=4.60 Hz, 2 H) 7.33 (s, 1 H) 7.50 (d, J=8.25 Hz, 1 H) 12.54 (br. s., 1 H). m/z (ESI) 422.0 (M+H)$^+$.

Example 68

4-(Isoquinolin-8-Yl)-N-(Thiazol-2-Yl)-3,4-Dihydro-2H-Benzo[B][1,4]Oxazine-7-Sulfonamide 2,2,2-Trifluoroacetate

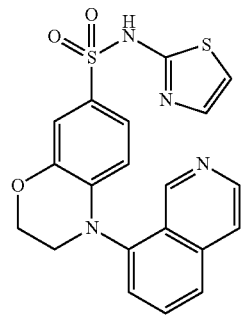 [SMILES: O=S(=O)(Nc1nccs1)c1ccc2c(c1)OCCN2c1cccc2ccncc12]

EXAMPLE 68 was synthesized in the same manner as EXAMPLE 49, using 8-bromoisoquinoline instead of 2-bromo-5-(trifluoromethyl)benzonitrile. $^1$H NMR (500 MHz, DMSO-$d_6$) δ ppm 3.74-3.87 (m, 1 H) 3.88-4.00 (m, 1 H) 4.43 (m, 1H) 4.53-4.65 (m, 1 H) 6.19 (d, J=8.48 Hz, 1 H) 6.78 (d, J=4.58 Hz, 1 H) 7.03 (dd, J=8.59, 2.06 Hz, 1 H) 7.16-7.27 (m, 2 H) 7.87 (d, J=7.33 Hz, 1 H) 8.06-8.21 (m, 2 H) 8.35 (d, J=6.07 Hz, 1 H) 8.67 (d, J=6.19 Hz, 1 H) 9.60 (s, 1 H) 12.56 (br. s, 1 H). m/z (ESI) 425.0 (M+H)$^+$.

Example 69

4-(Quinoxalin-6-Yl)-N-(Thiazol-2-Yl)-3,4-Dihydro-2H-Benzo[B][1,4]Oxazine-7-Sulfonamide 2,2,2-Trifluoroacetate

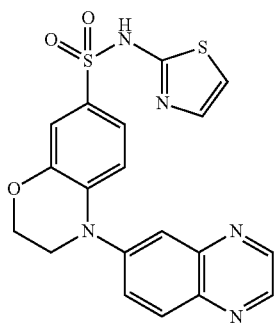 [SMILES: O=S(=O)(Nc1nccs1)c1ccc2c(c1)OCCN2c1ccc2nccnc2c1]

EXAMPLE 69 was synthesized in the same manner as EXAMPLE 49, using 6-bromoquinoxaline instead of 2-bromo-5-(trifluoromethyl)benzonitrile. $^1$H NMR (500 MHz, DMSO-$d_6$) δ ppm 3.90-3.96 (m, 2 H) 4.34-4.40 (m, 2 H) 6.80 (d, J=4.58 Hz, 1 H) 7.12 (d, J=8.59 Hz, 1 H) 7.18-7.26 (m, 3 H) 7.80 (d, J=2.41 Hz, 1 H) 7.88 (dd, J=9.11, 2.46 Hz, 1 H) 8.07 (d, J=9.05 Hz, 1 H) 8.83 (d, J=1.72 Hz, 1 H) 8.88 (d, J=1.72 Hz, 1 H) 12.63 (br. s., 1 H). m/z (ESI) 426.0 (M+H)$^+$.

Example 70

4-(Benzo[D]Thiazol-5-Yl)-N-(Thiazol-2-Yl)-3,4-Dihydro-2H-Benzo[B][1,4]Oxazine-7-Sulfonamide 2,2,2-Trifluoroacetate

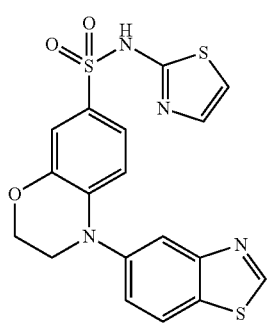 [SMILES: O=S(=O)(Nc1nccs1)c1ccc2c(c1)OCCN2c1ccc2scnc2c1]

EXAMPLE 70 was synthesized in the same manner as EXAMPLE 49, using 5-bromobenzo[d]thiazole instead of 2-bromo-5-(trifluoromethyl)benzonitrile. $^1$H NMR (500 MHz, DMSO-$d_6$) δ ppm 3.83 (d, J=4.35 Hz, 2 H) 4.30-4.40 (m, 2 H) 6.75 (d, J=8.59 Hz, 1 H) 6.78 (d, J=4.58 Hz, 1 H) 7.13 (dd, J=8.59, 2.06 Hz, 1 H) 7.17 (d, J=2.06 Hz, 1 H) 7.22 (d, J=4.70 Hz, 1 H) 7.48 (dd, J=8.48, 1.95 Hz, 1 H) 8.00 (d, J=1.95 Hz, 1 H) 8.20 (d, J=8.48 Hz, 1 H) 9.43 (s, 1 H) 12.56 (br. s., 1 H). m/z (ESI) 431.0 (M+H)$^+$.

Example 71

4-(Benzo[D]Thiazol-6-Yl)-N-(Thiazol-2-Yl)-3,4-Dihydro-2H-Benzo[B][1,4]Oxazine-7-Sulfonamide 2,2,2-Trifluoroacetate

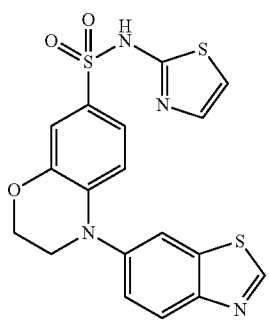 [SMILES: O=S(=O)(Nc1nccs1)c1ccc2c(c1)OCCN2c1ccc2ncsc2c1]

EXAMPLE 71 was synthesized in the same manner as EXAMPLE 49, using 6-bromobenzo[d]thiazole instead of 2-bromo-5-(trifluoromethyl)benzonitrile. $^1$H NMR (500 MHz, DMSO-$d_6$) δ ppm 3.74-3.84 (m, 2 H) 4.29-4.39 (m, 2 H) 6.73-6.82 (m, 2 H) 7.13 (dd, J=8.53, 2.12 Hz, 1 H) 7.18 (d, J=2.06 Hz, 1 H) 7.22 (d, J=4.70 Hz, 1 H) 7.50 (dd, J=8.71, 2.18 Hz, 1 H) 8.07-8.15 (m, 2 H) 9.35 (s, 1 H) 12.57 (br. s., 1 H). m/z (ESI) 431.0 (M+H)$^+$.

Example 72

4-(Benzo[D]Thiazol-4-Yl)-N-(Thiazol-2-Yl)-3,4-Dihydro-2H-Benzo[B][1,4]Oxazine-7-Sulfonamide 2,2,2-Trifluoroacetate

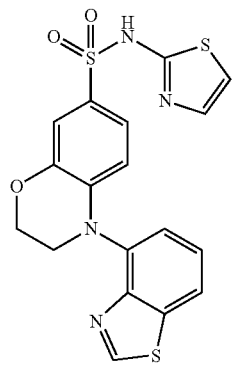 [SMILES: O=S(=O)(Nc1nccs1)c1ccc2c(c1)OCCN2c1cccc2scnc12]

EXAMPLE 72 was synthesized in the same manner as EXAMPLE 49, using 4-bromobenzo[d]thiazole instead of 2-bromo-5-(trifluoromethyl)benzonitrile. $^1$H NMR (500 MHz, DMSO-$d_6$) δ ppm 3.90 (t, J=4.35 Hz, 2 H) 4.33-4.40 (m, 2 H) 6.34 (d, J=8.59 Hz, 1 H) 6.77 (d, J=4.47 Hz, 1 H) 7.05 (dd, J=8.53, 2.12 Hz, 1 H) 7.17 (d, J=2.18 Hz, 1 H) 7.21 (d, J=4.58 Hz, 1 H) 7.47-7.52 (m, 1 H) 7.53-7.59 (m, 1 H) 8.10 (d, J=7.10 Hz, 1 H) 9.36 (s, 1 H) 12.55 (br. s., 1 H). m/z (ESI) 430.0 (M+H)$^+$.

Example 73

4-(6-Methylisoquinolin-5-Yl)-N-(Thiazol-2-Yl)-3,4-Dihydro-2H-Benzo[B][1,4]Oxazine-7-Sulfonamide 2,2,2-Trifluoroacetate

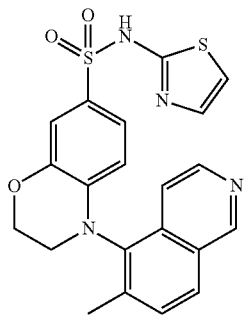 [SMILES: Cc1ccc2cnccc2c1N1CCOc2cc(S(=O)(=O)Nc3nccs3)ccc21]

EXAMPLE 73 was synthesized in the same manner as EXAMPLE 49, using 5-bromo-6-methylisoquinoline instead of 2-bromo-5-(trifluoromethyl)benzonitrile. $^1$H NMR (500 MHz, DMSO-$d_6$) δ ppm 2.36 (s, 3 H) 3.71-3.76 (m, 1 H) 4.06-4.14 (m, 1 H) 4.41-4.48 (m, 1 H) 4.52-4.59 (m, 1 H) 5.77 (d, J=8.59 Hz, 1 H) 6.77 (d, J=4.58 Hz, 1 H) 7.01-7.26 (m, 3 H) 7.66 (d, J=5.84 Hz, 1 H) 7.78 (d, J=8.36 Hz, 1 H) 8.20 (d, J=8.36 Hz, 1 H) 8.48 (d, J=5.96 Hz, 1 H) 9.46 (s, 1 H) 12.52 (br. s., 1 H). m/z (ESI) 439.0 (M+H)$^+$.

Example 74

4-(3,4-Dichlorophenyl)-N-(Thiazol-2-Yl)-3,4-Dihydro-2H-Benzo[B][1,4]Oxazine-7-Sulfonamide 2,2,2-Trifluoroacetate

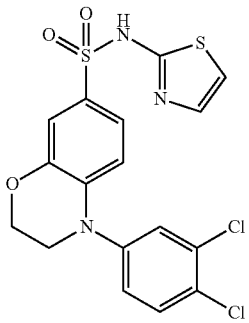 [SMILES: O=S(=O)(Nc1nccs1)c1ccc2c(c1)OCCN2c1ccc(Cl)c(Cl)c1]

EXAMPLE 74 was synthesized in the same manner as EXAMPLE 49, using 4-bromo-1,2-dichlorobenzene instead of 2-bromo-5-(trifluoromethyl)benzonitrile. $^1$H NMR (500 MHz, DMSO-$d_6$) δ ppm 3.72-3.75 (m, 2 H) 4.26-4.32 (m, 2 H) 6.79 (d, J=4.58 Hz, 1 H) 6.90 (d, J=8.48 Hz, 1 H) 7.07 (s, 1 H) 7.17 (s, 1 H) 7.22 (d, J=4.58 Hz, 1 H) 7.31 (dd, J=8.71, 2.63 Hz, 1 H) 7.58 (d, J=2.52 Hz, 1 H) 7.63 (d, J=8.71 Hz, 1 H) 12.59 (br. s., 1 H). m/z (ESI) 442.0 (M+H)$^+$.

Example 75

N-(Thiazol-2-Yl)-4-(M-Tolyl)-3,4-Dihydro-2H-Benzo[B][1,4]Oxazine-7-Sulfonamide 2,2,2-Trifluoroacetate

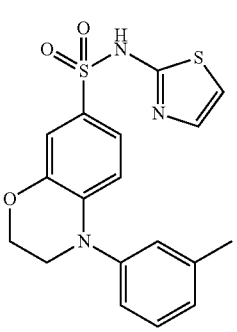 [SMILES: Cc1cccc(N2CCOc3cc(S(=O)(=O)Nc4nccs4)ccc32)c1]

EXAMPLE 75 was synthesized in the same manner as EXAMPLE 49, using 1-bromo-3-methylbenzene instead of 2-bromo-5-(trifluoromethyl)benzonitrile. $^1$H NMR (500 MHz, DMSO-$d_6$) δ ppm 2.31 (s, 3 H) 3.68-3.74 (m, 2 H) 4.25-4.33 (m, 2 H) 6.71 (d, J=8.48 Hz, 1 H) 6.78 (d, J=4.47 Hz, 1 H) 7.03 (d, J=7.68 Hz, 1H) 7.06-7.15 (m, 4 H) 7.22 (d, J=4.70 Hz, 1 H) 7.27-7.35 (m, 1 H) 12.54 (br. s., 1 H). m/z (ESI) 388.0 (M+H)$^+$.

Example 76

4-(4-Cyanophenyl)-N-(Thiazol-2-Yl)-3,4-Dihydro-2H-Benzo[B][1,4]Oxazine-7-Sulfonamide 2,2,2-Trifluoroacetate

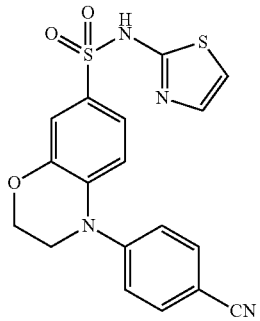 [SMILES: N#Cc1ccc(N2CCOc3cc(S(=O)(=O)Nc4nccs4)ccc32)cc1]

EXAMPLE 76 was synthesized in the same manner as EXAMPLE 49, using 4-bromobenzonitrile instead of 2-bromo-5-(trifluoromethyl)benzonitrile. $^1$H NMR (500 MHz, DMSO-$d_6$) δ ppm 3.77-3.82 (m, 2 H) 4.25-4.34 (m, 2 H) 6.81 (d, J=4.58 Hz, 1 H) 7.11-7.17 (m, 1 H) 7.17-7.26 (m, 3 H) 7.43 (d, J=8.82 Hz, 2 H) 7.79 (d, J=8.71 Hz, 2 H) 12.63 (br. s., 1 H). m/z (ESI) 399.0 (M+H)$^+$.

Example 77

4-(3-Methoxyphenyl)-N-(Thiazol-2-Yl)-3,4-Dihydro-2H-Benzo[B][1,4]Oxazine-7-Sulfonamide 2,2,2-Trifluoroacetate

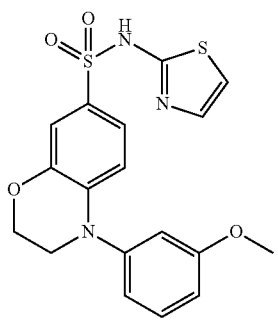 [SMILES: COc1cccc(N2CCOc3cc(S(=O)(=O)Nc4nccs4)ccc32)c1]

EXAMPLE 77 was synthesized in the same manner as EXAMPLE 49, using 1-bromo-3-methoxybenzene instead of 2-bromo-5-(trifluoromethyl)benzonitrile. $^1$H NMR (500 MHz, DMSO-d$_6$) δ ppm 3.67-3.74 (m, 2 H) 3.75 (s, 3 H) 4.26-4.33 (m, 2 H) 6.71-6.82 (m, 3 H) 6.83-6.90 (m, 2 H) 7.10-7.16 (m, 2 H) 7.22 (d, J=4.70 Hz, 1 H) 7.28-7.36 (m, 1 H) 12.55 (br. s., 1 H). m/z (ESI) 403.1 (M+H)$^+$.

Example 78

4-(3-Fluoro-2-Methylphenyl)-N-(Thiazol-2-Yl)-3,4-Dihydro-2H-Benzo[B][1,4]Oxazine-7-Sulfonamide 2,2,2-Trifluoroacetate

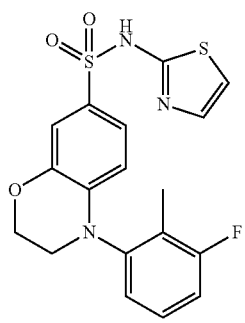 [SMILES: Cc1c(F)cccc1N1CCOc2cc(S(=O)(=O)Nc3nccs3)ccc21]

EXAMPLE 78 was synthesized in the same manner as EXAMPLE 49, using 1-bromo-3-fluoro-2-methylbenzene instead of 2-bromo-5-(trifluoromethyl)benzonitrile. $^1$H NMR (500 MHz, DMSO-d$_6$) δ ppm 2.06 (d, J=1.60 Hz, 3 H) 3.51-3.60 (m, 1 H) 3.69-3.77 (m, 1 H) 4.30-4.41 (m, 2 H) 6.11 (d, J=8.48 Hz, 1 H) 6.77 (d, J=4.70 Hz, 1 H) 7.10 (dd, J=8.48, 2.06 Hz, 1 H) 7.12-7.23 (m, 4 H) 7.30-7.39 (m, 1 H) 12.53 (br. s., 1 H). m/z (ESI) 406.0 (M+H)$^+$.

Example 79

4-(5-Fluoro-2-Methylphenyl)-N-(Thiazol-2-Yl)-3,4-Dihydro-2H-Benzo[B][1,4]Oxazine-7-Sulfonamide 2,2,2-Trifluoroacetate

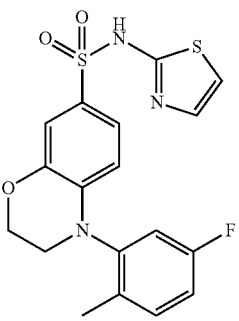 [SMILES: Cc1ccc(F)cc1N1CCOc2cc(S(=O)(=O)Nc3nccs3)ccc21]

EXAMPLE 79 was synthesized in the same manner as EXAMPLE 49, using 2-bromo-4-fluoro-1-methylbenzene instead of 2-bromo-5-(trifluoromethyl)benzonitrile. $^1$H NMR (500 MHz, DMSO-d$_6$) δ ppm 2.10 (s, 3 H) 3.47-3.54 (m, 1 H) 3.62-3.70 (m, 1 H) 4.25-4.38 (m, 2 H) 5.99 (d, J=8.36 Hz, 1 H) 6.76 (d, J=4.70 Hz, 1 H) 6.86 (dd, J=8.42, 2.81 Hz, 1 H) 6.94 (d, J=2.98 Hz, 1 H) 7.06-7.11 (m, 2 H) 7.16-7.22 (m, 2 H) 12.49 (br. s., 1 H).

Example 80

4-(2-Fluoro-5-Methylphenyl)-N-(Thiazol-2-Yl)-3,4-Dihydro-2H-Benzo[B][1,4]Oxazine-7-Sulfonamide 2,2,2-Trifluoroacetate

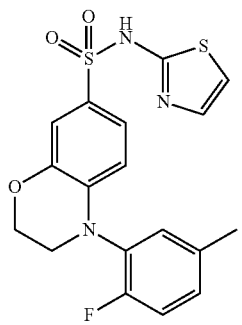 [SMILES: Cc1ccc(F)c(N2CCOc3cc(S(=O)(=O)Nc4nccs4)ccc32)c1]

EXAMPLE 80 was synthesized in the same manner as EXAMPLE 49, using 2-bromo-1-fluoro-4-methylbenzene instead of 2-bromo-5-(trifluoromethyl)benzonitrile. $^1$H NMR (500 MHz, DMSO-d$_6$) δ ppm 2.23 (s, 3H) 3.64-3.70 (m, 2 H) 4.26-4.33 (m, 2 H) 6.59 (d, J=8.36 Hz, 1 H) 6.78 (d, J=4.47 Hz, 1 H) 7.09-7.23 (m, 5 H) 7.23-7.28 (m, 1 H) 12.54 (br. s., 1 H). m/z (ESI) 406.0 (M+H)$^+$.

Example 81

4-(4-Fluoro-3-Methylphenyl)-N-(Thiazol-2-Yl)-3,4-Dihydro-2H-Benzo[B][1,4]Oxazine-7-Sulfonamide 2,2,2-Trifluoroacetate

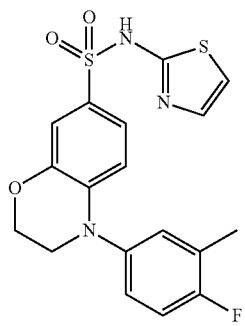 [SMILES: Cc1cc(N2CCOc3cc(S(=O)(=O)Nc4nccs4)ccc32)ccc1F]

EXAMPLE 81 was synthesized in the same manner as EXAMPLE 49, using 4-bromo-1-fluoro-2-methylbenzene instead of 2-bromo-5-(trifluoromethyl)benzonitrile. $^1$H NMR (500 MHz, DMSO-$d_6$) δ ppm 2.30 (s, 3 H) 3.65-3.71 (m, 2 H) 4.29-4.35 (m, 2 H) 6.34-6.39 (m, 1 H) 6.78 (d, J=4.58 Hz, 1 H) 7.12-7.17 (m, 3 H) 7.19-7.24 (m, 2 H) 7.25-7.29 (m, 1 H) 12.55 (br. s., 1 H). m/z (ESI) 406.0 (M+H)$^+$.

Example 82

4-(3-Fluoro-4-Methylphenyl)-N-(Thiazol-2-Yl)-3,4-Dihydro-2H-Benzo[B][1,4]Oxazine-7-Sulfonamide 2,2,2-Trifluoroacetate

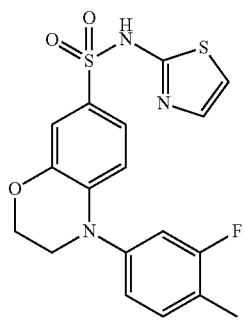 [SMILES: Cc1ccc(N2CCOc3cc(S(=O)(=O)Nc4nccs4)ccc32)cc1F]

EXAMPLE 82 was synthesized in the same manner as EXAMPLE 49, using 4-bromo-2-fluoro-1-methylbenzene instead of 2-bromo-5-(trifluoromethyl)benzonitrile. $^1$H NMR (500 MHz, DMSO-$d_6$) δ ppm 2.22 (s, 3 H) 3.68-3.73 (m, 2 H) 4.25-4.32 (m, 2 H) 6.76-6.81 (m, 2 H) 7.05 (dd, J=8.19, 2.12 Hz, 1 H) 7.10-7.16 (m, 3 H) 7.22 (d, J=4.70 Hz, 1 H) 7.28-7.35 (m, 1 H) 12.56 (br. s., 1 H). m/z (ESI) 405.1 (M+H)$^+$.

Example 83

4-(2,5-Difluorophenyl)-N-(Thiazol-2-Yl)-3,4-Dihydro-2H-Benzo[B][1,4]Oxazine-7-Sulfonamide 2,2,2-Trifluoroacetate

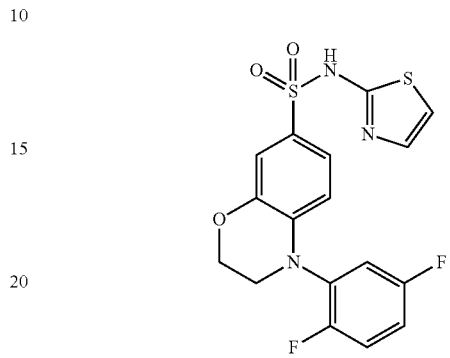

EXAMPLE 83 was synthesized in the same manner as EXAMPLE 49, using 2-bromo-1,4-difluorobenzene instead of 2-bromo-5-(trifluoromethyl)benzonitrile. $^1$H NMR (500 MHz, DMSO-$d_6$) δ ppm 3.67-3.76 (m, 2 H) 4.30-4.36 (m, 2 H) 6.44-6.51 (m, 1 H) 6.78 (d, J=4.58 Hz, 1 H) 7.13-7.24 (m, 4 H) 7.36-7.45 (m, 2 H) 12.58 (br. s., 1 H). m/z (ESI) 409.0 (M+H)$^+$.

Example 84

4-(3,4-Difluorophenyl)-N-(Thiazol-2-Yl)-3,4-Dihydro-2H-Benzo[B][1,4]Oxazine-7-Sulfonamide 2,2,2-Trifluoroacetate

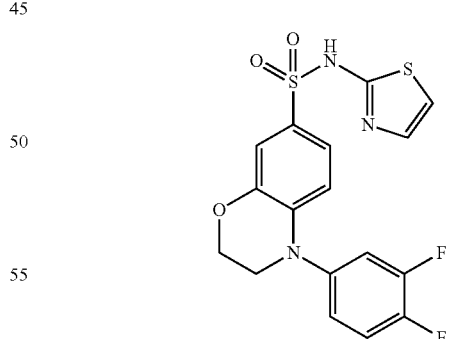

EXAMPLE 84 was synthesized in the same manner as EXAMPLE 49, using 4-bromo-1,2-difluorobenzene instead of 2-bromo-5-(trifluoromethyl)benzonitrile. $^1$H NMR (500 MHz, DMSO-$d_6$) δ ppm 3.67-3.73 (m, 2 H) 4.27-4.33 (m, 2 H) 6.75 (d, J=8.71 Hz, 1 H) 6.78 (d, J=4.70 Hz, 1 H) 7.11-7.19 (m, 3 H) 7.22 (d, J=4.58 Hz, 1 H) 7.42-7.52 (m, 2 H) 12.56 (br. s., 1 H). m/z (ESI) 410.0 (M+H)$^+$.

Example 85

4-(2-(1,2,3,6-Tetrahydropyridin-4-Yl)-4-(Trifluoromethyl)Phenyl)-N-(Thiazol-5-Yl)-3,4-Dihydro-2H-Benzo[B][1,4]Oxazine-7-Sulfonamide 2,2,2-Trifluoroacetate

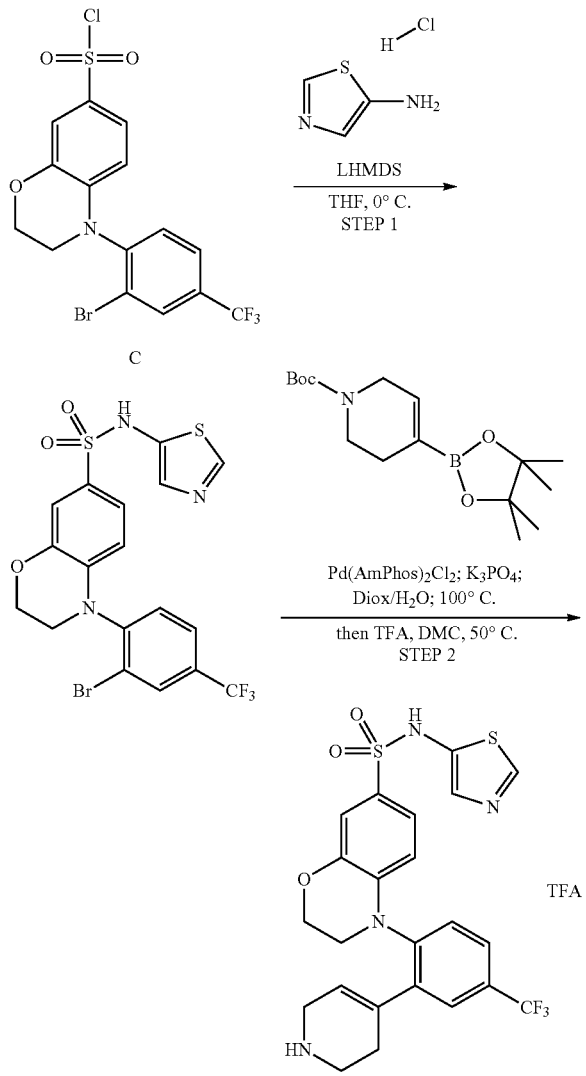

Step 1: 4-(2-Bromo-4-(Trifluoromethyl)Phenyl)-N-(Thiazol-5-Yl)-3,4-Dihydro-2H-Benzo[B][1,4]Oxazine-7-Sulfonamide

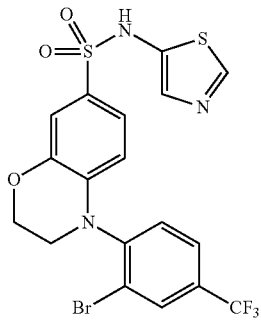 [SMILES: O=S(=O)(Nc1cncs1)c1ccc2c(c1)OCCN2c1ccc(C(F)(F)F)cc1Br]

A flask containing thiazol-5-amine hydrochloride (0.093 g, 0.684 mmol), 4-(2-bromo-4-(trifluoromethyl)phenyl)-3,4-dihydro-2H-benzo[b][1,4]oxazine-7-sulfonyl chloride (INTERMEDIATE C, 0.284 g, 0.622 mmol), and THF (4.15 mL) was cooled to 0° C. LHMDS (1.0 M in THF) (1.866 mL, 1.866 mmol) was added dropwise and the reaction was stirred for 5 minutes at 0° C. The reaction was quenched with saturated ammonium chloride solution, diluted with ethyl acetate and washed with water. The aqueous layer was extracted with ethyl acetate, and the combined organic layers were dried with sodium sulfate, filtered, and concentrated. The material was purified via silica gel column chromatography (40 g, gradient elution 0 to 100% EtOAc:Heptane) to afford 4-(2-bromo-4-(trifluoromethyl)phenyl)-N-(thiazol-5-yl)-3,4-dihydro-2H-benzo[b][1,4]oxazine-7-sulfonamide (0.083 g, 0.160 mmol) as an orange oily solid. $^1$H NMR (400 MHz, DMSO-$d_6$) δ=10.66 (s, 1 H), 8.69 (d, J=0.9 Hz, 1 H), 8.21 (d, J=1.6 Hz, 1 H), 7.91 (dd, J=1.5, 8.3 Hz, 1 H), 7.75 (d, J=7.8 Hz, 1 H), 7.35 (d, J=0.9 Hz, 1 H), 7.12 (d, J=2.2 Hz, 1 H), 7.05 (dd, J=2.2, 8.6 Hz, 1 H), 6.24 (d, J=8.6 Hz, 1 H), 4.37 (d, J=17.2 Hz, 2 H), 3.85-3.63 (m, 2 H). m/z (ESI) 520.2 (M+H)$^+$.

Step 2, Example 85: 4-(2-(1,2,3,6-Tetrahydropyridin-4-Yl)-4-(Trifluoromethyl)Phenyl)-N-(Thiazol-5-Yl)-3,4-Dihydro-2H-Benzo[B][1,4]Oxazine-7-Sulfonamide 2,2,2-Trifluoroacetate

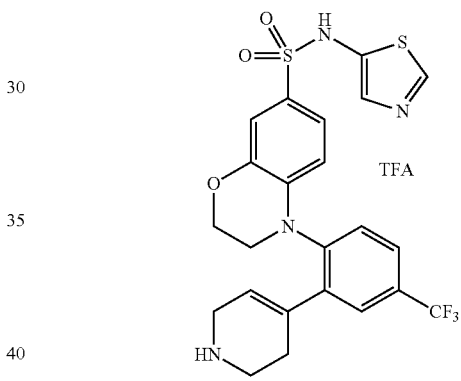

A microwave vial was charged with 4-(2-bromo-4-(trifluoromethyl)phenyl)-N-(thiazol-5-yl)-3,4-dihydro-2H-benzo[b][1,4]oxazine-7-sulfonamide (0.076 g, 0.146 mmol), tert-butyl 4-(4,4,5,5-tetramethyl-1,3,2-dioxaborolan-2-yl)-5,6-dihydropyridine-1(2 H)-carboxylate (0.068 g, 0.219 mmol), Pd(AmPhos$_2$)Cl$_2$ (10.34 mg, 0.015 mmol), and potassium phosphate (0.093 g, 0.438 mmol). Dioxane (0.649 mL) and water (0.325 mL) were added, the vial was flushed with argon and sealed, and microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was dissolved in DCM and TFA (0.1 mL, 1.298 mmol) was added. The reaction was stirred at 50° C. for one hour. The reaction was concentrated and the material was purified via silica gel column chromatography (12 g, gradient elution 0 to 10% MeOH:DCM) to afford 4-(2-(1,2,3,6-tetrahydropyridin-4-yl)-4-(trifluoromethyl)phenyl)-N-(thiazol-5-yl)-3,4-dihydro-2H-benzo[b][1,4]oxazine-7-sulfonamide 2,2,2-trifluoroacetate (0.069 g, 0.108 mmol) as a light yellow solid. $^1$H NMR (400 MHz, DMSO-$d_6$) δ ppm 10.71 (br. s., 1 H), 8.81 (br. s., 2 H), 8.70 (s, 1 H), 7.81-7.75 (m, 1 H), 7.63 (s, 1 H), 7.58 (d, J=8.2 Hz, 1 H), 7.35 (s, 1 H), 7.11 (d, J=2.2 Hz, 1 H), 7.06 (dd, J=2.1, 8.6 Hz, 1 H), 6.46 (d, J=8.6 Hz, 1 H), 5.86 (br. s., 1 H), 4.31 (d, J=4.1 Hz, 2 H), 3.66 (br. s., 2 H), 3.62 (t, J=4.1 Hz, 2 H), 3.17 (br. s., 3H), 2.42 (br. s., 1 H). m/z (ESI) 523.4 (M+H)+.

Example 86

N-(Pyrimidin-2-Yl)-4-(2-(1,2,3,6-Tetrahydropyridin-4-Yl)-4-(Trifluoromethyl)Phenyl)-3,4-Dihydro-2H-Benzo[B][1,4]Oxazine-7-Sulfonamide

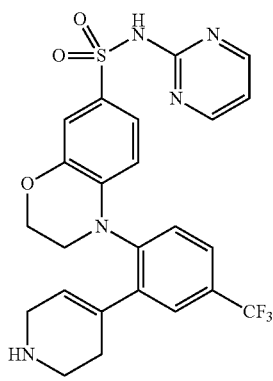 [SMILES: O=S(=O)(Nc1ncccn1)c1ccc2c(c1)OCCN2c1ccc(C(F)(F)F)cc1C1=CCNCC1]

A roundbottom flask was charged with tert-butyl 4-(2-(7-((perfluorophenoxy)sulfonyl)-2H-benzo[b][1,4]oxazin-4(3H)-yl)-5-(trifluoromethyl)phenyl)-5,6-dihydropyridine-1(2H)-carboxylate (INTERMEDIATE AA, 48.52 mg, 0.069 mmol), pyrimidin-2-amine (7.84 mg, 0.082 mmol), and THF (343 μl) to give a clear, lightly-colored solution. The flask was cooled in an ice-bath for 5 min, then lithium bis(trimethylsilyl)amide (1M in THF) (144 μl, 0.144 mmol) was added dropwise over 30 s to give a light-yellow solution. After 5 min, the cooling bath was removed. After 20 min, the mixture was diluted with TFA (0.5 mL), then concentrated. The residue was taken up in DCM (1 mL) and TFA (0.5 mL) and stirred for 20 min. The mixture was concentrated, and the residue was dissolved in MeOH and loaded onto a 500-mg SCX-2 ion exchange column. The column was eluted with MeOH then with 2N ammonia in methanol. The basic fraction was concentrated. The residue was further purified by chromatography on silica gel (12 g, eluting with 5 to 10% MeOH/DCM, then with 20 to 40% of 2N ammonia in methanol solution dissolved in DCM). The fractions containing product were combined and concentrated. The residue was taken up in DCM and filtered through cotton. The filtrate was concentrated, and the residue was taken up in 10% MeOH/DCM and filtered through cotton. The filtrate was concentrated to give N-(pyrimidin-2-yl)-4-(2-(1,2,3,6-tetrahydropyridin-4-yl)-4-(trifluoromethyl)phenyl)-3,4-dihydro-2H-benzo[b][1,4]oxazine-7-sulfonamide (13.66 mg, 0.026 mmol) as a light-yellow solid. $^1$H NMR (400 MHz, DMSO-$d_6$) δ ppm 8.37 (d, J=4.7 Hz, 2 H), 7.69 (d, J=8.5 Hz, 1 H), 7.59-7.48 (m, 2 H), 7.33 (s, 1 H), 7.25 (dd, J=1.8, 8.6 Hz, 1 H), 6.83 (t, J=4.6 Hz, 1 H), 6.41 (d, J=8.6 Hz, 1 H), 5.83 (br. s., 1 H), 4.25 (br. s., 2H), 3.59 (br. s., 2 H), 3.38 (br. s., 2 H), 2.87 (br. s., 2 H), 2.33 (br. s., 1 H), 2.23 (br. s., 1 H). m/z (ESI) 518.4 (M+H)+.

Example 87

N-(Pyridazin-3-Yl)-4-(2-(1,2,3,6-Tetrahydropyridin-4-Yl)-4-(Trifluoromethyl)Phenyl)-3,4-Dihydro-2H-Benzo[B][1,4]Oxazine-7-Sulfonamide

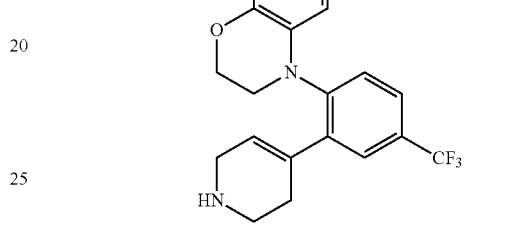

A round bottom flask was charged with tert-butyl 44247-((perfluorophenoxy)sulfonyl)-2H-benzo[b][1,4]oxazin-4(3H)-yl)-5-(trifluoromethyl)phenyl)-5,6-dihydropyridine-1(2H)-carboxylate (INTERMEDIATE AA, 29.24 mg, 0.041 mmol), pyridazin-3-amine (5.90 mg, 0.062 mmol, TCI America, Portland, Oreg.), and THF (207 μL) to give a clear, lightly-colored solution with a small amount of fine precipitate. The flask was cooled in a dry ice-acetone bath for 5 min, then lithium bis(trimethylsilyl)amide (1M in THF) (87 μL, 0.087 mmol) was added dropwise over 30 s to give a light-yellow solution. After 10 min, the flask was transferred to in an ice-bath. The mixture was stirred for 30 min, then TFA (3 drops) was added via syringe. The mixture was concentrated, and the residue was dissolved in DCM (1 mL) and TFA (0.5 mL). After 20 min, the mixture was concentrated, and the residue was dissolved in MeOH and loaded onto a 500-mg SCX-2 ion exchange column. The column was eluted with MeOH then with 2N ammonia in methanol. The basic fraction was concentrated. The residue was further purified by chromatography on silica gel (12 g column, 10% MeOH/DCM, then 20% of a 2N ammonia in methanol solution dissolved in DCM) to give N-(pyridazin-3-yl)-4-(2-(1,2,3,6-tetrahydropyridin-4-yl)-4-(trifluoromethyl)phenyl)-3,4-dihydro-2H-benzo[b][1,4]oxazine-7-sulfonamide (13.49 mg, 0.026 mmol) as an off-white solid after concentration from DCM/heptane. $^1$H NMR (400 MHz, DMSO-$d_6$) δ ppm 8.34 (dd, J=1.4, 4.1 Hz, 1 H), 7.78-7.67 (m, 1 H), 7.63-7.42 (m, 4 H), 7.21 (d, J=2.2 Hz, 1 H), 7.16 (dd, J=2.2, 8.5 Hz, 1 H), 6.43 (d, J=8.5 Hz, 1 H), 5.84 (br. s., 1 H), 4.27 (br. s., 2 H), 3.59 (t, J=4.2 Hz, 2 H), 3.46 (br. s., 2 H), 2.95 (br. s., 2 H), 2.43-2.22 (m, 3 H). m/z (ESI) 518.4 (M+H)+.

Example 88

N-(Pyrazin-2-Yl)-4-(2-(1,2,3,6-Tetrahydropyridin-4-Yl)-4-(Trifluoromethyl)Phenyl)-3,4-Dihydro-2H-Benzo[B][1,4]Oxazine-7-Sulfonamide

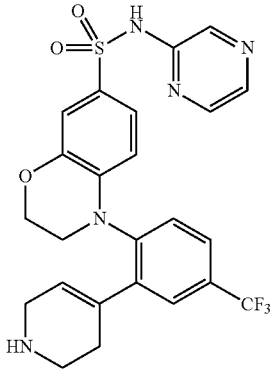 [SMILES: O=S(=O)(Nc1cnccn1)c1ccc2c(c1)OCCN2c1ccc(C(F)(F)F)cc1C1=CCNCC1]

A round-bottom flask was charged with tert-butyl 4-(2-(7-((perfluorophenoxy)sulfonyl)-2H-benzo[b][1,4]oxazin-4(3H)-yl)-5-(trifluoromethyl)phenyl)-5,6-dihydropyridine-1(2H)-carboxylate (INTERMEDIATE AA, 37.7 mg, 0.053 mmol), pyrazin-2-amine (7.61 mg, 0.080 mmol, TCI America, Portland, Oreg.), and THF (1 mL) to give a clear, colorless solution. The flask was cooled in a dry ice-acetone bath for 5 min, then lithium bis(trimethylsilyl)amide (1M in THF) (112 µL, 0.112 mmol) was added dropwise over 30 s to give a light-yellow solution. After 20 min, the flask was lowered into an ice bath. After another 30 min, TFA (3 drops) was added via a syringe, and the mixture was concentrated. The residue was dissolved in DCM (1 mL) and TFA (0.5 mL). After 20 min, the mixture was concentrated, and the residue was dissolved in MeOH and loaded onto a 500 mg SCX-2 ion exchange column. The column was eluted with MeOH then with 2N ammonia in methanol. The basic fraction was concentrated. The residue was further purified by chromatography on silica gel (12 g column, 10% MeOH/DCM, then 20% of a 2N ammonia in methanol solution dissolved in DCM) to give N-(pyrazin-2-yl)-4-(2-(1,2,3,6-tetrahydropyridin-4-yl)-4-(trifluoromethyl)phenyl)-3,4-dihydro-2H-benzo[b][1,4]oxazine-7-sulfonamide (13.49 mg, 0.026 mmol) as an off-white solid. $^1$H NMR (400 MHz, DMSO-d$_6$) δ ppm 8.08 (s, 1 H), 8.02 (s, 1 H), 7.86 (br. s., 1 H), 7.72 (dd, J=1.7, 8.6 Hz, 2 H), 7.59 (d, J=1.9 Hz, 1 H), 7.54 (d, J=8.1 Hz, 1 H), 6.43 (d, J=8.5 Hz, 1 H), 5.87 (br. s., 1 H), 4.27 (br. s., 2 H), 3.61-3.53 (m, J=6.1 Hz, 5 H), 3.09 (br. s., 2 H), 2.39-2.30 (m, 1 H). m/z (ESI) 518.4 (M+H)$^+$.

Example 89

4-(2-Cyano-4-(Trifluoromethyl)Phenyl)-N-(Pyrimidin-4-Yl)-3,4-Dihydro-2H-Benzo[B][1,4]Oxazine-7-Sulfonamide

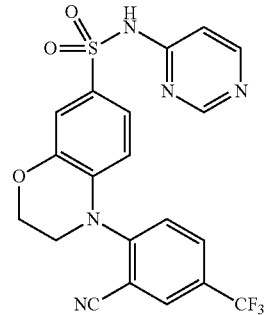 [SMILES: N#Cc1cc(C(F)(F)F)ccc1N1CCOc2cc(S(=O)(=O)Nc3ccncn3)ccc21]

A round bottom flask was charged with perfluorophenyl 4-(2-cyano-4-(trifluoromethyl)phenyl)-3,4-dihydro-2H-benzo[b][1,4]oxazine-7-sulfonate (INTERMEDIATE AB, 46.12 mg, 0.084 mmol), pyrimidin-4-amine (11.95 mg, 0.126 mmol), and THF (1 mL) to give a clear, colorless solution. The flask was cooled in a dry ice-acetone bath for 5 min, then lithium bis(trimethylsilyl)amide (1M in THF) (176 µL, 0.176 mmol) was added dropwise over 30 s to give a light-yellow solution. After 5 min, the flask was lowered into an ice bath for 1 h. Glacial acetic acid (2 drops) was added, and the mixture was concentrated under a vacuum. The product was purified by chromatography on silica gel (12 g column with 0 to 10% MeOH/DCM) to give 4-(2-cyano-4-(trifluoromethyl)phenyl)-N-(pyrimidin-4-yl)-3,4-dihydro-2H-benzo[b][1,4]oxazine-7-sulfonamide (25.2 mg, 0.055 mmol) as a light-yellow solid. $^1$H NMR (400 MHz, DMSO-d$_6$) δ ppm 12.10 (br. s., 1 H), 8.65 (s, 1 H), 8.42-8.35 (m, 2 H), 8.09 (dd, J=2.0, 8.8 Hz, 1 H), 7.74 (d, J=8.6 Hz, 1 H), 7.38 (d, J=2.1 Hz, 1 H), 7.31 (dd, J=2.2, 8.6 Hz, 1 H), 7.04 (d, J=6.0 Hz, 1 H), 6.80 (d, J=8.6 Hz, 1 H), 4.38-4.32 (m, 2 H), 3.89-3.84 (m, 2 H). m/z (ESI) 462.4 (M+H)$^+$.

Example 90

4-(2-Cyano-4-(Trifluoromethyl)Phenyl)-N-(Oxazol-2-Yl)-3,4-Dihydro-2H-Benzo[B][1,4]Oxazine-7-Sulfonamide

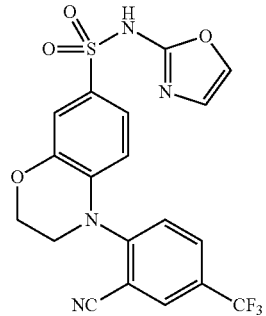 [SMILES: N#Cc1cc(C(F)(F)F)ccc1N1CCOc2cc(S(=O)(=O)Nc3ncco3)ccc21]

A round bottom flask was charged with perfluorophenyl 4-(2-cyano-4-(trifluoromethyl)phenyl)-3,4-dihydro-2H-benzo[b][1,4]oxazine-7-sulfonate (INTERMEDIATE AB, 40.69 mg, 0.074 mmol), oxazole-2-amine (9.32 mg, 0.11 mmol, Ryan Scientific, Mt. Pleasant, S.C.) and THF (1 mL) to give a clear, colorless solution. The flask was cooled in a dry ice-acetone bath for 5 min, then lithium bis(trimethylsilyl)amide (1M in THF) (155 µl, 0.155 mmol) was added dropwise over 30 s to give a light-yellow solution. After 5 min, the flask was lowered into an ice bath for 1 h. Additional portions of oxazole-2-amine (ca. 5 mg) and LHMDS solution (0.05 mL) were added in sequence. After an additional 45 min, glacial acetic acid (1 drop) was added. The mixture was concentrated under a vacuum. The product was purified by chromatography on silica gel (12 g column with 0 to 10% MeOH/DCM) to give 4-(2-cyano-4-(trifluoromethyl)phenyl)-N-(oxazol-2-yl)-3,4-dihydro-2H-benzo[b][1,4]oxazine-7-sulfonamide as a light-yellow solid. $^1$H NMR (400 MHz, DMSO-d$_6$) δ ppm 11.86 (br. s., 1 H), 8.38 (d, J=2.1 Hz, 1 H), 8.05 (dd, J=1.8, 8.8 Hz, 1 H), 7.71 (d, J=8.6 Hz, 1 H), 7.59 (d, J=1.7 Hz, 1 H), 7.31 (d, J=2.1 Hz, 1 H), 7.26-7.17 (m, 2 H), 6.80 (d, J=8.5 Hz, 1 H), 4.36-4.27 (m, 2 H), 3.87-3.82 (m, 2 H). m/z (ESI) 451.4 (M+H)+.

Example 91

4-(2-Cyano-4-(Trifluoromethyl)Phenyl)-N-(Isoxazol-5-Yl)-3,4-Dihydro-2H-Benzo[B][1,4]Oxazine-7-Sulfonamide

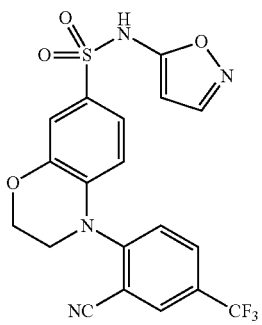 [SMILES: N#Cc1cc(C(F)(F)F)ccc1N1CCOc2cc(S(=O)(=O)Nc3ccno3)ccc21]

A round bottom flask was charged with perfluorophenyl 4-(2-cyano-4-(trifluoromethyl)phenyl)-3,4-dihydro-2H-benzo[b][1,4]oxazine-7-sulfonate (44.1 mg, 0.080 mmol), isoxazol-5-amine (10.1 mg, 0.12 mmol, Matrix Scientific, Columbia, S.C.) and THF (1 mL) to give a clear, colorless solution. The flask was cooled in a dry ice-acetone bath for 5 min, then lithium bis(trimethylsilyl)amide (1M in THF) (168 μl, 0.168 mmol) was added dropwise over 30 s to give a light-yellow solution. After 10 min, the flask was lowered into an ice bath for 45 min. Glacial acetic acid (1 drop) was added, and the mixture was concentrated under a vacuum. The product was purified by chromatography on silica gel (12 g column with 0 to 10% MeOH/DCM) to give 4-(2-cyano-4-(trifluoromethyl)phenyl)-N-(isoxazol-5-yl)-3,4-dihydro-2H-benzo[b][1,4]oxazine-7-sulfonamide (25.2 mg, 0.056 mmol) as a light-yellow solid. $^1$H NMR (400 MHz, DMSO-$d_6$) δ ppm 12.18 (br. s., 1 H), 8.42 (d, J=2.1 Hz, 1 H), 8.34 (d, J=2.0 Hz, 1 H), 8.11 (dd, J=2.0, 8.9 Hz, 1 H), 7.76 (d, J=8.6 Hz, 1 H), 7.30 (d, J=2.2 Hz, 1 H), 7.23 (dd, J=2.2, 8.7 Hz, 1 H), 6.80 (d, J=8.6 Hz, 1 H), 5.77 (d, J=1.9 Hz, 1 H), 4.40-4.35 (m, 2H), 3.89-3.86 (m, 2 H). m/z (ESI) 451.4 (M+H)+.

Example 92

4-(3-Chlorophenyl)-3-Oxo-N-(1,3,4-Thiadiazol-2-Yl)-3,4-Dihydro-2H-Benzo[B][1,4]Oxazine-7-Sulfonamide

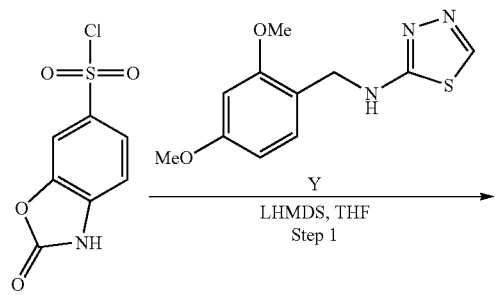

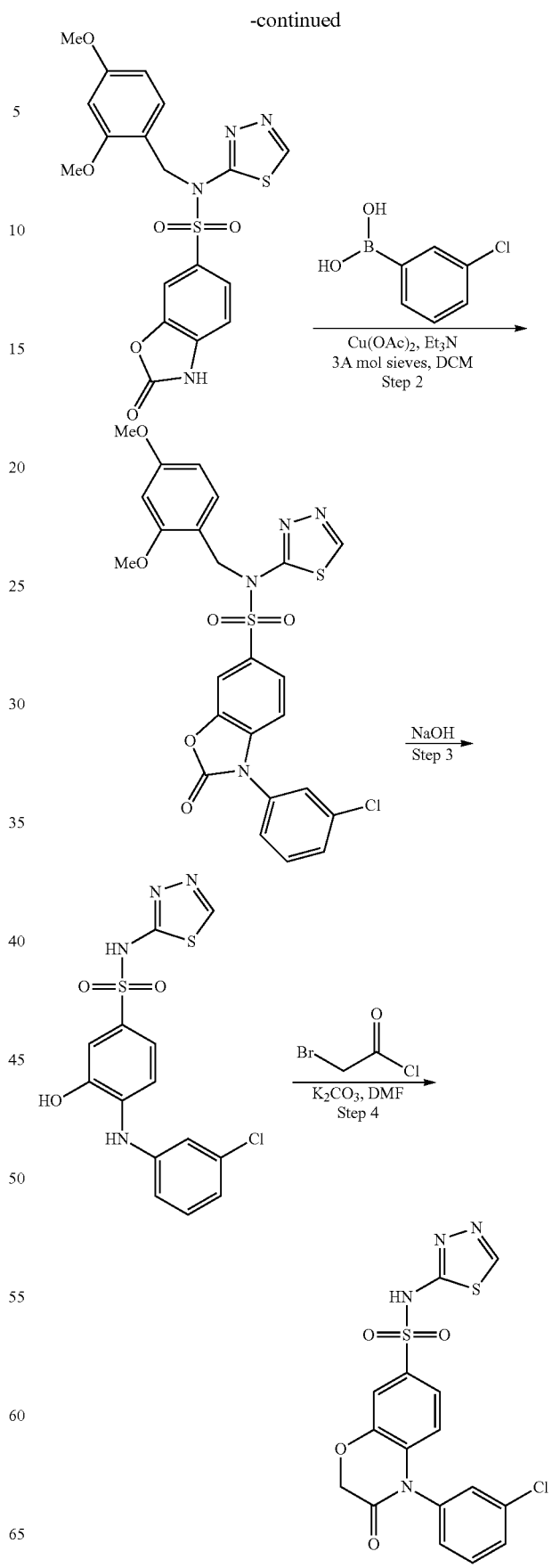

Step 1: N-(2,4-Dimethoxybenzyl)-2-Oxo-N-(1,3,4-Thiadiazol-2-Yl)-2,3-Dihydrobenzo[D]Oxazole-6-Sulfonamide

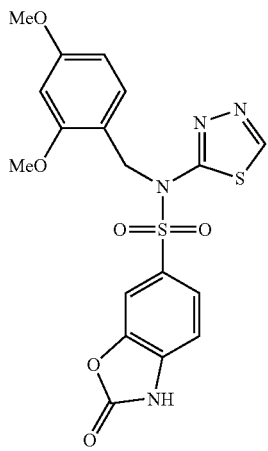 [SMILES: COc1ccc(CN(c2nncs2)S(=O)(=O)c2ccc3[nH]c(=O)oc3c2)c(OC)c1]

A round bottom flask was charged with N-(2,4-dimethoxybenzyl)-1,3,4-thiadiazol-2-amine (INTERMEDIATE Y) (0.689 g, 2.74 mmol), a septum and $N_2$ line were attached. THF (4.57 mL) was added and when the solution became homogeneous, it was cooled to −78° C. After 10 min, added a THF solution of 2-oxo-2,3-dihydrobenzo[d]oxazole-6-sulfonyl chloride (ASDI) (0.621 g, 2.66 mmol) dropwise over 5 minutes (still at −78° C.). When the addition was complete, the cold bath was removed and the mixture was allowed to warm to rt and stirred 18 h. The reaction mixture was poured into sat. aq. $NH_4Cl$, and DCM was added. The layers were separated and the organic layer was extracted with DCM (2×10 mL). The combined organic extracts were dried over $Na_2SO_4$ and concentrated under a vacuum. The solution was concentrated for purification by silica gel MPLC. The residue was taken up in minimal DCM and absorbed onto a 25 g loading cartridge and passed through silica gel column (40 g) using 98:2 Heptane:EtOAc to 100% EtOAc gradient to afford N-(2,4-dimethoxybenzyl)-2-oxo-N-(1,3,4-thiadiazol-2-yl)-2,3-dihydrobenzo[d]oxazole-6-sulfonamide (0.856 g, 1.909 mmol) as a white amorphous solid. m/z (ESI) 449.0 $(M+H)^+$.

Step 2: 3-(3-Chlorophenyl)-N-(2,4-Dimethoxybenzyl)-2-Oxo-N-(1,3,4-Thiadiazol-2-Yl)-2,3-Dihydrobenzo[D]Oxazole-6-Sulfonamide

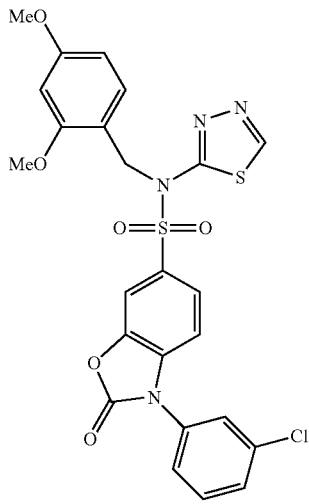 [SMILES: COc1ccc(CN(c2nncs2)S(=O)(=O)c2ccc3c(c2)oc(=O)n3-c2cccc(Cl)c2)c(OC)c1]

A sealable vial was charged with (3-chlorophenyl)boronic acid (25.6 mg, 0.164 mmol), N-(2,4-dimethoxybenzyl)-2-oxo-N-(1,3,4-thiadiazol-2-yl)-2,3-dihydrobenzo[d]oxazole-6-sulfonamide (48.9 mg, 0.109 mmol), 3 Å molecular sieves (powdered, 60 mg), DCM (545 µl), and triethylamine (45.6 µl, 0.327 mmol). Copper (II) acetate (39.6 mg, 0.218 mmol) was added as a solid in a single portion. The mixture was stirred at rt for 48 h. The reaction mixture was poured into a mixture of $NH_4OH$ and water (10% $NH_4OH$ in $H_2O$), extracted with DCM (2×10 mL), organic layers (which were an emulsion) were combined and washed with water (10 mL) then brine (20 mL), the emulsion resolved upon brine wash. The organic layers were dried ($Na_2SO_4$) and concentrated for purification by silica gel MPLC. The residue was taken up in minimal DCM and absorbed onto a 5 g loading cartridge and passed through a silica gel column (12 g) using 98:2 Heptane:EtOAc to 100% EtOAc gradient to afford 3-(3-chlorophenyl)-N-(2,4-dimethoxybenzyl)-2-oxo-N-(1,3,4-thiadiazol-2-yl)-2,3-dihydrobenzo[d]oxazole-6-sulfonamide (38.0 mg, 0.068 mmol) as a white amorphous solid. m/z (ESI) 559.2 $(M+H)^+$.

Step 3: 4-((3-Chlorophenyl)Amino)-3-Hydroxy-N-(1,3,4-Thiadiazol-2-Yl)Benzenesulfonamide

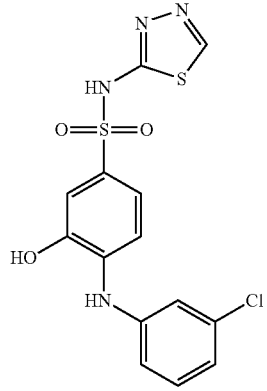 [SMILES: O=S(=O)(Nc1nncs1)c1ccc(Nc2cccc(Cl)c2)c(O)c1]

A sealable vial was charged with 3-(3-chlorophenyl)-N-(2,4-dimethoxybenzyl)-2-oxo-N-(1,3,4-thiadiazol-2-yl)-2,3-dihydrobenzo[d]oxazole-6-sulfonamide (38 mg, 0.068 mmol), and an aqueous solution of sodium hydroxide (2549 µL, 5.10 mmol) was added. The mixture was heated at 80° C. for 1 h, then poured into sat. aq. $NH_4Cl$. The solution became heterogeneous, extracted with DCM, product did not go into organic layer, even after addition of brine. Aqueous layer was lyophilized to give product along with salts. The mixture was dissolved in MeOH and filtered to remove the majority of salts. The filtrate was concentrated onto Celite® (diatomaceous earth) and eluted through a pre-equilibrated $C_{18}$ silica gel column (12 g) and eluted with a gradient of 95:5 1% formic acid in water: 1% formic acid in MeCN—10:90 1% formic acid in water: 1% formic acid in MeCN, followed by 100% IPA wash. The fractions containing desired product were concentrated to provide 4-((3-chlorophenyl)amino)-3-hydroxy-N-(1,3,4-thiadiazol-2-yl)benzenesulfonamide formate as a white amorphous solid. m/z (ESI) 383.1 $(M+H)^+$.

Step 4, Example 92: 4-(3-Chlorophenyl)-3-Oxo-N-(1,3,4-Thiadiazol-2-Yl)-3,4-Dihydro-2H-Benzo[B][1,4]Oxazine-7-Sulfonamide

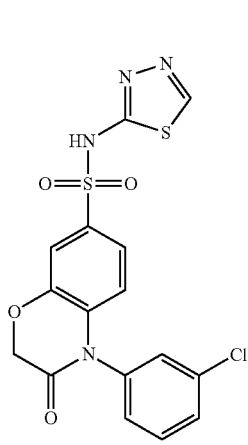 [SMILES: O=C1COc2cc(S(=O)(=O)Nc3nncs3)ccc2N1c1cccc(Cl)c1]

A sealable vial was charged with 4-((3-chlorophenyl)amino)-3-hydroxy-N-(1,3,4-thiadiazol-2-yl)benzenesulfonamide formate (14.0 mg, 0.033 mmol), potassium carbonate (22.56 mg, 0.163 mmol), then DMF (653 µl). A DMF solution of bromoacetyl chloride (224 µl, 0.036 mmol, 0.16 M) was added via syringe. The solution was maintained at rt for 2 h, then poured into sat. aq. NaHCO$_3$ and extracted with DCM (2×10 mL). Organic layers were combined, dried (Na$_2$SO$_4$) and concentrated. The residue was taken up in minimal MeOH and purified by preparative HPLC (15 to 90% CH$_3$CN:H$_2$O (1% TFA modifier, over 15 min; Column: Phenomenex 150×30 mm, 5 micron, C$_{18}$ column) Clean fractions were combined and concentrated to afford 4-(3-chlorophenyl)-3-oxo-N-(1,3,4-thiadiazol-2-yl)-3,4-dihydro-2H-benzo[b][1,4]oxazine-7-sulfonamide 2,2,2-trifluoroacetate (1.20 mg, 2.235 µmol) as a white amorphous solid. $^1$H NMR (400 MHz, MeOH) δ ppm 4.83-4.87 (m, 2 H) 6.53 (d, J=8.41 Hz, 1 H) 7.25-7.31 (m, 1 H) 7.40 (d, J=2.05 Hz, 1 H) 7.42-7.46 (m, 1 H) 7.51 (d, J=2.05 Hz, 1 H) 7.53-7.58 (m, 1 H) 8.46-8.55 (m, 1 H); m/z (ESI) 423.0 (M+H)$^+$.

Intermediate AC

N-(4-Methoxybenzyl)Pyrimidin-4-Amine

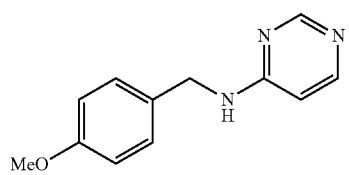

AC

N-(4-methoxybenzyl)pyrimidin-4-amine (INTERMEDIATE AC) was prepared in a manner analogous to INTERMEDIATE A wherein 1,2,4-thiadiazol-5-amine was replaced with pyrimidin-4-amine

Intermediate AD

4-Amino-3-Hydroxy-N-(4-Methoxybenzyl)-N-(Thiazol-2-Yl)Benzenesulfonamide

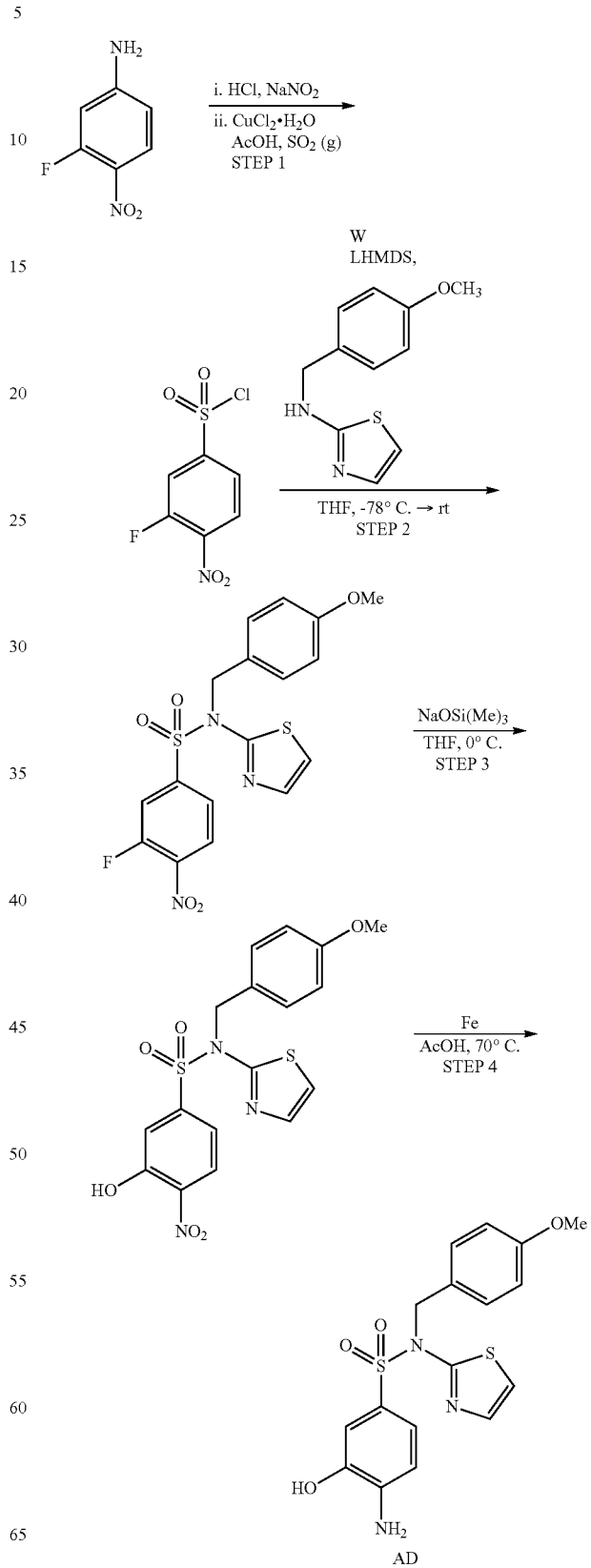

Step 1: 3-Fluoro-4-Nitrobenzene-1-Sulfonyl Chloride

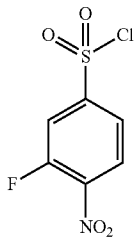

To a solution of 3-fluoro-4-nitroaniline (15 g, 96.1 mmol, Combi Blocks) in HCl (120 ml) was added NaNO$_2$ (7.9 g, 115.0 mmol, Qualigens) dissolved in water (10 ml) at 0° C. and the mixture was stirred for 30 minutes. Afterward, this diazonium salt was added to an ice-cold solution of CuCl$_2$.H$_2$O (14.4 g, 96.1 mmol, Aldrich) in AcOH (80 ml), saturated with SO$_2$ gas. The resulting mixture was stirred at 25° C.) for 1 h. After completion of reaction (monitored by TLC), the mixture was poured into ice-cold water and a solid precipitated. The solid was collected by filtration, washed with water and air dried to provide 14.2 g of 3-fluoro-4-nitrobenzene-1-sulfonyl chloride as brown solid in 62% yield. 1H-NMR (400 MHz, DMSO): δ 8.29 (t, J=7.2 Hz, 1H), 8.01 (dd, 2H).

Step 2: 3-Fluoro-N-(4-Methoxybenzyl)-4-Nitro-N-(Thiazol-2-Yl)Benzenesulfonamide

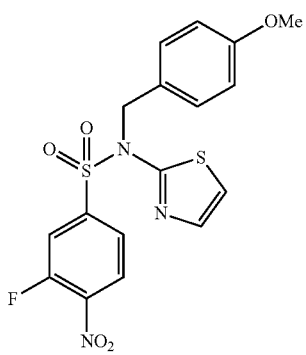 [SMILES: COc1ccc(CN(c2nccs2)S(=O)(=O)c2ccc([N+](=O)[O-])c(F)c2)cc1]

To a solution of N-(4-methoxybenzyl)thiazol-2-amine (1 g, 4.577 mmol) in THF (30 mL) was added LiHMDS (1.58 g, 9.09 mmol, Aldrich) at −78° C. and the reaction mixture was stirred at 25° C. for 15 min. Afterward, 3-fluoro-4-nitrobenzene-1-sulfonyl chloride (2.17 g, 9.09 mmol) dissolved in THF was added to the above mixture at −78° C. and reaction mixture was stirred at 25° C. for 1 h. The reaction mixture was cooled to 0° C. and quenched with ice water (70 mL). The organic compound was extracted with EtOAc, washed with water, dried over sodium sulfate and concentrated to get the crude material which was purified by silica gel column chromatography using a gradient of 0-40% EtOAc in hexanes as the eluent to afford 1.1 g of 3-fluoro-N-(4-methoxybenzyl)-4-nitro-N-(thiazol-2-yl)benzenesulfonamide as light yellow solid in 57.8% yield. 1H-NMR (400 MHz, DMSO): δ 8.12 (t, J=18.8 Hz, 1H), 8.09-8.07 (m, 1H), 7.84 (d, J=8.8 Hz, 1H), 7.49-7.53 (dd, 2H), 7.22-7.32 (m, 2H), 6.88-6.98 (m, 2H), 5.07 (s, 2H), 3.71 (s, 3H).

Step 3: 3-Hydroxy-N-(4-Methoxybenzyl)-4-Nitro-N-(Thiazol-2-Yl)Benzenesulfonamide

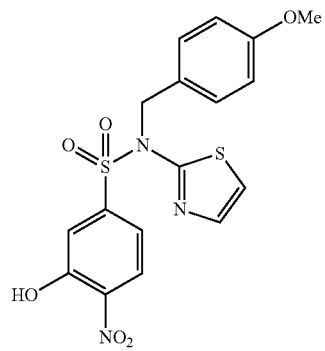

To a solution of 3-fluoro-N-(4-methoxybenzyl)-4-nitro-N-(thiazol-2-yl)benzenesulfonamide (9.0 g, 21.2 mmol) in THF (80 mL) was added a THF solution of NaOSi(Me)$_3$ (4.76 g, 42.5 mmoles, 1 M, Aldrich) at 0° C. and the resulting mixture was stirred at 25° C. for 2 h. After completion of the reaction (monitored by TLC), reaction mass was quenched with 1N HCl (70 mL). The organic compound was then extracted with EtOAc, washed with water, dried over sodium sulfate and concentrated to get the 9.20 g of crude material, 3-hydroxy-N-(4-methoxybenzyl)-4-nitro-N-(thiazol-2-yl)benzenesulfonamide as yellow semi-solid which was used for next step as is.

Step 4, Intermediate AD: 4-Amino-3-Hydroxy-N-(4-Methoxybenzyl)-N-(Thiazol-2-Yl)Benzenesulfonamide

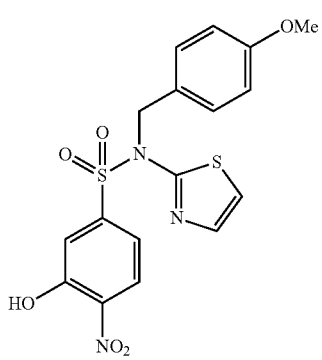 [SMILES: COc1ccc(CN(c2nccs2)S(=O)(=O)c2ccc([N+](=O)[O-])c(O)c2)cc1]

AD

To a solution of 3-hydroxy-N-(4-methoxybenzyl)-4-nitro-N-(thiazol-2-yl)benzenesulfonamide (9 g, 21.3 mmol) in AcOH (70 ml) was added Fe-powder (5.98 g, 106.0 mmol, Qualigens) and the resulting suspension was stirred at 70° C. for 2 h. The mixture was cooled to 25° C. The organic compound was extracted with EtOAc, washed with saturated aqueous solution of NaHCO$_3$, dried over sodium sulfate and concentrated. The resulting residue was purified by silica gel chromatography using a gradient of 0-50% EtOAc in hexanes as eluent to afford 5.5 g of 4-amino-3-hydroxy-N-(4-methoxybenzyl)-N-(thiazol-2-yl)benzenesulfonamide (INTERMEDIATE AD) as off white solid in 66.2% yield. 1H-NMR (400 MHz, DMSO): δ 9.82 (s, 1H), 7.37 (s, 1H), 7.29 (m, 1H), 7.21-7.25 (m, 2H), 7.08-7.09 (dd, 1H), 7.06 (s, 1H), 6.84 (d, J=8.8 Hz, 2H), 6.62 (d, J=8.4 Hz, 1H), 5.67 (s, 2H), 4.91 (s, 2H), 3.70 (s, 3H); m/z (ESI, positive ion) 392.1 (M+H).

Example 93

4-(2-Cyano-4-(Trifluoromethyl)Phenyl)-2-Methyl-N-(Thiazol-2-Yl)-3,4-Dihydro-2H-Benzo[B][1,4]Oxazine-7-Sulfonamide

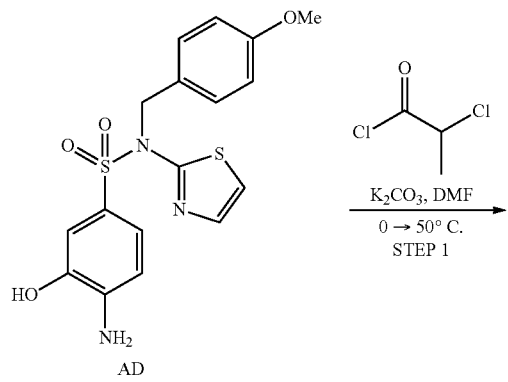

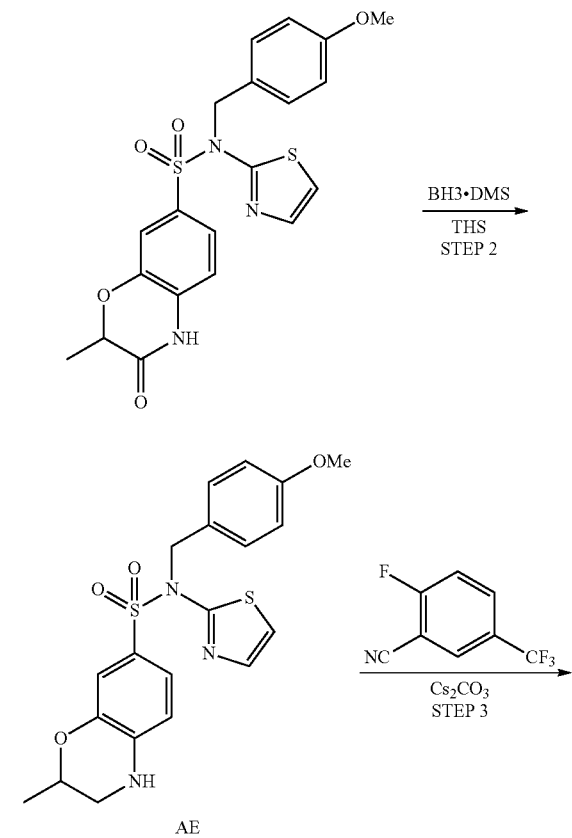

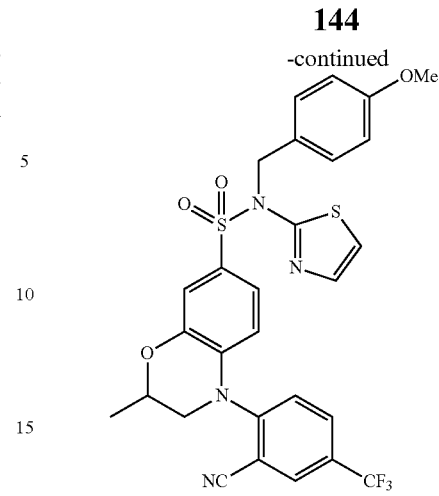

Step 1: N-(4-Methoxybenzyl)-2-Methyl-3-Oxo-N-(Thiazol-2-Yl)-3,4-Dihydro-2H-Benzo[B][1,4]Oxazine-7-Sulfonamide

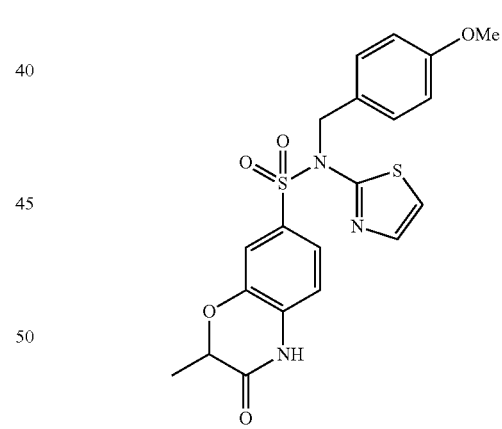

To a solution of 4-amino-3-hydroxy-N-(4-methoxybenzyl)-N-(thiazol-2-yl)benzenesulfonamide (INTERMEDIATE AD) (2.0 g, 5.12 mmol) in DMF (15 mL) was added K₂CO₃ (2.1 g, 15.3 mmol, Quaigens). To the above suspension was added 2-chloropropanoyl chloride (0.780 g, 6.15 mmol) at 0° C. and reaction mixture was stirred at 25° C. for 30 min, then heated 60° C. for 3 h. The reaction mixture was cooled to 25° C. The organic compound was extracted with EtOAc, washed with water, dried over sodium sulfate and concentrated. The resulting residue was purified by silica gel column chromatography using a gradient of 0-50% EtOAc in hexanes as the eluent to afford 1.45 g of N-(4-methoxybenzyl)-2-methyl-3-oxo-N-(thiazol-2-yl)-3,4-dihydro-2H-benzo[b][1,4]oxazine-7-sulfonamide as off white solid in 63.6% yield. 1H-NMR (400 MHz, DMSO): δ 7.45-7.46 (m, 2H), 7.40-7.44 (m, 1H), 7.23-7.26 (m, 3H), 7.02 (d, J=8.4 Hz, 1H), 6.85 (d, J=8.8 Hz, 2H), 5.19 (s, 2H), 3.70 (s, 3H), 1.44 (t, J=6.8 Hz, 3H); m/z (ESI, positive ion) 445.9 (M+H).

Step 2, Intermediate AE: N-(4-Methoxybenzyl)-2-Methyl-N-(Thiazol-2-Yl)-3,4-Dihydro-2H-Benzo[B][1,4]Oxazine-7-Sulfonamide

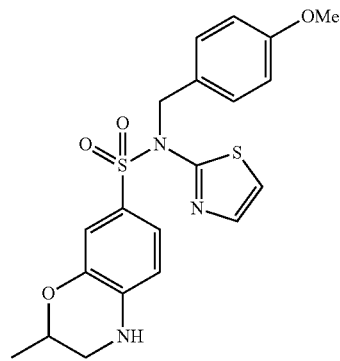

AE

To a solution of N-(4-methoxybenzyl)-2-methyl-3-oxo-N-(thiazol-2-yl)-3,4-dihydro-2H-benzo[b][1,4]oxazine-7-sulfonamide (1.45 g, 3.14 mmol) in THF (25 ml.) was added borane dimethyl sulfide (1M in THF) (0.343 g, 4.71 mmol, Aldrich) at 0° C. and reaction mixture was stirred at 25° C. for 5 h. The reaction mixture was quenched with MeOH (15 mL) and the solvent was removed under vacuum. The residue obtained was diluted with MeOH and stirred at 25° C. for 1 h, then concentrated in vacuo. The resulting residue was purified by silica gel column chromatography using a gradient of 0-50% EtOAc in hexanes as the eluent to afford 1.3 g of N-(4-methoxybenzyl)-2-methyl-N-(thiazol-2-yl)-3,4-dihydro-2H-benzo[b][1,4]oxazine-7-sulfonamide (INTERMEDIATE AE) as off white solid in 92% yield.

Step 3: 4-(2-Cyano-4-(Trifluoromethyl)Phenyl)-N-(4-Methoxybenzyl)-2-Methyl-N-(Thiazol-2-Yl)-3,4-Dihydro-2H-Benzo[B][1,4]Oxazine-7-Sulfonamide

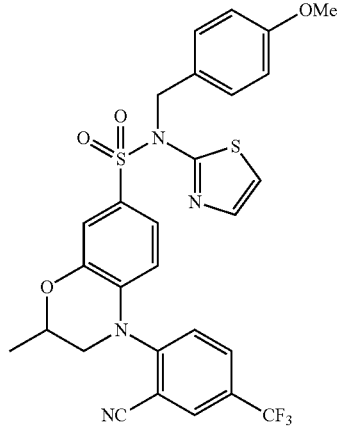 [SMILES: COc1ccc(CN(c2nccs2)S(=O)(=O)c2ccc3c(c2)OC(C)CN3c2ccc(C(F)(F)F)cc2C#N)cc1]

To a solution of N-(4-methoxybenzyl)-2-methyl-N-(thiazol-2-yl)-3,4-dihydro-2H-benzo[b][1,4]oxazine-7-sulfonamide (INTERMEDIATE AE) (1.3 g, 3.02 mmol) and 2-fluoro-5-(trifluoromethyl)benzonitrile in DMF (20 ml) was added Cs₂CO₃ (1.8 g, 5.56 mmol) at 25° C. and the reaction mixture was stirred at 90° C. for 2 h. The reaction mixture was poured into ice water and the resulting mixture was extracted with EtOAc. The layers were separated and the organic layer was washed with water, dried over sodium sulfate and concentrated. The resulting residue was purified by silica gel column chromatography using a gradient of 0-50% EtOAc in hexanes to afford 1.2 g of 4-(2-cyano-4-(trifluoromethyl)phenyl)-N-(4-methoxybenzyl)-2-methyl-N-(thiazol-2-yl)-3,4-dihydro-2H-benzo[b][1,4]oxazine-7-sulfonamide as off white solid in 75% yield. 1H-NMR (400 MHz, DMSO): 6.44 (s, 1H), 8.12 (d, J=8.8 Hz, 1H), 7.76 (d, J=8.4 Hz, 1H), 7.75-7.77 (m, 1H), 7.43-7.44 (m, 1H), 7.19-7.25 (m, 4H), 6.78-6.86 (m, 3H), 5.02 (s, 2H), 4.37-4.42 (m, 1H), 3.89-3.92 (m, 1H), 3.70 (s, 3H), 3.55-3.61 (m, 1H), 1.35 (s, 3H); m/z (ESI, positive ion) 601.0 (M+H)

Step 4, Example 93: 4-(2-Cyano-4-(Trifluoromethyl) Phenyl)-2-Methyl-N-(Thiazol-2-Yl)-3,4-Dihydro-2H-Benzo[B][1,4]Oxazine-7-Sulfonamide

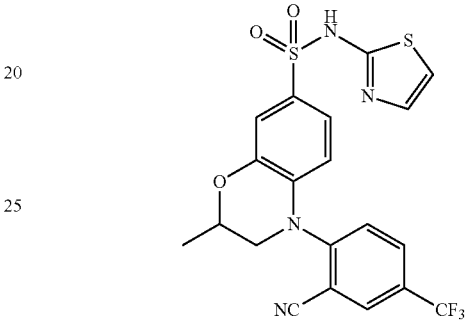

To a solution of -(2-cyano-4-(trifluoromethyl)phenyl)-N-(4-methoxybenzyl)-2-methyl-N-(thiazol-2-yl)-3,4-dihydro-2H-benzo[b][1,4]oxazine-7-sulfonamide (1.2 g, 2.00 mmol) in DCM (15 mL) was added TFA (1.14 g, 10.0 mmol, Qualigens) at 0° C. and the resulting solution was stirred at 25° C. for 2 h. The solvent was removed in vacuo and the resulting residue was dissolved in EtOAc, washed with saturated solution of NaHCO₃, dried over sodium sulfate and concentrated. The crude residue was triturated with pentane to afford 0.685 g of 4-(2-cyano-4-(trifluoromethyl)phenyl)-2-methyl-N-(thiazol-2-yl)-3,4-dihydro-2H-benzo[b][1,4]oxazine-7-sulfonamide as off white solid in 70.9% yield. ¹H NMR (400 MHz, DMSO) δ 12.66 (s, 1H), 8.39 (s, 1H), 8.05 (d, J=8.6 Hz, 1H), 7.70 (d, J=8.7 Hz, 1H), 7.20 (dd, J=16.9, 5.2 Hz, 3H), 6.80 (dd, J=21.2, 6.3 Hz, 2H), 4.38 (s, 1H), 3.89 (s, 1H), 3.54 (dd, J=12.6, 7.7 Hz, 1H), 1.34 (d, J=6.3 Hz, 3H); m/z (ESI) 480.9 (M+H).

Example 94

(S)-4-(2-Cyano-4-(Trifluoromethyl)Phenyl)-2-Methyl-N-(Thiazol-2-Yl)-3,4-Dihydro-2H-Benzo[B][1,4]Oxazine-7-Sulfonamide

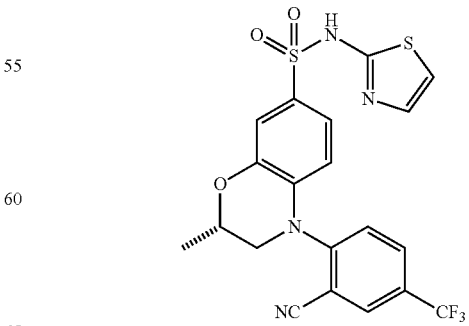

(S)-4-(2-cyano-4-(trifluoromethyl)phenyl)-2-methyl-N-(thiazol-2-yl)-3,4-dihydro-2H-benzo[b][1,4]oxazine-7-sulfonamide (absolute stereochemistry arbitrarily assigned) was obtained in enantioenriched form by chiral separation of racemic 4-(2-cyano-4-(trifluoromethyl)phenyl)-2-methyl-N-(thiazol-2-yl)-3,4-dihydro-2H-benzo[b][1,4]oxazine-7-sulfonamide (EXAMPLE 93) using supercritical fluid chromatography (SFC). The column used was Chiralcel OJ, 4.6×100 mm. The mobile phase was run under isocratic conditions; $CO_2$ with 20% MeOH co-solvent to provide (S)-4-(2-cyano-4-(trifluoromethyl)phenyl)-2-methyl-N-(thiazol-2-yl)-3,4-dihydro-2H-benzo[b][1,4]oxazine-7-sulfonamide (EXAMPLE 94) as the first eluting peak in 99% ee. $^1$H NMR and MS data were identical to that of the racemate (EXAMPLE 93).

Example 95

(R)-4-(2-Cyano-4-(Trifluoromethyl)Phenyl)-2-Methyl-N-(Thiazol-2-Yl)-3,4-Dihydro-2H-Benzo[B][1,4]Oxazine-7-Sulfonamide

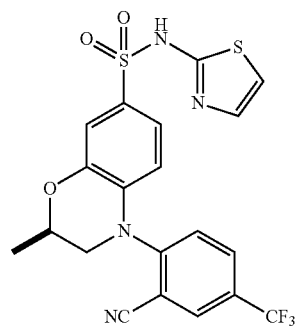 [SMILES: C[C@@H]1CN(c2ccc(C(F)(F)F)cc2C#N)c2ccc(S(=O)(=O)Nc3nccs3)cc2O1]

(R)-4-(2-cyano-4-(trifluoromethyl)phenyl)-2-methyl-N-(thiazol-2-yl)-3,4-dihydro-2H-benzo[b][1,4]oxazine-7-sulfonamide (absolute stereochemistry arbitrarily assigned) was obtained in enantioenriched form by chiral separation of racemic 4-(2-cyano-4-(trifluoromethyl)phenyl)-2-methyl-N-(thiazol-2-yl)-3,4-dihydro-2H-benzo[b][1,4]oxazine-7-sulfonamide (EXAMPLE 93) using supercritical fluid chromatography (SFC). The column used was Chiralcel OJ, 4.6×100 mm. The mobile phase was run under isocratic conditions; $CO_2$ with 20% MeOH co-solvent to provide (R)-4-(2-cyano-4-(trifluoromethyl)phenyl)-2-methyl-N-(thiazol-2-yl)-3,4-dihydro-2H-benzo[b][1,4]oxazine-7-sulfonamide (EXAMPLE 95) as the second eluting peak in 97% ee. $^1$H NMR and MS data were identical to that of the racemate (EXAMPLE 93).

Example 96

4-(2-Cyano-4-(Trifluoromethyl)Phenyl)-3-Methyl-N-(Thiazol-2-Yl)-3,4-Dihydro-2H-Benzo[B][1,4]Oxazine-7-Sulfonamide

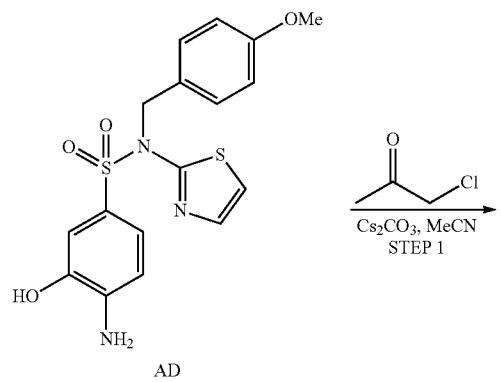

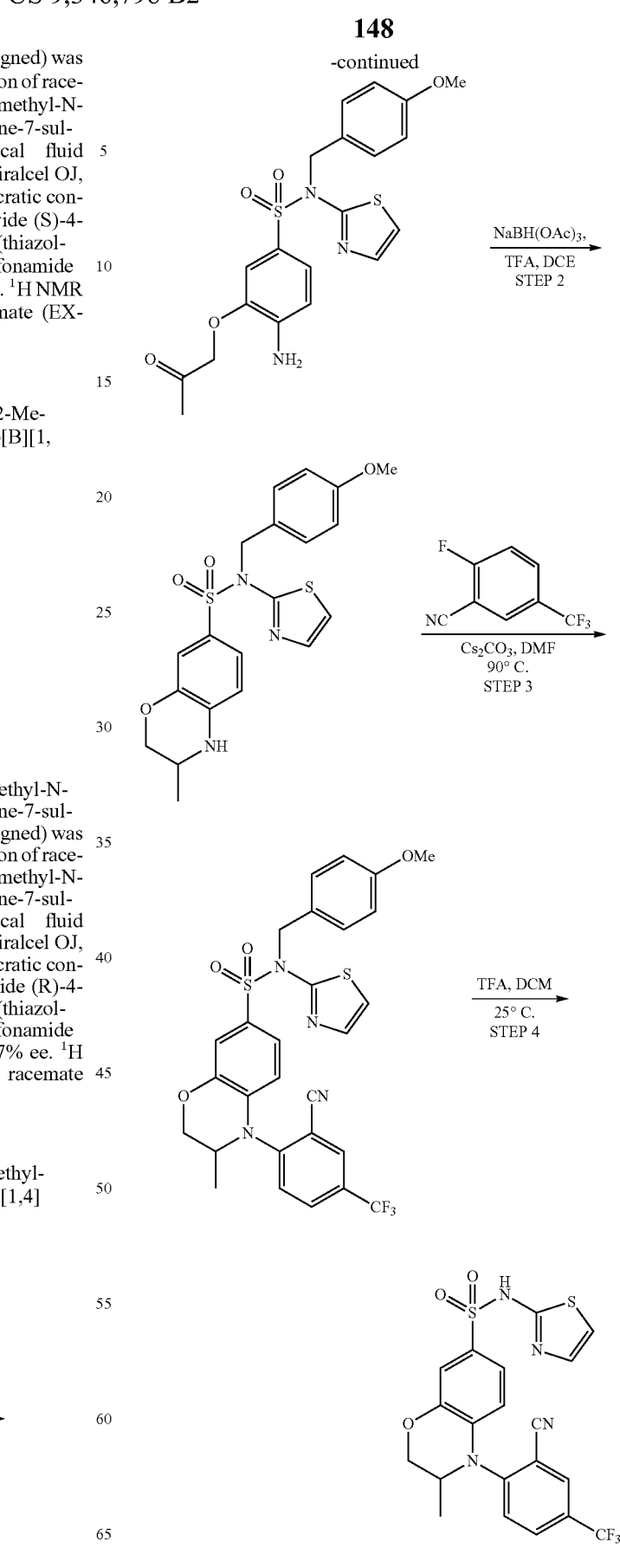

Step 1: 4-Amino-N-(4-Methoxybenzyl)-3-(2-Oxo-propoxy)-N-(Thiazol-2-Yl)Benzenesulfonamide

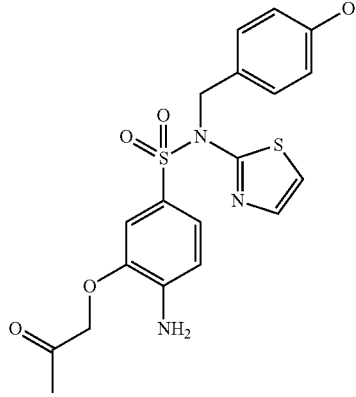

4-Amino-N-(4-methoxybenzyl)-3-(2-oxopropoxy)-1N-(thiazol-2-yl)benzenesulfonamide was prepared from INTERMEDIATE AD in the same manner as described for INTERMEDIATE Q, using 1-chloropropan-2-one instead of 2-bromo-1-phenylethanone.

Step 2: N-(4-Methoxybenzyl)-3-Methyl-N-(Thiazol-2-Yl)-3,4-Dihydro-2H-Benzo[B][1,4]Oxazine-7-Sulfonamide

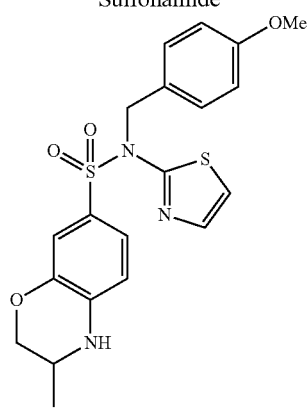

N-(4-methoxybenzyl)-3-methyl-N-(thiazol-2-yl)-3,4-dihydro-2H-benzo[b][1,4]oxazine-7-sulfonamide was prepared from 4-amino-N-(4-methoxybenzyl)-3-(2-oxopropoxy)-N-(thiazol-2-yl)benzenesulfonamide in a similar manner to that described for the synthesis of INTERMEDIATE R.

Step 3: 4-(2-Cyano-4-(Trifluoromethyl)Phenyl)-N-(4-Methoxybenzyl)-3-Methyl-N-(Thiazol-2-Yl)-3,4-Dihydro-2H-Benzo[B][1,4]Oxazine-7-Sulfonamide

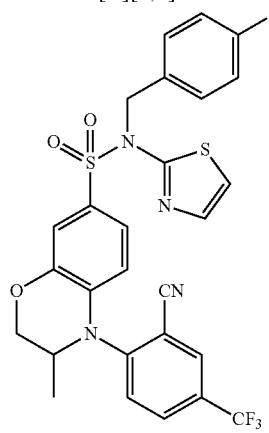

To a solution of N-(4-methoxybenzyl)-3-methyl-N-(thiazol-2-yl)-3,4-dihydro-2H-benzo[b][1,4]oxazine-7-sulfonamide (900 mg, 2.08 mmol) and 2-fluoro-5-(trifluoromethyl)benzonitrile (546 mg, 2.49 mmol, Alfa Aesar) in dimethylformamide (20 mL) was added $Cs_2CO_3$ (1.35 g, 4.16 mmol, GLR) and the mixture was heated at 90° C. for 3 h. The reaction mixture was cooled to room temperature and water (200 mL) was added. The aqueous layer was extracted with ethyl acetate (2×100 mL). The combined organic layer was dried over sodium sulfate, filtered and concentrated under reduced pressure to obtain the crude material which was further purified by column chromatography (silica gel 100-200 mesh and 0-3% methanol in dichloromethane) to obtain 4-(2-cyano-4-(trifluoromethyl)phenyl)-N-(4-methoxybenzyl)-3-methyl-N-(thiazol-2-yl)-3,4-dihydro-2H-benzo[b][1,4]oxazine-7-sulfonamide (700 mg, 56%) as off white solid. $^1$H NMR (400 MHz, DMSO) δ 8.50 (s, 1H), 8.17 (d, J=8.7 Hz, 1H), 7.77 (d, J=8.6 Hz, 1H), 7.44 (d, J=3.6 Hz, 1H), 7.35 (d, J=3.6 Hz, 1H), 7.30-7.12 (m, 4H), 6.85 (d, J=8.7 Hz, 2H), 6.55 (d, J=8.6 Hz, 1H), 5.02 (s, 2H), 4.23 (m, 2H), 4.19-4.06 (m, 1H), 3.70 (s, 3H), 1.21-1.09 (m, 3H); MS (ESI, positive ion) m/z 601.1 (M+H).

Step 4, Example 96: 4-(2-Cyano-4-(Trifluoromethyl)Phenyl)-3-Methyl-N-(Thiazol-2-Yl)-3,4-Dihydro-2H-Benzo[B][1,4]Oxazine-7-Sulfonamide

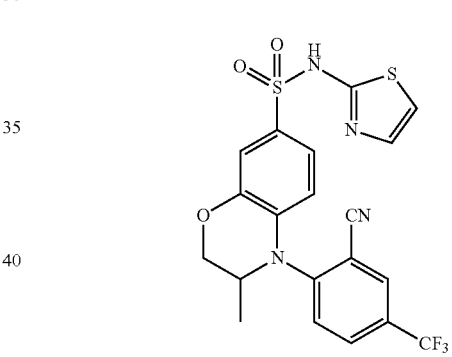

To a solution of 4-(2-cyano-4-(trifluoromethyl)phenyl)-N-(4-methoxybenzyl)-3-methyl-N-(thiazol-2-yl)-3,4-dihydro-2H-benzo[b][1,4]oxazine-7-sulfonamide (790 mg, 1.31 mmol) in dichloromethane (20 mL) was added TFA (2.0 mL, Spectrochem) at 0° C. and the mixture was allowed to stir at room temperature for 16 h. The reaction mixture was concentrated under reduced pressure to get the crude material which was basified (pH~9) with saturated aqueous $NaHCO_3$ solution. The aqueous layer was extracted with dichloromethane (2×100 mL). The combined organic layer was dried over sodium sulfate, filtered and concentrated under reduced pressure to get the crude material which was purified by column chromatography (silica gel 100-200 mesh, elution 0-5% methanol in dichloromethane) to obtain 4-(2-cyano-4-(trifluoromethyl)phenyl)-3-methyl-N-(thiazol-2-yl)-3,4-dihydro-2H-benzo[b][1,4]oxazine-7-sulfonamide (530 mg, 84%) as off white solid. $^1$H NMR (400 MHz, DMSO) δ 12.66 (s, 1H), 8.44 (s, 1H), 8.08 (d, J=7.5 Hz, 1H), 7.67 (d, J=8.4 Hz, 1H), 7.27-7.22 (m, 2H), 7.19 (d, J=8.5 Hz, 1H), 6.82 (d, J=4.5 Hz, 1H), 6.64 (d, J=8.5 Hz, 1H), 4.28-4.03 (m, 3H), 1.20 (d, J=6.5 Hz, 3H); MS (ESI, positive ion) m/z 481.1 (M+H).

Example 97

(R)-4-(2-Cyano-4-(Trifluoromethyl)Phenyl)-3-Methyl-N-(Thiazol-2-Yl)-3,4-Dihydro-2H-Benzo[B][1,4]Oxazine-7-Sulfonamide

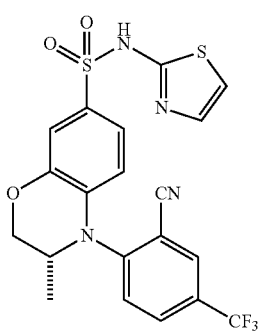 [SMILES: CC1COc2cc(S(=O)(=O)Nc3nccs3)ccc2N1c1ccc(C(F)(F)F)cc1C#N]

(R)-4-(2-cyano-4-(trifluoromethyl)phenyl)-3-methyl-N-(thiazol-2-yl)-3,4-dihydro-2H-benzo[b][1,4]oxazine-7-sulfonamide (absolute stereochemistry arbitrarily assigned) was obtained in enantioenriched form by chiral separation of racemic 4-(2-cyano-4-(trifluoromethyl)phenyl)-3-methyl-N-(thiazol-2-yl)-3,4-dihydro-2H-benzo[b][1,4]oxazine-7-sulfonamide (EXAMPLE 96) using supercritical fluid chromatography (SFC). The column used was Chiralcel OJ-H, 4.6×100 mm. The mobile phase was run under isocratic conditions; $CO_2$ with 20% MeOH co-solvent to provide (R)-4-(2-cyano-4-(trifluoromethyl)phenyl)-3-methyl-N-(thiazol-2-yl)-3,4-dihydro-2H-benzo[b][1,4]oxazine-7-sulfonamide (EXAMPLE 97) as the first eluting peak in 99% ee. $^1$H NMR and MS data were identical to that of the racemate (EXAMPLE 96).

Example 98

(S)-4-(2-Cyano-4-(Trifluoromethyl)Phenyl)-3-Methyl-N-(Thiazol-2-Yl)-3,4-Dihydro-2H-Benzo[B][1,4]Oxazine-7-Sulfonamide

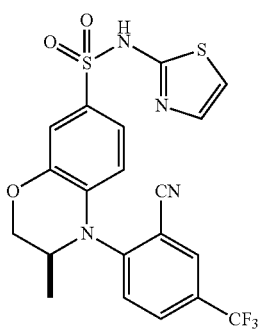 [SMILES: C[C@H]1COc2cc(S(=O)(=O)Nc3nccs3)ccc2N1c1ccc(C(F)(F)F)cc1C#N]

(S)-4-(2-cyano-4-(trifluoromethyl)phenyl)-3-methyl-N-(thiazol-2-yl)-3,4-dihydro-2H-benzo[b][1,4]oxazine-7-sulfonamide (absolute stereochemistry arbitrarily assigned) was obtained in enantioenriched form by chiral separation of racemic 4-(2-cyano-4-(trifluoromethyl)phenyl)-3-methyl-N-(thiazol-2-yl)-3,4-dihydro-2H-benzo[b][1,4]oxazine-7-sulfonamide (EXAMPLE 96) using supercritical fluid chromatography (SFC). The column used was Chiralcel OJ-H, 4.6×100 mm. The mobile phase was run under isocratic conditions; $CO_2$ with 20% MeOH co-solvent to provide (S)-4-(2-cyano-4-(trifluoromethyl)phenyl)-3-methyl-N-(thiazol-2-yl)-3,4-dihydro-2H-benzo[b][1,4]oxazine-7-sulfonamide (EXAMPLE 98) as the second eluting peak in 99% ee. $^1$H NMR and MS data were identical to that of the racemate (EXAMPLE 96).

Example 99

4-(3-Chloro-5-(Trifluoromethyl)Pyridin-2-Yl)-N-(Pyrimidin-4-Yl)-3,4-Dihydro-2H-Benzo[B][1,4]Oxazine-7-Sulfonamide

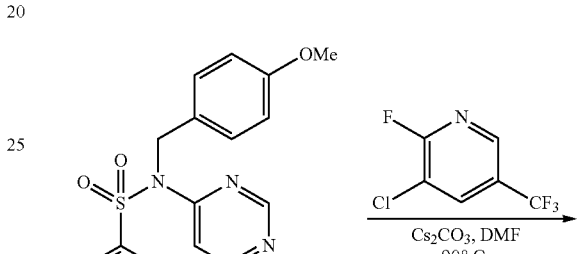

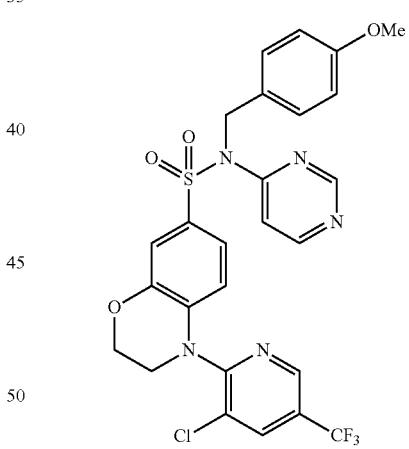

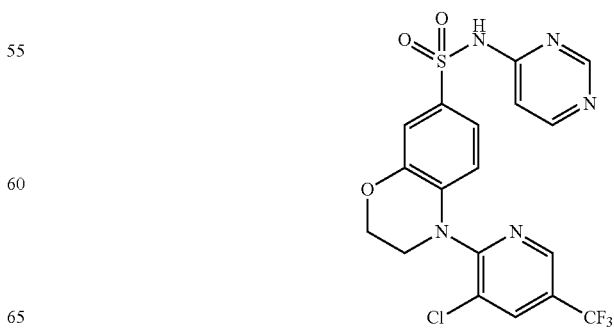

Step 1: N-(4-Methoxybenzyl)-N-(Pyrimidin-4-Yl)-3,4-Dihydro-2H-Benzo[B][1,4]Oxazine-7-Sulfonamide

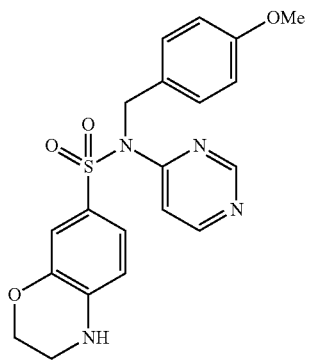 [SMILES: COc1ccc(CN(c2ccncn2)S(=O)(=O)c2ccc3c(c2)OCCN3)cc1]

N-(4-methoxybenzyl)-N-(pyrimidin-4-yl)-3,4-dihydro-2H-benzo[b][1,4]oxazine-7-sulfonamide was synthesized in a manner similar to that described for INTERMEDIATE L starting from 3-fluoro-4-nitrobenzenesulfonyl chloride (Matrix Scientific) and using INTERMEDIATE AC instead of N-(4-methoxybenzyl)-1,2,4-thiadiazol-5-amine.

Step 2: 4-(3-Chloro-5-(Trifluoromethyl)Pyridin-2-Yl)-N-(4-Methoxybenzyl)-N-(Pyrimidin-4-Yl)-3,4-Dihydro-2H-Benzo[B][1,4]Oxazine-7-Sulfonamide

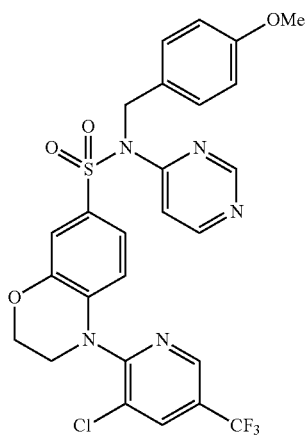 [SMILES: COc1ccc(CN(c2ccncn2)S(=O)(=O)c2ccc3c(c2)OCCN3c2ncc(C(F)(F)F)cc2Cl)cc1]

4-(3-Chloro-5-(trifluoromethyl)pyridin-2-yl)-N-(4-methoxybenzyl)-N-(pyrimidin-4-yl)-3,4-dihydro-2H-benzo[b][1,4]oxazine-7-sulfonamide was synthesized from N-(4-methoxybenzyl)-N-(pyrimidin-4-yl)-3,4-dihydro-2H-benzo[b][1,4]oxazine-7-sulfonamide and 3-chloro-2-fluoro-5-(trifluoromethyl)pyridine (Aldrich) in a manner similar to that described for EXAMPLE 94, Step 3.

Step 3, Example 99: 4-(3-Chloro-5-(Trifluoromethyl)Pyridin-2-Yl)-N-(Pyrimidin-4-Yl)-3,4-Dihydro-2H-Benzo[B][1,4]Oxazine-7-Sulfonamide

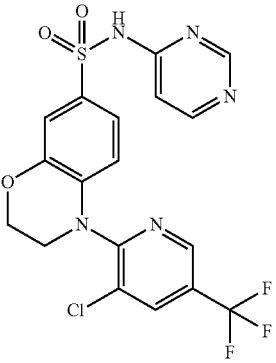 [SMILES: O=S(=O)(Nc1ccncn1)c1ccc2c(c1)OCCN2c1ncc(C(F)(F)F)cc1Cl]

4-(3-Chloro-5-(trifluoromethyl)pyridin-2-yl)-N-(pyrimidin-4-yl)-3,4-dihydro-2H-benzo[b][1,4]oxazine-7-sulfonamide was synthesized from 4-(3-chloro-5-(trifluoromethyl)pyridin-2-yl)-N-(4-methoxybenzyl)-N-(pyrimidin-4-yl)-3,4-dihydro-2H-benzo[b][1,4]oxazine-7-sulfonamide in a manner similar to that described for EXAMPLE 94, Step 4. $^1$H NMR (400 MHz, DMSO) δ 12.23 (s, 1H), 8.80 (d, J=2.2 Hz, 1H), 8.66 (s, 1H), 8.55 (d, J=2.2 Hz, 1H), 8.39 (s, 1H), 7.37 (d, J=2.4 Hz, 1H), 7.29 (dd, J=8.5, 2.3 Hz, 1H), 7.05 (s, 1H), 6.77 (d, J=8.6 Hz, 1H), 4.35 (t, J=4.2 Hz, 2H), 3.88 (t, J=4.3 Hz, 2H); MS (ESI, positive ion) m/z 472.0 (M+H).

Example 100

4-(2-Cyano-4-(Trifluoromethyl)Phenyl)-2-Ethyl-N-(Thiazol-2-Yl)-3,4-Dihydro-2H-Benzo[B][1,4]Oxazine-7-Sulfonamide

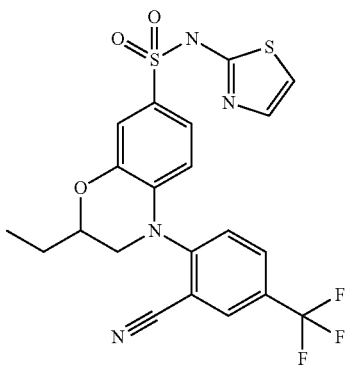 [SMILES: CCC1CN(c2ccc(C(F)(F)F)cc2C#N)c2ccc(S(=O)(=O)Nc3nccs3)cc2O1]

4-(2-Cyano-4-(trifluoromethyl)phenyl)-2-ethyl-N-(thiazol-2-yl)-3,4-dihydro-2H-benzo[b][1,4]oxazine-7-sulfonamide was synthesized in a manner similar to that described for EXAMPLE 93 using 2-chlorobutanoyl chloride instead of 2-chloropropanoyl chloride in Step 1. $^1$H NMR (400 MHz, DMSO) δ 12.52 (s, 1H), 8.39 (d, J=2.3 Hz, 1H), 8.06 (dd, J=8.6, 2.4 Hz, 1H), 7.72 (d, J=8.6 Hz, 1H), 7.26-7.21 (m, 2H), 7.17 (dd, J=8.4, 2.2 Hz, 1H), 6.80 (dd, J=6.4, 2.1 Hz, 2H), 4.30-4.06 (m, 1H), 3.89 (dd, J=12.4, 2.5 Hz, 1H), 3.59 (dd, J=12.5, 7.3 Hz, 1H), 1.83-1.58 (m, J=7.0 Hz, 2H), 0.99 (t, J=7.4 Hz, 3H); MS (ESI) m/z: 495.0 (M+H).

Example 101

(S)-4-(2-Cyano-4-(Trifluoromethyl)Phenyl)-2-Ethyl-N-(Thiazol-2-Yl)-3,4-Dihydro-2H-Benzo[B][1,4]Oxazine-7-Sulfonamide

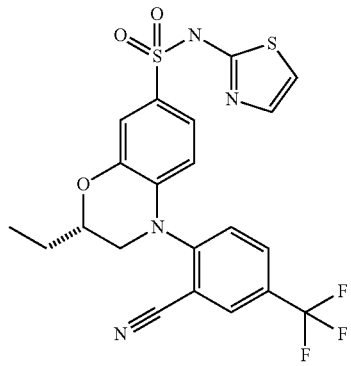

(S)-4-(2-Cyano-4-(trifluoromethyl)phenyl)-2-ethyl-N-(thiazol-2-yl)-3,4-dihydro-2H-benzo[b][1,4]oxazine-7-sulfonamide (absolute stereochemistry arbitrarily assigned) was obtained in enantioenriched form by chiral separation of racemic 4-(2-cyano-4-(trifluoromethyl)phenyl)-2-ethyl-N-(thiazol-2-yl)-3,4-dihydro-2H-benzo[b][1,4]oxazine-7-sulfonamide (EXAMPLE 100) using supercritical fluid chromatography (SFC). The column used was Chiralcel OJ-H, 4.6×100 mm. The mobile phase was run under isocratic conditions; $CO_2$ with 15% MeOH co-solvent to provide (S)-4-(2-cyano-4-(trifluoromethyl)phenyl)-2-ethyl-N-(thiazol-2-yl)-3,4-dihydro-2H-benzo[b][1,4]oxazine-7-sulfonamide (EXAMPLE 101) as the first eluting peak in 99% ee. $^1$H NMR and MS data were identical to that of the racemate (EXAMPLE 100).

Example 102

(R)-4-(2-Cyano-4-(Trifluoromethyl)Phenyl)-2-Ethyl-N-(Thiazol-2-Yl)-3,4-Dihydro-2H-Benzo[B][1,4]Oxazine-7-Sulfonamide

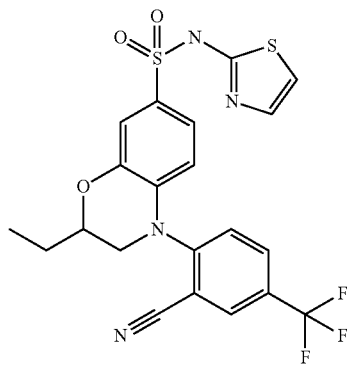

(R)-4-(2-cyano-4-(trifluoromethyl)phenyl)-2-ethyl-N-(thiazol-2-yl)-3,4-dihydro-2H-benzo[b][1,4]oxazine-7-sulfonamide (absolute stereochemistry arbitrarily assigned) was obtained in enantioenriched form by chiral separation of racemic 4-(2-cyano-4-(trifluoromethyl)phenyl)-2-ethyl-N-(thiazol-2-yl)-3,4-dihydro-2H-benzo[b][1,4]oxazine-7-sulfonamide (EXAMPLE 100) using supercritical fluid chromatography (SFC). The column used was Chiralcel OJ-H, 4.6×100 mm. The mobile phase was run under isocratic conditions; $CO_2$ with 15% MeOH co-solvent to provide (R)-4-(2-cyano-4-(trifluoromethyl)phenyl)-2-ethyl-N-(thiazol-2-yl)-3,4-dihydro-2H-benzo[b][1,4]oxazine-7-sulfonamide (EXAMPLE 102) as the second eluting peak in 99% ee. $^1$H NMR and MS data were identical to that of the racemate (EXAMPLE 100).

Example 103

4-(4-Chloro-2-Methoxyphenyl)-2-Methyl-N-(Thiazol-2-Yl)-3,4-Dihydro-2H-Benzo[B][1,4]Oxazine-7-Sulfonamide

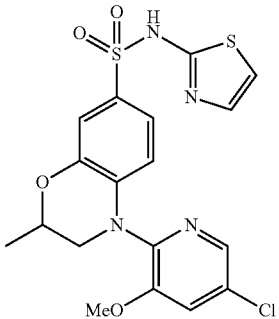 [SMILES: COc1cc(Cl)cnc1N1CC(C)Oc2cc(S(=O)(=O)Nc3nccs3)ccc21]

4-(4-chloro-2-methoxyphenyl)-2-methyl-N-(thiazol-2-yl)-3,4-dihydro-2H-benzo[b][1,4]oxazine-7-sulfonamide was synthesized from INTERMEDIATE AE in a manner similar to that described for EXAMPLE 49, using 1-bromo-4-chloro-2-methoxybenzene (Alfa Aesar) instead of 2-bromo-5-(trifluoromethyl)benzonitrile. $^1$H NMR (400 MHz, DMSO) δ 12.53 (s, 1H), 7.30 (d, J=8.3 Hz, 1H), 7.25 (d, J=2.3 Hz, 1H), 7.22 (d, J=4.7 Hz, 1H), 7.08 (q, J=4.1 Hz, 3H), 6.77 (d, J=4.5 Hz, 1H), 6.19 (d, J=8.4 Hz, 1H), 4.41-4.22 (m, 1H), 3.77 (s, 3H), 3.52 (dd, J=12.1, 2.7 Hz, 1H), 3.39 (dd, J=12.2, 7.6 Hz, 1H), 1.32 (d, J=6.3 Hz, 3H); MS (ESI) m/z: 451.9 (M+H).

Example 104

(S)-4-(4-Chloro-2-Methoxyphenyl)-2-Methyl-N-(Thiazol-2-Yl)-3,4-Dihydro-2H-Benzo[B][1,4]Oxazine-7-Sulfonamide

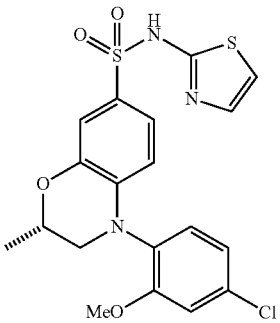 [SMILES: COc1cc(Cl)ccc1N1C[C@H](C)Oc2cc(S(=O)(=O)Nc3nccs3)ccc21]

(S)-4-(4-chloro-2-methoxyphenyl)-2-methyl-N-(thiazol-2-yl)-3,4-dihydro-2H-benzo[b][1,4]oxazine-7-sulfonamide (absolute stereochemistry arbitrarily assigned) was obtained in enantioenriched form by chiral separation of racemic 4-(4-chloro-2-methoxyphenyl)-2-methyl-N-(thiazol-2-yl)-3,4-dihydro-2H-benzo[b][1,4]oxazine-7-sulfonamide (EXAMPLE 103) using supercritical fluid chromatography (SFC). The column used was Chiralcel OJ-H, 4.6×100 mm. The mobile phase was run under isocratic conditions; $CO_2$ with 45% MeOH co-solvent to provide (S)-4-(4-chloro-2-methoxyphenyl)-2-methyl-N-(thiazol-2-yl)-3,4-dihydro-2H-benzo[b][1,4]oxazine-7-sulfonamide (EXAMPLE 104) as the first eluting peak in 99% ee. $^1$H NMR and MS data were identical to that of the racemate (EXAMPLE 103).

Example 105

(R)-4-(4-Chloro-2-Methoxyphenyl)-2-Methyl-N-(Thiazol-2-Yl)-3,4-Dihydro-2H-Benzo[B][1,4]Oxazine-7-Sulfonamide

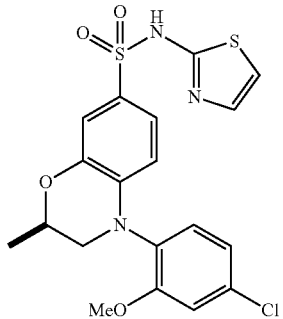 [SMILES: COc1cc(Cl)ccc1N1C[C@@H](C)Oc2cc(S(=O)(=O)Nc3nccs3)ccc21]

(R)-4-(4-chloro-2-methoxyphenyl)-2-methyl-N-(thiazol-2-yl)-3,4-dihydro-2H-benzo[b][1,4]oxazine-7-sulfonamide (absolute stereochemistry arbitrarily assigned) was obtained in enantio-enriched form by chiral separation of racemic 4-(4-chloro-2-methoxyphenyl)-2-methyl-N-(thiazol-2-yl)-3,4-dihydro-2H-benzo[b][1,4]oxazine-7-sulfonamide (EXAMPLE 103) using supercritical fluid chromatography (SFC). The column used was Chiralcel OJ-H, 4.6×100 mm. The mobile phase was run under isocratic conditions; $CO_2$ with 45% MeOH co-solvent to provide (R)-4-(4-chloro-2-methoxyphenyl)-2-methyl-N-(thiazol-2-yl)-3,4-dihydro-2H-benzo[b][1,4]oxazine-7-sulfonamide (EXAMPLE 105) as the second eluting peak in 99% ee. $^1$H NMR and MS data were identical to that of the racemate (EXAMPLE 103).

Example 106

4-(4-Cyano-2-Methoxyphenyl)-2-Methyl-N-(Thiazol-2-Yl)-3,4-Dihydro-2H-Benzo[B][1,4]Oxazine-7-Sulfonamide

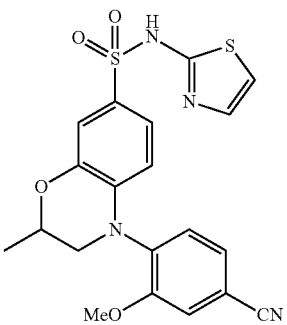 [SMILES: COc1cc(C#N)ccc1N1CC(C)Oc2cc(S(=O)(=O)Nc3nccs3)ccc21]

4-(4-cyano-2-methoxyphenyl)-2-methyl-N-(thiazol-2-yl)-3,4-dihydro-2H-benzo[b][1,4]oxazine-7-sulfonamide was synthesized from INTERMEDIATE AE in a manner similar to that described for EXAMPLE 49, using 4-bromo-3-methoxybenzonitrile (Combi-blocks) instead of 2-bromo-5-(trifluoromethyl)benzonitrile. $^1$H NMR (400 MHz, DMSO) δ 12.54 (s, 1H), 7.64 (d, J=1.8 Hz, 1H), 7.56-7.38 (m, 2H), 7.23 (d, J=4.5 Hz, 1H), 7.17-7.02 (m, 2H), 6.78 (d, J=4.8 Hz, 1H), 6.35 (d, J=8.4 Hz, 1H), 4.33 (ddd, J=11.7, 8.0, 5.9 Hz, 1H), 3.82 (s, 3H), 3.62 (dd, J=12.6, 2.5 Hz, 1H), 3.49-3.37 (m, 1H), 1.31 (d, J=6.2 Hz, 3H); MS (ESI) m/z: 443 (M+H).

Example 107

(S)-4-(4-Cyano-2-Methoxyphenyl)-2-Methyl-N-(Thiazol-2-Yl)-3,4-Dihydro-2H-Benzo[B][1,4]Oxazine-7-Sulfonamide

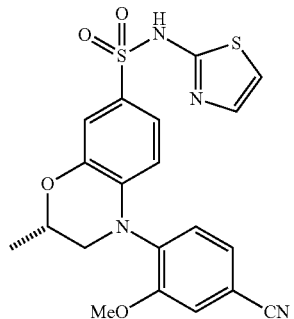 [SMILES: COc1cc(C#N)ccc1N1C[C@H](C)Oc2cc(S(=O)(=O)Nc3nccs3)ccc21]

(S)-4-(4-cyano-2-methoxyphenyl)-2-methyl-N-(thiazol-2-yl)-3,4-dihydro-2H-benzo[b][1,4]oxazine-7-sulfonamide (absolute stereochemistry arbitrarily assigned) was obtained in enantioenriched form by chiral separation of racemic 4-(4-cyano-2-methoxyphenyl)-2-methyl-N-(thiazol-2-yl)-3,4-dihydro-2H-benzo[b][1,4]oxazine-7-sulfonamide (EXAMPLE 106) using supercritical fluid chromatography (SFC). The column used was Chiralcel OJ-H, 4.6×100 mm. The mobile phase was run under isocratic conditions; $CO_2$ with 45% MeOH co-solvent to provide (S)-4-(4-cyano-2-methoxyphenyl)-2-methyl-N-(thiazol-2-yl)-3,4-dihydro-2H-benzo[b][1,4]oxazine-7-sulfonamide (EXAMPLE 107) as the first eluting peak in 99% ee. $^1$H NMR and MS data were identical to that of the racemate (EXAMPLE 106).

Example 108

(R)-4-(4-Cyano-2-Methoxyphenyl)-2-Methyl-N-(Thiazol-2-Yl)-3,4-Dihydro-2H-Benzo[B][1,4]Oxazine-7-Sulfonamide

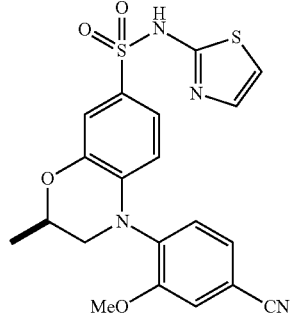 [SMILES: COc1cc(C#N)ccc1N1C[C@@H](C)Oc2cc(S(=O)(=O)Nc3nccs3)ccc21]

(R)-4-(4-cyano-2-methoxyphenyl)-2-methyl-N-(thiazol-2-yl)-3,4-dihydro-2H-benzo[b][1,4]oxazine-7-sulfonamide (absolute stereochemistry arbitrarily assigned) was obtained in enantioenriched form by chiral separation of racemic 4-(4-cyano-2-methoxyphenyl)-2-methyl-N-(thiazol-2-yl)-3,4-dihydro-2H-benzo[b][1,4]oxazine-7-sulfonamide (EXAMPLE 106) using supercritical fluid chromatography (SFC). The column used was Chiralcel OJ-H, 4.6×100 mm. The mobile phase was run under isocratic conditions; CO$_2$ with 45% MeOH co-solvent to provide (R)-4-(4-cyano-2-methoxyphenyl)-2-methyl-N-(thiazol-2-yl)-3,4-dihydro-2H-benzo[b][1,4]oxazine-7-sulfonamide (EXAMPLE 108) as the second eluting peak in 99% ee. $^1$H NMR and MS data were identical to that of the racemate (EXAMPLE 106).

Example 109

4-(3-Methoxy-6-Methyl-2-Pyridinyl)-N-1,3-Thiazol-2-Yl-3,4-Dihydro-2H-1,4-Benzoxazine-7-Sulfonamide

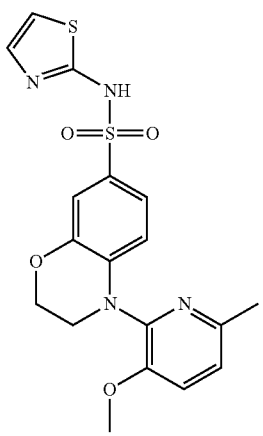 [SMILES: COc1ccc(C)nc1N1CCOc2cc(S(=O)(=O)Nc3nccs3)ccc21]

STEP 1: A resealable 1 gram reaction tube was charged with N-(4-methoxybenzyl)-N-(thiazol-2-yl)-3,4-dihydro-2H-benzo[b][1,4]oxazine-7-sulfonamide (INTERMEDIATE M, 0.100 g, 0.240 mmol), 2-bromo-3-methoxy-6-methylpyridine (Aces Pharma Inc., 00.073 g, 0.359 mmol), sodium tert-butoxide (0.046 g, 0.479 mmol), tris(dibenzylideneacetone)dipalladium(0) (0.022 g, 0.359 mmol) and xantphos (0.028 g, 0.048 mmol). After purging with N2, toluene (2.5 mL) was added. The vessel was sealed and shaken at 100° C. overnight. LCMS confirmed coupling product formation.

STEP 2: TFA (0.3 mL) was added to the crude reaction mixture from STEP 1 and shaking was resumed for 2 h at RT. The mixture was then filtered through a plug of Celite, washing with DCM. After genevac to remove excess acid and solvents, high throughput LC/MS directed purification using 0.1% NH$_4$OH in CH$_3$CN and water as a mobile phase afforded 4-(3-methoxy-6-methyl-2-pyridinyl)-N-1,3-thiazol-2-yl-3,4-dihydro-2H-1,4-benzoxazine-7-sulfonamide (0.057 g) as a solid. $^1$H NMR (500 MHz, DMSO-d$_6$) δ ppm 2.36 (s, 3 H), 3.70 (t, J=4.30 Hz, 2 H), 3.75 (s, 1 H) 4.30 (t, J=4.30 Hz, 2 H) 6.40 (d, J=8.59 Hz, 1 H) 6.78 (d, J=4.58 Hz, 1 H) 7.06-7.17 (m, 3 H) 7.18-7.27 (m, 1 H) 7.46 (d, J=8.36 Hz, 1 H) 12.57 (br. s., 1 H). m/z (ESI) 533.0 (M+H)$^+$. m/z (ESI) 419 (M+H)$^+$.

Example 110

4-(5-Fluoro-3-Methylpyridin-2-Yl)-N-(Thiazol-2-Yl)-3,4-Dihydro-2H-Benzo[B][1,4]Oxazine-7-Sulfonamide

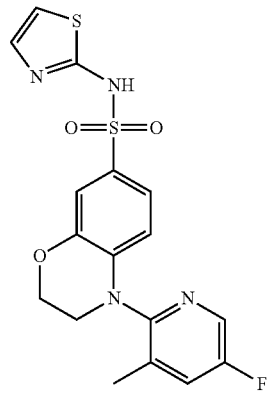 [SMILES: Cc1cc(F)cnc1N1CCOc2cc(S(=O)(=O)Nc3nccs3)ccc21]

4-(5-Fluoro-3-methylpyridin-2-yl)-N-(thiazol-2-yl)-3,4-dihydro-2H-benzo[b][1,4]oxazine-7-sulfonamide (EXAMPLE 110) (0.037 g) was prepared in the same manner as EXAMPLE 109, using 2-bromo-5-fluoro-3-methylpyridine (Sigma-Aldrich) instead of 2-bromo-3-methoxy-6-methylpyridine. $^1$H NMR (500 MHz, DMSO-d$_6$) δ ppm 2.19 (s, 3 H) 3.61-3.70 (m, 2 H) 4.31-4.42 (m, 2 H) 6.18 (d, J=8.59 Hz, 1 H) 6.78 (d, J=4.47 Hz, 1 H) 7.11 (dd, J=8.48, 2.06 Hz, 1 H) 7.15 (d, J=1.95 Hz, 1 H) 7.22 (d, J=4.70 Hz, 1 H) 7.79 (dd, J=8.99, 2.69 Hz, 1 H) 8.35 (d, J=2.86 Hz, 1 H) 12.54 (br. s., 1 H). m/z (ESI) 407 (M+H)$^+$.

Example 111

4-(5-Chloro-2-Methoxypyridin-3-Yl)-N-(Thiazol-2-Yl)-3,4-Dihydro-2H-Benzo[B][1,4]Oxazine-7-Sulfonamide

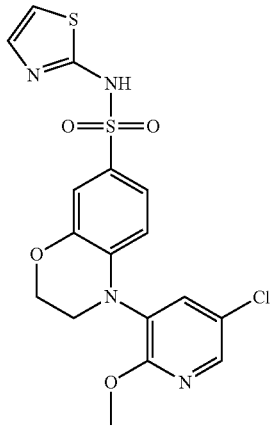 [SMILES: COc1ncc(Cl)cc1N1CCOc2cc(S(=O)(=O)Nc3nccs3)ccc21]

4-(5-Chloro-2-methoxypyridin-3-yl)-N-(thiazol-2-yl)-3,4-dihydro-2H-benzo[b][1,4]oxazine-7-sulfonamide (EXAMPLE 111) was prepared in the same manner as EXAMPLE 109, using 3-bromo-5-chloro-2-methoxypyridine (Matrix Scientific) instead of 2-bromo-3-methoxy-6-methylpyridine. $^1$HNMR (500 MHz, DMSO-d$_6$) δ ppm 3.58-3.70 (m, 2 H) 3.86 (s, 3 H) 4.24-4.33 (m, 2 H) 6.33 (d, J=8.36 Hz, 1 H) 6.78 (d, J=4.35 Hz, 1 H) 7.08-7.16 (m, 2 H) 7.22 (d, J=4.58 Hz, 1 H) 7.92 (d, J=2.41 Hz, 1 H) 8.18 (d, J=2.41 Hz, 1 H) 12.6 (br. s., 1 H). m/z (ESI) 439 (M+H)+.

Example 112

4-(4-Isopropylphenyl)-N-(Thiazol-2-Yl)-3,4-Dihydro-2H-Benzo[B][1,4]Oxazine-7-Sulfonamide

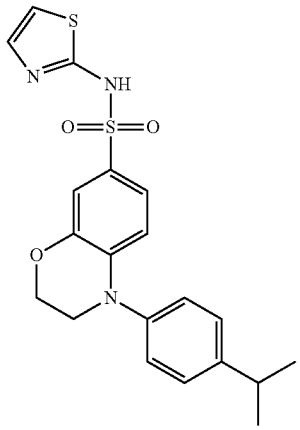 [SMILES: CC(C)c1ccc(N2CCOc3cc(S(=O)(=O)Nc4nccs4)ccc32)cc1]

4-(4-Isopropylphenyl)-N-(thiazol-2-yl)-3,4-dihydro-2H-benzo[b][1,4]oxazine-7-sulfonamide (EXAMPLE 112) (0.013 g) was prepared in the same manner as EXAMPLE 109, using 1-bromo-4-isopropylbenzene (Sigma-Aldrich) instead of 2-bromo-3-methoxy-6-methylpyridine. $^1$H NMR (500 MHz, DMSO-$d_6$) δ ppm 1.18-1.28 (m, 6 H) 2.75-2.95 (m, 1 H) 3.70 (d, J=5.04 Hz, 2 H) 4.25-4.33 (m, 2 H) 6.68 (d, J=8.25 Hz, 1 H) 6.78 (d, J=4.58 Hz, 1 H) 7.07-7.17 (m, 2 H) 7.19-7.25 (m, 3 H) 7.30 (d, J=8.36 Hz, 2 H) 12.53 (br. s., 1 H). m/z (ESI) 416 (M+H)+.

Example 113

N-(Thiazol-2-Yl)-4-(4-(2,2,2-Trifluoroethoxy)Phenyl)-3,4-Dihydro-2H-Benzo[B][1,4]Oxazine-7-Sulfonamide

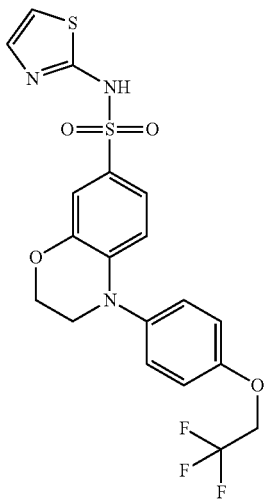 [SMILES: O=S(=O)(Nc1nccs1)c1ccc2c(c1)OCCN2c1ccc(OCC(F)(F)F)cc1]

N-(thiazol-2-yl)-4-(4-(2,2,2-trifluoroethoxy)phenyl)-3,4-dihydro-2H-benzo[b][1,4]oxazine-7-sulfonamide (EXAMPLE 113) (0.012 g) was prepared in the same manner as EXAMPLE 109, using 1-bromo-4-(2,2,2-trifluoroethoxy)benzene (Sigma-Aldrich) instead of 2-bromo-3-methoxy-6-methylpyridine. $^1$H NMR (500 MHz, DMSO-$d_6$) δ ppm 3.63-3.71 (m, 2 H) 4.26-4.35 (m, 2 H) 4.77 (q, J=8.90 Hz, 2 H) 6.53 (d, J=8.25 Hz, 1 H) 6.77 (d, J=4.70 Hz, 1 H) 7.03-7.17 (m, 4 H) 7.21 (d, J=4.58 Hz, 1 H) 7.29 (d, J=8.82 Hz, 2 H) 12.53 (br. s., 1 H). m/z (ESI) 472 (M+H)+.

Example 114

4-(2-Methoxy-5-(Trifluoromethyl)Phenyl)-N-(Thiazol-2-Yl)-3,4-Dihydro-2H-Benzo[B][1,4]Oxazine-7-Sulfonamide

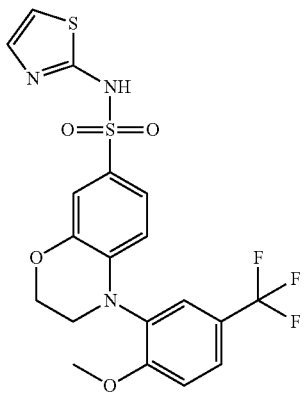 [SMILES: COc1ccc(C(F)(F)F)cc1N1CCOc2cc(S(=O)(=O)Nc3nccs3)ccc21]

4-(2-Methoxy-5-(trifluoromethyl)phenyl)-N-(thiazol-2-yl)-3,4-dihydro-2H-benzo[b][1,4]oxazine-7-sulfonamide (EXAMPLE 114) (0.013 g) was prepared in the same manner as EXAMPLE 109, using 2-bromo-1-methoxy-4-(trifluoromethyl)benzene (Sigma-Aldrich) instead of 2-bromo-3-methoxy-6-methylpyridine. $^1$H NMR (500 MHz, DMSO-$d_6$) δ ppm 3.66 (br. s., 2 H) 3.84 (s, 3 H) 4.31 (br. s., 2 H) 6.18 (d, J=8.48 Hz, 1 H) 6.77 (d, J=4.35 Hz, 1 H) 7.05-7.17 (m, 2 H) 7.21 (d, J=4.58 Hz, 1 H) 7.36 (d, J=8.71 Hz, 1 H) 7.65-7.75 (m, 2 H) 12.53 (br. s., 1 H). m/z (ESI) 472 (M+H)+.

Example 115

4-(3-Cyano-4-Methylphenyl)-N-(Thiazol-2-Yl)-3,4-Dihydro-2H-Benzo[B][1,4]Oxazine-7-Sulfonamide

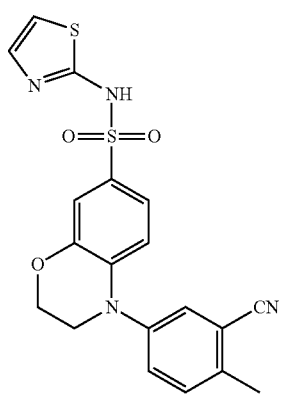 [SMILES: Cc1ccc(N2CCOc3cc(S(=O)(=O)Nc4nccs4)ccc32)cc1C#N]

4-(3-Cyano-4-methylphenyl)-N-(thiazol-2-yl)-3,4-dihydro-2H-benzo[b][1,4]oxazine-7-sulfonamide (EXAMPLE 115) (0.005 g) was prepared in the same manner as EXAMPLE 109, using 5-bromo-2-methylbenzonitrile (Sigma-Aldrich) instead of 2-bromo-3-methoxy-6-methylpyridine. $^1$H NMR (500 MHz, DMSO-$d_6$) δ ppm 2.47 (s, 3 H) 3.72 (br. s., 2 H) 4.29 (d, J=4.47 Hz, 2 H) 6.77-6.80 (m, 2 H) 7.14-7.18 (m, 2 H) 7.22 (d, J=4.12 Hz, 1 H) 7.49 (d, J=8.48 Hz, 1 H) 7.54-7.58 (m, 1 H) 7.72 (d, J=2.29 Hz, 1 H) 12.60 (br. s., 1 H). m/z (ESI) 413 (M+H)$^+$.

Example 116

4-(4-Cyano-3-Methylphenyl)-N-(Thiazol-2-Yl)-3,4-Dihydro-2H-Benzo[B][1,4]Oxazine-7-Sulfonamide

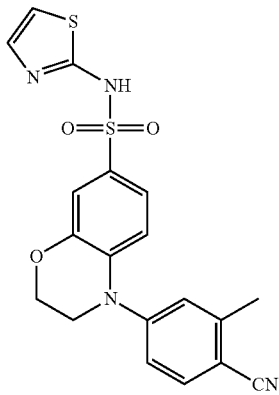 [SMILES: Cc1cc(N2CCOc3cc(S(=O)(=O)Nc4nccs4)ccc32)ccc1C#N]

4-(4-Cyano-3-methylphenyl)-N-(thiazol-2-yl)-3,4-dihydro-2H-benzo[b][1,4]oxazine-7-sulfonamide (EXAMPLE 116) (0.022 g) was prepared in the same manner as EXAMPLE 109, using 4-bromo-2-methylbenzonitrile (Sigma-Aldrich) instead of 2-bromo-3-methoxy-6-methylpyridine. $^1$H NMR (500 MHz, DMSO-$d_6$) δ ppm 2.45 (s, 3 H) 3.74-3.83 (m, 2 H) 4.23-4.36 (m, 2 H) 6.73-6.86 (m, 1 H) 7.09-7.28 (m, 5 H) 7.34 (s, 1 H) 7.72 (d, J=8.36 Hz, 1 H) 12.60 (br. s., 1 H). m/z (ESI) 413 (M+H)$^+$.

Example 117

4-(5-Cyanopyridin-3-Yl)-N-(Thiazol-2-Yl)-3,4-Dihydro-2H-Benzo[B][1,4]Oxazine-7-Sulfonamide

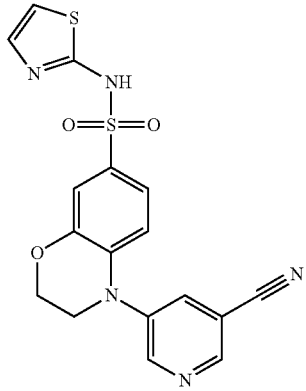 [SMILES: N#Cc1cncc(N2CCOc3cc(S(=O)(=O)Nc4nccs4)ccc32)c1]

4-(5-Cyanopyridin-3-yl)-N-(thiazol-2-yl)-3,4-dihydro-2H-benzo[b][1,4]oxazine-7-sulfonamide (EXAMPLE 117) (0.014 g) was prepared in the same manner as EXAMPLE 109, using 5-bromonicotinonitrile (Matrix Scientific) instead of 2-bromo-3-methoxy-6-methylpyridine. $^1$H NMR (500 MHz, DMSO-$d_6$) δ ppm 3.81 (d, J=4.58 Hz, 2 H) 4.27-4.37 (m, 2 H) 6.79 (d, J=4.58 Hz, 1 H) 7.01 (d, J=8.48 Hz, 1 H) 7.13-7.29 (m, 3 H) 8.26 (s, 1 H) 8.74 (d, J=1.49 Hz, 1 H) 8.85 (d, J=2.52 Hz, 1 H) 12.63 (br. s., 1 H). m/z (ESI) 400 (M+H)$^+$.

Example 118

4-(3-Cyano-4-Methoxyphenyl)-N-(Thiazol-2-Yl)-3,4-Dihydro-2H-Benzo[B][1,4]Oxazine-7-Sulfonamide

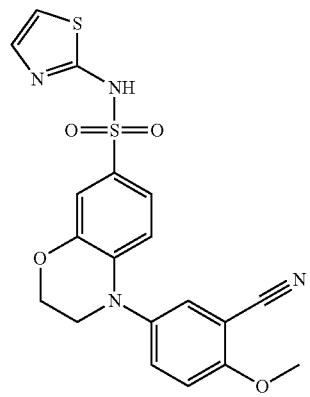 [SMILES: COc1ccc(N2CCOc3cc(S(=O)(=O)Nc4nccs4)ccc32)cc1C#N]

4-(3-Cyano-4-methoxyphenyl)-N-(thiazol-2-yl)-3,4-dihydro-2H-benzo[b][1,4]oxazine-7-sulfonamide (EXAMPLE 118) (0.009 g) was prepared in the same manner as EXAMPLE 109, using 5-bromo-2-methoxybenzonitrile (Sigma-Aldrich) instead of 2-bromo-3-methoxy-6-methylpyridine. $^1$H NMR (500 MHz, DMSO-$d_6$) δ ppm 3.68 (d, J=3.89 Hz, 2 H) 3.93 (s, 3 H) 4.26-4.36 (m, 2 H) 6.56 (d, J=8.36 Hz, 1 H) 6.77 (d, J=4.47 Hz, 1 H) 7.07-7.17 (m, 2 H) 7.21 (d, J=4.47 Hz, 1 H) 7.31 (d, J=9.05 Hz, 1 H) 7.60-7.69 (m, 1 H) 7.74 (d, J=2.63 Hz, 1 H). m/z (ESI) 429 (M+H)$^+$.

Example 119

4-(3,4-Dimethoxyphenyl)-N-(Thiazol-2-Yl)-3,4-Dihydro-2H-Benzo[B][1,4]Oxazine-7-Sulfonamide

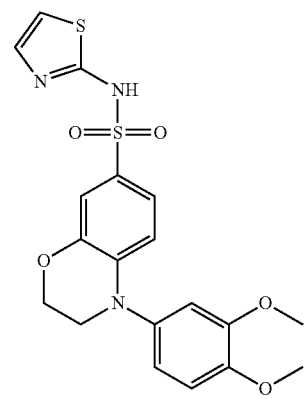 [SMILES: COc1ccc(N2CCOc3cc(S(=O)(=O)Nc4nccs4)ccc32)cc1OC]

4-(3,4-Dimethoxyphenyl)-N-(thiazol-2-yl)-3,4-dihydro-2H-benzo[b][1,4]oxazine-7-sulfonamide (EXAMPLE 119) (0.026 g) was prepared in the same manner as EXAMPLE 109, using 4-bromo-1,2-dimethoxybenzene (Sigma-Aldrich) instead of 2-bromo-3-methoxy-6-methylpyridine. $^1$H NMR (500 MHz, DMSO-$d_6$) δ ppm 3.68 (d, J=4.24 Hz, 2 H) 3.73 (s, 3 H) 3.77 (s, 3 H) 4.31 (t, J=4.12 Hz, 2 H) 6.55 (d, J=8.36 Hz, 1 H) 6.77 (d, J=4.47 Hz, 1 H) 6.83 (dd, J=8.48, 2.41 Hz, 1 H) 6.92 (d, J=2.29 Hz, 1 H) 7.00 (d, J=8.59 Hz, 1 H) 7.07-7.13 (m, 2 H) 7.21 (d, J=4.58 Hz, 1 H) 12.53 (br. s., 1 H). m/z (ESI) 434 (M+H)⁺.

Example 120

4-(2,4-Dimethoxyphenyl)-N-(Thiazol-2-Yl)-3,4-Dihydro-2H-Benzo[B][1,4]Oxazine-7-Sulfonamide

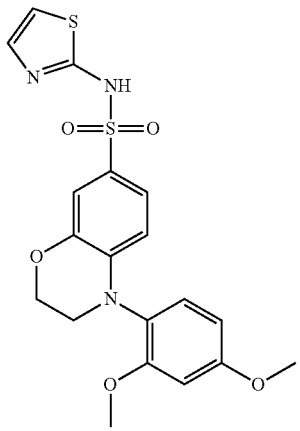 [SMILES: COc1ccc(N2CCOc3cc(S(=O)(=O)Nc4nccs4)ccc32)c(OC)c1]

4-(2,4-Dimethoxyphenyl)-N-(thiazol-2-yl)-3,4-dihydro-2H-benzo[b][1,4]oxazine-7-sulfonamide (EXAMPLE 120) (0.019 g) was prepared in the same manner as EXAMPLE 109, using 1-bromo-2,4-dimethoxybenzene (Sigma-Aldrich) instead of 2-bromo-3-methoxy-6-methylpyridine. ¹H NMR (500 MHz, DMSO-d₆) δ ppm 3.70-3.75 (m, 5 H) 3.77-3.81 (br. s., 3 H) 4.29-4.33 (m, 2 H) 6.73 (d, J=8.59 Hz, 1 H) 6.78 (d, J=4.47 Hz, 1 H) 7.11-7.16 (m, 2 H) 7.20-7.24 (m, 2 H) 7.31 (d, J=7.56 Hz, 1 H) 7.43 (t, J=7.79 Hz, 1 H) 12.55 (br. s., 1 H). m/z (ESI) 434 (M+H)⁺.

Example 121

4-(3,5-Dichloropyridin-2-Yl)-N-(Thiazol-2-Yl)-3,4-Dihydro-2H-Benzo[B][1,4]Oxazine-7-Sulfonamide

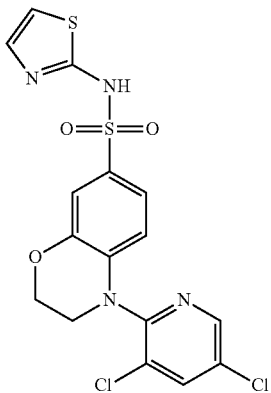 [SMILES: O=S(=O)(Nc1nccs1)c1ccc2c(c1)OCCN2c1ncc(Cl)cc1Cl]

4-(3,5-Dichloropyridin-2-yl)-N-(thiazol-2-yl)-3,4-dihydro-2H-benzo[b][1,4]oxazine-7-sulfonamide (EXAMPLE 121) (0.027 g) was prepared in the same manner as EXAMPLE 109, using 2-bromo-3,5-dichloropyridine (Sigma-Aldrich) instead of 2-bromo-3-methoxy-6-methylpyridine. ¹H NMR (500 MHz, DMSO-d₆) δ ppm 3.74-3.82 (m, 2 H) 4.25-4.37 (m, 2 H) 6.54 (d, J=8.59 Hz, 1 H) 6.79 (d, J=4.47 Hz, 1 H) 7.14 (dd, J=8.42, 2.12 Hz, 1 H) 7.17-7.28 (m, 2 H) 8.34 (d, J=2.29 Hz, 1 H) 8.50 (d, J=2.29 Hz, 1 H) 12.63 (br. s., 1 H). m/z (ESI) 444 (M+H)⁺.

Example 122

N-(Thiazol-2-Yl)-4-(6-(Trifluoromethyl)Pyridin-3-Yl)-3,4-Dihydro-2H-Benzo[B][1,4]Oxazine-7-Sulfonamide

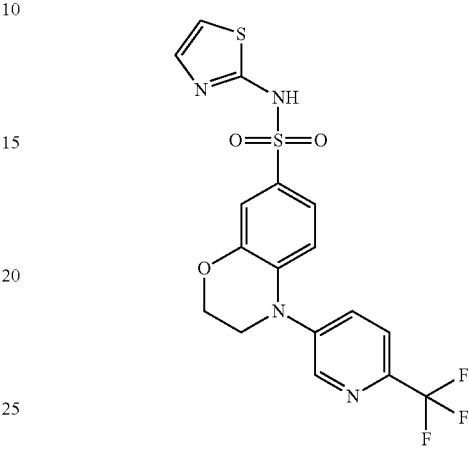

N-(thiazol-2-yl)-4-(6-(trifluoromethyl)pyridin-3-yl)-3,4-dihydro-2H-benzo[b][1,4]oxazine-7-sulfonamide (EXAMPLE 122) (0.040 g) was prepared in the same manner as EXAMPLE 109, using 5-bromo-2-(trifluoromethyl)pyridine (Sigma-Aldrich) instead of 2-bromo-3-methoxy-6-methylpyridine. ¹H NMR (500 MHz, DMSO-d₆) δ ppm 3.77-3.89 (m, 2 H) 4.24-4.39 (m, 2 H) 6.78 (d, J=4.35 Hz, 1 H) 6.96 (d, J=8.48 Hz, 1 H) 7.15-7.27 (m, 3 H) 8.11 (s, 1 H) 8.70 (s, 1 H) 8.87 (d, J=2.18 Hz, 1 H). m/z (ESI) 443 (M+H)⁺.

Example 123

4-(4-(1,1,2,2-Tetrafluoroethoxy)Phenyl)-N-(Thiazol-2-Yl)-3,4-Dihydro-2H-Benzo[B][1,4]Oxazine-7-Sulfonamide

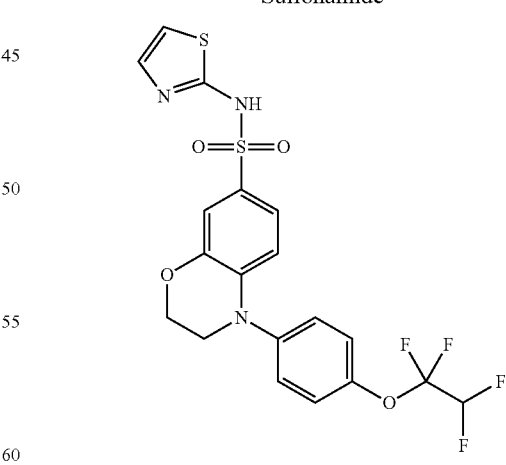

4-(4-(1,1,2,2-Tetrafluoroethoxy)phenyl)-N-(thiazol-2-yl)-3,4-dihydro-2H-benzo[b][1,4]oxazine-7-sulfonamide (EXAMPLE 123) (0.023 g) was prepared in the same manner as EXAMPLE 109, using 1-bromo-4-(1,1,2,2-tetrafluoroethoxy)benzene (Sigma-Aldrich) instead of 2-bromo-3-methoxy-6-methylpyridine. ¹H NMR (500 MHz, DMSO-d₆) δ ppm 3.67-3.77 (m, 2 H) 4.24-4.36 (m, 2 H) 6.75-6.83 (m, 2 H) 7.11-7.19 (m, 2 H) 7.22 (d, J=4.58 Hz, 1 H) 7.32 (m, J=8.82 Hz, 2 H) 7.40 (m, J=8.94 Hz, 2 H) 12.57 (s, 1 H). m/z (ESI) 490 (M+H)+.

Example 124

4-(3-Cyano-5-Methylphenyl)-N-(Thiazol-2-Yl)-3,4-Dihydro-2H-Benzo[B][1,4]Oxazine-7-Sulfonamide

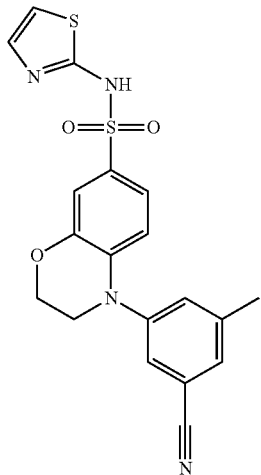 [SMILES: Cc1cc(C#N)cc(N2CCOc3cc(S(=O)(=O)Nc4nccs4)ccc32)c1]

4-(3-Cyano-5-methylphenyl)-N-(thiazol-2-yl)-3,4-dihydro-2H-benzo[b][1,4]oxazine-7-sulfonamide (EXAMPLE 124) (0.015 g) was prepared in the same manner as EXAMPLE 109, using 3-bromo-5-methylbenzonitrile (Sigma-Aldrich) instead of 2-bromo-3-methoxy-6-methylpyridine. $^1$H NMR (500 MHz, DMSO-$d_6$) δ ppm 2.35 (s, 3 H) 3.67-3.80 (m, 2 H) 4.23-4.35 (m, 2 H) 6.79 (d, J=4.58 Hz, 1 H) 6.87 (d, J=8.36 Hz, 1 H) 7.09-7.20 (m, 2 H) 7.22 (d, J=4.70 Hz, 1 H) 7.44 (s, 1 H) 7.49 (s, 1 H) 7.57 (s, 1 H) 12.57 (br. s., 1 H). m/z (ESI) 413 (M+H)+.

Example 125

4-(4-Chloro-3-(Trifluoromethyl)Phenyl)-N-(Thiazol-2-Yl)-3,4-Dihydro-2H-Benzo[B][1,4]Oxazine-7-Sulfonamide

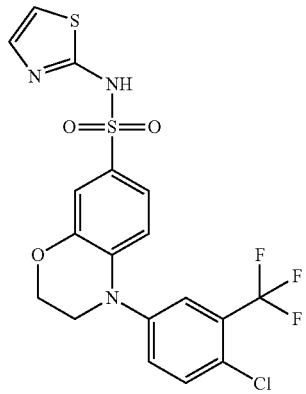 [SMILES: O=S(=O)(Nc1nccs1)c1ccc2c(c1)OCCN2c1ccc(Cl)c(C(F)(F)F)c1]

4-(4-Chloro-3-(trifluoromethyl)phenyl)-N-(thiazol-2-yl)-3,4-dihydro-2H-benzo[b][1,4]oxazine-7-sulfonamide (EXAMPLE 125) (0.006 g) was prepared in the same manner as EXAMPLE 109, using 4-bromo-1-chloro-2-(trifluoromethyl)benzene (Sigma-Aldrich) instead of 2-bromo-3-methoxy-6-methylpyridine. $^1$H NMR (500 MHz, DMSO-$d_6$) δ ppm 3.70-3.86 (m, 2 H) 4.24-4.39 (m, 2 H) 6.79 (d, J=4.58 Hz, 1 H) 6.92 (d, J=8.59 Hz, 1 H) 7.09-7.28 (m, 2 H) 7.55-7.66 (m, 1 H) 7.68-7.77 (m, 2 H) 12.60 (d, J=8.48 Hz, 1 H). m/z (ESI) 476 (M+H)+.

Example 126

4-(3-Chloro-4-(Trifluoromethyl)Phenyl)-N-(Thiazol-2-Yl)-3,4-Dihydro-2H-Benzo[B][1,4]Oxazine-7-Sulfonamide

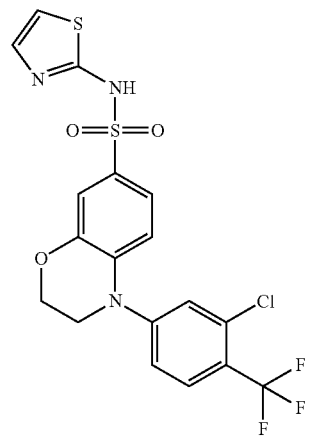 [SMILES: O=S(=O)(Nc1nccs1)c1ccc2c(c1)OCCN2c1ccc(C(F)(F)F)c(Cl)c1]

4-(3-Chloro-4-(trifluoromethyl)phenyl)-N-(thiazol-2-yl)-3,4-dihydro-2H-benzo[b][1,4]oxazine-7-sulfonamide (EXAMPLE 126) (0.009 g) was prepared in the same manner as EXAMPLE 109, using 4-bromo-2-chloro-1-(trifluoromethyl)benzene (Sigma-Aldrich) instead of 2-bromo-3-methoxy-6-methylpyridine. $^1$H NMR (500 MHz, DMSO-$d_6$) δ ppm 3.71-3.84 (m, 2 H) 4.25-4.36 (m, 2 H) 6.79 (d, J=4.58 Hz, 1 H) 6.92 (d, J=8.59 Hz, 1 H) 7.13-7.26 (m, 3 H) 7.55-7.67 (m, 1 H) 7.68-7.78 (m, 2 H) 12.60 (br. s., 1 H). m/z (ESI) 476 (M+H)+.

Example 127

4-(2,2-Difluorobenzo[D][1,3]Dioxol-5-Yl)-N-(Thiazol-2-Yl)-3,4-Dihydro-2H-Benzo[B][1,4]Oxazine-7-Sulfonamide

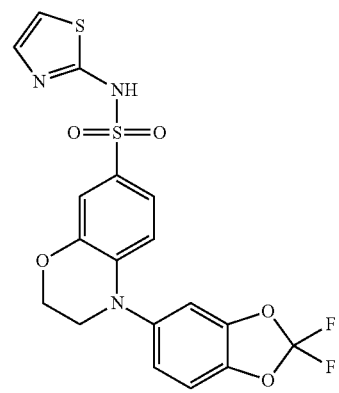 [SMILES: O=S(=O)(Nc1nccs1)c1ccc2c(c1)OCCN2c1ccc2c(c1)OC(F)(F)O2]

4-(2,2-Difluorobenzo[d][1,3]dioxol-5-yl)-N-(thiazol-2-yl)-3,4-dihydro-2H-benzo[b][1,4]oxazine-7-sulfonamide (EXAMPLE 127) (0.010 g) was prepared in the same manner as EXAMPLE 109, using 5-bromo-2,2-difluorobenzo[d][1,3]dioxole (Sigma-Aldrich) instead of 2-bromo-3-methoxy-6- methylpyridine. ¹H NMR (500 MHz, DMSO-d₆) δ ppm 3.62-3.75 (m, 2 H) 4.22-4.38 (m, 2 H) 6.67 (d, J=8.36 Hz, 1 H) 6.78 (d, J=4.58 Hz, 1 H) 7.07-7.18 (m, 3 H) 7.22 (d, J=4.70 Hz, 1 H) 7.40-7.55 (m, 2 H) 12.55 (br. s., 1 H). m/z (ESI) 454 (M+H)⁺.

Example 128

4-(2-Cyano-5-(Trifluoromethoxy)Phenyl)-N-(Thiazol-2-Yl)-3,4-Dihydro-2H-Benzo[B][1,4]Oxazine-7-Sulfonamide

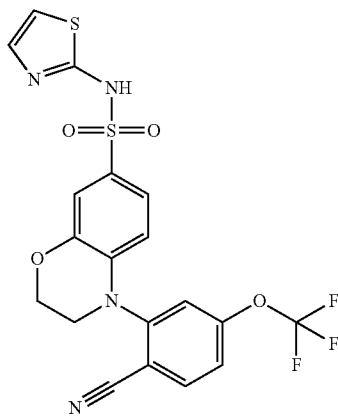 [SMILES: N#Cc1ccc(OC(F)(F)F)cc1N1CCOc2cc(S(=O)(=O)Nc3nccs3)ccc21]

4-(2-Cyano-5-(trifluoromethoxy)phenyl)-N-(thiazol-2-yl)-3,4-dihydro-2H-benzo[b][1,4]oxazine-7-sulfonamide (EXAMPLE 128) (0.003 g) was prepared in the same manner as EXAMPLE 109, using 5 2-bromo-4-(trifluoromethoxy)benzonitrile (Sigma-Aldrich) instead of 2-bromo-3-methoxy-6-methylpyridine. ¹H NMR (500 MHz, DMSO-d₆) δ ppm 3.81 (br. s., 2 H) 4.35 (d, J=3.78 Hz, 2 H) 6.63 (d, J=8.59 Hz, 1 H) 6.80 (d, J=4.24 Hz, 1 H) 7.10-7.28 (m, 3 H) 7.45 (d, J=9.05 Hz, 1 H) 7.61 (s, 1 H) 8.09 (d, J=8.71 Hz, 1 H) 12.55 (br. s., 1 H). m/z (ESI) 483 (M+H)⁺.

Example 129

4-(2,2-Difluorobenzo[D][1,3]Dioxol-4-Yl)-N-(Thiazol-2-Yl)-3,4-Dihydro-2H-Benzo[B][1,4]Oxazine-7-Sulfonamide

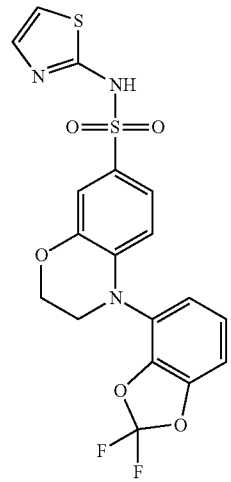 [SMILES: O=S(=O)(Nc1nccs1)c1ccc2c(c1)OCCN2c1cccc2c1OC(F)(F)O2]

4-(2,2-Difluorobenzo[d][1,3]dioxol-4-yl)-N-(thiazol-2-yl)-3,4-dihydro-2H-benzo[b][1,4]oxazine-7-sulfonamide (EXAMPLE 129) (0.017 g) was prepared in the same manner as EXAMPLE 109, using 4-bromo-2,2-difluorobenzo[d][1,3]dioxole (Sigma-Aldrich) instead of 2-bromo-3-methoxy-6-methylpyridine. ¹H NMR (500 MHz, DMSO-d₆) δ ppm 3.69-3.87 (m, 2 H) 4.26-4.41 (m, 2 H) 6.67 (d, J=9.16 Hz, 1 H) 6.80 (d, J=4.58 Hz, 1 H) 7.13-7.32 (m, 6 H) 12.60 (br. s., 1 H). m/z (ESI) 454 (M+H)⁺.

Example 130

4-(5-Chloropyridin-3-Yl)-N-(Thiazol-2-Yl)-3,4-Dihydro-2H-Benzo[B][1,4]Oxazine-7-Sulfonamide

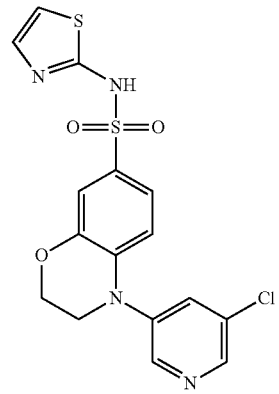 [SMILES: O=S(=O)(Nc1nccs1)c1ccc2c(c1)OCCN2c1cncc(Cl)c1]

4-(5-Chloropyridin-3-yl)-N-(thiazol-2-yl)-3,4-dihydro-2H-benzo[b][1,4]oxazine-7-sulfonamide (EXAMPLE 130) (0.010 g) was prepared in the same manner as EXAMPLE 109, using 3-bromo-5-chloropyridine (Sigma-Aldrich) instead of 2-bromo-3-methoxy-6-methylpyridine. ¹H NMR (500 MHz, DMSO-d₆) δ ppm 3.73-3.83 (m, 2 H) 4.24-4.37 (m, 2 H) 6.80 (d, J=4.58 Hz, 1 H) 6.94 (d, J=8.13 Hz, 1H) 7.15-7.27 (m, 3 H) 7.88-7.95 (m, 1 H) 8.39 (d, J=1.95 Hz, 1 H) 8.54 (d, J=2.18 Hz, 1 H) 12.59 (br. s., 1 H). m/z (ESI) 409 (M+H)⁺.

Example 131

4-(5-Methoxypyridin-3-Yl)-N-(Thiazol-2-Yl)-3,4-Dihydro-2H-Benzo[B][1,4]Oxazine-7-Sulfonamide

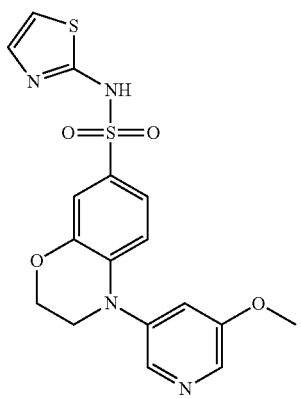 [SMILES: COc1cncc(N2CCOc3cc(S(=O)(=O)Nc4nccs4)ccc32)c1]

4-(5-Methoxypyridin-3-yl)-N-(thiazol-2-yl)-3,4-dihydro-2H-benzo[b][1,4]oxazine-7-sulfonamide (EXAMPLE 131) (0.024 g) was prepared in the same manner as EXAMPLE 109, using 5-bromo-2-(trifluoromethyl)pyridine (Sigma-Aldrich) instead of 2-bromo-3-methoxy-6-methylpyridine. $^1$H NMR (500 MHz, DMSO-d$_6$) δ ppm 3.70-3.80 (m, 2 H) 3.83 (s, 3 H) 4.27-4.41 (m, 2 H) 6.70-6.90 (m, 2 H) 7.12-7.20 (m, 2 H) 7.22 (d, J=4.58 Hz, 1 H) 7.35 (t, J=2.23 Hz, 1 H) 8.06-8.22 (m, 2 H) 12.58 (br. s., 1 H). m/z (ESI) 405 (M+H)$^+$.

Example 132

4-(2,6-Dimethylpyridin-3-Yl)-N-(Thiazol-2-Yl)-3,4-Dihydro-2H-Benzo[B][1,4]Oxazine-7-Sulfonamide

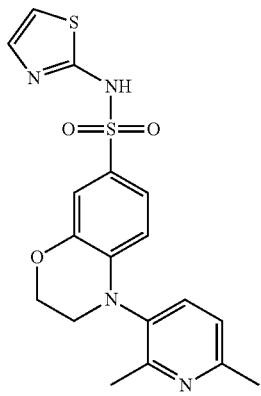 [SMILES: Cc1ccc(N2CCOc3cc(S(=O)(=O)Nc4nccs4)ccc32)c(C)n1]

4-(2,6-Dimethylpyridin-3-yl)-N-(thiazol-2-yl)-3,4-dihydro-2H-benzo[b][1,4]oxazine-7-sulfonamide (EXAMPLE 132) (0.039 g) was prepared in the same manner as EXAMPLE 109, using 3-bromo-2,6-dimethylpyridine (Sigma-Aldrich) instead of 2-bromo-3-methoxy-6-methylpyridine. $^1$H NMR (500 MHz, DMSO-d$_6$) δ ppm 2.39 (s, 3 H) 2.56-2.65 (m, 3 H) 3.80-3.88 (m, 4 H) 4.37 (br. s., 2 H) 6.17 (d, J=8.36 Hz, 1 H) 6.78 (d, J=4.58 Hz, 1 H) 7.11 (dd, J=8.48, 1.95 Hz, 1 H) 7.10 (d, J=4.58 Hz, 1 H) 7.21 (d, J=4.58 Hz, 1 H) 7.47 (d, J=7.10 Hz, 1 H) 7.96 (br. s., 1 H) 12.60 (s, 1 H). m/z (ESI) 403 (M+H)$^+$.

Example 133

4-(3,5-Dimethylpyridin-4-Yl)-N-(Thiazol-2-Yl)-3,4-Dihydro-2H-Benzo[B][1,4]Oxazine-7-Sulfonamide

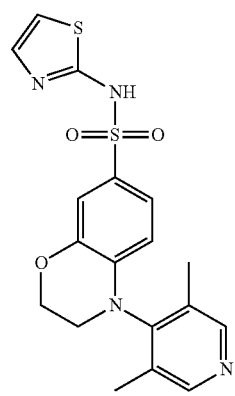 [SMILES: Cc1cncc(C)c1N1CCOc2cc(S(=O)(=O)Nc3nccs3)ccc21]

4-(3,5-Dimethylpyridin-4-yl)-N-(thiazol-2-yl)-3,4-dihydro-2H-benzo[b][1,4]oxazine-7-sulfonamide (EXAMPLE 133) (0.022 g) was prepared in the same manner as EXAMPLE 109, using 4-bromo-3,5-dimethylpyridine (Sigma-Aldrich) instead of 2-bromo-3-methoxy-6-methylpyridine. $^1$H NMR (500 MHz, DMSO-d$_6$) δ ppm 2.13 (s, 3 H) 2.29 (s, 3 H) 3.61-3.72 (m, 2 H) 4.36 (t, J=4.30 Hz, 2 H) 6.13 (d, J=8.48 Hz, 1 H) 6.78 (d, J=4.58 Hz, 1 H) 7.10 (dd, J=8.53, 2.12 Hz, 1 H) 7.14 (d, J=2.06 Hz, 1 H) 7.21 (d, J=4.58 Hz, 1 H) 7.60 (s, 1 H) 8.18 (s, 1 H) 12.55 (br. s., 1 H). m/z (ESI) 403 (M+H)$^+$.

Example 134

4-(2,5-Dimethylpyridin-4-Yl)-N-(Thiazol-2-Yl)-3,4-Dihydro-2H-Benzo[B][1,4]Oxazine-7-Sulfonamide

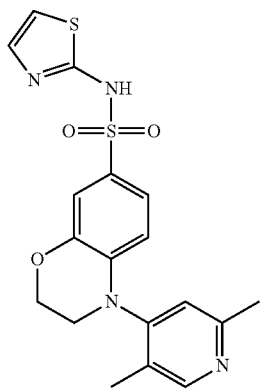 [SMILES: Cc1cc(N2CCOc3cc(S(=O)(=O)Nc4nccs4)ccc32)c(C)cn1]

4-(2,5-Dimethylpyridin-4-yl)-N-(thiazol-2-yl)-3,4-dihydro-2H-benzo[b][1,4]oxazine-7-sulfonamide (EXAMPLE 134) (0.041 g) was prepared in the same manner as EXAMPLE 109, using 4-bromo-2,5-dimethylpyridine (Sigma-Aldrich) instead of 2-bromo-3-methoxy-6-methylpyridine. $^1$H NMR (500 MHz, DMSO-d$_6$) δ ppm 2.14 (s, 3 H) 2.52 (s, 3 H) 3.73-3.76 (m, 2 H) 4.30-4.39 (m, 2 H) 6.56 (d, J=8.48 Hz, 1 H) 6.81 (d, J=4.58 Hz, 1 H) 7.18 (dd, J=8.48, 2.06 Hz, 1 H) 7.20-7.27 (m, 3 H) 7.43 (s, 1 H) 8.50 (s, 1 H) 12.66 (br. s., 1 H). m/z (ESI) 403 (M+H)$^+$.

Example 135

4-(3-Cyano-6-Methylpyridin-2-Yl)-N-(Thiazol-2-Yl)-3,4-Dihydro-2H-Benzo[B][1,4]Oxazine-7-Sulfonamide

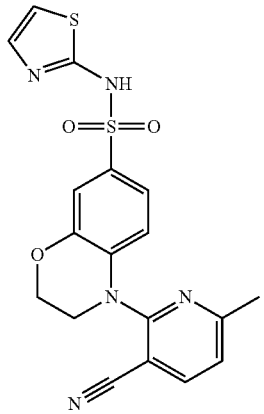 [SMILES: Cc1ccc(C#N)c(N2CCOc3cc(S(=O)(=O)Nc4nccs4)ccc32)n1]

4-(3-Cyano-6-methylpyridin-2-yl)-N-(thiazol-2-yl)-3,4-dihydro-2H-benzo[b][1,4]oxazine-7-sulfonamide (EXAMPLE 135) (0.007 g) was prepared in the same manner as EXAMPLE 109, using 2-bromo-6-methylnicotinonitrile (Sigma-Aldrich) instead of 2-bromo-3-methoxy-6-methylpyridine. $^1$H NMR (500 MHz, DMSO-$d_6$) δ ppm 2.48 (s, 3 H) 3.84-3.98 (m, 2 H) 4.25-4.38 (m, 2 H) 6.81 (d, J=4.58 Hz, 1 H) 6.98 (d, J=8.59 Hz, 1 H) 7.14-7.26 (m, 4 H) 8.19 (d, J=7.79 Hz, 1 H) 12.61 (br. s., 1 H). m/z (ESI) 414 (M+H)$^+$.

Example 136

4-(3,5-Difluoropyridin-2-Yl)-N-(Thiazol-2-Yl)-3,4-Dihydro-2H-Benzo[B][1,4]Oxazine-7-Sulfonamide

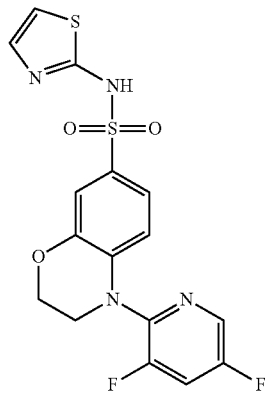 [SMILES: O=S(=O)(Nc1nccs1)c1ccc2c(c1)OCCN2c1ncc(F)cc1F]

4-(3,5-Difluoropyridin-2-yl)-N-(thiazol-2-yl)-3,4-dihydro-2H-benzo[b][1,4]oxazine-7-sulfonamide (EXAMPLE 136) (0.010 g) was prepared in the same manner as EXAMPLE 109, using 2-bromo-3,5-difluoropyridine (Sigma-Aldrich) instead of 2-bromo-3-methoxy-6-methylpyridine. $^1$H NMR (500 MHz, DMSO-$d_6$) δ ppm 3.80 (d, J=3.89 Hz, 2 H) 4.33 (d, J=4.35 Hz, 2 H) 6.70 (dd, J=8.53, 3.84 Hz, 1 H) 6.80 (d, J=4.81 Hz, 1 H) 7.11-7.21 (m, 2 H) 7.23 (d, J=4.70 Hz, 1 H) 8.07 (br. s., 1 H) 8.37 (d, J=2.52 Hz, 1 H). m/z (ESI) 411 (M+H)$^+$.

Example 137

4-(6-Methoxy-4-Methylpyridin-3-Yl)-N-(Thiazol-2-Yl)-3,4-Dihydro-2H-Benzo[B][1,4]Oxazine-7-Sulfonamide

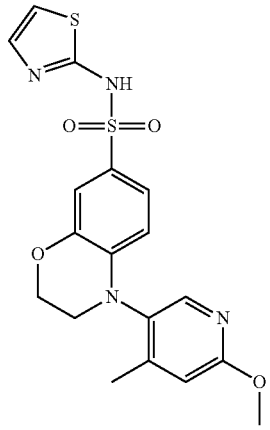 [SMILES: COc1cc(C)c(N2CCOc3cc(S(=O)(=O)Nc4nccs4)ccc32)cn1]

4-(6-Methoxy-4-methylpyridin-3-yl)-N-(thiazol-2-yl)-3,4-dihydro-2H-benzo[b][1,4]oxazine-7-sulfonamide (EXAMPLE 137) (0.014 g) was prepared in the same manner as EXAMPLE 109, using 5-bromo-2-methoxy-4-methylpyridine (Sigma-Aldrich) instead of 2-bromo-3-methoxy-6-methylpyridine.

Purification was accomplished with high throughput LC/MS using 0.1% TFA in CH$_3$CN and water as a mobile phase $^1$H NMR (500 MHz, DMSO-$d_6$) δ ppm 2.10 (s, 3 H) 3.85 (s, 3 H) 4.11 (br. s., 2 H) 4.36 (br. s., 2 H) 6.05 (d, J=8.48 Hz, 1 H) 6.59 (d, J=8.36 Hz, 1 H) 6.77-6.79 (m, 2 H) 6.84 (s, 1 H) 7.10 (br. s, 1 H) 7.20 (d, J=4.58 Hz, 1 H) 8.03-8.12 (br. s., 1 H). m/z (ESI) 419 (M+H)$^+$.

Example 138

4-(6-Ethoxypyridin-3-Yl)-N-(Thiazol-2-Yl)-3,4-Dihydro-2H-Benzo[B][1,4]Oxazine-7-Sulfonamide

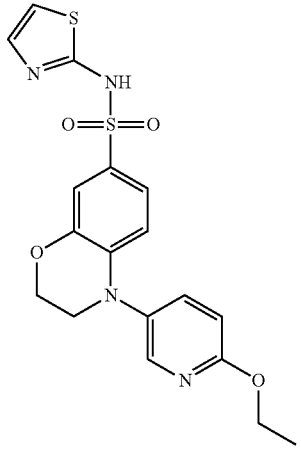 [SMILES: CCOc1ccc(N2CCOc3cc(S(=O)(=O)Nc4nccs4)ccc32)cn1]

4-(6-Ethoxypyridin-3-yl)-N-(thiazol-2-yl)-3,4-dihydro-2H-benzo[b][1,4]oxazine-7-sulfonamide (EXAMPLE 138) (0.029 g) was prepared in the same manner as EXAMPLE 109, using 5-bromo-2-ethoxypyridine (Sigma-Aldrich) instead of 2-bromo-3-methoxy-6-methylpyridine. Purification was accomplished with high throughput LC/MS using 0.1% TFA in CH$_3$CN and water as a mobile phase $^1$H NMR (500 MHz, DMSO-$d_6$) δ ppm 1.33 (t, J=7.05 Hz, 3 H) 3.59-3.79 (m, 2 H) 4.20-4.42 (m, 4 H) 6.47 (d, J=8.13 Hz, 1 H) 6.77 (d, J=4.47 Hz, 1 H) 6.87 (d, J=8.82 Hz, 1 H) 7.05-7.16 (m, 2 H) 7.21 (d, J=4.58 Hz, 1 H) 7.70 (dd, J=8.71, 2.75 Hz, 1 H) 8.13 (d, J=2.63 Hz, 1 H) 12.54 (br. s., 1 H). m/z (ESI) 419 (M+H)$^+$.

Example 139

4-(2,5-Dimethoxyphenyl)-N-(Thiazol-2-Yl)-3,4-Dihydro-2H-Benzo[B][1,4]Oxazine-7-Sulfonamide

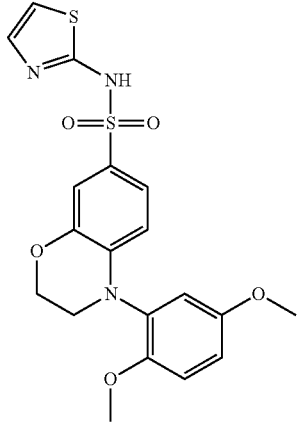 [SMILES: COc1ccc(OC)c(N2CCOc3cc(S(=O)(=O)Nc4nccs4)ccc32)c1]

4-(2,5-Dimethoxyphenyl)-N-(thiazol-2-yl)-3,4-dihydro-2H-benzo[b][1,4]oxazine-7-sulfonamide (EXAMPLE 139) (0.029 g) was prepared in the same manner as EXAMPLE 109, using 2-bromo-1,4-dimethoxybenzene (Sigma-Aldrich) instead of 2-bromo-3-methoxy-6-methylpyridine. Purification was accomplished with high throughput LC/MS using 0.1% TFA in CH$_3$CN and water as a mobile phase $^1$H NMR (500 MHz, DMSO-d$_6$) δ ppm 3.60-3.65 (m, 2 H) 3.68 (s, 3 H) 3.72 (s, 2H) 4.26-4.34 (m, 2 H) 6.22 (d, J=8.36 Hz, 1 H) 6.70-6.80 (m, 1 H) 6.84-6.94 (m, 1 H) 7.03-7.16 (m, 2 H) 7.17-7.24 (m, 1 H) 7.27-7.37 (m, 1 H) 7.39-7.48 (m, 1 H) 12.52 (br. s., 1 H). m/z (ESI) 434 (M+H)$^+$.

Example 140

4-(2-Methyl-4-(Trifluoromethoxy)Phenyl)-N-(Thiazol-2-Yl)-3,4-Dihydro-2H-Benzo[B][1,4]Oxazine-7-Sulfonamide

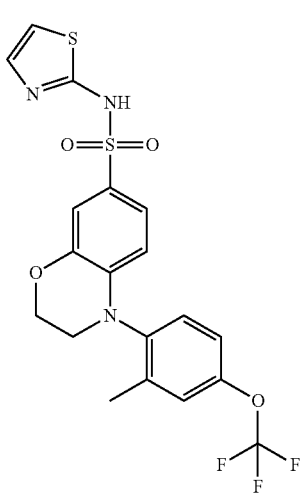 [SMILES: Cc1cc(OC(F)(F)F)ccc1N1CCOc2cc(S(=O)(=O)Nc3nccs3)ccc21]

4-(2-Methyl-4-(trifluoromethoxy)phenyl)-N-(thiazol-2-yl)-3,4-dihydro-2H-benzo[b][1,4]oxazine-7-sulfonamide (EXAMPLE 140) (0.034 g) was prepared in the same manner as EXAMPLE 109, using 2-bromo-1,4-dimethoxybenzene (Sigma-Aldrich) instead of 2-bromo-3-methoxy-6-methylpyridine. Purification was accomplished with high throughput LC/MS using 0.1% TFA in CH$_3$CN and water as a mobile phase $^1$H NMR (500 MHz, DMSO-d$_6$) δ ppm 2.18 (s, 3 H) 3.55 (d, J=12.94 Hz, 1 H) 3.65-3.78 (m, 1 H) 4.35 (d, J=3.55 Hz, 2 H) 6.05 (d, J=8.36 Hz, 1 H) 6.77 (d, J=4.47 Hz, 1 H) 7.07-7.17 (m, 2 H) 7.21 (d, J=4.58 Hz, 1 H) 7.30 (d, J=8.93 Hz, 1 H) 7.36-7.49 (m, 2 H) 12.53 (br. s., 1 H). m/z (ESI) 472 (M+H)$^+$.

Example 141

4-(4-(1H-Pyrazol-1-Yl)Phenyl)-N-(Thiazol-2-Yl)-3,4-Dihydro-2H-Benzo[B][1,4]Oxazine-7-Sulfonamide

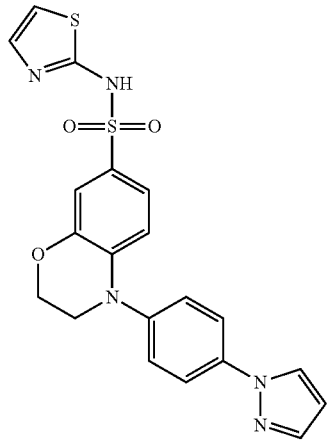 [SMILES: O=S(=O)(Nc1nccs1)c1ccc2c(c1)OCCN2c1ccc(-n2cccn2)cc1]

4-(4-(1H-pyrazol-1-yl)phenyl)-N-(thiazol-2-yl)-3,4-dihydro-2H-benzo[b][1,4]oxazine-7-sulfonamide (EXAMPLE 141) (0.037 g) was prepared in the same manner as EXAMPLE 109, using 1-(4-bromophenyl)-1H-pyrazole (Sigma-Aldrich) instead of 2-bromo-3-methoxy-6-methylpyridine. Purification was accomplished with high throughput LC/MS using 0.1% TFA in CH$_3$CN and water as a mobile phase $^1$H NMR (500 MHz, DMSO-d$_6$) δ ppm 3.69-3.81 (m, 2 H) 4.28-4.38 (m, 2 H) 6.55 (d, J=1.72 Hz, 1 H) 6.79 (d, J=8.13 Hz, 2 H) 7.09-7.18 (m, 2 H) 7.22 (d, J=4.58 Hz, 1 H) 7.43 (m, J=8.71 Hz, 2 H) 7.75 (s, 1 H) 7.88 (m, J=8.71 Hz, 2 H) 8.48 (d, J=2.40 Hz, 1 H) 12.56 (br. s., 1 H). m/z (ESI) 440 (M+H)$^+$.

Example 142

4-(2-Chloro-6-Cyanophenyl)-N-(Thiazol-2-Yl)-3,4-Dihydro-2H-Benzo[B][1,4]Oxazine-7-Sulfonamide

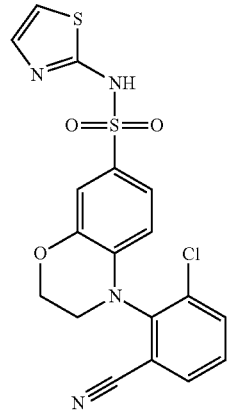 [SMILES: N#Cc1cccc(Cl)c1N1CCOc2cc(S(=O)(=O)Nc3nccs3)ccc21]

4-(2-Chloro-6-cyanophenyl)-N-(thiazol-2-yl)-3,4-dihydro-2H-benzo[b][1,4]oxazine-7-sulfonamide (EXAMPLE 142) (0.026 g) was prepared in the same manner as EXAMPLE 109, using 2-bromo-3-chlorobenzonitrile (Oakwood) instead of 2-bromo-3-methoxy-6-methylpyridine. Purification was accomplished with high throughput LC/MS using 0.1% TFA in CH$_3$CN and water as a mobile phase $^1$H NMR (500 MHz, DMSO-d$_6$) δ ppm 3.67-3.86 (m, 2 H) 4.29-4.50 (m, 2 H) 6.12 (d, J=8.48 Hz, 1 H) 6.79 (d, J=4.58 Hz, 1 H) 7.10-7.28 (m, 3 H) 7.65 (t, J=7.96 Hz, 1 H) 8.03 (dd, J=7.10, 5.61 Hz, 2 H) 12.59 (br. s., 1H). m/z (ESI) 433 (M+H)$^+$.

Example 143

4-(3,5-Dimethoxypyrazin-2-Yl)-N-(Thiazol-2-Yl)-3,4-Dihydro-2H-Benzo[B][1,4]Oxazine-7-Sulfonamide

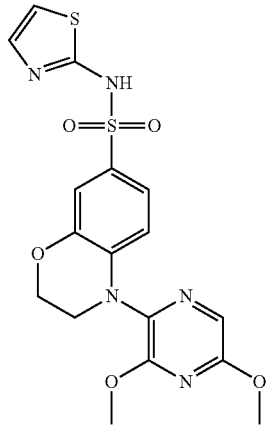 [SMILES: COc1cnc(N2CCOc3cc(S(=O)(=O)Nc4nccs4)ccc32)c(OC)n1]

4-(3,5-Dimethoxypyrazin-2-yl)-N-(thiazol-2-yl)-3,4-dihydro-2H-benzo[b][1,4]oxazine-7-sulfonamide (EXAMPLE 143) (0.068 g) was prepared in the same manner as EXAMPLE 109, using 2-bromo-3,5-dimethoxypyrazine (ACES Pharma) instead of 2-bromo-3-methoxy-6-methylpyridine. Purification was accomplished with high throughput LC/MS using 0.1% TFA in CH$_3$CN and water as a mobile phase $^1$H NMR (500 MHz, DMSO-d$_6$) δ ppm 3.61-3.74 (m, 2 H) 3.93 (s, 3 H) 3.95 (s, 3 H) 4.29 (t, J=4.24 Hz, 2 H) 6.41 (d, J=8.59 Hz, 1 H) 6.78 (d, J=4.47 Hz, 1 H) 7.04-7.19 (m, 2 H) 7.22 (d, J=4.70 Hz, 1 H) 7.72 (s, 1 H) 12.57 (br. s., 1 H). m/z (ESI) 436 (M+H)$^+$.

Example 144

4-(3,5-Dimethoxypyridin-2-Yl)-N-(Thiazol-2-Yl)-3,4-Dihydro-2H-Benzo[B][1,4]Oxazine-7-Sulfonamide

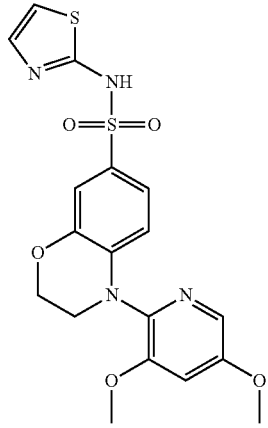 [SMILES: COc1cnc(N2CCOc3cc(S(=O)(=O)Nc4nccs4)ccc32)c(OC)c1]

4-(3,5-Dimethoxypyridin-2-yl)-N-(thiazol-2-yl)-3,4-dihydro-2H-benzo[b][1,4]oxazine-7-sulfonamide (EXAMPLE 144) (0.067 g) was prepared in the same manner as EXAMPLE 109, using 2-bromo-3,5-dimethoxypyridine (ACES Pharma) instead of 2-bromo-3-methoxy-6-methylpyridine. Purification was accomplished with high throughput LC/MS using 0.1% TFA in CH$_3$CN and water as a mobile phase $^1$H NMR (500 MHz, DMSO-d$_6$) δ ppm 3.59-3.71 (m, 2 H) 3.80 (br. s., 3 H) 3.88 (s, 3 H) 4.29 (t, J=4.24 Hz, 2 H) 6.28 (d, J=8.48 Hz, 1 H) 6.77 (d, J=4.58 Hz, 1 H) 7.00-7.15 (m, 2 H) 7.15-7.27 (m, 2 H) 7.78 (d, J=2.41 Hz, 1 H) 12.57 (br. s., 1 H). m/z (ESI) 435 (M+H)$^+$.

Example 145

4-(2-Methoxy-5-(Trifluoromethyl)Pyridin-3-Yl)-N-(Thiazol-2-Yl)-3,4-Dihydro-2H-Benzo[B][1,4]Oxazine-7-Sulfonamide

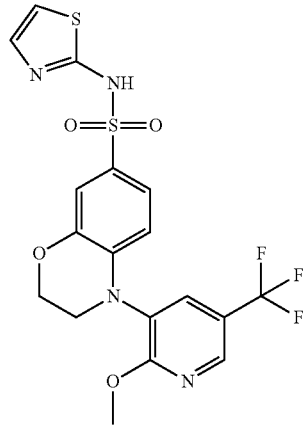 [SMILES: COc1ncc(C(F)(F)F)cc1N1CCOc2cc(S(=O)(=O)Nc3nccs3)ccc21]

4-(2-Methoxy-5-(trifluoromethyl)pyridin-3-yl)-N-(thiazol-2-yl)-3,4-dihydro-2H-benzo[b][1,4]oxazine-7-sulfonamide (EXAMPLE 145) (0.051 g) was prepared in the same manner as EXAMPLE 109, using 3-bromo-2-methoxy-5-(trifluoromethyl)pyridine (ACES Pharma) instead of 2-bromo-3-methoxy-6-methylpyridine. Purification was accomplished with high throughput LC/MS using 0.1% TFA in CH$_3$CN and water as a mobile phase $^1$H NMR (500 MHz, DMSO-d$_6$) δ ppm 3.47-3.57 (s, 3 H) 3.60-3.71 (m, 2 H) 4.21-4.35 (m, 2 H) 6.41 (d, J=8.25 Hz, 1 H) 6.77 (d, J=4.35 Hz, 1 H) 7.04-7.16 (m, 2 H) 7.21 (d, J=4.58 Hz, 1 H) 7.76 (d, J=2.41 Hz, 1 H) 8.40 (s, 1 H) 12.55 (br. s., 1 H). m/z (ESI) 473 (M+H)$^+$.

Example 146

4-(5-(Difluoromethoxy)-3-Methylpyridin-2-Yl)-N-(Thiazol-2-Yl)-3,4-Dihydro-2H-Benzo[B][1,4]Oxazine-7-Sulfonamide

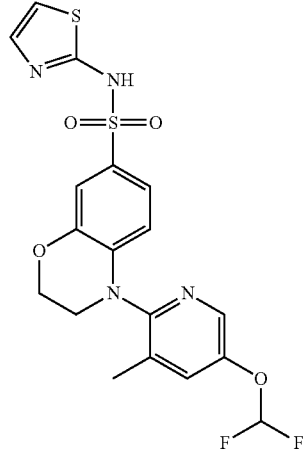 [SMILES: Cc1cc(OC(F)F)cnc1N1CCOc2cc(S(=O)(=O)Nc3nccs3)ccc21]

4-(5-(Difluoromethoxy)-3-methylpyridin-2-yl)-N-(thiazol-2-yl)-3,4-dihydro-2H-benzo[b][1,4]oxazine-7-sulfonamide (EXAMPLE 146) (0.049 g) was prepared in the same manner as EXAMPLE 109, using 2-bromo-5-(difluoromethoxy)-3-methylpyridine (Ellanova Laboratories) instead of 2-bromo-3-methoxy-6-methylpyridine. Purification was accomplished with high throughput LC/MS using 0.1% TFA in CH$_3$CN and water as a mobile phase $^1$H NMR (500 MHz, DMSO-d$_6$) δ ppm 2.20 (s, 3 H) 3.62-3.77 (m, 2 H) 4.36 (t, J=4.24 Hz, 2 H) 6.20 (d, J=8.48 Hz, 1 H) 6.78 (d, J=4.47 Hz, 1 H) 7.12 (dd, J=8.48, 2.06 Hz, 1 H) 7.14-7.18 (m, 1 H) 7.22 (d, J=4.58 Hz, 1 H) 7.71 (d, J=2.52 Hz, 1 H) 8.26 (d, J=2.63 Hz, 1 H) 12.58 (br. s., 1 H). m/z (ESI) 455 (M+H)$^+$.

Example 147

4-(2-(Pyridin-4-Yl)Phenyl)-N-(Thiazol-2-Yl)-3,4-Dihydro-2H-Benzo[B][1,4]Oxazine-7-Sulfonamide

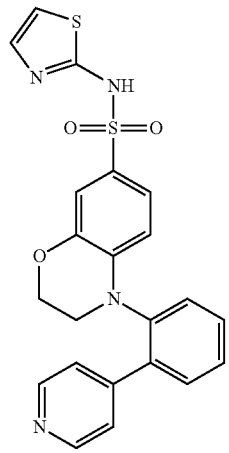 [SMILES: O=S(=O)(Nc1nccs1)c1ccc2c(c1)OCCN2c1ccccc1-c1ccncc1]

4-(2-(Pyridin-4-yl)phenyl)-N-(thiazol-2-yl)-3,4-dihydro-2H-benzo[b][1,4]oxazine-7-sulfonamide (EXAMPLE 147) (0.070 g) was prepared in the same manner as EXAMPLE 109, using 4-(2-iodophenyl)pyridine (HDH Pharma, Inc.) instead of 2-bromo-3-methoxy-6-methylpyridine. $^1$H NMR (500 MHz, DMSO-d$_6$) δ ppm 3.62 (d, J=11.11 Hz, 2 H) 4.01 (br. s., 1 H) 4.23 (d, J=11.68 Hz, 1 H) 6.32 (d, J=8.36 Hz, 1 H) 6.77 (d, J=4.47 Hz, 1 H) 7.00-7.11 (m, 2 H) 7.21 (d, J=4.47 Hz, 1 H) 7.40 (d, J=5.50 Hz, 2 H) 7.49 (t, J=7.05 Hz, 2H) 7.54-7.64 (m, 2 H) 8.56 (d, J=5.50 Hz, 2 H) 12.51 (br. s., 1 H). m/z (ESI) 451 (M+H)$^+$.

Example 148

4-(2-(1-Methyl-1H-Pyrazol-5-Yl)Phenyl)-N-(Thiazol-2-Yl)-3,4-Dihydro-2H-Benzo[B][1,4]Oxazine-7-Sulfonamide

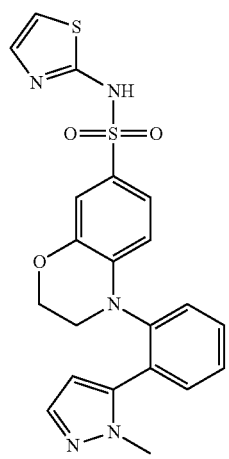 [SMILES: Cn1nccc1-c1ccccc1N1CCOc2cc(S(=O)(=O)Nc3nccs3)ccc21]

4-(2-(1-Methyl-1H-pyrazol-5-yl)phenyl)-N-(thiazol-2-yl)-3,4-dihydro-2H-benzo[b][1,4]oxazine-7-sulfonamide (EXAMPLE 148) (0.040 g) was prepared in the same manner as EXAMPLE 109, using 5-(2-bromophenyl)-1-methyl-1H-pyrazole (HDH Pharma, Inc.) instead of 2-bromo-3-methoxy-6-methylpyridine. $^1$H NMR (500 MHz, DMSO-d$_6$) δ ppm 3.16 (br. s., 1 H) 3.53 (br. s., 1 H) 3.64 (br. s., 2 H) 4.02 (br. s., 1 H) 4.17 (br. s., 1 H) 6.17 (s, 1 H) 6.41 (d, J=8.48 Hz, 1 H) 6.77 (d, J=4.12 Hz, 1 H) 7.00-7.13 (m, 2 H) 7.21 (d, J=4.47 Hz, 1 H) 7.38 (s, 1 H) 7.42-7.63 (m, 4 H) 12.52 (br. s., 1 H). m/z (ESI) 454 (M+H)$^+$.

Example 149

4-(2-(Tetrahydro-2H-Pyran-4-Yl)Phenyl)-N-(Thiazol-2-Yl)-3,4-Dihydro-2H-Benzo[B][1,4]Oxazine-7-Sulfonamide

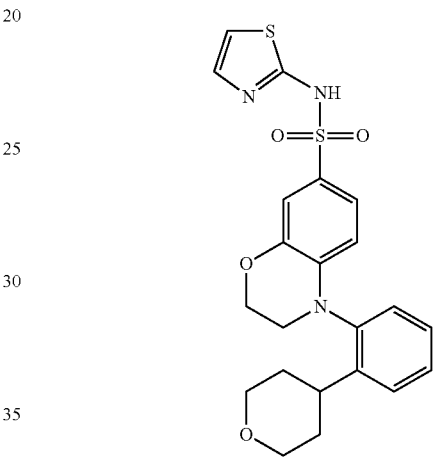

STEP 1: A microwave vial was charged N-(4-methoxybenzyl)-N-(thiazol-2-yl)-3,4-dihydro-2H-benzo[b][1,4]oxazine-7-sulfonamide (0.120 g, 0.287 μmol), 4-(2-iodophenyl)tetrahydro-2H-pyran (0.124 g, 0.431 μmol), sodium tert-butoxide (0.055 g, 0.575 μmol), tris(dibenzylideneacetone)dipalladium(0) (0.026 g, 0.029 μmol) and xantphos (0.033 g, 0.057 μmol). After purging with N$_2$, toluene (3 mL) was added and the vessel was sealed and heated in the microwave at 130° C. for 30 min. LCMS confirmed coupling product formation. The reaction mixture was concentrated and taken up in DCM, then passed through a 12 g silica gel plug, eluting with 1:1 EtOAC/hex to afford N-(4-methoxybenzyl)-4-(2-(tetrahydro-2H-pyran-4-yl)phenyl)-N-(thiazol-2-yl)-3,4-dihydro-2H-benzo[b][1,4]oxazine-7-sulfonamide as a semipure orange solid.

STEP 2: TFA (0.45 mL) was added dropwise to the material from STEP 1 and the mixture was allowed to stir at RT for 4 h. After genevac to remove excess acid and solvents, high throughput LC/MS directed purification using 0.1% NH$_4$OH in CH$_3$CN and water as a mobile phase afforded -(2-(tetrahydro-2H-pyran-4-yl)phenyl)-N-(thiazol-2-yl)-3,4-dihydro-2H-benzo[b][1,4]oxazine-7-sulfonamide (EXAMPLE 149) (0.018 g) as a solid. $^1$H NMR (500 MHz, DMSO-d$_6$) δ ppm 1.47 (d, J=12.23 Hz, 1 H) 1.53-1.62 (m, 1 H) 1.62-1.78 (m, 2 H) 2.89 (t, J=12.28 Hz, 1 H) 3.21-3.52 (m, 6 H) 4.31-4.35 (m, 2 H) 6.01 (d, J=8.50 Hz, 1H) 6.74 (d, J=8.40 Hz, 1 H) 6.77 (m, 3 H) 7.00-7.10 (m, 3 H) 7.20 (d, J=4.47 Hz, 1 H) 7.34 (s, 1 H) 12.53 (br. s., 1 H). m/z (ESI) 458 (M+H)$^+$.

Example 150

4-(4-Fluoro-2-Methoxyphenyl)-N-(Thiazol-2-Yl)-3,4-Dihydro-2H-Benzo[B][1,4]Oxazine-7-Sulfonamide

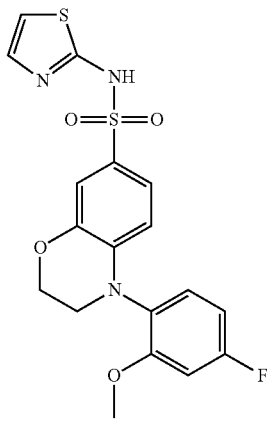 [SMILES: COc1cc(F)ccc1N1CCOc2cc(S(=O)(=O)Nc3nccs3)ccc21]

4-(4-Fluoro-2-methoxyphenyl)-N-(thiazol-2-yl)-3,4-dihydro-2H-benzo[b][1,4]oxazine-7-sulfonamide (EXAMPLE 150) (0.034 g) was prepared in the same manner as EXAMPLE 149, using 1-bromo-4-fluoro-2-methoxybenzene (Sigma-Aldrich) instead of 4-(2-iodophenyl)tetrahydro-2H-pyran. Purification was accomplished with high throughput LC/MS using 0.1% TFA in $CH_3CN$ and water as a mobile phase. $^1H$ NMR (400 MHz, DMSO-$d_6$) δ ppm 3.38 (br. s., 3 H) 3.52-3.66 (m, 2 H) 4.29 (t, J=4.25 Hz, 2 H) 6.14 (d, J=8.31 Hz, 1 H) 6.77 (d, J=4.50 Hz, 1 H) 6.86 (td, J=8.46, 2.84 Hz, 1 H) 6.98-7.15 (m, 3 H) 7.22 (d, J=4.60 Hz, 1 H) 7.33 (dd, J=8.71, 6.46 Hz, 1 H) 12.53 (br. s., 1 H). m/z (ESI) 422 $(M+H)^+$.

Example 151

4-(5-Fluoro-2-Methoxyphenyl)-N-(Thiazol-2-Yl)-3,4-Dihydro-2H-Benzo[B][1,4]Oxazine-7-Sulfonamide

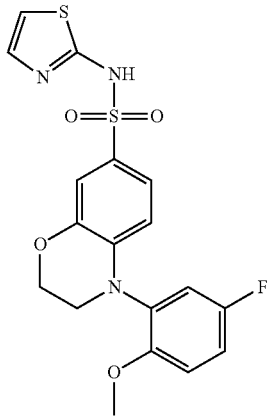 [SMILES: COc1ccc(F)cc1N1CCOc2cc(S(=O)(=O)Nc3nccs3)ccc21]

4-(5-Fluoro-2-methoxyphenyl)-N-(thiazol-2-yl)-3,4-dihydro-2H-benzo[b][1,4]oxazine-7-sulfonamide (EXAMPLE 151) (0.034 g) was prepared in the same manner as EXAMPLE 149, using 2-bromo-4-fluoro-1-methoxybenzene (Sigma-Aldrich) instead of 4-(2-iodophenyl)tetrahydro-2H-pyran. Purification was accomplished in three steps: (1) MPLC (Isco: using eluent 10-100% EtOAC/hexanes 10 min then 100% EtOAC) to afford the product in ~80% purity; (2) PE-AX column, eluting with MeOH; (3) Trituration with MeOH and filtration of the pure solid. $^1H$ NMR (400 MHz, DMSO-$d_6$) ppm 3.60-3.69 (m, 2 H) 3.71-3.77 (m, 3 H) 4.25-4.34 (m, 2 H) 6.22-6.28 (m, 1 H) 6.55 (d, J=3.62 Hz, 1 H) 6.74-6.82 (m, 1 H) 6.82-6.97 (m, 2 H) 7.07-7.13 (m, 1 H) 7.14-7.19 (m, 1 H) 7.22 (d, J=4.50 Hz, 1 H) 12.54 (br. s., 1 H). m/z (ESI) 422 $(M+H)^+$.

Example 152

4-(2-Cyano-4-(Trifluoromethyl)Phenyl)-N-(Thiazol-4-Yl)-3,4-Dihydro-2H-Benzo[B][1,4]Oxazine-7-Sulfonamide

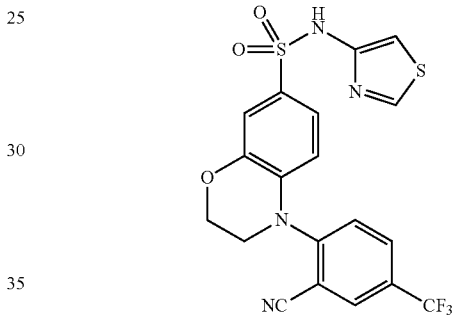

A 10-mL round-bottom flask was charged with perfluorophenyl 4-(2-cyano-4-(trifluoromethyl)phenyl)-3,4-dihydro-2H-benzo[b][1,4]oxazine-7-sulfonate (INTERMEDIATE AB) (48.92 mg, 0.089 mmol), thiazol-4-amine hydrochloride (Accel Pharmatech, East Brunswick, N.J., 15.78 mg, 0.116 mmol), and THF (889 µl) to give a suspension. The flask was cooled in a dry ice-acetone bath for 5 min, then lithium bis(trimethylsilyl)amide (1M in THF) (293 µl, 0.293 mmol) was added dropwise over 30 s to give a bright orange mixture. The mixture was stirred for 5 min, then the flask was lowered into an ice-water bath. After 2 h, additional portions of thiazol-4-amine hydrochloride (15.78 mg, 0.116 mmol) and lithium bis(trimethylsilyl)amide (1M in THF) (293 µl, 0.293 mmol) were added in sequence. Following an additional 1 h of stirring, the mixture was quenched with glacial acetic acid (1 drop), diluted with MeOH, and concentrated in vacuo. The residue was purified by chromatography on silica gel (12-g Redi-Sep Gold column, 0-10% MeOH/DCM) to give 4-(2-cyano-4-(trifluoromethyl)phenyl)-N-(thiazol-4-yl)-3,4-dihydro-2H-benzo[b][1,4]oxazine-7-sulfonamide (14.11 mg, 0.030 mmol, 34.0% yield) as a tan solid: $^1H$ NMR (400 MHz, DMSO-$d_6$) δ=10.96 (s, 1 H), 8.88 (d, J=2.2 Hz, 1 H), 8.41 (d, J=1.7 Hz, 1 H), 8.09 (dd, J=1.9, 8.8 Hz, 1 H), 7.72 (d, J=8.7 Hz, 1 H), 7.30 (d, J=2.2 Hz, 1 H), 7.20 (dd, J=2.2, 8.6 Hz, 1 H), 6.99 (d, J=2.2 Hz, 1 H), 6.79 (d, J=8.6 Hz, 1 H), 4.38-4.28 (m, 2 H), 3.90-3.81 (m, 2 H); m/z (ESI) 467.2 $(M+H)^+$.

Example 153

4-(2-Cyano-4-Methoxyphenyl)-N-(Thiazol-2-Yl)-3,4-Dihydro-2H-Benzo[B][1,4]Oxazine-7-Sulfonamide 2,2,2-Trifluoroacetate

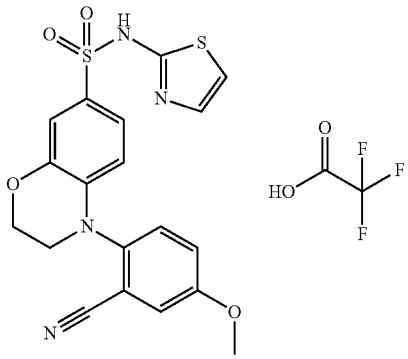 [SMILES: COc1ccc(N2CCOc3cc(S(=O)(=O)Nc4nccs4)ccc32)c(C#N)c1 ; O=C(O)C(F)(F)F]

A microwave vial was charged with N-(4-methoxybenzyl)-N-(thiazol-2-yl)-3,4-dihydro-2H-benzo[b][1,4]oxazine-7-sulfonamide (INTERMEDIATE M, 0.125 g, 0.299 mmol), 2-bromo-5-methoxybenzonitrile (ASDI, 0.111 g, 0.524 mmol), Xantphos (0.035 g, 0.060 mmol), Pd$_2$(dba)$_3$ (0.027 g, 0.030 mmol) and sodium tert-butoxide (0.058 g, 0.599 mmol). The mixture was diluted with Toluene (2.00 ml), and purged with nitrogen, and heated at 130° C. in the microwave for 30 minutes. After cooling to RT, trifluoroacetic acid (0.577 ml, 7.48 mmol) was added to the crude reaction mixture, and the reaction was stirred at RT for 2 h ( ), after which the crude reaction was filtered over a plug of Celite (washing with minimal DCM to flush through the product). The reactions were then dried overnight in a hood and purified using reverse phase mass-directed HPLC. The column used was a Waters Xbridge C18 19×100 mm 10 micron column. The mobile phase was run under gradient conditions using Water and CH$_3$CN with 0.1% trifluoroacetic acid. $^1$H NMR (500 MHz, DMSO-d$_6$) δ ppm 12.57 (br. s., 1 H) 7.55 (d, J=2.86 Hz, 1 H) 7.51 (d, J=8.94 Hz, 1 H) 7.37 (dd, J=8.94, 2.86 Hz, 1 H) 7.21 (d, J=4.47 Hz, 1 H) 7.16 (d, J=1.83 Hz, 1 H) 7.13 (dd, J=8.48, 1.95 Hz, 1 H) 6.78 (d, J=4.47 Hz, 1 H) 6.29 (d, J=8.59 Hz, 1 H) 4.31-4.37 (m, 2 H) 3.84 (s, 3 H) 3.68-3.73 (m, 2 H). m/z (ESI) 428.1 (M+H)$^+$.

Example 154

4-(4-(1H-Imidazol-1-Yl)Phenyl)-N-(Thiazol-2-Yl)-3,4-Dihydro-2H-Benzo[B][1,4]Oxazine-7-Sulfonamide 2,2,2-Trifluoroacetate

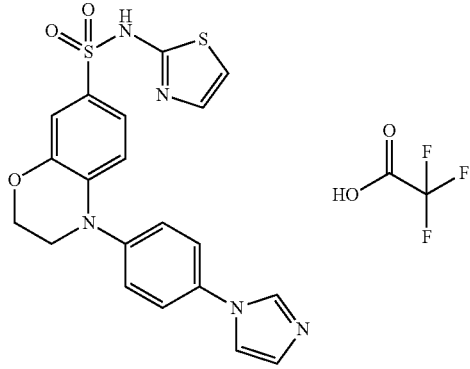 [SMILES: O=S(=O)(Nc1nccs1)c1ccc2c(c1)OCCN2c1ccc(-n2ccnc2)cc1 ; O=C(O)C(F)(F)F]

EXAMPLE 154 was synthesized in the same manner as EXAMPLE 153, using 1-(4-bromophenyl)-1H-imidazole (ASDI) instead of 2-bromo-5-methoxybenzonitrile. $^1$H NMR (500 MHz, DMSO-d$_6$) δ ppm 12.64 (br. s, 1 H) 9.47 (s, 1 H) 8.19 (s, 1 H) 7.76-7.85 (m, 3 H) 7.51-7.56 (m, 2 H) 7.14-7.25 (m, 3 H) 6.89 (d, J=8.36 Hz, 1 H) 6.80 (d, J=4.58 Hz, 1 H) 4.30-4.36 (m, 2 H) 3.76-3.81 (m, 2 H). m/z (ESI) 439.1 (M+H)$^+$.

Example 155

4-(4-Chloro-3-Fluorophenyl)-N-(Thiazol-2-Yl)-3,4-Dihydro-2H-Benzo[B][1,4]Oxazine-7-Sulfonamide 2,2,2-Trifluoroacetate

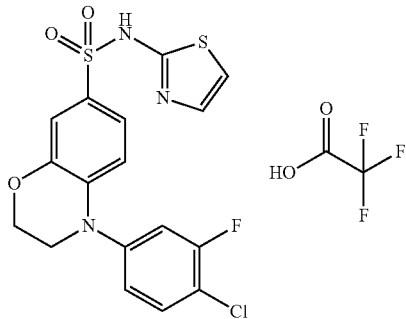 [SMILES: O=S(=O)(Nc1nccs1)c1ccc2c(c1)OCCN2c1ccc(Cl)c(F)c1 ; O=C(O)C(F)(F)F]

EXAMPLE 155 was synthesized in the same manner as EXAMPLE 153, using 4-bromo-1-chloro-2-fluorobenzene (ASDI) instead of 2-bromo-5-methoxybenzonitrile. $^1$H NMR (500 MHz, DMSO-d$_6$) δ ppm 12.60 (br. s., 1 H) 7.54-7.61 (m, 1 H) 7.39 (dd, J=11.03, 2.21 Hz, 1 H) 7.22 (d, J=4.47 Hz, 1 H) 7.14-7.19 (m, 3 H) 6.94 (d, J=8.25 Hz, 1 H) 6.79 (d, J=4.53 Hz, 1 H) 4.26-4.31 (m, 2 H) 3.71-3.75 (m, 2 H). m/z (ESI) 428.0 (M+H)$^+$.

Example 156

4-(4-Chloro-3-Methylphenyl)-N-(Thiazol-2-Yl)-3,4-Dihydro-2H-Benzo[B][1,4]Oxazine-7-Sulfonamide 2,2,2-Trifluoroacetate

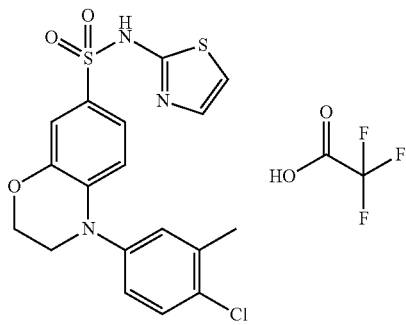 [SMILES: Cc1cc(N2CCOc3cc(S(=O)(=O)Nc4nccs4)ccc32)ccc1Cl ; O=C(O)C(F)(F)F]

EXAMPLE 156 was synthesized in the same manner as EXAMPLE 153, using 4-bromo-1-chloro-2-methylbenzene (ASDI) instead of 2-bromo-5-methoxybenzonitrile. $^1$H NMR (500 MHz, DMSO-d$_6$) δ ppm 2.32 (s, 3 H) 3.68-3.74 (m, 2 H) 4.26-4.32 (m, 2 H) 6.76 (d, J=8.48 Hz, 1 H) 6.78 (d, J=4.47

Hz, 1H) 7.10-7.18 (m, 3 H) 7.22 (d, J=4.58 Hz, 1 H) 7.32 (d, J=2.41 Hz, 1 H) 7.44 (d, J=8.48 Hz, 1 H) 12.56 (br. s., 1 H). m/z (ESI) 424.0 (M+H)+.

Example 157

N-(Thiazol-2-Yl)-4-(2-(Trifluoromethyl)Phenyl)-3,4-Dihydro-2H-Benzo[B][1,4]Oxazine-7-Sulfonamide 2,2,2-Trifluoroacetate

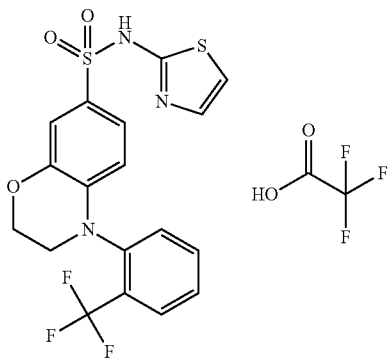 [SMILES: O=S(=O)(Nc1nccs1)c1ccc2c(c1)OCCN2c1ccccc1C(F)(F)F ; O=C(O)C(F)(F)F]

EXAMPLE 157 was synthesized in the same manner as EXAMPLE 153, using 1-bromo-2-(trifluoromethyl)benzene (ASDI) instead of 2-bromo-5-methoxybenzonitrile. $^1$H NMR (500 MHz, DMSO-d$_6$) δ ppm 3.41-3.48 (m, 1 H) 3.68-3.76 (m, 1 H) 4.23-4.32 (m, 1 H) 4.37-4.44 (m, 1 H) 5.97 (d, J=8.53 Hz, 1 H) 6.77 (d, J=4.64 Hz, 1 H) 7.08 (d, J=8.53 Hz, 1 H) 7.14 (d, J=1.95 Hz, 1 H) 7.21 (d, J=4.58 Hz, 1 H) 7.61-7.67 (m, 2 H) 7.80-7.86 (m, 1 H) 7.90 (d, J=7.79 Hz, 1 H) 12.55 (br. s., 1 H). m/z (ESI) 424.0 (M+H)+.

Example 158

4-(3-Methoxypyridin-4-Yl)-N-(Thiazol-2-Yl)-3,4-Dihydro-2H-Benzo[B][1,4]Oxazine-7-Sulfonamide

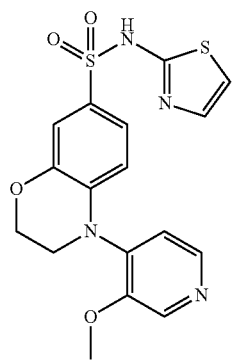 [SMILES: COc1cnccc1N1CCOc2cc(S(=O)(=O)Nc3nccs3)ccc21]

EXAMPLE 158 was synthesized in the same manner as EXAMPLE 153, using 4-bromo-3-methoxypyridine hydrochloride (Milestone Pharmtec) instead of 2-bromo-5-methoxybenzonitrile. The crude product was purified by reverse-phase preparative HPLC using a Phenomenex Luna column, 5 micron, C18(2), 100 Å, 150×30 mm, 0.1% TFA in CH$_3$CN/H$_2$O, gradient 25% to 90% over 20 min to provide impure material. The positive fractions were combined and concentrated in vacuo, and further purified via 5-g SCX column (product eluted with ammonia/methanol wash) to yield 4-(3-methoxypyridin-4-yl)-N-(thiazol-2-yl)-3,4-dihydro-2H-benzo[b][1,4]oxazine-7-sulfonamide (0.100 g, 0.247 mmol, 83% yield) as a light-yellow solid. $^1$H NMR (400 MHz, DMSO-d$_6$) δ ppm 3.66-3.73 (m, 2 H) 3.87 (s, 3 H) 4.25-4.33 (m, 2 H) 6.48 (d, J=8.41 Hz, 1 H) 6.79 (d, J=4.60 Hz, 1 H) 7.10-7.17 (m, 2 H) 7.23 (d, J=4.69 Hz, 1 H) 7.29 (d, J=5.09 Hz, 1 H) 8.22 (d, J=5.09 Hz, 1 H) 8.45 (s, 1 H) 12.59 (br. s., 1 H). m/z (ESI) 405.0 (M+H)+.

Example 159

4-(2-Cyano-6-Fluorophenyl)-N-(Thiazol-2-Yl)-3,4-Dihydro-2H-Benzo[B][1,4]Oxazine-7-Sulfonamide

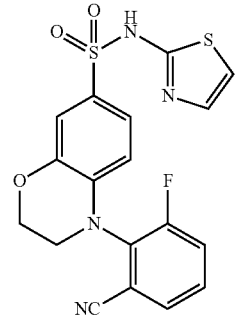 [SMILES: N#Cc1cccc(F)c1N1CCOc2cc(S(=O)(=O)Nc3nccs3)ccc21]

EXAMPLE 159 was synthesized in the same manner as EXAMPLE 158, using 2-bromo-3-fluorobenzonitrile (Indofine Chemical Company) instead of 4-bromo-3-methoxypyridine hydrochloride. $^1$H NMR (400 MHz, DMSO-d$_6$) δ ppm 3.73-3.80 (m, 2 H) 4.33-4.38 (m, 2 H) 6.34 (dd, J=8.41, 1.37 Hz, 1 H) 6.79 (d, J=4.60 Hz, 1 H) 7.14-7.18 (m, 1 H) 7.20 (d, J=2.05 Hz, 1 H) 7.23 (d, J=4.69 Hz, 1 H) 7.59-7.66 (m, 1 H) 7.80 (ddd, J=10.39, 8.68, 1.37 Hz, 1 H) 7.86 (d, J=7.63 Hz, 1H) 12.61 (br. s., 1 H). m/z (ESI) 417.0 (M+H)+.

Example 160

4-(8-Oxo-5,6,7,8-Tetrahydronaphthalen-2-Yl)-N-(Thiazol-2-Yl)-3,4-Dihydro-2H-Benzo[B][1,4]Oxazine-7-Sulfonamide 2,2,2-Trifluoroacetate

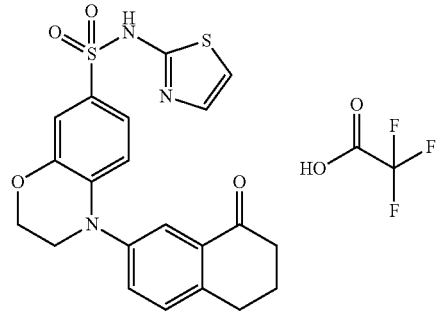 [SMILES: O=C1CCCc2ccc(N3CCOc4cc(S(=O)(=O)Nc5nccs5)ccc43)cc21 ; O=C(O)C(F)(F)F]

EXAMPLE 160 was synthesized in the same manner as EXAMPLE 153, using 7-bromo-3,4-dihydronaphthalen-1(2H)-one (ASDI) instead of 2-bromo-5-methoxybenzonitrile. $^1$H NMR (500 MHz, DMSO-d$_6$) δ ppm 1.98-2.11 (m, 2 H)

2.61 (t, J=6.30 Hz, 2 H) 2.94 (t, J=5.70 Hz, 2 H) 3.70-3.75 (m, 2 H) 4.24-4.34 (m, 2 H) 6.70 (d, J=8.59 Hz, 1 H) 6.78 (d, J=4.18 Hz, 1 H) 7.10-7.17 (m, 2 H) 7.22 (d, J=4.58 Hz, 1 H) 7.42 (d, J=8.31 Hz, 1 H) 7.48-7.53 (m, 1 H) 7.71 (d, J=2.06 Hz, 1 H) 12.56 (br. s., 1 H). m/z (ESI) 441.1 (M+H)+.

Example 161

4-(4-(Dimethylamino)-3,5-Dimethylphenyl)-N-(Thiazol-2-Yl)-3,4-Dihydro-2H-Benzo[B][1,4]Oxazine-7-Sulfonamide 2,2,2-Trifluoroacetate

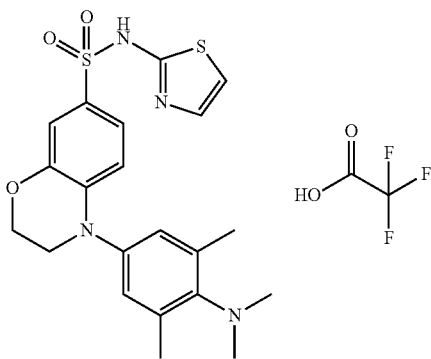 [SMILES: Cc1cc(N2CCOc3cc(S(=O)(=O)Nc4nccs4)ccc32)cc(C)c1N(C)C ; O=C(O)C(F)(F)F]

EXAMPLE 161 was synthesized in the same manner as EXAMPLE 153, using 4-bromo-N,N,2,6-tetramethylaniline (ASDI) instead of 2-bromo-5-methoxybenzonitrile. $^1$H NMR (500 MHz, DMSO-d$_6$) δ ppm 2.29 (s, 6 H) 2.86 (s, 6 H) 3.63-3.69 (m, 2 H) 4.24-4.29 (m, 2 H) 6.70 (d, J=8.99 Hz, 1 H) 6.78 (d, J=4.58 Hz, 1 H) 6.96 (s, 2 H) 7.10-7.15 (m, 2 H) 7.21 (d, J=4.58 Hz, 1 H) 12.64 (br. s, 1 H). m/z (ESI) 444.1 (M+H)+.

Example 162

4-(3-Ethoxyphenyl)-N-(Thiazol-2-Yl)-3,4-Dihydro-2H-Benzo[B][1,4]Oxazine-7-Sulfonamide 2,2,2-Trifluoroacetate

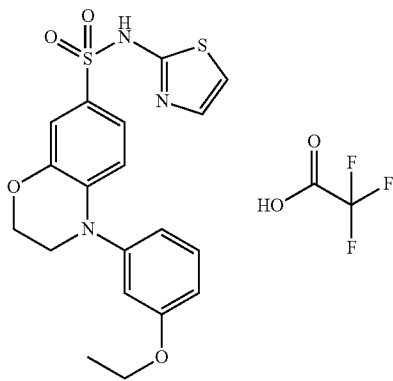 [SMILES: CCOc1cccc(N2CCOc3cc(S(=O)(=O)Nc4nccs4)ccc32)c1 ; O=C(O)C(F)(F)F]

EXAMPLE 162 was synthesized in the same manner as EXAMPLE 153, using 1-bromo-3-ethoxybenzene (ASDI) instead of 2-bromo-5-methoxybenzonitrile. $^1$H NMR (500 MHz, DMSO-d$_6$) δ ppm 1.31 (t, J=6.99 Hz, 3 H) 3.67-3.74 (m, 2 H) 4.02 (q, J=6.99 Hz, 2 H) 4.25-4.32 (m, 2 H) 6.74-6.81 (m, 3 H) 6.82-6.87 (m, 2 H) 7.10-7.15 (m, 2 H) 7.22 (d, J=4.47 Hz, 1 H) 7.28-7.34 (m, 1 H) 12.55 (br. s., 1 H). m/z (ESI) 417.1 (M+H)+.

Example 163

4-(3-Chloro-4-Methylphenyl)-N-(Thiazol-2-Yl)-3,4-Dihydro-2H-Benzo[B][1,4]Oxazine-7-Sulfonamide 2,2,2-Trifluoroacetate

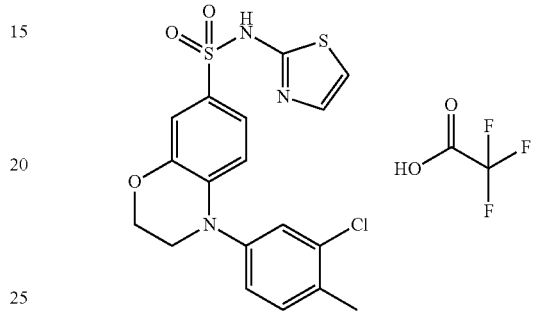

EXAMPLE 163 was synthesized in the same manner as EXAMPLE 153, using 4-bromo-2-chloro-1-methylbenzene (ASDI) instead of 2-bromo-5-methoxybenzonitrile. $^1$H NMR (500 MHz, DMSO-d$_6$) δ ppm 2.22-2.35 (m, 3 H) 3.64-3.75 (m, 2 H) 4.23-4.33 (m, 2 H) 6.73 (d, J=8.02 Hz, 1 H) 6.78 (d, J=4.52 Hz, 1 H) 7.02-7.17 (m, 2 H) 7.17-7.27 (m, 2 H) 7.29-7.45 (m, 2 H) 12.56 (br. s., 1 H). m/z (ESI) 421.0 (M+H)+.

Example 164

4-(5-Cyano-2-Fluorophenyl)-N-(Thiazol-2-Yl)-3,4-Dihydro-2H-Benzo[B][1,4]Oxazine-7-Sulfonamide 2,2,2-Trifluoroacetate

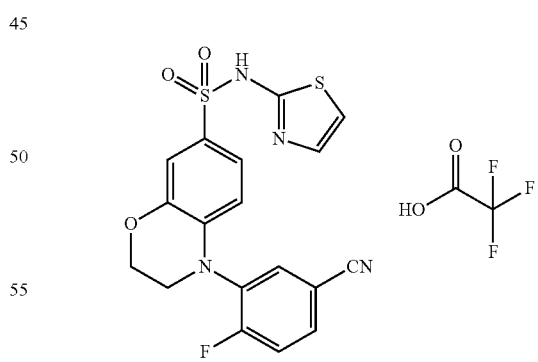

EXAMPLE 164 was synthesized in the same manner as EXAMPLE 153, using 3-bromo-4-fluorobenzonitrile (ASDI) instead of 2-bromo-5-methoxybenzonitrile. $^1$H NMR (500 MHz, DMSO-d$_6$) δ ppm 3.70-3.76 (m, 2 H) 4.30-4.37 (m, 2 H) 6.47 (dd, J=8.08, 2.58 Hz, 1 H) 6.79 (d, J=4.35 Hz, 1 H) 7.13-7.19 (m, 2 H) 7.22 (d, J=4.58 Hz, 1 H) 7.60 (dd, J=10.71, 8.65 Hz, 1 H) 7.82-7.88 (m, 1 H) 8.07 (dd, J=7.45, 1.95 Hz, 1 H) 12.59 (br. s., 1 H). m/z (ESI) 416.0 (M+H)+.

Example 165

4-Phenyl-N-(Thiazol-2-Yl)-3,4-Dihydro-2H-Benzo[B][1,4]Oxazine-7-Sulfonamide

EXAMPLE 165 was synthesized in the same manner as EXAMPLE 153, using bromobenzene (TCI America) instead of 2-bromo-5-methoxybenzonitrile. After concentration, the crude material was absorbed directly onto a 12-g RediSep Gold column and purified by silica-gel chromatography, eluting with a gradient of 0% to 100% ethyl acetate in heptanes to provide slightly impure product. The impure material was further purified using a 500-mg SCX column (product eluted with methanol wash) to yield 4-phenyl-N-(thiazol-2-yl)-3,4-dihydro-2H-benzo[b][1,4]oxazine-7-sulfonamide (0.021 g, 0.056 mmol, 23.48% yield) as a tan solid.

$^1$H NMR (400 MHz, DMSO-$d_6$) δ ppm 3.70-3.76 (m, 2 H) 4.28-4.34 (m, 2 H) 6.73 (d, J=8.41 Hz, 1 H) 6.78 (d, J=4.70 Hz, 1 H) 7.10-7.16 (m, 2 H) 7.18-7.24 (m, 2 H) 7.28-7.33 (m, 2 H) 7.40-7.46 (m, 2 H) 12.55 (br. S., 1 H). m/z (ESI) 374.0 (M+H)$^+$.

Example 166

4-(Quinolin-8-Yl)-N-(Thiazol-2-Yl)-3,4-Dihydro-2H-Benzo[B][1,4]Oxazine-7-Sulfonamide 2,2,2-Trifluoroacetate EXAMPLE 166 was synthesized in the same manner as EXAMPLE 153, using 8-bromoquinoline (ASDI) instead of 2-bromo-5-methoxybenzonitrile. $^1$H NMR (400 MHz, DMSO-$d_6$) δ ppm 3.83-3.93 (m, 2 H) 4.41 (t, J=4.35 Hz, 2 H) 6.08 (d, J=8.61 Hz, 1 H) 6.76 (d, J=4.60 Hz, 1 H) 6.98 (dd, J=8.51, 2.15 Hz, 1 H) 7.16 (d, J=2.05 Hz, 1 H) 7.21 (d, J=4.60 Hz, 1 H) 7.58 (dd, J=8.31, 4.11 Hz, 1 H) 7.66-7.72 (m, 1 H) 7.76-7.81 (m, 1 H) 8.00 (dd, J=8.17, 1.42 Hz, 1 H) 8.47 (dd, J=8.36, 1.71 Hz, 1 H) 8.87 (dd, J=4.11, 1.76 Hz, 1 H) 12.50 (br. S., 1 H). m/z (ESI) 425.0 (M+H)$^+$.

Example 167

4-(4-Cyano-3-(Trifluoromethoxy)Phenyl)-N-(Thiazol-2-Yl)-3,4-Dihydro-2H-Benzo[B][1,4]Oxazine-7-Sulfonamide EXAMPLE 167 was synthesized in the same manner as EXAMPLE 153, using 4-bromo-2-(trifluoromethoxy)benzonitrile (CombiBlocks) instead of 2-bromo-5-methoxybenzonitrile. After concentration, the crude material was absorbed directly onto a 12-g RediSep Gold column and purified by silica-gel chromatography, eluting with a gradient of 0% to 100% ethyl acetate in heptanes to provide 4-(4-cyano-3-(trifluoromethoxy)phenyl)-N-(thiazol-2-yl)-3,4-dihydro-2H-benzo[b][1,4]oxazine-7-sulfonamide (0.104 g, 0.216 mmol, 90% yield) as a yellow solid. $^1$H NMR (400 MHz, DMSO-$d_6$) δ ppm 3.82-3.89 (m, 2 H) 4.29-4.34 (m, 2 H) 6.82 (d, J=4.60 Hz, 1 H) 7.18-7.30 (m, 4 H) 7.43-7.48 (m, 2 H) 7.93 (d, J=8.80 Hz, 1 H) 12.67 (br. S., 1 H). m/z (ESI) 483.0 (M+H)$^+$.

Example 168

4-(2-Isopropyl-5-Methylphenyl)-N-(Thiazol-2-Yl)-3,4-Dihydro-2H-Benzo[B][1,4]Oxazine-7-Sulfonamide 2,2,2-Trifluoroacetate EXAMPLE 168 was synthesized in the same manner as EXAMPLE 153, using 2-bromo-1-isopropyl-4-methylbenzene (ASDI) instead of 2-bromo-5-methoxybenzonitrile. $^1$H NMR (500 MHz, DMSO-d$_6$) δ ppm 1.18 (d, J=6.76 Hz, 6 H) 2.09 (s, 3 H) 2.86 (dt, J=13.96, 6.97 Hz, 1 H) 3.65-3.78 (m, 2 H) 4.27-4.41 (m, 2 H) 6.00 (d, J=8.48 Hz, 1 H) 6.76 (d, J=4.47 Hz, 1 H) 7.07-7.17 (m, 4 H) 7.20 (d, J=4.47 Hz, 1 H) 7.27 (d, J=7.68 Hz, 1 H) 12.50 (br. S., 1 H). m/z (ESI) 430.0 (M+H)$^+$.

Example 169

4-(3-Chloro-2-Methylphenyl)-N-(Thiazol-2-Yl)-3,4-Dihydro-2H-Benzo[B][1,4]Oxazine-7-Sulfonamide 2,2,2-Trifluoroacetate

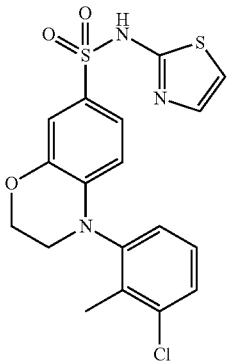

EXAMPLE 169 was synthesized in the same manner as EXAMPLE 153, using 1-bromo-3-chloro-2-methylbenzene (ASDI) instead of 2-bromo-5-methoxybenzonitrile. $^1$H NMR (500 MHz, DMSO-d$_6$) δ ppm 2.19 (s, 3 H) 3.51-3.58 (m, 1 H) 3.68-3.76 (m, 1 H) 4.32-4.39 (m, 2 H) 6.06 (d, J=8.48 Hz, 1 H) 6.77 (d, J=4.47 Hz, 1 H) 7.10 (dd, J=8.48, 2.06 Hz, 1 H) 7.14 (d, J=1.95 Hz, 1 H) 7.21 (d, J=4.58 Hz, 1 H) 7.28-7.38 (m, 2 H) 7.46 (d, J=7.79 Hz, 1 H) 12.53 (br. S., 1 H). m/z (ESI) 421.0 (M+H)$^+$.

Example 170

4-(4-Chloro-2-Fluorophenyl)-N-(Thiazol-2-Yl)-3,4-Dihydro-2H-Benzo[B][1,4]Oxazine-7-Sulfonamide 2,2,2-Trifluoroacetate

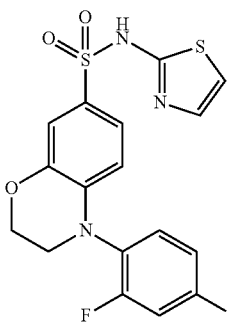

EXAMPLE 170 was synthesized in the same manner as EXAMPLE 153, using 1-bromo-4-chloro-2-fluorobenzene (ASDI) instead of 2-bromo-5-methoxybenzonitrile. $^1$H NMR (500 MHz, DMSO-d$_6$) δ ppm 3.64-3.74 (m, 2 H) 4.29-4.37 (m, 2 H) 6.36-6.45 (m, 1 H) 6.78 (d, J=4.41 Hz, 1 H) 7.10-7.17 (m, 2 H) 7.21 (d, J=4.52 Hz, 1 H) 7.35-7.42 (m, 1 H) 7.46-7.54 (m, 1 H) 7.60 (dd, J=10.80, 2.03 Hz, 1 H) 12.57 (br. S., 1 H). m/z (ESI) 426.0 (M+H)$^+$.

Example 171

4-(2,3-Dichlorophenyl)-N-(Thiazol-2-Yl)-3,4-Dihydro-2H-Benzo[B][1,4]Oxazine-7-Sulfonamide 2,2,2-Trifluoroacetate

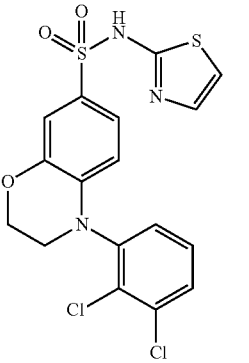
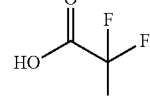

EXAMPLE 171 was synthesized in the same manner as EXAMPLE 153, using 1-bromo-2,3-dichlorobenzene (ASDI) instead of 2-bromo-5-methoxybenzonitrile. $^1$H NMR (500 MHz, DMSO-d$_6$) δ ppm 3.60-3.76 (m, 2 H) 4.26-4.41 (m, 2 H) 6.17 (d, J=8.53 Hz, 1 H) 6.78 (d, J=4.24 Hz, 1 H) 7.12 (dd, J=8.51, 1.98 Hz, 1 H) 7.16 (d, J=1.89 Hz, 1 H) 7.21 (d, J=4.58 Hz, 1 H) 7.46-7.54 (m, 2 H) 7.64-7.69 (m, 1 H) 12.56 (br. s., 1 H). m/z (ESI) 441.0 (M+H)$^+$.

Example 172

4-(3-(Difluoromethoxy)Phenyl)-N-(Thiazol-2-Yl)-3,4-Dihydro-2H-Benzo[B][1,4]Oxazine-7-Sulfonamide 2,2,2-Trifluoroacetate

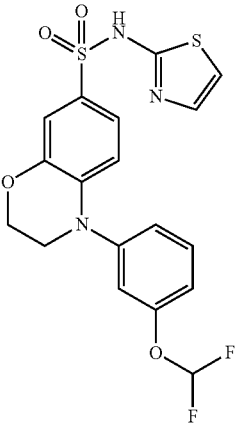
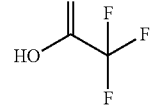

EXAMPLE 172 was synthesized in the same manner as EXAMPLE 153, using 1-bromo-3-(difluoromethoxy)benzene (ASDI) instead of 2-bromo-5-methoxybenzonitrile. $^1$H NMR (500 MHz, DMSO-d$_6$) δ ppm 3.71-3.79 (m, 2 H) 4.24-4.33 (m, 2 H) 6.79 (d, J=4.52 Hz, 1 H) 6.88 (d, J=8.25 Hz, 1

H) 6.97 (d, J=8.48 Hz, 1 H) 7.11 (d, J=1.95 Hz, 1 H) 7.14-7.20 (m, 3 H) 7.22 (d, J=4.53 Hz, 1 H) 7.26 (s, 1 H) 7.41-7.48 (m, 1 H) 12.57 (br. s., 1 H). m/z (ESI) 440.0 (M+H)⁺.

Example 173

N-(Thiazol-2-Yl)-4-(3-(Trifluoromethyl)Phenyl)-3,4-Dihydro-2H-Benzo[B][1,4]Oxazine-7-Sulfonamide 2,2,2-Trifluoroacetate

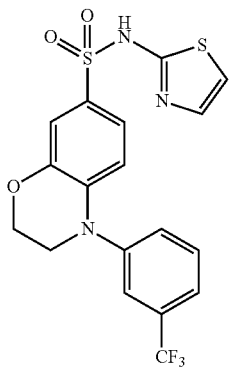

EXAMPLE 173 was synthesized in the same manner as EXAMPLE 153, using 1-bromo-3-(trifluoromethyl)benzene (ASDI) instead of 2-bromo-5-methoxybenzonitrile. ¹H NMR (500 MHz, DMSO-d₆) δ ppm 3.76-3.82 (m, 2 H) 4.27-4.35 (m, 2 H) 6.79 (d, J=4.52 Hz, 1 H) 6.85 (d, J=8.53 Hz, 1 H) 7.13-7.20 (m, 2 H) 7.22 (d, J=4.52 Hz, 1 H) 7.48-7.54 (m, 1 H) 7.59-7.68 (m, 3 H) 12.61 (br. s., 1 H). m/z (ESI) 442.0 (M+H)⁺.

Example 174

4-(3-(Cyanomethyl)Phenyl)-N-(Thiazol-2-Yl)-3,4-Dihydro-2H-Benzo[B][1,4]Oxazine-7-Sulfonamide 2,2,2-Trifluoroacetate

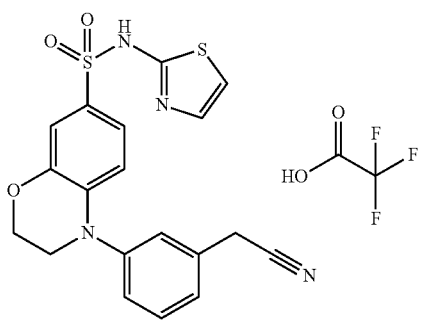 [SMILES: N#CCc1cccc(N2CCOc3cc(S(=O)(=O)Nc4nccs4)ccc32)c1 ; O=C(O)C(F)(F)F]

EXAMPLE 174 was synthesized in the same manner as EXAMPLE 153, using 2-(3-bromophenyl)acetonitrile (ASDI) instead of 2-bromo-5-methoxybenzonitrile. ¹H NMR (500 MHz, DMSO-d₆) δ ppm 3.71-3.75 (m, 2 H) 4.04 (s, 2 H) 4.27-4.33 (m, 2 H) 6.77-6.82 (m, 2 H) 7.11-7.19 (m, 3 H) 7.22 (d, J=4.70 Hz, 1 H) 7.25-7.31 (m, 2 H) 7.42-7.47 (m, 1 H) 12.57 (br. s., 1 H). m/z (ESI) 413.0 (M+H)⁺.

Example 175

4-(3-Cyano-4-Fluorophenyl)-N-(Thiazol-2-Yl)-3,4-Dihydro-2H-Benzo[B][1,4]Oxazine-7-Sulfonamide 2,2,2-Trifluoroacetate

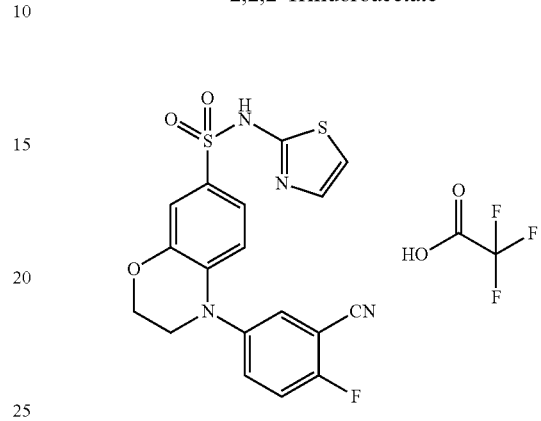

EXAMPLE 175 was synthesized in the same manner as EXAMPLE 153, using 5-bromo-2-fluorobenzonitrile (ASDI) instead of 2-bromo-5-methoxybenzonitrile. ¹H NMR (500 MHz, DMSO-d₆) δ ppm 3.68-3.75 (m, 2 H) 4.27-4.34 (m, 2 H) 6.76 (d, J=8.59 Hz, 1 H) 6.79 (d, J=4.58 Hz, 1 H) 7.12-7.18 (m, 2 H) 7.22 (d, J=4.58 Hz, 1 H) 7.56 (m, J=9.00, 9.00 Hz, 1 H) 7.71-7.76 (m, 1 H) 7.91 (dd, J=5.56, 2.81 Hz, 1 H) 12.58 (br. s., 1 H). m/z (ESI) 417.0 (M+H)⁺.

Example 176

4-(2,4-Difluorophenyl)-N-(Thiazol-2-Yl)-3,4-Dihydro-2H-Benzo[B][1,4]Oxazine-7-Sulfonamide 2,2,2-Trifluoroacetate

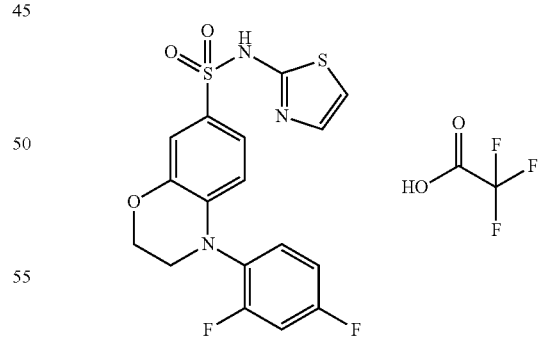

EXAMPLE 176 was synthesized in the same manner as EXAMPLE 153, using 1-bromo-2,4-difluorobenzene (ASDI) instead of 2-bromo-5-methoxybenzonitrile. ¹H NMR (500 MHz, DMSO-d₆) δ ppm 3.65-3.70 (m, 2 H) 4.29-4.36 (m, 2 H) 6.32 (dd, J=8.99, 1.89 Hz, 1 H) 6.78 (d, J=4.47 Hz, 1 H) 7.11-7.16 (m, 2 H) 7.18-7.24 (m, 2 H) 7.40-7.47 (m, 1 H) 7.54 (td, J=9.02, 6.01 Hz, 1 H) 12.56 (br. s., 1H). m/z (ESI) 409.0 (M+H)⁺.

Example 177

4-(2-Cyano-4-Fluorophenyl)-N-(Thiazol-2-Yl)-3,4-Dihydro-2H-Benzo[B][1,4]Oxazine-7-Sulfonamide

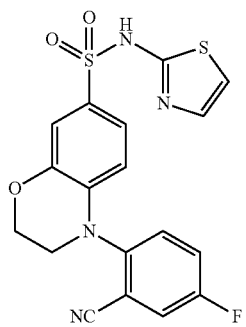 [SMILES: N#Cc1cc(F)ccc1N1CCOc2cc(S(=O)(=O)Nc3nccs3)ccc21]

EXAMPLE 177 was synthesized in the same manner as EXAMPLE 153, using 2-bromo-5-fluorobenzonitrile (Matrix Scientific) instead of 2-bromo-5-methoxybenzonitrile. After TFA deprotection and concentration in vacuo, upon attempts to take the crude material up in DCM for MPLC purification, a white solid started to precipitate out of solution, and after allowing it to settle, the solids were filtered and washed with DCM to yield pure final compound. Upon drying over high vacuum, 4-(2-cyano-4-fluorophenyl)-N-(thiazol-2-yl)-3,4-dihydro-2H-benzo[b][1,4]oxazine-7-sulfonamide (0.027 g, 0.065 mmol, 27.1% yield) was obtained as a white solid. $^1$H NMR (400 MHz, DMSO-$d_6$) δ ppm 3.71-3.77 (m, 2 H) 4.32-4.37 (m, 2 H) 6.42 (d, J=8.51 Hz, 1 H) 6.79 (d, J=4.60 Hz, 1 H) 7.14 (dd, J=8.51, 2.05 Hz, 1 H) 7.18 (d, J=2.05 Hz, 1 H) 7.22 (d, J=4.69 Hz, 1 H) 7.62-7.73 (m, 2 H) 7.98 (dd, J=8.31, 2.93 Hz, 1 H) 12.59 (br. s., 1 H). m/z (ESI) 417.0 (M+H)$^+$.

Example 178

4-(5-Chloro-2-Methylphenyl)-N-(Thiazol-2-Yl)-3,4-Dihydro-2H-Benzo[B][1,4]Oxazine-7-Sulfonamide 2,2,2-Trifluoroacetate

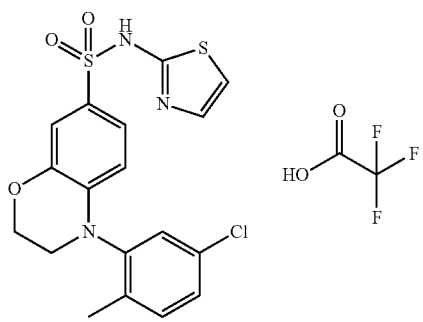 [SMILES: Cc1ccc(Cl)cc1N1CCOc2cc(S(=O)(=O)Nc3nccs3)ccc21 ; O=C(O)C(F)(F)F]

EXAMPLE 178 was synthesized in the same manner as EXAMPLE 153, using 2-bromo-4-chloro-1-methylbenzene (ASDI) instead of 2-bromo-5-methoxybenzonitrile. $^1$H NMR (500 MHz, DMSO-$d_6$) δ ppm 2.12 (s, 3 H) 3.64-3.81 (m, 2 H) 4.26-4.40 (m, 2 H) 6.06 (d, J=8.36 Hz, 1 H) 6.77 (d, J=4.12 Hz, 1H) 7.08-7.15 (m, 2 H) 7.21 (d, J=4.58 Hz, 1 H) 7.32-7.36 (m, 1 H) 7.38-7.43 (m, 2 H) 12.53 (br. s., 1 H). m/z (ESI) 424.0 (M+H)$^+$.

Example 179

4-(2-(Difluoromethoxy)Phenyl)-N-(Thiazol-2-Yl)-3,4-Dihydro-2H-Benzo[B][1,4]Oxazine-7-Sulfonamide 2,2,2-Trifluoroacetate

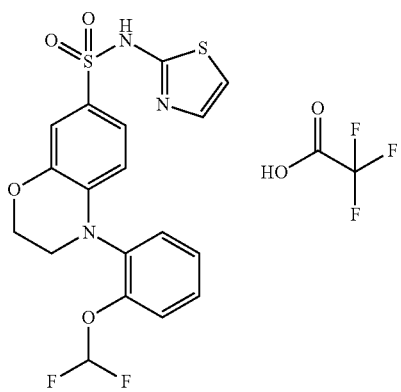 [SMILES: O=S(=O)(Nc1nccs1)c1ccc2c(c1)OCCN2c1ccccc1OC(F)F ; O=C(O)C(F)(F)F]

EXAMPLE 179 was synthesized in the same manner as EXAMPLE 153, using 1-bromo-2-(difluoromethoxy)benzene (ASDI) instead of 2-bromo-5-methoxybenzonitrile. $^1$H NMR (500 MHz, DMSO-$d_6$) δ ppm 3.61-3.69 (m, 2 H) 4.27-4.33 (m, 2 H) 6.26 (d, J=8.53 Hz, 1 H) 6.77 (d, J=4.47 Hz, 1 H) 7.05-7.15 (m, 3 H) 7.21 (d, J=4.58 Hz, 1 H) 7.33-7.49 (m, 4 H) 12.53 (br. s., 1 H). m/z (ESI) 440.0 (M+H)$^+$.

Example 180

4-(2,5-Dichlorophenyl)-N-(Thiazol-2-Yl)-3,4-Dihydro-2H-Benzo[B][1,4]Oxazine-7-Sulfonamide 2,2,2-Trifluoroacetate

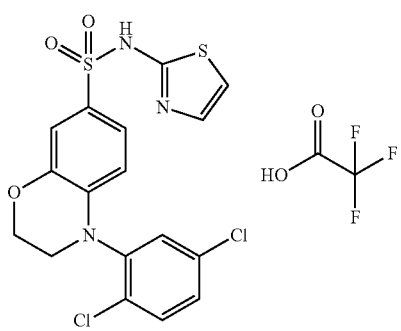 [SMILES: O=S(=O)(Nc1nccs1)c1ccc2c(c1)OCCN2c1cc(Cl)ccc1Cl ; O=C(O)C(F)(F)F]

EXAMPLE 180 was synthesized in the same manner as EXAMPLE 153, using 2-bromo-1,4-dichlorobenzene (ASDI) instead of 2-bromo-5-methoxybenzonitrile. $^1$H NMR (500 MHz, DMSO-$d_6$) δ ppm 3.57-3.67 (m, 1 H) 3.68-3.77 (m, 1 H) 4.24-4.41 (m, 2 H) 6.20 (d, J=8.36 Hz, 1 H) 6.78 (d, J=4.18 Hz, 1 H) 7.10-7.17 (m, 2 H) 7.21 (d, J=4.58 Hz, 1 H) 7.43-7.51 (m, 1 H) 7.64-7.70 (m, 2 H) 12.55 (br. s., 1 H). m/z (ESI) 442.0 (M+H)$^+$.

Example 181

4-(4-Cyano-2-Methoxyphenyl)-N-(Thiazol-2-Yl)-3,4-Dihydro-2H-Benzo[B][1,4]Oxazine-7-Sulfonamide 2,2,2-Trifluoroacetate

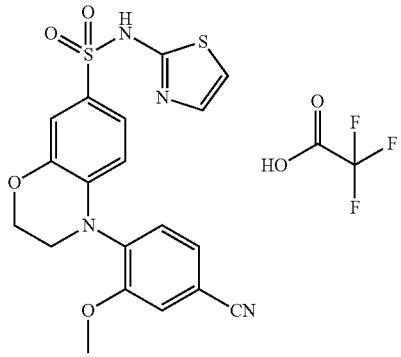 [SMILES: COc1cc(C#N)ccc1N1CCOc2cc(S(=O)(=O)Nc3nccs3)ccc21 ; O=C(O)C(F)(F)F]

EXAMPLE 181 was synthesized in the same manner as EXAMPLE 158, using 4-bromo-3-methoxybenzonitrile instead of 4-bromo-3-methoxypyridine hydrochloride. SCX column purification was not used. $^1$H NMR (400 MHz, DMSO-d$_6$) δ ppm 3.64-3.68 (m, 2 H) 3.83 (s, 3 H) 4.27-4.31 (m, 2 H) 6.34 (d, J=8.51 Hz, 1 H) 6.78 (d, J=4.60 Hz, 1 H) 7.11 (dd, J=8.51, 2.15 Hz, 1 H) 7.14 (d, J=2.05 Hz, 1 H) 7.22 (d, J=4.60 Hz, 1 H) 7.43-7.52 (m, 2 H) 7.64 (d, J=1.56 Hz, 1 H) 12.56 (br. s., 1 H). m/z (ESI) 429.0 (M+H)$^+$.

Example 182

4-(2-Methoxy-4-(Trifluoromethyl)Phenyl)-N-(Thiazol-2-Yl)-3,4-Dihydro-2H-Benzo[B][1,4]Oxazine-7-Sulfonamide

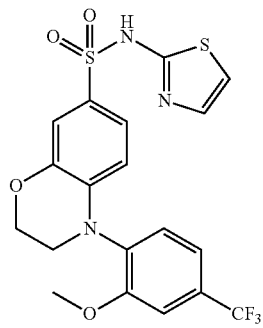 [SMILES: COc1cc(C(F)(F)F)ccc1N1CCOc2cc(S(=O)(=O)Nc3nccs3)ccc21]

EXAMPLE 182 was synthesized in the same manner as EXAMPLE 158, using 1-bromo-2-methoxy-4-(trifluoromethyl)benzene (CombiBlocks Inc.) instead of 4-bromo-3-methoxypyridine hydrochloride. $^1$H NMR (400 MHz, DMSO-d$_6$) δ ppm 3.63-3.69 (m, 2 H) 3.85 (s, 3 H) 4.27-4.33 (m, 2 H) 6.30 (d, J=8.51 Hz, 1 H) 6.78 (d, J=4.50 Hz, 1 H) 7.07-7.12 (m, 1 H) 7.13 (d, J=2.15 Hz, 1 H) 7.22 (d, J=4.60 Hz, 1 H) 7.38 (dd, J=8.17, 1.32 Hz, 1 H) 7.44 (d, J=1.66 Hz, 1 H) 7.51 (d, J=7.82 Hz, 1 H) 12.55 (br. s., 1H. m/z (ESI) 472.0 (M+H)$^+$.

Example 183

N-(Thiazol-2-Yl)-4-(5-(Trifluoromethyl)Pyridin-2-Yl)-3,4-Dihydro-2H-Benzo[B][1,4]Oxazine-7-Sulfonamide

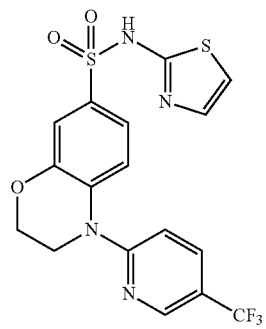 [SMILES: O=S(=O)(Nc1nccs1)c1ccc2c(c1)OCCN2c1ccc(C(F)(F)F)cn1]

EXAMPLE 183 was synthesized in the same manner as EXAMPLE 158, using 2-bromo-5-(trifluoromethyl)pyridine instead of 4-bromo-3-methoxypyridine hydrochloride. $^1$H NMR (400 MHz, DMSO-d$_6$) δ ppm 4.03-4.12 (m, 2 H) 4.26-4.37 (m, 2 H) 6.83 (d, J=4.60 Hz, 1 H) 7.21-7.30 (m, 3 H) 7.41 (d, J=8.90 Hz, 1H) 7.59-7.67 (m, 1 H) 8.00 (dd, J=9.10, 2.45 Hz, 1 H) 8.65 (dd, J=1.61, 0.83 Hz, 1 H) 12.70 (br. s., 1 H). m/z (ESI) 443.0 (M+H)$^+$.

Example 184

4-(2-Cyano-5-(Trifluoromethyl)Phenyl)-N-(Thiazol-2-Yl)-3,4-Dihydro-2H-Benzo[B][1,4]Oxazine-7-Sulfonamide

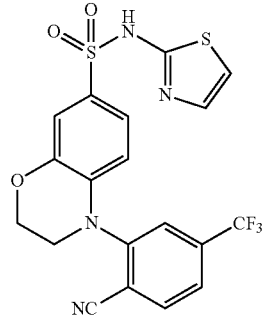 [SMILES: N#Cc1ccc(C(F)(F)F)cc1N1CCOc2cc(S(=O)(=O)Nc3nccs3)ccc21]

EXAMPLE 184 was synthesized in the same manner as EXAMPLE 158, using 2-bromo-4-(trifluoromethyl)benzonitrile (Beta Pharma, Inc) instead of 4-bromo-3-methoxypyridine hydrochloride. Purification by SCX column was not needed for this compound. $^1$H NMR (400 MHz, DMSO-d$_6$) δ ppm 3.78-3.89 (m, 2 H) 4.31-4.42 (m, 2 H) 6.61 (d, J=8.51 Hz, 1 H) 6.80 (d, J=4.69 Hz, 1 H) 7.16 (dd, J=8.51, 2.05 Hz, 1 H) 7.20-7.26 (m, 2 H) 7.80 (dd, J=8.12, 1.08 Hz, 1 H) 7.98 (s, 1 H) 8.18 (d, J=8.02 Hz, 1 H) 12.63 (br. s., 1 H). m/z (ESI) 467.0 (M+H)+.

Example 185

N-(Thiazol-2-Yl)-4-(3-(Trifluoromethoxy)Phenyl)-3,4-Dihydro-2H-Benzo[B][1,4]Oxazine-7-Sulfonamide

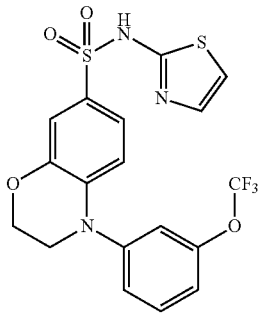 [SMILES: O=S(=O)(Nc1nccs1)c1ccc2c(c1)OCCN2c1cccc(OC(F)(F)F)c1]

EXAMPLE 185 was synthesized in the same manner as EXAMPLE 158, using 1-bromo-3-(trifluoromethoxy)benzene instead of 4-bromo-3-methoxypyridine hydrochloride. $^1$H NMR (400 MHz, DMSO-d$_6$) δ ppm 3.72-3.79 (m, 2 H) 4.27-4.33 (m, 2 H) 6.79 (d, J=4.69 Hz, 1 H) 6.90 (d, J=8.41 Hz, 1 H) 7.12-7.19 (m, 3 H) 7.23 (d, J=4.60 Hz, 1 H) 7.28-7.32 (m, 1 H) 7.35 (dd, J=8.12, 1.37 Hz, 1 H) 7.49-7.56 (m, 1 H) 12.59 (br. s., 1 H). m/z (ESI) 458.0 (M+H)+.

Example 186

4-(4-Chloro-2-Methoxyphenyl)-N-(Thiazol-2-Yl)-3,4-Dihydro-2H-Benzo[B][1,4]Oxazine-7-Sulfonamide

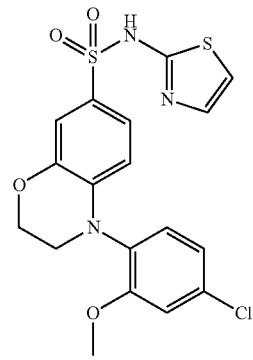 [SMILES: COc1cc(Cl)ccc1N1CCOc2cc(S(=O)(=O)Nc3nccs3)ccc21]

EXAMPLE 186 was synthesized in the same manner as EXAMPLE 167, using 2-bromo-5-chloroanisole instead of 4-bromo-2-(trifluoromethoxy)benzonitrile. Prior to silica gel purification, the material was cleaned using a 2-g SCX column (crude material eluted with methanol wash). $^1$H NMR (400 MHz, DMSO-d$_6$) δ ppm 3.55-3.63 (m, 2 H) 3.78 (s, 3 H) 4.25-4.32 (m, 2 H) 6.19 (d, J=8.41 Hz, 1H) 6.77 (d, J=4.60 Hz, 1 H) 7.05-7.09 (m, 1 H) 7.09-7.11 (m, 2 H) 7.19-7.23 (m, 1 H) 7.25 (d, J=2.25 Hz, 1 H) 7.31 (d, J=8.41 Hz, 1 H) 12.53 (br. s., 1 H). m/z (ESI) 438.0 (M+H)+.

Example 187

4-(2-Cyano-3-Fluorophenyl)-N-(Thiazol-2-Yl)-3,4-Dihydro-2H-Benzo[B][1,4]Oxazine-7-Sulfonamide

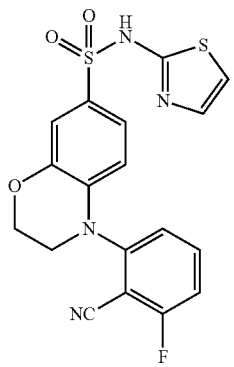 [SMILES: N#Cc1c(F)cccc1N1CCOc2cc(S(=O)(=O)Nc3nccs3)ccc21]

EXAMPLE 187 was synthesized in the same manner as EXAMPLE 167, using 2-bromo-6-fluorobenzonitrile (0.072 g, 0.359 mmol) instead of 4-bromo-2-(trifluoromethoxy)benzonitrile. $^1$H NMR (400 MHz, DMSO-d$_6$) δ ppm 3.78-3.83 (m, 2 H) 4.31-4.35 (m, 2 H) 6.71 (d, J=8.51 Hz, 1 H) 6.80 (d, J=4.50 Hz, 1H) 7.17 (dd, J=8.51, 2.05 Hz, 1 H) 7.21 (d, J=2.15 Hz, 1 H) 7.23 (d, J=4.69 Hz, 1H) 7.35-7.42 (m, 2 H) 7.80 (td, J=8.39, 6.80 Hz, 1 H) 12.62 (br. S., 1 H). m/z (ESI) 417.0 (M+H)+.

Example 188

4-(2-Cyano-5-Fluorophenyl)-N-(Thiazol-2-Yl)-3,4-Dihydro-2H-Benzo[B][1,4]Oxazine-7-Sulfonamide

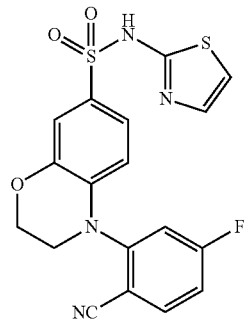 [SMILES: COc1ccc(C#N)c(N2CCOc3cc(S(=O)(=O)Nc4nccs4)ccc32)c1]

EXAMPLE 188 was synthesized in the same manner as EXAMPLE 167, using 2-bromo-4-fluorobenzonitrile (Matrix Scientific) instead of 4-bromo-2-(trifluoromethoxy)benzonitrile. $^1$H NMR (400 MHz, DMSO-d$_6$) δ ppm 3.76-3.84 (m, 2 H) 4.30-4.39 (m, 2 H) 6.62 (d, J=8.51 Hz, 1 H) 6.80 (d, J=4.40 Hz, 1H) 7.12-7.25 (m, 3 H) 7.34 (td, J=8.41, 2.54 Hz, 1 H) 7.52 (dd, J=10.17, 2.35 Hz, 1 H) 8.03 (dd, J=8.66, 6.21 Hz, 1 H) 12.62 (br. s., 1 H). m/z (ESI) 417.0 (M+H)+.

Example 189

4-(2-Cyano-5-Methoxyphenyl)-N-(Thiazol-2-Yl)-3,4-Dihydro-2H-Benzo[B][1,4]Oxazine-7-Sulfonamide

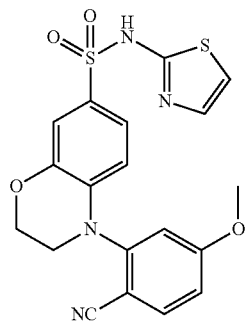

EXAMPLE 189 was synthesized in the same manner as EXAMPLE 167, using 2-bromo-4-methoxybenzonitrile (J&W PharmLab) instead of 4-bromo-2-(trifluoromethoxy)benzonitrile. $^1$H NMR (400 MHz, DMSO-$d_6$) δ ppm 3.73-3.79 (m, 2 H) 3.83 (s, 3 H) 4.31-4.37 (m, 2 H) 6.49 (d, J=8.41 Hz, 1 H) 6.79 (d, J=4.60 Hz, 1 H) 7.04 (dd, J=8.71, 2.54 Hz, 1 H) 7.10-7.19 (m, 3 H) 7.22 (d, J=4.69 Hz, 1 H) 7.85 (d, J=8.71 Hz, 1 H) 12.59 (br. s., 1 H). m/z (ESI) 429.0 (M+H)$^+$.

Example 190

4-(4-Methoxypyridin-3-Yl)-N-(Thiazol-2-Yl)-3,4-Dihydro-2H-Benzo[B][1,4]Oxazine-7-Sulfonamide

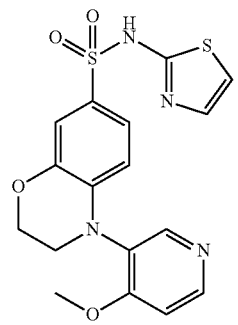

EXAMPLE 190 was synthesized in the same manner as EXAMPLE 167, using 3-bromo-4-methoxypyridine (Small Molecules, Inc.) instead of 4-bromo-2-(trifluoromethoxy)benzonitrile. $^1$H NMR (400 MHz, DMSO-$d_6$) δ ppm 12.55 (br. s., 1 H) 8.51-8.60 (m, 2 H) 7.42 (d, J=6.06 Hz, 1 H) 7.22 (d, J=4.69 Hz, 1 H) 7.07-7.16 (m, 2 H) 6.78 (d, J=4.60 Hz, 1 H) 6.28 (d, J=8.41 Hz, 1 H) 4.24-4.39 (m, 2 H) 3.92 (s, 3 H) 3.62-3.70 (m, 2 H). m/z (ESI) 405.0 (M+H)$^+$.

Example 191

4-(2-Chloro-4-Cyanophenyl)-N-(Thiazol-2-Yl)-3,4-Dihydro-2H-Benzo[B][1,4]Oxazine-7-Sulfonamide

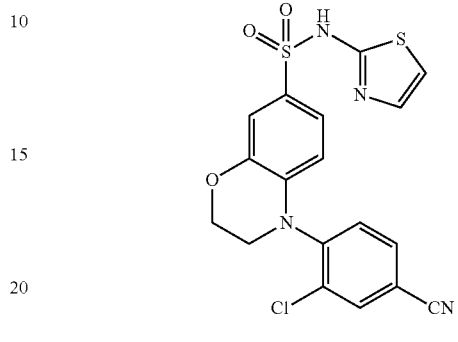

EXAMPLE 191 was synthesized in the same manner as EXAMPLE 167, using 4-bromo-3-chlorobenzonitrile instead of 4-bromo-2-(trifluoromethoxy)benzonitrile. $^1$H NMR (400 MHz, DMSO-$d_6$) δ ppm 3.68-3.76 (m, 2 H) 4.34 (t, J=4.30 Hz, 2H) 6.35 (d, J=8.51 Hz, 1 H) 6.79 (d, J=4.60 Hz, 1 H) 7.13 (dd, J=8.51, 2.15 Hz, 1H) 7.18 (d, J=2.05 Hz, 1 H) 7.23 (d, J=4.40 Hz, 1 H) 7.68 (d, J=8.31 Hz, 1 H) 7.92 (dd, J=8.31, 1.86 Hz, 1 H) 8.23 (d, J=1.86 Hz, 1 H) 12.59 (br. s., 1 H). m/z (ESI) 433.0 (M+H)$^+$.

Example 192

4-(5-Chloro-2-Cyanophenyl)-N-(Thiazol-2-Yl)-3,4-Dihydro-2H-Benzo[B][1,4]Oxazine-7-Sulfonamide

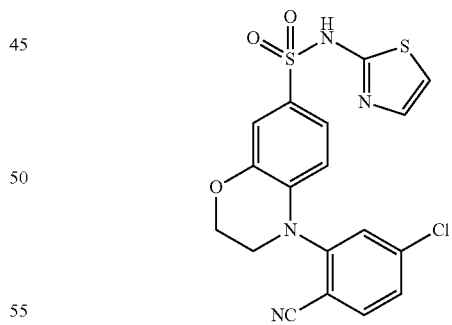

EXAMPLE 192 was synthesized in the same manner as EXAMPLE 167, using 2-bromo-4-chlorobenzonitrile (Matrix Scientific) instead of 4-bromo-2-(trifluoromethoxy)benzonitrile. $^1$H NMR (400 MHz, DMSO-$d_6$) δ ppm 3.76-3.81 (m, 2 H) 4.31-4.37 (m, 2 H) 6.60 (d, J=8.51 Hz, 1 H) 6.80 (d, J=4.40 Hz, 1H) 7.17 (dd, J=8.41, 2.15 Hz, 1 H) 7.20 (d, J=2.05 Hz, 1 H) 7.23 (d, J=4.89 Hz, 1H) 7.54 (dd, J=8.41, 2.05 Hz, 1 H) 7.72 (d, J=2.05 Hz, 1 H) 7.97 (d, J=8.41 Hz, 1H) 12.61 (br. s., 1 H). m/z (ESI) 433.0 (M+H)$^+$.

Example 193

4-(4-Chloro-2-(Difluoromethoxy)Phenyl)-N-(Thiazol-2-Yl)-3,4-Dihydro-2H-Benzo[B][1,4]Oxazine-7-Sulfonamide 2,2,2-Trifluoroacetate

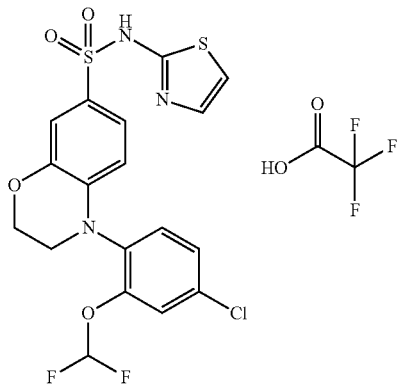 [SMILES: O=S(=O)(Nc1nccs1)c1ccc2c(c1)OCCN2c1ccc(Cl)cc1OC(F)F ; O=C(O)C(F)(F)F]

Step 1:
1-Bromo-4-Chloro-2-(Difluoromethoxy)Benzene

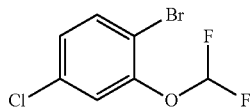

To a solution of 2-bromo-5-chlorophenol (4.34 g, 20.92 mmol, Ark Pharm) in N,N-dimethylformamide (21.79 ml, 20.92 mmol) was added sodium chlorodifluoroacetate (7.34 g, 48.1 mmol), cesium carbonate (9.54 g, 29.3 mmol), and water (2.179 ml, 20.92 mmol). The reaction was heated at 100° C. for 16 h.

After 16 h, the reaction was partitioned between EtOAc (100 mL) and water (50 mL). The aqueous layer was extracted with EtOAc (2×70 mL). The organic portions were combined and washed with water (2×50 mL), 10% aq citric acid (1×30 mL), and brine, dried over MgSO₄, filtered, and concentrated to provide 1-bromo-4-chloro-2-(difluoromethoxy)benzene (4.35 g, 16.90 mmol, 81% yield) as a colorless oil. The material was used without further purification.

Example 193

4-(4-Chloro-2-(Difluoromethoxy)Phenyl)-N-(Thiazol-2-Yl)-3,4-Dihydro-2H-Benzo[B][1,4]Oxazine-7-Sulfonamide 2,2,2-Trifluoroacetate

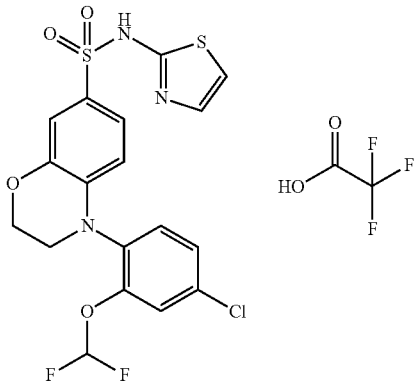 [SMILES: O=S(=O)(Nc1nccs1)c1ccc2c(c1)OCCN2c1ccc(Cl)cc1OC(F)F ; O=C(O)C(F)(F)F]

EXAMPLE 193 was synthesized in the same manner as EXAMPLE 167, using 1-bromo-4-chloro-2-(difluoromethoxy)benzene (EXAMPLE 193, Step 1) instead of 4-bromo-2-(trifluoromethoxy)benzonitrile. After silica-gel chromatography and concentration in vacuo, the material was taken up in DCM, and triturated. The solids were filtered and washed with DCM to yield 4-(4-chloro-2-(difluoromethoxy)phenyl)-N-(thiazol-2-yl)-3,4-dihydro-2H-benzo[b][1,4]oxazine-7-sulfonamide (0.040 g, 0.084 mmol, 35.2% yield) as a light yellow solid. $^1$H NMR (400 MHz, DMSO-d₆) δ ppm 12.55 (br. s., 1 H) 7.49-7.52 (m, 1 H) 7.48 (d, J=2.15 Hz, 1 H) 7.41-7.45 (m, 1 H) 7.22 (t, J=72 Hz, 1H) 7.21 (s, 1 H) 7.13-7.14 (m, 1 H) 7.09-7.13 (m, 1 H) 6.78 (d, J=4.50 Hz, 1 H) 6.31 (d, J=8.41 Hz, 1H) 4.28-4.33 (m, 2 H) 3.64 (t, J=4.06 Hz, 2 H). m/z (ESI) 474.0 (M+H)⁺.

Example 194

4-(2-Cyano-5-Methylphenyl)-N-(Thiazol-2-Yl)-3,4-Dihydro-2H-Benzo[B][1,4]Oxazine-7-Sulfonamide

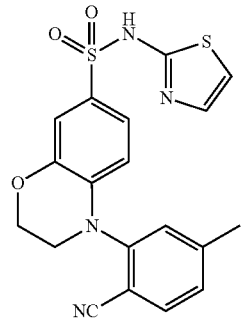 [SMILES: Cc1ccc(C#N)c(N2CCOc3cc(S(=O)(=O)Nc4nccs4)ccc32)c1]

EXAMPLE 194 was synthesized in the same manner as EXAMPLE 167, using 2-bromo-4-methylbenzonitrile instead of 4-bromo-2-(trifluoromethoxy)benzonitrile. $^1$H NMR (400 MHz, DMSO-d₆) δ ppm 2.38 (s, 3 H) 3.65-3.79 (m, 2 H) 4.26-4.38 (m, 2 H) 6.45 (d, J=8.51 Hz, 1 H) 6.79 (d, J=4.60 Hz, 1 H) 7.15 (dd, J=8.46, 2.10 Hz, 1 H) 7.18 (d, J=2.05 Hz, 1 H) 7.22 (d, J=4.69 Hz, 1 H) 7.30 (dd, J=7.92, 0.68 Hz, 1 H) 7.41 (s, 1 H) 7.82 (d, J=7.92 Hz, 1 H) 12.59 (br. s., 1 H). m/z (ESI) 413.0 (M+H)⁺.

Example 195

4-(4-Chloro-2-Methylphenyl)-N-(Thiazol-2-Yl)-3,4-Dihydro-2H-Benzo[B][1,4]Oxazine-7-Sulfonamide

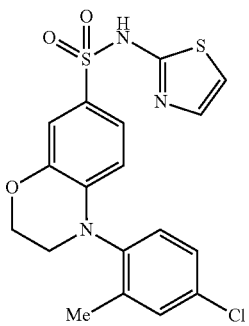 [SMILES: Cc1cc(Cl)ccc1N1CCOc2cc(S(=O)(=O)Nc3nccs3)ccc21]

EXAMPLE 195 was synthesized in the same manner as EXAMPLE 167, using 1-bromo-4-chloro-2-methylbenzene instead of 4-bromo-2-(trifluoromethoxy)benzonitrile. $^1$H NMR (400 MHz, DMSO-d₆) δ ppm 2.14 (s, 3 H) 3.49-3.56 (m, 1 H) 3.67-3.75 (m, 1 H) 4.30-4.37 (m, 2 H) 6.05 (d, J=8.41

Hz, 1 H) 6.77 (d, J=4.60 Hz, 1 H) 7.07-7.11 (m, 1 H) 7.12 (d, J=2.15 Hz, 1 H) 7.21 (d, J=4.60 Hz, 1 H) 7.29-7.33 (m, 1 H) 7.34-7.39 (m, 1 H) 7.47 (d, J=2.35 Hz, 1 H) 12.53 (br. s., 1 H). m/z (ESI) 422.0 (M+H)+.

Example 196

4-(2-Methyl-4-(Trifluoromethyl)Phenyl)-N-(Thiazol-2-Yl)-3,4-Dihydro-2H-Benzo[B][1,4]Oxazine-7-Sulfonamide

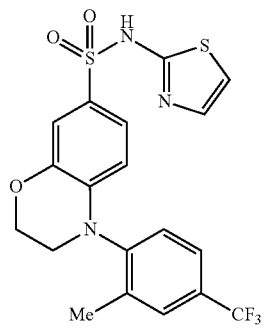 [SMILES: Cc1cc(C(F)(F)F)ccc1N1CCOc2cc(S(=O)(=O)Nc3nccs3)ccc21]

EXAMPLE 196 was synthesized in the same manner as EXAMPLE 167, using 1-bromo-2-methyl-4-(trifluoromethyl)benzene (Oakwood) instead of 4-bromo-2-(trifluoromethoxy)benzonitrile. ¹H NMR (400 MHz, DMSO-d₆) δ ppm 2.23 (s, 3 H) 3.50-3.65 (m, 1 H) 3.68-3.83 (m, 1 H) 4.29-4.41 (m, 2 H) 6.12 (d, J=8.51 Hz, 1 H) 6.78 (d, J=4.60 Hz, 1 H) 7.11 (dd, J=8.51, 2.15 Hz, 1 H) 7.15 (d, J=2.15 Hz, 1 H) 7.21 (d, J=4.60 Hz, 1 H) 7.51 (d, J=8.22 Hz, 1 H) 7.66 (d, J=8.60 Hz, 1H) 7.73-7.79 (m, 1 H) 12.54 (br. s., 1 H). m/z (ESI) 456.0 (M+H)+.

Example 197

4-Nitrophenyl 7-(N-(Thiazol-2-Yl)Sulfamoyl)-2H-Benzo[B][1,4]Oxazine-4(3 H)-Carboxylate

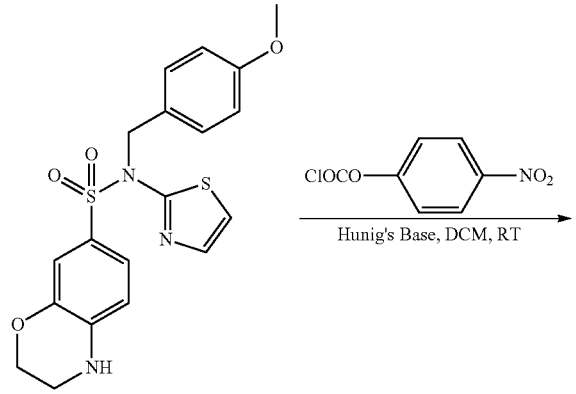

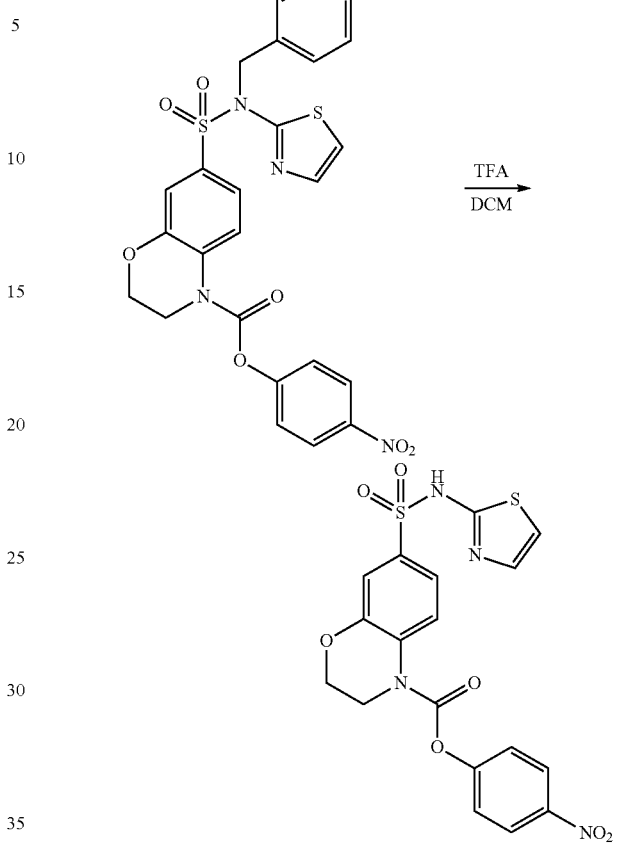

Step 1: 4-Nitrophenyl 7-(N-(4-Methoxybenzyl)-N-(Thiazol-2-Yl)Sulfamoyl)-2H-Benzo[B][1,4]Oxazine-4(3 H)-Carboxylate

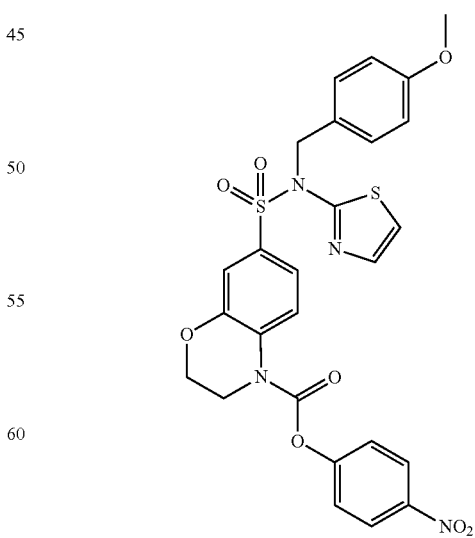

To a stirred solution of N-(4-methoxybenzyl)-N-(thiazol-2-yl)-3,4-dihydro-2H-benzo[b][1,4]oxazine-7-sulfonamide (INTERMEDIATE M, 0.200 g, 0.479 mmol) and Hunig's base (0.092 ml, 0.527 mmol) in DCM (2.395 ml) was added 4-nitrophenyl chloroformate (0.097 g, 0.479 mmol) (change from colorless to light yellow solution). The reaction was stirred at RT overnight, at which point starting material remained. Additional 4-nitrophenyl chloroformate (0.097 g, 0.479 mmol) was added and the reaction was stirred overnight once more until completion. After concentration in vacuo, the material was purified via MPLC (12-g Redi Sep Gold) eluting with 0-100% ethyl acetate in heptanes, to yield 4-nitrophenyl 7-(N-(4-methoxybenzyl)-N-(thiazol-2-yl)sulfamoyl)-2H-benzo[b][1,4]oxazine-4(3H)-carboxylate as a white solid. m/z (ESI) 583.0 (M+H)+.

Step 2, Example 197: 4-Nitrophenyl 7-(N-(Thiazol-2-Yl)Sulfamoyl)-2H-Benzo[B][1,4]Oxazine-4(3H)-Carboxylate

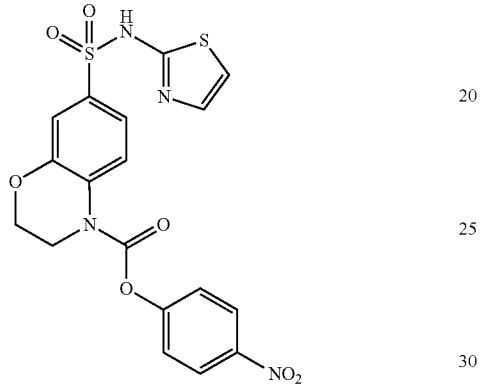

To a solution of 4-nitrophenyl 7-(N-(4-methoxybenzyl)-N-(thiazol-2-yl)sulfamoyl)-2H-benzo[b][1,4]oxazine-4(3H)-carboxylate (0.050 g, 0.086 mmol) in DCM (0.172 ml) was added trifluoroacetic acid (0.165 ml, 2.146 mmol). The reaction was stirred at RT for 15 minutes until complete deprotection. The reaction was concentrated in vacuo and purified via 500-mg SCX column (product eluted cleanly with methanol wash) to yield, after concentration, 4-nitrophenyl 7-(N-(thiazol-2-yl)sulfamoyl)-2H-benzo[b][1,4]oxazine-4(3H)-carboxylate (0.036 g, 0.078 mmol, 91% yield) as a white solid. $^1$H NMR (400 MHz, DMSO-$d_6$) δ ppm 12.73 (br. s., 1 H) 8.28-8.38 (m, 2 H) 8.06 (d, J=8.71 Hz, 1 H) 7.55-7.64 (m, 2 H) 7.34 (dd, J=8.75, 2.20 Hz, 1 H) 7.22-7.30 (m, 2 H) 6.83 (d, J=4.60 Hz, 1 H) 4.36-4.48 (m, 2 H) 4.02-4.11 (m, 2 H). m/z (ESI) 462.9 (M+H)+.

Example 198

4-(3-Cyano-2'-Fluoro-[1,1'-Biphenyl]-4-Yl)-N-(Thiazol-2-Yl)-3,4-Dihydro-2H-Benzo[B][1,4]Oxazine-7-Sulfonamide

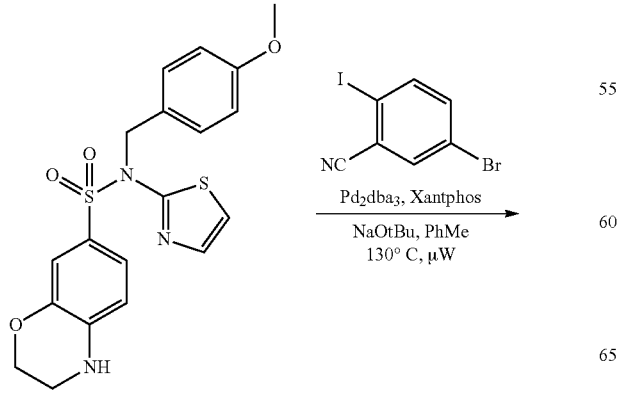

Step 1: 4-(4-Bromo-2-Cyanophenyl)-N-(4-Methoxybenzyl)-N-(Thiazol-2-Yl)-3,4-Dihydro-2H-Benzo[B][1,4]Oxazine-7-Sulfonamide

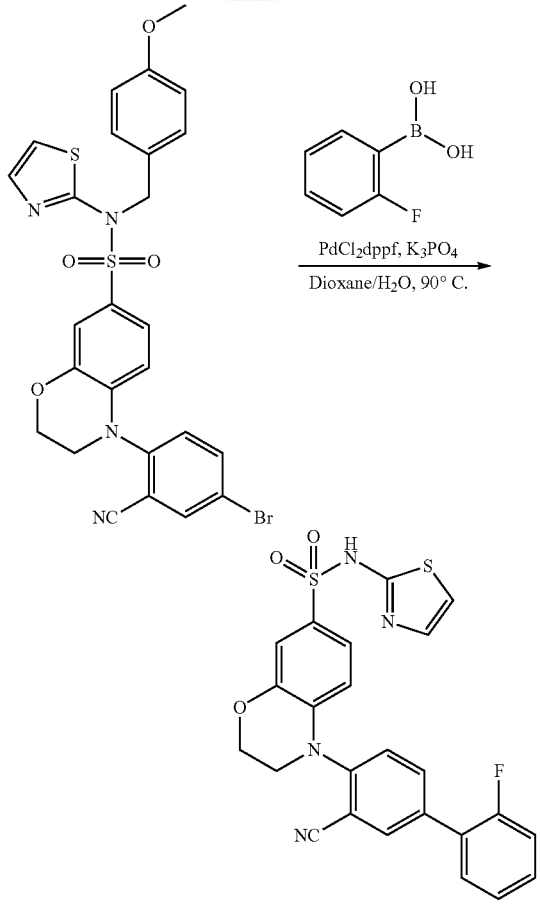

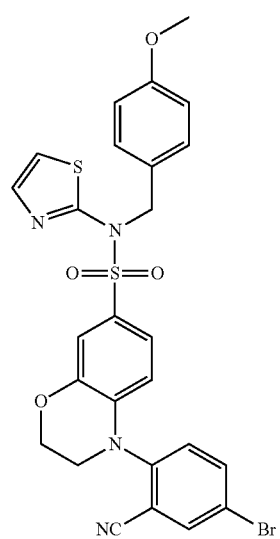 [SMILES: COc1ccc(CN(c2nccs2)S(=O)(=O)c2ccc3c(c2)OCCN3c2ccc(Br)cc2C#N)cc1]

A microwave vial was charged with N-(4-methoxybenzyl)-N-(thiazol-2-yl)-3,4-dihydro-2H-benzo[b][1,4]oxazine-7-sulfonamide (Intermediate M, 0.320 g, 0.766 mmol), Xantphos (0.089 g, 0.153 mmol), 5-bromo-2-iodobenzonitrile (Combi-Blocks) (0.354 g, 1.150 mmol), Pd$_2$(dba)$_3$ (0.070 g, 0.077 mmol) and sodium tert-butoxide (0.147 g, 1.533 mmol). The mixture was diluted with toluene (7.66 ml), and purged with nitrogen, and stirred at 130° C. in the microwave for 30 minutes, until clean conversion to the desired product. The reaction was filtered over a plug of Celite, washing well with DCM. The filtrate was concentrated in vacuo and the crude material was directly adsorbed onto a 12-g RediSep Gold column and purified by silica gel chromatography, eluting with a gradient of 0% to 100% ethyl acetate in heptane, to provide 4-(4-bromo-2-cyanophenyl)-N-(4-methoxybenzyl)-N-(thiazol-2-yl)-3,4-dihydro-2H-benzo[b][1,4]oxazine-7-sulfonamide (0.248 g, 0.415 mmol, 54.2% yield) as yellow solid.

Step 2, Example 198: 4-(3-Cyano-2'-Fluoro-[1,1'-Biphenyl]-4-Yl)-N-(Thiazol-2-Yl)-3,4-Dihydro-2H-Benzo[B][1,4]Oxazine-7-Sulfonamide

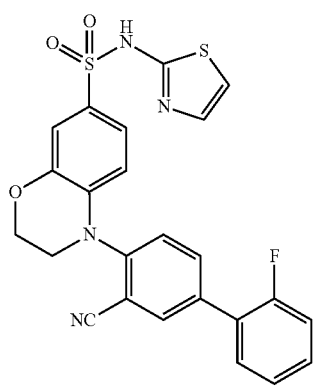 [SMILES: N#Cc1cc(-c2ccccc2F)ccc1N1CCOc2cc(S(=O)(=O)Nc3nccs3)ccc21]

A solution of PdCl$_2$(dppf)-CH$_2$Cl$_2$ adduct (0.017 g, 0.021 mmol), 4-(4-bromo-2-cyanophenyl)-N-(4-methoxybenzyl)-N-(thiazol-2-yl)-3,4-dihydro-2H-benzo[b][1,4]oxazine-7-sulfonamide (0.124 g, 0.208 mmol), (2-fluorophenyl)boronic acid (0.032 g, 0.228 mmol, Aldrich) and potassium phosphate (0.220 g, 1.038 mmol) in dioxane (0.553 ml)/water (0.277 ml) was heated to 90° C. for 1 h until completion. The reaction was cooled to RT and then diluted with DCM and washed with water. The organics were dried via phase separator (Radleys Discovery Technologies) and concentrated in vacuo. The material was taken up in a mixture of DCM and methanol, and further purified using a 2-g SCX column (product eluted with methanol wash). After concentration, DCM (1.0 mL) and TFA (0.5 mL) were added and stirred at RT for 3 h until complete deprotection. The reaction was concentrated in vacuo and purified via silica-gel chromatography, eluting with 0-100% ethyl acetate in heptanes to yield, after concentration, 4-(3-cyano-2'-fluoro-[1,1'-biphenyl]-4-yl)-N-(thiazol-2-yl)-3,4-dihydro-2H-benzo[b][1,4]oxazine-7-sulfonamide (0.082 g, 0.166 mmol, 80% yield). $^1$H NMR (400 MHz, DMSO-d$_6$) δ ppm 3.79-3.86 (m, 2 H) 4.32-4.40 (m, 2 H) 6.64 (d, J=8.51 Hz, 1 H) 6.80 (d, J=4.50 Hz, 1 H) 7.17-7.21 (m, 1 H) 7.21-7.24 (m, 2 H) 7.31-7.40 (m, 2 H) 7.45-7.53 (m, 1 H) 7.60-7.68 (m, 2 H) 7.95 (dt, J=8.56, 1.83 Hz, 1 H) 8.11 (s, 1 H) 12.62 (br. S., 1 H). m/z (ESI) 493.0 (M+H)$^+$.

Example 199

4-(3-Cyano-4'-Fluoro-[1,1'-Biphenyl]-4-Yl)-N-(Thiazol-2-Yl)-3,4-Dihydro-2H-Benzo[B][1,4]Oxazine-7-Sulfonamide

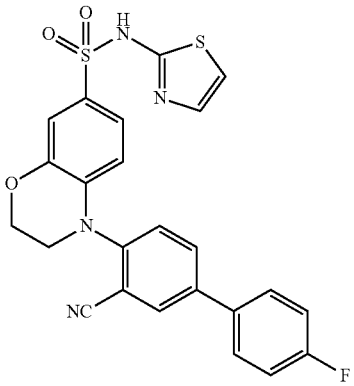 [SMILES: N#Cc1cc(-c2ccc(F)cc2)ccc1N1CCOc2cc(S(=O)(=O)Nc3nccs3)ccc21]

EXAMPLE 199 was synthesized in the same manner as EXAMPLE 198, using (4-fluorophenyl)boronic acid (Aldrich) in Step 2 instead of (2-fluorophenyl)boronic acid. $^1$H NMR (400 MHz, DMSO-d$_6$) δ ppm 3.76-3.84 (m, 2 H) 4.32-4.39 (m, 2 H) 6.58 (d, J=8.41 Hz, 1 H) 6.80 (d, J=4.30 Hz, 1 H) 7.17 (dd, J=8.51, 2.05 Hz, 1 H) 7.21 (d, J=2.05 Hz, 1 H) 7.23 (d, J=4.79 Hz, 1 H) 7.30-7.38 (m, 2 H) 7.63 (d, J=8.61 Hz, 1 H) 7.79-7.86 (m, 2 H) 8.07 (dd, J=8.46, 2.40 Hz, 1 H) 8.25 (d, J=2.25 Hz, 1 H) 12.60 (br. S., 1 H). m/z (ESI) 492.9 (M+H)$^+$.

Example 200

4-(3-Cyano-3'-Fluoro-[1,1'-Biphenyl]-4-Yl)-N-(Thiazol-2-Yl)-3,4-Dihydro-2H-Benzo[B][1,4]Oxazine-7-Sulfonamide

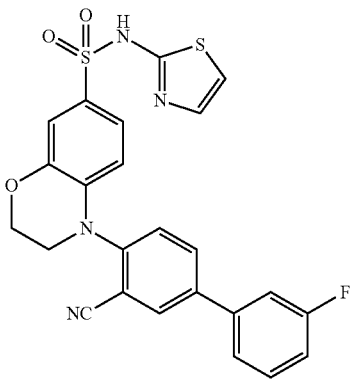 [SMILES: N#Cc1cc(-c2cccc(F)c2)ccc1N1CCOc2cc(S(=O)(=O)Nc3nccs3)ccc21]

EXAMPLE 200 was synthesized in the same manner as EXAMPLE 198, using (3-fluorophenyl)boronic acid (Aldrich) instead of (2-fluorophenyl)boronic acid in Step 2. $^1$H NMR (400 MHz, DMSO-d$_6$) δ ppm 3.78-3.87 (m, 2 H) 4.33-4.41 (m, 2 H) 6.61 (d, J=8.51 Hz, 1 H) 6.80 (d, J=4.60 Hz, 1 H) 7.15-7.31 (m, 4 H) 7.55 (td, J=7.97, 6.16 Hz, 1 H) 7.62-7.71 (m, 3 H) 8.13 (dd, J=8.56, 2.30 Hz, 1H) 8.32 (d, J=2.35 Hz, 1 H) 12.61 (br. s., 1 H). m/z (ESI) 493.0 (M+H)$^+$.

Example 201

4-(3'-Fluoro-3-Methoxy-[1,1'-Biphenyl]-4-Yl)-N-(Thiazol-2-Yl)-3,4-Dihydro-2H-Benzo[B][1,4]Oxazine-7-Sulfonamide

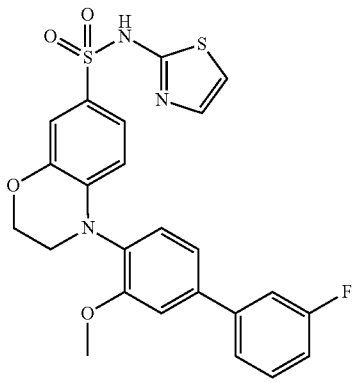 [SMILES: COc1cc(-c2cccc(F)c2)ccc1N1CCOc2cc(S(=O)(=O)Nc3nccs3)ccc21]

Step 1: 4-Bromo-3'-Fluoro-3-Methoxy-1,1'-Biphenyl

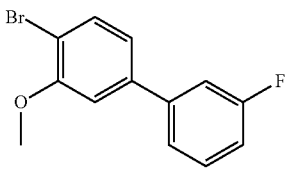 [SMILES: COc1cc(-c2cccc(F)c2)ccc1Br]

A solution of PdCl$_2$(dppf)-CH$_2$Cl$_2$ adduct (0.065 g, 0.080 mmol), 1-bromo-4-iodo-2-methoxybenzene (CombiBlocks, 0.250 g, 0.799 mmol), 3-fluorophenylboronic acid (0.123 g, 0.879 mmol) and potassium phosphate (0.848 g, 3.99 mmol) in dioxane (2.130 ml)/water (1.065 ml) was heated to 90° C. overnight. The reaction was diluted with DCM and separated from the aqueous via phase separator (Radleys Discovery Technologies). After concentration in vacuo, the material was purified via MPLC (12-g Redi Sep Gold), eluting with 0-100% ethyl acetate in heptanes to yield, after concentration, 4-bromo-3'-fluoro-3-methoxy-1,1'-biphenyl as an orange oil, which was used without further purification.

Step 2, Example 201: 4-(3'-Fluoro-3-Methoxy-[1,1'-Biphenyl]-4-Yl)-N-(Thiazol-2-Yl)-3,4-Dihydro-2H-Benzo[B][1,4]Oxazine-7-Sulfonamide

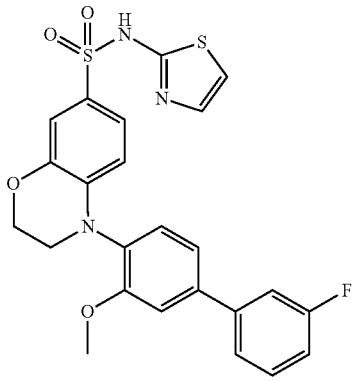 [SMILES: COc1cc(-c2cccc(F)c2)ccc1N1CCOc2cc(S(=O)(=O)Nc3nccs3)ccc21]

EXAMPLE 201 was synthesized in the same manner as EXAMPLE 167, using 4-bromo-3'-fluoro-3-methoxy-1,1'-biphenyl (Step 1) instead of 4-bromo-2-(trifluoromethoxy) benzonitrile. $^1$H NMR (400 MHz, DMSO-d$_6$) δ ppm 3.63-3.69 (m, 2 H) 3.87 (s, 3 H) 4.31 (t, J=4.30 Hz, 2 H) 6.24-6.31 (m, 1 H) 6.77 (d, J=4.40 Hz, 1 H) 7.07-7.13 (m, 2 H) 7.18-7.26 (m, 2 H) 7.36-7.39 (m, 2 H) 7.42-7.47 (m, 1 H) 7.52 (td, J=8.02, 6.26 Hz, 1 H) 7.58-7.64 (m, 2 H) 12.53 (br. s., 1 H). m/z (ESI) 498.0 (M+H)$^+$.

Example 202

4-(2-Cyano-4-Isopropylphenyl)-N-(Thiazol-2-Yl)-3,4-Dihydro-2H-Benzo[B][1,4]Oxazine-7-Sulfonamide

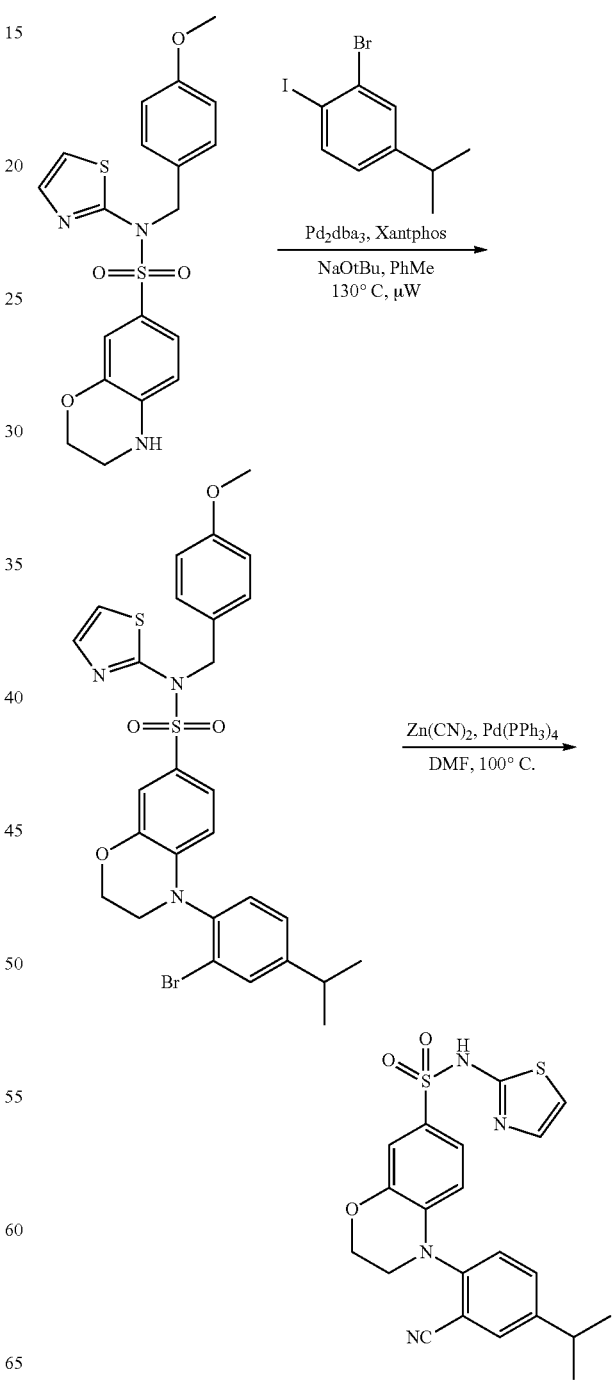

Step 1: 4-(2-Bromo-4-Isopropylphenyl)-N-(4-Methoxybenzyl)-N-(Thiazol-2-Yl)-3,4-Dihydro-2H-Benzo[B][1,4]Oxazine-7-Sulfonamide

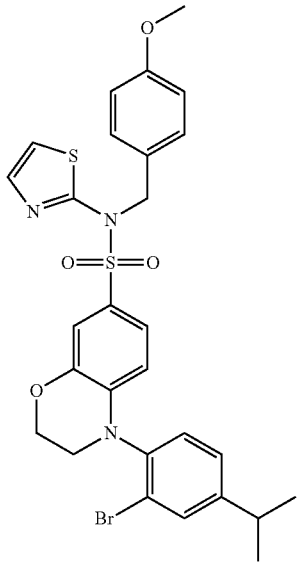 [SMILES: COc1ccc(CN(c2nccs2)S(=O)(=O)c2ccc3c(c2)OCCN3c2ccc(C(C)C)cc2Br)cc1]

A microwave vial was charged with 2-bromo-1-iodo-4-isopropylbenzene (Oakwood, 0.117 g, 0.359 mmol), N-(4-methoxybenzyl)-N-(thiazol-2-yl)-3,4-dihydro-2H-benzo[b][1,4]oxazine-7-sulfonamide (INTERMEDIATE M, 0.150 g, 0.359 mmol), Xantphos (0.042 g, 0.072 mmol), Pd$_2$(dba)$_3$ (0.033 g, 0.036 mmol) and sodium tert-butoxide (0.069 g, 0.719 mmol). The mixture was diluted with toluene (3.59 ml), and purged with nitrogen, and stirred at 130° C. in the microwave for 30 minutes, until clean conversion to the desired product. After completion, the reaction was filtered over a plug of Celite, washing well with DCM. The filtrate was concentrated in vacuo. The crude material was purified using a 5-g SCX column (product eluted with methanol wash to yield 4-(2-bromo-4-isopropylphenyl)-N-(4-methoxybenzyl)-N-(thiazol-2-yl)-3,4-dihydro-2H-benzo[b][1,4]oxazine-7-sulfonamide (0.175 g, 0.285 mmol, 79% yield) as an orange oil. m/z (ESI) 614.0 (M+H)$^+$.

Step 2, Example 202: 4-(2-Cyano-4-Isopropylphenyl)-N-(Thiazol-2-Yl)-3,4-Dihydro-2H-Benzo[B][1,4]Oxazine-7-Sulfonamide

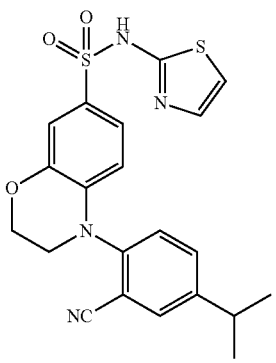 [SMILES: CC(C)c1ccc(N2CCOc3cc(S(=O)(=O)Nc4nccs4)ccc32)c(C#N)c1]

A reaction vial was charged with 4-(2-bromo-4-isopropylphenyl)-N-(4-methoxybenzyl)-N-(thiazol-2-yl)-3,4-dihydro-2H-benzo[b][1,4]oxazine-7-sulfonamide (0.175 g, 0.285 mmol), Pd(PPh$_3$)$_4$ (0.049 g, 0.043 mmol), and zinc cyanide (0.050 g, 0.427 mmol), and DMF (1.139 ml) was added. The reaction was sealed and heated to 100° C. overnight until complete conversion to the desired product. The reaction was diluted with ethyl acetate and filtered over a membrane, washing with ethyl acetate. The filtrate was then washed with small amounts of water (×4) to remove residual DMF. The organics were dried over sodium sulfate, filtered and concentrated in vacuo to yield a crude yellow oil. The oil was dissolved in methanol and was loaded onto a 2-g SCX column (product eluted with methanol wash). After concentration, the crude product was diluted with DCM (2.0 mL) and TFA (1.0 mL) was added and the reaction was stirred at RT for 30 minutes until complete deprotection. The reaction was then concentrated in vacuo, and was purified by silica gel chromatography eluting with 0-100% ethyl acetate in heptanes to yield 4-(2-cyano-4-isopropylphenyl)-N-(thiazol-2-yl)-3,4-dihydro-2H-benzo[b][1,4]oxazine-7-sulfonamide (0.055 g, 0.125 mmol, 43.8% yield). $^1$H NMR (400 MHz, DMSO-d$_6$) δ ppm 1.23 (d, J=6.94 Hz, 6 H) 2.93-3.05 (m, 1 H) 3.72-3.77 (m, 2 H) 4.30-4.36 (m, 2 H) 6.42 (d, J=8.41 Hz, 1 H) 6.79 (d, J=4.60 Hz, 1 H) 7.13-7.17 (m, 1 H) 7.18 (d, J=2.15 Hz, 1 H) 7.22 (d, J=4.60 Hz, 1 H) 7.49 (d, J=8.41 Hz, 1 H) 7.68 (dd, J=8.46, 2.20 Hz, 1 H) 7.83 (d, J=2.15 Hz, 1 H) 12.58 (br. s., 1 H). m/z (ESI) 441.3 (M+H)$^+$.

Example 203

4-(2-Cyano-4-Ethylphenyl)-N-(Thiazol-2-Yl)-3,4-Dihydro-2H-Benzo[B][1,4]Oxazine-7-Sulfonamide

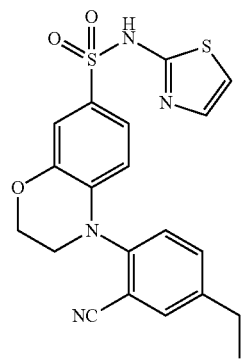 [SMILES: CCc1ccc(N2CCOc3cc(S(=O)(=O)Nc4nccs4)ccc32)c(C#N)c1]

EXAMPLE 203 was synthesized in the same manner as EXAMPLE 202, using 2-bromo-4-ethyl-1-iodobenzene (Oakwood) instead of 2-bromo-1-iodo-4-isopropylbenzene. $^1$H NMR (400 MHz, DMSO-d$_6$) δ ppm 1.21 (t, J=7.58 Hz, 3H) 2.68 (q, J=7.56 Hz, 2 H) 3.71-3.77 (m, 2 H) 4.30-4.37 (m, 2 H) 6.40 (d, J=8.51 Hz, 1 H) 6.79 (d, J=4.50 Hz, 1 H) 7.14 (dd, J=8.46, 2.10 Hz, 1 H) 7.18 (d, J=2.05 Hz, 1 H) 7.22 (d, J=4.69 Hz, 1 H) 7.48 (d, J=8.31 Hz, 1 H) 7.64 (dd, J=8.36, 2.10 Hz, 1 H) 7.80 (d, J=2.15 Hz, 1 H) 12.58 (br. s., 1 H). m/z (ESI) 427.0 (M+H)$^+$.

Example 204

4-(2-(1,2-Dihydroxyethyl)-4-(Trifluoromethyl)Phenyl)-N-(Thiazol-2-Yl)-3,4-Dihydro-2H-Benzo[B][1,4]Oxazine-7-Sulfonamide

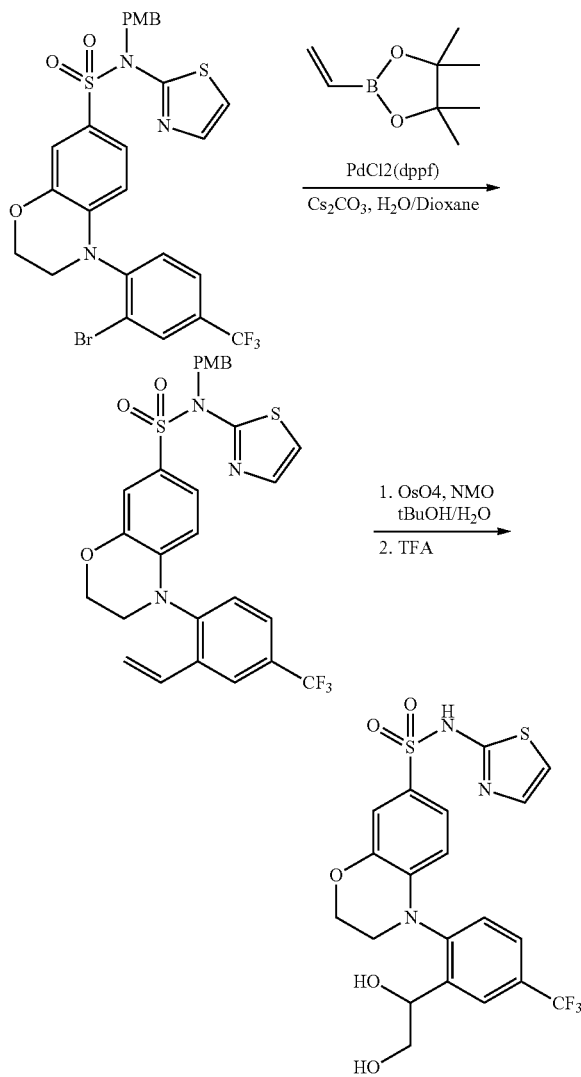

Step 1: N-(4-Methoxybenzyl)-N-(Thiazol-2-Yl)-4-(4-(Trifluoromethyl)-2-Vinylphenyl)-3,4-Dihydro-2H-Benzo[B][1,4]Oxazine-7-Sulfonamide

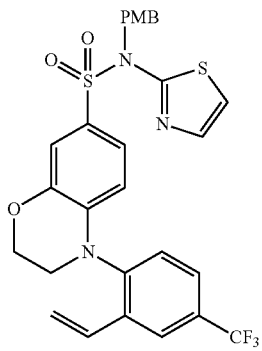

In a reaction vial flushed with nitrogen, 4,4,5,5-tetramethyl-2-vinyl-1,3,2-dioxaborolane (1.080 ml, 6.38 mmol), 4-(2-bromo-4-(trifluoromethyl)phenyl)-N-(4-methoxybenzyl)-N-(thiazol-2-yl)-3,4-dihydro-2H-benzo[b][1,4]oxazine-7-sulfonamide (EXAMPLE 53, Step 1; 1.022 g, 1.596 mmol), PdCl$_2$(dppf)-CH$_2$Cl$_2$ adduct (0.065 g, 0.080 mmol), and cesium carbonate (1.560 g, 4.79 mmol) were combined in dioxane (7.18 ml) and water (0.798 ml). The vial was sealed and heated at 100° C. overnight. The reaction was diluted with ethyl acetate and extracted with water. The aqueous layer was then back extracted with ethyl acetate (×3). The organics were combined and dried over sodium sulfate, filtered and concentrated to yield crude material, which was then purified via silica gel chromatography (eluting with 0-100% ethyl acetate in heptanes) to yield N-(4-methoxybenzyl)-N-(thiazol-2-yl)-4-(4-(trifluoromethyl)-2-vinylphenyl)-3,4-dihydro-2H-benzo[b][1,4]oxazine-7-sulfonamide (0.787 g, 1.339 mmol, 84% yield) as a light yellow solid. m/z (ESI) 588.3 (M+H)$^+$.

Step 2, Example 204: 4-(2-(1,2-Dihydroxyethyl)-4-(Trifluoromethyl)Phenyl)-N-(Thiazol-2-Yl)-3,4-Dihydro-2H-Benzo[B][1,4]Oxazine-7-Sulfonamide

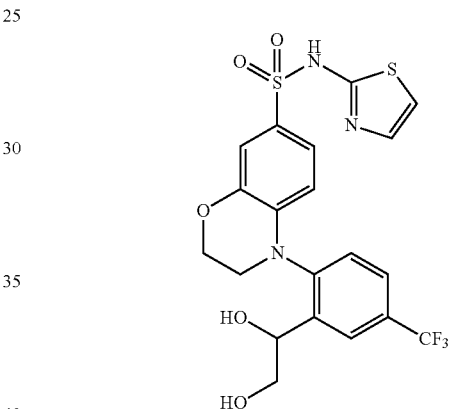

N-(4-methoxybenzyl)-N-(thiazol-2-yl)-4-(4-(trifluoromethyl)-2-vinylphenyl)-3,4-dihydro-2H-benzo[b][1,4]oxazine-7-sulfonamide (0.787 g, 1.339 mmol) and 4-methylmorpholine n-oxide (0.314 g, 2.68 mmol) was dissolved in a mixture of THF (4.46 ml) and water (2.232 ml), and to the reaction was added, dropwise, osmium tetroxide, 4% solution in water (0.818 ml, 0.134 mmol). The reaction was stirred at RT for 3 h. The reaction was quenched with 5 mL of a sat. aq. sodium thiosulfate solution, and was then extracted with DCM (3×10). The organics were dried via phase separator (Radleys Discovery Technologies) and concentrated in vacuo to yield crude 4-(2-(1,2-dihydroxyethyl)-4-(trifluoromethyl)phenyl)-N-(4-methoxybenzyl)-N-(thiazol-2-yl)-3,4-dihydro-2H-benzo[b][1,4]oxazine-7-sulfonamide as a light yellow solid. The material was purified via silica-gel chromatography, eluting with 0-100% ethyl acetate in heptane, to yield 4-(2-(1,2-dihydroxyethyl)-4-(trifluoromethyl)phenyl)-N-(4-methoxybenzyl)-N-(thiazol-2-yl)-3,4-dihydro-2H-benzo[b][1,4]oxazine-7-sulfonamide as a light yellow oil. The PMB-protected intermediate (200 mg) was diluted with DCM (1.7 mL) and TFA (1.0 mL) was added. The reaction was stirred at RT for 1 h until complete deprotection of the sulfonamide. The reaction was concentrated in vacuo, and purified via silica gel chromatography (12-g RediSep Gold, eluting with 0-100% ethyl acetate in heptane with a 2% methanol modifier) to yield 4-(2-(1,2-dihydroxyethyl)-4-(trifluoromethyl)phenyl)-N-(thiazol-2-yl)-3,4-dihydro-2H-benzo[b][1,4]oxazine-7-sulfonamide (0.033 g, 0.066 mmol, 4.91% yield) as a white solid. $^1$H NMR (400 MHz, DMSO-$d_6$) δ ppm 12.53 (br. s., 1 H) 7.93 (dd, J=7.58, 1.61 Hz, 1 H) 7.69-7.77 (m, 1 H) 7.46-7.54 (m, 1 H) 7.21 (dd, J=4.55, 1.22 Hz, 1 H) 7.13-7.16 (m, 1 H) 7.06-7.11 (m, 1 H) 6.75-6.80 (m, 1 H) 6.09-6.21 (m, 1 H) 5.41-5.46 (m, 1 H) 4.74-4.81 (m, 1 H) 4.66-4.74 (m, 1 H) 4.32-4.43 (m, 2 H) 3.35-3.68 (m, 4 H). m/z (ESI) 502.0 (M+H)$^+$.

Example 205

4-(2-Methoxyphenyl)-N-(Thiazol-2-Yl)-3,4-Dihydro-2H-Benzo[B][1,4]Oxazine-7-Sulfonamide

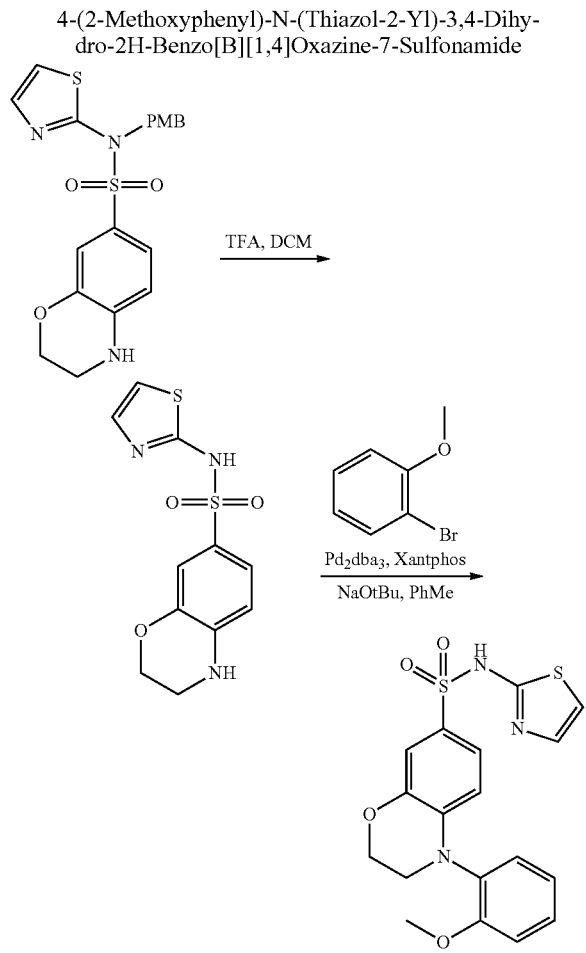

Step 1: N-(Thiazol-2-Yl)-3,4-Dihydro-2H-Benzo[B][1,4]Oxazine-7-Sulfonamide

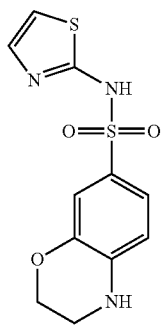 [SMILES: O=S(=O)(Nc1nccs1)c1ccc2c(c1)OCCN2]

N-(4-methoxybenzyl)-N-(thiazol-2-yl)-3,4-dihydro-2H-benzo[b][1,4]oxazine-7-sulfonamide (Intermediate M; 0.200 g, 0.479 mmol) was dissolved in DCM (1.597 ml) and TFA (0.923 ml, 11.98 mmol) was added. The reaction was stirred at RT for 20 minutes at which time it was concentrated in vacuo. The crude reaction was purified via 2-g SCX column (product eluted with ammonia/methanol wash) to yield N-(thiazol-2-yl)-3,4-dihydro-2H-benzo[b][1,4]oxazine-7-sulfonamide (0.142 g, 0.478 mmol, 100% yield). m/z (ESI) 298.2 (M+H)$^+$.

Step 2, Example 205: 4-(2-Methoxyphenyl)-N-(Thiazol-2-Yl)-3,4-Dihydro-2H-Benzo[B][1,4]Oxazine-7-Sulfonamide

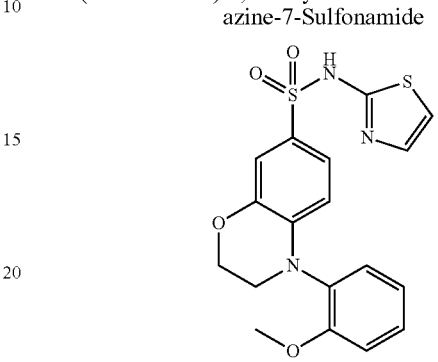

A microwave vial was charged with 1-bromo-2-methoxybenzene (0.056 ml, 0.454 mmol), N-(thiazol-2-yl)-3,4-dihydro-2H-benzo[b][1,4]oxazine-7-sulfonamide (0.090 g, 0.303 mmol), Xantphos (0.035 g, 0.061 mmol), Pd$_2$(dba)$_3$ (0.028 g, 0.030 mmol) and sodium tert-butoxide (0.087 g, 0.908 mmol). The mixture was diluted with toluene (3.03 ml), and purged with nitrogen, and stirred at 130° C. in the microwave for 15 minutes, until clean conversion to the desired product. The reaction was filtered over a plug of Celite, washing well with DCM. The filtrate was concentrated in vacuo and further purified using a 2-g SCX column (product eluted with methanol wash). The crude material was concentrated and absorbed directly onto a 12-g RediSep Gold column and purified by silica-gel chromatography, eluting with a gradient of 0% to 100% ethyl acetate in heptanes to provide 4-(2-methoxyphenyl)-N-(thiazol-2-yl)-3,4-dihydro-2H-benzo[b][1,4]oxazine-7-sulfonamide as a yellow solid. $^1$H NMR (400 MHz, DMSO-$d_6$) δ ppm 3.59-3.65 (m, 2 H) 3.74 (s, 3 H) 4.29 (t, J=4.35 Hz, 2 H) 6.16 (d, J=8.41 Hz, 1 H) 6.76 (d, J=4.60 Hz, 1 H) 7.00-7.04 (m, 1 H) 7.04-7.11 (m, 2H) 7.17 (dd, J=8.31, 1.27 Hz, 1 H) 7.21 (d, J=4.60 Hz, 1 H) 7.28 (dd, J=7.78, 1.61 Hz, 1 H) 7.31-7.37 (m, 1 H) 12.52 (br. s., 1 H). m/z (ESI) 404.0 (M+H)$^+$.

Example 206

4-(2-(Hydroxymethyl)-4-(Trifluoromethyl)Phenyl)-N-(Thiazol-2-Yl)-3,4-Dihydro-2H-Benzo[B][1,4]Oxazine-7-Sulfonamide

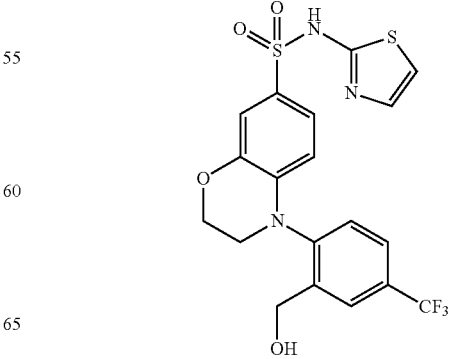

To a solution of 4-(2-(1,2-dihydroxyethyl)-4-(trifluoromethyl)phenyl)-N-(4-methoxybenzyl)-N-(thiazol-2-yl)-3,4-dihydro-2H-benzo[b][1,4]oxazine-7-sulfonamide (from EXAMPLE 204, intermediate in Step 2; 0.100 g, 0.161 mmol) in THF (0.619 ml)/water (0.619 ml) was added sodium periodate (0.052 g, 0.241 mmol). The reaction mixture was stirred at RT for 2 h. Upon completion, the reaction was filtered and washed well with THF. The filtrate was concentrated in vacuo and 4-(2-formyl-4-(trifluoromethyl)phenyl)-N-(4-methoxybenzyl)-N-(thiazol-2-yl)-3,4-dihydro-2H-benzo[b][1,4]oxazine-7-sulfonamide was carried on without purification. To a solution of 4-(2-formyl-4-(trifluoromethyl)phenyl)-N-(4-methoxybenzyl)-N-(thiazol-2-yl)-3,4-dihydro-2H-benzo[b][1,4]oxazine-7-sulfonamide (0.095 g, 0.161 mmol, 100% yield) in methanol (1.609 ml, 0.161 mmol) was added sodium borohydride (0.012 g, 0.322 mmol) at 0° C. (turned from yellow to clear solution upon addition), and the reaction was stirred in the ice-bath for 30 minutes until completion. The reaction was quenched with sat ammonium chloride solution (aq) and washed with DCM (×2). After drying via phase separator (Radley's Discovery Technology), the organics were concentrated in vacuo to yield an orange oil. The oil was taken up in DCM, and TFA was added (color change from orange solution to light pink). The reaction was stirred for 1 h until complete deprotection. The material was concentrated in vacuo and purified via silica gel chromatography, eluting with 0-100% ethyl acetate in heptane to yield 4-(2-(hydroxymethyl)-4-(trifluoromethyl)phenyl)-N-(thiazol-2-yl)-3,4-dihydro-2H-benzo[b][1,4]oxazine-7-sulfonamide (0.017 g, 0.036 mmol, 22.41% yield) as a white solid. $^1$H NMR (400 MHz, DMSO-$d_6$) δ ppm 3.58 (br. s., 1 H) 3.66-3.79 (m, 1 H) 4.30-4.37 (m, 2 H) 4.38-4.58 (m, 2 H) 5.42 (t, J=5.48 Hz, 1H) 6.12 (d, J=8.51 Hz, 1 H) 6.78 (d, J=4.50 Hz, 1 H) 7.10 (dd, J=8.46, 2.10 Hz, 1H) 7.15 (d, J=2.05 Hz, 1 H) 7.21 (d, J=4.60 Hz, 1 H) 7.53 (d, J=8.31 Hz, 1 H) 7.73 (d, J=8.22 Hz, 1 H) 7.92 (s, 1 H) 12.55 (br. s., 1 H). m/z (ESI) 472.0 (M+H)$^+$.

Example 207

4-(2-(2,3-Dihydroxypropyl)-4-(Trifluoromethyl)Phenyl)-N-(Thiazol-2-Yl)-3,4-Dihydro-2H-Benzo[B][1,4]Oxazine-7-Sulfonamide

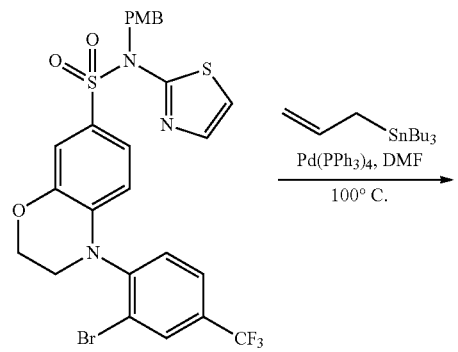

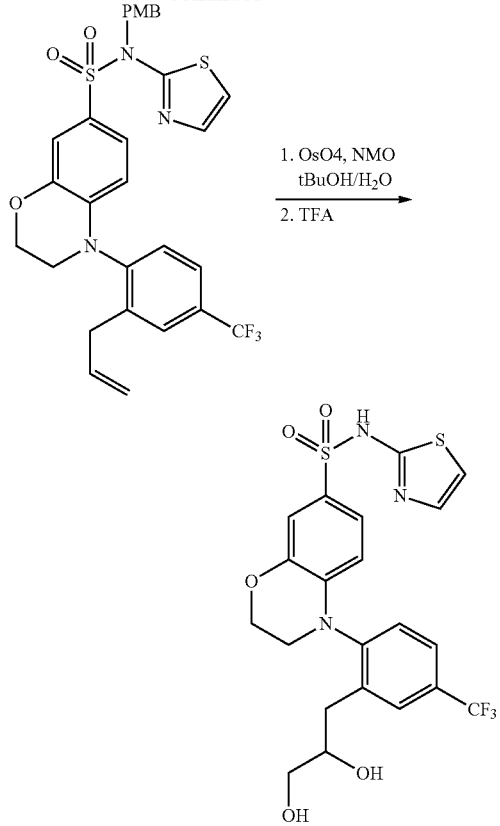

Step 1: 4-(2-Allyl-4-(Trifluoromethyl)Phenyl)-N-(4-Methoxybenzyl)-N-(Thiazol-2-Yl)-3,4-Dihydro-2H-Benzo[B][1,4]Oxazine-7-Sulfonamide

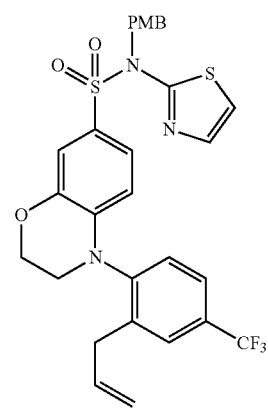

A reaction vial was charged with 4-(2-bromo-4-(trifluoromethyl)phenyl)-N-(4-methoxybenzyl)-N-(thiazol-2-yl)-3,4-dihydro-2H-benzo[b][1,4]oxazine-7-sulfonamide (EXAMPLE 53, Step 1; 0.347 g, 0.542 mmol) and Pd(PPh$_3$)$_4$ (0.031 g, 0.027 mmol), and then diluted with DMF (1.084 ml). After purging with nitrogen, allyltributyltin (0.202 ml, 0.650 mmol) was added and the reaction was heated to 100° C. for 30 minutes until completion. The reaction was concentrated in vacuo and purified via silica-gel chromatography (12-g RediSep Gold column), eluting with 0-30% ethyl acetate in heptanes) to yield 4-(2-allyl-4-(trifluoromethyl)phenyl)-N-(4-methoxybenzyl)-N-(thiazol-2-yl)-3,4-dihydro-2H-benzo[b][1,4]oxazine-7-sulfonamide (0.312 g, 0.519 mmol, 96% yield) as a yellow oil. m/z (ESI) 602.1 (M+H)$^+$.

Step 2, Example 207: 4-(2-(2,3-Dihydroxypropyl)-4-(Trifluoromethyl)Phenyl)-N-(Thiazol-2-Yl)-3,4-Dihydro-2H-Benzo[B][1,4]Oxazine-7-Sulfonamide

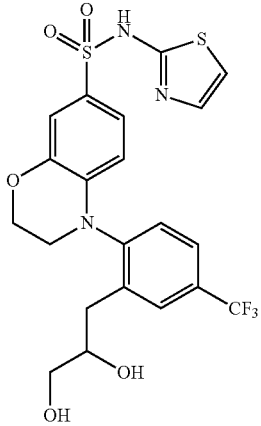 [SMILES: O=S(=O)(Nc1nccs1)c1ccc2c(c1)OCCN2c1ccc(C(F)(F)F)cc1CC(O)CO]

EXAMPLE 207 was synthesized in the same manner as step 2 of EXAMPLE 204, using 4-(2-allyl-4-(trifluoromethyl)phenyl)-N-(4-methoxybenzyl)-N-(thiazol-2-yl)-3,4-dihydro-2H-benzo[b][1,4]oxazine-7-sulfonamide instead of N-(4-methoxybenzyl)-N-(thiazol-2-yl)-4-(4-(trifluoromethyl)-2-vinylphenyl)-3,4-dihydro-2H-benzo[b][1,4]oxazine-7-sulfonamide. $^1$H NMR (400 MHz, DMSO-d$_6$) δ ppm 12.53 (br. s., 1 H) 7.82 (dd, J=9.59, 1.66 Hz, 1 H) 7.62-7.71 (m, 1 H) 7.51 (t, J=8.36 Hz, 1 H) 7.21 (d, J=4.69 Hz, 1 H) 7.13 (d, J=2.05 Hz, 1 H) 7.08 (dd, J=8.56, 2.01 Hz, 1 H) 6.77 (d, J=4.79 Hz, 1 H) 6.02-6.12 (m, 1 H) 4.66 (dd, J=12.03, 5.58 Hz, 1 H) 4.56-4.63 (m, 1 H) 4.32-4.41 (m, 2 H) 3.48-3.83 (m, 3H) 3.19-3.30 (m, 2 H) 2.76-2.92 (m, 1 H) 2.37-2.48 (m, 1 H). m/z (ESI) 516.0 (M+H)$^+$.

Example 208

(S)-4-(2-(2,3-Dihydroxypropyl)-4-(Trifluoromethyl)Phenyl)-N-(Thiazol-2-Yl)-3,4-Dihydro-2H-Benzo[B][1,4]Oxazine-7-Sulfonamide

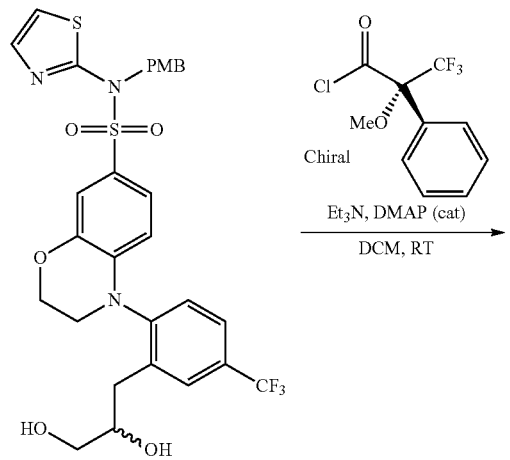

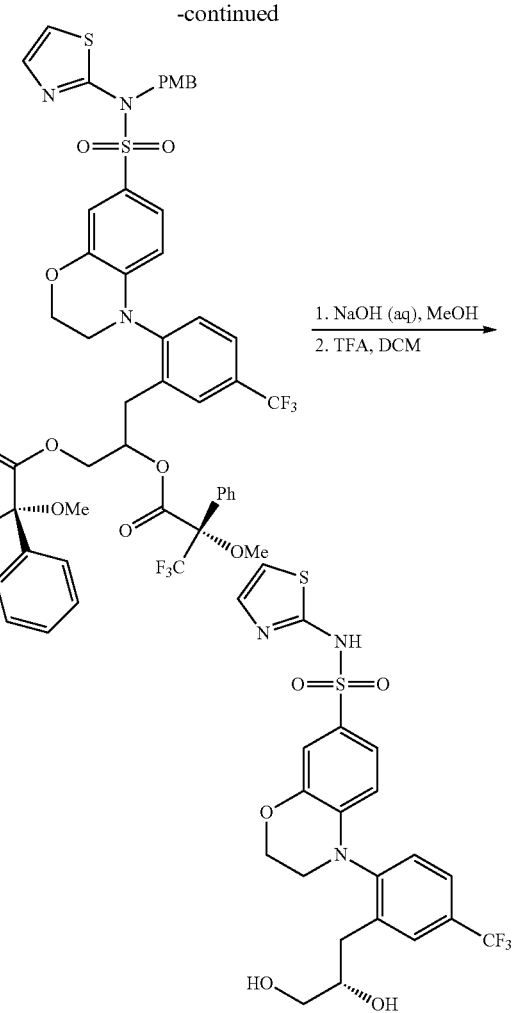

Step 1: (2S,2'S)-3-(2-(7-(N-(4-Methoxybenzyl)-N-(Thiazol-2-Yl)Sulfamoyl)-2H-Benzo[B][1,4]Oxazin-4(3H)-Yl)-5-(Trifluoromethyl)Phenyl)Propane-1,2-Diyl Bis(3,3,3-Trifluoro-2-Methoxy-2-Phenylpropanoate)

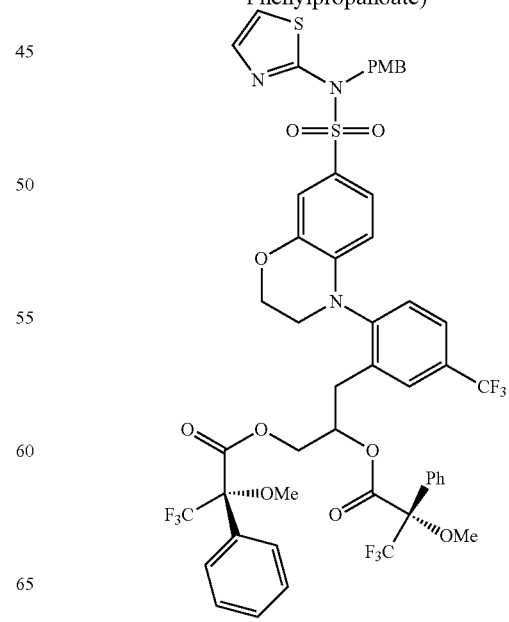

4-(2-(2,3-dihydroxypropyl)-4-(trifluoromethyl)phenyl)-N-(4-methoxybenzyl)-N-(thiazol-2-yl)-3,4-dihydro-2H-benzo[b][1,4]oxazine-7-sulfonamide (from EXAMPLE 207, Step 2, prior to TFA deprotection; 0.200 g, 0.315 mmol) was diluted in DCM (1.573 ml) and (S)-3,3,3-trifluoro-2-methoxy-2-phenylpropanoyl chloride (0.271 ml, 1.573 mmol) was added, along with triethylamine (0.132 ml, 0.944 mmol) and a catalytic amount of DMAP. The reaction was stirred overnight until complete conversion to the bis-ester. The reaction was concentrated in vacuo and purified via MPLC, eluting with 0-100% ethyl acetate in heptane to yield (2S,2'S)-3-(2-(7-(N-(4-methoxybenzyl)-N-(thiazol-2-yl)sulfamoyl)-2H-benzo[b][1,4]oxazin-4(3H)-yl)-5-(trifluoromethyl)phenyl)propane-1,2-diylbis(3,3,3-trifluoro-2-methoxy-2-phenylpropanoate) (0.300 g, 0.281 mmol, 89% yield) as a white solid. Diastereomeric separation was performed using supercritical fluid chromatography (SFC). The column used was AD-H 2×25 cm 5 micron. The mobile phase was run under isocratic conditions; $CO_2$ with (25)% isopropanol co-solvent containing 0.2% diethylamine modifier to obtain both (2S,2'S)—(S)-3-(2-(7-(N-(4-methoxybenzyl)-N-(thiazol-2-yl)sulfamoyl)-2H-benzo[b][1,4]oxazin-4(3H)-yl)-5-(trifluoromethyl)phenyl)propane-1,2-diylbis(3,3,3-trifluoro-2-methoxy-2-phenylpropanoate) and (2S,2'S)—(R)-3-(2-(7-(N-(4-methoxybenzyl)-N-(thiazol-2-yl)sulfamoyl)-2H-benzo[b][1,4]oxazin-4(3H)-yl)-5-(trifluoromethyl)phenyl)propane-1,2-diylbis(3,3,3-trifluoro-2-methoxy-2-phenylpropanoate) were obtained in diastereoenriched form (de>99).

Step 2, Example 208: (S)-4-(2-(2,3-Dihydroxypropyl)-4-(Trifluoromethyl)Phenyl)-N-(Thiazol-2-Yl)-3,4-Dihydro-2H-Benzo[B][1,4]Oxazine-7-Sulfonamide

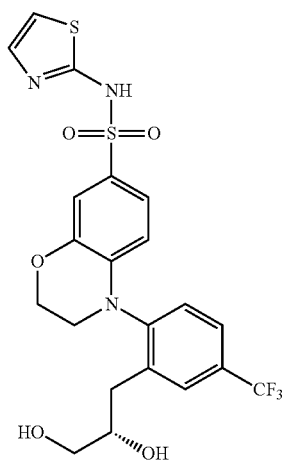 [SMILES: O=S(=O)(Nc1nccs1)c1ccc2c(c1)OCCN2c1ccc(C(F)(F)F)cc1C[C@H](O)CO]

(2S,2'S)—(S)-3-(2-(7-(N-(4-methoxybenzyl)-N-(thiazol-2-yl)sulfamoyl)-2H-benzo[b][1,4]oxazin-4(3H)-yl)-5-(trifluoromethyl)phenyl)propane-1,2-diyl bis(3,3,3-trifluoro-2-methoxy-2-phenylpropanoate) (second eluting peak from diastereomer purification (Step 1); absolute stereochemistry arbitrarily assigned; 0.149 g, 0.140 mmol) was dissolved in MeOH (1.395 ml) and sodium hydroxide (2N aq. solution) (0.070 ml, 0.140 mmol) was added, and the reaction was stirred for 4 h at RT, at which time no conversion was observed. NaOMe in Methanol was added (0.070 mL) and stirred at RT for 20 minutes until complete cleavage of the bis-ester. The reaction was diluted with ammonium chloride solution (aq), and extracted with DCM (×2). The combined organics were dried via phase separator, and concentrated in vacuo. (S)-4-(2-(2,3-dihydroxypropyl)-4-(trifluoromethyl)phenyl)-N-(4-methoxybenzyl)-N-(thiazol-2-yl)-3,4-dihydro-2H-benzo[b][1,4]oxazine-7-sulfonamide was taken on crude. The material was dissolved in DCM (2.0 mL), and TFA (1.0 mL) was added. The reaction was stirred for 2 h at which time it was concentrated in vacuo. The crude material was purified via silica gel chromatography (4-g Silicycle column) eluting with 0-100% ethyl acetate in heptane to (S)-4-(2-(2,3-dihydroxypropyl)-4-(trifluoromethyl)phenyl)-N-(thiazol-2-yl)-3,4-dihydro-2H-benzo[b][1,4]oxazine-7-sulfonamide (0.014 g, 0.027 mmol, 19.47% yield) as a white solid. $^1$H NMR and MS data were identical to that of the racemate (EXAMPLE 207).

Example 209

(R)-4-(2-(2,3-Dihydroxypropyl)-4-(Trifluoromethyl)Phenyl)-N-(Thiazol-2-Yl)-3,4-Dihydro-2H-Benzo[B][1,4]Oxazine-7-Sulfonamide

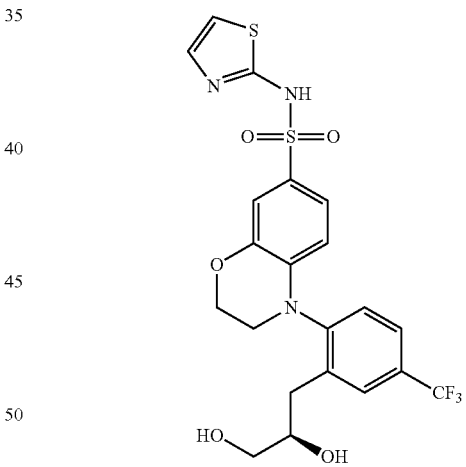

EXAMPLE 209 was synthesized in the same manner as EXAMPLE 208, using (2S,2'S)—(R)-3-(2-(7-(N-(4-methoxybenzyl)-N-(thiazol-2-yl)sulfamoyl)-2H-benzo[b][1,4]oxazin-4(3H)-yl)-5-(trifluoromethyl)phenyl)propane-1,2-diyl bis(3,3,3-trifluoro-2-methoxy-2-phenylpropanoate) in step 2 (first eluting peak from diastereomer purification (Step 1); absolute stereochemistry arbitrarily assigned) to yield (R)-4-(2-(2,3-dihydroxypropyl)-4-(trifluoromethyl)phenyl)-N-(thiazol-2-yl)-3,4-dihydro-2H-benzo[b][1,4]oxazine-7-sulfonamide (0.018 g, 0.035 mmol, 28.5% yield) as a white solid. $^1$H NMR and MS data were identical to that of the racemate (EXAMPLE 207).

Example 210

4-(4-Chloro-2-(2,3-Dihydroxypropyl)Phenyl)-N-(Thiazol-2-Yl)-3,4-Dihydro-2H-Benzo[B][1,4]Oxazine-7-Sulfonamide

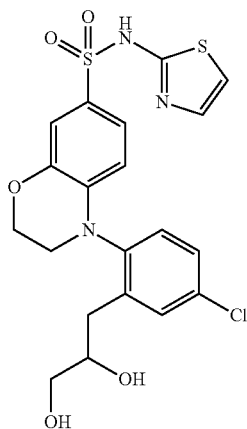 [SMILES: O=S(=O)(Nc1nccs1)c1ccc2c(c1)OCCN2c1ccc(Cl)cc1CC(O)CO]

EXAMPLE 210 was synthesized in the same manner as EXAMPLE 207, using 4-(2-bromo-4-chlorophenyl)-N-(4-methoxybenzyl)-N-(thiazol-2-yl)-3,4-dihydro-2H-benzo[b][1,4]oxazine-7-sulfonamide (EXAMPLE 52, Step 1) in Step 1 instead of 4-(2-bromo-4-(trifluoromethyl)phenyl)-N-(4-methoxybenzyl)-N-(thiazol-2-yl)-3,4-dihydro-2H-benzo[b][1,4]oxazine-7-sulfonamide. $^1$H NMR (400 MHz, DMSO-d$_6$) δ ppm 2.30-2.46 (m, 1 H) 2.64-2.85 (m, 1 H) 3.14-3.24 (m, 1 H) 3.25-3.32 (m, 2 H) 3.43-3.79 (m, 3 H) 4.27-4.41 (m, 2 H) 4.62 (br. s., 1 H) 6.03 (dd, J=8.46, 6.90 Hz, 1 H) 6.77 (d, J=4.21 Hz, 1 H) 7.07 (dd, J=8.51, 2.15 Hz, 1 H) 7.11 (d, J=2.15 Hz, 1 H) 7.21 (d, J=4.50 Hz, 1 H) 7.26-7.34 (m, 1 H) 7.35-7.41 (m, 1 H) 7.51 (dd, J=8.66, 2.49 Hz, 1 H) 12.52 (br. s., 1 H). m/z (ESI) 482.0 (M+H)$^+$.

Example 211

4-(2-(2-Hydroxyethyl)-4-(Trifluoromethyl)Phenyl)-N-(Thiazol-2-Yl)-3,4-Dihydro-2H-Benzo[B][1,4]Oxazine-7-Sulfonamide

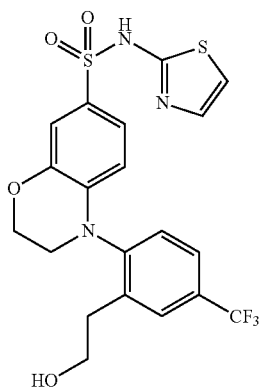 [SMILES: O=S(=O)(Nc1nccs1)c1ccc2c(c1)OCCN2c1ccc(C(F)(F)F)cc1CCO]

To a solution of 4-(2-(2,3-dihydroxypropyl)-4-(trifluoromethyl)phenyl)-N-(4-methoxybenzyl)-N-(thiazol-2-yl)-3, 4-dihydro-2H-benzo[b][1,4]oxazine-7-sulfonamide (from EXAMPLE 207, intermediate from Step 2; 0.100 g, 0.157 mmol) in THF (0.605 ml)/water (0.605 ml) was added sodium periodate (0.050 g, 0.236 mmol). The reaction mixture was stirred at RT for 50 minutes (reaction turned from white slurry to yellow upon addition of sodium periodate). Upon completion, the reaction was filtered and washed well with THF. The filtrate was concentrated in vacuo to yield crude N-(4-methoxybenzyl)-4-(2-(2-oxoethyl)-4-(trifluoromethyl)phenyl)-N-(thiazol-2-yl)-3,4-dihydro-2H-benzo[b][1,4]oxazine-7-sulfonamide, which was dissolved in methanol (1.573 ml, 0.157 mmol) and to the solution was added sodium borohydride (0.012 g, 0.315 mmol) at 0° C. (turned from yellow to clear solution upon addition), and the reaction was stirred in the ice-bath for 20 minutes until completion. The reaction was quenched with sat. ammonium chloride solution (aq) and washed with DCM (×2). After drying via phase separator (Radley's Discovery Technology), the organics were concentrated in vacuo to yield an orange oil. The oil was taken up in DCM, and TFA was added (color change from orange solution to light pink). The reaction was stirred for 6 h, at which time product was observed (along with TFA adduct of the alcohol). Upon concentrating in vacuo, the material fully converted to the TFA adduct. The material was dissolved in methanol, and a few drops of sodium methoxide solution (in methanol) were added. After 1 h, the reaction was neutralized with ammonium chloride solution (aq) and was extracted with DCM (×2) and then the organics were dried via phase separator, and concentrated in vacuo. Upon attempting to dissolve the crude material in DCM for silica gel chromatography, the material would not go into solution. Instead, methanol was added (solubilizing it) and then it was purified via 2-g SCX column (product eluted with methanol wash) to yield product (with some impurities) as a white solid. The material was lastly purified via silica gel chromatography, eluting with 0-100% ethyl acetate in heptane to yield 4-(2-(2-hydroxyethyl)-4-(trifluoromethyl)phenyl)-N-(thiazol-2-yl)-3,4-dihydro-2H-benzo[b][1,4]oxazine-7-sulfonamide as a white solid. $^1$H NMR (400 MHz, DMSO-d$_6$) δ ppm 2.69-2.76 (m, 2 H) 3.53-3.62 (m, 3 H) 3.72-3.80 (m, 1 H) 4.32-4.42 (m, 2 H) 4.68 (t, J=5.28 Hz, 1 H) 6.08 (d, J=8.51 Hz, 1 H) 6.78 (d, J=4.60 Hz, 1 H) 7.09 (dd, J=8.51, 2.15 Hz, 1 H) 7.14 (d, J=2.05 Hz, 1 H) 7.21 (d, J=4.50 Hz, 1 H) 7.52 (d, J=8.51 Hz, 1 H) 7.69 (dd, J=8.46, 2.01 Hz, 1 H) 7.81 (d, J=1.76 Hz, 1 H) 12.54 (br. s., 1 H). m/z (ESI) 486.0 (M+H)$^+$.

Example 212

6-Chloro-4-(2-Cyano-4-(Trifluoromethyl)Phenyl)-N-(Thiazol-2-Yl)-3,4-Dihydro-2H-Benzo[B][1,4]Oxazine-7-Sulfonamide

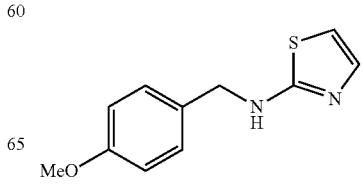

-continued

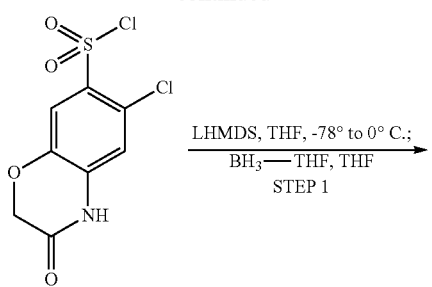

LHMDS, THF, -78° to 0° C.;
BH₃—THF, THF
STEP 1

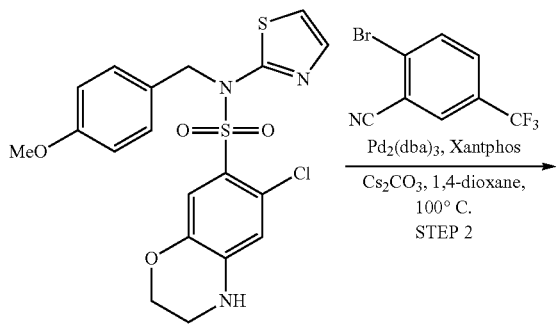

Pd₂(dba)₃, Xantphos
Cs₂CO₃, 1,4-dioxane,
100° C.
STEP 2

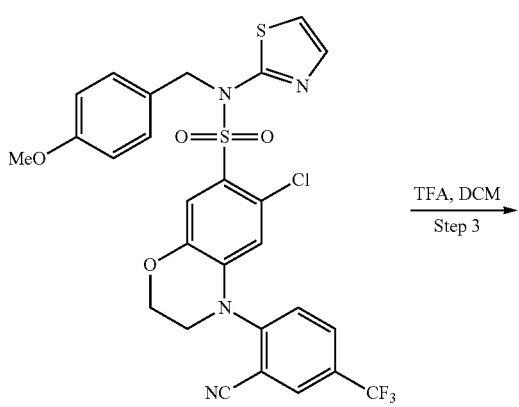

TFA, DCM
Step 3

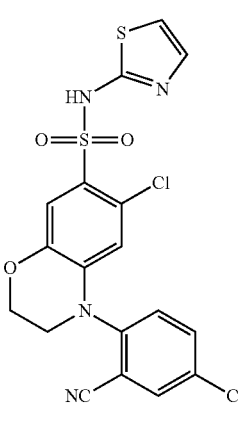

Step 1: 6-Chloro-N-(4-Methoxybenzyl)-N-(Thiazol-2-Yl)-3,4-Dihydro-2H-Benzo[B][1,4]Oxazine-7-Sulfonamide

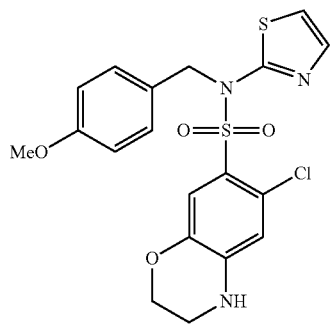 [SMILES: COc1ccc(CN(c2nccs2)S(=O)(=O)c2cc3c(cc2Cl)NCCO3)cc1]

A 250-mL round-bottom flask was charged with 6-chloro-3-oxo-3,4-dihydro-2h-1-4-benzoxazine-7-sulfonyl chloride (Enamine, Kiev, Ukraine, 3.849 g, 13.64 mmol), N-(4-methoxybenzyl)thiazol-2-amine (3.61 g, 16.37 mmol), and THF (68.2 ml) to give a thick suspension. The flask was sonicated for 30 s, then cooled in a dry ice-acetone bath for 10 min. Lithium bis(trimethylsilyl)amide (1M in THF) (30.0 ml, 30.0 mmol) was added dropwise over 5 min. After another 5 min, the flask was transferred to an ice-bath. After 1 h of stirring, an additional portion of base solution (5 mL) was added. After 10 min, the mixture was diluted with saturated aq. ammonium chloride (150 mL) and water (50 mL). The mixture was extracted with EtOAc (3×). The combined organic extracts were dried over sodium sulfate, filtered, and concentrated. The residue was concentrated from DCM (2×). The resulting solid was taken up in THF (100 mL) to give a thin suspension. The flask was cooled in an ice-bath for 5 min, then borane-tetrahydrofuran complex (1M in THF) (1.173 g, 13.64 mmol). Following the addition, the cooling bath was removed. After 2 h, borane-tetrahydrofuran complex (1M in THF) from another bottle (30 mL) was added. Some bubbling was observed, and the mixture lightened. After 16 h of stirring, the mixture was quenched by the careful addition of MeOH (20 mL). After 2 h, the mixture was concentrated, then concentrated from MeOH/DCM. The residual oil was treated with MeOH, and the resulting mixture was stirred for 5 h. The sides of the flask were scraped with a spatula, and the flask was cooled in an ice-bath for 10 min. The mixture was then filtered, and the collected solid was washed with ice-cold MeOH (2×), dried under a stream of N2 (g), then dried under vacuum to give 6-chloro-N-(4-methoxybenzyl)-N-(thiazol-2-yl)-3,4-dihydro-2H-benzo[b][1,4]oxazine-7-sulfonamide (2.3249 g, 5.14 mmol, 37.7% yield) as a white solid: $^1$H NMR (400 MHz, DMSO-$d_6$) δ=7.41 (d, J=3.5 Hz, 1 H), 7.30-7.19 (m, 5 H), 6.85 (d, J=8.7 Hz, 2 H), 6.68 (s, 1 H), 5.15 (s, 2 H), 4.12 (t, J=4.3 Hz, 2 H), 3.71 (s, 3 H), 3.37 (d, J=2.2 Hz, 2 H); m/z (ESI) 452.2 (M+H)$^+$.

Step 2: 6-Chloro-4-(2-Cyano-4-(Trifluoromethyl)Phenyl)-N-(4-Methoxybenzyl)-N-(Thiazol-2-Yl)-3,4-Dihydro-2H-Benzo[B][1,4]Oxazine-7-Sulfonamide

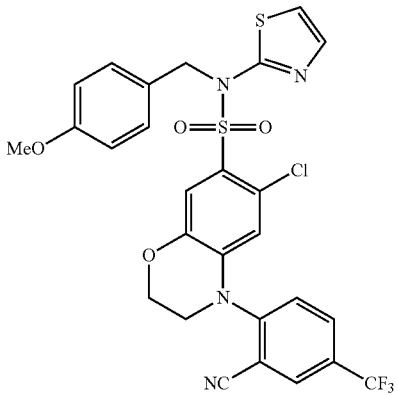 [SMILES: COc1ccc(CN(c2nccs2)S(=O)(=O)c2cc3c(cc2Cl)N(c2ccc(C(F)(F)F)cc2C#N)CCO3)cc1]

A 150-mL pressure vessel was charged with 6-chloro-N-(4-methoxybenzyl)-N-(thiazol-2-yl)-3,4-dihydro-2H-benzo[b][1,4]oxazine-7-sulfonamide (2.32 g, 5.13 mmol), 2-bromo-5-(trifluoromethyl)benzonitrile (2.57 g, 10.27 mmol), Xantphos (0.594 g, 1.027 mmol), Pd$_2$(dba)$_3$ (0.470 g, 0.513 mmol), and cesium carbonate (5.02 g, 15.40 mmol). The vessel was flushed with Ar (g), then 1,4-dioxane (51.3 ml) was added. The vessel was sealed and placed in a 100° C. heating bath for 16 h. The mixture was cooled to room temperature, diluted with water, and extracted with EtOAc (3×). The combined organic extracts were dried over sodium sulfate, filtered, and concentrated. The crude product was purified by chromatography on silica gel (50-g Redi-Sep Gold column, 25-g silica gel loading column, 25-75% EtOAc/Heptane) to give 6-chloro-4-(2-cyano-4-(trifluoromethyl)phenyl)-N-(4-methoxybenzyl)-N-(thiazol-2-yl)-3,4-dihydro-2H-benzo[b][1,4]oxazine-7-sulfonamide as a yellow solid: $^1$H NMR (400 MHz, DMSO-d$_6$) δ=8.46 (d, J=2.1 Hz, 1 H), 8.15 (dd, J=1.8, 8.7 Hz, 1 H), 7.81 (d, J=8.5 Hz, 1 H), 7.50 (s, 1 H), 7.45 (d, J=3.6 Hz, 1 H), 7.32 (d, J=3.5 Hz, 1 H), 7.28-7.21 (m, 2 H), 6.90-6.78 (m, 3 H), 5.17 (s, 2 H), 4.40-4.34 (m, 2 H), 3.91-3.85 (m, 2 H), 3.71 (s, 3 H); m/z (ESI) 621.0 (M+H)$^+$.

Step 3, Example 212: 6-Chloro-4-(2-Cyano-4-(Trifluoromethyl)Phenyl)-N-(Thiazol-2-Yl)-3,4-Dihydro-2H-Benzo[B][1,4]Oxazine-7-Sulfonamide

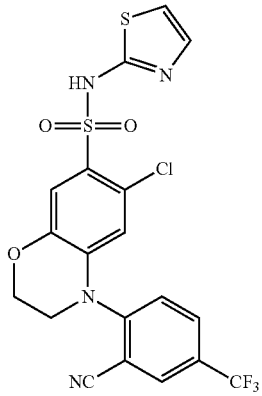 [SMILES: N#Cc1cc(C(F)(F)F)ccc1N1CCOc2cc(S(=O)(=O)Nc3nccs3)c(Cl)cc21]

A round-bottom flask was charged with 6-chloro-4-(2-cyano-4-(trifluoromethyl)phenyl)-N-(4-methoxybenzyl)-N-(thiazol-2-yl)-3,4-dihydro-2H-benzo[b][1,4]oxazine-7-sulfonamide (3.36 g, 5.41 mmol), DCM (20 mL), and TFA (8 mL). The resulting solution was stirred for 2 h, then the mixture was diluted with MeOH. It became cloudy, so it was filtered through celite with the aid of MeOH. The filtrate was concentrated in vacuo. The crude product was purified by chromatography on silica gel (120-g Redi-Sep Gold column, 0-10% MeOH/DCM) to afford 6-chloro-4-(2-cyano-4-(trifluoromethyl)phenyl)-n-(thiazol-2-yl)-3,4-dihydro-2h-benzo[b][1,4]oxazine-7-sulfonamide as a white powder: $^1$H NMR (400 MHz, DMSO-d$_6$) δ=12.79 (br. s., 1 H), 8.42 (d, J=2.2 Hz, 1 H), 8.10 (dd, J=2.0, 8.9 Hz, 1 H), 7.76 (d, J=8.6 Hz, 1 H), 7.48 (s, 1 H), 7.27 (d, J=4.6 Hz, 1 H), 6.84 (d, J=4.6 Hz, 1 H), 6.80 (s, 1 H), 4.37-4.33 (m, 2H), 3.88-3.84 (m, 2 H); m/z (ESI) 501.0 (M+H)$^+$.

Example 213

6-Cyano-4-(2-Methoxy-4-(Trifluoromethyl)Phenyl)-N-(Thiazol-2-Yl)-3,4-Dihydro-2H-Benzo[B][1,4]Oxazine-7-Sulfonamide

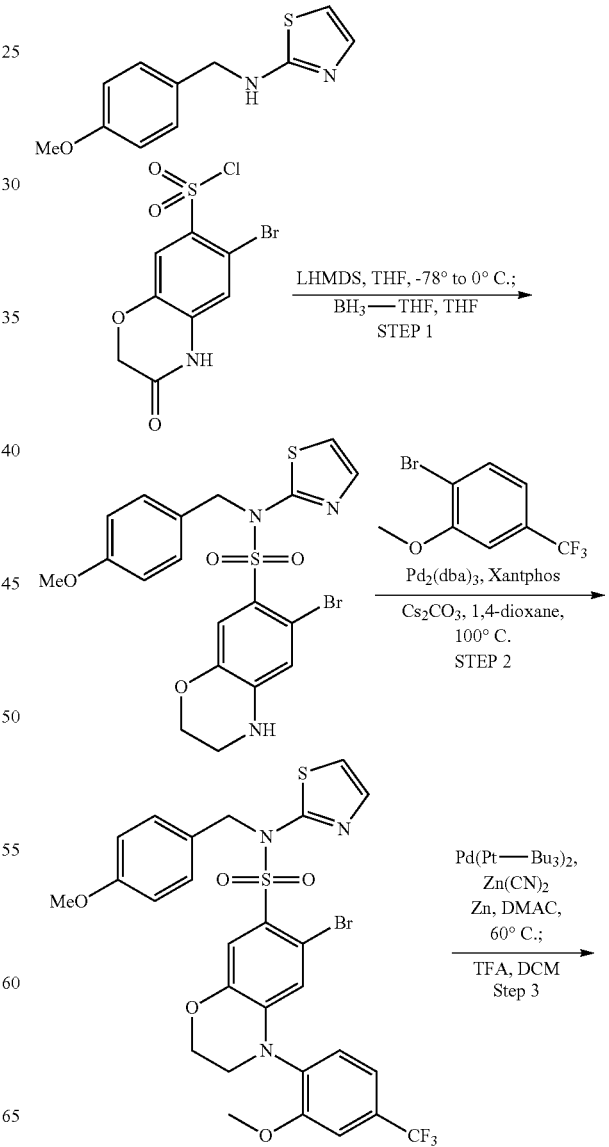

-continued

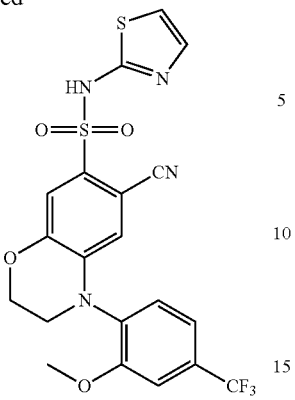

Step 1: 6-Bromo-N-(4-Methoxybenzyl)-N-(Thiazol-2-Yl)-3,4-Dihydro-2H-Benzo[B][1,4]Oxazine-7-Sulfonamide

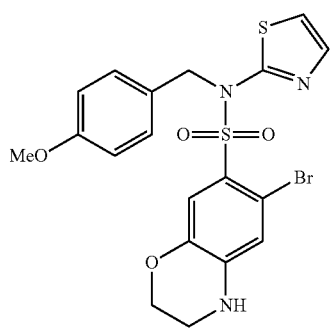 [SMILES: COc1ccc(CN(c2nccs2)S(=O)(=O)c2cc3c(cc2Br)NCCO3)cc1]

A 50-mL round-bottom flask was charged with 6-bromo-3-oxo-3,4-dihydro-2H-benzo[b][1,4]oxazine-7-sulfonyl chloride (Enamine, Kiev, Ukraine, 1.002 g, 3.07 mmol), N-(4-methoxybenzyl)thiazol-2-amine (0.811 g, 3.68 mmol), and THF (15.34 ml) to give a thick suspension. The flask was cooled in a dry ice-acetone bath for 10 min. Lithium bis(trimethylsilyl)amide (1M in THF) (6.75 ml, 6.75 mmol) was added dropwise over 5 min. After another 5 min, the flask was transferred to an ice-bath. After 25 min, the mixture was diluted with saturated aq. ammonium chloride and water. The mixture was extracted with EtOAc (3×). The combined organic extracts were dried over sodium sulfate, filtered, and concentrated. The residue was concentrated from DCM (2×, to help remove residual EtOAc and water). The flask was flushed with Ar (g), and the mixture was taken up in THF (15 mL) to give a thin suspension. Borane-tetrahydrofuran complex (1M in THF) (7.67 ml, 7.67 mmol) was added over 20 s, resulting in some bubbling and then a clear, amber solution. The mixture was stirred overnight for 16 h, then MeOH (ca. 20 mL) was added carefully. The resulting solution was stirred for 3 h, and the mixture was concentrated. The residue was concentrated from MeOH (1×), then from MeOH/DCM (3×). The residue was taken up in MeOH, which formed a partial slurry with some floating gummy solid. The mixture was sonicated for 2 min, then stirred vigorously for 4 h. The mixture was filtered, and the collected solids were washed with MeOH (2×), then dried under a stream of N2 (g) overnight. The material was dried further under high vac to give 6-bromo-N-(4-methoxybenzyl)-N-(thiazol-2-yl)-3,4-dihydro-2H-benzo[b][1,4]oxazine-7-sulfonamide (391.2 mg, 0.788 mmol, 25.7% yield) as an off-white solid: m/z (ESI) 495.9 (M+H)+.

Step 2: 6-Bromo-4-(2-Methoxy-4-(Trifluoromethyl)Phenyl)-N-(4-Methoxybenzyl)-N-(Thiazol-2-Yl)-3,4-Dihydro-2H-Benzo[B][1,4]Oxazine-7-Sulfonamide

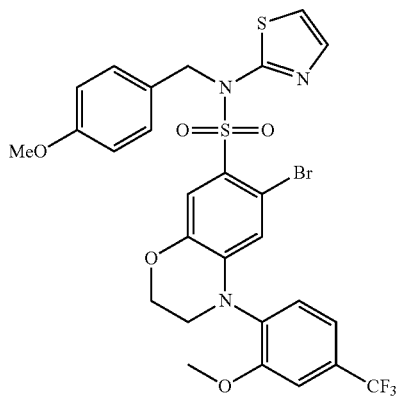 [SMILES: COc1ccc(CN(c2nccs2)S(=O)(=O)c2cc3c(cc2Br)N(c2ccc(C(F)(F)F)cc2OC)CCO3)cc1]

A vial was charged with 6-bromo-N-(4-methoxybenzyl)-N-(thiazol-2-yl)-3,4-dihydro-2H-benzo[b][1,4]oxazine-7-sulfonamide (107.43 mg, 0.216 mmol), 1-bromo-2-methoxy-4-(trifluoromethyl)benzene (Sigma-Aldrich, St. Louis, Mo., 193 mg, 0.757 mmol), Xantphos (25.04 mg, 0.043 mmol), Pd2(dba)3 (19.82 mg, 0.022 mmol), and cesium carbonate (212 mg, 0.649 mmol). The vessel was flushed with Ar (g), then 1,4-dioxane (2164 μl) was added. The vessel was sealed and placed in a 100° C. heating bath for 20 h. The mixture was cooled to room temperature, diluted with EtOAc, and filtered through celite. The filtrate was concentrated, and the residue was purified by chromatography on silica gel (12-g Redi-Sep Gold column, 0-50% EtOAc/Heptane) to give 6-bromo-4-(2-methoxy-4-(trifluoromethyl)phenyl)-N-(4-methoxybenzyl)-N-(thiazol-2-yl)-3,4-dihydro-2H-benzo[b][1,4]oxazine-7-sulfonamide (67 mg, 0.100 mmol, 46.2% yield) as a yellow foam: m/z (ESI) 670.2 (M+H)+.

Step 3, Example 213: 6-Cyano-4-(2-Methoxy-4-(Trifluoromethyl)Phenyl)-N-(Thiazol-2-Yl)-3,4-Dihydro-2H-Benzo[B][1,4]Oxazine-7-Sulfonamide

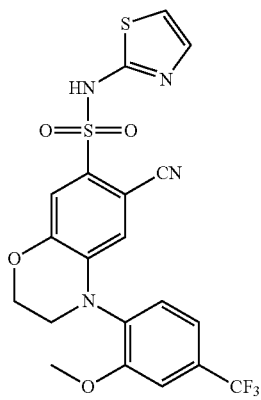 [SMILES: COc1cc(C(F)(F)F)ccc1N1CCOc2cc(S(=O)(=O)Nc3nccs3)c(C#N)cc21]

A vial was charged with 6-bromo-4-(2-methoxy-4-(trifluoromethyl)phenyl)-N-(4-methoxybenzyl)-N-(thiazol-2-yl)-3,4-dihydro-2H-benzo[b][1,4]oxazine-7-sulfonamide (67 mg, 0.100 mmol), dicyanozinc (23.46 mg, 0.200 mmol), bis(tri-t-butylphosphine)palladium(0) (5.11 mg, 9.99 μmol), and zinc (1.960 mg, 0.030 mmol). The vial was flushed with Ar (g), then N,N-dimethylacetamide (500 μl) was added. The vial was sealed and placed in a 60° C. heating bath for 5 h. Additional portions of dicyanozinc (23.46 mg, 0.200 mmol) and bis(tri-t-butylphosphine)palladium(0) (ca. 8.5 mg) were added, and the vial was returned to the heat for 2 h. The mixture was diluted with EtOAc, then washed with water (2×), washed with brine, dried over sodium sulfate, filtered, and concentrated. The residue was taken up in DCM (1 mL) and TFA (0.5 mL). After 35 min, the mixture was diluted with MeOH and concentrated. The residue was purified by chromatography on 12-g Redi-Sep Gold column (20-70% EtOAc/Heptane, product eluted late) to give ca. 16 mg of a white solid. The material was rechromatographed twice on 12-g Redi-Sep Gold columns, once with 3% MeOH/DCM, then with 0-4% MeOH/DCM to give 6-cyano-4-(2-methoxy-4-(trifluoromethyl)phenyl)-n-(thiazol-2-yl)-3,4-dihydro-2h-benzo[b][1,4]oxazine-7-sulfonamide as a white solid that was about 91% pure by LCMS and NMR: $^1$H NMR (400 MHz, DMSO-d$_6$) δ=12.91 (br. s., 1 H), 7.56 (d, J=8.1 Hz, 1 H), 7.49-7.40 (m, 2 H), 7.36 (s, 1 H), 7.28 (d, J=4.6 Hz, 1 H), 6.87 (d, J=4.6 Hz, 1 H), 6.60 (s, 1 H), 4.43-4.38 (m, 2 H), 3.87 (s, 3 H), 3.71 (t, J=4.3 Hz, 2 H); m/z (ESI) 497.2 (M+H)$^+$.

To a 10-20 ml microwave vial charged with N-(4-methoxybenzyl)-N-(thiazol-2-yl)-3,4-dihydro-2H-benzo[b][1,4]oxazine-7-sulfonamide (INTERMEDIATE M) (0.05 g, 0.120 mmol), 3-bromo-2-methoxy-6-(trifluoromethyl)pyridine (Anichem) (0.046 g, 0.180 mmol), sodium t-butoxide (0.029 ml, 0.240 mmol), xantphos (0.014 g, 0.024 mmol), and Pd$_2$(dba)$_3$ (10.97 mg, 0.012 mmol) was added toluene (1.198 ml). The mixture was purged with argon and the vessel was sealed and irradiated at 130° C. for 30 mins. LC-MS indicated complete conversion to desired product (PMB protected, m/z=593). To the mixture was added TFA (200 μl) and the resulting mixture stirred at room temperature for 2 hrs. The mixture was filtered through celite and the filtrate dried under reduced pressure. The crude material was purified with a 25 g HP spherical silica column (15 μm, Interchim) ramping EtOAc in heptane (0-50%, then isocratic at 50%, 10% DCM isocratic throughout) providing product as a film which was lyophilized yielding an off-white solid. The material was further purified with preparative RP-HPLC ramping ACN in H$_2$O (10-90%, 0.1% TFA) affording 4-(2-methoxy-6-(trifluoromethyl)pyridin-3-yl)-N-(thiazol-2-yl)-3,4-dihydro-2H-benzo[b][1,4]oxazine-7-sulfonamide (10 mg, 18%). $^1$H NMR (400 MHz, DMSO-d$_6$) δ ppm 3.67-3.72 (m, 2 H) 3.92 (s, 3 H) 4.29-4.33 (m, 2 H) 6.44 (d, J=8.51 Hz, 1 H) 6.79 (d, J=4.60 Hz, 1 H) 7.13 (dd, J=8.51, 2.15 Hz, 1 H) 7.16 (d, J=2.05 Hz, 1 H) 7.22 (d, J=4.60 Hz, 1 H) 7.56 (d, J=7.92 Hz, 1 H) 7.90-7.97 (m, 1 H). m/z (ESI) 473.2 (M+H)$^+$.

Example 214

4-(2-Methoxy-6-(Trifluoromethyl)Pyridin-3-Yl)-N-(Thiazol-2-Yl)-3,4-Dihydro-2H-Benzo[B][1,4]Oxazine-7-Sulfonamide Example 215

4-(2-Cyano-4-(Trifluoromethyl)Phenyl)-6-Fluoro-N-(Thiazol-2-Yl)-3,4-Dihydro-2H-Benzo[B][1,4]Oxazine-7-Sulfonamide

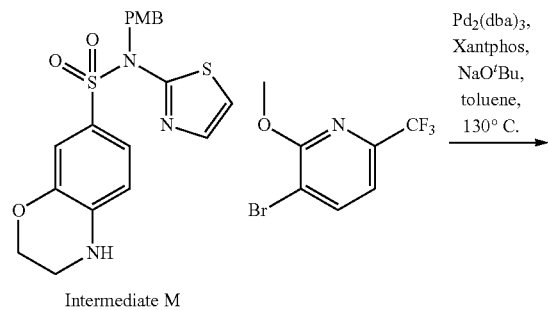

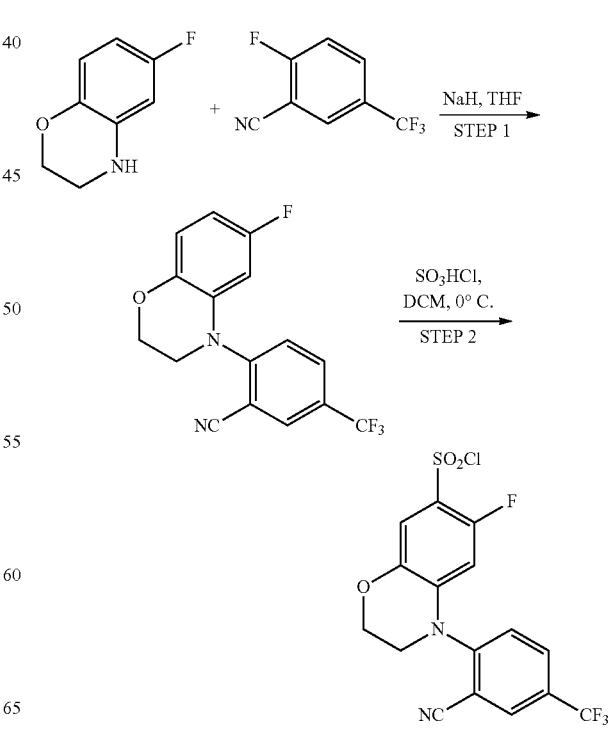

-continued

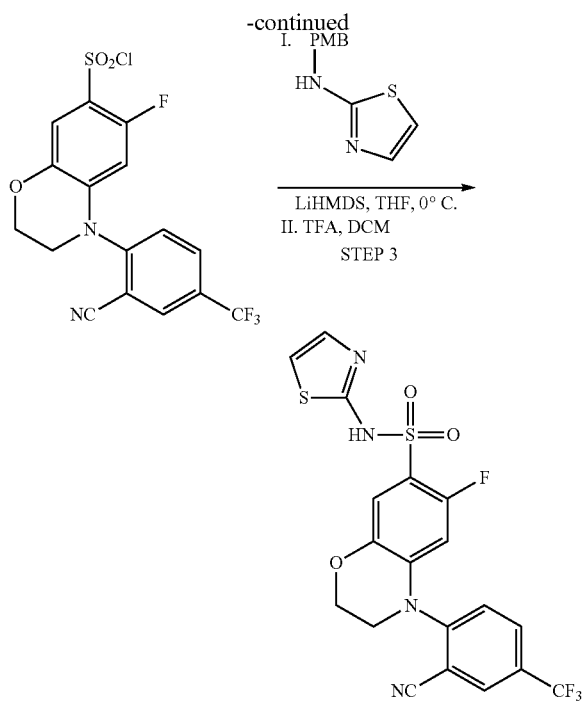

LiHMDS, THF, 0° C.
II. TFA, DCM
STEP 3

Step 1: 2-(6-Fluoro-2H-Benzo[B][1,4]Oxazin-4(3 H)-Y1)-5-(Trifluoromethyl)Benzonitrile

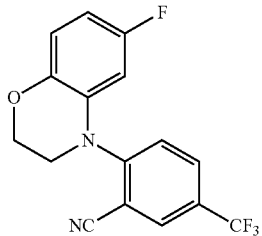 [SMILES: N#Cc1cc(C(F)(F)F)ccc1N1CCOc2ccc(F)cc21]

A 250 ml round bottom flask charged with 6-fluoro-3,4-dihydro-2H-benzo[b][1,4]oxazine (5.00 g, 32.6 mmol) was dried under high vacuum and placed under nitrogen prior to the addition of THF (131 ml). The solution was cooled in an ice water bath for 10 mins prior to the addition of sodium hydride (60% in mineral oil) (1.436 g, 35.9 mmol), added carefully in two portions 5 mins apart. The resulting suspension was stirred for 15 min at 0° C. then 90 min at room temp yielding a brownish suspension. To the suspension was added 2-fluoro-5-(trifluoromethyl)benzonitrile (6.79 g, 35.9 mmol) at room temperature. The mixture was stirred at 60° C. overnight affording about 75% conversion according to LC-MS. The dark solution was cooled in an ice water bath and carefully added to a stirred flask of water/ice/NH$_4$Cl which was extracted with EtOAc (2×). The combined organics were dried with Na$_2$SO$_4$, filtered, and dried under reduced pressure. The crude residue was purified with a 120 g ISCO gold column (load column loaded with crude brown oil directly with DCM rinsing) ramping EtOAc in heptane (0-25%, then isocratic at 25%) providing product cleanly (3.65 g, yellow solid) as well as a large portion which coeluted with starting amine and other minor impurities. The mixture was dried under reduced pressure and passed through a 25 g SCX-2 column, then a second 25 g SCX-2 column since after the first wash some dark materials eluted through. DCM was used as the eluent providing 2-(6-fluoro-2H-benzo[b][1,4]oxazin-4(3 H)-yl)-5-(trifluoromethyl)benzonitrile as a tan solid (3.0 g) (6.65 g total, 63%). $^1$H NMR (400 MHz, CHLOROFORM-d) δ ppm 3.84-3.91 (m, 2 H) 4.26-4.31 (m, 2 H) 6.53 (dd, J=9.93, 2.89 Hz, 1 H) 6.64 (ddd, J=9.00, 7.82, 2.93 Hz, 1 H) 6.90 (dd, J=8.95, 5.33 Hz, 1 H) 7.55 (d, J=8.71 Hz, 1 H) 7.76 (ddd, J=8.71, 2.25, 0.59 Hz, 1H) 7.95 (dd, J=1.57, 0.68 Hz, 1 H). m/z (ESI) 323.1 (M+H)$^+$.

Step 2: 4-(2-Cyano-4-(Trifluoromethyl)Phenyl)-6-Fluoro-3,4-Dihydro-2H-Benzo[B][1,4]Oxazine-7-Sulfonyl Chloride

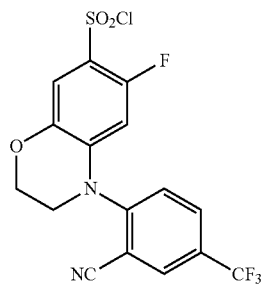 [SMILES: N#Cc1cc(C(F)(F)F)ccc1N1CCOc2cc(S(=O)(=O)Cl)c(F)cc21]

To a vial charged with 2-(6-fluoro-2H-benzo[b][1,4]oxazin-4(3 H)-yl)-5-(trifluoromethyl)benzonitrile (1.85 g, 5.74 mmol) was added DCM (23 mL). The resulting solution was cooled in an ice water bath prior to the addition of chlorosulfonic acid (1.526 ml, 22.96 mmol), faster than dropwise. After 30 min of stirring LC-MS of the resulting yellow/brown solution indicated desired product mass as the main mass (M+23) with consumption of starting material. The solution was added to ice water, and extracted 2× with DCM. The combined organics were dried with Na$_2$SO$_4$, filtered, and dried under reduced pressure. The crude material was purified with a 25 g SNAP column ramping EtOAc in heptane (0-25%, then isocratic at 25%, 10% DCM throughout) providing product as a white foam 4-(2-cyano-4-(trifluoromethyl)phenyl)-6-fluoro-3,4-dihydro-2H-benzo[b][1,4]oxazine-7-sulfonyl chloride (1.80 g, 4.28 mmol, 74.5% yield). $^1$H NMR (400 MHz, CHLOROFORM-d) δ ppm 3.87-3.94 (m, 2 H) 4.40-4.49 (m, 2 H) 6.37 (d, J=11.15 Hz, 1 H) 7.50 (d, J=6.46 Hz, 1 H) 7.64 (d, J=8.51 Hz, 1 H) 7.94-8.01 (m, 1 H) 8.09 (dd, J=1.57, 0.59 Hz, 1 H). m/z (ESI) 443.1 (M+Na)$^+$.

Step 3, Example 215: 4-(2-Cyano-4-(Trifluoromethyl)Phenyl)-6-Fluoro-N-(Thiazol-2-Y1)-3,4-Dihydro-2H-Benzo[B][1,4]Oxazine-7-Sulfonamide

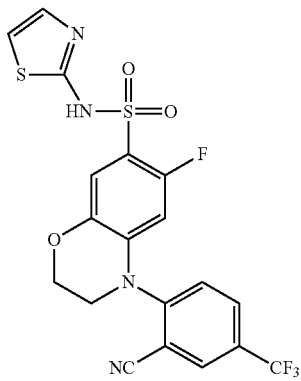 [SMILES: N#Cc1cc(C(F)(F)F)ccc1N1CCOc2cc(S(=O)(=O)Nc3nccs3)c(F)cc21]

To a vial charged with N-(4-methoxybenzyl)thiazol-2-amine (2.83 g, 12.86 mmol) was added THF (38.2 ml) and the mixture cooled in an ice water bath prior to the addition of lithium bis(trimethylsilyl)amide, 1.0M solution in tetrahydrofuran (14.03 ml, 14.03 mmol), faster than dropwise. After 15 min, a solution of 4-(2-cyano-4-(trifluoromethyl)phenyl)-6-fluoro-3,4-dihydro-2H-benzo[b][1,4]oxazine-7-sulfonyl chloride (4.92 g, 11.69 mmol) in THF (30 ml) was added. The mixture was allowed to warm to rt over 1.5 h, providing a brown solution and product as the primary species according to LC-MS (m/z=605). The solution was added to ice, diluted with EtOAc and extracted with water (brine added to help resolve emulsion). The layers were separated and the aqueous phase was extracted with EtOAc. The combined organics were dried with Na$_2$SO$_4$, filtered, and dried under reduced pressure. To the crude material was added DCM (70 ml) and the resulting light brown solution cooled in an ice water bath prior to the addition of TFA (20 ml) and the mixture stirred at 0° C. for 20 mins and at room temperature for 1 h affording a purplish solution. The mixture was concentrated under reduced pressure and the resulting brownish oil purified with a 330 g ISCO gold column ramping EtOAc in heptane (0-45%, then isocratic at 45% with 10% DCM isocratic throughout, sample loaded with DCM providing product (~3.9 g) as a slightly off-white solid. The solid was triturated with MeOH to afford a white solid, 4-(2-cyano-4-(trifluoromethyl)phenyl)-6-fluoro-N-(thiazol-2-yl)-3,4-dihydro-2H-benzo[b][1,4]oxazine-7-sulfonamide (3.208 g, 6.62 mmol, 56.6% yield). $^1$H NMR (400 MHz, DMSO-d$_6$) δ ppm 3.80-3.88 (m, 2 H) 4.28-4.35 (m, 2 H) 6.64 (d, J=11.64 Hz, 1 H) 6.84 (d, J=4.69 Hz, 1 H) 7.23 (d, J=6.75 Hz, 1 H) 7.27 (d, J=4.60 Hz, 1 H) 7.77 (d, J=8.61 Hz, 1 H) 8.09 (dd, J=8.90, 1.96 Hz, 1 H) 8.41 (d, J=1.66 Hz, 1 H) 12.81 (s, 1 H). m/z (ESI) 485.2 (M+H)$^+$.

Example 216

4-(2-Cyano-4-(Trifluoromethyl)Phenyl)-8-Fluoro-N-(Thiazol-2-Yl)-3,4-Dihydro-2H-Benzo[B][1,4]Oxazine-7-Sulfonamide

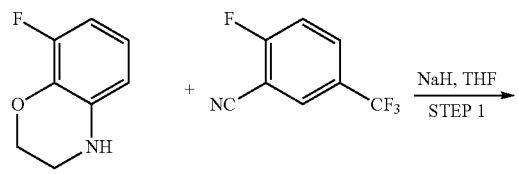

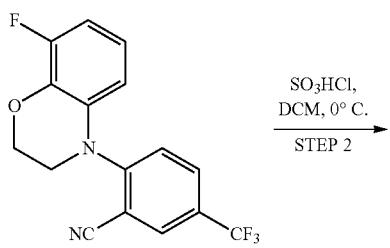

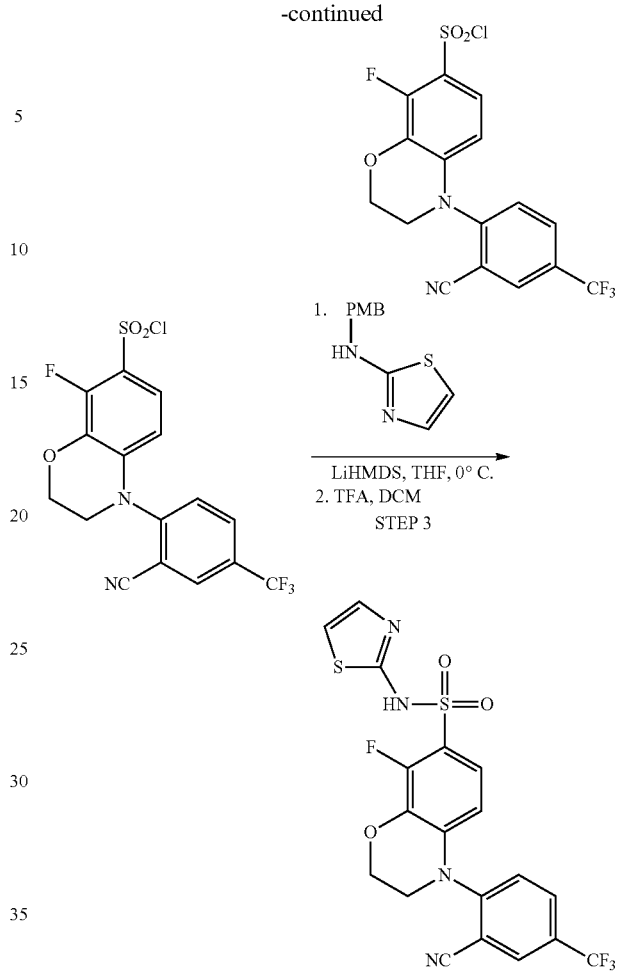

Step 1: 2-(8-Fluoro-2H-Benzo[B][1,4]Oxazin-4(3H)-Yl)-5-(Trifluoromethyl)Benzonitrile

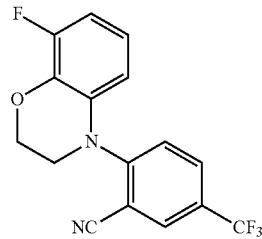 [SMILES: N#Cc1cc(C(F)(F)F)ccc1N1CCOc2c(F)cccc21]

To a flask charged with 8-fluoro-3,4-dihydro-2H-benzo[b][1,4]oxazine (AAT Pharmaceuticals) (0.237 g, 1.547 mmol) was added THF (6.19 ml). The solution was cooled in an ice water bath prior to the addition of sodium hydride (60% in mineral oil) (0.068 g, 1.702 mmol). The resulting suspension was stirred for 30 min at 0° C., the 30 min at rt. The resulting pale yellow suspension was cooled in an ice water bath prior to the addition of 2-fluoro-5-(trifluoromethyl)benzonitrile (0.322 g, 1.702 mmol). The resulting mixture was stirred for 30 min at 0° C., then 1 hr at room temperature. The mixture was heated to 60° C. overnight then at reflux for 2 hr. The mixture was cooled to room temperature and added carefully to ice water and extracted with EtOAc (2×). The combined organics were dried with Na$_2$SO$_4$, filtered and dried under reduced pressure. The crude material was purified with a 25 g SNAP column ramping EtOAc in heptane (0-25%, 10% DCM throughout) yielding product, obtained as a yellow oil, 2-(8-fluoro-2H-benzo[b][1,4]oxazin-4(3H)-yl)-5-(trifluoromethyl)benzonitrile (0.168 g, 0.521 mmol, 33.7% yield). $^1$H NMR (400 MHz, CHLOROFORM-d) δ ppm 3.89-3.97 (m, 2 H) 4.36 (dd, J=4.94, 3.86 Hz, 2 H) 6.61 (dt, J=7.78, 1.79 Hz, 1 H) 6.70-6.80 (m, 2 H) 7.50 (d, J=8.80 Hz, 1 H) 7.71-7.77 (m, 1 H) 7.92-7.95 (m, 1 H). m/z (ESI) 323.1 (M+H)$^+$.

Step 2: 4-(2-Cyano-4-(Trifluoromethyl)Phenyl)-8-Fluoro-3,4-Dihydro-2H-Benzo[B][1,4]Oxazine-7-Sulfonyl Chloride

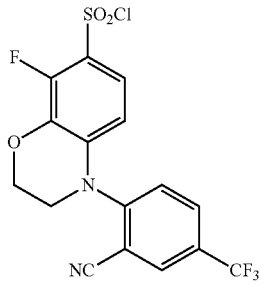 [SMILES: N#Cc1cc(C(F)(F)F)ccc1N1CCOc2c1ccc(S(=O)(=O)Cl)c2F]

To a vial charged with 2-(8-fluoro-2H-benzo[b][1,4]oxazin-4(3H)-yl)-5-(trifluoromethyl)benzonitrile (0.168 g, 0.521 mmol) was added DCM (2.085 ml). The resulting solution was cooled in an ice water bath prior to the addition of chlorosulfonic acid (0.139 ml, 2.085 mmol), faster than dropwise. After 30 mins the solution was added to ice water, and mixture was extracted 2× with EtOAc. The combined organics were dried with Na$_2$SO$_4$, filtered, and dried under reduced pressure. The crude material was purified with a 25 g SNAP column ramping EtOAc in heptane (0-25%, then isocratic at 25%, 10% DCM throughout) providing product as a white foam, 4-(2-cyano-4-(trifluoromethyl)phenyl)-8-fluoro-3,4-dihydro-2H-benzo[b][1,4]oxazine-7-sulfonyl chloride (0.127 g, 0.302 mmol, 57.9% yield). $^1$H NMR (400 MHz, CHLOROFORM-d) δ ppm 3.91-3.99 (m, 2 H) 4.52 (dd, J=5.14, 3.67 Hz, 2 H) 6.42 (dd, J=9.19, 1.66 Hz, 1 H) 7.34 (dd, J=9.19, 6.75 Hz, 1 H) 7.60 (d, J=8.51 Hz, 1 H) 7.95 (dd, J=8.56, 1.81 Hz, 1 H) 8.07 (d, J=2.15 Hz, 1 H). m/z (ESI) 443.1 (M+Na)$^+$.

Step 3, Example 216: 4-(2-Cyano-4-(Trifluoromethyl)Phenyl)-8-Fluoro-N-(Thiazol-2-Yl)-3,4-Dihydro-2H-Benzo[B][1,4]Oxazine-7-Sulfonamide

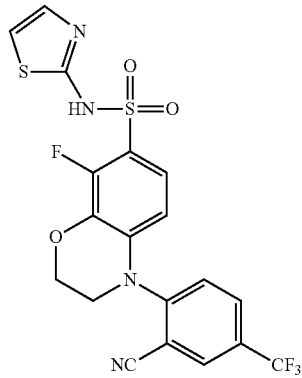 [SMILES: N#Cc1cc(C(F)(F)F)ccc1N1CCOc2c1ccc(S(=O)(=O)Nc1nccs1)c2F]

To a vial charged with N-(4-methoxybenzyl)thiazol-2-amine (0.036 g, 0.162 mmol) was added THF (0.482 ml) and the mixture cooled in an ice water bath prior to the addition of lithium bis(trimethylsilyl)amide, 1.0M solution in tetrahydrofuran (0.177 ml, 0.177 mmol), faster than dropwise. After 15 mins of stirring a solution of 4-(2-cyano-4-(trifluoromethyl)phenyl)-8-fluoro-3,4-dihydro-2H-benzo[b][1,4]oxazine-7-sulfonyl chloride (0.062 g, 0.147 mmol) in THF (0.5 ml) was added dropwise, then washed with 0.2 ml THF and added. The mixture was allowed to warm to rt over 1 hr providing a turbid brown mixture with product as the primary species according to LC-MS (m/z=605). To the turbid brown solution was added MeOH and the mixture concentrated under reduced pressure. To the crude residue was added DCM (2 ml) and TFA (0.2 ml). After 2 hr, the mixture was concentrated under reduced pressure and purified with a 25 g SNAP column ramping EtOAc in heptane (0-75%, 10% DCM throughout) to yield product as a sticky white solid, which was lyophilized from MeOH/H$_2$O affording product as a fluffy white solid, 4-(2-cyano-4-(trifluoromethyl)phenyl)-8-fluoro-N-(thiazol-2-yl)-3,4-dihydro-2H-benzo[b][1,4]oxazine-7-sulfonamide (0.04 g, 0.083 mmol, 56.0% yield). $^1$H NMR (400 MHz, DMSO-d$_6$) δ ppm 3.83-3.95 (m, 2 H) 4.34-4.46 (m, 2 H) 6.56 (dd, J=8.90, 1.27 Hz, 1 H) 6.84 (d, J=4.60 Hz, 1 H) 7.17 (dd, J=8.85, 7.29 Hz, 1 H) 7.27 (d, J=4.60 Hz, 1 H) 7.76 (d, J=8.61 Hz, 1 H) 8.11 (dd, J=8.80, 2.05 Hz, 1 H) 8.42 (d, J=1.76 Hz, 1 H) 12.80 (br. s., 1 H). m/z (ESI) 485.2 (M+H)$^+$.

Example 217

4-(4-Cyano-2-Methoxyphenyl)-6-Fluoro-N-(Thiazol-2-Yl)-3,4-Dihydro-2H-Benzo[B][1,4]Oxazine-7-Sulfonamide

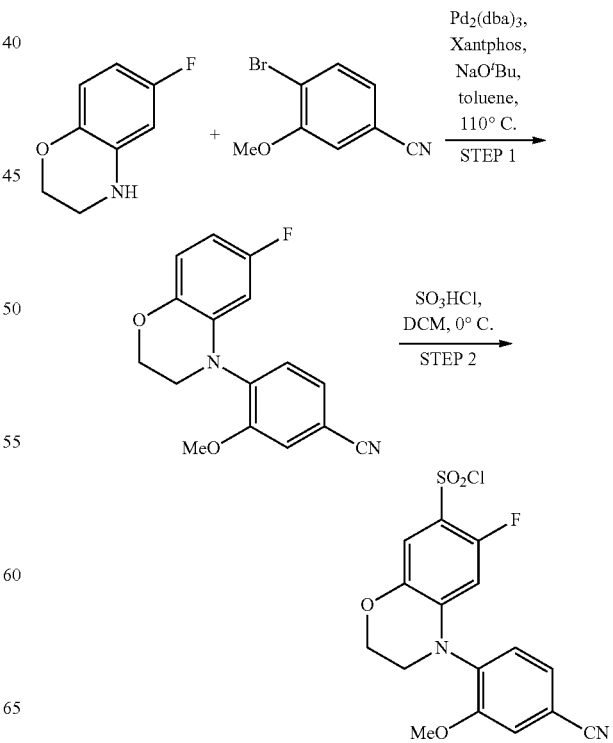

241

-continued

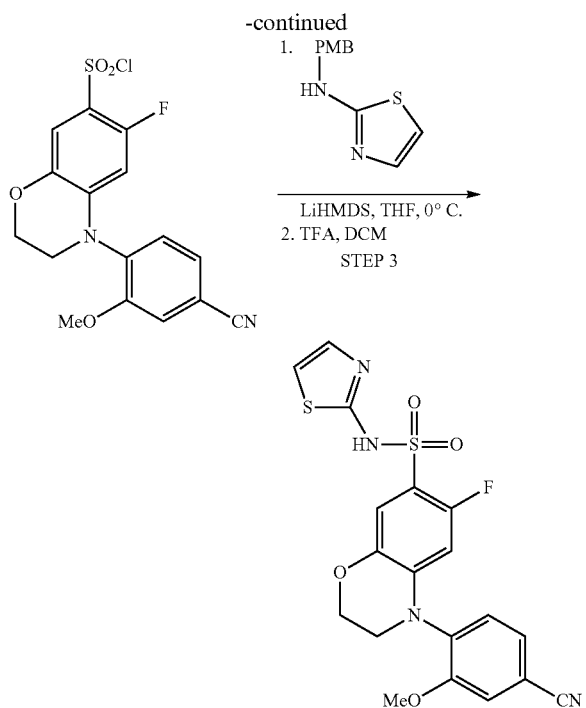

Step 1: 4-(6-Fluoro-2H-Benzo[B][1,4]Oxazin-4(3 H)-Yl)-3-Methoxybenzonitrile

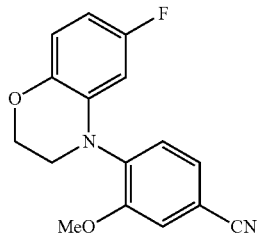 [SMILES: COc1cc(C#N)ccc1N1CCOc2ccc(F)cc21]

To a 10-20 ml microwave vial charged with 6-fluoro-3,4-dihydro-2h-benzo[1,4]oxazine (Ark Pharm) (0.150 g, 0.979 mmol), 4-bromo-3-methoxybenzonitrile (Combi-Blocks) (0.312 g, 1.469 mmol), and sodium t-butoxide (0.240 ml, 1.959 mmol) was added Toluene (9.79 ml). The mixture was purged with argon prior to the additions of xantphos (0.113 g, 0.196 mmol) and tris(dibenzylideneacetone)dipalladium (0) (0.090 g, 0.098 mmol). The mixture was irradiated at 110° C. for 30 min. The resulting dark suspension was filtered through celite and the filtrate dried under reduced pressure and purified with a 50 g SNAP column ramping EtOAc in heptane (0-40%, 10% DCM throughout) providing product as a light brown foam 4-(6-fluoro-2H-benzo[b][1,4]oxazin-4(3 H)-yl)-3-methoxybenzonitrile (0.255 g, 0.897 mmol, 92% yield). $^1$H NMR (400 MHz, DMSO-d$_6$) δ ppm 3.58-3.65 (m, 2 H) 4.19-4.26 (m, 2 H) 6.07 (dd, J=10.95, 2.93 Hz, 1 H) 6.47 (td, J=8.51, 2.93 Hz, 1 H) 6.79 (dd, J=8.80, 5.58 Hz, 1 H) 7.41-7.45 (m, 1 H) 7.45-7.51 (m, 1 H) 7.62 (d, J=1.66 Hz, 1 H). m/z (ESI) 285.2 (M+H)$^+$.

242

Step 2: 4-(4-Cyano-2-Methoxyphenyl)-6-Fluoro-3,4-Dihydro-2H-Benzo[B][1,4]Oxazine-7-Sulfonyl Chloride

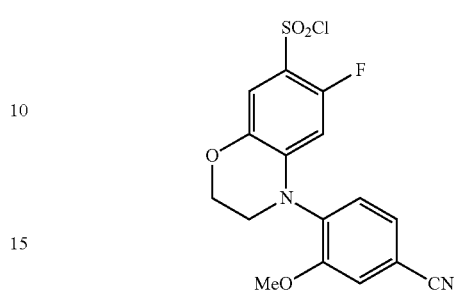

To a vial charged with 4-(6-fluoro-2H-benzo[b][1,4]oxazin-4(3 H)-yl)-3-methoxybenzonitrile (0.234 g, 0.823 mmol) was added DCM (3.29 ml). The resulting solution was cooled to −78° C. and chlorosulfonic acid (0.137 ml, 2.058 mmol) was added faster than dropwise. After 30 min the mixture was warmed to 0° C. and the mixture was allowed to stir and warm to rt over 3 hr. LC-MS indicated conversion to the desired product mass (M+23). The reaction mixture was added to ice carefully and EtOAc was used to wash reaction vial. The resulting mixture was extracted with EtOAc (2×). The layers were separated and the cloudy aqueous phase was diluted with brine and extracted once more with EtOAc. The combined organics were dried with Na$_2$SO$_4$, filtered, and concentrated under reduced pressure. The crude material was purified with a 40 g silicycle HP column ramping EtOAc in heptane (0-50%) providing product 4-(4-cyano-2-methoxyphenyl)-6-fluoro-3,4-dihydro-2H-benzo[b][1,4]oxazine-7-sulfonyl chloride (0.093 g, 0.243 mmol, 29.5% yield) as a light yellow solid. m/z (ESI) 405.2 (M+Na)$^+$.

Step 3, Example 217: 4-(4-Cyano-2-Methoxyphenyl)-6-Fluoro-N-(Thiazol-2-Yl)-3,4-Dihydro-2H-Benzo[B][1,4]Oxazine-7-Sulfonamide

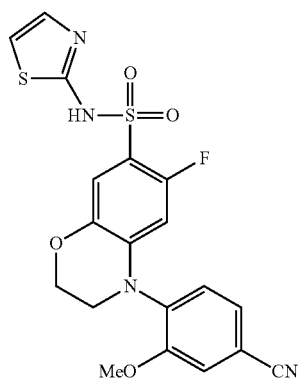 [SMILES: COc1cc(C#N)ccc1N1CCOc2cc(S(=O)(=O)Nc3nccs3)c(F)cc21]

To a vial charged with N-(4-methoxybenzyl)thiazol-2-amine (0.055 g, 0.250 mmol) was added THF (0.743 ml) and the mixture cooled in an ice water bath prior to the addition of lithium bis(trimethylsilyl)amide, 1.0M solution in tetrahydrofuran (0.273 ml, 0.273 mmol), faster than dropwise. After 15 mins of stirring a solution of 4-(4-cyano-2-methoxyphenyl)-6-fluoro-3,4-dihydro-2H-benzo[b][1,4]oxazine-7-sulfonyl chloride (0.087 g, 0.227 mmol) in THF (0.6 ml) was added dropwise, then washed with 0.2 ml THF and added. The mixture was stirred for 1 hr (ice melt) providing a brown solution and product as the primary species according to LC-MS (m/z=567) with consumption of starting material. The solution was added to ice, the mixture diluted with EtOAc and extracted with water and EtOAc. The combined organics were dried with Na$_2$SO$_4$, filtered, and dried under reduced pressure. To the crude material, a light yellow/brown foam (115 mg) was added DCM (5 ml) and TFA (1.5 ml) and the mixture stirred at room temp for 60 mins affording about 85% conversion to desired product. Stirring for another hr did not afford further conversion. Additional TFA (1 ml) was added and stirring at room temperature continued. After another hr LC-MS indicated no further conversion.

The dark solution was dried under reduced pressure and the crude residue purified with a 25 g HP spherical silica column (15 m spherical, Interchim) ramping EtOAc in heptane (0-100%, 10% DCM throughout) providing product which had coeluted with a minor non-polar impurity according to TLC. The material was repurified with a 2 g PE-AX column loading and washing with MeOH, then eluting product with 10% v/v conc. HCl in MeOH. The acidic wash was dried under reduced pressure and the material dissolved in MeOH and filtered through a 500 mg Si-carbonate plug. The sticky solid obtained upon drying was lyophilized from MeOH/H$_2$O to provide product 4-(4-cyano-2-methoxyphenyl)-6-fluoro-N-(thiazol-2-yl)-3,4-dihydro-2H-benzo[b][1,4]oxazine-7-sulfonamide (0.037 g, 0.083 mmol, 36.5% yield) as a white solid. $^1$H NMR (400 MHz, DMSO-d$_6$) δ ppm 3.66 (t, J=4.30 Hz, 2 H) 3.84 (s, 3 H) 4.24-4.31 (m, 2 H) 6.04 (d, J=12.03 Hz, 1 H) 6.82 (d, J=4.50 Hz, 1 H) 7.14 (d, J=6.75 Hz, 1 H) 7.25 (d, J=4.79 Hz, 1 H) 7.52 (s, 2 H) 7.67 (s, 1 H) 12.72 (br. s., 1 H). m/z (ESI) 447.2 (M+H)$^+$.

Example 218

4-(2-Cyano-4-(Trifluoromethyl)Phenyl)-5-Fluoro-N-(Thiazol-2-Yl)-3,4-Dihydro-2H-Benzo[B][1,4]Oxazine-7-Sulfonamide

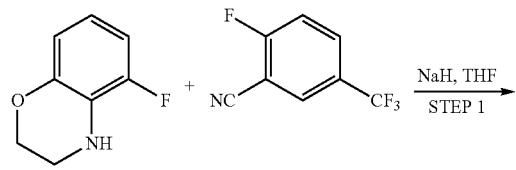

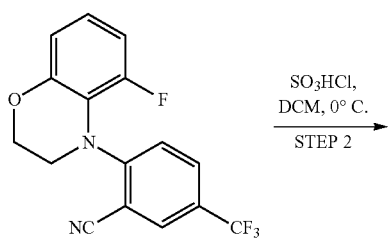

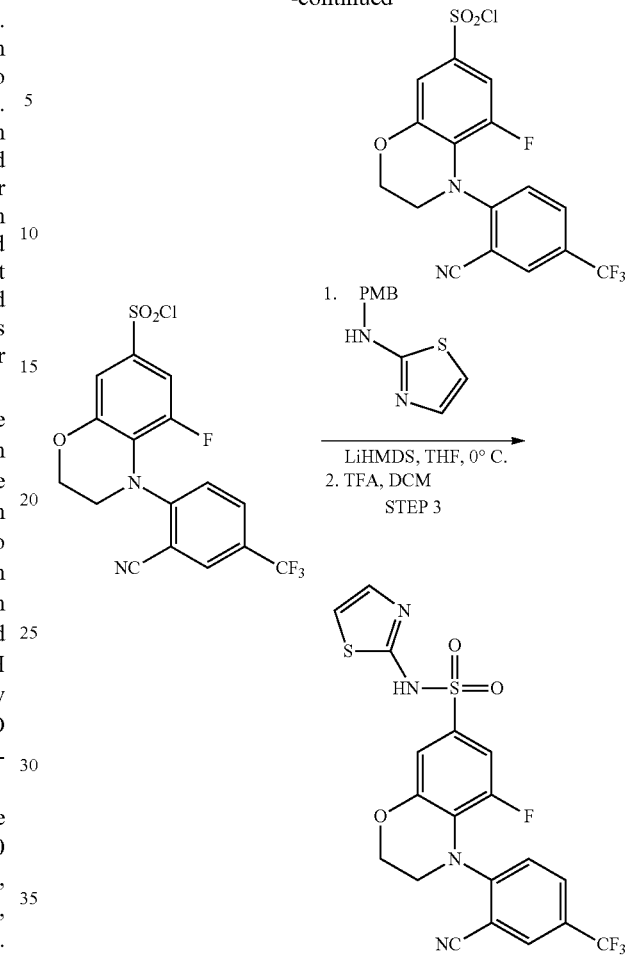

Step 1: 2-(5-Fluoro-2H-Benzo[B][1,4]Oxazin-4(3H)-Yl)-5-(Trifluoromethyl)Benzonitrile

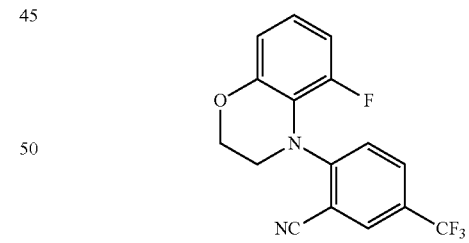

To a flask charged with 5-fluoro-3,4-dihydro-2H-benzo[b][1,4]oxazine (Combi-Blocks) (0.321 g, 2.096 mmol) was added THF (8.38 ml). The solution was cooled in an ice water bath prior to the addition of sodium hydride (60% in mineral oil) (0.092 g, 2.306 mmol). The resulting suspension was stirred for 30 mins at 0° C., the 30 mins at room temp. The resulting pale yellow suspension was cooled in an ice water bath prior to the addition of 2-fluoro-5-(trifluoromethyl)benzonitrile (Matrix Scientific) (0.436 g, 2.306 mmol). The mixture was stirred for 5 mins at 0° C., the 1 hr at room temperature when LC-MS indicated all starting material present. The tannish suspension was heated to reflux overnight providing a brown solution with about 80% conversion to product according to LC-MS. The mixture was cooled to room temperature and carefully added to ice water which was extracted with EtOAc (2×). The combined organics were dried with Na₂SO₄, filtered and dried under reduced pressure. The crude residue was purified with a 25 g column (25 m spherical silica gel, Interchim) ramping EtOAc in heptane (0-35%, with 10% DCM throughout) providing product which had partially coeluted with starting amine. The material obtained was filtered through a 5 g SCX-2 column washing with MeOH. The MeOH wash contained product, obtained as an off-white solid 2-(5-fluoro-2H-benzo[b][1,4]oxazin-4(3H)-yl)-5-(trifluoromethyl)benzonitrile (0.450 g, 1.396 mmol, 66.6% yield). ¹H NMR (400 MHz, CHLOROFORM-d) δ ppm 3.91-3.97 (m, 2 H) 4.22 (br. s., 2 H) 6.68 (ddd, J=10.86, 8.22, 1.37 Hz, 1 H) 6.82 (dt, J=8.41, 1.37 Hz, 1 H) 7.00 (td, J=8.31, 5.97 Hz, 1 H) 7.14 (dd, J=8.71, 2.25 Hz, 1 H) 7.67 (ddd, J=8.73, 2.23, 0.59 Hz, 1 H) 7.90 (dd, J=1.57, 0.59 Hz, 1 H). m/z (ESI) 323.3 (M+H)⁺.

Step 2: 4-(2-Cyano-4-(Trifluoromethyl)Phenyl)-5-Fluoro-3,4-Dihydro-2H-Benzo[B][1,4]Oxazine-7-Sulfonyl Chloride

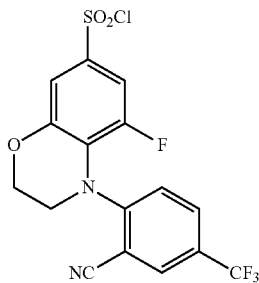 [SMILES: N#Cc1cc(C(F)(F)F)ccc1N1CCOc2cc(S(=O)(=O)Cl)cc(F)c21]

To a vial charged with 2-(5-fluoro-2H-benzo[b][1,4]oxazin-4(3H)-yl)-5-(trifluoromethyl)benzonitrile (0.445 g, 1.381 mmol) was added DCM (5.52 ml). The resulting solution was cooled in an ice water bath prior to the addition of chlorosulfonic acid (0.367 ml, 5.52 mmol), faster than dropwise. After 90 mins of stirring LC-MS of the resulting yellow/brown suspension indicated two peaks (~2:1) with desired product mass as the main mass (M+23) with consumption of starting material. The mixture was added to ice, diluted with water and extracted with EtOAc (2×). The combined organics were dried under reduced pressure and purified with a 40 HP spherical silica column (15 m spherical, Interchim) ramping EtOAc in heptane (0-35%, 10% DCM throughout) yielding near complete separation of isomers. NMR analysis of the first eluted peak confirmed the desired regiochemistry 4-(2-cyano-4-(trifluoromethyl)phenyl)-5-fluoro-3,4-dihydro-2H-benzo[b][1,4]oxazine-7-sulfonyl chloride (0.123 g, 0.292 mmol, 21.17% yield). ¹H NMR (400 MHz, CHLOROFORM-d) δ ppm 3.91-4.02 (m, 2 H) 4.37 (br. s., 2 H) 6.97 (dd, J=9.10, 1.56 Hz, 1 H) 7.20 (d, J=8.61 Hz, 1 H) 7.64 (dd, J=9.10, 7.34 Hz, 1 H) 7.77 (dd, J=8.61, 2.15 Hz, 1 H) 7.97 (d, J=1.76 Hz, 1 H). m/z (ESI) 443.1 (M+Na)⁺.

Step 3, Example 218: 4-(2-Cyano-4-(Trifluoromethyl)Phenyl)-5-Fluoro-N-(Thiazol-2-Yl)-3,4-Dihydro-2H-Benzo[B][1,4]Oxazine-7-Sulfonamide

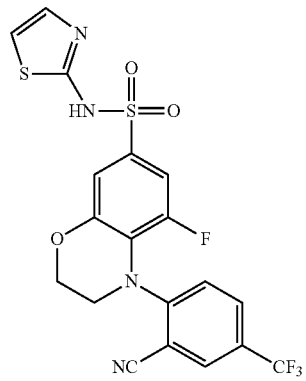 [SMILES: N#Cc1cc(C(F)(F)F)ccc1N1CCOc2cc(S(=O)(=O)Nc3nccs3)cc(F)c21]

To a vial charged with N-(4-methoxybenzyl)thiazol-2-amine (0.071 g, 0.322 mmol) was added THF (0.955 ml) and the mixture cooled in an ice water bath prior to the addition of lithium bis(trimethylsilyl)amide, 1.0M solution in tetrahydrofuran (0.351 ml, 0.351 mmol), faster than dropwise. After 15 mins of stirring a solution of 4-(2-cyano-4-(trifluoromethyl)phenyl)-5-fluoro-3,4-dihydro-2H-benzo[b][1,4]oxazine-7-sulfonyl chloride (0.123 g, 0.292 mmol) in THF (0.5 ml) was added dropwise, then washed with 0.2 ml THF and added. The mixture was stirred for 1 hr (ice melt) providing a turbid brown mixture with product as the primary species according to LC-MS (m/z=605). To the turbid brown solution was added MeOH and the mixture dried under reduced pressure. To the crude residue was added DCM (2 ml) and TFA (0.2 ml). After 2 hr the mixture was dried under reduced pressure and purified with a 25 g SNAP column ramping EtOAc in heptane (0-75%, 10% DCM throughout) to yield product as a sticky white solid which was lyophilized from MeOH/H₂O affording product as a fluffy white solid, 4-(2-cyano-4-(trifluoromethyl)phenyl)-5-fluoro-N-(thiazol-2-yl)-3,4-dihydro-2H-benzo[b][1,4]oxazine-7-sulfonamide (0.074 g, 0.153 mmol, 52.3% yield). ¹H NMR (400 MHz, DMSO-d₆) δ ppm 3.39 (br. s., 2 H) 3.80-4.20 (m, 2 H) 6.87 (d, J=4.50 Hz, 1 H) 7.12 (dd, J=10.71, 2.01 Hz, 1 H) 7.20 (t, J=1.66 Hz, 1 H) 7.30 (d, J=4.69 Hz, 1 H) 7.41 (d, J=8.80 Hz, 1 H) 7.91-7.96 (m, 1 H) 8.35 (d, J=2.15 Hz, 1 H) 12.83 (br. s., 1 H). m/z (ESI) 485.2 (M+H)⁺.

Example 219

4-(4-Cyano-2-Methoxybenzyl)-N-(Thiazol-2-Yl)-3,4-Dihydro-2H-Benzo[B][1,4]Oxazine-7-Sulfonamide

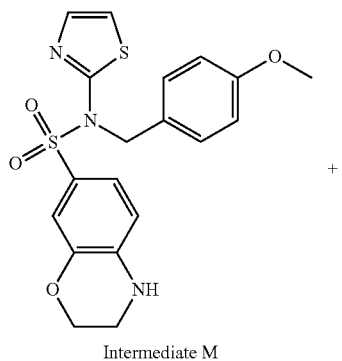

Intermediate M

247
-continued

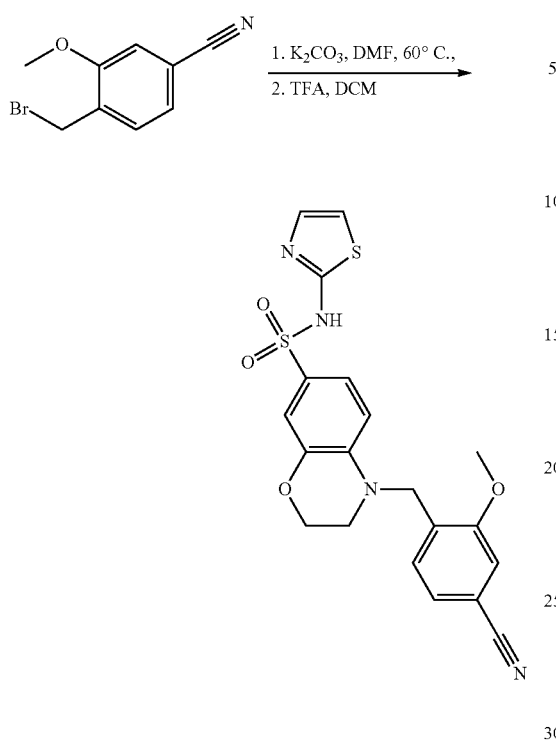

In a vial charged with N-(4-methoxybenzyl)-N-(thiazol-2-yl)-3,4-dihydro-2H-benzo[b][1,4]oxazine-7-sulfonamide (INTERMEDIATE M) (0.05 g, 0.120 mmol), 4-cyano-2-methoxybenzyl bromide (Carbocore) (0.027 g, 0.120 mmol) and potassium carbonate (0.036 g, 0.263 mmol) was added DMF (0.479 ml). The vessel was sealed and shaken at 60° C. for 3 days.

The mixture was cooled to room temperature and the DMF solution decanted from the solid salts and dried under reduced pressure. To the mixture was added DCM (2 ml) and TFA (0.2 ml). The mixture was shaken at room temperature at 2 h affording PMB cleavage. The mixture was dried under reduced pressure and the crude residue purified with a 25 g HP spherical silica column (Interchim, 15 m) ramping EtOAc in heptane (0-100%, 10% DCM throughout) providing product which contained minor impurities. The material was repurified with a Gilson RP-HPLC (ACN in H$_2$O, 10-90%, 0.1% TFA throughout) providing product which was free-based with a 2 g SCX-2 column washing with MeOH, then 2M NH$_3$ in MeOH. The basic wash was dried under reduced pressure and lyophilized from MeOH/H$_2$O providing product as a white solid, 4-(4-cyano-2-methoxybenzyl)-N-(thiazol-2-yl)-3,4-dihydro-2H-benzo[b][1,4]oxazine-7-sulfonamide (0.025 g, 0.056 mmol, 47.2% yield). $^1$H NMR (400 MHz, DMSO-d$_6$) δ ppm 3.41-3.49 (m, 2 H) 3.90 (s, 3 H) 4.17-4.25 (m, 2 H) 4.47 (s, 2 H) 6.30-6.39 (m, 2 H) 6.87 (d, J=3.81 Hz, 1 H) 7.05 (dq, J=4.43, 2.18 Hz, 2 H) 7.22 (d, J=7.73 Hz, 1 H) 7.34 (dd, J=7.78, 1.42 Hz, 1 H) 7.48 (d, J=1.37 Hz, 1 H). m/z (ESI) 443.1 (M+H)$^+$.

248

Example 220

4-Benzyl-N-(Thiazol-2-Yl)-3,4-Dihydro-2H-Benzo [B][1,4]Oxazine-7-Sulfonamide

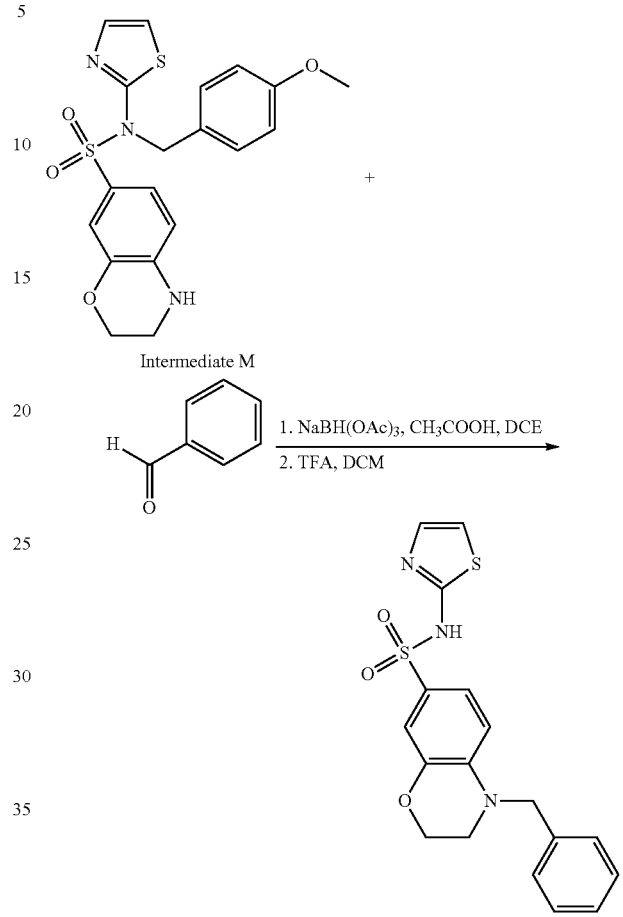

To a vial charged with N-(4-methoxybenzyl)-N-(thiazol-2-yl)-3,4-dihydro-2H-benzo[b][1,4]oxazine-7-sulfonamide (INTERMEDIATE M) (50 mg, 0.120 mmol) was added DCE (479 nl), acetic acid (10.28 µl, 0.180 mmol) and benzaldehyde (18.24 µl, 0.180 mmol). The mixture was shaken at room temperature for 10 min prior to the addition of sodium triacetoxyborohydride (76 mg, 0.359 mmol). The mixture was shaken at rt overnight yielding product (PMB protected) as the major species. To the mixture was added TFA (100 nl) and the mixture shaken at room temperature for 1 hr then at 80° C. for 1 hr. The mixture was concentrated under reduced pressure and purified with a 25 g HP spherical silica column (15 nm spherical, Interchim) ramping DCM:MeOH (90:10) in DCM (0-50%), monitoring at 215 nm providing product which had coeluted with minor impurities (51 mg). The material was repurified with Gilson RP-HPLC dissolving in DMSO/MeOH ramping ACN in H$_2$O (10-90%, 0.1% TFA throughout). The product containing eluents were filtered through a 2 g SCX-2 column washing with MeOH, then 2 M NH$_3$ in MeOH. The basic wash was dried under reduced pressure and lyophilized from MeOH/H$_2$O providing product as an off-white solid, 4-benzyl-N-(thiazol-2-yl)-3,4-dihydro-2H-benzo[b][1,4]oxazine-7-sulfonamide (6 mg, 0.015 mmol, 12.93% yield). $^1$H NMR (500 MHz, DMSO-d$_6$) ppm 3.45-3.50 (m, 2 H) 4.23 (t, J=4.33 Hz, 2 H) 4.56 (s, 2 H) 6.68 (d, J=8.55 Hz, 1 H) 6.75 (d, J=4.49 Hz, 1 H) 7.03 (d, J=2.24 Hz, 1 H) 7.14 (dd, J=8.49, 2.08 Hz, 1 H) 7.19 (d, J=4.49 Hz, 1 H) 7.26 (d, J=7.37 Hz, 3 H) 7.31-7.36 (m, 2 H) 12.48 (br. s., 1 H). m/z (ESI) 388.2 (M+H)+.

Example 221

4-((5-Methyl-3-Phenylisoxazol-4-Yl)Methyl)-N-(Thiazol-2-Yl)-3,4-Dihydro-2H-Benzo[B][1,4]Oxazine-7-Sulfonamide

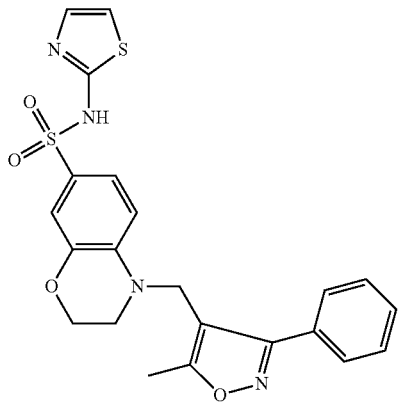 [SMILES: Cc1onc(-c2ccccc2)c1CN1CCOc2cc(S(=O)(=O)Nc3nccs3)ccc21]

To a flask charged with N-(4-methoxybenzyl)-N-(thiazol-2-yl)-3,4-dihydro-2H-benzo[b][1,4]oxazine-7-sulfonamide (INTERMEDIATE M) (0.104 g, 0.25 mmol) was added DMF (0.7 ml), and cooled in an ice water bath prior to the addition of NaH (60% in mineral oil) (10 mg, 0.25 mmol). The mixture was stirred for 45 min at 0° C., then 30 min at rt. To a separate vial charged with 4-(bromomethyl)-5-methyl-3-phenylisoxazole (Sigma Aldrich) (35 mg, 0.25 mmol) was added DMF (0.3 ml), then the solution of deprotonated amine. The resulting mixture was sealed and shaken at room temperature overnight. The mixture was quenched with the addition of MeOH, then concentrated under reduced pressure and purified with NH$_4$OH modified reverse-phase-HPLC affording 4-((5-methyl-3-phenylisoxazol-4-yl)methyl)-N-(thiazol-2-yl)-3,4-dihydro-2H-benzo[b][1,4]oxazine-7-sulfonamide (14.6 mg, 12%). $^1$H NMR (500 MHz, DMSO-d$_6$) δ=12.50 (br. s., 1 H), 7.60 (dd, J=1.7, 7.7 Hz, 2 H), 7.48-7.40 (m, 3 H), 7.21 (d, J=4.6 Hz, 1 H), 7.15 (dd, J=2.1, 8.5 Hz, 1 H), 6.99 (d, J=2.2 Hz, 1 H), 6.82-6.75 (m, 2 H), 4.37 (s, 2 H), 4.03-3.95 (m, 2 H), 3.13-3.07 (m, 2 H), 2.47 (s, 3 H); m/z (ESI) 469.0 (M+H)+.

Example 222

4-((1H-Pyrrolo[3,2-B]Pyridin-3-Yl)Methyl)-N-(Thiazol-2-Yl)-3,4-Dihydro-2H-Benzo[B][1,4]Oxazine-7-Sulfonamide

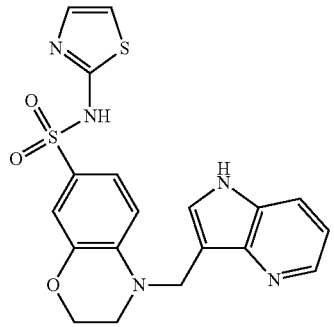 [SMILES: O=S(=O)(Nc1nccs1)c1ccc2c(c1)OCCN2Cc1c[nH]c2cccnc12]

Prepared in an identical manner to EXAMPLE 220 except using DMF as the solvent and 1H-pyrrolo[3,2-b]pyridine-3-carbaldehyde (Ark Pharm) (37 mg, 0.25 mmol) affording 4-((1H-pyrrolo[3,2-b]pyridin-3-yl)methyl)-N-(thiazol-2-yl)-3,4-dihydro-2H-benzo[b][1,4]oxazine-7-sulfonamide (5.2 mg, 5%). $^1$H NMR (500 MHz, DMSO-d$_6$) δ ppm 3.62 (t, J=4.30 Hz, 2 H) 4.17 (t, J=4.35 Hz, 2 H) 4.68 (s, 2 H) 6.74 (d, J=4.58 Hz, 1 H) 6.96 (d, J=2.06 Hz, 1 H) 7.07-7.13 (m, 2 H) 7.13-7.22 (m, 2 H) 7.65 (d, J=2.52 Hz, 1 H) 7.73 (dd, J=8.13, 1.26 Hz, 1 H) 8.35 (dd, J=4.52, 1.32 Hz, 1 H) 11.22 (br. s., 1 H) 12.44 (br. s., 1 H). m/z (ESI) 427.9 (M+H)+.

Example 223

4-(2-Methoxy-4-(Trifluoromethyl)Phenyl)-3-Oxo-N-(Thiazol-2-Yl)-3,4-Dihydro-2H-Benzo[B][1,4]Oxazine-7-Sulfonamide

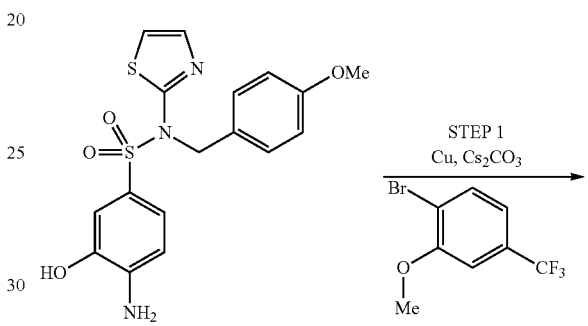

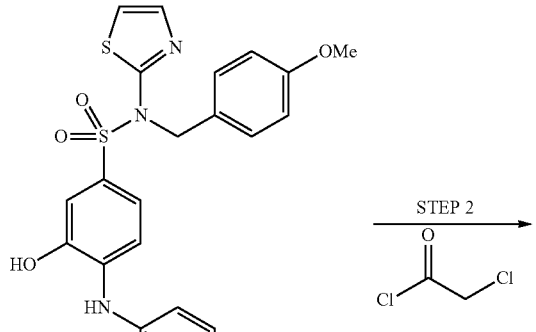

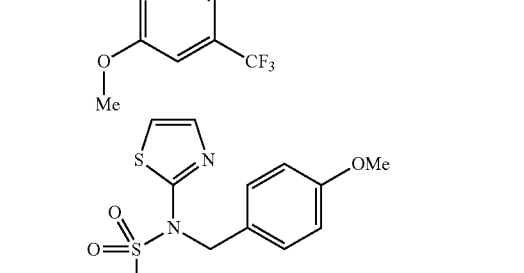

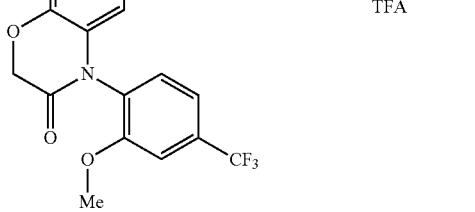

-continued

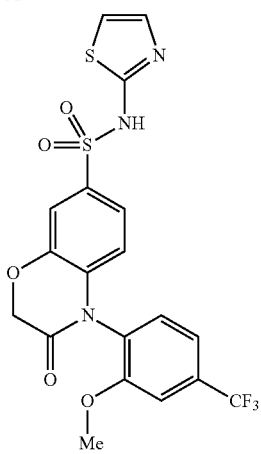

Step 1: 3-Hydroxy-4-((2-Methoxy-4-(Trifluoromethyl)Phenyl)Amino)-N-(4-Methoxybenzyl)-N-(Thiazol-2-Yl)Benzenesulfonamide

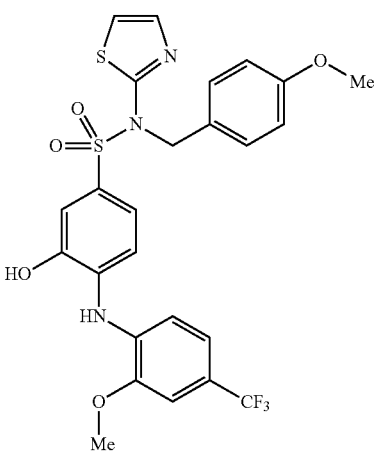 [SMILES: COc1ccc(CN(c2nccs2)S(=O)(=O)c2ccc(Nc3ccc(C(F)(F)F)cc3OC)c(O)c2)cc1]

In a 10-mL sealed tube under $N_2$ was dissolved INTERMEDIate AD (573 mg, 1.46 mmol), 1-bromo-2-methoxy-4-(trifluoromethyl)benzene (373 mg, 1.46 mmol), cesium carbonate (1.43 g, 4.39 mmol) and copper(I) iodide (139 mg, 0.732 mmol) in 3 mL of DMF. The reaction vessel was covered from light and the mixture stirred and heated at 90° C. After 12 h, the reaction mixture was diluted with DCM then neutralized with $NH_4Cl$ (sat.) and sodium 2,2'4(2-((carboxylatomethyl)(2-hydroxyethyl)amino)ethyl)azanediyl)diacetate hydrate (10 g) (copper chelator). The aqueous phase was extracted 3× with DCM. The layers were separated and the organic layer was dried over $Na_2SO_4$, filtered and concentrated under reduced pressure. The crude mixture was purified by MPLC (ISCO) with Hexanes:AcOEt 100:0 to 0:100 to afforded 3-hydroxy-4-((2-methoxy-4-(trifluoromethyl)phenyl)amino)-N-(4-methoxybenzyl)-N-(thiazol-2-yl)benzenesulfonamide (350 mg, 0.619 mmol, 42.3% yield) as a yellow solid. m/z (ESI) 566.0 (M+H)+.

Step 2: 4-(2-Methoxy-4-(Trifluoromethyl)Phenyl)-N-(4-Methoxybenzyl)-3-Oxo-N-(Thiazol-2-Yl)-3,4-Dihydro-2H-Benzo[B][1,4]Oxazine-7-Sulfonamide

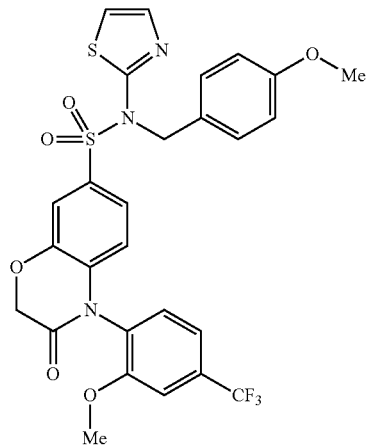 [SMILES: COc1ccc(CN(c2nccs2)S(=O)(=O)c2ccc3c(c2)OCC(=O)N3c2ccc(C(F)(F)F)cc2OC)cc1]

In a 10-mL round bottom flask under $N_2$ was dissolved cesium carbonate (807 mg, 2.48 mmol) and 3-hydroxy-4-((2-methoxy-4-(trifluoromethyl)phenyl)amino)-N-(4-methoxybenzyl)-N-(thiazol-2-yl)benzenesulfonamide (350 mg, 0.619 mmol) in 4 mL of DMF followed by a slow addition of chloroacetyl chloride (0.099 mL, 1.24 mmol) at rt. After 1 h the reaction mixture was neutralized with $H_2O$ and ice and the product 4-(2-methoxy-4-(trifluoromethyl)phenyl)-N-(4-methoxybenzyl)-3-oxo-N-(thiazol-2-yl)-3,4-dihydro-2H-benzo[b][1,4]oxazine-7-sulfonamide was collected as a solid and dried under reduced pressure and used directly in the next step.

Step 3, Example 223: 4-(2-Methoxy-4-(Trifluoromethyl)Phenyl)-3-Oxo-N-(Thiazol-2-Yl)-3,4-Dihydro-2H-Benzo[B][1,4]Oxazine-7-Sulfonamide

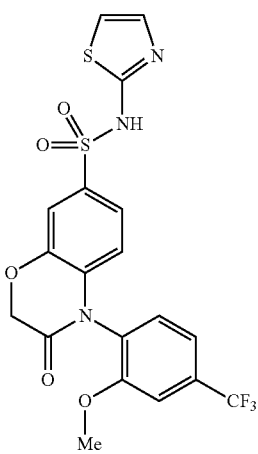 [SMILES: COc1cc(C(F)(F)F)ccc1N1C(=O)COc2cc(S(=O)(=O)Nc3nccs3)ccc21]

In a 25-mL round bottom flask was dissolved 4-(2-methoxy-4-(trifluoromethyl)phenyl)-N-(4-methoxybenzyl)-3-oxo-N-(thiazol-2-yl)-3,4-dihydro-2H-benzo[b][1,4]oxazine-7-sulfonamide in 4 mL of DCM then treated with TFA (2.384 mL, 30.9 mmol). After 30 min the reaction mixture was concentrated under reduced pressure and purified by MPLC (ISCO) with DCM:MeOH 100:0 to 90:10 to afforded 4-(2-methoxy-4-(trifluoromethyl)phenyl)-3-oxo-N-(thiazol-2-yl)-3,4-dihydro-2H benzo[b][1,4]oxazine-7-sulfonamide (250 mg, 0.515 mmol, 83.0% yield from INTERMEDIate AB2) as a white solid. $^1$H NMR (400 MHz, DMSO-$d_6$) δ ppm 3.81 (s, 3 H) 4.91 (s, 2 H) 6.41 (d, J=8.41 Hz, 1 H) 6.83 (d, J=4.60 Hz, 1 H) 7.26 (d, J=4.60 Hz, 1 H) 7.34 (dd, J=8.36, 2.01 Hz, 1 H) 7.38 (d, J=1.96 Hz, 1 H) 7.51 (d, J=8.12 Hz, 1 H) 7.55-7.65 (m, 2 H) 12.75 (br. s., 1 H). m/z (ESI) 486.0 (M+H)$^+$.

Example 225

4-(5-Cyano-2-Methoxyphenyl)-N-(Thiazol-2-Yl)-3,4-Dihydro-2H-Benzo[B][1,4]Oxazine-7-Sulfonamide

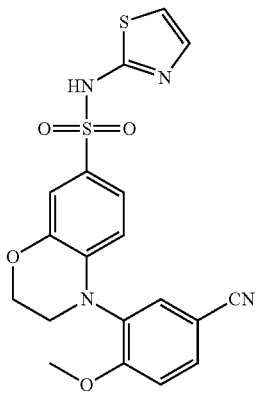 [SMILES: COc1ccc(C#N)cc1N1CCOc2cc(S(=O)(=O)Nc3nccs3)ccc21]

A vial was charged with N-(4-methoxybenzyl)-N-(thiazol-2-yl)-3,4-dihydro-2H-benzo[b][1,4]oxazine-7-sulfonamide (INTERMEDIate M) (80 mg, 0.192 mmol), 3-bromo-4-methoxybenzonitrile (81 mg, 0.383 mmol), Xantphos (22.17 mg, 0.038 mmol), Pd$_2$(dba)$_3$ (17.55 mg, 0.019 mmol), and cesium carbonate (187 mg, 0.575 mmol). The vessel was flushed with Ar (g), then 1,4-dioxane (1916 µl) was added. The vessel was sealed and placed in a 100° C. heating bath for 20 h. The mixture was filtered through celite with the aid of EtOAc. The filtrate was concentrated, and the residue was dissolved in DCM (1 mL) and TFA (0.5 mL). After 4 h, mixture was diluted with MeOH, then concentrated. The residue was purified by chromatography on silica gel (12-g Redi-Sep Gold column, 0-5% MeOH/DCM). The material this obtained was further purified by chromatography on silica gel (12-g Redi-Sep Gold column, 50-100% EtOAc/Heptane). The resulting solid was taken up in EtOAc, sonicated, and filtered. The collected solid was washed with EtOAc (2×), dried under a stream of N$_2$ (g), then dried under vacuum to give 4-(5-cyano-2-methoxyphenyl)-N-(thiazol-2-yl)-3,4-dihydro-2H-benzo[b][1,4]oxazine-7-sulfonamide (58 mg, 0.135 mmol, 70.6% yield) as an off-white solid: $^1$H NMR (400 MHz, DMSO-$d_6$) δ=12.55 (br. s., 1 H), 7.92-7.77 (m, 2 H), 7.34 (d, J=8.5 Hz, 1 H), 7.22 (d, J=4.5 Hz, 1 H), 7.16-7.06 (m, 2 H), 6.78 (d, J=4.5 Hz, 1 H), 6.21 (d, J=8.4 Hz, 1 H), 4.30 (br. s., 2 H), 3.85 (s, 3 H), 3.63 (br. s., 2 H); m/z (ESI) 429.2 (M+H)$^+$.

Example 226

4-(4-Cyano-2-Methylphenyl)-N-(Thiazol-2-Yl)-3,4-Dihydro-2H-Benzo[B][1,4]Oxazine-7-Sulfonamide

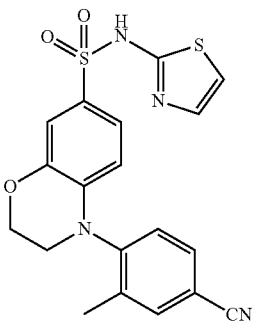 [SMILES: Cc1cc(C#N)ccc1N1CCOc2cc(S(=O)(=O)Nc3nccs3)ccc21]

EXAMPLE 226 was synthesized in a similar manner to EXAMPLE 167, using 4-bromo-3-methylbenzonitrile instead of 4-bromo-2-(trifluoromethoxy)benzonitrile to yield 4-(4-cyano-2-methylphenyl)-N-(thiazol-2-yl)-3,4-dihydro-2H-benzo[b][1,4]oxazine-7-sulfonamide (0.089 g, 0.216 mmol, 90% yield) as an off-white solid. $^1$H NMR (400 MHz, DMSO-$d_6$) δ ppm 2.18 (s, 3 H) 3.51-3.66 (m, 1 H) 3.73 (s, 1 H) 4.36 (t, J=4.21 Hz, 2 H) 6.15 (d, J=8.41 Hz, 1 H) 6.78 (d, J=4.60 Hz, 1 H) 7.11 (dd, J=8.51, 2.15 Hz, 1 H) 7.16 (d, J=2.05 Hz, 1 H) 7.21 (d, J=4.60 Hz, 1 H) 7.48 (d, J=8.22 Hz, 1 H) 7.77 (dd, J=8.22, 1.57 Hz, 1 H) 7.86 (d, J=1.37 Hz, 1 H) 12.55 (br. s., 1 H). m/z (ESI) 413.0 (M+H)$^+$.

Example 228

N,N-Diethyl-2-(7-(N-(Thiazol-2-Yl)Sulfamoyl)-2H-Benzo[B][1,4]Oxazin-4(3H)-Yl)Acetamide

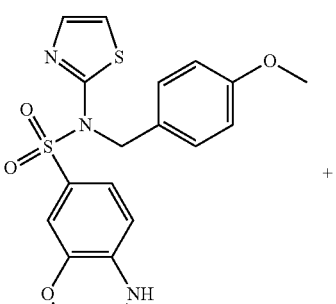

Intermediate M

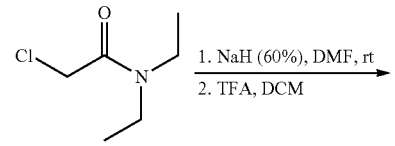

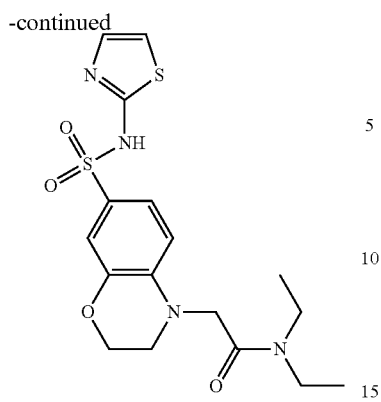

To a flask charged with N-(4-methoxybenzyl)-N-(thiazol-2-yl)-3,4-dihydro-2H-benzo[b][1,4]oxazine-7-sulfonamide (INTERMEDIate M) (0.104 g, 0.25 mmol) was added DMF (0.7 ml), and cooled in an ice water bath prior to the addition of NaH (60% in mineral oil) (10 mg, 0.25 mmol). The mixture was stirred for 45 min at 0° C., then 30 min at room temperature. To a separate vial charged with 2-chloro-N,N-diethylacetamide (37 mg, 0.25 mmol) was added DMF (0.3 ml), then the solution of deprotonated amine. The resulting mixture was sealed and shaken at rt overnight. The mixture was quenched with the addition of MeOH, then dried under reduced pressure and purified with NH$_4$OH modified RP-HPLC affording N,N-diethyl-2-(7-(N-(thiazol-2-yl)sulfamoyl)-2H-benzo[b][1,4]oxazin-4(3 H)-yl)acetamide (27.4 mg, 27%). $^1$H NMR (500 MHz, DMSO-d$_6$) δ ppm 1.01 (t, J=7.05 Hz, 3 H) 1.18 (t, J=7.10 Hz, 3 H) 3.21-3.27 (m, 2 H) 3.36 (br. s., 2 H) 3.39-3.45 (m, 2 H) 4.18 (t, J=4.35 Hz, 2 H) 4.26 (s, 2 H) 6.49 (d, J=8.71 Hz, 1 H) 6.75 (d, J=4.35 Hz, 1 H) 7.00 (d, J=2.06 Hz, 1 H) 7.13 (dd, J=8.59, 2.06 Hz, 1 H) 7.19 (d, J=4.58 Hz, 1 H) 12.47 (br. s., 1 H). m/z (ESI) 411.1 (M+H)$^+$.

Example 229

4-(2-(2-Methoxyethoxy)Phenyl)-N-(Thiazol-2-Yl)-3,4-Dihydro-2H-Benzo[B][1,4]Oxazine-7-Sulfonamide

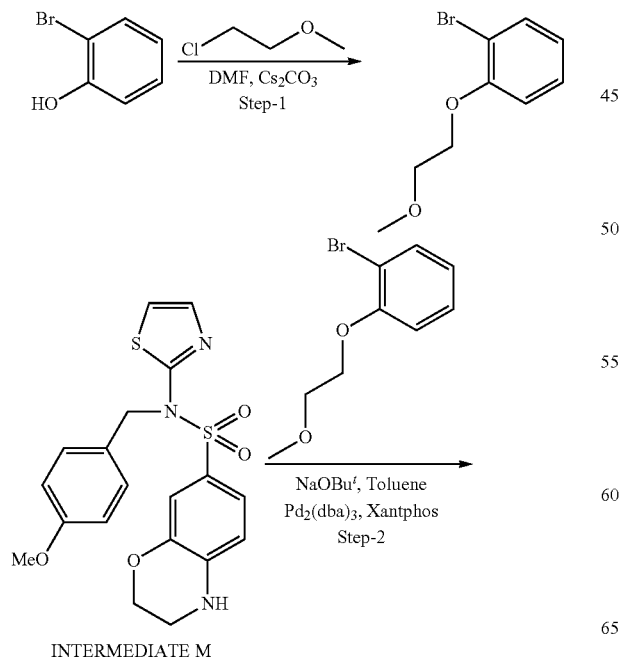

INTERMEDIATE M

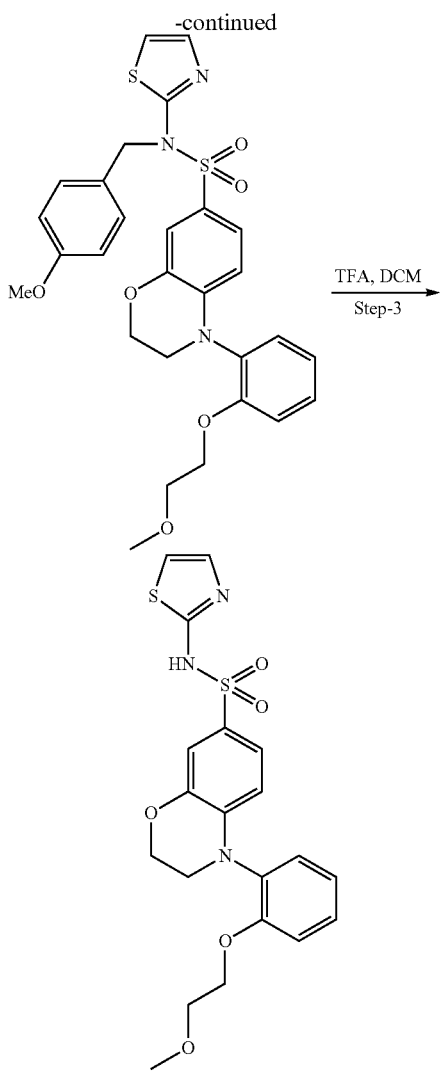

Step 1: 1-Bromo-2-(2-Methoxyethoxy)Benzene

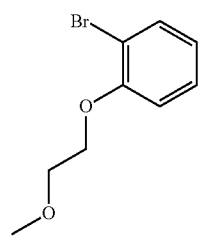

To a solution of 2-bromophenol (500.0 mg, 2.89 mmol) in DMF (5 mL) was added cesium carbonate (2.82 g, 8.67 mmol). To this mixture was added 1-chloro-2-methoxyethane (0.26 mL, 2.89 mmol, Aldrich) and the mixture was heated at 90° C. for 4 h. After completion, the reaction mixture was diluted with water (3 mL) and extracted with ethyl acetate (2×10 mL). The organic layer was dried over sodium sulfate and concentrated under reduced pressure to get 1-bromo-2-(2-methoxyethoxyl)benzene (400 mg, 60.2%) as clear liquid that was used as such for next step without any purification. $^1$H NMR (400 MHz, DMSO) δ 7.57 (dd, J=7.9, 1.5 Hz, 1H), 7.39-7.24 (m, 1H), 7.13-7.05 (m, 1H), 6.89 (td, J=7.7, 1.2 Hz, 1H), 4.17 (t, J=4.6 Hz, 2H), 3.69 (t, J=4.6 Hz, 2H), 3.33 (s, 3H). MS (ESI, positive ion) m/z: 231.08 (M+1).

Step 2: N-(4-Methoxybenzyl)-4-(2-(2-Methoxyethoxy)Phenyl)-N-(Thiazol-2-Yl)-3,4-Dihydro-2H-Benzo[B][1,4]Oxazine-7-Sulfonamide

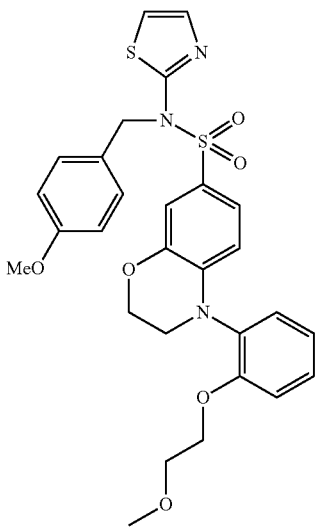 [SMILES: COCCOc1ccccc1N1CCOc2cc(S(=O)(=O)N(Cc3ccc(OC)cc3)c3nccs3)ccc21]

A mixture of 1-bromo-2-(2-methoxyethoxyl)benzene (302.0 mg, 1.31 mmol), INTERMEDIate M (500 mg, 1.19 mmol), Pd$_2$(dba)$_3$ (76.0 mg, 0.0837 mmol), Xantphos (69.0 mg, 0.119 mmol) and sodium-tert-butoxide (229.0 mg, 2.39 mmol) in toluene (10 mL) was degassed with nitrogen for 10 minutes. The reaction mixture was subjected for heating at 100° C. for 1 h under microwave. After completion, the reaction mixture was diluted with water (10 mL) and extracted with ethyl acetate (3×15 mL). The organic layer was dried over sodium sulfate and concentrated under reduced pressure to obtain the crude material which was purified by combiflash column chromatography (column size: 12 g; elution: 12% ethyl acetate in hexane) to get N-(4-methoxybenzyl)-4-(2-(2-methoxyethoxyl)phenyl)-N-(thiazol-2-yl)-3,4-dihydro-2H-benzo[b][1,4]oxazine-7-sulfonamide (300 mg, 44.2%) as yellow solid. MS (ESI, positive ion) m/z: 568.03 (M+1).

Step 3, Example 229: 4-(2-(2-Methoxyethoxy)Phenyl)-N-(Thiazol-2-Yl)-3,4-Dihydro-2H-Benzo[B][1,4]Oxazine-7-Sulfonamide

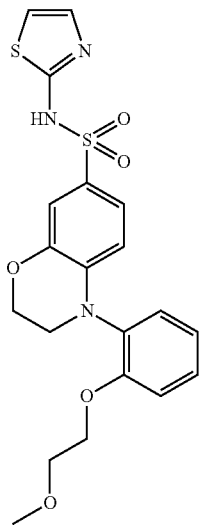 [SMILES: COCCOc1ccccc1N1CCOc2cc(S(=O)(=O)Nc3nccs3)ccc21]

To a solution of N-(4-methoxybenzyl)-4-(2-(2-methoxyethoxyl)phenyl)-N-(thiazol-2-yl)-3,4-dihydro-2H-benzo[b][1,4]oxazine-7-sulfonamide (300 mg, 0.529 mmol) in DCM (6 mL) was added TFA (3 mL) at 0° C. The reaction mixture was stirred at ambient temperature for 2 h. After completion, the reaction mixture was quenched with saturated sodium bicarbonate solution (10 mL) and extracted with DCM (2×10 mL). The organic layer was dried over sodium sulfate and concentrated reduced pressure to obtain the crude material (36% by LCMS) that was purified by prep purification to obtain 4-(2-(2-methoxyethoxyl)phenyl)-N-(thiazol-2-yl)-3,4-dihydro-2H-benzo[b][1,4]oxazine-7-sulfonamide (38 mg, 16.1%) as white solid. $^1$H NMR (400 MHz, DMSO) δ 12.49 (s, 1H), 7.38-7.25 (m, 2H), 7.25-7.13 (m, 2H), 7.14-6.95 (m, 3H), 6.75 (d, J=4.6 Hz, 1H), 6.22 (d, J=8.5 Hz, 1H), 4.28 (t, J=4.3 Hz, 2H), 4.07 (dd, J=5.6, 3.5 Hz, 2H), 3.62 (t, J=4.1 Hz, 2H), 3.47 (t, J=4.5 Hz, 2H), 3.10 (s, 3H); MS (ESI, positive ion) m/z: 448.09 (M+1).

Example 230

4-(2-(Methylsulfonyl)Phenyl)-N-(Thiazol-2-Yl)-3,4-Dihydro-2H-Benzo[B][1,4]Oxazine-7-Sulfonamide

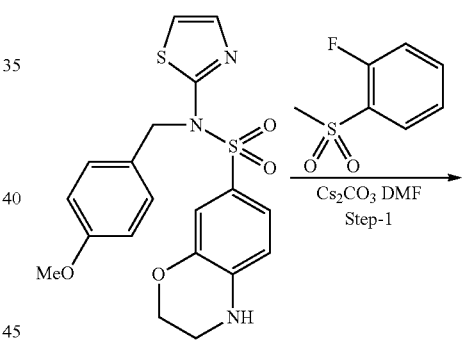

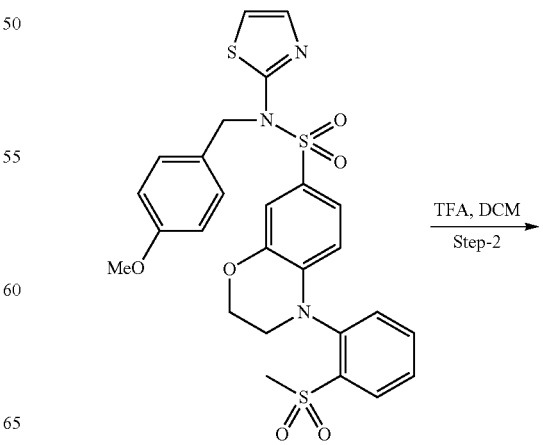

259
-continued

Step 1: N-(4-Methoxybenzyl)-4-(2-(Methylsulfonyl)Phenyl)-N-(Thiazol-2-Yl)-3,4-Dihydro-2H-Benzo[B][1,4]Oxazine-7-Sulfonamide

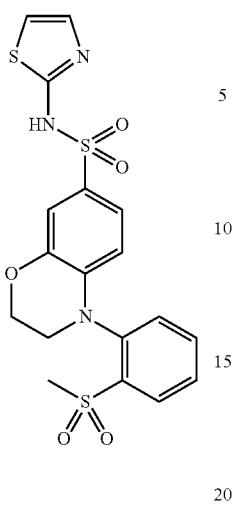

To a solution of INTERMEDIate M (300 mg, 0.717 mmol) and 1-fluoro-2-(methylsulfonyl)benzene (149.0 mg, 0.861 mmol, Apollo) in DMF was added cesium carbonate (467.0 mg, 1.43 mmol). The reaction mixture was heated at 90° C. for 16 h. After completion, the reaction mixture was diluted with water (10 mL) and extracted with ethyl acetate (2×10 mL). The organic layer was dried over sodium sulfate and concentrated under reduced pressure to obtain the crude material which was purified by combiflash column chromatography (column size: 12 g; elution: 12% ethyl acetate in hexane) to provide N-(4-methoxybenzyl)-4-(2-(methylsulfonyl)phenyl)-N-(thiazol-2-yl)-3,4-dihydro-2H-benzo[b][1,4]oxazine-7-sulfonamide (200 mg, 48.8%) as yellow solid. MS (ESI, positive ion) m/z: 572.02 (M+1).

260

Step 2, Example 230: 4-(2-(Methylsulfonyl)Phenyl)-N-(Thiazol-2-Yl)-3,4-Dihydro-2H-Benzo[B][1,4]Oxazine-7-Sulfonamide To a solution of N-(4-methoxybenzyl)-4-(2-(methylsulfonyl)phenyl)-N-(thiazol-2-yl)-3,4-dihydro-2H-benzo[b][1,4]oxazine-7-sulfonamide (200 mg, 0.350 mmol) in DCM (5 mL) was added TFA (2 mL) at 0° C. The reaction mixture was stirred at ambient temperature for 2 h. After completion, the reaction mixture was quenched with saturated aqueous sodium bicarbonate solution (10 mL) and extracted with DCM (2×10 mL). The organic layer was dried over sodium sulfate and concentrated under reduced pressure to obtain the crude material (71% by LCMS) that was purified by prep purification to obtain 4-(2-(methylsulfonyl)phenyl)-N-(thiazol-2-yl)-3,4-dihydro-2H-benzo[b][1,4]oxazine-7-sulfonamide (28 mg, 17.8%) as white solid. $^1$H NMR (400 MHz, DMSO) δ 12.51 (s, 1H), 8.07 (d, J=7.8 Hz, 1H), 7.85 (t, J=7.7 Hz, 1H), 7.77-7.54 (m, 2H), 7.19 (dd, J=15.2, 3.4 Hz, 2H), 7.08 (dd, J=8.7, 2.1 Hz, 1H), 6.77 (d, J=4.7 Hz, 1H), 6.21 (d, J=8.5 Hz, 1H), 4.42 (dt, J=10.9, 3.3 Hz, 1H), 4.34 (dd, J=10.9, 5.4 Hz, 1H), 3.61 (t, J=3.9 Hz, 2H), 3.18 (s, 3H); MS (ESI, positive ion) m/z: 452.0 (M+1).

Example 231

4-(2-(Pyrimidin-5-Yl)Phenyl)-N-(Thiazol-2-Yl)-3,4-Dihydro-2H-Benzo[B][1,4]Oxazine-7-Sulfonamide

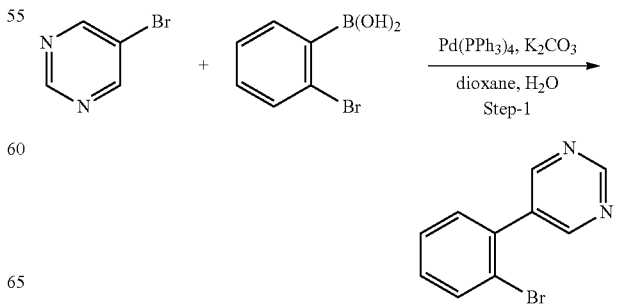

-continued

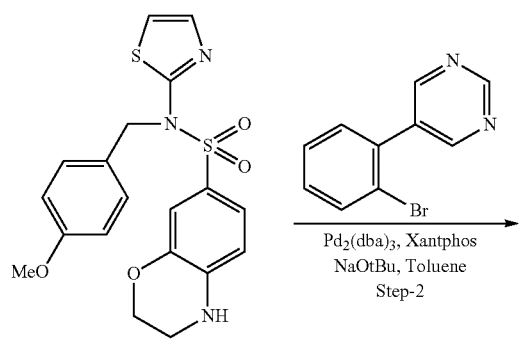

INTERMEDIATE M

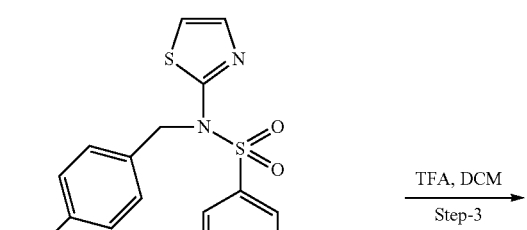

TFA, DCM
Step-3

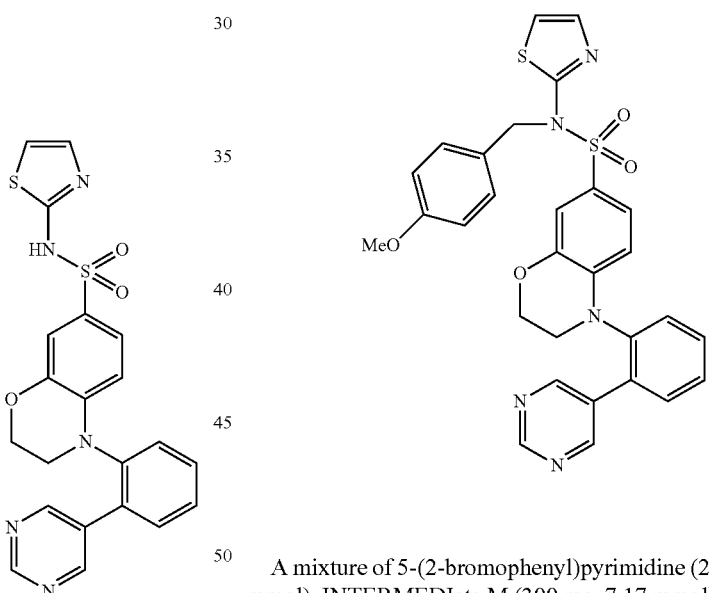

Step 1: 5-(2-Bromophenyl)Pyrimidine

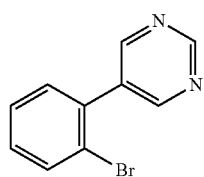 [SMILES: Brc1ccccc1-c1cncnc1]

A mixture of 5-bromopyrimidine (500 mg, 3.14 mmol, Aldrich), (2-bromophenyl)boronic acid (947 mg, 4.71 mmol, Aldrich), Pd(PPh$_3$)$_4$ (363 mg, 0.314 mmol, GLR) and potassium carbonate (2.17 g, 15.7 mmol, Qualigens) in 1,4-dioxane:water (5.8 mL:2.9 mL) was degassed for 10 min. The reaction mixture was subjected to microwave heating for 30 minutes at 100° C. After completion, the reaction mixture was diluted with water (10 mL) and ethyl acetate (25 mL). The layers were separated. The organic layer was dried over sodium sulfate and concentrated under reduced pressure to obtain crude material which was purified by combiflash column chromatography (column size: 12 g; elution: 15% ethyl acetate in hexane) to get 5-(2-bromophenyl)pyrimidine (400 mg, 30.5%) as yellow solid. $^1$H NMR (400 MHz, CDCl$_3$) δ 9.24 (s, 1H), 8.83 (s, 2H), 7.73 (d, J=7.9 Hz, 1H), 7.48-7.42 (m, 1H), 7.33 (d, J=7.4 Hz, 2H); MS (ESI, positive ion) m/z: 234.98 (M+1).

Step 2: N-(4-Methoxybenzyl)-4-(2-(Pyrimidin-5-Yl)
Phenyl)-N-(Thiazol-2-Yl)-3,4-Dihydro-2H-Benzo
[B][1,4]Oxazine-7-Sulfonamide A mixture of 5-(2-bromophenyl)pyrimidine (251 mg, 1.07 mmol), INTERMEDIate M (300 mg, 7.17 mmol), Pd$_2$(dba)$_3$ (65 mg, 0.0717 mmol), Xantphos (82 mg, 0.143 mmol) and sodium-tert-butoxide (137 mg, 1.43 mmol) in toluene (8 mL) was degassed for 10 min. The reaction mixture was subjected to microwave heating for 1 h at 100° C. After completion, the reaction mixture was diluted with water (10 mL) and extracted with ethyl acetate (3×15 mL). The organic layer was dried over sodium sulfate and concentrated under reduced pressure to obtain the crude material which was purified by combiflash column chromatography (column size: 12 g; elution: 35% ethyl acetate in hexane) to get N-(4-methoxybenzyl)-4-(2-(pyrimidin-5-yl)phenyl)-N-(thiazol-2-yl)-3,4-dihydro-2H-benzo[b][1,4]oxazine-7-sulfonamide as yellow solid (250 mg, 41.0%); MS (ESI, positive ion) m/z: 572.0 (M+1).

263

Step 3, Example 231: 4-(2-(Pyrimidin-5-Yl)Phenyl)-N-(Thiazol-2-Yl)-3,4-Dihydro-2H-Benzo[B][1,4]Oxazine-7-Sulfonamide

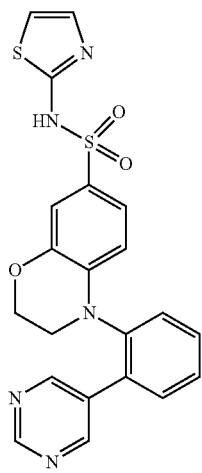 [SMILES: O=S(=O)(Nc1nccs1)c1ccc2c(c1)OCCN2c1ccccc1-c1cncnc1]

To a solution of N-(4-methoxybenzyl)-4-(2-(pyrimidin-5-yl)phenyl)-N-(thiazol-2-yl)-3,4-dihydro-2H-benzo[b][1,4]oxazine-7-sulfonamide (250 mg, 0.437 mmol) in DCM (5 mL) was added TFA (2 mL) at 0° C. The reaction mixture was stirred at ambient temperature for 2 h. After completion, the reaction mixture was quenched with saturated aqueous sodium bicarbonate solution (8 mL) and extracted with DCM (2×10 mL). The organic layer was dried over sodium sulfate and concentrated under reduced pressure to obtain the crude material (69.61% by LCMS) that was purified by prep purification to obtain 4-(2-(pyrimidin-5-yl)phenyl)-N-(thiazol-2-yl)-3,4-dihydro-2H-benzo[b][1,4]oxazine-7-sulfonamide (60 mg, 30.4%) as white solid. $^1$H NMR (400 MHz, DMSO) δ 12.51 (s, 1H), 9.06 (s, 1H), 8.83 (s, 2H), 7.61 (td, J=6.9, 2.0 Hz, 2H), 7.58-7.48 (m, 2H), 7.21 (d, J=4.7 Hz, 1H), 7.01 (td, J=4.8, 4.2, 1.8 Hz, 2H), 6.77 (d, J=4.7 Hz, 1H), 6.21 (d, J=9.0 Hz, 1H), 4.30 (dt, J=11.1, 3.2 Hz, 1H), 4.03 (ddd, J=10.9, 8.6, 2.7 Hz, 1H), 3.76 (ddd, J=11.3, 8.3, 3.0 Hz, 1H), 3.44 (dt, J=12.3, 3.1 Hz, 1H); MS (ESI, positive ion) m/z: 452.1 (M+1).

Example 232

4-(4-Cyano-2-Methoxyphenyl)-3-Oxo-N-(Thiazol-2-Yl)-3,4-Dihydro-2H-Benzo[B][1,4]Oxazine-7-Sulfonamide

STEP 1

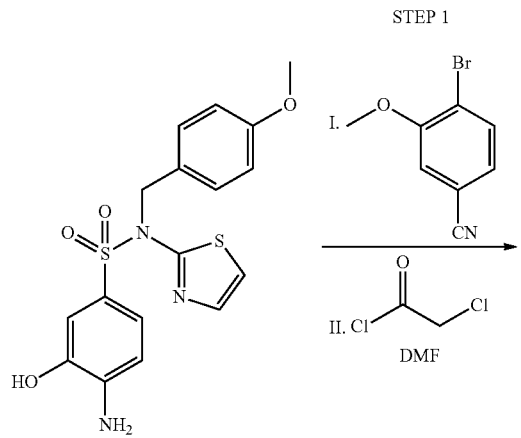

INTERMEDIATE AD

264

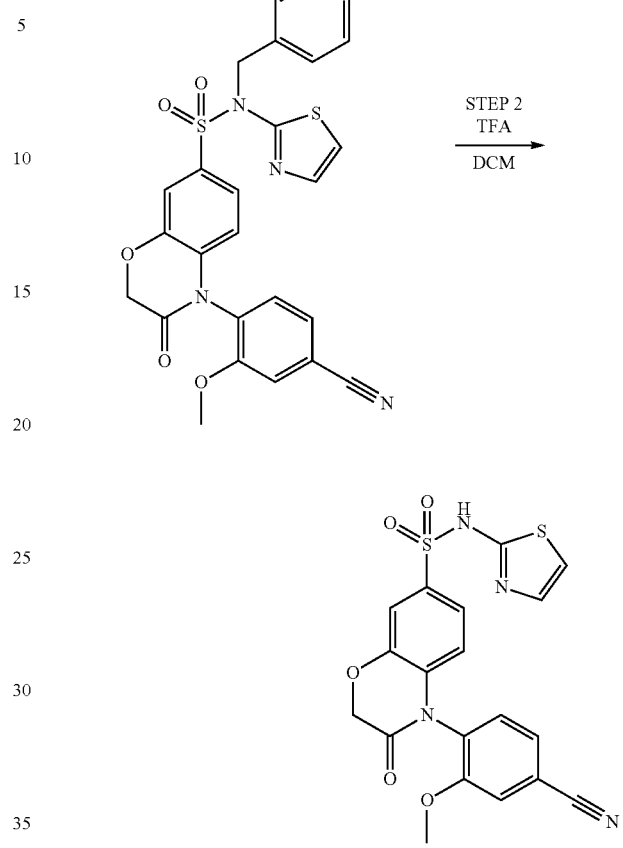

Step 1: 4-(4-Cyano-2-Methoxyphenyl)-N-(4-Methoxybenzyl)-3-Oxo-N-(Thiazol-2-Yl)-3,4-Dihydro-2H-Benzo[B][1,4]Oxazine-7-Sulfonamide

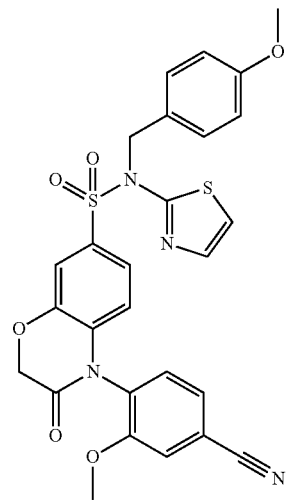 [SMILES: COc1ccc(CN(c2nccs2)S(=O)(=O)c2ccc3c(c2)OCC(=O)N3c2ccc(C#N)cc2OC)cc1]

A microwave vial was charged with 4-amino-3-hydroxy-N-(4-methoxybenzyl)-N-(thiazol-2-yl)benzenesulfonamide (0.185 g, 0.472 mmol) (INTERMEDIate AD), cesium carbonate (0.384 g, 1.179 mmol), 4-bromo-3-methoxybenzonitrile (0.05 g, 0.236 mmol, Combi Blocks) and copper(i) iodide (0.011 g, 0.059 mmol). The vial was sealed and flushed with argon, and wrapped with aluminum foil to exclude light, then DMF (0.5 mL) was added. The reaction was heated to 110° C. for 2 hr to give intermediate 4-((4-cyano-2-methoxyphenyl)amino)-3-hydroxy-N-(4-methoxybenzyl)-N-(thiazol-2-yl)benzenesulfonamide. The reaction was cooled to rt, and chloroacetic acid chloride was added dropwise (0.038 ml, 0.472 mmol). The solution was maintained at rt for 30 min. At this time, 10 mL of saturated ammonium chloride solution was added, and the mixture was further diluted with 10 mL of DCM. The layers were separated and the aqueous layer was extracted with DCM (2×10 mL). To the aqueous layer was added n-(2-hydroxyethyl)ethylenediaminetriacetic acid, trisodium salt hydrate (500 mg, Sigma Aldrich) to aqueous to decomplex Cu from the product. The resulting aqueous solution was extracted with DCM (1×10 mL). The combined organics were dried (Na$_2$SO$_4$), filtered, and concentrated in vacuo. The crude product, 4-(4-cyano-2-methoxyphenyl)-N-(4-methoxybenzyl)-3-oxo-N-(thiazol-2-yl)-3,4-dihydro-2H-benzo[b][1,4]oxazine-7-sulfonamide (0.133 g, 0.236 mmol, 100% yield) was taken forward without further purification.

Step 2, Example 232: 4-(4-Cyano-2-Methoxyphenyl)-3-Oxo-N-(Thiazol-2-Yl)-3,4-Dihydro-2H-Benzo[B][1,4]Oxazine-7-Sulfonamide

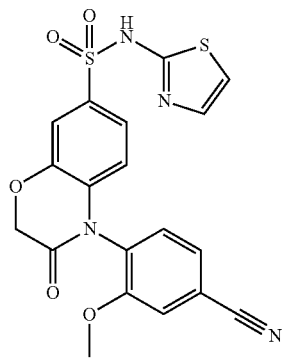 [SMILES: COc1cc(C#N)ccc1N1C(=O)COc2cc(S(=O)(=O)Nc3nccs3)ccc21]

Dissolved 4-(4-cyano-2-methoxyphenyl)-N-(4-methoxybenzyl)-3-oxo-N-(thiazol-2-yl)-3,4-dihydro-2H-benzo[b][1,4]oxazine-7-sulfonamide (133 mg, 0.236 mmol) in 500 µl of DCM in a 10 mL rbf (wrapped with aluminum foil to exclude light) and added trifloroacetic acid (500 µl, 5.91 mmol). The solution was maintained at rt for 30 min until reaction was complete by LCMS. The reaction mixture was concentrated via rotary evaporation then purified using reverse-phase HPLC with a Waters-Xbridge C18, 19×100 mm, 10 µm column with a gradient 5-95% acetonitrile and water with 0.1% NHOH to give 4-(4-cyano-2-methoxyphenyl)-3-oxo-N-(thiazol-2-yl)-3,4-dihydro-2H-benzo[b][1,4]oxazine-7-sulfonamide (23 mg, 0.052 mmol, 22% yield). 1H NMR (500 MHz, DMSO-d6) δ ppm 3.78 (s, 3 H) 4.89 (s, 2 H) 6.39 (d, J=8.48 Hz, 1 H) 6.80 (d, J=4.47 Hz, 1 H) 7.23 (d, J=4.47 Hz, 1 H) 7.28-7.35 (m, 1 H) 7.35-7.49 (m, 1 H) 7.53-7.66 (m, 2 H) 7.80 (s, 1 H). m/z ESI 441.0 (M−H)$^-$.

Example 233

4-(4-Chloro-2-Methoxyphenyl)-3-Oxo-N-(Thiazol-2-Yl)-3,4-Dihydro-2H-Benzo[B][1,4]Oxazine-7-Sulfonamide

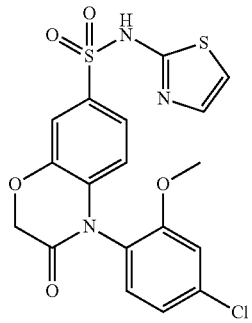 [SMILES: COc1cc(Cl)ccc1N1C(=O)COc2cc(S(=O)(=O)Nc3nccs3)ccc21]

EXAMPLE 233 was synthesized in the same manner as EXAMPLE 232, using 2-bromo-5-chloroanisole instead of 4-bromo-3-methoxybenzonitrile. $^1$H NMR (400 MHz, DMSO-d$_6$) δ ppm 3.74 (s, 3 H) 4.88 (s, 2 H) 6.42 (d, J=8.41 Hz, 1 H) 6.83 (d, J=4.60 Hz, 1 H) 7.19 (dd, J=8.36, 2.20 Hz, 1 H) 7.26 (d, J=4.60 Hz, 1 H) 7.31-7.40 (m, 4 H) 12.74 (br. s., 1 H). m/z ESI 452.1 (M+H)$^+$.

Example 234

4-(2-Cyano-4-(Trifluoromethyl)Phenyl)-3-Oxo-N-(Thiazol-2-Yl)-3,4-Dihydro-2H-Benzo[B][1,4]Oxazine-7-Sulfonamide

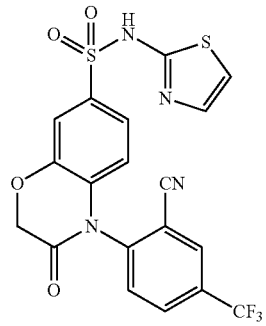 [SMILES: N#Cc1cc(C(F)(F)F)ccc1N1C(=O)COc2cc(S(=O)(=O)Nc3nccs3)ccc21]

EXAMPLE 234 was synthesized in the same manner as EXAMPLE 232, using 2-bromo-5-(trifluoromethyl)benzonitrile (Apollo Scientific, Ltd) instead of 4-bromo-3-methoxybenzonitrile. $^1$H NMR (400 MHz, DMSO-d$_6$) δ ppm 4.92-5.09 (m, 2 H) 6.56 (d, J=8.51 Hz, 1 H) 6.84 (d, J=4.79 Hz, 1 H) 7.26 (d, J=4.40 Hz, 1 H) 7.36 (d, J=8.61 Hz, 1 H) 7.44 (s, 1 H) 7.99 (d, J=8.41 Hz, 1 H) 8.37 (d, J=7.82 Hz, 1 H) 8.69 (s, 1 H) 12.79 (br. s., 1 H). m/z ESI 480.9 (M+H)$^+$.

Example 235

4-(2-Methoxyphenyl)-3-Oxo-N-(Thiazol-2-Yl)-3,4-Dihydro-2H-Benzo[B][1,4]Oxazine-7-Sulfonamide

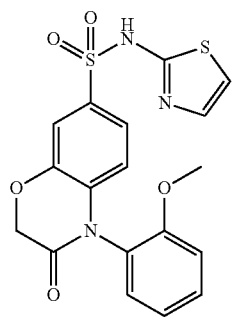 [SMILES: COc1ccccc1N1C(=O)COc2cc(S(=O)(=O)Nc3nccs3)ccc21]

EXAMPLE 235 was synthesized in the same manner as EXAMPLE 232, using 2-iodoanisole instead of 4-bromo-3-methoxybenzonitrile and heating to only 70° C. $^1$H NMR (400 MHz, DMSO-d$_6$) δ ppm 3.71 (s, 3 H) 4.88 (d, J=1.96 Hz, 2 H) 6.37 (d, J=8.41 Hz, 1 H) 6.83 (d, J=4.60 Hz, 1 H) 7.12 (td, J=7.58, 1.17 Hz, 1 H) 7.23-7.28 (m, 2 H) 7.29-7.37 (m, 3 H) 7.51 (dd, J=7.43, 1.76 Hz, 1 H) 12.74 (br. s., 1 H). m/z ESI 417.9 (M+H)$^+$.

Example 236

4-(2-Methoxy-5-(Trifluoromethyl)Phenyl)-3-Oxo-N-(Thiazol-2-Yl)-3,4-Dihydro-2H-Benzo[B][1,4]Oxazine-7-Sulfonamide

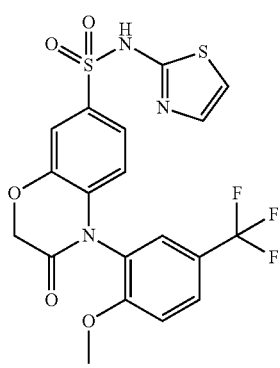 [SMILES: COc1ccc(C(F)(F)F)cc1N1C(=O)COc2cc(S(=O)(=O)Nc3nccs3)ccc21]

4-(2-Methoxy-5-(trifluoromethyl)phenyl)-3-oxo-N-(thiazol-2-yl)-3,4-dihydro-2H-benzo[b][1,4]oxazine-7-sulfonamide (14 mg, 0.029 mmol, 10.52% yield) was prepared in a similar fashion to EXAMPLE 232, starting from INTERMEDIate AD and 2-bromo-1-methoxy-4-(trifluoromethyl)benzene (0.07 g, 0.274 mmol, Apollo Scientific) instead of 4-bromo-3-methoxybenzonitrile. 1H NMR (500 MHz, DMSO-d6) δ ppm 3.81 (s, 3 H) 4.88 (s, 2 H) 6.38 (d, J=8.42 Hz, 1 H) 6.80 (d, J=4.52 Hz, 1 H) 7.23 (d, J=4.52 Hz, 1 H) 7.28-7.40 (m, 1 H) 7.47 (d, J=8.71 Hz, 1 H) 7.83 (s, 1 H) 7.91 (d, J=8.71 Hz, 1 H). m/z ESI 486.0 (M+H)$^+$.

Example 238

4-(2-Methoxyphenyl)-N-(1,2,4-Thiadiazol-5-Yl)-3,4-Dihydro-2H-Benzo[B][1,4]Oxazine-7-Sulfonamide

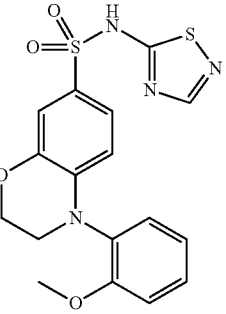

A vial was charged with N-(1,2,4-thiadiazol-5-yl)-3,4-dihydro-2H-benzo[b][1,4]oxazine-7-sulfonamide (94.2 mg, 0.316 mmol) (INTERMEDIate Z), Xantphos (36.5 mg, 0.063 mmol), Pd$_2$(dba)$_3$ (28.9 mg, 0.032 mmol), and sodium tert-butoxide (91 mg, 0.947 mmol). The vial was flushed with Ar (g), then toluene (1579 µl) and 1-bromo-2-methoxybenzene (Aldrich Inc., St. Louis, Mo., 58.5 µl, 0.474 mmol) were added. The vial was heated to 130° C. for 6 h in a Biotage Initiator microwave reactor. The mixture was treated with 5 drops of AcOH, then diluted with MeOH and filtered through celite. The filtrate was concentrated, and the residue was purified by chromatography on silica gel (25-g Interchim column, 0-5% MeOH/DCM). The resulting solid was taken up in DCM/MeOH and loaded onto a 1-g PEAX column (Biotage, LLC). The column was eluted with MeOH, then with a 10% conc. HCl/MeOH solution. The acidic fraction was concentrated to give ca. 28 mg of a yellow oily solid. The material was purified by chromatography on silica gel (12-g Redi-Sep Gold column, 3% MeOH/DCM) to give 4-(2-methoxyphenyl)-N-(1,2,4-thiadiazol-5-yl)-3,4-dihydro-2H-benzo[b][1,4]oxazine-7-sulfonamide (11 mg, 0.027 mmol, 8.61% yield) as an off-white solid. $^1$H NMR (400 MHz, DMSO-d$_6$) δ=8.41 (s, 1 H), 7.39-7.26 (m, 2 H), 7.18 (dd, J=1.1, 8.3 Hz, 1 H), 7.09 (qd, J=2.2, 4.5 Hz, 2 H), 7.04 (dt, J=1.3, 7.6 Hz, 1 H), 6.21-6.15 (m, 1 H), 4.30 (t, J=4.3 Hz, 2 H), 3.75 (s, 3 H), 3.65-3.59 (m, 2 H). m/z (ESI) 405.2 (M+H)±.

Example 239

4-(2-Bromo-4-(Trifluoromethyl)Phenyl)-3-Oxo-N-(Thiazol-2-Yl)-3,4-Dihydro-2H-Benzo[B][1,4]Oxazine-7-Sulfonamide

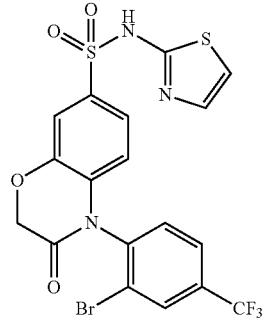 [SMILES: O=C1COc2cc(S(=O)(=O)Nc3nccs3)ccc2N1c1ccc(C(F)(F)F)cc1Br]

EXAMPLE 239 was synthesized in the same manner as EXAMPLE 232, running STEP 1 at 25° C. for 16 h (instead of 110° C. for 2 h), and using 2-bromo-1-iodo-4-(trifluoromethyl)benzene (Oakwood Products) instead of 4-bromo-3- methoxybenzonitrile. The intermediate from STEP 1, 4-(2-bromo-4-(trifluoromethyl)phenyl)-N-(4-methoxybenzyl)-3-oxo-N-(thiazol-2-yl)-3,4-dihydro-2H-benzo[b][1,4]oxazine-7-sulfonamide, was purified via MPLC silica gel chromatography with a gradient of (0-100%) Hexanes:EtOAc. The final product, 4-(2-bromo-4-(trifluoromethyl)phenyl)-3-oxo-n-(thiazol-2-yl)-3,4-dihydro-2h-benzo[b][1,4]oxazine-7-sulfonamide, obtained from STEP 2 was subjected to an aqueous work up, added saturated ammonium chloride (2 mL) and DCM (2 mL), extracted with DCM (3×2 mL), dried over Na2SO4 and concentrated via rotary evaporation to provide 4-(2-bromo-4-(trifluoromethyl)phenyl)-3-oxo-N-(thiazol-2-yl)-3,4-dihydro-2H-benzo[b][1,4]oxazine-7-sulfonamide (18 mg, 0.034 mmol, 73.5% yield) as an offwhite solid. $^1$H NMR (400 MHz, DMSO-$d_6$) δ ppm 4.95 (s, 2 H) 6.39 (d, J=8.51 Hz, 1 H) 6.84 (d, J=4.50 Hz, 1 H) 7.26 (d, J=4.60 Hz, 1 H) 7.35 (dd, J=8.46, 2.01 Hz, 1 H) 7.41 (d, J=2.05 Hz, 1 H) 7.84 (d, J=8.41 Hz, 1 H) 8.03 (dd, J=8.12, 1.86 Hz, 1 H) 8.33 (d, J=1.37 Hz, 1 H). m/z ESI 534.0 (M+H)$^+$.

Example 240

4-(2-Fluoro-4-(Trifluoromethyl)Phenyl)-3-Oxo-N-(Thiazol-2-Yl)-3,4-Dihydro-2H-Benzo[B][1,4]Oxazine-7-Sulfonamide

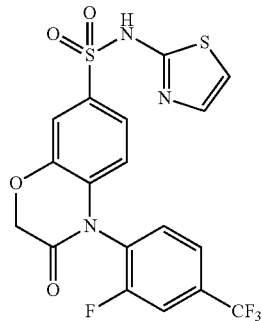 [SMILES: O=C1COc2cc(S(=O)(=O)Nc3nccs3)ccc2N1c1ccc(C(F)(F)F)cc1F]

EXAMPLE 240 was synthesized in the same manner as EXAMPLE 232, running the STEP 1 at 70° C. for 2 h (instead of 110° C. for 2 h), and using 1-bromo-2-fluoro-4-(trifluoromethyl)benzene (Matrix Scientific) instead of 4-bromo-3-methoxybenzonitrile. $^1$H NMR (500 MHz, DMSO-$d_6$) δ ppm 4.67 (br. s., 2 H) 6.79 (d, J=4.47 Hz, 1 H) 7.06-7.17 (m, 1 H) 7.22 (d, J=4.01 Hz, 1 H) 7.27-7.48 (m, 3 H) 7.63 (d, J=11.57 Hz, 1 H) 7.83 (s, 1 H). m/z ESI 474.0 (M+H)$^+$.

Example 241

4-(2-Chloro-4-(Trifluoromethyl)Phenyl)-3-Oxo-N-(Thiazol-2-Yl)-3,4-Dihydro-2H-Benzo[B][1,4]Oxazine-7-Sulfonamide

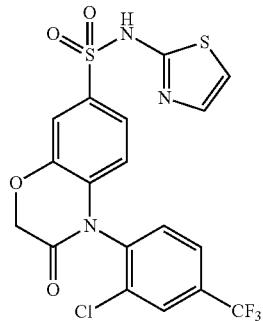 [SMILES: O=C1COc2cc(S(=O)(=O)Nc3nccs3)ccc2N1c1ccc(C(F)(F)F)cc1Cl]

EXAMPLE 241 was synthesized in the same manner as EXAMPLE 232, running STEP 1 at 25° C. for 16 h (instead of 110° C. for 2 h), and using 2-chloro-1-iodo-4-(trifluoromethyl)benzene (Alfa Aesar) instead of 4-bromo-3-methoxybenzonitrile. $^1$H NMR (500 MHz, DMSO-$d_6$) δ ppm 4.92-5.00 (m, 2 H) 6.42 (d, J=8.48 Hz, 1 H) 6.77-6.85 (m, 1 H) 7.16-7.37 (m, 2 H) 7.42 (d, J=1.95 Hz, 1 H) 7.87 (d, J=8.31 Hz, 1 H) 7.99 (d, J=8.30 Hz, 1 H) 8.23 (s, 1 H) m/z ESI 490.0 (M+H)$^+$.

Example 242

4-(2-(1-Hydroxyethyl)Phenyl)-3-Oxo-N-(Thiazol-2-Yl)-3,4-Dihydro-2H-Benzo[B][1,4]Oxazine-7-Sulfonamide

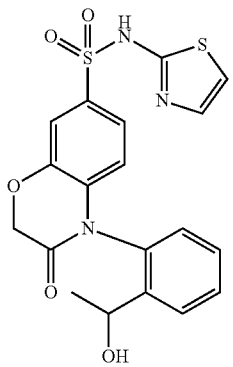 [SMILES: CC(O)c1ccccc1N1C(=O)COc2cc(S(=O)(=O)Nc3nccs3)ccc21]

EXAMPLE 242 was synthesized in the same manner as EXAMPLE 232, using 1-(2-bromophenyl)ethanol (Acros Organics) instead of 4-bromo-3-methoxybenzonitrile. $^1$H NMR (500 MHz, DMSO-$d_6$) δ ppm 1.18 (d, J=6.36 Hz, 3 H) 4.49 (d, J=6.19 Hz, 1 H) 4.80-5.00 (m, 2 H) 6.36 (d, J=8.48 Hz, 1 H) 6.81 (d, J=4.52 Hz, 1 H) 7.10-7.28 (m, 2 H) 7.28-7.46 (m, 3 H) 7.54 (t, J=7.13 Hz, 1 H) 7.73 (d, J=7.85 Hz, 1 H). m/z ESI 432.0 (M+H)$^+$.

Example 243

4-(4-Chloro-2-Cyanophenyl)-N-(Pyrimidin-4-Yl)-3,4-Dihydro-2H-Benzo[B][1,4]Oxazine-7-Sulfonamide

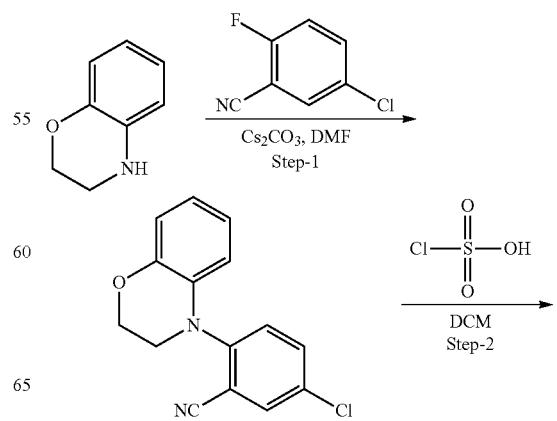

-continued

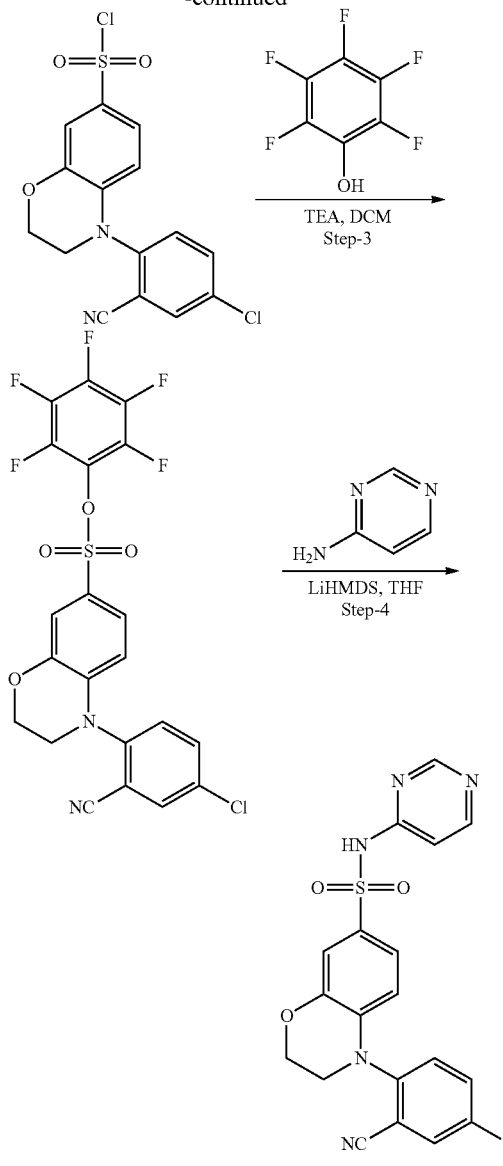

Step 1: 2-(2H-Benzo[B][1,4]Oxazin-4(3H)-Yl)-5-Chlorobenzonitrile

To a solution of 3,4-dihydro-2H-benzo[b][1,4]oxazine (500 mg, 3.69 mmol, Tyger Scientific) and 5-chloro-2-fluorobenzonitrile (573 mg, 3.69 mmol) in DMF (10 mL) was added cesium carbonate (3.61 g, 11.0 mmol). The reaction mixture was heated at 100° C. for 24 h. After completion, the reaction mixture was quenched with ice water (10 mL) and extracted with ethyl acetate (2×15 mL). The organic layer was dried over sodium sulfate and concentrated to get crude material which was purified by column chromatography (12 g column: elution: 5% ethyl acetate in hexane) to provide 2-(2h-benzo[b][1,4]oxazin-4(3h)-yl)-5-chlorobenzonitrile (480 mg, 48.4%) as yellow solid. LCMS (ESI) m/z 270.02 (M+H).

Step 2: 4-(4-Chloro-2-Cyanophenyl)-3,4-Dihydro-2H-Benzo[B][1,4]Oxazine-7-Sulfonyl Chloride

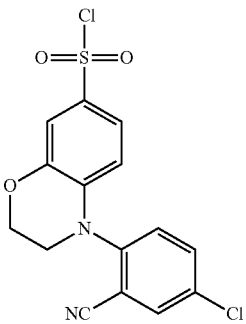 [SMILES: N#Cc1cc(Cl)ccc1N1CCOc2cc(S(=O)(=O)Cl)ccc21]

To a solution of 2-(2h-benzo[b][1,4]oxazin-4(3h)-yl)-5-chlorobenzonitrile (480 mg, 1.77 mmol) in DCM (5 mL) was added chlorosulfonic acid (0.47 mL, 7.11 mmol) at 0° C. The reaction mixture was stirred at room temperature for 2 h. After completion, reaction mixture was poured into ice water (10 mL), quenched with solid sodium bicarbonate (pH~9-10) and extracted with ethyl acetate (2×15 mL). The organic layer was dried over sodium sulfate and concentrated under reduced pressure to provide 4-(4-chloro-2-cyanophenyl)-3,4-dihydro-2H-benzo[b][1,4]oxazine-7-sulfonyl chloride (480 mg, 73.3%) as yellow solid. The compound was used in the next step without further purification. LCMS (ESI) m/z: 367.98 (M+H).

Step 3: Perfluorophenyl 4-(4-Chloro-2-Cyanophenyl)-3,4-Dihydro-2H-Benzo[B][1,4]Oxazine-7-Sulfonate

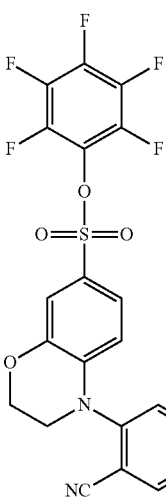

To a solution of 4-(4-chloro-2-cyanophenyl)-3,4-dihydro-2H-benzo[b][1,4]oxazine-7-sulfonyl chloride (480 mg, 1.30 mmol) in DCM (5 mL) was added pentafluorophenol (240 mg, 1.30 mmol) at 0° C. Triethylamine (0.27 mL, 1.95 mmol) was added at 0° C. and the reaction mixture was stirred at room temperature for 1 h. After completion, the reaction mixture was diluted with DCM (3 mL) and concentrated under reduced pressure. The crude mass was purified by combi flash column chromatography (12 g column; elution: 7% ethyl acetate in hexane) to provide perfluorophenyl 4-(4- chloro-2-cyanophenyl)-3,4-dihydro-2H-benzo[b][1,4]ox-azine-7-sulfonate (370 mg, 54.9%) as clear liquid. $^1$H NMR (400 MHz, DMSO) δ 8.22 (d, J=2.5 Hz, 1H), 7.96 (dd, J=8.7, 2.5 Hz, 1H), 7.70 (d, J=8.7 Hz, 1H), 7.38 (d, J=2.2 Hz, 1H), 7.31 (dd, J=8.7, 2.3 Hz, 1H), 6.59 (d, J=8.7 Hz, 1H), 4.41 (s, 2H), 3.86 (s, 2H); LCMS (ESI) m/z; 516.02 (M+H).

Step 4, Example 243: 4-(4-Chloro-2-Cyanophenyl)-N-(Pyrimidin-4-Yl)-3,4-Dihydro-2H-Benzo[B][1,4]Oxazine-7-Sulfonamide

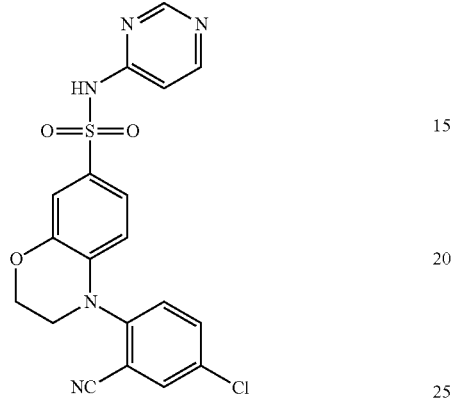

To a solution of perfluorophenyl 4-(4-chloro-2-cyanophenyl)-3,4-dihydro-2H-benzo[b][1,4]oxazine-7-sulfonate (370 mg, 0.717 mmol) and 4-amino pyrimidine (102 mg, 1.07 mmol) in THF (5 mL) was added LiHMDS (1M in THF, 1.43 mL, 1.43 mmol) at −78° C. The reaction mixture was stirred at −78° C. for 5 min and at 0° C. for 1 h. After completion, the reaction mixture was quenched with 2-3 drops of acetic acid and concentrated under reduced pressure. The crude mass was purified by combi flash column chromatography (12 g column; elution: 2.5% methanol in DCM) to provide 4-(4-chloro-2-cyanophenyl)-N-(pyrimidin-4-yl)-3,4-dihydro-2H-benzo[b][1,4]oxazine-7-sulfonamide (48 mg, 15.6%) as an off-white solid. $^1$H NMR (400 MHz, DMSO) δ 11.87 (s, 1H), 8.66 (s, 1H), 8.40 (s, 1H) 8.15 (d, J=2.4 Hz, 1H), 7.86 (dd, J=8.7, 2.5 Hz, 1H), 7.60 (d, J=8.8 Hz, 1H), 7.12-6.96 (m, 1H), 7.43-7.24 (m, 2H), 6.56 (d, J=8.6 Hz, 1H), 4.34 (s, 2H), 3.77 (s, 2H); LCMS (ESI) m/z; 427.95 (M+H).

Example 244

2-(7-(N-(Thiazol-2-Yl)Sulfamoyl)-2H-Benzo[B][1,4]Oxazin-4(3H)-Yl)Benzamide

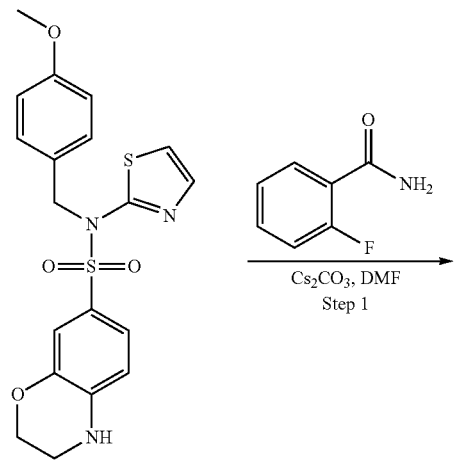

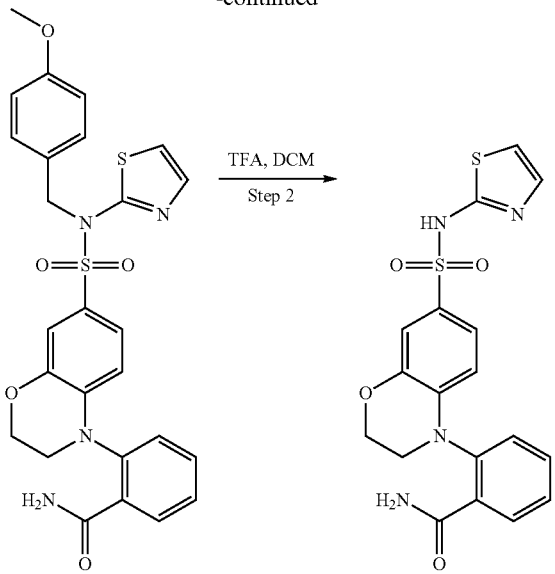

Step 1: 2-(7-(N-(4-Methoxybenzyl)-N-(Thiazol-2-Yl)Sulfamoyl)-2H-Benzo[B][1,4]Oxazin-4(3H)-Yl)Benzamide

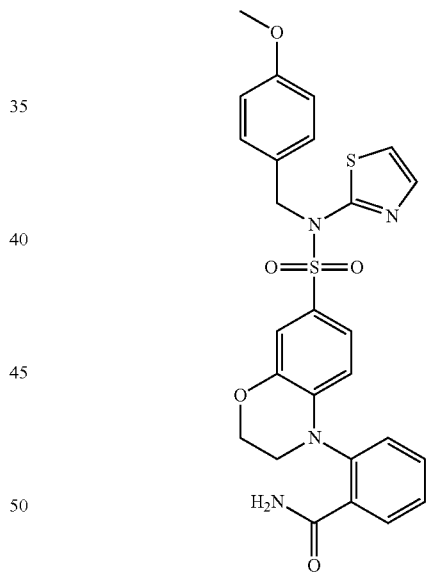

To a solution of INTERMEDIate M (900 mg, 2.08 mmol) and 2-fluorobenzamide (293 mg, 2.08 mmol, Aldrich) in DMF (10 mL) was added cesium carbonate (1.01 g, 3.12 mmol). The reaction mixture was heated at 90° C. for 48 h. After completion, the reaction mixture was diluted with ethyl acetate (30 mL) and water (20 mL). The layers were separated and the organic layer was dried over sodium sulfate and concentrated under reduced pressure to obtain crude material which was purified by combi flash silica gel column chromatography (column size: 40 g, elution: 25% ethyl acetate in hexane) to provide 2-(7-(N-(4-methoxybenzyl)-N-(thiazol-2-yl)sulfamoyl)-2H-benzo[b][1,4]oxazin-4(3H)-yl)benzamide (800 mg, 71.4%); LCMS (ESI) m/z; 537.12 (M+H).

Step 2, Example 244: 2-(7-(N-(Thiazol-2-Yl)Sulfa-moyl)-2H-Benzo[B][1,4]Oxazin-4(3H)-Yl)Benzamide

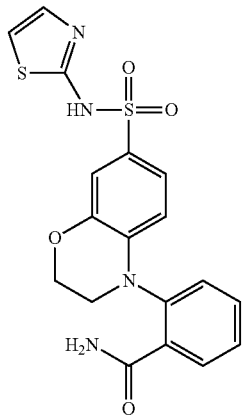 [SMILES: NC(=O)c1ccccc1N1CCOc2cc(S(=O)(=O)Nc3nccs3)ccc21]

To a solution of 2-(7-(N-(4-methoxybenzyl)-N-(thiazol-2-yl)sulfamoyl)-2H-benzo[b][1,4]oxazin-4(3H)-yl)benzamide (800 mg, 1.48 mmol) in DCM (15 mL) was added TFA (1.6 mL, Spectrochem) at 0° C. The reaction mixture was stirred at ambient temperature for 2 h. After completion, the reaction mixture was quenched with saturated aqueous sodium bicarbonate solution (20 mL) and extracted with DCM (2×15 mL). The combined organic layers were dried over sodium sulfate and concentrated under reduced pressure. The resulting residue was purified by prep purification to obtain 2-(7-(N-(thiazol-2-yl)sulfamoyl)-2H-benzo[b][1,4]oxazin-4(3H)-yl)benzamide (21 mg, 3.38%) as white solid. $^1$H NMR (400 MHz, DMSO) δ 12.54 (s, 1H), 7.68 (s, 1H), 7.55 (t, J=7.8 Hz, 2H), 7.37 (dt, J=15.2, 7.7 Hz, 3H), 7.21 (d, J=4.6 Hz, 1H), 7.09 (d, J=1.9 Hz, 1H), 7.04 (dd, J=8.5, 2.0 Hz, 1H), 6.77 (d, J=4.4 Hz, 1H), 6.26 (d, J=8.5 Hz, 1H), 4.29-4.27 (s, 2H), 3.71-3.68 (m, 2H). LCMS (ESI) m/z; 417.5 (M+H).

Example 245

4-(4-Fluoro-2-Methoxyphenyl)-3-Oxo-N-(Thiazol-2-Yl)-3,4-Dihydro-2H-Benzo[B][1,4]Oxazine-7-Sulfonamide

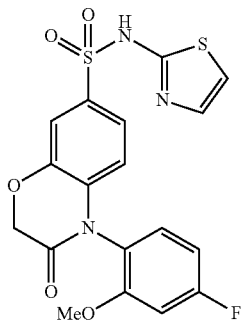 [SMILES: COc1cc(F)ccc1N1C(=O)COc2cc(S(=O)(=O)Nc3nccs3)ccc21]

EXAMPLE 245 was synthesized in the same manner as EXAMPLE 232, running STEP 1 at 80° C. for 2 h (instead of 110° C. for 2 h), using 1-bromo-4-fluoro-2-methoxybenzene (Sigma Aldrich) instead of 4-bromo-3-methoxybenzonitrile. $^1$H NMR (500 MHz, DMSO-d$_6$) δ ppm 3.73 (s, 3 H) 4.87 (s, 2 H) 6.39 (d, J=8.48 Hz, 1 H) 6.78 (d, J=3.67 Hz, 1 H) 6.95 (td, J=8.42, 2.52 Hz, 1 H) 7.12-7.24 (m, 2 H) 7.27-7.43 (m, 3 H); LCMS (ESI) m/z: 436.0 (M+H)$^+$.

Example 246

4-(5-Fluoro-2-Methoxyphenyl)-3-Oxo-N-(Thiazol-2-Yl)-3,4-Dihydro-2H-Benzo[B][1,4]Oxazine-7-Sulfonamide

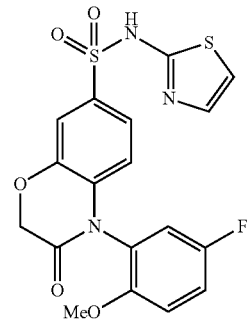 [SMILES: COc1ccc(F)cc1N1C(=O)COc2cc(S(=O)(=O)Nc3nccs3)ccc21]

EXAMPLE 246 was synthesized in the same manner as EXAMPLE 232, running STEP 1 at 80° C. for 2 h (instead of 110° C. for 2 h), using 2-bromo-4-fluoro-1-methoxybenzene (Sigma Aldrich) instead of 4-bromo-3-methoxybenzonitrile. $^1$H NMR (500 MHz, DMSO-d$_6$) δ ppm 3.70 (m, 3 H) 4.88 (s, 2 H) 6.43 (d, J=8.42 Hz, 1 H) 6.81 (d, J=4.12 Hz, 1 H) 7.21-7.41 (m, 6 H); LCMS (ESI) m/z: 436.0 (M+H)$^+$.

Example 247

4-(2-Methyl-4-(Trifluoromethyl)Phenyl)-3-Oxo-N-(Thiazol-2-Yl)-3,4-Dihydro-2H-Benzo[B][1,4]Oxazine-7-Sulfonamide

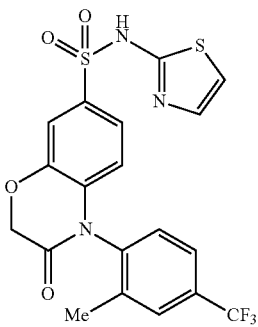

EXAMPLE 247 was synthesized in the same manner as EXAMPLE 232, running STEP 1 at 80° C. for 2 h (instead of 110° C. for 2 h), using 1-bromo-2-methyl-4-(trifluoromethyl)benzene (Oakwood Products) instead of 4-bromo-3-methoxybenzonitrile. $^1$H NMR (500 MHz, DMSO-d$_6$) δ ppm 2.12 (s, 3 H) 4.91 (d, J=15.12 Hz, 1 H) 5.00 (d, J=15.12 Hz, 1 H) 6.32 (d, J=8.42 Hz, 1 H) 6.81 (d, J=4.12 Hz, 1 H) 7.23 (d, J=3.89 Hz, 1 H) 7.34 (dd, J=8.39, 1.63 Hz, 1 H) 7.37-7.46 (m, 1 H) 7.56 (d, J=8.13 Hz, 1 H) 7.77 (d, J=7.45 Hz, 1 H) 7.89 (s, 1 H), LCMS (ESI) m/z: 470.0 (M+H)$^+$.

277

Example 248

4-(2-Methoxy-4-(Trifluoromethyl)Phenyl)-3-Oxo-N-(1,2,4-Thiadiazol-5-Yl)-3,4-Dihydro-2H-Benzo[B][1,4]Oxazine-7-Sulfonamide

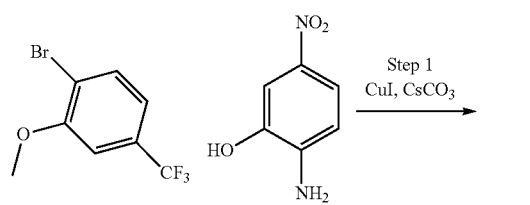

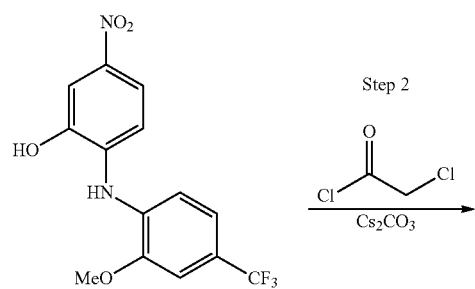

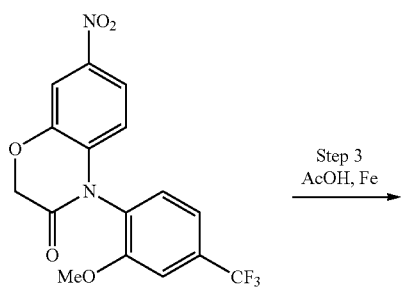

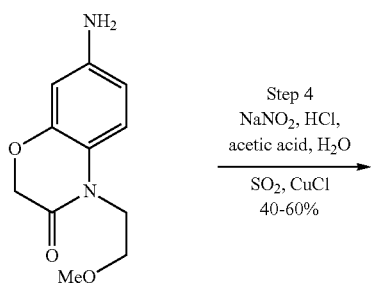

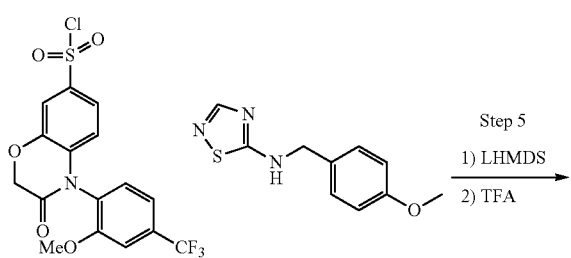

278

-continued

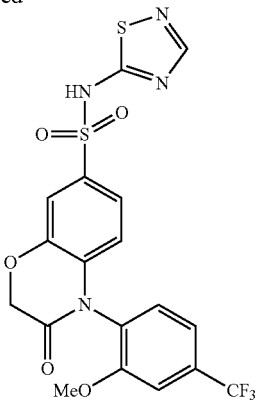

Step 1: 2-(2-Methoxy-4-(Trifluoromethyl)Phenyl)Amino)-5-Nitrophenol

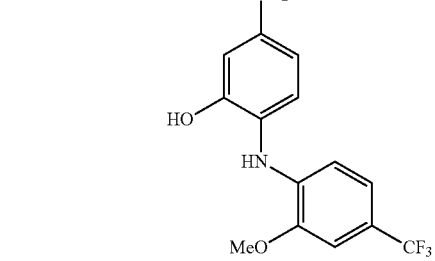

Dissolved 2-amino-5-nitrophenol (4.0 g, 26.0 mmol), cesium carbonate (23.25 g, 71.4 mmol), and copper(i) iodide (4.94 g, 26.0 mmol) in DMF (43.3 ml) in a 250 mL sealed tube and stirred at 25° C. for 30 min. Then added 1-bromo-2-methoxy-4-(trifluoromethyl)benzene (5.52 g, 21.63 mmol) and stirred for 18 h at 100° C. Added acetic acid (8.67 ml, 151 mmol) to neutralize base and product. Diluted the reaction with a solution of DCM/MeOH/NH4OH (90:10:1) and filtered through a frit of silica to remove some of the copper and base, rinsing with more of the solution. The collected eluent was concentrated, then purified using silica gel chromatography using a gradient of (0-100%) Hex:EtOAc to yield 2-((2-methoxy-4-(trifluoromethyl)phenyl)amino)-5-nitrophenol (1.75 g, 5.33 mmol, 24.65% yield) as a yellow solid.

Step 2: 4-(2-Methoxy-4-(Trifluoromethyl)Phenyl)-7-Nitro-2H-Benzo[B][1,4]Oxazin-3(4H)-One

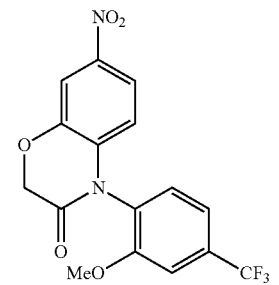

To a flask charged with 2-((2-methoxy-4-(trifluoromethyl)phenyl)amino)-5-nitrophenol (1.75 g, 5.33 mmol) and cesium carbonate (8.69 g, 26.7 mmol) was added DMF (21.33 ml) followed by chloroacetyl chloride (0.854 ml, 10.66 mmol), dropwise over 5 min. The resulting solution was maintained at rt for 1 h. Quenched reaction with saturated ammonium chloride (25 mL) and diluted with EtOAc (25 mL). Separated layers, and extracted aqueous layer with EtOAc (3×25 mL). The combined organic layers were dried over Na2SO4, filtered, and concentrated via rotary evaporation to provide 4-(2-methoxy-4-(trifluoromethyl)phenyl)-7-nitro-2H-benzo[b][1,4]oxazin-3(4H)-one (2.10 g, 5.70 mmol, 107% yield) as a yellow solid. The crude product was used in the next step without further purification.

Step 3: 7-Amino-4-(2-Methoxy-4-(Trifluoromethyl) Phenyl)-2H-Benzo[B][1,4]Oxazin-3(4H)-One

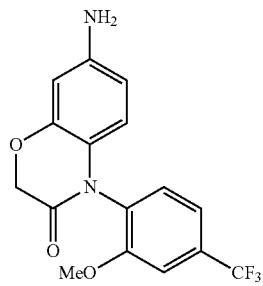 [SMILES: COc1cc(C(F)(F)F)ccc1N1C(=O)COc2cc([N+](=O)[O-])ccc21]

4-(2-Methoxy-4-(trifluoromethyl)phenyl)-7-nitro-2H-benzo[b][1,4]oxazin-3(4H)-one (2.1 g, 5.70 mmol) was dissolved in THF (22.81 ml) and acetic acid (17.95 ml, 314 mmol) in a 250 mL rbf, and iron (3.18 g, 57.0 mmol) was added. The flask was sealed and heated to 70° C. for 1 hr until the reaction was complete by LCMS. The reaction was cooled to RT, diluted with THF (50 mL), and filtered through Celite, washing well with 200 mL of THF. The filtrate was concentrated via rotary evaporation, and partitioned between sat. aq. sodium bicarbonate solution (50 mL) and EtOAc (50 mL). The layers were separated, and the aqueous was then extracted two times with EtOAc (2×50 mL). The combined organics were washed with brine, dried over sodium sulfate, filtered and concentrated to a brown oil. The oil was loaded onto a silica column and purified by MPLC with a gradient Heptanes:EtOAc column (0-100%). Fractions were combined and concentrated to give 7-amino-4-(2-methoxy-4-(trifluoromethyl)phenyl)-2H-benzo[b][1,4]oxazin-3(4H)-one (1.434 g, 4.24 mmol, 74.3% yield) as an off-white foamy solid.

Step 4: 4-(2-Methoxy-4-(Trifluoromethyl)Phenyl)-3-Oxo-3,4-Dihydro-2H-Benzo[B][1,4]Oxazine-7-Sulfonyl Chloride

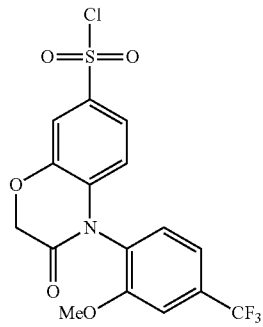 [SMILES: COc1cc(C(F)(F)F)ccc1N1C(=O)COc2cc(S(=O)(=O)Cl)ccc21]

Dissolve 7-amino-4-(2-methoxy-4-(trifluoromethyl)phenyl)-2H-benzo[b][1,4]oxazin-3(4H)-one (1.4 g, 4.14 mmol) in hydrogen chloride (2.096 ml, 24.83 mmol) and acetic acid (4.74 ml, 83 mmol) in a 250 mL rbf and cooled to 0° C. Added sodium nitrite (0.314 g, 4.55 mmol) dissolved in water (0.746 ml, 41.4 mmol) and let stir at 0° C. for 30 min until azide formation by LCMS. Then bubbled sulfur dioxide (0.265 g, 4.14 mmol) gas into solution for 5 minutes and added copper (I) chloride (0.205 g, 2.069 mmol), then bubbled more sulfur dioxide into the solution for 5 minutes. Let stir at rt for 3 hr until reaction was complete by LCMS. Quenched reaction over ice, added EtOAc (100 mL) and brine (100 mL) and extracted 3 times with EtOAc (3×100 mL). Dried organics over Na2SO4 and concentrated via rotary evaporation. Purified 4-(2-methoxy-4-(trifluoromethyl)phenyl)-3-oxo-3,4-dihydro-2H-benzo[b][1,4]oxazine-7-sulfonyl chloride (1.041 g, 2.468 mmol, 59.6% yield) via MPLC with a gradient Hex: EtOAc column (0-100%) which was isolated as an off-white solid.

Step 5, Example 248: 4-(2-Methoxy-4-(Trifluoromethyl)Phenyl)-3-Oxo-N-(1,2,4-Thiadiazol-5-Yl)-3,4-Dihydro-2H-Benzo[B][1,4]Oxazine-7-Sulfonamide

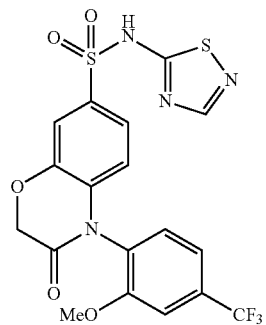 [SMILES: COc1cc(C(F)(F)F)ccc1N1C(=O)COc2cc(S(=O)(=O)Nc3ncns3)ccc21]

To a vial charged with 4-(2-methoxy-4-(trifluoromethyl)phenyl)-3-oxo-3,4-dihydro-2H-benzo[b][1,4]oxazine-7-sulfonyl chloride (120 mg, 0.285 mmol) and N-(4-methoxybenzyl)-1,2,4-thiadiazol-5-amine (69.3 mg, 0.313 mmol) was added THF (948 µl) and the mixture cooled in a dry ice bath at −78 C. Then lithium bis(trimethylsilyl)amide (341 µl, 0.341 mmol) was added dropwise. The mixture was stirred at −78 C for 30 min, then warmed to 0 C for 30 min until conversion to the product by LCMS. The solution was added to ice, diluted with EtOAc (5 mL) and brine (5 mL) and extracted three times with EtOAc (3×5 mL). The combined organics were dried with $Na_2SO_4$, filtered, and dried under reduced pressure. To the crude material was added DCM (1 ml) and TFA (548 µl, 7.11 mmol) and the mixture stirred at rt for 1 hr until deprotection occurred by LCMS. The mixture was concentrated and purified using reverse-phase HPLC with a Waters-Xbridge C18, 19×100 mm, 10 m column with a gradient 5-95% acetonitrile and water with 0.1% TFA to give 4-(2-methoxy-4-(trifluoromethyl)phenyl)-3-oxo-N-(1,2,4-thiadiazol-5-yl)-3,4-dihydro-2H-benzo[b][1,4]oxazine-7-sulfonamide (80 mg, 0.164 mmol, 57.0% yield). $^1$H NMR (500 MHz, DMSO-$d_6$) δ ppm 3.81 (s, 3 H) 4.89 (s, 2 H) 6.38 (d, J=8.42 Hz, 1 H) 7.31 (dd, J=8.45, 1.86 Hz, 1 H) 7.36 (d, J=1.89 Hz, 1 H) 7.50 (d, J=8.08 Hz, 1 H) 7.55-7.62 (m, 2 H) 8.15 (s, 1 H). m/z ESI 485.0 (M−H)$^-$.

Example 250

4-(4-Cyano-2-Methoxyphenyl)-N-(Pyrimidin-4-Yl)-3,4-Dihydro-2H-Benzo[B][1,4]Oxazine-7-Sulfonamide

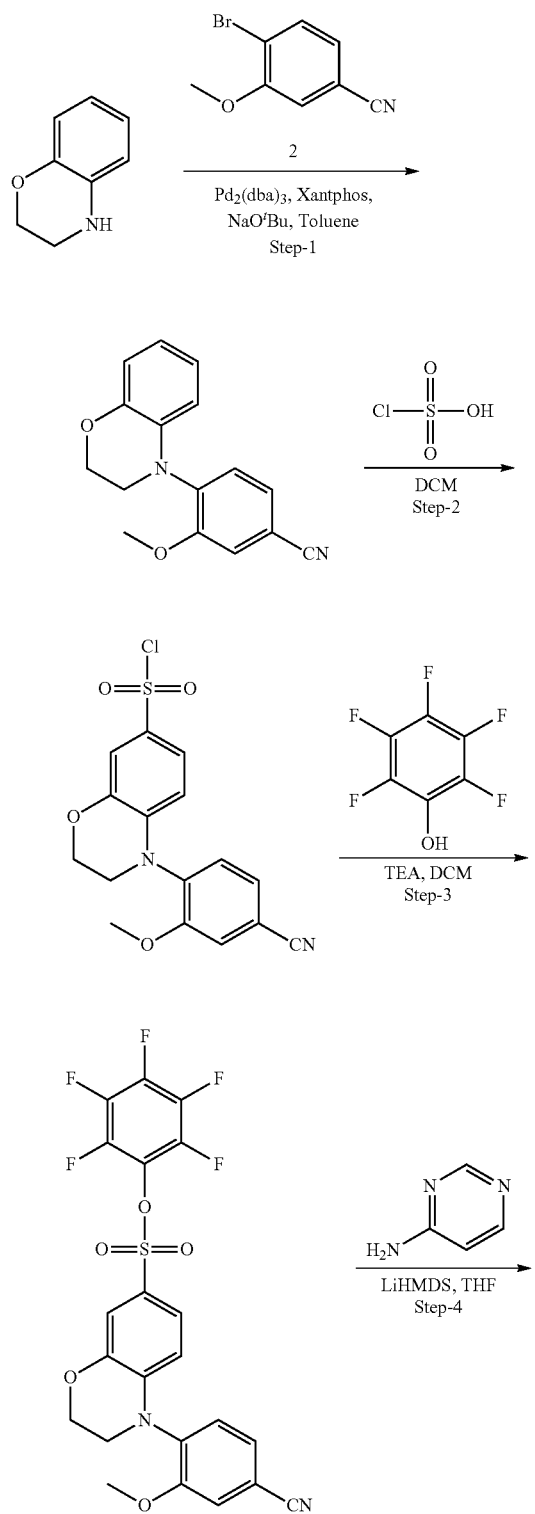

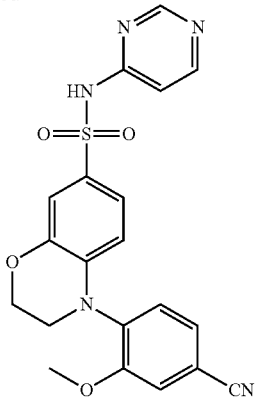 [SMILES: COc1cc(C#N)ccc1N1CCOc2cc(S(=O)(=O)Nc3ccncn3)ccc21]

Step 1: 4-(2H-Benzo[B][1,4]Oxazin-4(3H)-Yl)-3-Methoxybenzonitrile

A mixture of 3,4-dihydro-2H-benzo[b][1,4]oxazine (500 mg, 3.69 mmol), 4-bromo-3-methoxybenzonitrile (784 mg, 3.69 mmol), Pd$_2$(dba)$_3$ (271 mg, 0.295 mmol), Xantphos (342 mg, 0.591 mmol) and sodium-tert-butoxide (590 mg, 6.14 mmol) in toluene (10 mL) was degassed for 10 minutes. The reaction mixture was heated at 100° C. for 1 h under microwave conditions. After completion, the reaction mixture was diluted with water (10 mL) and extracted with ethyl acetate (3×15 mL). The organic layer was dried over sodium sulfate and concentrated under reduced pressure to obtain the crude material which was purified by combi flash column chromatography (column size: 24 g; elution: 5% ethyl acetate in hexane) to obtain 4-(2H-benzo[b][1,4]oxazin-4(3H)-yl)-3-methoxybenzonitrile (790 mg, 80.2%) as yellow solid. m/z (ESI) 266.0 (M+H)$^+$.

Step 2: 4-(4-Cyano-2-Methoxyphenyl)-3,4-Dihydro-2H-Benzo[B][1,4]Oxazine-7-Sulfonyl Chloride To a solution of 4-(2H-benzo[b][1,4]oxazin-4(3H)-yl)-3-methoxybenzonitrile (790 mg, 2.96 mmol) in DCM (10 mL) was added chlorosulfonic acid (0.79 mL, 11.8 mmol) at 0° C. The reaction mixture was stirred at room temperature for 2 h. After completion, reaction mixture was poured into ice water (15 mL), quenched with solid sodium bicarbonate (pH~9-10) and the aqueous layer was extracted with ethyl acetate (2×20 mL). The organic layer was dried over sodium sulfate and concentrated to get 4-(4-cyano-2-methoxyphenyl)-3,4-dihydro-2H-benzo[b][1,4]oxazine-7-sulfonyl chloride as a sticky yellow solid (220 mg, 20.3%) which was used without further purification in the next step.

Step 3: Perfluorophenyl 4-(4-Cyano-2-Methoxyphenyl)-3,4-Dihydro-2H-Benzo[B][1,4]Oxazine-7-Sulfonate To a solution of 4-(4-cyano-2-methoxyphenyl)-3,4-dihydro-2H-benzo[b][1,4]oxazine-7-sulfonyl chloride (220 mg, 0.603 mmol) in DCM (5 mL) was added pentafluorophenol (110 mg, 0.603 mmol) at 0° C. Triethylamine (0.12 mL, 0.904 mmol) was added at 0° C. and the reaction mixture was stirred at room temperature for 1 h. After completion, the reaction mixture was diluted with DCM (3 mL) and concentrated under reduced pressure. The crude mass thus obtained was purified by column chromatography (12 g column; elution: 5% ethyl acetate in hexane) to get perfluorophenyl 4-(4-cyano-2-methoxyphenyl)-3,4-dihydro-2H-benzo[b][1,4]oxazine-7-sulfonate (180 mg, 58.4%) as a clear liquid. m/z (ESI) 512.0 (M+H)$^+$.

Step 4: 4-(4-Cyano-2-Methoxyphenyl)-N-(Pyrimidin-4-Yl)-3,4-Dihydro-2H-Benzo[B][1,4]Oxazine-7-Sulfonamide To a solution of perfluorophenyl 4-(4-cyano-2-methoxyphenyl)-3,4-dihydro-2H-benzo[b][1,4]oxazine-7-sulfonate (180 mg, 0.351 mmol) and 4-amino pyrimidine (50 mg, 0.527 mmol) in THF (5 mL) was added LiHMDS (1M in THF, 0.7 mL, 0.703 mmol) at −78° C. The reaction mixture was stirred at same temperature for 5 minutes and at 0° C. for 1 h. After completion, reaction mixture was quenched with 2-3 drops of acetic acid and concentrated under reduced pressure. The crude mass was purified by prep purification to obtain 4-(4-cyano-2-methoxyphenyl)-N-(pyrimidin-4-yl)-3,4-dihydro-2H-benzo[b][1,4]oxazine-7-sulfonamide (13 mg, 11.3%) as a white solid. m/z (ESI) 423.0 (M+H)$^+$. $^1$H NMR (400 MHz, DMSO) δ 11.88 (s, 1H), 8.64 (s, 1H), 8.36 (d, J=5.8 Hz, 1H), 7.65 (s, 1H), 7.55-7.43 (m, 2H), 7.35-7.15 (m, 2H), 7.00 (d, J=5.9 Hz, 1H), 6.34 (d, J=8.6 Hz, 1H), 4.30 (t, J=4.0 Hz, 2H), 3.81 (s, 3H), 3.67-3.65 (m, 2H).

Example 251

4-(4-Chloro-2-Cyanophenyl)-2-(Methoxymethyl)-N-(Thiazol-2-Yl)-3,4-Dihydro-2H-Benzo[B][1,4]Oxazine-7-Sulfonamide

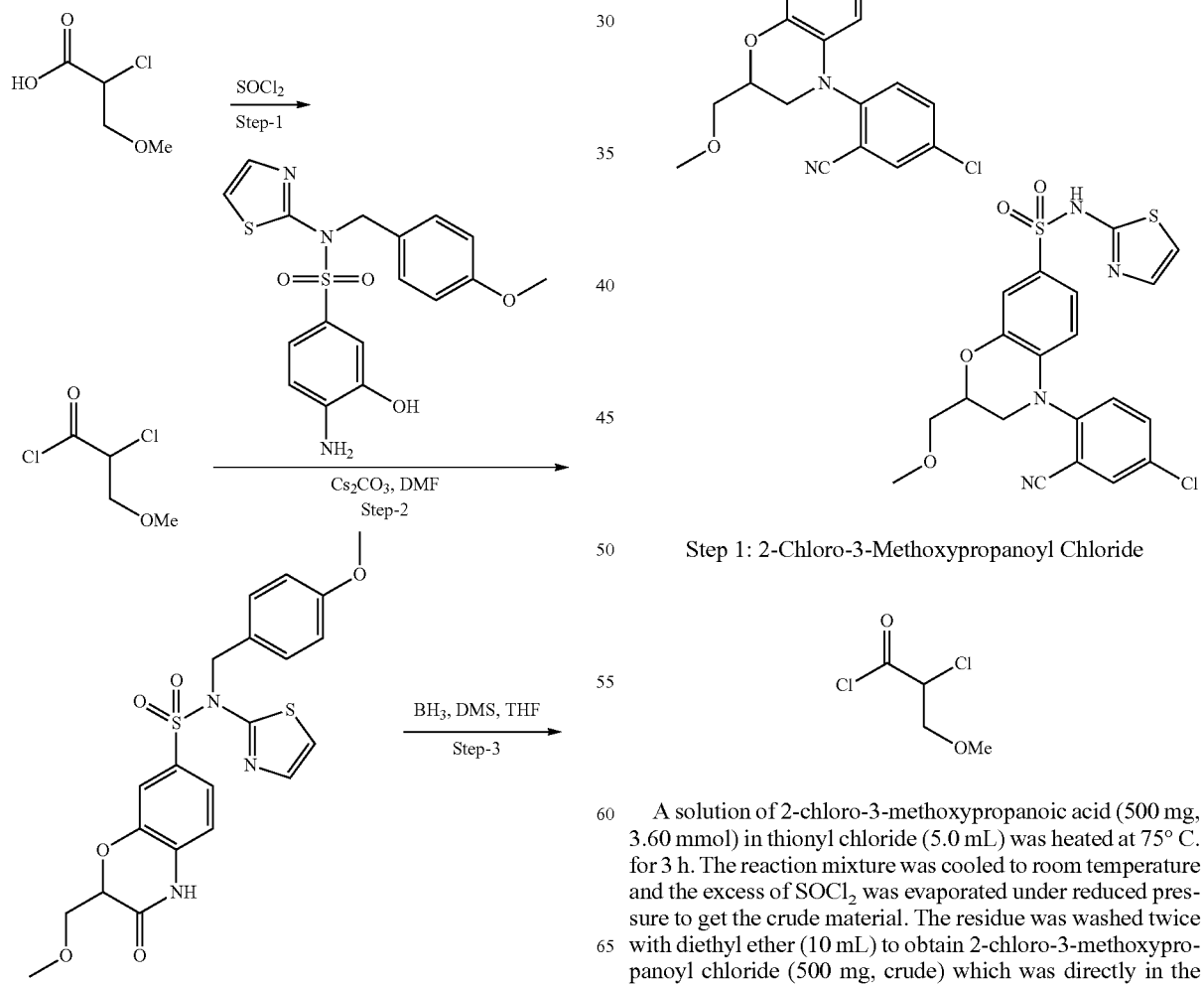

Step 1: 2-Chloro-3-Methoxypropanoyl Chloride

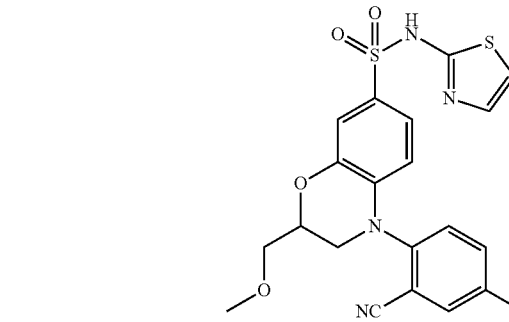

A solution of 2-chloro-3-methoxypropanoic acid (500 mg, 3.60 mmol) in thionyl chloride (5.0 mL) was heated at 75° C. for 3 h. The reaction mixture was cooled to room temperature and the excess of SOCl$_2$ was evaporated under reduced pressure to get the crude material. The residue was washed twice with diethyl ether (10 mL) to obtain 2-chloro-3-methoxypropanoyl chloride (500 mg, crude) which was directly in the next step.

Step 2: N-(4-Methoxybenzyl)-2-(Methoxymethyl)-3-Oxo-N-(Thiazol-2-Yl)-3,4-Dihydro-2H-Benzo[B][1,4]Oxazine-7-Sulfonamide

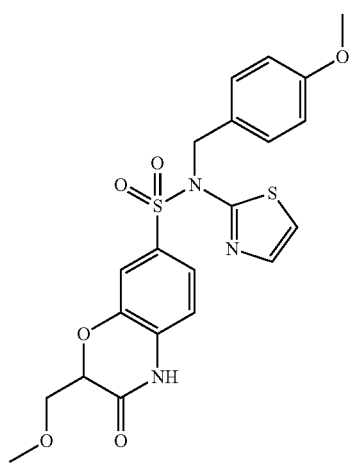

To a solution of 2-chloro-3-methoxypropanoyl chloride (500 mg, 3.18 mmol) and 4-amino-3-hydroxy-N-(4-methoxybenzyl)-N-(thiazol-2-yl)benzenesulfonamide (Intermediate AD; 1.04 g, 2.65 mmol) in DMF (20 mL) was added $Cs_2CO_3$ (2.59 g, 7.95 mmol). The reaction mixture was stirred at ambient temperature for 16 h. The reaction mixture was diluted with water (200 mL) and extracted with ethyl acetate (2×100 mL). The combined organic layers were dried over sodium sulfate, filtered and concentrated under reduced pressure to obtain the crude material which was further purified by column chromatography (silica gel 100-200 mesh and 0-30% ethyl acetate in hexane) to obtain N-(4-methoxybenzyl)-2-(methoxymethyl)-3-oxo-N-(thiazol-2-yl)-3,4-dihydro-2H-benzo[b][1,4]oxazine-7-sulfonamide (500 mg, 33.1%) as an off white solid. m/z (ESI) 476.1 (M+H)$^+$.

Step 3: N-(4-Methoxybenzyl)-2-(Methoxymethyl)-N-(Thiazol-2-Yl)-3,4-Dihydro-2H-Benzo[B][1,4]Oxazine-7-Sulfonamide

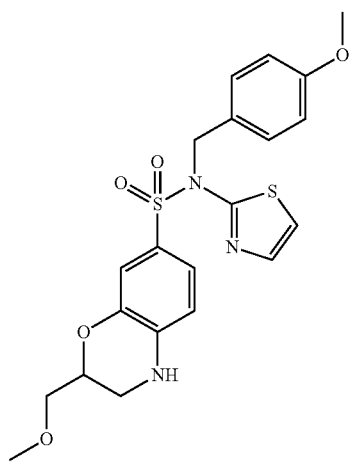

To a solution of N-(4-methoxybenzyl)-2-(methoxymethyl)-3-oxo-N-(thiazol-2-yl)-3,4-dihydro-2H-benzo[b][1,4]oxazine-7-sulfonamide (500 mg, 1.05 mmol) in THF (10 mL) was added $BH_3$.DMS (0.15 mL, 1.57 mmol, Aldrich) at 0° C. The reaction mixture was stirred at ambient temperature for 16 h. After completion, the reaction mixture was quenched with methanol (7 mL) and was azeotroped with methanol (3×15 mL). The solvent was removed under reduced pressure and the crude material thus obtained was purified by column chromatography (silica: 100-200; elution: 30% ethyl acetate in hexane) to get pure N-(4-methoxybenzyl)-2-(methoxymethyl)-N-(thiazol-2-yl)-3,4-dihydro-2H-benzo[b][1,4]oxazine-7-sulfonamide (350 mg, 71.6%) as a brown solid. m/z (ESI) 462.2 (M+H)$^+$.

Step 4: 4-(4-Chloro-2-Cyanophenyl)-N-(4-Methoxybenzyl)-2-(Methoxymethyl)-N-(Thiazol-2-Yl)-3,4-Dihydro-2H-Benzo[B][1,4]Oxazine-7-Sulfonamide

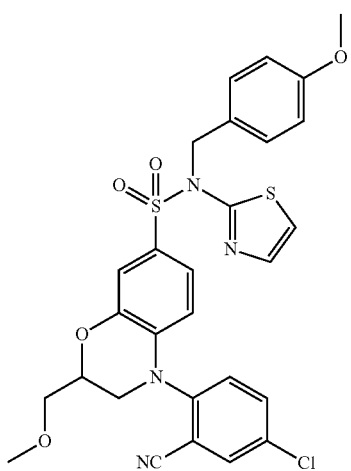

To a solution of N-(4-methoxybenzyl)-2-(methoxymethyl)-N-(thiazol-2-yl)-3,4-dihydro-2H-benzo[b][1,4]oxazine-7-sulfonamide (150 mg, 0.324 mmol) and 5-chloro-2-fluorobenzonitrile (50.55 mg, 0.324 mmol, Aldrich) in DMF (5.0 mL) was added $Cs_2CO_3$ (210 mg, 7.95 mmol) and the reaction mixture was heated at 80° C. for 16 h. The reaction mixture was diluted with water (100 mL) and extracted with ethyl acetate (2×50 mL). The combined organic layers were dried over sodium sulfate, filtered and concentrated under reduced pressure to obtain the crude material which was purified by column chromatography (silica gel 100-200 mesh and 0-30% ethyl acetate in hexane) to obtain 4-(4-chloro-2-cyanophenyl)-N-(4-methoxybenzyl)-2-(methoxymethyl)-N-(thiazol-2-yl)-3,4-dihydro-2H-benzo[b][1,4]oxazine-7-sulfonamide (170 mg, 87.6%) as an off white solid. m/z (ESI) 596.8 (M+H)$^+$.

Step 5: 4-(4-Chloro-2-Cyanophenyl)-2-(Methoxymethyl)-N-(Thiazol-2-Yl)-3,4-Dihydro-2H-Benzo[B][1,4]Oxazine-7-Sulfonamide

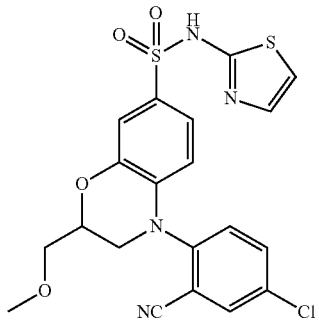 [SMILES: COCC1CN(c2ccc(Cl)cc2C#N)c2ccc(S(=O)(=O)Nc3nccs3)cc2O1]

To a solution of 4-(4-chloro-2-cyanophenyl)-N-(4-methoxybenzyl)-2-(methoxymethyl)-N-(thiazol-2-yl)-3,4-dihydro-2H-benzo[b][1,4]oxazine-7-sulfonamide (170 mg, 0.28 mmol) in dichloromethane (10 mL) was added trifluroacetic acid (0.7 mL, Spectrochem) at 0° C. and the mixture was allowed to stir at room temperature for 4 h. The volatiles were removed under reduced pressure and the residue was basified (pH~10) with saturated aqueous NaHCO$_3$ solution. The aqueous layer was extracted with dichloromethane (2×100 mL). The combined organic layers were dried over sodium sulfate, filtered and concentrated under reduced pressure to get the crude material which was further purified by column chromatography (silica gel 100-200 mesh, 0-2% methanol in dichloromethane) to obtain 4-(4-chloro-2-cyanophenyl)-2-(methoxymethyl)-N-(thiazol-2-yl)-3,4-dihydro-2H-benzo[b][1,4]oxazine-7-sulfonamide (70 mg, 51.5%) as an off white solid. m/z (ESI) 476.8 (M+H)$^+$. $^1$H NMR (400 MHz, DMSO) δ 12.71 (s, 1H), 8.13 (d, J=2.5 Hz, 1H), 7.84 (dd, J=8.8, 2.5 Hz, 1H), 7.59 (d, J=8.8 Hz, 1H), 7.35-7.04 (m, 3H), 6.80 (d, J=4.6 Hz, 1H), 6.57 (d, J=8.5 Hz, 1H), 4.46 (d, J=4.6 Hz, 1H), 3.80-3.76 (m, 1H), 3.65-3.57 (m, 3H), 3.29 (s, 3H).

Example 252

4-(2-(1,2-Dihydroxyethyl)Phenyl)-N-(Thiazol-2-Yl)-3,4-Dihydro-2H-Benzo[B][1,4]Oxazine-7-Sulfonamide

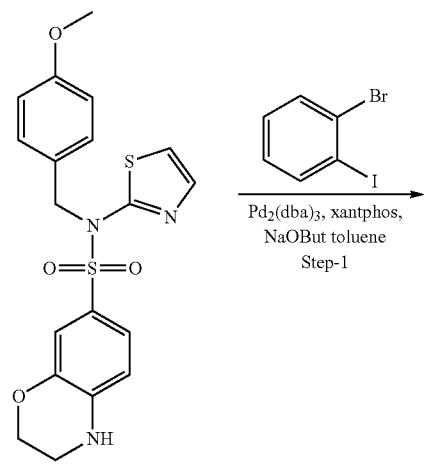

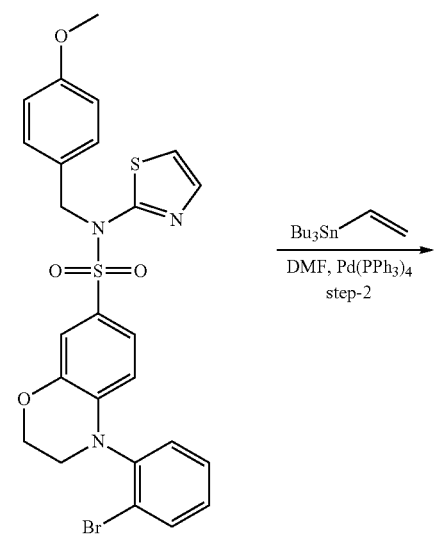

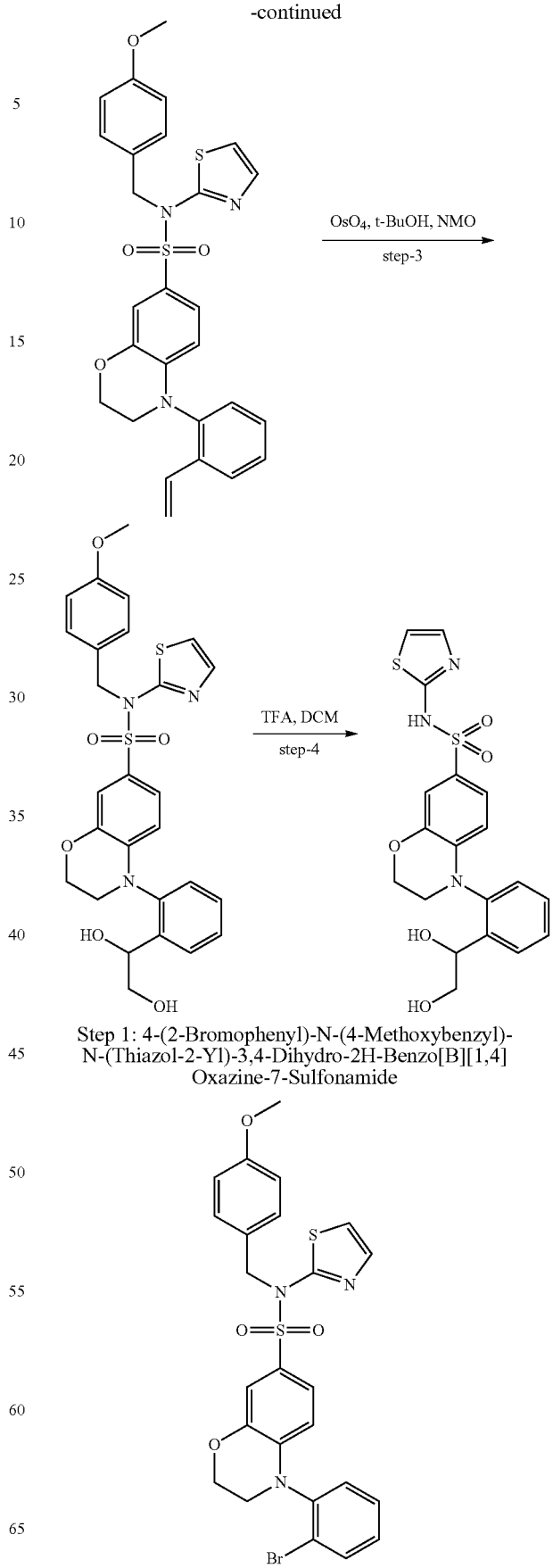

Step 1: 4-(2-Bromophenyl)-N-(4-Methoxybenzyl)-N-(Thiazol-2-Yl)-3,4-Dihydro-2H-Benzo[B][1,4]Oxazine-7-Sulfonamide

289

A mixture of N-(4-methoxybenzyl)-N-(thiazol-2-yl)-3,4-dihydro-2H-benzo[b][1,4]oxazine-7-sulfonamide (Intermediate M; 1.0 g, 2.392 mmol), 1-bromo-2-iodobenzene (1.0 g, 3.588 mmol, Aldrich), Pd$_2$(dba$_3$)$_2$ (138 mg, 0.239 mmol), Xantphos (437 mg, 0.478 mmol) and sodium-tert-butoxide (459 mg, 4.784 mmol) in toluene (20 mL) was degassed with nitrogen for 10 minutes. The reaction mixture was subjected to microwave for 1 h at 100° C. After completion, reaction mixture was diluted with water (10 mL) and extracted with ethyl acetate (3×15 mL). The organic layer was dried over sodium sulfate and concentrated under reduced pressure to obtain the crude material which was purified by combiflash column chromatography (column size: 12 g; elution: 12% ethyl acetate in hexane) to get 4-(2-bromophenyl)-N-(4-methoxybenzyl)-N-(thiazol-2-yl)-3,4-dihydro-2H-benzo[b][1,4]oxazine-7-sulfonamide as a yellow coloured solid (1.2 g, 88.2%). m/z (ESI) 571.9 (M+H)$^+$.

Step 2: N-(4-Methoxybenzyl)-N-(Thiazol-2-Yl)-4-(2-Vinylphenyl)-3,4-Dihydro-2H-Benzo[B][1,4]Oxazine-7-Sulfonamide

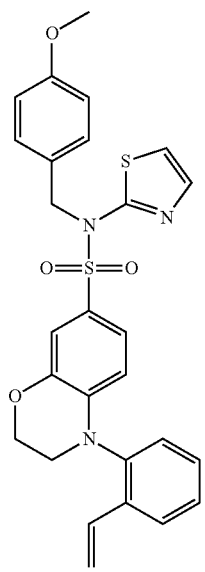 [SMILES: C=Cc1ccccc1N1CCOc2cc(S(=O)(=O)N(Cc3ccc(OC)cc3)c3nccs3)ccc21]

A mixture of 4-(2-bromophenyl)-N-(4-methoxybenzyl)-N-(thiazol-2-yl)-3,4-dihydro-2H-benzo[b][1,4]oxazine-7-sulfonamide (1.2 g, 2.626 mmol), tributyl(vinyl)stannane (3.0 g, 10.5 mmol, Finar), Pd(PPh$_3$)$_4$ (303 mg, 0.131 mmol) in DMF (15 mL) was degassed with nitrogen for 10 minutes. The reaction mixture was subjected to microwave irradiation for 2 h at 100° C. After completion, the reaction mixture was diluted with water (10 mL) and extracted with ethyl acetate (3×15 mL). The organic layer was dried over sodium sulfate and concentrated under reduced pressure to obtain crude material which was purified by combi flash column chromatography (column size: 12 g; elution: 0-5% ethyl acetate in hexane) to get N-(4-methoxybenzyl)-N-(thiazol-2-yl)-4-(2-vinylphenyl)-3,4-dihydro-2H-benzo[b][1,4]oxazine-7-sulfonamide (750 mg, 68.0%) as a yellow solid. m/z (ESI) 520.1 (M+H)$^+$.

290

Step 3: 4-(2-(1,2-Dihydroxyethyl)Phenyl)-N-(4-Methoxybenzyl)-N-(Thiazol-2-Yl)-3,4-Dihydro-2H-Benzo[B][1,4]Oxazine-7-Sulfonamide

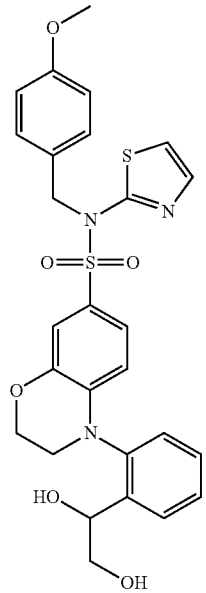 [SMILES: COc1ccc(CN(c2nccs2)S(=O)(=O)c2ccc3c(c2)OCCN3c2ccccc2C(O)CO)cc1]

To a solution of N-(4-methoxybenzyl)-N-(thiazol-2-yl)-4-(2-vinylphenyl)-3,4-dihydro-2H-benzo[b][1,4]oxazine-7-sulfonamide (750 mg, 1.445 mmol) in t-BuOH (10 mL) and water (5 mL) was added NMO (338 mg, 2.890 mmol, Aldrich) followed by OsO$_4$ (4% in water) (0.7 mL, 0.144 mmol, Aldrich) at 0° C. The reaction mixture was stirred at ambient temperature for 12 h. After completion, the reaction mixture was quenched with saturated aqueous ammonium chloride solution (10 mL) and extracted with DCM (2×10 mL). The organic layer was dried over sodium sulfate and concentrated reduced pressure to obtain crude 4-(2-(1,2-dihydroxyethyl)phenyl)-N-(4-methoxybenzyl)-N-(thiazol-2-yl)-3,4-dihydro-2H-benzo[b][1,4]oxazine-7-sulfonamide (300 mg, 37.5%) which was used in the next step without purification. m/z (ESI) 553.9 (M+H)$^+$.

Step 4: 4-(2-(1,2-Dihydroxyethyl)Phenyl)-N-(Thiazol-2-Yl)-3,4-Dihydro-2H-Benzo[B][1,4]Oxazine-7-Sulfonamide

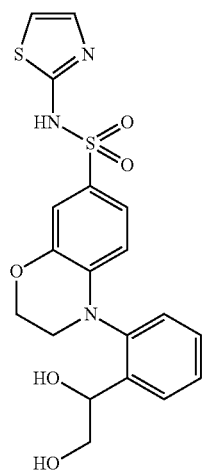 [SMILES: O=S(=O)(Nc1nccs1)c1ccc2c(c1)OCCN2c1ccccc1C(O)CO]

To a solution of 4-(2-(1,2-dihydroxyethyl)phenyl)-N-(4-methoxybenzyl)-N-(thiazol-2-yl)-3,4-dihydro-2H-benzo[b][1,4]oxazine-7-sulfonamide (300 mg, 0.585 mmol) in DCM (5 mL) was added TFA (0.7 mL, Spectrochem) at 0° C. The reaction mixture was stirred at ambient temperature for 2 h. After completion, the reaction mixture was quenched with saturated aqueous sodium bicarbonate solution (10 mL) and extracted with DCM (2×10 mL). The organic layer was dried over sodium sulfate and concentrated under reduced pressure to obtain the crude material which was purified by prep HPLC to obtain 4-(2-(1,2-dihydroxyethyl)phenyl)-N-(thiazol-2-yl)-3,4-dihydro-2H-benzo[b][1,4]oxazine-7-sulfonamide (14 mg, 5.9%) as a white solid. m/z (ESI) 434.0 (M+H)$^+$. $^1$H NMR (400 MHz, DMSO) δ 12.48 (s, 1H), 7.61 (d, J=5.0 Hz, 1H), 7.37 (d, J=4.5 Hz, 2H), 7.23 (t, J=7.7 Hz, 1H), 7.16 (d, J=4.3 Hz, 1H), 7.11 (s, 1H), 7.05 (d, J=8.6 Hz, 1H), 6.71 (d, J=4.2 Hz, 1H), 6.05 (d, J=8.5 Hz, 1H), 5.16 (s, 1H), 4.66 (d, J=25.7 Hz, 2H), 4.34 (q, J=10.8, 10.3 Hz, 2H), 3.77 (t, J=8.3 Hz, 1H), 3.68-3.45 (m, 3H).

Example 253

4-(2-(2-Hydroxy-2-Methylpropoxy)Phenyl)-N-(Thiazol-2-Yl)-3,4-Dihydro-2H-Benzo[B][1,4]Oxazine-7-Sulfonamide

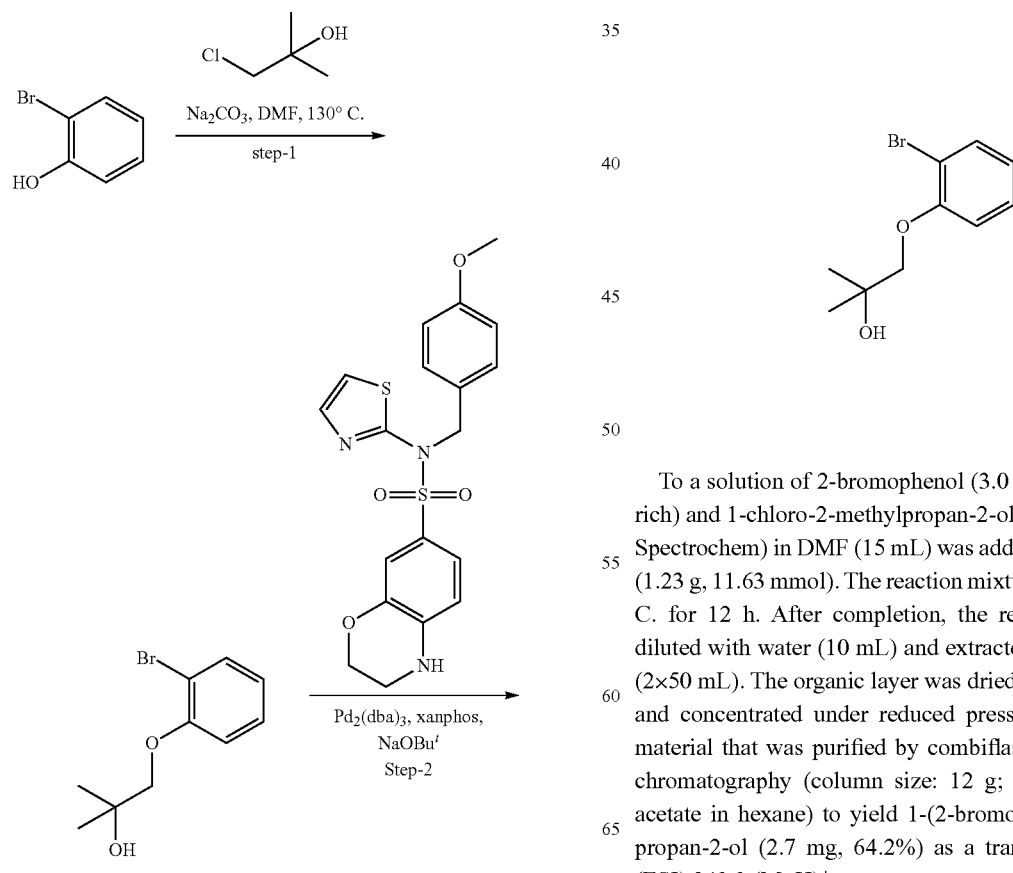

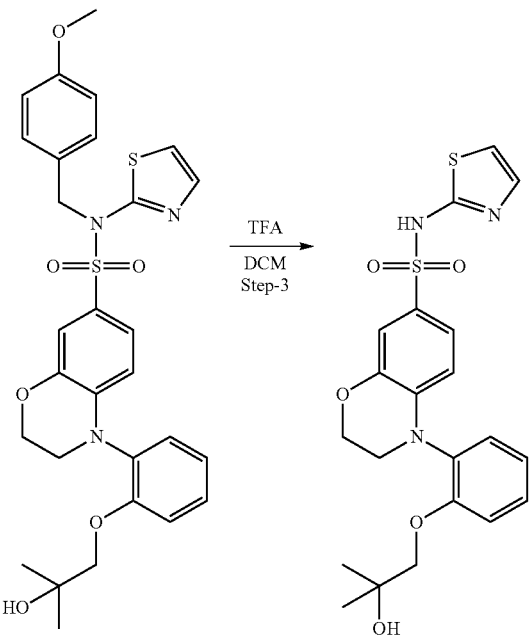

Step 1: 1-(2-Bromophenoxy)-2-Methylpropan-2-Ol

To a solution of 2-bromophenol (3.0 g, 1.745 mmol, Aldrich) and 1-chloro-2-methylpropan-2-ol (2.8 g, 6.397 mmol, Spectrochem) in DMF (15 mL) was added sodium carbonate (1.23 g, 11.63 mmol). The reaction mixture was heated at 90° C. for 12 h. After completion, the reaction mixture was diluted with water (10 mL) and extracted with ethyl acetate (2×50 mL). The organic layer was dried over sodium sulfate and concentrated under reduced pressure to obtain crude material that was purified by combiflash silica gel column chromatography (column size: 12 g; elution: 0-5% ethyl acetate in hexane) to yield 1-(2-bromophenoxy)-2-methylpropan-2-ol (2.7 mg, 64.2%) as a transparent liquid. m/z (ESI) 243.3 (M+H)$^+$.

Step 2: 4-(2-(2-Hydroxy-2-Methylpropoxy)Phenyl)-N-(4-Methoxybenzyl)-N-(Thiazol-2-Yl)-3,4-Dihydro-2H-Benzo[B][1,4]Oxazine-7-Sulfonamide

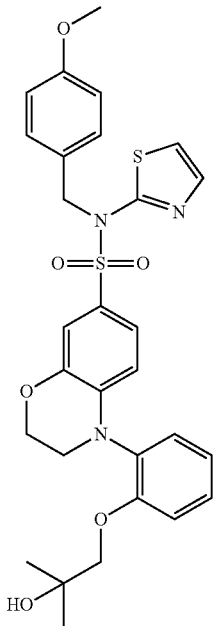 [SMILES: COc1ccc(CN(c2nccs2)S(=O)(=O)c2ccc3c(c2)OCCN3c2ccccc2OCC(C)(C)O)cc1]

A mixture of N-(4-methoxybenzyl)-N-(thiazol-2-yl)-3,4-dihydro-2H-benzo[b][1,4]oxazine-7-sulfonamide (Intermediate M; 700 mg, 1.674 mmol), 1-(2-bromophenoxy)-2-methylpropan-2-ol (2.8 g, 11.722 mmol), Pd$_2$(dba$_3$)$_2$ (96 mg, 0.1674 mmol), Xantphos (306 mg, 0.3349 mmol) and sodium-tert-butoxide (402 mg, 4.186 mmol) in toluene (15 mL) was degassed with nitrogen for 10 minutes. The reaction mixture was subjected to microwave for 1 h at 100° C. After completion, reaction mixture was diluted with water (10 mL) and extracted with ethyl acetate (3×15 mL). The organic layer was dried over sodium sulfate and concentrated under reduced pressure to obtain crude material, which was purified by combiflash silica gel column chromatography (column size: 12 g; elution: 12% ethyl acetate in hexane) to yield 4-(2-(2-hydroxy-2-methylpropoxy)phenyl)-N-(4-methoxybenzyl)-N-(thiazol-2-yl)-3,4-dihydro-2H-benzo[b][1,4]oxazine-7-sulfonamide (600 mg, 88.2%). m/z (ESI) 582.1 (M+H)$^+$.

Step 3: 4-(2-(2-Hydroxy-2-Methylpropoxy)Phenyl)-N-(Thiazol-2-Yl)-3,4-Dihydro-2H-Benzo[B][1,4]Oxazine-7-Sulfonamide

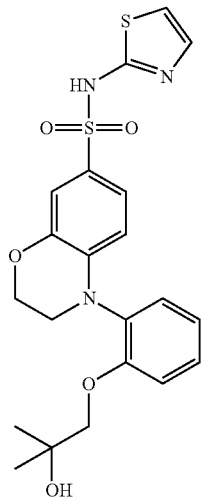 [SMILES: CC(C)(O)COc1ccccc1N1CCOc2cc(S(=O)(=O)Nc3nccs3)ccc21]

To a solution of 4-(2-(2-hydroxy-2-methylpropoxy)phenyl)-N-(4-methoxybenzyl)-N-(thiazol-2-yl)-3,4-dihydro-2H-benzo[b][1,4]oxazine-7-sulfonamide (600 mg, 0.585 mmol) in DCM (5 mL) was added TFA (1.4 mL, Spectrochem) at 0° C. The reaction mixture was stirred at ambient temperature for 2 h. After completion, the reaction mixture was quenched with saturated sodium bicarbonate solution (10 mL) and extracted with DCM (2×10 mL). The organic layer was dried over sodium sulfate and concentrated under reduced pressure to obtain the crude material which was purified by prep HPLC purification to obtain 4-(2-(2-hydroxy-2-methylpropoxy)phenyl)-N-(thiazol-2-yl)-3,4-dihydro-2H-benzo[b][1,4]oxazine-7-sulfonamide (120 mg, 26.0%) as a white solid. m/z (ESI) 461.8 (M+H)$^+$. $^1$H NMR (400 MHz, DMSO) δ 12.50 (s, 1H), 7.38-7.24 (m, 2H), 7.20 (d, J=4.6 Hz, 1H), 7.16-6.95 (m, 4H), 6.76 (d, J=4.3 Hz, 1H), 6.23-6.00 (m, 1H), 4.46 (s, 1H), 4.31 (d, J=3.9 Hz, 2H), 3.61-3.58 (m, 4H), 0.83 (s, 6H).

Example 254

4-(2-(Prop-1-En-2-Yl)Phenyl)-N-(Thiazol-2-Yl)-3,4-Dihydro-2H-Benzo[B][1,4]Oxazine-7-Sulfonamide

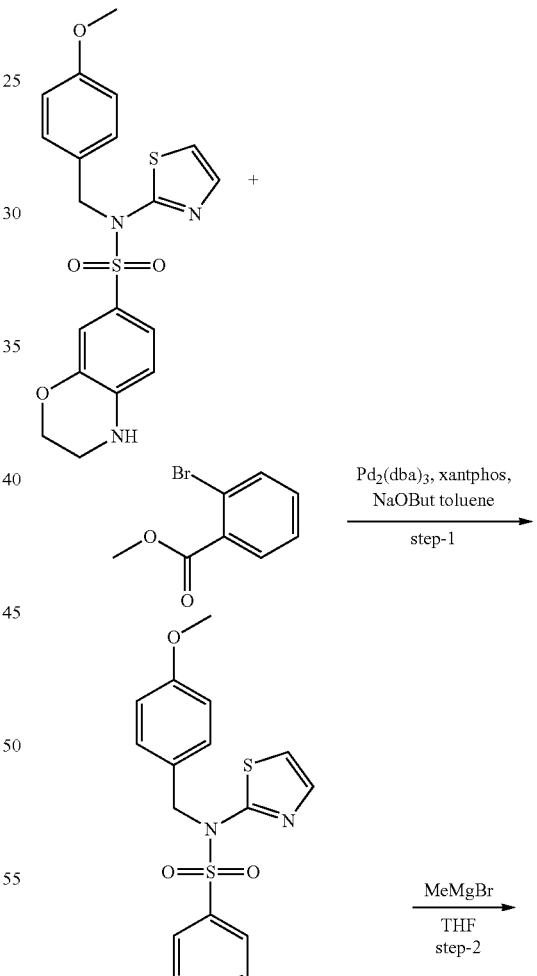

-continued

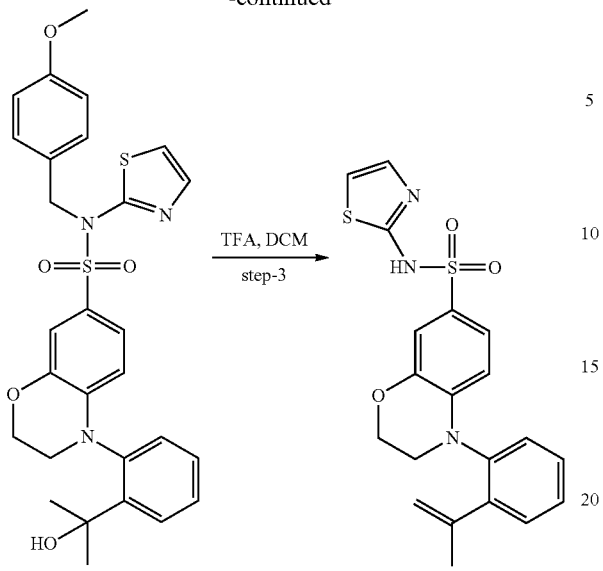

Step 1: Methyl 2-(7-(N-(4-Methoxybenzyl)-N-(Thiazol-2-Yl)Sulfamoyl)-2H-Benzo[B][1,4]Oxazin-4(3H)-Yl)Benzoate

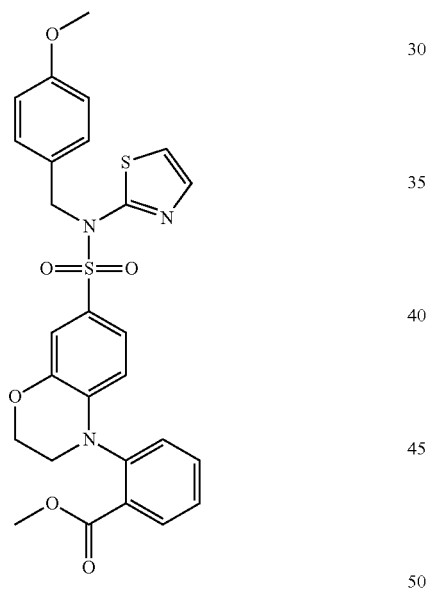

A mixture of N-(4-methoxybenzyl)-N-(thiazol-2-yl)-3,4-dihydro-2H-benzo[b][1,4]oxazine-7-sulfonamide (Intermediate M; 500 mg, 1.196 mmol), methyl 2-bromobenzoate (687 mg, 2.99 mmol, Spectrochem), Pd$_2$(dba$_3$)$_2$ (109 mg, 0.119 mmol), Xantphos (138 mg, 0.239 mmol) and sodium-tert-butoxide (229 mg, 2.392 mmol) in toluene (10 mL) was degassed for 10 minutes. The reaction mixture was subjected to microwave for 1 h at 100° C. After completion, reaction mixture was diluted with water (10 mL) and extracted with ethyl acetate (3×15 mL). The organic layer was dried over sodium sulfate and concentrated under reduced pressure to obtain the crude material which was purified by combi flash column chromatography (column size: 12 g; elution: 0-20% ethyl acetate in hexane) to get methyl 2-(7-(N-(4-methoxybenzyl)-N-(thiazol-2-yl)sulfamoyl)-2H-benzo[b][1,4]oxazin-4(3H)-yl)benzoate (500 mg, 75.7%) as a yellow solid. MS (ESI, positive ion) m/z; 552.1 (M+1)

Step 2: 4-(2-(2-Hydroxypropan-2-Yl)Phenyl)-N-(4-Methoxybenzyl)-N-(Thiazol-2-Yl)-3,4-Dihydro-2H-Benzo[B][1,4]Oxazine-7-Sulfonamide

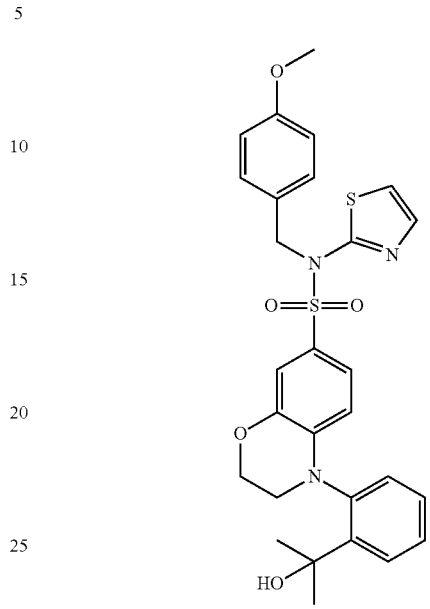

To a solution of methyl 2-(7-(N-(4-methoxybenzyl)-N-(thiazol-2-yl)sulfamoyl)-2H-benzo[b][1,4]oxazin-4(3H)-yl) benzoate (400 mg, 0.725 mmol) in THF (10 mL) was added methyl magnesium bromide (1M in THF) (1.7 mL, mmol, Aldrich) at −78° C. The reaction mixture was stirred at ambient temperature for 5 h. After completion, the reaction mixture was quenched with saturated aqueous ammonium chloride solution (10 mL) and extracted with DCM (2×10 mL). The organic layer was dried over sodium sulfate and concentrated under reduced pressure to obtain the crude material that was purified by prep HPLC to obtain 4-(2-(2-hydroxypropan-2-yl)phenyl)-N-(4-methoxybenzyl)-N-(thiazol-2-yl)-3,4-dihydro-2H-benzo[b][1,4]oxazine-7-sulfonamide as a white solid (300 mg, 75%). MS (ESI, positive ion) m/z; 552.1 (M+1)

Step 3: 4-(2-(Prop-1-En-2-Yl)Phenyl)-N-(Thiazol-2-Yl)-3,4-Dihydro-2H-Benzo[B][1,4]Oxazine-7-Sulfonamide

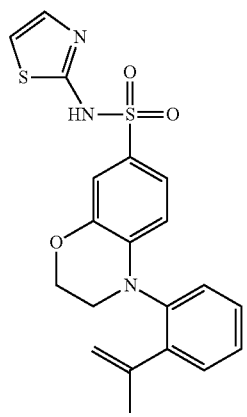 [SMILES: C=C(C)c1ccccc1N1CCOc2cc(S(=O)(=O)Nc3nccs3)ccc21]

To a solution of 4-(2-(2-hydroxypropan-2-yl)phenyl)-N-(4-methoxybenzyl)-N-(thiazol-2-yl)-3,4-dihydro-2H-benzo[b][1,4]oxazine-7-sulfonamide (300 mg, 0.543 mmol) in DCM (5 mL) was added TFA (0.4 mL, Spectrochem) at 0° C. The reaction mixture was stirred at ambient temperature for 2 h. After completion, the reaction mixture was quenched with saturated sodium bicarbonate solution (10 mL) and extracted with DCM (2×10 mL). The organic layer was dried over sodium sulfate and concentrated under reduced pressure to obtain crude material (47% by LCMS) that was purified by prep HPLC to obtain 4-(2-(prop-1-en-2-yl)phenyl)-N-(thiazol-2-yl)-3,4-dihydro-2H-benzo[b][1,4]oxazine-7-sulfonamide as a white solid (45 mg, 20.0%). MS (ESI, positive ion) m/z; 414.1 (M+1). $^1$H NMR (400 MHz, DMSO) δ 12.51 (s, 1H), 7.50-7.26 (m, 4H), 7.21 (d, J=4.6 Hz, 1H), 7.16-6.94 (m, 1H), 6.77 (d, J=4.5 Hz, 1H), 6.23 (d, J=8.4 Hz, 1H), 5.10 (s, 1H), 4.96 (s, 1H), 4.41-4.08 (m, 2H), 3.52 (d, J=11.7 Hz, 2H), 1.96 (s, 3H).

Example 255

4-(2-(6-Hydroxypyridin-3-Yl)Phenyl)-N-(Thiazol-2-Yl)-3,4-Dihydro-2H-Benzo[B][1,4]Oxazine-7-Sulfonamide 2,2,2-Trifluoroacetate

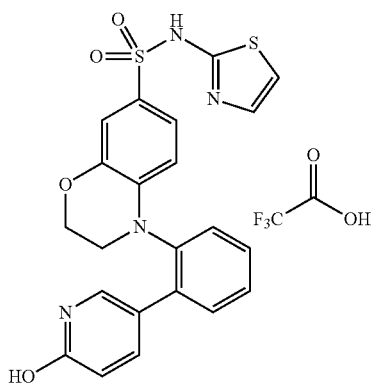

A microwave vial was charged with 4-(2-bromophenyl)-N-(4-methoxybenzyl)-N-(thiazol-2-yl)-3,4-dihydro-2H-benzo[b][1,4]oxazine-7-sulfonamide (From Example 252, Step 1; 34.89 mg, 0.061 mmol), 5-(4,4,5,5-tetramethyl-1,3,2-dioxaborolan-2-yl)pyridin-2-ol (Aldrich Co., 40.4 mg, 0.183 mmol), potassium carbonate (42.1 mg, 0.305 mmol), and Pd(Ph$_3$P)$_4$ (7.04 mg, 6.09 μmol). The vial was flushed with Ar (g), then 1,4-dioxane (0.3 mL) and water (0.1 mL). The vial was sealed and heated in a Biotage Initiator microwave reactor for 70 min at 90° C. The mixture was extracted with EtOAc (3×). The combined organic extracts were concentrated. The residue was taken up in DCM (1 mL), and the resulting solution was cooled in an ice-water bath for 5 min. TFA (0.5 mL) was added dropwise. The resulting mixture was warmed to room temperature and stirred overnight. The mixture was diluted with MeOH and concentrated. The residue was purified by chromatography on silica gel (25-g Interchim 15-micron column, 0-10% MeOH/DCM) to give 4-(2-(6-hydroxypyridin-3-yl)phenyl)-N-(thiazol-2-yl)-3,4-dihydro-2H-benzo[b][1,4]oxazine-7-sulfonamide 2,2,2-trifluoroacetate as a light-pink solid. $^1$H NMR (400 MHz, DMSO-d$_6$) δ=7.49-7.30 (m, 6 H), 7.21 (d, J=4.6 Hz, 1 H), 7.11-7.02 (m, 2 H), 6.77 (d, J=4.7 Hz, 1 H), 6.32-6.25 (m, 2 H), 4.31-4.24 (m, 1 H), 4.13-4.03 (m, 1 H), 3.67-3.60 (m, 1 H), 3.37 (td, J=2.9, 12.9 Hz, 1 H). m/z (ESI) 467.1 (M+H)$^+$.

Example 256

2-(2-(7-(N-(Thiazol-2-Yl)Sulfamoyl)-2H-Benzo[B][1,4]Oxazin-4(3 H)-Yl)Phenoxy)Acetamide

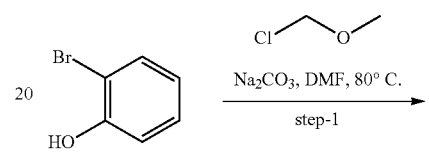

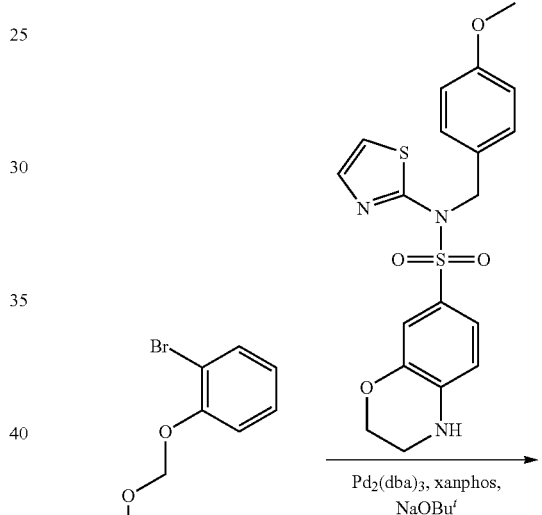

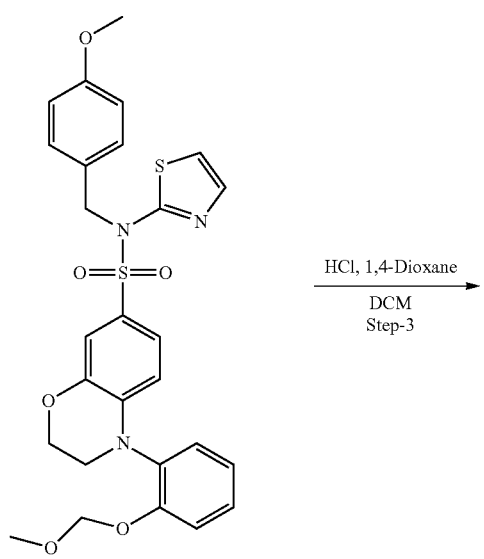

-continued

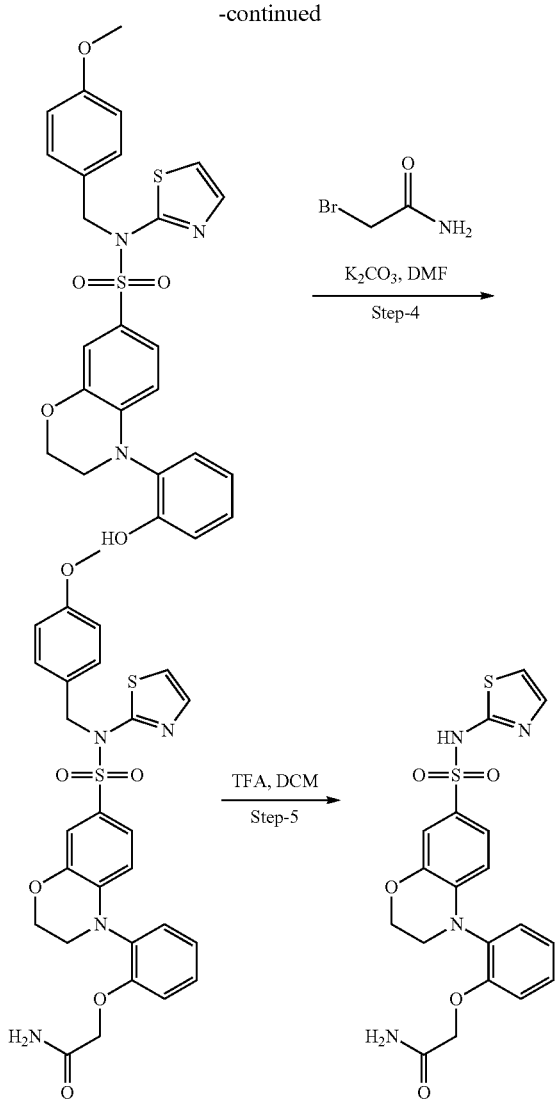

Step 1: 1-Bromo-2-(Methoxymethoxy)Benzene

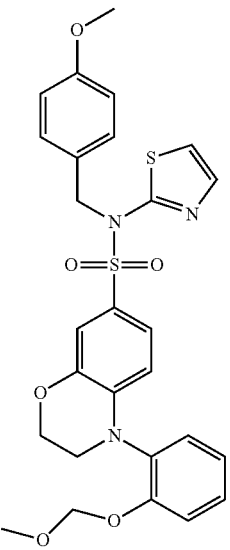 [SMILES: COCOc1ccccc1N1CCOc2cc(S(=O)(=O)N(Cc3ccc(OC)cc3)c3nccs3)ccc21]

To a solution of 2-bromophenol (5.0 g, 28.90 mmol) and chloro(methoxy)methane (3.4 g, 43.35 mmol) in DMF (50 mL) was added sodium carbonate (18.7 g, 57.8 mmol). The reaction mixture was heated at 80° C. for 12 h. After completion, the reaction mixture was diluted with water (100 mL) and extracted with ethyl acetate (2×100 mL). The organic layer was washed with water (3×100 mL), dried over sodium sulfate and concentrated under reduced pressure to yield desired 1-bromo-2-(methoxymethoxy)benzene (4.2 g, 67.7%) as a clear liquid, which was used without further purification.

Step 2: N-(4-Methoxybenzyl)-4-(2-(Methoxymethoxy)Phenyl)-N-(Thiazol-2-Yl)-3,4-Dihydro-2H-Benzo[B][1,4]Oxazine-7-Sulfonamide A mixture of N-(4-methoxybenzyl)-N-(thiazol-2-yl)-3,4-dihydro-2H-benzo[b][1,4]oxazine-7-sulfonamide (Intermediate M; 500 mg, 1.19 mmol), 1-bromo-2-(methoxymethoxy)benzene (1.2 g, 5.98 mmol), Pd$_2$(dba)$_3$ (109 mg, 0.119 mmol, GLR), Xantphos (138 mg, 0.23 mmol, GLR) and sodium-tert-butoxide (229 mg, 2.39 mmol) in toluene (15 mL) was degassed with nitrogen for 10 minutes. The reaction mixture was heated at 100° C. for 1 h under microwave. After completion, the reaction mixture was diluted with water (15 mL) and extracted with ethyl acetate (3×15 mL). The organic layer was dried over sodium sulfate and concentrated under reduced pressure to obtain the crude material which was purified by combiflash column chromatography (column size: 12 g; elution: 0-20% ethyl acetate in hexane) to yield N-(4-methoxybenzyl)-4-(2-(methoxymethoxy)phenyl)-N-(thiazol-2-yl)-3,4-dihydro-2H-benzo[b][1,4]oxazine-7-sulfonamide (600 mg, 90.7%). MS (ESI, positive ion) m/z; 554.1 (M+1).

Step 3: 4-(2-Hydroxyphenyl)-N-(4-Methoxybenzyl)-N-(Thiazol-2-Yl)-3,4-Dihydro-2H-Benzo[B][1,4]Oxazine-7-Sulfonamide

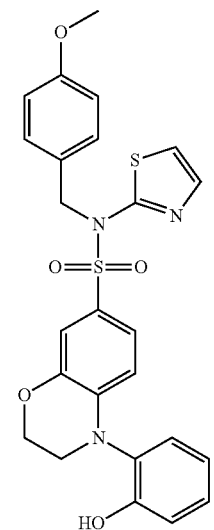 [SMILES: COc1ccc(CN(c2nccs2)S(=O)(=O)c2ccc3c(c2)OCCN3c2ccccc2O)cc1]

301

To a solution of N-(4-methoxybenzyl)-4-(2-(methoxymethoxy)phenyl)-N-(thiazol-2-yl)-3,4-dihydro-2H-benzo[b][1,4]oxazine-7-sulfonamide (600 mg, 2.169 mmol) in DCM (20 mL) was added 20% HCl in 1,4-Dioxane (2.0 mL) at 0° C. The reaction mixture was stirred at ambient temperature for 2 h. After completion, the reaction mixture was quenched with saturated aqueous sodium bicarbonate solution (20 mL) and extracted with DCM (2×20 mL). The organic layer was dried over sodium sulfate and concentrated under reduced pressure to obtain 4-(2-hydroxyphenyl)-N-(4-methoxybenzyl)-N-(thiazol-2-yl)-3,4-dihydro-2H-benzo[b][1,4]oxazine-7-sulfonamide as a yellow solid (550 mg, 99%) which was used for next step without purification.

MS (ESI, positive ion) m/z; 510.1 (M+1)

Step 4: 2-(2-(7-(N-(4-Methoxybenzyl)-N-(Thiazol-2-Yl)Sulfamoyl)-2H-Benzo[B][1,4]Oxazin-4(3H)-Yl)Phenoxy)Acetamide

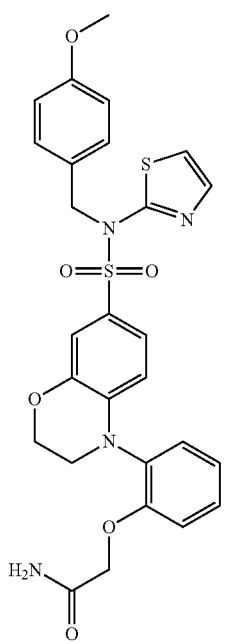 [SMILES: COc1ccc(CN(c2nccs2)S(=O)(=O)c2ccc3c(c2)OCCN3c2ccccc2OCC(N)=O)cc1]

To a solution of 4-(2-hydroxyphenyl)-N-(4-methoxybenzyl)-N-(thiazol-2-yl)-3,4-dihydro-2H-benzo[b][1,4]oxazine-7-sulfonamide (550 mg, 1.080 mmol), 2-bromoacetamide (704 mg, 5.108 mmol, Aldrich) in DMF (10 mL) was added potassium carbonate (528 mg, 3.83 mmol). The reaction mixture was heated at 80° C. for 12 h. After completion, the reaction mixture was cooled to room temperature, diluted with water (50 mL) and extracted with ethyl acetate (2×50 mL). The combined organic layer was washed with water (50 mL), dried over sodium sulfate and concentrated under reduced pressure to obtain the crude material which was purified by combiflash column chromatography (column size: 12 g; elution: 0-60% ethyl acetate in hexane) to get 2-(2-(7-(N-(4-methoxybenzyl)-N-(thiazol-2-yl)sulfamoyl)-2H-benzo[b][1,4]oxazin-4(3H)-yl)phenoxy)acetamide (300 mg, 49.0%). MS (ESI, positive ion) m/z; 567.1 (M+1)

302

Step 5: 2-(2-(7-(N-(Thiazol-2-Yl)Sulfamoyl)-2H-Benzo[B][1,4]Oxazin-4(3H)-Yl)Phenoxy) Acetamide

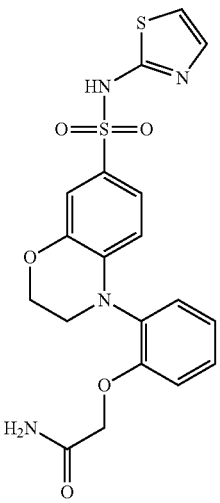 [SMILES: NC(=O)COc1ccccc1N1CCOc2cc(S(=O)(=O)Nc3nccs3)ccc21]

To a solution of 2-(2-(7-(N-(4-methoxybenzyl)-N-(thiazol-2-yl)sulfamoyl)-2H-benzo[b][1,4]oxazin-4(3H)-yl)phenoxy)acetamide (300 mg, 0.53 mmol) in DCM (30 mL) was added TFA (0.5 mL) at 0° C. The reaction mixture was stirred at ambient temperature for 5 h. After completion, the reaction mixture was quenched with saturated aqueous sodium bicarbonate solution (50 mL) and extracted with ethyl acetate (2×50 mL). The organic layer was dried over sodium sulfate and concentrated under reduced pressure to obtain the crude material which was purified by prep HPLC purification to obtain 2-(2-(7-(N-(thiazol-2-yl)sulfamoyl)-2H-benzo[b][1,4]oxazin-4(3H)-yl)phenoxy)acetamide (55 mg, 13.7%) as an off white solid.

MS (ESI, positive ion) m/z; 447.1 (M+1). $^1$H NMR (400 MHz, DMSO) δ 12.51 (s, 1H), 7.39-7.25 (m, 3H), 7.21 (d, J=4.6 Hz, 1H), 7.18-6.98 (m, 5H), 6.76 (d, J=4.4 Hz, 1H), 6.30 (d, J=8.5 Hz, 1H), 4.47 (s, 2H), 4.31 (t, J=4.1 Hz, 2H), 3.69-3.67 (m, 2H).

Example 257

4-(2-(Cyanomethoxy)Phenyl)-N-(Thiazol-2-Yl)-3,4-Dihydro-2H-Benzo[B][1,4]Oxazine-7-Sulfonamide

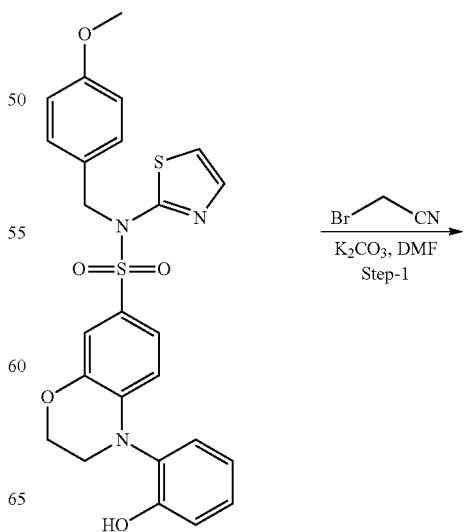

303

-continued

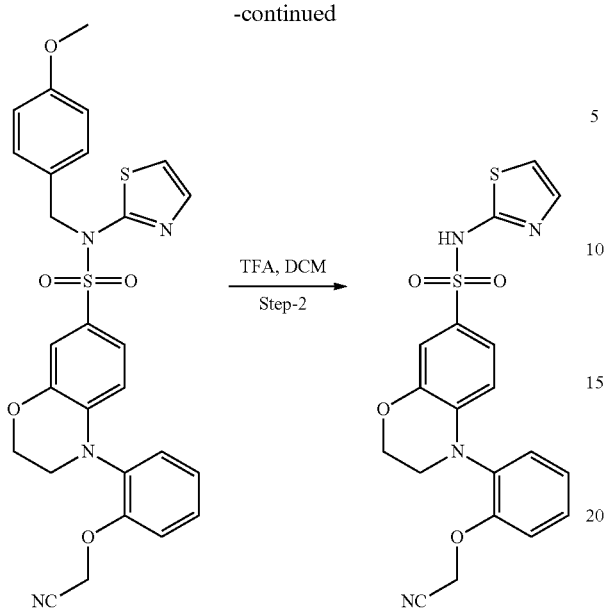

Step 1: 4-(2-Hydroxyphenyl)-N-(4-Methoxybenzyl)-N-(Thiazol-2-Yl)-3,4-Dihydro-2H-Benzo[B][1,4]Oxazine-7-Sulfonamide

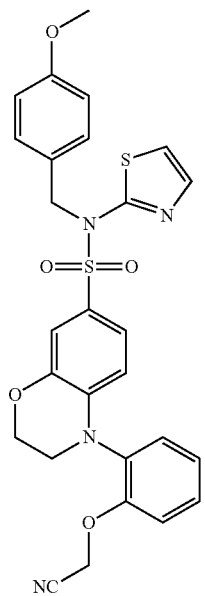 [SMILES: COc1ccc(CN(c2nccs2)S(=O)(=O)c2ccc3c(c2)OCCN3c2ccccc2OCC#N)cc1]

To a solution of 4-(2-hydroxyphenyl)-N-(4-methoxybenzyl)-N-(thiazol-2-yl)-3,4-dihydro-2H-benzo[b][1,4]oxazine-7-sulfonamide (From Example 256, Step 3; 550 mg, 1.080 mmol) and 2-bromoacetonitrile (194 mg, 1.62 mmol) in DMF (10 mL) was added potassium carbonate (447 mg, 3.24 mmol). The reaction mixture was heated at 80° C. for 12 h. After completion, the reaction mixture was cooled to room temperature, diluted with water (50 mL) and extracted with ethyl acetate (2×50 mL). The combined organic layer was washed with water (3×50 mL), dried over sodium sulfate and concentrated under reduced pressure to obtain the crude material which was purified by combiflash column chromatography (column size: 12 g; elution: 0-30% ethyl acetate in hexane) to yield 4-(2-(cyanomethoxy)phenyl)-N-(4-methoxybenzyl)-N-(thiazol-2-yl)-3,4-dihydro-2H-benzo[b][1,4]oxazine-7-sulfonamide (200 mg, 33.8%). MS (ESI, positive ion) m/z; 549.1 (M+1)

304

Step 2: 4-(2-(Cyanomethoxy)-Phenyl)-N-(Thiazol-2-Yl)-3,4-Dihydro-2H-Benzo[B][1,4]Oxazine-7-Sulfonamide

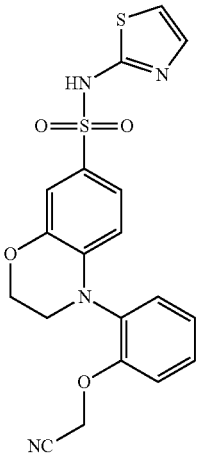 [SMILES: N#CCOc1ccccc1N1CCOc2cc(S(=O)(=O)Nc3nccs3)ccc21]

To a solution of 4-(2-(cyanomethoxy)phenyl)-N-(4-methoxybenzyl)-N-(thiazol-2-yl)-3,4-dihydro-2H-benzo[b][1,4]oxazine-7-sulfonamide (200 mg, 0.364 mmol) in DCM (30 mL) was added TFA (0.5 mL) at 0° C. The reaction mixture was stirred at ambient temperature for 2 h. After completion, the reaction mixture was quenched with saturated aqueous sodium bicarbonate solution (20 mL) and extracted with ethyl acetate (2×50 mL). The combined organic layer was dried over sodium sulfate and concentrated under reduced pressure to obtain the crude product which was purified by prep HPLC purification to obtain 4-(2-(cyanomethoxy)phenyl)-N-(thiazol-2-yl)-3,4-dihydro-2H-benzo[b][1,4]oxazine-7-sulfonamide as a white solid (39 mg, 25%). MS (ESI, positive ion) m/z; 429.0 (M+1). $^1$H NMR (400 MHz, DMSO) δ 12.50 (s, 1H), 7.42-7.36 (m, 2H), 7.36-7.30 (m, 1H), 7.23-7.15 (m, 2H), 7.12 (d, J=2.0 Hz, 1H), 7.08 (dd, J=8.5, 2.1 Hz, 1H), 6.77 (d, J=4.5 Hz, 1H), 6.19 (d, J=8.5 Hz, 1H), 5.18 (s, 2H), 4.32 (t, J=4.2 Hz, 2H), 3.64 (t, J=4.2 Hz, 2H).

Example 258

4-(2-(2-Hydroxypropan-2-Yl)Phenyl)-N-(Thiazol-2-Yl)-3,4-Dihydro-2H-Benzo[B][1,4]Oxazine-7-Sulfonamide

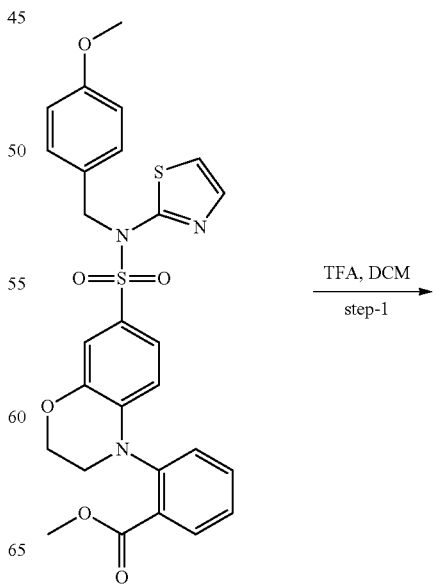

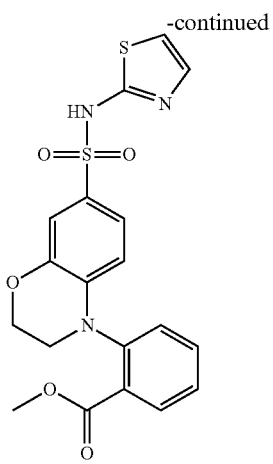

Step 1: Methyl-2-(7-(N-(Thiazol-2-Yl)Sulfamoyl)-2H-Benzo[B][1,4]Oxazin-4(3H)-Yl) Benzoate

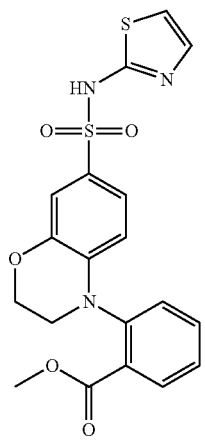 [SMILES: COC(=O)c1ccccc1N1CCOc2cc(S(=O)(=O)Nc3nccs3)ccc21]

To a solution of methyl 2-(7-(N-(4-methoxybenzyl)-N-(thiazol-2-yl)sulfamoyl)-2H-benzo[b][1,4]oxazin-4(3H)-yl) benzoate (From example 254, step 1; 1.2 g, 2.784 mmol) in DCM (40 mL) was added TFA (2.0 mL) at 0° C. The reaction mixture was stirred at ambient temperature for 5 h. After completion, the reaction mixture was quenched with saturated aqueous sodium bicarbonate solution (20 mL) and the aqueous layer was extracted with DCM (2×20 mL). The organic layer was dried over sodium sulfate and concentrated under reduced pressure to obtain the crude material which was purified by combiflash column chromatography (column size: 12 g; elution: 0-50% ethyl acetate in hexane) to get methyl 2-(7-(N-(thiazol-2-yl)sulfamoyl)-2H-benzo[b][1,4] oxazin-4(3H)-yl)benzoate as a yellow solid (400 mg, 42.7%).

MS (ESI, positive ion) m/z; 431.9 (M+1).

Step 2: 4-(2-(2-Hydroxypropan-2-Yl)Phenyl)-N-(Thiazol-2-Yl)-3,4-Dihydro-2H-Benzo[B][1,4]Oxazine-7-Sulfonamide

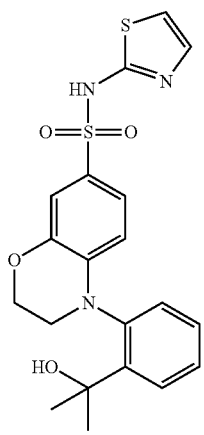 [SMILES: CC(C)(O)c1ccccc1N1CCOc2cc(S(=O)(=O)Nc3nccs3)ccc21]

To a solution of methyl 2-(7-(N-(thiazol-2-yl)sulfamoyl)-2H-benzo[b][1,4]oxazin-4(3H)-yl)benzoate (400 mg, 0.928 mmol) in THF (10 mL) was added MeMgBr (1.5 mL, 1 M in THF, 1.5 mmol) drop-wise at −78° C. The reaction mixture was stirred at ambient temperature for 2 h. After completion, the reaction mixture was quenched with saturated aqueous ammonium chloride solution (10 mL) and extracted with ethyl acetate (2×15 mL). The organic layer was dried over sodium sulfate and concentrated reduced pressure to obtain the crude compound which was purified by prep HPLC purification to obtain 4-(2-(2-hydroxypropan-2-yl)phenyl)-N-(thiazol-2-yl)-3,4-dihydro-2H-benzo[b][1,4]oxazine-7-sulfonamide as a white solid (55 mg, 13.7%). MS (ESI, positive ion) m/z; 432.10 (M+1). $^1$H NMR (400 MHz, DMSO) δ 12.53 (s, 1H), 7.84-7.81 (m, 1H), 7.40-7.34 (m, 2H), 7.20-7.15 (m, 2H), 7.15-7.11 (m, 2H), 6.77 (d, J=4.5 Hz, 1H), 5.91 (d, J=8.5 Hz, 1H), 5.07 (s, 1H), 4.38 (dt, J=17.9, 10.0 Hz, 2H), 3.64 (t, J=9.0 Hz, 1H), 3.46 (d, J=12.3 Hz, 1H), 1.43 (d, J=10.4 Hz, 6H).

Example 259

4-(2-Ethylphenyl)-N-(Thiazol-2-Yl)-3,4-Dihydro-2H-Benzo[B][1,4]Oxazine-7-Sulfonamide

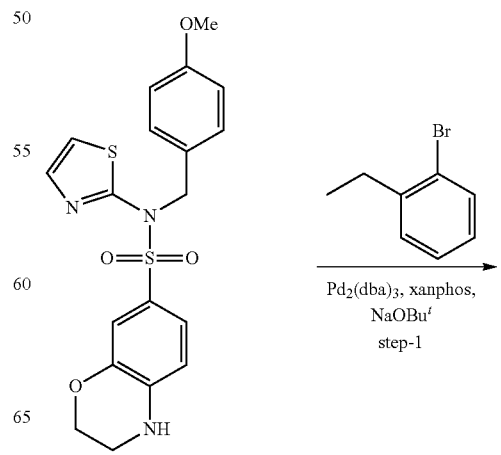

307
-continued

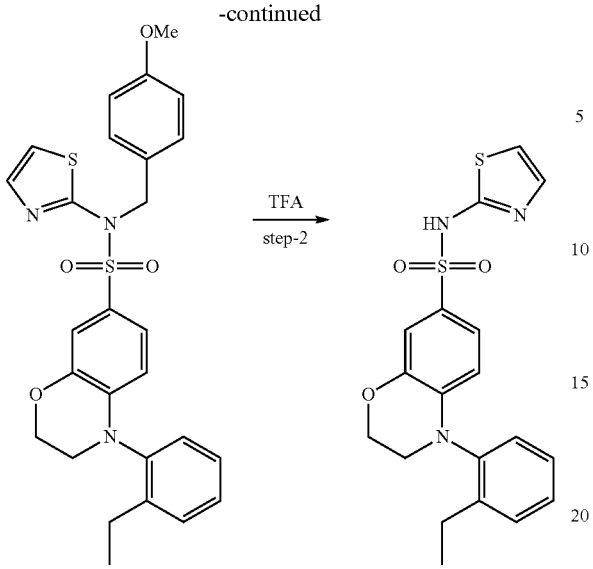

Step 1: 4-(2-Ethylphenyl)-N-(4-Methoxybenzyl)-N-(Thiazol-2-Yl)-3,4-Dihydro-2H-Benzo[B][1,4]Oxazine-7-Sulfonamide

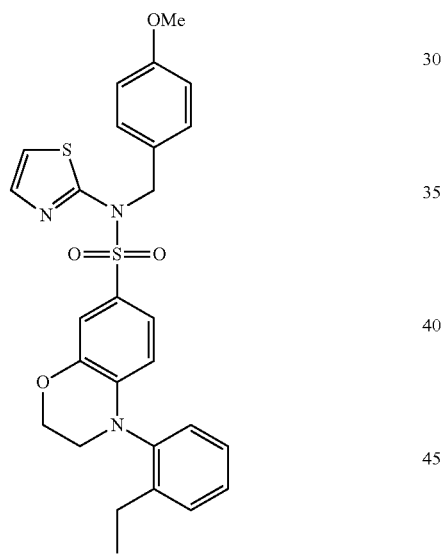

A mixture of N-(4-methoxybenzyl)-N-(thiazol-2-yl)-3,4-dihydro-2H-benzo[b][1,4]oxazine-7-sulfonamide (1.0 g, 2.39 mmol), 1-bromo-2-ethylbenzene (572.0 mg, 3.11 mmol, Aldrich), Pd$_2$(dba)$_3$ (218 mg, 0.23 mmol, GLR), Xantphos (276 mg, 0.46 mmol, GLR) and sodium-tert-butoxide (458 mg, 4.784 mmol) in toluene (20 mL) was degassed with nitrogen for 10 minutes. The reaction mixture was heated at 100° C. for 1 h under microwave irradiation. After completion, reaction mixture was diluted with water (10 mL) and extracted with ethyl acetate (3×50 mL). The combined organic layer was dried over sodium sulfate and concentrated under reduced pressure to obtain the crude material which was purified by combiflash column chromatography (column size: 12 g; elution: 0-20% ethyl acetate in hexane) to obtain 4-(2-ethylphenyl)-N-(4-methoxybenzyl)-N-(thiazol-2-yl)-3,4-dihydro-2H-benzo[b][1,4]oxazine-7-sulfonamide (400 mg, 33%) as a brown solid. MS (ESI, positive ion) m/z; 522.1 (M+1)

308

Step 2: 4-(2-Ethylphenyl)-N-(Thiazol-2-Yl)-3,4-Dihydro-2H-Benzo[B][1,4]Oxazine-7-Sulfonamide

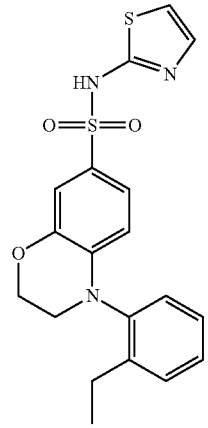 [SMILES: CCc1ccccc1N1CCOc2cc(S(=O)(=O)Nc3nccs3)ccc21]

To a solution of 4-(2-ethylphenyl)-N-(4-methoxybenzyl)-N-(thiazol-2-yl)-3,4-dihydro-2H-benzo[b][1,4]oxazine-7-sulfonamide (400 mg, 0.77 mmol) in DCM (50 mL) was added TFA (2.0 mL) at 0° C. The reaction mixture was stirred at ambient temperature for 2 h. After completion, the reaction mixture was quenched with saturated aqueous sodium bicarbonate solution (20 mL) and extracted with ethyl acetate (2×50 mL). The combined organic layer was dried over sodium sulfate and concentrated under reduced pressure to obtain the crude product which was purified by prep HPLC purification to obtain 4-(2-ethylphenyl)-N-(thiazol-2-yl)-3,4-dihydro-2H-benzo[b][1,4]oxazine-7-sulfonamide (176 mg, 56.9%) as a white solid. MS (ESI, positive ion) m/z; 402.3 (M+1). $^1$H NMR (400 MHz, DMSO) δ 12.51 (s, 1H), 7.42-7.38 (m, 1H), 7.33 (dt, J=4.4, 2.0 Hz, 2H), 7.29-7.24 (m, 1H), 7.21 (d, J=4.6 Hz, 1H), 7.12 (d, J=2.0 Hz, 1H), 7.08 (dd, J=8.5, 2.0 Hz, 1H), 6.77 (d, J=4.4 Hz, 1H), 6.00 (d, J=8.5 Hz, 1H), 4.34 (dd, J=10.2, 3.1 Hz, 2H), 3.74 (dt, J=7.3, 3.8 Hz, 1H), 3.51 (d, J=12.5 Hz, 1H), 2.47-2.44 (m, 2H), 1.11 (t, J=7.5 Hz, 3H).

Example 260

4-(2-(Pyridin-4-Yloxy)Phenyl)-N-(Thiazol-2-Yl)-3,4-Dihydro-2H-Benzo[B][1,4]Oxazine-7-Sulfonamide

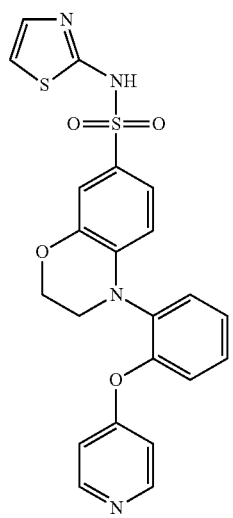 [SMILES: O=S(=O)(Nc1nccs1)c1ccc2c(c1)OCCN2c1ccccc1Oc1ccncc1]

A microwave vial containing a suspension of 4-(2-bromophenoxy)pyridine (0.180 g, 0.719 mmol), N-(4-methoxybenzyl)-N-(thiazol-2-yl)-3,4-dihydro-2H-benzo[b][1,4]oxazine-7-sulfonamide (Intermediate M; 0.2 g, 0.479 mmol), sodium t-butoxide (0.117 ml, 0.958 mmol), Xantphos (0.111 g, 0.192 mmol) and tris(dibenzylideneacetone)dipalladium (0) (0.088 g, 0.096 mmol) in toluene (4.79 ml) was purged with nitrogen and was microwave irradiated at 100° C. for 45 min. Reaction mixture was diluted with EtOAc (100 mL) and washed with water (2×50 mL). The organic layer was dried over anhydrous sodium sulfate, concentrated and purified by preperative LC/MS-2 System Column: XBridge 19×100 mm 12230326114 03 Mobile phase: 0.1% NH4OH in water/acetonitrile Flow rate: 40 ml/min Inj: 2200 uL. Gradient: 10 min5-50% shallow; 10 min10-60% shallow to obtain N-(4-methoxybenzyl)-4-(2-(pyridin-4-yloxy)phenyl)-N-(thiazol-2-yl)-3,4-dihydro-2H-benzo[b][1,4]oxazine-7-sulfonamide (0.108 g, 0.184 mmol, 38.4% yield) as yellow solid. The material was then dissolved in DCM (1 mL) and TFA was added (1 ml). The reaction mixture was concentrated and purified by MPLC (Biotage Isolera One; PuriFlash HP, 15p., 80 g), eluting with DCM:MeOH (90:10) to obtain 4-(2-(pyridin-4-yloxy)phenyl)-N-(thiazol-2-yl)-3,4-dihydro-2H-benzo[b][1,4]oxazine-7-sulfonamide (0.03 g, 0.064 mmol, 13.42% yield) as an off white solid. $^1$H NMR (400 MHz, DMSO-$d_6$) δ ppm 12.57 (br. s., 1 H) 8.30-8.34 (m, 2 H) 7.50-7.54 (m, 1 H) 7.41-7.45 (m, 2 H) 7.33-7.38 (m, 1 H) 7.23 (d, J=4.60 Hz, 1 H) 7.13 (dd, J=8.51, 2.15 Hz, 1 H) 7.02 (d, J=2.15 Hz, 1 H) 6.79 (d, J=4.60 Hz, 1 H) 6.64-6.68 (m, 2 H) 6.43 (d, J=8.51 Hz, 1 H) 3.56 (br. s., 2 H) 3.29 (br. s., 1H); MS (ESI, positive ion) m/z; 467.1 (M+1)

Example 261

4-(2-((2-Cyanopropan-2-Yl)Oxy)Phenyl)-N-(Thiazol-2-Yl)-3,4-Dihydro-2H-Benzo[B][1,4]Oxazine-7-Sulfonamide

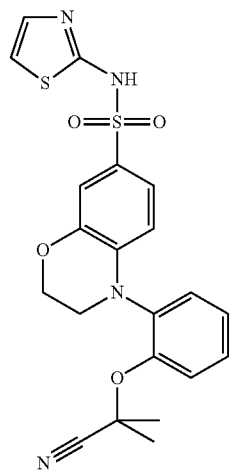 [SMILES: CC(C)(C#N)Oc1ccccc1N1CCOc2cc(S(=O)(=O)Nc3nccs3)ccc21]

A microwave vial containing a suspension of 2-(2-bromophenoxy)-2-methylpropanenitrile (0.173 g, 0.719 mmol), N-(4-methoxybenzyl)-N-(thiazol-2-yl)-3,4-dihydro-2H-benzo[b][1,4]oxazine-7-sulfonamide (Intermediate M; 0.2 g, 0.479 mmol), sodium t-butoxide (0.117 ml, 0.958 mmol), Xantphos (0.111 g, 0.192 mmol) and tris(dibenzylideneacetone)dipalladium (0) (0.088 g, 0.096 mmol) in toluene (9.58 ml) was purged with nitrogen and was microwave irradiated at 110° C. for 30 min. Reaction mixture was diluted with EtOAc (50 mL) and washed with saturated NaCl solution. Organic layer was concentrated and purified by preperative LC/MS-2 System Column: XBridge 19×100 mm 12230326114 03 Mobile phase: 0.1% NH4OH in water/acetonitrile Flow rate: 40 ml/min Inj: 2200 uL. Gradient: 10 min5-50% shallow; 10 min10-60% shallow to obtain 4-(2-((2-cyanopropan-2-yl)oxy)phenyl)-N-(4-methoxybenzyl)-N-(thiazol-2-yl)-3,4-dihydro-2H-benzo[b][1,4]oxazine-7-sulfonamide (44 mg, 0.076 mmol, 16% yield). To the material was then added DCM (1 mL) and TFA (4 drops) and stirred at ambient temperature for 2 h The reaction mixture was concentrated and purified by preperative LC/MS-2 System Column: XBridge 19×100 mm 12230326114 03 Mobile phase: 0.1% NH4OH in water/acetonitrile Flow rate: 40 ml/min Inj: 2200 uL. Gradient: 10 min5-50% shallow; 10 min10-60% shallow to obtain 4-(2-((2-cyanopropan-2-yl)oxy)phenyl)-N-(thiazol-2-yl)-3,4-dihydro-2H-benzo[b][1,4]oxazine-7-sulfonamide (3.8 mg, 0.008 mmol, 1.6% yield). $^1$H NMR (500 MHz, DMSO-$d_6$) δ ppm 7.43 (dd, J=8.12, 1.28 Hz, 1 H) 7.39 (dd, J=7.85, 1.55 Hz, 1 H) 7.31-7.37 (m, 1 H) 7.21-7.27 (m, 1 H) 7.11-7.14 (m, 2 H) 7.08 (dd, J=8.55, 2.14 Hz, 1 H) 6.66 (d, J=4.38 Hz, 1 H) 6.34 (d, J=8.44 Hz, 1 H) 5.75 (s, 1 H) 4.26-4.32 (m, 2 H) 3.60-3.65 (m, 2 H) 1.55 (br. s., 6 H); MS (ESI, positive ion) m/z; 457.0 (M+1)

Example 262

4-(2-(Hydroxymethyl)-4-(Trifluoromethyl) Phenyl)-3-Oxo-N-(Thiazol-2-Yl)-3,4-Dihydro-2H-Benzo[B][1,4]Oxazine-7-Sulfonamide

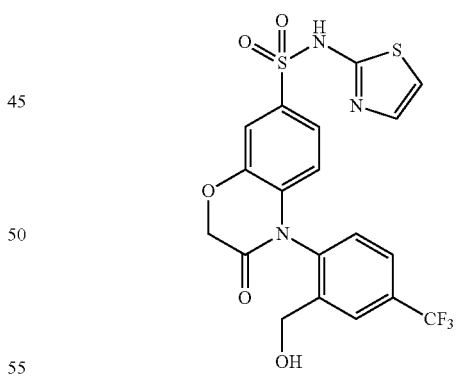

4-(2-(hydroxymethyl)-4-(trifluoromethyl)phenyl)-3-oxo-N-(thiazol-2-yl)-3,4-dihydro-2H-benzo[b][1,4]oxazine-7-sulfonamide was prepared in a similar fashion to Example 223, starting from INTERMEDIate AD and (2-bromo-5-(trifluoromethyl)phenyl)methanol (SynQuest Laboratories) instead of 1-bromo-2-methoxy-4-(trifluoromethyl)benzene. Purification was achieved using reverse-phase HPLC with a Waters-Xbridge C18, 19×100 mm, 10 μm column with a gradient 5-95% acetonitrile and water with 0.1% TFA modifier. m/z ESI 486.2 (M+H)$^+$.

Example 263

(+/−)-4-(2-Methoxy-4-(Trifluoromethyl)Phenyl)-2-Methyl-3-Oxo-N-(Thiazol-2-Yl)-3,4-Dihydro-2H-Benzo[B][1,4]Oxazine-7-Sulfonamide

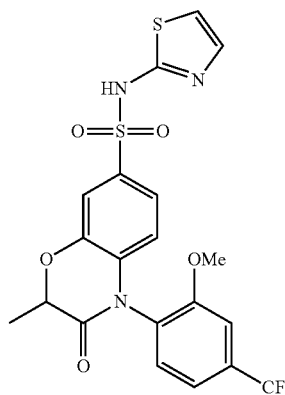

(+/−)-4-(2-methoxy-4-(trifluoromethyl)phenyl)-2-methyl-3-oxo-N-(thiazol-2-yl)-3,4-dihydro-2H-benzo[b][1,4]oxazine-7-sulfonamide was prepared in a similar fashion to Example 223, starting from 3-hydroxy-4-((2-methoxy-4-(trifluoromethyl)phenyl)amino)-N-(4-methoxybenzyl)-N-(thiazol-2-yl)benzenesulfonamide) (from Step 1, Example 223) and 2-chloropropanoyl chloride instead chloroacetyl chloride. Purification was achieved using reverse-phase HPLC with a Waters-Xbridge C18, 19×100 mm, 10 m column with a gradient 5-95% acetonitrile and water with 0.1% ammonium hydroxide modifier. 1H NMR (500 MHz, DMSO-d6) δ 1.53 (dd, J=16.93, 6.73 Hz, 3 H) 2.54 (s, 3 H) 3.79 (s, 1 H) 4.97-5.04 (m, 1 H) 6.40 (d, J=8.48 Hz, 1 H) 6.83 (d, J=4.58 Hz, 1H) 7.26 (d, J=4.52 Hz, 1 H) 7.30-7.42 (m, 2 H) 7.45-7.63 (m, 3 H). m/z ESI 500.0 (M+H)+.

Example 264

(S)-4-(2-Methoxy-4-(Trifluoromethyl)Phenyl)-2-Methyl-3-Oxo-N-(Thiazol-2-Yl)-3,4-Dihydro-2H-Benzo[B][1,4]Oxazine-7-Sulfonamide

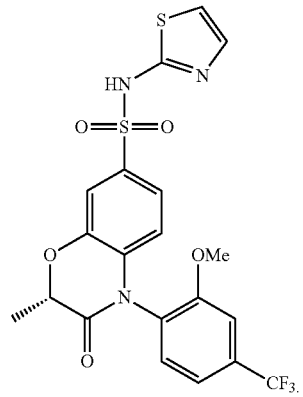 [SMILES: COc1cc(C(F)(F)F)ccc1N1C(=O)C(C)Oc2cc(S(=O)(=O)Nc3nccs3)ccc21]

*Chiral center randomly assigned

Chiral separation of racemic 4-(2-methoxy-4-(trifluoromethyl)phenyl)-2-methyl-3-oxo-N-(thiazol-2-yl)-3,4-dihydro-2H-benzo[b][1,4]oxazine-7-sulfonamide (Example 263) was achieved using supercritical fluid chromatography with a mobile phase: 80% CO2/20% methanol with 0.2% diethylamine and stationary phase of 2 cm×15 cm Chiralpak AD-H column (Chiral Technologies). (S)-4-(2-methoxy-4-(trifluoromethyl)phenyl)-2-methyl-3-oxo-N-(thiazol-2-yl)-3,4-dihydro-2H-benzo[b][1,4]oxazine-7-sulfonamide was isolated as an off-white solid. m/z ESI 500.2 (M+H)+.

Example 265

(R)-4-(2-Methoxy-4-(Trifluoromethyl)Phenyl)-2-Methyl-3-Oxo-N-(Thiazol-2-Yl)-3,4-Dihydro-2H-Benzo[B][1,4]Oxazine-7-Sulfonamide

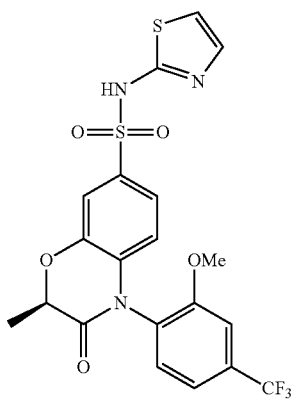

*Chiral center randomly assigned

Purified according to Example 264; m/z ESI 500.2 (M+H)+.

Example 266

4-(2-Methoxy-4-(Trifluoromethyl)Phenyl)-2,2-Dimethyl-3-Oxo-N-(Thiazol-2-Yl)-3,4-Dihydro-2H-Benzo[B][1,4]Oxazine-7-Sulfonamide

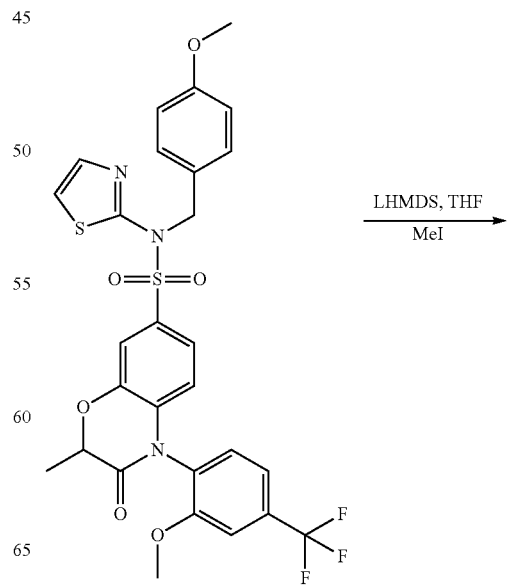

-continued

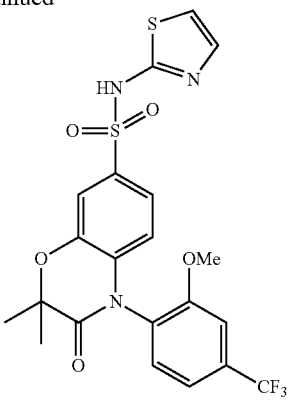

4-(2-Methoxy-4-(trifluoromethyl)phenyl)-N-(4-methoxybenzyl)-2-methyl-3-oxo-N-(thiazol-2-yl)-3,4-dihydro-2H-benzo[b][1,4]oxazine-7-sulfonamide (from the product of Step 2 in Example 263; 110 mg, 0.178 mmol) was dissolved in THF (710 µl) in a 5 mL vial and cooled to 0° C. Lithium bis(trimethylsilyl)amide (1.0 m solution in THF, 69.1 µl, 0.355 mmol) was added dropwise, followed by methyl iodide (16.65 µl, 0.266 mmol), and the reaction was stirred for 30 min at 0° C. until reaction was complete by LCMS. Saturated ammonium chloride solution (aq; 5 mL) was added to the reaction mixture and it was warmed to RT, then extracted with EtOAc (3×5 mL), dried organics over $Na_2SO_4$, filtered and concentrated via rotary evaporation. Crude 4-(2-methoxy-4-(trifluoromethyl)phenyl)-N-(4-methoxybenzyl)-2,2-dimethyl-3-oxo-N-(thiazol-2-yl)-3,4-dihydro-2H-benzo[b][1,4]oxazine-7-sulfonamide was dissolved in DCM (177 µl) then treated with 2,2,2-trifluoroacetic acid (328 µl, 4.42 mmol) and stirred at rt for 30 min until reaction was complete by LCMS. The reaction mixture was concentrated and purified via reverse-phase HPLC with a Waters-Xbridge C18, 19×100 mm, 10 µm column with a gradient 5-95% acetonitrile and water with 0.1% TFA modifier to yield title compound. m/z ESI 514.0 $(M+H)^+$.

Nav 1.7 and Nav 1.5 In Vitro Assays

HEK 293 cells stably transfected with either Nav 1.7 or with Nav 1.5 were recorded in population patch-clamp mode with the IonWorks® Quattro automated electrophysiology system in accordance with the manufacturer's specifications (Molecular Devices, LLC, Sunnyvale, Calif.). Sodium channel currents were measured in response to a train of depolarizations that induced successively greater inactivation.

Cells were held at −110 mV for three seconds (Nav 1.7) or half a second (Nav 1.5) from a holding voltage of −15 mV, then put through a series of 26 pulses of 150 msec duration to −20 mV at a frequency of 5 Hz. Cells were then left unclamped for a period of 3 to 8 minutes while a single concentration of test compound was added. Cells were then reclamped and put through the same voltage protocol. Current at the end of the $26^{th}$ pulse to −20 mV was subtracted from the peak current evoked by the $26^{th}$ pulse to −20 mV to correct for leak current. Percent block was calculated for each concentration in duplicate, and $IC_{50}$ curves were fitted to percent block as a function of concentration. Data for compounds of the present invention are shown in the table below. It is noted that more than one experiment may have been conducted and the number presented may be the average of the results of more than one experiment.

Nav 1.7 In Vitro PX Assay

HEK 293 cells stably transfected with human Nav1.7 were recorded in whole cell voltage clamp mode with the PatchXpress automated electrophysiology system (Molecular Devices, LLC, Sunnyvale, Calif.). Compound effects were measured on a partially inactivated state of the sodium channel. Cells were clamped to a holding potential yielding 20 to 50% inactivation. To elicit sodium current, channels were activated by pulsing to −10 mV for 20 msec. This voltage protocol was repeated at a rate of 0.1 Hz throughout the experiment. A single concentration of test compound was applied to cells for a duration of 3 minutes. Peak sodium current was measured at the end of the compound addition period to determine percent inhibition. Three to five cells were tested per concentration, and $IC_{50}$ curves were fitted to percent inhibition as a function of concentration.

| Example No. | Nav 1.7 IWQ $IC_{50}$ (µM) | Nav 1.7 PX $IC_{50}$ (µM) | Nav 1.5 IWQ IC50 (µM) |
|---|---|---|---|
| 1 | 0.0113 | 0.0589 | >10.0 |
| 2 | 0.00783 | 0.0386 | >10.0 |
| 3 | 0.0108 | 0.0577 | 1.87 |
| 4 | 0.00933 | 0.0576 | 0.944 |
| 5 | 0.245 | 0.322 | 4.03 |
| 6 | 0.0818 | 0.306 | 2.29 |
| 7 | 0.0044 | 0.0237 | 0.349 |
| 8 | 7.58 | 16 | >10.0 |
| 9 | 0.876 | 6.32 | >10.0 |
| 10 | 4.61 | 6.75 | >10.0 |
| 11 | 3.21 | 12.6 | >10.0 |
| 12 | 24.5* | | >10.0 |
| 13 | 1.72 | 5.16 | >10.0 |
| 14 | 9.31 | | 8.25 |
| 15 | 6.11 | | >10.0 |
| 16 | 1.86 | 11.9 | >10.0 |
| 17 | 3.63 | 24.1* | >10.0 |
| 18 | 1.04 | 0.946 | >10.0 |
| 19 | 1.18 | 4.89 | >10.0 |
| 20 | 7.6 | 33.2* | |
| 21 | 0.0158 | 0.162 | 1.33 |
| 22 | 0.0105 | 0.134 | >10.0 |
| 23 | 0.0298 | 0.659 | 5.41 |
| 24 | 0.834 | 4.27 | >10.0 |
| 25 | 0.0123 | 0.146 | 0.214 |
| 26 | 0.0105 | 0.102 | 0.306 |
| 27 | 1.25 | 10.7 | >10.0 |
| 28 | 0.656 | 2.65 | >10.0 |
| 29 | 0.0095 | 0.079 | 0.634 |
| 30 | 0.142 | 0.756 | >10.0 |
| 31 | 0.016 | 0.0914 | 1.46 |
| 32 | 0.0725 | 0.534 | 4.77 |
| 33 | 0.141 | 1.19 | >10.0 |
| 34 | 2.45 | 3.46 | >10.0 |
| 35 | 0.0435 | 0.138 | >10.0 |
| 36 | 0.0315 | 0.145 | >10.0 |
| 37 | 0.207 | 2.2 | >10.0 |
| 38 | 0.013 | 0.0794 | 0.254 |
| 39 | 0.333 | 9.22 | >10.0 |
| 40 | 0.713 | 4.32 | >10.0 |
| 41 | 0.111 | 0.64 | 4.93 |
| 42 | 0.121 | 1.54 | >10.0 |
| 43 | 0.115 | 0.975 | 1.85 |
| 44 | 0.014 | 0.0687 | 3.59 |
| 45 | 0.0062 | 0.135 | 1.2 |
| 46 | 0.165 | 1.08 | >10.0 |
| 47 | 0.0145 | 0.303 | 7.93 |
| 48 | 0.0285 | 0.719 | >10.0 |
| 49 | 0.015 | 0.193 | 1.15 |
| 50 | 0.117 | 0.315 | 0.957 |
| 51 | 0.0045 | 0.364 | >10.0 |
| 52 | 0.0045 | 0.0355 | |
| 53 | 0.0225 | 0.203 | 0.554 |
| 54 | 0.0115 | 0.585 | 0.731 |
| 55 | 2.92 | 19.9 | >10.0 |
| 56 | 0.051 | 0.265 | 4.79 |
| 57 | 0.154 | 1.93 | 6.7 |

| Example No. | Nav 1.7 IWQ IC$_{50}$ (µM) | Nav 1.7 PX IC$_{50}$ (µM) | Nav 1.5 IWQ IC50 (µM) |
|---|---|---|---|
| 58 | 0.225 | 2.55 | 6.3 |
| 59 | 0.015 | 0.252 | 5.57 |
| 60 | 1.47 | 24.4* | >10.0 |
| 61 | 0.679 | 2.43 | >10.0 |
| 62 | 0.049 | 0.282 | >10.0 |
| 63 | 0.027 | 0.144 | 2.67 |
| 64 | 0.418 | 1.07 | >10.0 |
| 65 | 0.024 | 0.0244 | 5.28 |
| 66 | 3.73 | 22.8* | >10.0 |
| 67 | 0.381 | 0.442 | 5.33 |
| 68 | 0.158 | 1.75 | 4.83 |
| 69 | 3.78 | 33.9* | 4.44 |
| 70 | 0.638 | 5.69 | >10.0 |
| 71 | 0.605 | 5.32 | >10.0 |
| 72 | 3.76 | 5.76 | >10.0 |
| 73 | 7.58 |  | >10.0 |
| 74 | 5.24 | 4.07 | 6.08 |
| 75 | 0.182 | 0.706 | 7.37 |
| 76 | 0.871 | 9.23 | 6.03 |
| 77 | 0.141 | 2.07 | >10.0 |
| 78 | 0.249 | 2.22 | >10.0 |
| 79 | 0.216 | 1.18 | >10.0 |
| 80 | 0.126 | 0.34 | 5.64 |
| 81 | 0.288 | 1.65 | >10.0 |
| 82 | 7.37 |  | >10.0 |
| 83 | 0.114 | 1.11 | >10.0 |
| 84 | 0.326 | 3.04 | 3.81 |
| 85 | 41.1* |  | >10.0 |
| 86 | 0.32 | 0.851 | 2.26 |
| 87 | 0.026 | 0.381 | >10.0 |
| 88 | 0.224 | 0.737 | >10.0 |
| 89 | 0.0285 | 0.464 | 1.14 |
| 90 | 0.924 | 2.59 | >10.0 |
| 91 | 3.64 | 9.21 | >10.0 |
| 92 | 26.4* |  | >10.0 |
| 93 | 0.0785 | 0.566 | 1.84 |
| 94 | 0.0085 | 0.149 | 0.724 |
| 95 | 0.0705 | 0.293 | 6.67 |
| 96 | 0.823 | 1.89 | 1.4 |
| 97 | 0.208 | 0.772 | 0.851 |
| 98 | 0.996 | 3.43 | >10.0 |
| 99 | 0.327 | 4.97 | >10.0 |
| 100 | 0.679 | 5.79 | >10.0 |
| 101 | 0.367 | 3.63 | 8.5 |
| 102 | 1.39 | 8.89 | >10.0 |
| 103 | 0.04 | 0.422 | 9.59 |
| 104 | 0.11 | 0.657 | >10.0 |
| 105 | 0.0535 | 0.894 | >10.0 |
| 106 | 0.0425 | 0.288 | >10.0 |
| 107 | 0.0285 | 0.309 | >10.0 |
| 108 | 0.0455 | 0.303 | >10.0 |
| 109 | 0.249 | 1.98 | >10.0 |
| 110 | 1.7 | 39.2* | >10.0 |
| 111 | 0.0335 | 1.05 | 3.03 |
| 112 | 1.66 | 12.2 | >10.0 |
| 113 | 0.891 | 2.72 | 3.37 |
| 114 | 0.0405 | 0.278 | 5.06 |
| 115 | 1.28 | 5.57 | 7.73 |
| 116 | 0.841 | 4.95 | 7.36 |
| 117 | 2.14 |  | >10.0 |
| 118 | 0.66 | 18.1 | >10.0 |
| 119 | 2.53 |  | >10.0 |
| 120 | 0.796 | 2.24 | >10.0 |
| 121 | 0.397 | 4.5 | >10.0 |
| 122 | 0.615 | 2.9 | 7.03 |
| 123 | 1.07 | 4.72 | 5.81 |
| 124 | 0.16 | 2.69 | 2.33 |
| 125 | 0.571 | 4.04 | 6.55 |
| 126 | 1.24 | 14.2 | >10.0 |
| 127 | 0.475 | 1.32 | >10.0 |
| 128 | 0.0695 | 0.912 | 3.69 |
| 129 | 0.263 | 2.9 | >10.0 |
| 130 | 0.635 | 5.29 | 6.2 |
| 131 | 1.31 | 23.3 | >10.0 |
| 132 | 3.56 |  | >10.0 |
| 133 | 1.59 | 20.2* | >10.0 |
| 134 | 1.34 | 17.1 | >10.0 |
| 135 | 2.68 | 22.6* | >10.0 |
| 136 | 2.98 | 27.4* | >10.0 |
| 137 | 0.914 | 21.7 | >10.0 |
| 138 | 0.86 | 11.5 | 3.83 |
| 139 | 0.0695 | 0.415 | 7.04 |
| 140 | 0.451 | 1.34 | 6.6 |
| 141 | 0.671 | 6.42 | 2.5 |
| 142 | 2.21 | 33.9* | >10.0 |
| 143 | 1.01 | 9.07 | >10.0 |
| 144 | 0.894 | 7.67 | >10.0 |
| 145 | 0.235 | 11.8 | 7.38 |
| 146 | 0.416 | 4.73 | 5.22 |
| 147 | 0.107 | 1.99 | >10.0 |
| 148 | 0.0665 | 0.782 | >10.0 |
| 149 | 0.198 | 2.55 | >10.0 |
| 150 | 0.017 | 0.192 | 5.58 |
| 151 | 0.0135 | 0.158 | >10.0 |
| 152 | 1.63 | 2.78 | 9.42 |
| 153 | 2.69 | 13.8 | >10.0 |
| 154 | 2.69 | 13.7 | >10.0 |
| 155 | 2.37 | 12.6 | >10.0 |
| 156 | 2.28 | 2.6 | 3.93 |
| 157 | 1.66 | 8.02 | >10.0 |
| 158 | 1.49 | 4.51 | >10.0 |
| 159 | 1.42 | 8.15 | >10.0 |
| 160 | 1.1 | 7.1 | >10.0 |
| 161 | 0.808 | 2.37 | 3.49 |
| 162 | 0.742 | 2.85 | >10.0 |
| 163 | 0.733 | 1.55 | 3.14 |
| 164 | 0.727 | 3.19 | >10.0 |
| 165 | 0.7 | 3.75 | >10.0 |
| 166 | 0.683 | 11.1 | >10.0 |
| 167 | 0.652 | 6.15 | >10.0 |
| 168 | 0.643 | 3.25 | >10.0 |
| 169 | 0.601 | 0.416 | >10.0 |
| 170 | 0.401 | 2.62 | >10.0 |
| 171 | 0.274 | 0.961 | 6.44 |
| 172 | 0.244 | 0.936 | >10.0 |
| 173 | 0.236 | 1.65 | >10.0 |
| 174 | 0.211 | 0.822 | 2.01 |
| 175 | 0.202 | 1.39 | 5.08 |
| 176 | 0.191 | 1.82 | >10.0 |
| 177 | 0.178 | 1.49 | >10.0 |
| 178 | 0.129 | 0.678 | 5.6 |
| 179 | 0.112 | 0.75 | 5.64 |
| 180 | 0.104 | 0.85 | 6.94 |
| 181 | 0.0075 | 0.175 | >10.0 |
| 182 | 0.064 | 0.124 | 1.99 |
| 183 | 0.177 | 3.32 | >10.0 |
| 184 | 0.186 | 0.392 | 3.17 |
| 185 | 0.335 | 2.62 | 7.62 |
| 186 | 0.0115 | 0.0676 | 7.72 |
| 187 | 0.417 | 7.73 | >10.0 |
| 188 | 0.0753 | 1.22 | 3.62 |
| 189 | 0.385 | 3.1 | 7.59 |
| 190 | 0.309 | 5.17 | >10.0 |
| 191 | 0.14 | 0.976 | >10.0 |
| 192 | 0.0525 | 0.769 | 1.61 |
| 193 | 0.103 | 0.684 | 1.56 |
| 194 | 0.163 | 1.37 | 3.59 |
| 195 | 0.233 | 1.1 | >10.0 |
| 196 | 0.396 | 0.898 | 5.7 |
| 197 | 2.53 | 27.8* | >10.0 |
| 198 | 0.627 | 0.339 | 1.88 |
| 199 | 0.469 | 0.387 | 1.22 |
| 200 | 0.144 | 0.15 | 0.854 |
| 201 | 0.143 | 0.773 | 4.83 |
| 202 | 0.0935 | 0.428 | 0.686 |
| 203 | 0.0875 | 0.469 | 1.09 |
| 204 | 0.0475 | 0.343 | 0.637 |
| 205 | 0.038 | 0.382 | >10.0 |
| 206 | 0.0315 | 0.174 | 1.14 |
| 207 | 0.025 | 0.0867 | 3.11 |

| Example No. | Nav 1.7 IWQ IC$_{50}$ (µM) | Nav 1.7 PX IC$_{50}$ (µM) | Nav 1.5 IWQ IC50 (µM) |
| --- | --- | --- | --- |
| 208 | 0.0185 | 0.258 | 0.896 |
| 209 | 0.0125 | 0.165 | 0.497 |
| 210 | 0.0125 | 0.226 | 6.11 |
| 211 | 0.0055 | 0.229 | 0.471 |
| 212 | 0.0213 | 0.373 | 0.736 |
| 213 | | 0.455 | |
| 214 | 0.0685 | 0.8 | >10.0 |
| 215 | 0.00986 | 0.183 | 0.203 |
| 216 | 0.034 | 0.516 | 5.73 |
| 217 | 0.008 | 0.207 | 1.31 |
| 218 | 0.193 | 1.99 | 0.385 |
| 219 | 5.19 | 26.2* | >10.0 |
| 220 | 0.864 | 17.2 | >10.0 |
| 221 | 0.564 | 3.03 | >10.0 |
| 222 | 3.43 | 33.8* | >10.0 |
| 223 | 0.012 | 0.218 | >10.0 |
| 225 | | 0.303 | |
| 226 | 0.0365 | 0.74 | >10.0 |
| 228 | 20.0* | | >10.0 |
| 229 | | 3.16 | |
| 230 | | 33.6 | |
| 231 | | 19.8 | |
| 232 | | 2.01 | |
| 233 | | 0.327 | |
| 234 | | 1.45 | |
| 235 | | 0.896 | |
| 236 | | 0.513 | |
| 238 | | 0.135 | |
| 239 | | 0.35 | |
| 240 | | 11.9 | |
| 241 | | 0.483 | |
| 242 | | 5.82 | |
| 243 | | 1.88 | |
| 244 | | 5.01 | |
| 245 | | 0.615 | |
| 246 | | 0.54 | |
| 247 | | 0.403 | |
| 248 | | 0.175 | |
| 250 | | 0.91 | |
| 251 | | 27.8* | |
| 252 | | 3.67 | |
| 253 | | 27.0* | |
| 254 | | 2.42 | |
| 255 | | 0.975 | |
| 256 | | 2.22 | |
| 257 | | 0.408 | |
| 258 | | 1.31 | |
| 259 | | 1.6 | |
| 260 | | 2.26 | |
| 261 | | 3.6 | |
| 262 | | 3.35 | |
| 263 | | 0.457 | |
| 264 | | 0.596 | |
| 265 | | 0.728 | |
| 266 | | 5.62 | |

*percent inhibition at 4.9 µM

The compounds of the present invention may also be tested in the following in vivo assays.

Rat Formalin Model of Persistent Pain

On the test day, animals (Naïve, male Sprague Dawley rats) weighing between 260-300 g at the start of testing can be obtained from Harlan (Indianapolis, Ind.). All animals may be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing and at least 30 minutes prior to test onset, animals can be acclimated to the individual testing chambers. At test time, each animal can be gently wrapped in a towel with the left hindpaw exposed. A dilute solution of formalin (2.5%) in phosphate buffered saline can be injected subcutaneously into the dorsal surface of the left hindpaw in a volume to 50 µL with a 30 g needle. Immediately following injection, a small metal band can be affixed to the plantar side of the left hindpaw with a drop of LOCTITE (adhesive). Animals may be then placed into the testing chambers and the number of flinches can be recorded between 10 to 40 minutes after formalin injection. A flinch is defined as a quick and spontaneous movement of the injected hindpaw not associated with ambulation. Flinches can be quantified with the aid of the Automated Nociception Analyzer built by the University of California, San Diego Department of Anesthesiology. Individual data can be expressed as a % maximal potential effect (% MPE) calculated with the following formula: (−(Individual score−Vehicle average score)/Vehicle average score))*100=% MPE Statistical analysis can be performed by analysis of variance (ANOVA), with post-hoc analysis using Bonferroni compared to the vehicle group for a significant main effect. Data can be represented as mean % MPE+/−standard error for each group.

Mouse Formalin Model of Persistent Pain

On the test day, animals (Naïve, male C57Bl/6 mice) weighing between 22-30 g at the start of testing were obtained from Harlan (Frederick, Md.). All animals are housed under a 12/12 h light/dark cycle with lights on at 0600. Rodents are housed up to four per cage on solid bottom cages with corn cob bedding and have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing, animals are acclimated to the individual testing chambers for 5 minutes immediately preceding the test. At test time, each animal is gently wrapped in a glove with the left hind paw exposed. A dilute solution of formalin (2.0%) in phosphate buffered saline is injected subcutaneously into the dorsal surface of the left hindpaw in a volume to 20 µL with a 30 g needle. Animals are then placed into the testing chambers and the time the animal spends licking and/or lifting the hind paw is recorded for up to one hour. Individual data can be expressed as a % reversal calculated with the following formula: (1−(Drug group average score−Vehicle group average score))*100=% Reversal Statistical analysis is performed by analysis of variance (ANOVA), with post-hoc analysis using Dunett's multiple comparison test compared to the vehicle group for any significant main effect. Data can be represented as mean+/− standard error for each group.

Rat Open Field Assay

On the test day, animals (Naïve, male C57Bl/6 mice) weighing between 22-30 g at the start of testing were obtained from Harlan (Frederick, Md.). All animals are housed under a 12/12 h light/dark cycle with lights on at 0600. Rodents are housed up to four per cage on solid bottom cages with corn cob bedding and have access to food and water ad libitum. Animals should be allowed to habituate to the vivarium for at least five days before testing is begun and should be brought into a room separate from the testing room at least 30 minutes prior to dosing. Animals are pretreated with the appropriate test compound either by oral gavage or intraperitoneal injection at the desired pretreatment time (typically two hours before test onset) and then are returned to their home cages until the pretreatment has elapsed. At test time, animal are transferred to the open field testing room in their home cages. Each animal is placed in a separate testing chamber and the motion tracking system is started. The house lights in the testing room should be turned off and the animals can be allowed to explore the novel open field for 30 minutes. An automated motion tracker, made by Kinder Scientific, Poway, Calif., is used to capture animal exploration with the aid of infrared photo beams to detect animal movement. These behaviors include basic movement and vertical rearing, which are used as the primary endpoints for this assay. At the end of the test, house lights are turned on and the animals should be removed from the testing apparatus. Data can be expressed as a percent change from the vehicle control using the following equation.

(1−(Test mean/Vehicle mean))*100=% Change.

Statistical analysis can be performed by analysis of variance (ANOVA), with post-hoc analysis using Dunnett's multiple comparison test to follow up significant main effects. Data can be represented as mean+/−standard error for each group.

CFA-Thermal Assay

Animals (Naïve, male Sprague Dawley rats) weighing between 260-300 g at the start of testing) can be obtained from Harlan (Indianapolis, Ind.). All animals can be housed under a 12/12 h light/dark cycle with lights on at 0600. Rodents may be housed two to a cage on solid bottom cages with corn cob bedding with access to food and water ad libitum. Animals can be allowed to habituate to the vivarium for at least five days before testing was begun and may be brought into the testing room at least 30 minutes prior to dosing. The Complete Freund's Adjuvant (CFA)-thermal assay may use a three continuous day testing schedule consisting of a habituation day, a baseline day, and a test day. On day 1, animals can be brought into the testing room, labeled, and placed in their individual testing boxes on the testing apparatus. Animals may be allowed to explore this environment for at least an hour without actually being tested. After habituating, animals can be placed back in their home cages and returned to the vivarium. On day 2, animals can be brought back into the testing room and placed on the testing apparatus and allowed to calm down (typically 30-45 minutes). A basal thermal threshold should be then taken with the following procedure: once calm, a Ugo Basile plantar device is placed under the animals left hindpaw; the start button is depressed turning on a steadily increasing thermal source and a timer; when the animal reaches its thermal threshold it will flinch its hindpaw, stopping the timer and the thermal stimulus. This latency to flinch can be recorded three times for each animal, with at least 5 minutes between trials, and the mean score can be used as the animal's baseline threshold. After testing, animals can be injected intraplantarly with a 25 µg/50 µl of complete Freund's adjuvant into the left hindpaw. Animals are then returned to their home cages and returned to the vivarium. On test day, animals can be again placed on the thermal testing apparatus and their post-CFA baselines obtained with the procedure outlined above. Animals can be pretreated with the appropriate test compound either by oral gavage or intraperitoneal injection at the desired pretreatment time (typically two hours before test onset) and then can be returned to their home cages. Thirty minutes prior to testing, animals can be placed on the apparatus again. Once the pretreatment time has elapsed, animals can be again tested with the procedure above. Data may be expressed as a percent maximal potential effect with the following formula:

((Post-Drug Mean−Pre-Drug Mean)/(Baseline Mean−Pre-Drug Mean))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Spinal Nerve Ligation (Chung)

Animals (Naïve, male Sprague Dawley rats) weighing between 150-200 g at the start of first time testing can be obtained from Harlan (Indianapolis, Ind.). All animals may be housed under a 12/12 h light/dark cycle with lights on at 0600. Rodents can be housed two to a cage on solid bottom cages with corn cob bedding with access to food and water ad libitum. Animals may be allowed to habituate to the vivarium for at least five days before testing is begun. Surgery may be then performed based on the method described by Kim and Chung (1992). Briefly, animals can be placed under isoflurane anesthesia and placed in a sterile surgical field. The area of the lumbar spine is excised and the spinal nerves at L4-L5 are exposed. The L5 spinal nerve is identified and tightly ligated with 5-0 silk suture. The muscle may be closed with absorbable suture and the skin with wound clip. Animals may be returned to the vivarium for 7-14 days and monitored daily. On test day, animals can be brought into the testing room and placed on a wire mesh floor in individual testing chambers. They may be allowed to acclimate to the chambers until they are calm. A series of Semmes-Weinstein monofilaments (von Frey hairs) with calibrated bending forces are then applied to determine a hyperalgesic baseline following the method set forth by Chaplan et al. (1994). Briefly, filaments are applied with an increasing force (if there was not reaction to the previous stimulus) or decreasing force (if there was a reaction to the previous stimulus) until a baseline value is reached. Animals are then pretreated with the appropriate test compound either by oral gavage or intraperitoneal injection at the desired pretreatment time (typically two hours before test onset) and then returned to their home cages. Thirty minutes prior to testing, animals are placed on the apparatus again. After the pretreatment time had elapsed, the procedure above is repeated to determine drug efficacy. Data can be expressed as the mean gram force to elicit a nociceptive behavior. Statistical analysis can be performed by analysis of variance (ANOVA), with post-hoc analysis using Bonferroni compared to the vehicle group for a significant main effect.

What is claimed is:

1. A compound of Formula I, or a pharmaceutically acceptable salt thereof,

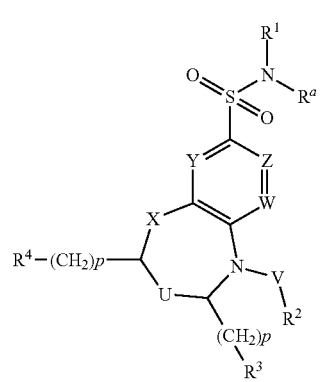

I wherein:
- $R^a$ is hydrogen, $C_{1-6}$alkyl or a three to eight membered cycloalkyl group, where the cycloalkyl group may be unsubstituted or substituted with from 1 to 3 substitutents independently selected from halo, $C_{1-6}$alkyl, —CN, —CF$_3$, —OH, —OCF$_3$ or —OC$_{1-6}$alkyl;
- X is O;
- Each of W, Y and Z are independently CR$^5$;
- U is absent;
- V is absent, —C(R$^d$)$_2$—, (C=O) or —(C=O)N(R$^d$)—;
- $R^b$ is hydrogen, $C_{1-6}$alkyl, —(C=O)NR$^d$R$^d$, —S(=O)$_2$NR$^d$ or —(C=O)C$_{1-6}$alkyl;
- $R^1$ is a five to six membered heteroaryl group having from one to three heteroatoms independently selected from O, N or S, where the heteroaryl group may be unsubstituted or substituted with from 1 to 3 substituents independently selected from a B group, halo, $C_{1-6}$alkyl, —CN, —CF$_3$, —OH, —OCF$_3$, —OC$_{1-6}$alkyl or —(CH$_2$)$_n$NR$^d$R$^d$;
- $R^2$ is a five to ten membered aryl group or a five to ten membered heteroaryl group having from one to three heteroatoms independently selected from O, N or S, where the aryl or heteroaryl group may be unsubstituted or substituted with from 1 to 3 substituents independently selected from an A group, halo, —N$_3$, —CF$_3$, —OH, —OCF$_3$, $C_{1-6}$alkyl, —OC$_{1-6}$alkyl, —CN, —(CH$_2$)$_n$NR$^d$R$^d$, —O(CH$_2$)$_m$OR$^c$, —NR$^d$ five to ten membered aryl, —NR$^d$ five to ten membered heteroaryl, —CO$_2$H, —SR$^d$, —S(=O)$_2$R$^d$, —O-three to eight membered cycloalkyl or —NR$^d$(CH$_2$)$_m$OR$^c$, and heteroaryl group having from one to three heteroatoms independently selected from O, N or S, and the aryl, heteroaryl or cycloalkyl group can be unsubstituted or substituted with from 1 to 3 substituents independently selected from halo, $C_{1-6}$alkyl, —CN, —CF$_3$, —OH, —OCF$_3$, —OC$_{1-6}$alkyl or —(CH$_2$)$_n$NR$^d$R$^d$;
- A is a five to six membered aryl group, a five to six membered heteroaryl group, a three to six membered cycloalkyl group or a three to six membered heterocycloalkyl group, wherein the heteroaryl or heterocycloalkyl group has from one to three heteroatoms independently selected from O, N or S, and where the aryl, heteroaryl cycloalkyl or heterocycloalkyl group may be unsubstituted or substituted with from 1 to 4 substituents independently selected from halo, —CF$_3$, —OH, —OCF$_3$, $C_{1-6}$alkyl, —OC$_{1-6}$alkyl, —CN, —(CH$_2$)$_n$NR$^d$R$^d$, —O(CH$_2$)$_m$OR$^c$, —(C=O)NR$^d$R$^d$, —S(=O)$_2$NR$^d$, NR$^d$(C=O)NR$^d$R$^d$, —NR$^d$S(=O)$_2$NR$^d$, —(C=N)OC$_{1-6}$alkyl, —S(=O)$_2$R$^d$ or —NR$^d$(CH$_2$)$_m$OR$^c$;
- B is a five to six membered aryl group, a five to six membered heteroaryl group, a three to six membered cycloalkyl group or a three to six membered heterocycloalkyl group, wherein the heteroaryl or heterocycloalkyl group has from one to three heteroatoms independently selected from O, N or S, and where the aryl, heteroaryl cycloalkyl or heterocycloalkyl group may be unsubstituted or substituted with from 1 to 4 substituents independently selected from halo, —CF$_3$, —OH, —OCF$_3$, $C_{1-6}$alkyl, —OC$_{1-6}$alkyl, —CN, —(CH$_2$)$_n$NR$^d$R$^d$, —O(CH$_2$)$_m$OR$^c$, —(C=O)NR$^d$R$^d$, —S(=O)$_2$NR$^d$, —NR$^d$(C=O)NR$^d$R$^d$, —NR$^d$S(=O)$_2$NR$^d$, —(C=N)OC$_{1-6}$alkyl, —S(=O)$_2$R$^d$ or —NR$^d$(CH$_2$)$_m$OR$^c$;
- each $R^c$ is independently hydrogen, $C_{1-6}$alkyl, a three to eight membered cycloalkyl group, a five to 10 membered aryl group, a five to ten membered heteroaryl group or a three to eight membered heteroacylcoalkyl group; where the heteroaryl or heterocycloalkyl group has from one to three heteroatoms independently selected from O, N or S, and where the aryl, heteroaryl, cycloalkyl or heterocycloalkyl group may be unsubstituted or substituted with from 1 to 4 substituents independently selected from halo, —CF$_3$, —OH, —OCF$_3$, —OH, $C_{1-6}$alkyl, —OC$_{1-6}$alkyl, —CN, —(CH$_2$)$_n$NR$^d$R$^d$, —O(CH$_2$)$_m$OR$^c$, —(C=O)NR$^d$R$^d$, —S(=O)$_2$NR$^d$, —N(R$^d$)$_2$—NR$^d$(C=O)NR$^d$R$^d$, —NR$^d$S(=O)$_2$NR$^d$, —(C=N)OC$_{1-6}$alkyl, —S(=O)$_2$R$^d$ or —NR$^d$(CH$_2$)$_m$OR$^c$;
- each $R^d$ is independently hydrogen or $C_{1-6}$alkyl, -aryl, —Oaryl, heteroaryl, —Oheteroaryl, cycloalkyl or heterocycloalkyl group, where the —Oaryl, heteroaryl, —Oheteroaryl, cycloalkyl or heterocycloalkyl group may be unsubstituted or substituted with from 1 to 4 substituents independently selected from halo, —CF$_3$, —OH, —CH$_2$F, —CF$_2$H, —OH, —OCF$_3$, $C_{1-6}$alkyl, —OC$_{1-6}$alkyl, or —CN;
- each $R^3$ is independently hydrogen, $C_{1-6}$alkyl, —OC$_{1-6}$alkyl, $C_{1-6}$haloalkyl, —OC$_{1-6}$haloalkyl, a five or six membered aryl or —Oaryl group, or a five or six membered heteroaryl or —Oheteroaryl group, a three to eight membered cycloalkyl group or a three to eight membered heterocycloalkyl group, where the heteroaryl, —Oheteroaryl or heterocycloalkyl group has from one to three heteroatoms independently selected from O, N or S, and where the aryl, —Oaryl, heteroaryl, —Oheteroaryl, cycloalkyl or heterocycloalkyl group may be unsubstituted or substituted with from 1 to 4 substituents independently selected from halo, —CF$_3$, —OH, —CH$_2$F, —CF$_2$H, —OH, —OCF$_3$, $C_{1-6}$alkyl, —OC$_{1-6}$alkyl, —CN, —(CH$_2$)$_n$NR$^d$R$^d$, or $R^3$ together with the ring carbon to which it is attached can be a (C=O) group;
- each $R^4$ is independently hydrogen, $C_{1-6}$alkyl, —OC$_{1-6}$alkyl, $C_{1-6}$haloalkyl, —OC$_{1-6}$haloalkyl, a five or six membered aryl or —Oaryl group, or a five or six membered heteroaryl or —Oheteroaryl group, a three to eight membered cycloalkyl group or a three to eight membered heterocycloalkyl group, where the heteroaryl, —Oheteroaryl or heterocycloalkyl group has from one to three heteroatoms independently selected from O, N or S, and where the aryl, —Oaryl, heteroaryl, —Oheteroaryl, cycloalkyl or heterocycloalkyl group may be unsubstituted or substituted with from 1 to 4 substituents independently selected from halo, —CF$_3$, —OH, —CH$_2$F, —CF$_2$H, —OH, —OCF$_3$, $C_{1-6}$alkyl, —OC$_{1-6}$alkyl, —CN, —(CH$_2$)$_n$NR$^d$R$^d$, or $R^3$ together with the ring carbon to which it is attached can be a (C=O) group;
- each $R^5$ is independently hydrogen, halo, —CN, —OC$_{1-6}$alkyl, $C_{1-6}$alkyl, —CF$_3$, —OH, —CF$_2$H, —OCF$_3$, —OCF$_2$H, or —OCFH$_2$;
- each n is independently 0 to 3;
- each m is independently 1 to 3, and
- each p is independently 0 to 3,
- provided that the compound of Formula I is not N-(5-chloro-1,3-thiazol-2yl)-4-(2-chloro-4-(trifluoromethyl)phenyl)-3,4-dihydro-2H-1,4-benzoxazine-7-sulfonamide;
- 4-(2-chloro-4-(trifluoromethyl)phenyl)-N-(3-methyl-1,2,4-oxadiazol-5-yl)-3,4-dihydro-2H-1,4-benzoxazine-7-sulfonamide;

4-(2-chloro-4-(trifluoromethyl)phenyl)-N-(3-cyano-1,2,4-thiadiazol-5-yl)-3,4-dihydro-2H-1,4-benzoxazine-7-sulfonamide;

4-(2-chloro-4-(trifluoromethyl)phenyl)-N-(5-methyl-1,2,4-oxadiazol-3-yl)-3,4-dihydro-2H-1,4-benzoxazine-7-sulfonamide;

4-(2-chloro-4-(trifluoromethyl)phenyl)-N-(5-methyl-4-(trifluoromethyl)-1,3-thiazol-2-yl)-3,4-dihydro-2H-1,4-benzoxazine-7-sulfonamide;

4-(2-chloro-4-(trifluoromethyl)phenyl)-N-1,3-thiazol-5-yl-3,4-dihydro-2H-1,4-benzoxazine-7-sulfonamide;

4-(2-chloro-4-(trifluoromethyl)phenyl)-N-(5-methyl-3-isoxazolyl)-3,4-dihydro-2H-1,4-benzoxazine-7-sulfonamide;

4-(2-chloro-4-(trifluoromethyl)phenyl)-N-(1-methyl-1H-imidazol-4-yl)-3,4-dihydro-2H-1,4-benzoxazine-7-sulfonamide;

4-(2-chloro-4-(trifluoromethyl)phenyl)-N-(5-methyl-1,3,4-oxadiazol-2-yl)-3,4-dihydro-2H-1,4-benzoxazine-7-sulfonamide;

4-(2-chloro-4-(trifluoromethyl)phenyl)-N-(2,4-difluorophenyl)-3,4-dihydro-2H-1,4-benzoxazine-7-sulfonamide;

4-(2-chloro-4-(trifluoromethyl)phenyl)-N-4-isoxazolyl-3,4-dihydro-2H-1,4-benzoxazine-7-sulfonamide;

4-(2-chloro-4-(trifluoromethyl)phenyl)-N-1,3,4-oxadiazol-2-yl-3,4-dihydro-2H-1,4-benzoxazine-7-sulfonamide;

4-(2-bromo-4-(trifluoromethyl)phenyl)-N-1,3-thiazol-5-yl-3,4-dihydro-2H-1,4-benzoxazine-7-sulfonamide; or 4-(2-(1,2,3,6-tetrahydro-4-pyridinyl)-4-(trifluoromethyl)phenyl)-N-1,3-thiazol-5-yl-3,4-dihydro-2H-1,4-benzoxazine-7-sulfonamide.

2. The compound in accordance with claim 1, or a pharmaceutically acceptable salt thereof, wherein:

each $R^a$ is independently hydrogen or $C_{1-6}$alkyl;

Each of Y, Z and W are CH or CF;

V is absent;

$R^b$ is hydrogen, $C_{1-6}$alkyl or —(C=O)$C_{1-6}$alkyl;

$R^1$ is a five to six membered heteroaryl group having from one to three heteroatoms independently selected from O, N or S, where the heteroaryl group may be unsubstituted or substituted with from 1 to 3 substituents independently selected from halo, $C_{1-6}$alkyl, —CN, —CF$_3$, —OCF$_3$ or —(CH$_2$)$_n$NR$^d$R$^d$;

$R^2$ is a five to ten membered aryl group or heteroaryl group having from one to three heteroatoms independently selected from O, N or S, where the aryl or heteroaryl group may be unsubstituted or substituted with from 1 to 3 substituents independently selected from an A group, halo, —N$_3$, —CF$_3$, —OH, —OCF$_3$, $C_{1-6}$alkyl, —OC$_{1-6}$alkyl, —CN, —(CH$_2$)$_n$NR$^d$R$^d$, —O(CH$_2$)$_m$OR$^c$ or —NR$^d$(CH$_2$)$_m$OR$^c$;

A is a five to six membered aryl group, or a five to six membered heteroaryl or three to six membered heterocycloalkyl group, where the heteroaryl or heterocycloalkyl group has from one to three heteroatoms independently selected from O, N or S, and where the aryl, heteroaryl or heterocycloalkyl group may be unsubstituted or substituted with from 1 to 3 substituents independently selected from halo, —CF$_3$, —OH, —OCF$_3$, $C_{1-6}$alkyl, —OC$_{1-6}$alkyl, —CN, —(CH$_2$)$_n$NR$^d$R$^d$, —O(CH$_2$)$_m$OR, or —NR$^d$(CH$_2$)$_m$OR$^c$;

each $R^c$ is independently hydrogen or $C_{1-6}$alkyl;

each $R^3$ is independently hydrogen, $C_{1-6}$alkyl, —OC$_{1-6}$alkyl, a five to six membered aryl group, or a five to six membered heteroaryl group having from one to three heteroatoms independently selected from O, N or S, or $R^3$ together with the ring carbon to which it is attached can be a (C=O) group;

each $R^4$ is independently hydrogen, $C_{1-6}$alkyl, —OC$_{1-6}$alkyl, a five or six membered aryl group, or a five or six membered heteroaryl group having from one to three heteroatoms independently selected from O, N or S;

each $R^5$ is independently hydrogen, halo, —CN, —OC$_{1-6}$alkyl, $C_{1-6}$alkyl, —CF$_3$ or —OCF$_3$;

each n is independently 0 to 3;

each m is independently 1 to 3; and each p is 0.

3. The compound, or a pharmaceutically acceptable salt thereof, in accordance with claim 2 wherein $R^a$ is hydrogen.

4. The compound, or a pharmaceutically acceptable salt thereof, in accordance with claim 3 wherein $R^3$ is hydrogen.

5. The compound, or a pharmaceutically acceptable salt thereof, in accordance with claim 4 wherein $R^4$ is hydrogen and $R^5$ is hydrogen or F.

6. The compound in accordance with claim 2 wherein $R^1$ is a six membered heteroaryl group having from one to three heteroatoms independently selected from O, N or S, where the heteroaryl group may be unsubstituted or substituted with from 1 to 3 substituents independently selected from halo, $C_{1-6}$alkyl, or —(CH$_2$)$_n$NR$^d$R$^d$.

7. The compound, or a pharmaceutically acceptable salt thereof, in accordance with claim 2 wherein $R^1$ is selected from

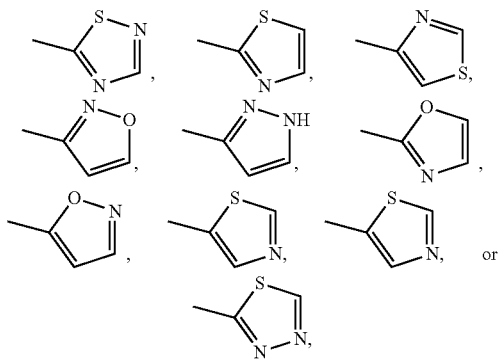

which may be unsubstituted or substituted with from 1 to 3 substituents independently selected from halo, $C_{1-6}$alkyl, or —(CH$_2$)$_n$NR$^d$R$^d$.

8. The compound, or a pharmaceutically acceptable salt thereof, in accordance with claim 2 wherein $R^2$ is substituted phenyl.

9. The compound, or a pharmaceutically acceptable salt thereof, in accordance with claim 8 wherein $R^2$ is disubstituted phenyl, where the substituents are located at the ortho and para positions with respect to the point of attachment of the phenyl ring to the rest of the molecule.

10. The compound, or a pharmaceutically acceptable salt thereof, in accordance with claim 8 wherein $R^2$ is substituted phenyl having at least one A substituent.

11. The compound, or a pharmaceutically acceptable salt thereof, in accordance with claim 10 wherein A is selected from pyrazolyl, dihydropyridinyl, tetrahydropyridinyl, pyridinyl, piperazinyl, or pyrimidinyl, which groups may be unsubstituted or substituted with from 1 to 3 substituents independently selected from halo, —CF$_3$, —OCF$_3$, $C_{1-6}$alkyl, —OC$_{1-6}$alkyl, —CN, —(CH$_2$)$_n$NR$^d$R$^d$, —O(CH$_2$)$_m$OR$^c$ or —NR$^d$(CH$_2$)$_m$OR$^c$.

12. The compound, or a pharmaceutically acceptable salt thereof, in accordance with claim 2 wherein $R^2$ is substituted phenyl wherein one substituent is an A group located at an ortho position with respect to the point of attachment of the phenyl ring to the rest of the molecule and any other substituents are located at the remaining positions.

13. The compound, or a pharmaceutically acceptable salt thereof, in accordance with claim 2 wherein $R^2$ is selected from unsubstituted or substituted quinoline, isoquinoline, naphthalene, quinoxaline, or benozothiazole.

14. The compound, or a pharmaceutically acceptable salt thereof, in accordance with claim 2 wherein Y is CH and each of Z and W, independently, is CH or CF.

15. The compound, or a pharmaceutically acceptable salt thereof, in accordance with claim 1 selected from:
- 4-(2-bromo-4-(trifluoromethyl)phenyl)-N-(1,2,4-thiadiazol-5-yl)-3,4-dihydro-2H-benzo[b][1,4]oxazine-7-sulfonamide;
- 4-(2-chloro-4-(trifluoromethyl)phenyl)-N-(1,2,4-thiadiazol-5-yl)-3,4-dihydro-2H-benzo[b][1,4]oxazine-7-sulfonamide;
- 4-(2-(1-methyl-1H-pyrazol-5-yl)-4-(trifluoromethyl)phenyl)-N-(1,2,4-thiadiazol-5-yl)-3,4-dihydro-2H-benzo[b][1,4]oxazine-7-sulfonamide;
- 4-(2-(1H-pyrazol-4-yl)-4-(trifluoromethyl)phenyl)-N-(1,2,4-thiadiazol-5-yl)-3,4-dihydro-2H-benzo[b][1,4]oxazine-7-sulfonamide;
- 4-(2-chloro-4-(trifluoromethyl)phenyl)-N-(thiazol-2-yl)-3,4-dihydro-2H-benzo[b][1,4]oxazine-7-sulfonamide;
- tert-butyl 4-(2-(7-(n-(1,2,4-thiadiazol-5-yl)sulfamoyl)-2H-benzo[b][1,4]oxazin-4(3H)-yl)-5-(trifluoromethyl)phenyl)-5,6-dihydropyridine-1(2H)-carboxylate;
- 4-(2-(1,2,3,6-tetrahydropyridin-4-yl)-4-(trifluoromethyl)phenyl)-N-(1,2,4-thiadiazol-5-yl)-3,4-dihydro-2H-benzo[b][1,4]oxazine-7-sulfonamide;
- N-(3-(aminomethyl)-1,2,4-thiadiazol-5-yl)-4-(2-chloro-4-(trifluoromethyl)phenyl)-3,4-dihydro-2H-benzo[b][1,4]oxazine-7-sulfonamide;
- 4-(2-chloro-4-(trifluoromethyl)phenyl)-N-(6-chloropyrimidin-4-yl)-3,4-dihydro-2H-benzo[b][1,4]oxazine-7-sulfonamide;
- 4-(2-chloro-4-(trifluoromethyl)phenyl)-N-(3-methyl-1,2,4-thiadiazol-5-yl)-3,4-dihydro-2H-benzo[b][1,4]oxazine-7-sulfonamide;
- 4-(2-chloro-4-(trifluoromethyl)phenyl)-N-(thiazol-4-yl)-3,4-dihydro-2H-benzo[b][1,4]oxazine-7-sulfonamide;
- 4-(2-chloro-4-(trifluoromethyl)phenyl)-N-(5-methylthiazol-2-yl)-3,4-dihydro-2H-benzo[b][1,4]oxazine-7-sulfonamide;
- 4-(2-chloro-4-(trifluoromethyl)phenyl)-N-(isoxazol-3-yl)-3,4-dihydro-2H-benzo[b][1,4]oxazine-7-sulfonamide;
- 4-(2-chloro-4-(trifluoromethyl)phenyl)-N-(1-(2-(dimethylamino)ethyl)-1H-pyrazol-3-yl)-3,4-dihydro-2H-benzo[b][1,4]oxazine-7-sulfonamide;
- 4-(2-chloro-4-(trifluoromethyl)phenyl)-N-(1-methyl-1H-pyrazol-3-yl)-3,4-dihydro-2H-benzo[b][1,4]oxazine-7-sulfonamide;
- 4-(2-chloro-4-(trifluoromethyl)phenyl)-N-(pyrimidin-2-yl)-3,4-dihydro-2H-benzo[b][1,4]oxazine-7-sulfonamide;
- 4-(2-chloro-4-(trifluoromethyl)phenyl)-N-(5-fluoropyridin-2-yl)-3,4-dihydro-2H-benzo[b][1,4]oxazine-7-sulfonamide;
- 4-(2(pyridine-3-yl)-4-(trifluoromethyl)phenyl)-N-(1,2,4-thiadiazol-5-yl)-3,4-dihydro-2H-benzo[b][1,4]oxazine-7-sulfonamide;
- 4-(2-(1-methyl-1,2,3,6-terrahydropyridin-4-yl)-4-(trifluoromethyl)phenyl)-N-(1,2,4-thiadiazol-5-yl)-3,4-dihydro-2H-benzo[b][1,4]oxazine-7-sulfonamide;
- 4-(2-(pyrimidin-5-yl)-4-(trifluoromethyl)phenyl)-N-(1,2,4-thiadiazol-5-yl)-3,4-dihydro-2H-benzo[b][1,4]oxazine-7-sulfonamide;
- 4-(2-chloro-4-(trifluoromethyl)phenyl)-N-(oxazol-2-yl)-3,4-dihydro-2H-benzo[b][1,4]oxazine-7-sulfonamide;
- 4-(2-(3,6-dihydro-2H-pyran-4-yl)-4-(trifluoromethyl)phenyl)-N-(1,2,4-thiadiazol-5-yl)-3,4-dihydro-2H-benzo[b][1,4]oxazine-7-sulfonamide;
- 4-(2-(pyridin-4-yl)-4-(trifluoromethyl)phenyl)-N-(1,2,4-thiadiazol-5-yl)-3,4-dihydro-2H-benzo[b][1,4]oxazine-7-sulfonamide;
- 4-(2-chloro-4-(trifluoromethyl)phenyl)-N-(pyridazin-3-yl)-3,4-dihydro-2H-benzo[b][1,4]oxazine-7-sulfonamide;
- 4-(2-chloro-4-(trifluoromethyl)phenyl)-N-(1,3,4-thiadiazol-2-yl)-3,4-dihydro-2H-benzo[b][1,4]oxazine-7-sulfonamide;
- 4-(2-(2-aminopyridin-4-yl)-4-(trifluoromethyl)phenyl)-N-(1,2,4-thiadiazol-5-yl)-3,4-dihydro-2H-benzo[b][1,4]oxazine-7-sulfonamide;
- 4-phenyl-N-(1,2,4-thiadiazol-5-yl)-3,4-dihydro-2H-benzo[b][1,4]oxazine-7-sulfonamide;
- 4-(2-cyano-4-(trifluoromethyl)phenyl)-N-(1,2,4-thiadiazol-5-yl)-3,4-dihydro-2H-benzo[b][1,4]oxazine-7-sulfonamide;
- 4-(2-chloro-4-(trifluoromethyl)phenyl)-N-(pyrimidin-4-yl)-3,4-dihydro-2H-benzo[b][1,4]oxazine-7-sulfonamide;
- 4-(quinolin-5-yl)-N-(1,2,4-thiadiazol-5-yl)-3,4-dihydro-2H-benzo[b][1,4]oxazine-7-sulfonamide;
- 3-phenyl-N-(1,2,4-thiadiazol-5-yl)-4-(4-(trifluoromethyl)phenyl)-3,4-dihydro-2H-benzo[b][1,4]oxazine-7-sulfonamide;
- N-(1,2,4-thiadiazol-5-yl)-4-(3-(trifluoromethoxy)phenyl)-3,4-dihydro-2H-benzo[b][1,4]oxazine-7-sulfonamide;
- 4-(naphthalen-1-yl)-N-(1,2,4-thiadiazol-5-yl)-3,4-dihydro-2H-benzo[b][1,4]oxazine-7-sulfonamide;
- 4-(4-methoxyphenyl)-N-(1,2,4-thiadiazol-5-yl)-3,4-dihydro-2H-benzo[b][1,4]oxazine-7-sulfonamide;
- 4-(2-(1,2,3,6-tetrahydropyridin-4-yl)-4-(trifluoromethyl)phenyl)-N-(thiazol-2-yl)-3,4-dihydro-2H-benzo[b][1,4]oxazine-7-sulfonamide;
- 4-(4-(2-methoxyethoxyl)phenyl)-N-(1,2,4-thiadiazol-5-yl)-3,4-dihydro-2H-benzo[b][1,4]oxazine-7-sulfonamide;
- 4-(4-chlorophenyl)-N-(thiazol-2-yl)-3,4-dihydro-2H-benzo[b][1,4]oxazine-7-sulfonamide;
- 4-(3-chlorophenyl)-N-(thiazol-2-yl)-3,4-dihydro-2H-benzo[b][1,4]oxazine-7-sulfonamide;
- 4-(2-(1-methyl-1H-pyrazol-5-yl)-4-(trifluoromethyl)phenyl)-N-(thiazol-2-yl)-3,4-dihydro-2H-benzo[b][1,4]oxazine-7-sulfonamide;
- 4-(2-bromo-4-(trifluoromethyl)phenyl)-N-(thiazol-2-yl)-3,4-dihydro-2H-benzo[b][1,4]oxazine-7-sulfonamide;
- 4-(2-(1-methyl-1,2,3,6-tetrahydropyridin-4-yl)-4-(trifluoromethyl)phenyl)-N-(thiazol-2-yl)-3,4-dihydro-2H-benzo[b][1,4]oxazine-7-sulfonamide;
- N-(pyrimidin-4-yl)-4-(2-(1,2,3,6-tetrahydropyridin-4-yl)-4-(trifluoromethyl)phenyl)-3,4-dihydro-2H-benzo[b][1,4]oxazine-7-sulfonamide;
- 4-(2-chlorophenyl)-N-(thiazol-2-yl)-3,4-dihydro-2H-benzo[b][1,4]oxazine-7-sulfonamide;

4-(2-bromo-4-(trifluoromethyl)phenyl)-N-(pyrimidin-4-yl)-3,4-dihydro-2H-benzo[b][1,4]oxazine-7-sulfonamide;

4-(2-((2-methoxyethyl)amino)-4-(trifluoromethyl)phenyl)-N-(pyrimidin-4-yl)-3,4-dihydro-2H-benzo[b][1,4]oxazine-7-sulfonamide;

4-(2-cyano-4-(trifluoromethyl)phenyl)-N-(thiazol-2-yl)-3,4-dihydro-2H-benzo[b][1,4]oxazine-7-sulfonamide;

4-(2-(4-methylpiperazin-1-yl)-4-(trifluoromethyl)phenyl)-N-(thiazol-2-yl)-3,4-dihydro-2H -benzo[b][1,4]oxazine-7-sulfonamide;

4-(2-(1-methyl-1,2,3,6-tetrahydropyridin-4-yl)-4-(trifluoromethyl)phenyl)-N-(pyrimidin-4-yl)-3,4-dihydro-2H-benzo[b][1,4]oxazine-7-sulfonamide;

4-(4-chloro-2-(1,2,3,6-tetrahydropyridin-4-yl)phenyl)-N-(thiazol-2-yl)-3,4-dihydro-2H-benzo[b][1,4]oxazine-7-sulfonamide;

4-(2-(pyridin-4-yl)-4-(trifluoromethyl)phenyl)-N-(thiazol-2-yl)-3,4-dihydro-2H-benzo[b][1,4]oxazine-7-sulfonamide;

4-(2-(pyrimidin-5-yl)-4-(trifluoromethyl)phenyl)-N-(thiazol-2-yl)-3,4-dihydro-2H-benzo[b][1,4]oxazine-7-sulfonamide;

4-(2-chloro-4-(trifluoromethyl)phenyl)-N-(isoxazol-5-yl)-3,4-dihydro-2H-benzo[b][1,4]oxazine-7-sulfonamide;

4-(4-chloro-2-cyanophenyl)-N-(thiazol-2-yl)-3,4-dihydro-2H-benzo[b][1,4]oxazine-7-sulfonamide;

4-(2-cyanophenyl)-N-(1,2,4-thiadiazol-5-yl)-3,4-dihydro-2H-benzo[b][1,4]oxazine-7-sulfonamide;

4-(2-cyanophenyl)-N-(thiazol-2-yl)-3,4-dihydro-2H-benzo[b][1,4]oxazine-7-sulfonamide;

4-(2-(1,2,3,6-tetrahydropyridin-4-yl)phenyl)-N-(thiazol-2-yl)-3,4-dihydro-2H-benzo[b][1,4]oxazine-7-sulfonamide;

4-(2-bromo-4-(trifluoromethyl)phenyl)-N-(pyridin-2-yl)-3,4-dihydro-2H-benzo[b][1,4]oxazine-7-sulfonamide;

4-(2-bromo-4-(trifluoromethyl)phenyl)-N-(thiazol-4-yl)-3,4-dihydro-2H-benzo[b][1,4]oxazine-7-sulfonamide;

N-(pyridin-2-yl)-4-(2-(1,2,3,6-tetrahydropyridin-4-yl)-4-(trifluoromethyl)phenyl)-3,4-dihydro-2H-benzo[b][1,4]oxazine-7-sulfonamide;

4-(2-(1,2,3,6-tetrahydropyridin-4-yl)-4-(trifluoromethyl)phenyl)-N-(thiazol-4-yl)-3,4-dihydro-2H-benzo[b][1,4]oxazine-7-sulfonamide;

4-(4-azido-2-bromophenyl)-N-(thiazol-2-yl)-3,4-dihydro-2H-benzo[b][1,4]oxazine-7-sulfonamide;

4-(4-azido-2-(1,2,3,6-tetrahydropyridin-4-yl)phenyl)-N-(thiazol-2-yl)-3,4-dihydro-2H-benzo[b][1,4]oxazine-7-sulfonamide;

4-(quinolin-6-yl)-N-(thiazol-2-yl)-3,4-dihydro-2H-benzo[b][1,4]oxazine-7-sulfonamide;

4-(2-chloro-5-methylphenyl)-N-(thiazol-2-yl)-3,4-dihydro-2H-benzo[b][1,4]oxazine-7-sulfonamide;

4-(isoquinolin-8-yl)-N-(thiazol-2-yl)-3,4-dihydro-2H-benzo[b][1,4]oxazine-7-sulfonamide;

4-(quinoxalin-6-yl)-N-(thiazol-2-yl)-3,4-dihydro-2H-benzo[b][1,4]oxazine-7-sulfonamide;

4-(benzo[d]thiazol-5-yl)-N-(thiazol-2-yl)-3,4-dihydro-2H-benzo[b][1,4]oxazine-7-sulfonamide;

4-(benzo[d]thiazol-6-yl)-N-(thiazol-2-yl)-3,4-dihydro-2H-benzo[b][1,4]oxazine-7-sulfonamide;

4-(benzo[d]thiazol-4-yl)-N-(thiazol-2-yl)-3,4-dihydro-2H-benzo[b][1,4]oxazine-7-sulfonamide;

4-(6-methylisoquinolin-5-yl)-N-(thiazol-2-yl)-3,4-dihydro-2H-benzo[b][1,4]oxazine-7-sulfonamide;

4-(3,4-dichlorophenyl)-N-(thiazol-2-yl)-3,4-dihydro-2H-benzo[b][1,4]oxazine-7-sulfonamide;

N-(thiazol-2-yl)-4-(m-tolyl)-3,4-dihydro-2H-benzo[b][1,4]oxazine-7-sulfonamide;

4-(4-cyanophenyl)-N-(thiazol-2-yl)-3,4-dihydro-2H-benzo[b][1,4]oxazine-7-sulfonamide;

4-(3-methoxyphenyl)-N-(thiazol-2-yl)-3,4-dihydro-2H-benzo[b][1,4]oxazine-7-sulfonamide;

4-(3-fluoro-2-methylphenyl)-N-(thiazol-2-yl)-3,4-dihydro-2H-benzo[b][1,4]oxazine-7-sulfonamide;

4-(5-fluoro-2-methylphenyl)-N-(thiazol-2-yl)-3,4-dihydro-2H-benzo[b][1,4]oxazine-7-sulfonamide;

4-(2-fluoro-5-methylphenyl)-N-(thiazol-2-yl)-3,4-dihydro-2H-benzo[b][1,4]oxazine-7-sulfonamide;

4-(4-fluoro-3-methylphenyl)-N-(thiazol-2-yl)-3,4-dihydro-2H-benzo[b][1,4]oxazine-7-sulfonamide;

4-(3-fluoro-4-methylphenyl)-N-(thiazol-2-yl)-3,4-dihydro-2H-benzo[b][1,4]oxazine-7-sulfonamide;

4-(2,5-difluorophenyl)-N-(thiazol-2-yl)-3,4-dihydro-2H-benzo[b][1,4]oxazine-7-sulfonamide;

4-(3,4-difluorophenyl)-N-(thiazol-2-yl)-3,4-dihydro-2H-benzo[b][1,4]oxazine-7-sulfonamide;

4-(2-(1,2,3,6-tetrahydropyridin-4-yl)-4-(trifluoromethyl)phenyl)-N-(thiazol-5-yl)-3,4-dihydro-2H-benzo[b][1,4]oxazine-7-sulfonamide;

N-(pyrimidin-2-yl)-4-(2-(1,2,3,6-tetrahydropyridin-4-yl)-4-(trifluoromethyl)phenyl)-3,4-dihydro-2H-benzo[b][1,4]oxazine-7-sulfonamide;

N-(pyridazin-3-yl)-4-(2-(1,2,3,6-tetrahydropyridin-4-yl)-4-(trifluoromethyl)phenyl)-3,4-dihydro-2H-benzo[b][1,4]oxazine-7-sulfonamide;

N-(pyrazin-2-yl)-4-(2-(1,2,3,6-tetrahydropyridin-4-yl)-4-(trifluoromethyl)phenyl)-3,4-dihydro-2H-benzo[b][1,4]oxazine-7-sulfonamide;

4-(2-cyano-4-(trifluoromethyl)phenyl)-N-(pyrimidin-4-yl)-3,4-dihydro-2H-benzo[b][1,4]oxazine-7-sulfonamide;

4-(2-cyano-4-(trifluoromethyl)phenyl)-N-(oxazol-2-yl)-3,4-dihydro-2H-benzo[b][1,4]oxazine-7-sulfonamide;

4-(2-cyano-4-(trifluoromethyl)phenyl)-N-(isoxazol-5-yl)-3,4-dihydro-2H-benzo[b][1,4]oxazine-7-sulfonamide; or 4-(3-chlorophenyl)-3-oxo-N-(1,3,4-thiadiazol-2-yl)-3,4-dihydro-2H-benzo[b][1,4]oxazine-7-sulfonamide.

16. A compound, or a pharmaceutically acceptable salt thereof, in accordance with claim 1 selected from:

(2S)-4-(2-cyano-4-(trifluoromethyl)phenyl)-2-methyl-N-1,3-thiazol-2-yl-3,4-dihydro-2H-1,4-benzoxazine-7-sulfonamide;

(2R)-4-(2-cyano-4-(trifluoromethyl)phenyl)-2-methyl-N-1,3-thiazol-2-yl-3,4-dihydro-2H-1,4-benzoxazine-7-sulfonamide;

(3R)-4-(2-cyano-4-(trifluoromethyl)phenyl)-3-methyl-N-1,3-thiazol-2-yl-3,4-dihydro-2H-1,4-benzoxazine-7-sulfonamide;

(3S)-4-(2-cyano-4-(trifluoromethyl)phenyl)-3-methyl-N-1,3-thiazol-2-yl-3,4-dihydro-2H-1,4-benzoxazine-7-sulfonamide;

(2R)-4-(4-chloro-2-methoxyphenyl)-2-methyl-N-1,3-thiazol-2-yl-3,4-dihydro-2H-1,4-benzoxazine-7-sulfonamide;

(2R)-4-(4-cyano-2-methoxyphenyl)-2-methyl-N-1,3-thiazol-2-yl-3,4-dihydro-2H-1,4-benzoxazine-7-sulfonamide;

(2S)-4-(4-cyano-2-methoxyphenyl)-2-methyl-N-1,3-thiazol-2-yl-3,4-dihydro-2H-1,4-benzoxazine-7-sulfonamide;

4-(5-chloro-2-methoxy-3-pyridinyl)-N-1,3-thiazol-2-yl-3,4-dihydro-2H-1,4-benzoxazine-7-sulfonamide;
4-(2-methoxy-5-(trifluoromethyl)phenyl)-N-1,3-thiazol-2-yl-3,4-dihydro-2H-1,4-benzoxazine-7-sulfonamide;
4-(3-cyano-5-methylphenyl)-N-1,3-thiazol-2-yl-3,4-dihydro-2H-1,4-benzoxazine-7-sulfonamide;
4-(2-cyano-5-(trifluoromethoxy)phenyl)-N-1,3-thiazol-2-yl-3,4-dihydro-2H-1,4-benzoxazine-7-sulfonamide;
4-(2,2-difluoro-1,3-benzodioxol-4-yl)-N-1,3-thiazol-2-yl-3,4-dihydro-2H-1,4-benzoxazine-7-sulfonamide;
4-(2,5-dimethoxyphenyl)-N-1,3-thiazol-2-yl-3,4-dihydro-2H-1,4-benzoxazine-7-sulfonamide;
4-(2-methyl-4-(trifluoromethoxy)phenyl)-N-1,3-thiazol-2-yl-3,4-dihydro-2H-1,4-benzoxazine-7-sulfonamide;
4-(4-(1H-pyrazol-1-yl)phenyl)-N-1,3-thiazol-2-yl-3,4-dihydro-2H-1,4-benzoxazine-7-sulfonamide;
4-(2-methoxy-5-(trifluoromethyl)-3-pyridinyl)-N-1,3-thiazol-2-yl-3,4-dihydro-2H-1,4-benzoxazine-7-sulfonamide;
4-(2-(4-pyridinyl)phenyl)-N-1,3-thiazol-2-yl-3,4-dihydro-2H-1,4-benzoxazine-7-sulfonamide;
4-(2-(1-methyl-1H-pyrazol-5-yl)phenyl)-N-1,3-thiazol-2-yl-3,4-dihydro-2H-1,4-benzoxazine-7-sulfonamide;
4-(4-fluoro-2-methoxyphenyl)-N-1,3-thiazol-2-yl-3,4-dihydro-2H-1,4-benzoxazine-7-sulfonamide;
4-(5-fluoro-2-methoxyphenyl)-N-1,3-thiazol-2-yl-3,4-dihydro-2H-1,4-benzoxazine-7-sulfonamide;
4-(2,3-dichlorophenyl)-N-1,3-thiazol-2-yl-3,4-dihydro-2H-1,4-benzoxazine-7-sulfonamide;
4-(3-(difluoromethoxy)phenyl)-N-1,3-thiazol-2-yl-3,4-dihydro-2H-1,4-benzoxazine-7-sulfonamide;
N-1,3-thiazol-2-yl-4-(3-(trifluoromethyl)phenyl)-3,4-dihydro-2H-1,4-benzoxazine-7-sulfonamide;
4-(3-(cyanomethyl)phenyl)-N-1,3-thiazol-2-yl-3,4-dihydro-2H-1,4-benzoxazine-7-sulfonamide;
4-(3-cyano-4-fluorophenyl)-N-1,3-thiazol-2-yl-3,4-dihydro-2H-1,4-benzoxazine-7-sulfonamide;
4-(2,4-difluorophenyl)-N-1,3-thiazol-2-yl-3,4-dihydro-2H-1,4-benzoxazine-7-sulfonamide;
4-(2-cyano-4-fluorophenyl)-N-1,3-thiazol-2-yl-3,4-dihydro-2H-1,4-benzoxazine-7-sulfonamide;
4-(5-chloro-2-methylphenyl)-N-1,3-thiazol-2-yl-3,4-dihydro-2H-1,4-benzoxazine-7-sulfonamide;
4-(2-(difluoromethoxy)phenyl)-N-1,3-thiazol-2-yl-3,4-dihydro-2H-1,4-benzoxazine-7-sulfonamide;
4-(2,5-dichlorophenyl)-N-1,3-thiazol-2-yl-3,4-dihydro-2H-1,4-benzoxazine-7-sulfonamide;
4-(4-cyano-2-methoxyphenyl)-N-1,3-thiazol-2-yl-3,4-dihydro-2H-1,4-benzoxazine-7-sulfonamide;
4-(2-methoxy-4-(trifluoromethyl)phenyl)-N-1,3-thiazol-2-yl-3,4-dihydro-2H-1,4-benzoxazine-7-sulfonamide;
N-1,3-thiazol-2-yl-4-(5-(trifluoromethyl)-2-pyridinyl)-3,4-dihydro-2H-1,4-benzoxazine-7-sulfonamide;
4-(2-cyano-5-(trifluoromethyl)phenyl)-N-1,3-thiazol-2-yl-3,4-dihydro-2H-1,4-benzoxazine-7-sulfonamide;
4-(4-chloro-2-methoxyphenyl)-N-1,3-thiazol-2-yl-3,4-dihydro-2H-1,4-benzoxazine-7-sulfonamide;
4-(2-cyano-5-fluorophenyl)-N-1,3-thiazol-2-yl-3,4-dihydro-2H-1,4-benzoxazine-7-sulfonamide;
4-(5-chloro-2-cyanophenyl)-N-1,3-thiazol-2-yl-3,4-dihydro-2H-1,4-benzoxazine-7-sulfonamide;
4-(4-chloro-2-(difluoromethoxy)phenyl)-N-1,3-thiazol-2-yl-3,4-dihydro-2H-1,4-benzoxazine-7-sulfonamide;
4-(2-cyano-5-methylphenyl)-N-1,3-thiazol-2-yl-3,4-dihydro-2H-1,4-benzoxazine-7-sulfonamide;
4-(4-chloro-2-methylphenyl)-N-1,3-thiazol-2-yl-3,4-dihydro-2H-1,4-benzoxazine-7-sulfonamide;
4-(3-cyano-3'-fluoro-4-biphenylyl)-N-1,3-thiazol-2-yl-3,4-dihydro-2H-1,4-benzoxazine-7-sulfonamide;
4-(3'-fluoro-3-methoxy-4-biphenylyl)-N-1,3-thiazol-2-yl-3,4-dihydro-2H-1,4-benzoxazine-7-sulfonamide;
4-(2-cyano-4-(1-methylethyl)phenyl)-N-1,3-thiazol-2-yl-3,4-dihydro-2H-1,4-benzoxazine-7-sulfonamide;
4-(2-cyano-4-ethylphenyl)-N-1,3-thiazol-2-yl-3,4-dihydro-2H-1,4-benzoxazine-7-sulfonamide;
4-(2-((1R)-1,2-dihydroxyethyl)-4-(trifluoromethyl)phenyl)-N-1,3-thiazol-2-yl-3,4-dihydro-2H-1,4-benzoxazine-7-sulfonamide;
4-(2-((1S)-1,2-dihydroxyethyl)-4-(trifluoromethyl)phenyl)-N-1,3-thiazol-2-yl-3,4-dihydro-2H-1,4-benzoxazine-7-sulfonamide;
4-(2-methoxyphenyl)-N-1,3-thiazol-2-yl-3,4-dihydro-2H-1,4-benzoxazine-7-sulfonamide;
4-(2-(hydroxymethyl)-4-(trifluoromethyl)phenyl)-N-1,3-thiazol-2-yl-3,4-dihydro-2H-1,4-benzoxazine-7-sulfonamide;
4-(2-((2R)-2,3-dihydroxypropyl)-4-(trifluoromethyl)phenyl)-N-1,3-thiazol-2-yl-3,4-dihydro-2H-1,4-benzoxazine-7-sulfonamide;
4-(2-((2S)-2,3-dihydroxypropyl)-4-(trifluoromethyl)phenyl)-N-1,3-thiazol-2-yl-3,4-dihydro-2H-1,4-benzoxazine-7-sulfonamide;
4-(4-chloro-2-((2R)-2,3-dihydroxypropyl)phenyl)-N-1,3-thiazol-2-yl-3,4-dihydro-2H-1,4-benzoxazine-7-sulfonamide;
4-(4-chloro-2-((2S)-2,3-dihydroxypropyl)phenyl)-N-1,3-thiazol-2-yl-3,4-dihydro-2H-1,4-benzoxazine-7-sulfonamide;
6-chloro-4-(2-cyano-4-(trifluoromethyl)phenyl)-N-1,3-thiazol-2-yl-3,4-dihydro-2H-1,4-benzoxazine-7-sulfonamide;
4-(2-methoxy-6-(trifluoromethyl)-3-pyridinyl)-N-1,3-thiazol-2-yl-3,4-dihydro-2H-1,4-benzoxazine-7-sulfonamide;
4-(2-cyano-4-(trifluoromethyl)phenyl)-6-fluoro-N-1,3-thiazol-2-yl-3,4-dihydro-2H-1,4-benzoxazine-7-sulfonamide;
4-(2-cyano-4-(trifluoromethyl)phenyl)-8-fluoro-N-1,3-thiazol-2-yl-3,4-dihydro-2H-1,4-benzoxazine-7-sulfonamide;
4-(4-cyano-2-methoxyphenyl)-6-fluoro-N-1,3-thiazol-2-yl-3,4-dihydro-2H-1,4-benzoxazine-7-sulfonamide;
4-(2-cyano-4-(trifluoromethyl)phenyl)-5-fluoro-N-1,3-thiazol-2-yl-3,4-dihydro-2H-1,4-benzoxazine-7-sulfonamide; or
4-(2-methoxy-4-(trifluoromethyl)phenyl)-3-oxo-N-1,3-thiazol-2-yl-3,4-dihydro-2H-1,4-benzoxazine-7-sulfonamide.

17. A method of treating pain, the method comprising administering to a patient in need thereof a therapeutically effective amount of a compound in accordance with claim 2, or a pharmaceutically acceptable salt thereof.

18. The method of claim 17 wherein the treatment is for chronic pain, acute pain, neuropathic pain, pain associated with rheumatoid arthritis, pain associated with osteoarthritis, pain associated with cancer or a cough selected from the group consisting of post viral cough, viral cough, and acute viral cough.

19. A pharmaceutical composition comprising a compound in accordance with claim 2, or a pharmaceutically acceptable salt thereof, and a pharmaceutically acceptable excipient.

* * * * *